US007344861B2

(12) United States Patent
Jacobs et al.

(10) Patent No.: US 7,344,861 B2

(45) Date of Patent: Mar. 18, 2008

(54) SECRETED PROTEINS AND POLYNUCLEOTIDES ENCODING THEM

(75) Inventors: Kenneth Jacobs, Newton, MA (US); John M. McCoy, Reading, MA (US); Edward R. LaVallie, Harvard, MA (US); Lisa A. Collins-Racie, Acton, MA (US); David Merberg, Acton, MA (US); Michael J. Agostino, Andover, MA (US); Robert J. Steininger, II, Cambridge, MA (US); Vikki Spaulding, Billerica, MA (US); Gordon G. Wong, Brookline, MA (US); Hilary F. Clark, San Francisco, CA (US); Kim Fechtel, Arlington, MA (US); Cheryl Evans, Germantown, MD (US); Maurice Treacy, Dublin (IE)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 11/395,249

(22) Filed: Apr. 3, 2006

(65) Prior Publication Data

US 2006/0177904 A1 Aug. 10, 2006

Related U.S. Application Data

(63) Continuation of application No. 10/616,263, filed on Jul. 8, 2003, now abandoned, which is a continuation of application No. 09/374,046, filed on Aug. 13, 1999, now abandoned.

(60) Provisional application No. 60/148,424, filed on Aug. 11, 1999, provisional application No. 60/132,020, filed on Apr. 30, 1999, provisional application No. 60/120,575, filed on Feb. 18, 1999, provisional application No. 60/119,931, filed on Feb. 12, 1999, provisional application No. 60/115,234, filed on Jan. 8, 1999, provisional application No. 60/105,368, filed on Oct. 23, 1998, provisional application No. 60/099,229, filed on Sep. 4, 1998, provisional application No. 60/096,815, filed on Aug. 17, 1998, provisional application No. 60/096,622, filed on Aug. 14, 1998.

(51) Int. Cl.

| | |
|---|---|
| *C12N 5/10* | (2006.01) |
| *C12N 15/12* | (2006.01) |
| *C12N 15/62* | (2006.01) |

(52) U.S. Cl. .................... 435/69.1; 536/23.5; 435/325; 435/252.3; 435/254.11; 435/320.1

(58) Field of Classification Search ..................... None
See application file for complete search history.

(56) References Cited

U.S. PATENT DOCUMENTS

| | | | | |
|---|---|---|---|---|
| 5,643,781 A | 7/1997 | Suzuki | ....................... | 435/325 |
| 5,798,224 A | 8/1998 | Suzuki | ...................... | 435/69.1 |
| 6,133,232 A | 10/2000 | De Robertis et al. | ......... | 514/12 |
| 6,972,325 B2 * | 12/2005 | Fong et al. | ................. | 530/399 |

FOREIGN PATENT DOCUMENTS

| | | |
|---|---|---|
| WO | WO 94/14960 A2 | 7/1994 |
| WO | WO 98/45436 | 10/1998 |
| WO | WO 99/31236 | 6/1999 |

OTHER PUBLICATIONS

Eck & Wilson in Goodman & Gilman's The Pharmacological Basis of Therapeutics, Ninth Edition, McGraw-Hill New York, 1996.*

Callard & Gearing (1994) The Cytokine Factsbook. Academic Press Ltd., pp. 39-40.*

Reeck et al. Cell, vol. 50, p. 667.*

Rieger et al. Glossary of Genetics and Cytogenetics (1976), pp. 16-19.*

Bossy et al. "Conservation of neural nicotinic acetylcholine receptors from *Drosophila* to vertebrate central nervous systems" *EMBO J.* 7(3):611-618 (Jun. 1988).

GenBank Accession No. AA057573 for Soares retina N2b4HR Homo sapiens cDNA clone Image: 381523 3', similar to WP:T12G3.4 CE06440 Strictosidine Synthase Like;, mRNA sequence (Feb. 2, 1997).

GenBank Accession No. AA179549 for Stratagene HeLa cell s3 937216 Homo sapiens cDNA clone IMAGE:612765 3', mRNA sequence (Dec. 31, 1996).

GenBank Accession No. AA287697 for NCI_CGAP_GCB1 Homo sapiens cDNA clone IMAGE:701234 5',mRNA sequence (Aug. 13, 1997).

GenBank Accession No. AL035661 for Human DNA sequence from clone RP4-568C11 on chromosome 10p11.21-11.23 (Mar. 15, 1999).

Doerks, et al., TIG vol. 14, No. 6, pp. 248-250 Jun. 1998.

GenBank Accession No. AA292131 for zr58h08.r1 Soares_NhHMPu_S1 Homo sapiens cDNA clone IMAGE:667647 5', mRNA sequence.

GenBank Accession No. AA292132 for zr58h08.s1 Soares_NhHMPu_S1 Homo sapiens cDNA clone IMAGE:667647 3', mRNA sequence.

GenBank Accession No. AA320829 for EST23234 Adipose tissue, white II Homo sapiens cDNA 5' end, mRNA sequence.

GenBank Accession No. AA328473 for EST31956 Embryo, 12 week I Homo sapiens cDNA 5'end, mRNA sequence.

GenBank Accession No. AA329081 for EST31956 Embryo, 12 week I Homo sapiens cDNA 5' end, mRNA sequence.

GenBank Accession No. AA342606 for EST48158 Fetal spleen Homo sapiens cDNA 3' end, mRNA sequence.

GenBank Accession No. AA375083 for EST87308 HSC172 cells I Homo sapiens cDNA 5' end, mRNA sequence.

GenBank Accession No. AA532364 for nj12a08.s1 NCI_CGAP_Pr22 Homo sapiens cDNA clone IMAGE:986102 3', mRNA sequence.

GenBank Accession No. AA558554 for nl69g02.s1 NCI_CGAP_Pr4.1 Homo sapiens cDNA clone IMAGE:1045970 similar to TR:G307329 G307329 PROTOCADHERIN 43;, mRNA sequence.

(Continued)

*Primary Examiner*—Prema Mertz

(74) *Attorney, Agent, or Firm*—Fitzpatrick, Cella, Harper & Scinto

(57) ABSTRACT

Novel polynucleotides and the proteins encoded thereby are disclosed.

5 Claims, 3 Drawing Sheets

OTHER PUBLICATIONS

GenBank Accession No. AA584313 for nn79g06.s1 NCI_CGAP_Co9 Homo sapiens cDNA clone IMAGE:1090138 3', mRNA sequence.
GenBank Accession No. AA604083 for no72a05.s1 NCI_CGAP_AA1 Homo sapiens cDNA clone IMAGE:1112336 3', mRNA sequence.
GenBank Accession No. AA678070 for zi12g09.s1 Soares_fetal_liver_spleen_1NFLS_S1 Homo sapiens cDNA clone IMAGE:430624 3', mRNA sequence.
GenBank Accession No. AA704401 for zj21g02.s1 Soares_fetal_liver_spleen_1NFLS_S1 Homo sapiens cDNA clone IMAGE:450962 3', mRNA sequence.
GenBank Accession No. AA828004 for of10d08.s1 NCI_CGAP_Co12 Homo sapiens cDNA clone IMAGE:1420719 3', mRNA sequence.
GenBank Accession No. AA961517 for oq79b01.s1 NCI_CGAP_Kid6 Homo sapiens cDNA clone IMAGE:1592521 3', mRNA sequence.
GenBank Accession No. AB002343 for Human mRNA for KIAA0345 gene, complete cds.
GenBank Accession No. AF029343 for Homo sapiens protocadherin 68 (PCH68) mRNA, complete cds.
GenBank Accession No. AF042192 for *Xenopus laevis* paraxial protocadherin mRNA, complete cds.
GenBank Accession No. AF052685 Home sapiens protocadherin 43 gene, exon 3, exon 4, and complete cds.
GenBank Accession No. A1040077 for ox52a10.x1 Soares_total_fetus_Nb2HF8_9w Homo sapiens cDNA clone IMAGE:1659930 3', mRNA sequence.
GenBank Accession No. A1088690 for qa12a02.x1 NCI_CGAP_Brn23 Homo sapiens cDNA clone IMAGE:1686506 3', mRNA sequence.
GenBank Accession No. A1243359 for qh30g06.x1 Soares_NFL_T_GBC_S1 Homo sapiens cDNA clone IMAGE:1846234 3', mRNA sequence.
GenBank Accession No. AI129871 for qc35c10.x1 Soares_pregnant_uterus_NbHPU Homo sapiens cDNA clone IMAGE:1711602 3', mRNA sequence.
GenBank Accession No. A1245928 for qk33c10.X1 NCI_CGAP_Co8 Homo sapiens cDNA clone IMAGE:18707703', mRNA sequence.
GenBank Accession No. AI347052 for qp54g11.x1 NCI_CGAP_Co8 Homo sapiens cDNA clone IMAGE:1926884 3', mRNA sequence.
GenBank Accession No. A1358874 for qy24b08.x1 NCI_CGAP_Brn 23 Homo sapiens cDNA clone IMAGE:2012919 3', mRNA sequence.
GenBank Accession No. AI369507 for ta67h11.x1 Soares_total_fetus_Nb2HF8_9w Homo sapiens cDNA clone IMAGE:2049189 3', mRNA sequence.
GenBank Accession No. AI424628 for tf34g06.x1 NCI-CGAP-Brn23 Homo sapiens cDNA clone IMAGE:2098138 3', mRNA sequence.
GenBank Accession No. AI750440 for cn02h12.x2 Normal Human Trabecular Bone Cells Homo sapiens cDNA clone NHTBC-cn02h12 random, mRNA sequence.
GenBank Accession No. AI750441 for cn02h12.y2 Normal Human Trabecular Bone Cells Homo sapiens cDNA clone NHTBC_cn02h12 random, mRNA sequence.
GenBank Accession No. C01861 for HUMGS0003835 Human adult (K. Okubo) Homo sapiens cDNA, mRNA sequence.
GenBank Accession No. D81553 for HUM172F01B Human fetal brain (T Fujiwara) Homo sapiens cDNA clone GEN-172F01 5', mRNA sequence.
GenBank Accession No. F13763 for HSFII099 Stratagene cat#937212 (1992) Homo sapiens cDNA clone FII099 3', mRNA sequence.
GenBank Accession No. H88270 for yw18a10.r1 Morton Fetal Cochlea Homo sapiens cDNA clone IMAGE:252570 5', mRNA sequence.
GenBank Accession No. H88271 for yw18a10.s1 Morton Fetal Cochlea Homo sapiens cDNA clone IMAGE:252570 3', mRNA sequence.
GenBank Accession No. H88539 for yw22g06.s1 Morton Fetal Cochlea Homo sapiens cDNA clone IMAGE:253018 3', mRNA sequence.
GenBank Accession No. H88587 for yw22g06.r1 Morton Fetal Cochlea Homo sapiens cDNA clone IMAGE:253018 5', mRNA sequence.
GenBank Accession No. H88655 for yw23d04.s1 Morton Fetal Cochlea Homo sapiens cDNA clone IMAGE:253063 3', mRNA sequence.
GenBank Accession No. H88699 for yw23d04.r1 Morton Fetal Cochlea Homo sapiens cDNA clone IMAGE:253063 5', mRNA sequence.
GenBank Accession No. L11373 for Human protocadherin 43 mRNA, complete cds for abbreviated PC43.
GenBank Accession No. L43592 for *Rattus norvegicus* protocadherin-3 (pcdh3) mRNA, complete cds.
GenBank Accession No. N63129 for yz36g10.s1 Morton Fetal Cochlea Homo sapiens cDNA clone IMAGE:285186 3', mRNA sequence.
GenBank Accession No. R49144 for yg69h04.s1 Soares infant brain 1NIB Homo sapiens cDNA clone IMAGE:38816 3', mRNA sequence.
GenBank Accession No. R68257 for yh98h07.s1 Soares placenta Nb2HP Homo sapiens cDNA clone IMAGE:137821 3', mRNA sequence.
GenBank Accession No. R68551 for yh98h07.r1 Soares placenta Nb2HP Homo sapiens cDNA clone IMAGE 137821 5', nRNA sequence.
GenBank Accession No. W48094 for mc85c01.r1 Soares mouse embryo NbME 13.5 14.5 Mus musculus cDNA clone IMAGE:355296 5', mRNA sequence.
GenBank Accession No. W55718 for md14e08.r1 Soares mouse embryo NbME 13.5 14.5 Mus musculus cDNA clone IMAGE:368390 5', mRNA sequence.
GenBank Accession No. W72511 for zd64f08.s1 Soares_fetal_heart_NbHH19W Homo sapiens cDNA clone IMAGE:345447 3', mRNA sequence.
GenBank Accession No. W76069 for zd64f08.r1 Soares_fetal_heart_NbHH19W Homo sapiens cDNA clone IMAGE:345447 5', mRNA sequence.
GenBank Accession No. Y08715 for Mus musculus mRNA for vascular cadherin-2.
Nollet, F. et al. "Phylogenetic Analysis of the Cadherin Superfamily allows Identification of Six Major Subfamilies Besides Several Solitary Members" *J. Mol. Biol.* 229:551-572 (2000).
Sago, H. et al. "Cloning, Expression, and Chromosomal Localization of a Novel Cadherin-Related Protein, Protocadherin-3" *Genomics* 29:631-640 (1995).
Sano, K. et al. "Protocadherins: a large family of cadherin-related molecules in central nervous system" *The EMBO Journal* 12(6):2249-2256 (1993).
Suzuki, S.T. "Recent Progress in Protocadherin Research" *Experimental Cell Research* 261: 13-18 (2000).
Wu, Q. et al. "Large exons encoding multiple ectodomains are a characteristic feature of protocadherin genes" *PNAS* 97(7):3124-3219 (Mar. 28, 2000).
Yagi, T. et al. "Cadherin superfamily genes: functions, genomic organization, and neurologic diversity" *Genes & Development* 14:1169-1180 (2000).
Mikayama et al. Proc. Natl. Acad. Sci. USA vol. 9, pp. 10056-10060 (1993).
Voet et al. Biochemistry, *John Wiley & Sons, Inc.* pp. 126-128 and 228-234 (1990).
Skolnick, et al. Nature Biotechnology, Mar. 2000. vol. 18, pp. 283-287.
Eck, et al., "Gene-Based Therapy", Goodman & Gilman's The Pharmacological Basis of Therapeutics, Ninth Edition, McGraw-Hill, New York, 1996, pp. 77-101.
Reeck, et al. "'Homology' in Proteins and Nucleic Acids: A Terminology Muddle and a Way out of It.", Cell, vol. 50, pp. 667.

Skolnick, et al., "Structural genomics and its importance for gene function analysis", Nature Biotechnology, vol. 18, pp. 283-287, Mar. 2000.

Ganong, Review of Medical Physiology, 17th edition, Appleton & Lange, pp. 220, 446, 1995.

Creighton, Proteins: Structures and Molecules Principles, Freeman & Co., New York, pp. 70-73, 1984.

Callard, et al., The Cytokine Factsbook, Academic Press Ltd. pp. 39-40, 1994.

* cited by examiner

SECRETED PROTEINS AND POLYNUCLEOTIDES ENCODING THEM

This application is a continuation of application Ser. No. 10/616,263, filed Jul. 8, 2003 now abandoned, which is a continuation of application Ser. No. 09/374,046, filed Aug. 13, 1999, now abandoned which is a continuation-in-part of the following applications:

(1) provisional application Ser. No. 60/096,622, filed Aug. 14, 1998;
(2) provisional application Ser. No. 60/096,815, filed Aug. 17, 1998;
(3) provisional application Ser. No. 60/099,229, filed Sep. 4, 1998;
(4) provisional application Ser. No. 60/105,368, filed Oct. 23, 1998;
(5) provisional application Ser. No. 60/115,234, filed Jan. 8, 1999;
(6) provisional application Ser. No. 60/119,931, filed Feb. 12, 1999;
(7) provisional application Ser. No. 60/120,575, filed Feb. 18, 1999;
(8) provisional application Ser. No. 60/132,020, filed Apr. 30, 1999;
(9) provisional application Ser. No. 60/148,424, filed Aug. 11, 1999; all of which are incorporated by reference herein.

FIELD OF THE INVENTION

The present invention provides novel polynucleotides and proteins encoded by such polynucleotides, along with therapeutic, diagnostic and research utilities for these polynucleotides and proteins.

BACKGROUND OF THE INVENTION

Technology aimed at the discovery of protein factors (including e.g., cytokines, such as lymphokines, interferons, CSFs and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization cloning techniques, have advanced the state of the art by making available large numbers of DNA/amino acid sequences for proteins that are known to have biological activity by virtue of their secreted nature in the case of leader sequence cloning, or by virtue of the cell or tissue source in the case of PCR-based techniques. It is to these proteins and the polynucleotides encoding them that the present invention is directed.

SUMMARY OF THE INVENTION

In one embodiment, the present invention provides a composition comprising an isolated polynucleotide selected from the group consisting of:

(a) a polynucleotide comprising the nucleotide sequence of SEQ ID NO:1;
(b) a polynucleotide comprising the nucleotide sequence of SEQ ID NO:1 from nucleotide 87 to nucleotide 821;
(c) a polynucleotide comprising the nucleotide sequence of SEQ ID NO:1 from nucleotide 120 to nucleotide 821;
(d) a polynucleotide comprising the nucleotide sequence of SEQ ID NO:1 from nucleotide 1 to nucleotide 1625;
(e) a polynucleotide comprising the nucleotide sequence of the full-length protein coding sequence of clone co62_12 deposited under accession number ATCC 98825;
(f) a polynucleotide encoding the full-length protein encoded by the cDNA insert of clone co62_12 deposited under accession number ATCC 98825;
(g) a polynucleotide comprising the nucleotide sequence of a mature protein coding sequence of clone co62_12 deposited under accession number ATCC 98825;
(h) a polynucleotide encoding a mature protein encoded by the cDNA insert of clone co62_12 deposited under accession number ATCC 98825;
(i) a polynucleotide encoding a protein comprising the amino acid sequence of SEQ ID NO:2;
(j) a polynucleotide encoding a protein comprising a fragment of the amino acid sequence of SEQ ID NO:2 having biological activity, the fragment comprising eight contiguous amino acids of SEQ ID NO:2;
(k) a polynucleotide which is an allelic variant of a polynucleotide of (a)-(h) above;
(l) a polynucleotide which encodes a species-homologue of the protein of (i) or (j) above;
(m) a polynucleotide that hybridizes under stringent conditions to any one of the polynucleotides specified in (a)-(j); and
(n) a polynucleotide that hybridizes under stringent conditions to any one of the polynucleotides specified in (a)-(j) and that has a length that is at least 25% of the length of SEQ ID NO:1.

Preferably, such polynucleotide comprises the nucleotide sequence of SEQ ID NO:1 from nucleotide 87 to nucleotide 821; the nucleotide sequence of SEQ ID NO:1 from nucleotide 120 to nucleotide 821; the nucleotide sequence of SEQ ID NO:1 from nucleotide 1 to nucleotide 1625; the nucleotide sequence of the full-length protein coding sequence of clone co62_12 deposited under accession number ATCC 98825; or the nucleotide sequence of a mature protein coding sequence of clone co62_12 deposited under accession number ATCC 98825. In other preferred embodiments, the polynucleotide encodes the full-length or a mature protein encoded by the cDNA insert of clone co62_12 deposited under accession number ATCC 98825. In further preferred embodiments, the present invention provides a polynucleotide encoding a protein comprising a fragment of the amino acid sequence of SEQ ID NO:2 having biological activity, the fragment preferably comprising eight (more preferably twenty, most preferably thirty) contiguous amino acids of SEQ ID NO:2, or a polynucleotide encoding a protein comprising a fragment of the amino acid sequence of SEQ ID NO:2 having biological activity, the fragment comprising the amino acid sequence from amino acid 117 to amino acid 126 of SEQ ID NO:2.

Other embodiments provide the gene corresponding to the cDNA sequence of SEQ ID NO:1.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:

(aa) SEQ ID NO:1, but excluding the poly(A) tail at the 3' end of SEQ ID NO:1; and (ab) the nucleotide sequence of the cDNA insert of clone co62__12 deposited under accession number ATCC 98825;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of;

(ba) SEQ ID NO:1, but excluding the poly(A) tail at the 3' end of SEQ ID NO:1; and (bb) the nucleotide sequence of the cDNA insert of clone co62__12 deposited under accession number ATCC 98825;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:1, and extending contiguously from a nucleotide sequence corresponding to the 5' end of SEQ ID NO:1 to a nucleotide sequence corresponding to the 3' end of SEQ ID NO:1, but excluding the poly(A) tail at the 3' end of SEQ ID NO:1. Also preferably the polynucleotide isolated according to the above process comprises a nucleotide sequence corresponding to the cDNA sequence of SEQ ID NO:1 from nucleotide 87 to nucleotide 821, and extending contiguously from a nucleotide sequence corresponding to the 5' end of said sequence of SEQ ID NO:1 from nucleotide 87 to nucleotide 821, to a nucleotide sequence corresponding to the 3' end of said sequence of SEQ ID NO:1 from nucleotide 87 to nucleotide 821. Also preferably the polynucleotide isolated according to the above process comprises a nucleotide sequence corresponding to the cDNA sequence of SEQ ID NO:1 from nucleotide 120 to nucleotide 821, and extending contiguously from a nucleotide sequence corresponding to the 5' end of said sequence of SEQ ID NO:1 from nucleotide 120 to nucleotide 821, to a nucleotide sequence corresponding to the 3' end of said sequence of SEQ ID NO:1 from nucleotide 120 to nucleotide 821. Also preferably the polynucleotide isolated according to the above process comprises a nucleotide sequence corresponding to the cDNA sequence of SEQ ID NO:1 from nucleotide 1 to nucleotide 1625, and extending contiguously from a nucleotide sequence corresponding to the 5' end of said sequence of SEQ ID NO:1 from nucleotide 1 to nucleotide 1625, to a nucleotide sequence corresponding to the 3' end of said sequence of SEQ ID NO:1 from nucleotide 1 to nucleotide 1625.

In other embodiments, the present invention provides a composition comprising a protein, wherein said protein comprises an amino acid sequence selected from the group consisting of:

(a) the amino add sequence of SEQ ID NO:2;

(b) a fragment of the amino acid sequence of SEQ ID NO:2, the fragment comprising eight contiguous amino acids of SEQ ID NO:2; and (c) the amino acid sequence encoded by the cDNA insert of clone co62__12 deposited under accession number ATCC 98825;

the protein being substantially free from other mammalian proteins. Preferably such protein comprises the amino add sequence of SEQ ID NO:2. In further preferred embodiments, the present invention provides a protein comprising a fragment of the amino acid sequence of SEQ ID NO:2 having biological activity, the fragment preferably comprising eight (more preferably twenty, most preferably thirty) contiguous amino acids of SEQ ID NO:2, or a protein comprising a fragment of the amino acid sequence of SEQ ID NO:2 having biological activity, the fragment comprising the amino acid sequence from amino acid 117 to amino acid 126 of SEQ ID NO:2.

In one embodiment, the present invention provides a composition comprising an isolated polynucleotide selected from the group consisting of:

(a) a polynucleotide comprising the nucleotide sequence of SEQ ID NO:3;

(b) a polynucleotide comprising the nucleotide sequence of SEQ ID NO:3 from nucleotide 9 to nucleotide 1013;

(c) a polynucleotide comprising the nucleotide sequence of SEQ ID NO:3 from nucleotide 96 to nucleotide 1013;

(d) a polynucleotide comprising the nucleotide sequence of the full-length protein coding sequence of clone lo311__8 deposited under accession number ATCC 98825;

(e) a polynucleotide encoding the full-length protein encoded by the cDNA insert of clone lo311__8 deposited under accession number ATCC 98825;

(f) a polynucleotide comprising the nucleotide sequence of a mature protein coding sequence of clone lo311__8 deposited under accession number ATCC 98825;

(g) a polynucleotide encoding a mature protein encoded by the cDNA insert of clone lo311__8 deposited under accession number ATCC 98825;

(h) a polynucleotide encoding a protein comprising the amino acid sequence of SEQ ID NO:4;

(i) a polynucleotide encoding a protein comprising a fragment of the amino acid sequence of SEQ ID NO:4 having biological activity, the fragment comprising eight contiguous amino acids of SEQ ID NO:4;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:3.

Preferably, such polynucleotide comprises the nucleotide sequence of SEQ ID NO:3 from nucleotide 9 to nucleotide 1013; the nucleotide sequence of SEQ ID NO:3 from nucleotide 96 to nucleotide 1013; the nucleotide sequence of the full-length protein coding sequence of clone lo311__8 deposited under accession number ATCC 98825; or the nucleotide sequence of a mature protein coding sequence of clone lo311__8 deposited under accession number ATCC 98825. In other preferred embodiments, the polynucleotide encodes the full-length or a mature protein encoded by the cDNA insert of clone lo311__8 deposited under accession number ATCC 98825. In further preferred embodiments, the present invention provides a polynucleotide encoding a protein comprising a fragment of the amino acid sequence of SEQ ID NO:4 having biological activity, the fragment preferably comprising eight (more preferably twenty, most preferably thirty) contiguous amino acids of SEQ ID NO:4, or a polynucleotide encoding a protein comprising a fragment of the amino acid sequence of SEQ ID NO:4 having biological activity, the fragment comprising the amino acid sequence from amino acid 162 to amino acid 171 of SEQ ID NO:4.

Other embodiments provide the gene corresponding to the cDNA sequence of SEQ ID NO:3.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:3, but excluding the poly(A) tail at the 3' end of SEQ ID NO:3; and
    (ab) the nucleotide sequence of the cDNA insert of clone lo311_8 deposited under accession number ATCC 98825;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:3, but excluding the poly(A) tail at the 3' end of SEQ ID NO:3; and
    (bb) the nucleotide sequence of the cDNA insert of clone lo311_8 deposited under accession number ATCC 98825;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:3, and extending contiguously from a nucleotide sequence corresponding to the 5' end of SEQ ID NO:3 to a nucleotide sequence corresponding to the 3' end of SEQ ID NO:3, but excluding the poly(A) tail at the 3' end of SEQ ID NO:3. Also preferably the polynucleotide isolated according to the above process comprises a nucleotide sequence corresponding to the cDNA sequence of SEQ ID NO:3 from nucleotide 9 to nucleotide 1013, and extending contiguously from a nucleotide sequence corresponding to the 5' end of said sequence of SEQ ID NO:3 from nucleotide 9 to nucleotide 1013, to a nucleotide sequence corresponding to the 3' end of said sequence of SEQ ID NO:3 from nucleotide 9 to nucleotide 1013. Also preferably the polynucleotide isolated according to the above process comprises a nucleotide sequence corresponding to the cDNA sequence of SEQ ID NO:3 from nucleotide 96 to nucleotide 1013, and extending contiguously from a nucleotide sequence corresponding to the 5' end of said sequence of SEQ ID NO:3 from nucleotide 96 to nucleotide 1013, to a nucleotide sequence corresponding to the 3' end of said sequence of SEQ ID NO:3 from nucleotide 96 to nucleotide 1013.

In other embodiments, the present invention provides a composition comprising a protein, wherein said protein comprises an amino acid sequence selected from the group consisting of:

(a) the amino acid sequence of SEQ ID NO:4;
(b) a fragment of the amino acid sequence of SEQ ID NO:4, the fragment comprising eight contiguous amino acids of SEQ ID NO:4; and
(c) the amino acid sequence encoded by the cDNA insert of clone lo311_8 deposited under accession number ATCC 98825;

the protein being substantially free from other mammalian proteins. Preferably such protein comprises the amino acid sequence of SEQ ID NO:4. In further preferred embodiments, the present invention provides a protein comprising a fragment of the amino acid sequence of SEQ ID NO:4 having biological activity, the fragment preferably comprising eight (more preferably twenty, most preferably thirty) contiguous amino acids of SEQ ID NO:4, or a protein comprising a fragment of the amino acid sequence of SEQ ID NO:4 having biological activity, the fragment comprising the amino acid sequence from amino acid 162 to amino acid 171 of SEQ ID NO:4.

In one embodiment, the present invention provides a composition comprising an isolated polynucleotide selected from the group consisting of:

(a) a polynucleotide comprising the nucleotide sequence of SEQ ID NO:5;
(b) a polynucleotide comprising the nucleotide sequence of SEQ ID NO:5 from nucleotide 352 to nucleotide 825;
(c) a polynucleotide comprising the nucleotide sequence of the full-length protein coding sequence of clone ns197_1 deposited under accession number ATCC 98825;
(d) a polynucleotide encoding the full-length protein encoded by the cDNA insert of clone ns197_1 deposited under accession number ATCC 98825;
(e) a polynucleotide comprising the nucleotide sequence of a mature protein coding sequence of clone ns197_1 deposited under accession number ATCC 98825;
(f) a polynucleotide encoding a mature protein encoded by the cDNA insert of clone ns197_1 deposited under accession number ATCC 98825;
(g) a polynucleotide encoding a protein comprising the amino acid sequence of SEQ ID NO:6;
(h) a polynucleotide encoding a protein comprising a fragment of the amino acid sequence of SEQ ID NO:6 having biological activity, the fragment comprising eight contiguous amino acids of SEQ ID NO:6;
(i) a polynucleotide which is an allelic variant of a polynucleotide of (a)-(f) above;
(j) a polynucleotide which encodes a species homologue of the protein of (g) or (h) above;
(k) a polynucleotide that hybridizes under stringent conditions to any one of the polynucleotides specified in (a)-(h); and
(l) a polynucleotide that hybridizes under stringent conditions to any one of the polynucleotides specified in (a)-(h) and that has a length that is at least 25% of the length of SEQ ID NO:5.

Preferably, such polynucleotide comprises the nucleotide sequence of SEQ ID NO:5 from nucleotide 352 to nucleotide 825; the nucleotide sequence of the full-length protein coding sequence of clone ns197_1 deposited under accession number ATCC 98825; or the nucleotide sequence of a mature protein coding sequence of clone ns197_1 deposited under accession number ATCC 98825. In other preferred embodiments, the polynucleotide encodes the full-length or a mature protein encoded by the cDNA insert of clone ns197_1 deposited under accession number ATCC 98825. In further preferred embodiments, the present invention provides a polynucleotide encoding a protein comprising a fragment of the amino acid sequence of SEQ ID NO:6 having biological activity, the fragment preferably comprising eight (more preferably twenty, most preferably thirty) contiguous amino acids of SEQ ID NO:6, or a polynucleotide encoding a protein comprising a fragment of the amino acid sequence of SEQ ID NO:6 having biological activity, the fragment comprising the amino acid sequence from amino acid 74 to amino acid 83 of SEQ ID NO:6.

Other embodiments provide the gene corresponding to the cDNA sequence of SEQ ID NO:5.

Further embodiments of the invention provide isolated polynucleotides produced according to a process selected from the group consisting of:

(a) a process comprising the steps of:
   (i) preparing one or more polynucleotide probes that hybridize in 6×SSC at 65 degrees C. to a nucleotide sequence selected from the group consisting of:
      (aa) SEQ ID NO:5, but excluding the poly(A) tail at the 3' end of SEQ ID NO:5; and
      (ab) the nucleotide sequence of the cDNA insert of clone ns197_1 deposited under accession number ATCC 98825;
   (ii) hybridizing said probe(s) to human genomic DNA in conditions at least as stringent as 4×SSC at 50 degrees C.; and
   (iii) isolating the DNA polynucleotides detected with the probe(s); and
(b) a process comprising the steps of:
   (i) preparing one or more polynucleotide primers that hybridize in 6×SSC at 65 degrees C. to a nucleotide sequence selected from the group consisting of:
      (ba) SEQ ID NO:5, but excluding the poly(A) tail at the 3' end of SEQ ID NO:5; and
      (bb) the nucleotide sequence of the cDNA insert of clone ns197_1 deposited under accession number ATCC 98825;
   (ii) hybridizing said primer(s) to human genomic DNA in conditions at least as stringent as 4×SSC at 50 degrees C.;
   (iii) amplifying human DNA sequences; and
   (iv) isolating the polynucleotide products of step (b) (iii).

Preferably the polynucleotide isolated according to the above process comprises a nucleotide sequence corresponding to the cDNA sequence of SEQ ID NO:5, and extending contiguously from a nucleotide sequence corresponding to the 5' end of SEQ ID NO:5 to a nucleotide sequence corresponding to the 3' end of SEQ ID NO:5, but excluding the poly(A) tail at the 3' end of SEQ ID NO:5. Also preferably the polynucleotide isolated according to the above process comprises a nucleotide sequence corresponding to the cDNA sequence of SEQ ID NO:5 from nucleotide 352 to nucleotide 825, and extending contiguously from a nucleotide sequence corresponding to the 5' end of said sequence of SEQ ID NO:5 from nucleotide 352 to nucleotide 825, to a nucleotide sequence corresponding to the 3' end of said sequence of SEQ ID NO:5 from nucleotide 352 to nucleotide 825.

In other embodiments, the present invention provides a composition comprising a protein, wherein said protein comprises an amino acid sequence selected from the group consisting of:

(a) the amino acid sequence of SEQ ID NO:6;
(b) a fragment of the amino acid sequence of SEQ ID NO:6, the fragment comprising eight contiguous amino acids of SEQ ID NO:6; and
(c) the amino acid sequence encoded by the cDNA insert of clone ns197_1 deposited under accession number ATCC 98825;

the protein being substantially free from other mammalian proteins. Preferably such protein comprises the amino acid sequence of SEQ ID NO:6. In further preferred embodiments, the present invention provides a protein comprising a fragment of the amino acid sequence of SEQ ID NO:6 having biological activity, the fragment preferably comprising eight (more preferably twenty, most preferably thirty) contiguous amino acids of SEQ ID NO:6, or a protein comprising a fragment of the amino acid sequence of SEQ ID NO:6 having biological activity, the fragment comprising the amino acid sequence from amino acid 74 to amino acid 83 of SEQ ID NO:6.

In one embodiment, the present invention provides a composition comprising an isolated polynucleotide selected from the group consisting of:

(a) a polynucleotide comprising the nucleotide sequence of SEQ ID NO:7;
(b) a polynucleotide comprising the nucleotide sequence of SEQ ID NO:7 from nucleotide 86 to nucleotide 829;
(c) a polynucleotide comprising the nucleotide sequence of SEQ ID NO:7 from nucleotide 149 to nucleotide 829;
(d) a polynucleotide comprising the nucleotide sequence of the full-length protein coding sequence of clone pj193_5 deposited under accession number ATCC 98825;
(e) a polynucleotide encoding the full-length protein encoded by the cDNA insert of clone pj193_5 deposited under accession number ATCC 98825;
(f) a polynucleotide comprising the nucleotide sequence of a mature protein coding sequence of clone pj193_5 deposited under accession number ATCC 98825;
(g) a polynucleotide encoding a mature protein encoded by the cDNA insert of clone pj193_5 deposited under accession number ATCC 98825;
(h) a polynucleotide encoding a protein comprising the amino acid sequence of SEQ ID NO:8;
(i) a polynucleotide encoding a protein comprising a fragment of the amino acid sequence of SEQ ID NO:8 having biological activity, the fragment comprising eight contiguous amino acids of SEQ ID NO:8;
(j) a polynucleotide which is an allelic variant of a polynucleotide of (a)-(g) above;
(k) a polynucleotide which encodes a species homologue of the protein of (h) or (i) above;
(l) a polynucleotide that hybridizes under stringent conditions to any one of the polynucleotides specified in (a)-(i); and
(m) a polynucleotide that hybridizes under stringent conditions to any one of the polynucleotides specified in (a)-(i) and that has a length that is at least 25% of the length of SEQ ID NO:7.

Preferably, such polynucleotide comprises the nucleotide sequence of SEQ ID NO:7 from nucleotide 86 to nucleotide 829; the nucleotide sequence of SEQ ID NO:7 from nucleotide 149 to nucleotide 829; the nucleotide sequence of the full-length protein coding sequence of clone pj193_5 deposited under accession number ATCC 98825; or the nucleotide sequence of a mature protein coding sequence of clone pj193_5 deposited under accession number ATCC 98825. In other preferred embodiments, the polynucleotide encodes the full-length or a mature protein encoded by the cDNA insert of clone pj193_5 deposited under accession number ATCC 98825. In further preferred embodiments, the present invention provides a polynucleotide encoding a protein comprising a fragment of the amino acid sequence of SEQ ID NO:8 having biological activity, the fragment preferably comprising eight (more preferably twenty, most preferably thirty) contiguous amino acids of SEQ ID NO:8, or a polynucleotide encoding a protein comprising a fragment of the amino acid sequence of SEQ ID NO:8 having biological activity, the fragment comprising the amino acid sequence from amino acid 119 to amino acid 128 of SEQ ID NO:8.

Other embodiments provide the gene corresponding to the cDNA sequence of SEQ ID NO:7.

Further embodiments of the invention provide isolated polynucleotides produced according to a process selected from the group consisting of:

- (a) a process comprising the steps of:
  - (i) preparing one or more polynucleotide probes that hybridize in 6×SSC at 65 degrees C. to a nucleotide sequence selected from the group consisting of:
    - (aa) SEQ ID NO:7, but excluding the poly(A) tail at the 3' end of SEQ ID NO:7; and
    - (ab) the nucleotide sequence of the cDNA insert of clone pj193_5 deposited under accession number ATCC 98825;
  - (ii) hybridizing said probe(s) to human genomic DNA in conditions at least as stringent as 4×SSC at 50 degrees C.; and
  - (iii) isolating the DNA polynucleotides detected with the probe(s); and
- (b) a process comprising the steps of:
  - (i) preparing one or more polynucleotide primers that hybridize in 6×SSC at 65 degrees C. to a nucleotide sequence selected from the group consisting of:
    - (ba) SEQ ID NO:7, but excluding the poly(A) tail at the 3' end of SEQ ID NO:7; and
    - (bb) the nucleotide sequence of the cDNA insert of clone pj193_5 deposited under accession number ATCC 98825;
  - (ii) hybridizing said primer(s) to human genomic DNA in conditions at least as stringent as 4×SSC at 50 degrees C.;
  - (iii) amplifying human DNA sequences; and
  - (iv) isolating the polynucleotide products of step (b) (iii).

Preferably the polynucleotide isolated according to the above process comprises a nucleotide sequence corresponding to the cDNA sequence of SEQ ID NO:7, and extending contiguously from a nucleotide sequence corresponding to the 5' end of SEQ ID NO:7 to a nucleotide sequence corresponding to the 3' end of SEQ ID NO:7, but excluding the poly(A) tail at the 3' end of SEQ ID NO:7. Also preferably the polynucleotide isolated according to the above process comprises a nucleotide sequence corresponding to the cDNA sequence of SEQ ID NO:7 from nucleotide 86 to nucleotide 829, and extending contiguously from a nucleotide sequence corresponding to the 5' end of said sequence of SEQ ID NO:7 from nucleotide 86 to nucleotide 829, to a nucleotide sequence corresponding to the 3' end of said sequence of SEQ ID NO:7 from nucleotide 86 to nucleotide 829. Also preferably the polynucleotide isolated according to the above process comprises a nucleotide sequence corresponding to the cDNA sequence of SEQ ID NO:7 from nucleotide 149 to nucleotide 829, and extending contiguously from a nucleotide sequence corresponding to the 5' end of said sequence of SEQ ID NO:7 from nucleotide 149 to nucleotide 829, to a nucleotide sequence corresponding to the 3' end of said sequence of SEQ ID NO:7 from nucleotide 149 to nucleotide 829.

In other embodiments, the present invention provides a composition comprising a protein, wherein said protein comprises an amino acid sequence selected from the group consisting of:

- (a) the amino acid sequence of SEQ ID NO:8;
- (b) a fragment of the amino acid sequence of SEQ ID NO:8, the fragment comprising eight contiguous amino acids of SEQ ID NO:8; and
- (c) the amino acid sequence encoded by the cDNA insert of clone pj193_5 deposited under accession number ATCC 98825;

the protein being substantially free from other mammalian proteins. Preferably such protein comprises the amino acid sequence of SEQ ID NO:8. In further preferred embodiments, the present invention provides a protein comprising a fragment of the amino acid sequence of SEQ ID NO:8 having biological activity, the fragment preferably comprising eight (more preferably twenty, most preferably thirty) contiguous amino acids of SEQ ID NO:8, or a protein comprising a fragment of the amino acid sequence of SEQ ID NO:8 having biological activity, the fragment comprising the amino acid sequence from amino acid 119 to amino acid 128 of SEQ ID NO:8.

In one embodiment, the present invention provides a composition comprising an isolated polynucleotide selected from the group consisting of:

- (a) a polynucleotide comprising the nucleotide sequence of SEQ ID NO:9;
- (b) a polynucleotide comprising the nucleotide sequence of SEQ ID NO:9 from nucleotide 174 to nucleotide 1292;
- (c) a polynucleotide comprising the nucleotide sequence of the full-length protein coding sequence of clone pj317_2 deposited under accession number ATCC 98825;
- (d) a polynucleotide encoding the full-length protein encoded by the cDNA insert of clone pj317_2 deposited under accession number ATCC 98825;
- (e) a polynucleotide comprising the nucleotide sequence of a mature protein coding sequence of clone pj317_2 deposited under accession number ATCC 98825;
- (f) a polynucleotide encoding a mature protein encoded by the cDNA insert of clone pj317_2 deposited under accession number ATCC 98825;
- (g) a polynucleotide encoding a protein comprising the amino acid sequence of SEQ ID NO:10;
- (h) a polynucleotide encoding a protein comprising a fragment of the amino acid sequence of SEQ ID NO:10 having biological activity, the fragment comprising eight contiguous amino acids of SEQ ID NO:10;
- (i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:9.

Preferably, such polynucleotide comprises the nucleotide sequence of SEQ ID NO:9 from nucleotide 174 to nucleotide 1292; the nucleotide sequence of the full-length protein coding sequence of clone pj317_2 deposited under accession number ATCC 98825; or the nucleotide sequence of a mature protein coding sequence of clone pj317_2 deposited under accession number ATCC 98825. In other preferred embodiments, the polynucleotide encodes the full-length or a mature protein encoded by the cDNA insert of clone pj317_2 deposited under accession number ATCC 98825. In further preferred embodiments, the present invention provides a polynucleotide encoding a protein comprising a fragment of the amino acid sequence of SEQ ID NO:10 having biological activity, the fragment preferably comprising eight (more preferably twenty, most preferably thirty) contiguous amino acids of SEQ ID NO:10, or a polynucleotide encoding a protein comprising a fragment of the amino acid sequence of SEQ ID NO:10 having biological activity, the fragment comprising the amino add sequence from amino acid 181 to amino acid 190 of SEQ ID NO:10.

Other embodiments provide the gene corresponding to the cDNA sequence of SEQ ID NO:9.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:9, but excluding the poly(A) tail at the 3' end of SEQ ID NO:9; and
    (ab) the nucleotide sequence of the cDNA insert of clone pj317_2 deposited under accession number ATCC 98825;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:9, but excluding the poly(A) tail at the 3' end of SEQ ID NO:9; and
    (bb) the nucleotide sequence of the cDNA insert of clone pj317_2 deposited under accession number ATCC 98825;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:9, and extending contiguously from a nucleotide sequence corresponding to the 5' end of SEQ ID NO:9 to a nucleotide sequence corresponding to the 3' end of SEQ ID NO:9, but excluding the poly(A) tail at the 3' end of SEQ ID NO:9. Also preferably the polynucleotide isolated according to the above process comprises a nucleotide sequence corresponding to the cDNA sequence of SEQ ID NO:9 from nucleotide 174 to nucleotide 1292, and extending contiguously from a nucleotide sequence corresponding to the 5' end of said sequence of SEQ ID NO:9 from nucleotide 174 to nucleotide 1292, to a nucleotide sequence corresponding to the 3' end of said sequence of SEQ ID NO:9 from nucleotide 174 to nucleotide 1292.

In other embodiments, the present invention provides a composition comprising a protein, wherein said protein comprises an amino acid sequence selected from the group consisting of:

(a) the amino acid sequence of SEQ ID NO:10;

(b) a fragment of the amino acid sequence of SEQ ID NO:10, the fragment comprising eight contiguous amino acids of SEQ ID NO:10; and (c) the amino acid sequence encoded by the cDNA insert of clone pj317_2 deposited under accession number ATCC 98825;

the protein being substantially free from other mammalian proteins. Preferably such protein comprises the amino acid sequence of SEQ ID NO:10. In further preferred embodiments, the present invention provides a protein comprising a fragment of the amino acid sequence of SEQ ID NO:10 having biological activity, the fragment preferably comprising eight (more preferably twenty, most preferably thirty) contiguous amino acids of SEQ ID NO:10, or a protein comprising a fragment of the amino acid sequence of SEQ ID NO:10 having biological activity, the fragment comprising the amino acid sequence from amino acid 181 to amino acid 190 of SEQ ID NO:10.

In one embodiment, the present invention provides a composition comprising an isolated polynucleotide selected from the group consisting of:

(a) a polynucleotide comprising the nucleotide sequence of SEQ ID NO:11;

(b) a polynucleotide comprising the nucleotide sequence of SEQ ID NO:11 from nucleotide 7 to nucleotide 2517;

(c) a polynucleotide comprising the nucleotide sequence of SEQ ID NO:11 from nucleotide 904 to nucleotide 2517;

(d) a polynucleotide comprising the nucleotide sequence of the full-length protein coding sequence of clone pt332_1 deposited under accession number ATCC 98825;

(e) a polynucleotide encoding the full-length protein encoded by the cDNA insert of clone pt332_1 deposited under accession number ATCC 98825;

(f) a polynucleotide comprising the nucleotide sequence of a mature protein coding sequence of clone pt332_1 deposited under accession number ATCC 98825;

(g) a polynucleotide encoding a mature protein encoded by the cDNA insert of clone pt332_1 deposited under accession number ATCC 98825;

(h) a polynucleotide encoding a protein comprising the amino acid sequence of SEQ ID NO:12;

(i) a polynucleotide encoding a protein comprising a fragment of the amino acid sequence of SEQ ID NO:12 having biological activity, the fragment comprising eight contiguous amino acids of SEQ ID NO:12;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:11.

Preferably, such polynucleotide comprises the nucleotide sequence of SEQ ID NO:11 from nucleotide 7 to nucleotide 2517; the nucleotide sequence of SEQ ID NO:11 from nucleotide 904 to nucleotide 2517; the nucleotide sequence of the full-length protein coding sequence of clone pt332_1 deposited under accession number ATCC 98825; or the nucleotide sequence of a mature protein coding sequence of clone pt332_1 deposited under accession number ATCC 98825. In other preferred embodiments, the polynucleotide encodes the full-length or a mature protein encoded by the cDNA insert of clone pt332_1 deposited under accession number ATCC 98825. In further preferred embodiments, the present invention provides a polynucleotide encoding a protein comprising a fragment of the amino acid sequence of SEQ ID NO:12 having biological activity, the fragment preferably comprising eight (more preferably twenty, most preferably thirty) contiguous amino acids of SEQ ID NO:12, or a polynucleotide encoding a protein comprising a fragment of the amino acid sequence of SEQ ID NO:12 having biological activity, the fragment comprising the amino acid sequence from amino acid 413 to amino acid 422 of SEQ ID NO:12.

Other embodiments provide the gene corresponding to the cDNA sequence of SEQ ID NO:11.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:11, but excluding the poly(A) tail at the 3' end of SEQ ID NO:11; and
    (ab) the nucleotide sequence of the cDNA insert of clone pt332_1 deposited under accession number ATCC 98825;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:11, but excluding the poly(A) tail at the 3' end of SEQ ID NO:11; and
    (bb) the nucleotide sequence of the cDNA insert of clone pt332_1 deposited under accession number ATCC 98825;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:11, and extending contiguously from a nucleotide sequence corresponding to the 5' end of SEQ ID NO:11 to a nucleotide sequence corresponding to the 3' end of SEQ ID NO:11, but excluding the poly(A) tail at the 3' end of SEQ ID NO:11. Also preferably the polynucleotide isolated according to the above process comprises a nucleotide sequence corresponding to the cDNA sequence of SEQ ID NO:11 from nucleotide 7 to nucleotide 2517, and extending contiguously from a nucleotide sequence corresponding to the 5' end of said sequence of SEQ ID NO:11 from nucleotide 7 to nucleotide 2517, to a nucleotide sequence corresponding to the 3' end of said sequence of SEQ ID NO:11 from nucleotide 7 to nucleotide 2517. Also preferably the polynucleotide isolated according to the above process comprises a nucleotide sequence corresponding to the cDNA sequence of SEQ ID NO:11 from nucleotide 904 to nucleotide 2517, and extending contiguously from a nucleotide sequence corresponding to the 5' end of said sequence of SEQ ID NO:11 from nucleotide 904 to nucleotide 2517, to a nucleotide sequence corresponding to the 3' end of said sequence of SEQ ID NO:11 from nucleotide 904 to nucleotide 2517.

In other embodiments, the present invention provides a composition comprising a protein, wherein said protein comprises an amino acid sequence selected from the group consisting of:

(a) the amino acid sequence of SEQ ID NO:12;

(b) a fragment of the amino acid sequence of SEQ ID NO:12, the fragment comprising eight contiguous amino acids of SEQ ID NO:12; and (c) the amino acid sequence encoded by the cDNA insert of clone pt332_1 deposited under accession number ATCC 98825;

the protein being substantially free from other mammalian proteins. Preferably such protein comprises the amino acid sequence of SEQ ID NO:12. In further preferred embodiments, the present invention provides a protein comprising a fragment of the amino acid sequence of SEQ ID NO:12 having biological activity, the fragment preferably comprising eight (more preferably twenty, most preferably thirty) contiguous amino acids of SEQ ID NO:12, or a protein comprising a fragment of the amino acid sequence of SEQ ID NO:12 having biological activity, the fragment comprising the amino acid sequence from amino acid 413 to amino acid 422 of SEQ ID NO:12.

In one embodiment, the present invention provides a composition comprising an isolated polynucleotide selected from the group consisting of:

(a) a polynucleotide comprising the nucleotide sequence of SEQ ID NO:13;

(b) a polynucleotide comprising the nucleotide sequence of SEQ ID NO:13 from nucleotide 18 to nucleotide 257;

(c) a polynucleotide comprising the nucleotide sequence of the full-length protein coding sequence of clone qc297_15 deposited under accession number ATCC 98825;

(d) a polynucleotide encoding the full-length protein encoded by the cDNA insert of clone qc297_15 deposited under accession number ATCC 98825;

(e) a polynucleotide comprising the nucleotide sequence of a mature protein coding sequence of clone qc297_15 deposited under accession number ATCC 98825;

(f) a polynucleotide encoding a mature protein encoded by the cDNA insert of clone qc297__15 deposited under accession number ATCC 98825;

(g) a polynucleotide encoding a protein comprising the amino acid sequence of SEQ ID NO:14;

(h) a polynucleotide encoding a protein comprising a fragment of the amino acid sequence of SEQ ID NO:14 having biological activity, the fragment comprising eight contiguous amino acids of SEQ ID NO:14;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:13.

Preferably, such polynucleotide comprises the nucleotide sequence of SEQ ID NO:13 from nucleotide 18 to nucleotide 257; the nucleotide sequence of the full-length protein coding sequence of clone qc297__15 deposited under accession number ATCC 98825; or the nucleotide sequence of a mature protein coding sequence of clone qc297__15 deposited under accession number ATCC 98825. In other preferred embodiments, the polynucleotide encodes the full-length or a mature protein encoded by the cDNA insert of clone qc297__15 deposited under accession number ATCC 98825. In further preferred embodiments, the present invention provides a polynucleotide encoding a protein comprising a fragment of the amino acid sequence of SEQ ID NO:14 having biological activity, the fragment preferably comprising eight (more preferably twenty, most preferably thirty) contiguous amino acids of SEQ ID NO:14, or a polynucleotide encoding a protein comprising a fragment of the amino acid sequence of SEQ ID NO:14 having biological activity, the fragment comprising the amino acid sequence from amino acid 35 to amino acid 44 of SEQ ID NO:14.

Other embodiments provide the gene corresponding to the cDNA sequence of SEQ ID NO:13.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:13, but excluding the poly(A) tail at the 3' end of SEQ ID NO:13; and (ab) the nucleotide sequence of the cDNA insert of clone qc297__15 deposited under accession number ATCC 98825;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:13, but excluding the poly(A) tail at the 3' end of SEQ ID NO:13; and (bb) the nucleotide sequence of the cDNA insert of clone qc297__15 deposited under accession number ATCC 98825;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:13, and extending contiguously from a nucleotide sequence corresponding to the 5' end of SEQ ID NO:13 to a nucleotide sequence corresponding to the 3' end of SEQ ID NO:13, but excluding the poly(A) tail at the 3' end of SEQ ID NO:13. Also preferably the polynucleotide isolated according to the above process comprises a nucleotide sequence corresponding to the cDNA sequence of SEQ ID NO:13 from nucleotide 18 to nucleotide 257, and extending contiguously from a nucleotide sequence corresponding to the 5' end of said sequence of SEQ ID NO:13 from nucleotide 18 to nucleotide 257, to a nucleotide sequence corresponding to the 3' end of said sequence of SEQ ID NO:13 from nucleotide 18 to nucleotide 257.

In other embodiments, the present invention provides a composition comprising a protein, wherein said protein comprises an amino acid sequence selected from the group consisting of:

(a) the amino acid sequence of SEQ ID NO:14;

(b) a fragment of the amino acid sequence of SEQ ID NO:14, the fragment comprising eight contiguous amino acids of SEQ ID NO:14; and (c) the amino acid sequence encoded by the cDNA insert of clone qc297__15 deposited under accession number ATCC 98825;

the protein being substantially free from other mammalian proteins. Preferably such protein comprises the amino acid sequence of SEQ ID NO:14. In further preferred embodiments, the present invention provides a protein comprising a fragment of the amino acid sequence of SEQ ID NO:14 having biological activity, the fragment preferably comprising eight (more preferably twenty, most preferably thirty) contiguous amino acids of SEQ ID NO:14, or a protein comprising a fragment of the amino acid sequence of SEQ ID NO:14 having biological activity, the fragment comprising the amino acid sequence from amino acid 35 to amino acid 44 of SEQ ID NO:14.

In one embodiment, the present invention provides a composition comprising an isolated polynucleotide selected from the group consisting of:

(a) a polynucleotide comprising the nucleotide sequence of SEQ ID NO:15;

(b) a polynucleotide comprising the nucleotide sequence of SEQ ID NO:15 from nucleotide 21 to nucleotide 2432;

(c) a polynucleotide comprising the nucleotide sequence of the full-length protein coding sequence of clone qg596__12 deposited under accession number ATCC 98825;

(d) a polynucleotide encoding the full-length protein encoded by the cDNA insert of clone qg596__12 deposited under accession number ATCC 98825;

(e) a polynucleotide comprising the nucleotide sequence of a mature protein coding sequence of clone qg596__12 deposited under accession number ATCC 98825;

(f) a polynucleotide encoding a mature protein encoded by the cDNA insert of clone qg596_12 deposited under accession number ATCC 98825;

(g) a polynucleotide encoding a protein comprising the amino acid sequence of SEQ ID NO:16;

(h) a polynucleotide encoding a protein comprising a fragment of the amino acid sequence of SEQ ID NO:16 having biological activity, the fragment comprising eight contiguous amino acids of SEQ ID NO:16;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:15.

Preferably, such polynucleotide comprises the nucleotide sequence of SEQ ID NO:15 from nucleotide 21 to nucleotide 2432; the nucleotide sequence of the full-length protein coding sequence of clone qg596_12 deposited under accession number ATCC 98825; or the nucleotide sequence of a mature protein coding sequence of clone qg596_12 deposited under accession number ATCC 98825. In other preferred embodiments, the polynucleotide encodes the full-length or a mature protein encoded by the cDNA insert of clone qg596_12 deposited under accession number ATCC 98825. In further preferred embodiments, the present invention provides a polynucleotide encoding a protein comprising a fragment of the amino acid sequence of SEQ ID NO:16 having biological activity, the fragment preferably comprising eight (more preferably twenty, most preferably thirty) contiguous amino acids of SEQ ID NO:16, or a polynucleotide encoding a protein comprising a fragment of the amino acid sequence of SEQ ID NO:16 having biological activity, the fragment comprising the amino add sequence from amino acid 397 to amino acid 406 of SEQ ID NO:16.

Other embodiments provide the gene corresponding to the cDNA sequence of SEQ ID NO:15.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:15, but excluding the poly(A) tail at the 3' end of SEQ ID NO:15; and (ab) the nucleotide sequence of the cDNA insert of clone qg596_12 deposited under accession number ATCC 98825;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:15, but excluding the poly(A) tail at the 3' end of SEQ ID NO:15; and (bb) the nucleotide sequence of the cDNA insert of clone qg596_12 deposited under accession number ATCC 98825;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:15, and extending contiguously from a nucleotide sequence corresponding to the 5' end of SEQ ID NO:15 to a nucleotide sequence corresponding to the 3' end of SEQ ID NO:15, but excluding the poly(A) tail at the 3' end of SEQ ID NO:15. Also preferably the polynucleotide isolated according to the above process comprises a nucleotide sequence corresponding to the cDNA sequence of SEQ ID NO:15 from nucleotide 21 to nucleotide 2432, and extending contiguously from a nucleotide sequence corresponding to the 5' end of said sequence of SEQ ID NO:15 from nucleotide 21 to nucleotide 2432, to a nucleotide sequence corresponding to the 3' end of said sequence of SEQ ID NO:15 from nucleotide 21 to nucleotide 2432.

In other embodiments, the present invention provides a composition comprising a protein, wherein said protein comprises an amino acid sequence selected from the group consisting of:

(a) the amino acid sequence of SEQ ID NO:16;

(b) a fragment of the amino acid sequence of SEQ ID NO:16, the fragment comprising eight contiguous amino acids of SEQ ID NO:16; and (c) the amino acid sequence encoded by the cDNA insert of clone qg596_12 deposited under accession number ATCC 98825;

the protein being substantially free from other mammalian proteins. Preferably such protein comprises the amino acid sequence of SEQ ID NO:16. In further preferred embodiments, the present invention provides a protein comprising a fragment of the amino acid sequence of SEQ ID NO:16 having biological activity, the fragment preferably comprising eight (more preferably twenty, most preferably thirty) contiguous amino acids of SEQ ID NO:16, or a protein comprising a fragment of the amino acid sequence of SEQ ID NO:16 having biological activity, the fragment comprising the amino acid sequence from amino acid 397 to amino acid 406 of SEQ ID NO:16.

In one embodiment, the present invention provides a composition comprising an isolated polynucleotide selected from the group consisting of:

(a) a polynucleotide comprising the nucleotide sequence of SEQ ID NO:17;

(b) a polynucleotide comprising the nucleotide sequence of SEQ ID NO:17 from nucleotide 339 to nucleotide 2105;

(c) a polynucleotide comprising the nucleotide sequence of SEQ ID NO:17 from nucleotide 501 to nucleotide 2105;

(d) a polynucleotide comprising the nucleotide sequence of the full-length protein coding sequence of clone rb649_3 deposited under accession number ATCC 98825;

(e) a polynucleotide encoding the full-length protein encoded by the cDNA insert of clone rb649_3 deposited under accession number ATCC 98825;

(f) a polynucleotide comprising the nucleotide sequence of a mature protein coding sequence of clone rb649_3 deposited under accession number ATCC 98825;

(g) a polynucleotide encoding a mature protein encoded by the cDNA insert of clone rb649_3 deposited under accession number ATCC 98825;

(h) a polynucleotide encoding a protein comprising the amino acid sequence of SEQ ID NO:18;

(i) a polynucleotide encoding a protein comprising a fragment of the amino acid sequence of SEQ ID NO:18 having biological activity, the fragment comprising eight contiguous amino acids of SEQ ID NO:18;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:17.

Preferably, such polynucleotide comprises the nucleotide sequence of SEQ ID NO:17 from nucleotide 339 to nucleotide 2105; the nucleotide sequence of SEQ ID NO:17 from nucleotide 501 to nucleotide 2105; the nucleotide sequence of the full-length protein coding sequence of clone rb649_3 deposited under accession number ATCC 98825; or the nucleotide sequence of a mature protein coding sequence of clone rb649_3 deposited under accession number ATCC 98825. In other preferred embodiments, the polynucleotide encodes the full-length or a mature protein encoded by the cDNA insert of clone rb649_3 deposited under accession number ATCC 98825. In further preferred embodiments, the present invention provides a polynucleotide encoding a protein comprising a fragment of the amino acid sequence of SEQ ID NO:18 having biological activity, the fragment preferably comprising eight (more preferably twenty, most preferably thirty) contiguous amino acids of SEQ ID NO:18, or a polynucleotide encoding a protein comprising a fragment of the amino acid sequence of SEQ ID NO:18 having biological activity, the fragment comprising the amino acid sequence from amino add 289 to amino acid 298 of SEQ ID NO:18.

Other embodiments provide the gene corresponding to the cDNA sequence of SEQ ID NO:17.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:17, but excluding the poly(A) tail at the 3' end of SEQ ID NO:17; and (ab) the nucleotide sequence of the cDNA insert of clone rb649_3 deposited under accession number ATCC 98825;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:17, but excluding the poly(A) tail at the 3' end of SEQ ID NO:17; and (bb) the nucleotide sequence of the cDNA insert of clone rb649_3 deposited under accession number ATCC 98825;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:17, and extending contiguously from a nucleotide sequence corresponding to the 5' end of SEQ ID NO:17 to a nucleotide sequence corresponding to the 3' end of SEQ ID NO:17, but excluding the poly(A) tail at the 3' end of SEQ ID NO:17. Also preferably the polynucleotide isolated according to the above process comprises a nucleotide sequence corresponding to the cDNA sequence of SEQ ID NO:17 from nucleotide 339 to nucleotide 2105, and extending contiguously from a nucleotide sequence corresponding to the 5' end of said sequence of SEQ ID NO:17 from nucleotide 339 to nucleotide 2105, to a nucleotide sequence corresponding to the 3' end of said sequence of SEQ ID NO:17 from nucleotide 339 to nucleotide 2105. Also preferably the polynucleotide isolated according to the above process comprises a nucleotide sequence corresponding to the cDNA sequence of SEQ ID NO:17 from nucleotide 501 to nucleotide 2105, and extending contiguously from a nucleotide sequence corresponding to the 5' end of said sequence of SEQ ID NO:17 from nucleotide 501 to nucleotide 2105, to a nucleotide sequence corresponding to the 3' end of said sequence of SEQ ID NO:17 from nucleotide 501 to nucleotide 2105.

In other embodiments, the present invention provides a composition comprising a protein, wherein said protein comprises an amino acid sequence selected from the group consisting of:

(a) the amino acid sequence of SEQ ID NO:18;

(b) a fragment of the amino acid sequence of SEQ ID NO:18, the fragment comprising eight contiguous amino acids of SEQ ID NO:18; and (c) the amino acid sequence encoded by the cDNA insert of clone rb649_3 deposited under accession number ATCC 98825;

the protein being substantially free from other mammalian proteins. Preferably such protein comprises the amino acid sequence of SEQ ID NO:18. In further preferred embodiments, the present invention provides a protein comprising a fragment of the amino acid sequence of SEQ ID NO:18 having biological activity, the fragment preferably comprising eight (more preferably twenty, most preferably thirty) contiguous amino acids of SEQ ID NO:18, or a protein comprising a fragment of the amino acid sequence of SEQ ID NO:18 having biological activity, the fragment comprising the amino acid sequence from amino acid 289 to amino acid 298 of SEQ ID NO:18.

In one embodiment, the present invention provides a composition comprising an isolated polynucleotide selected from the group consisting of:

(a) a polynucleotide comprising the nucleotide sequence of SEQ ID NO:19;

(b) a polynucleotide comprising the nucleotide sequence of SEQ ID NO:19 from nucleotide 509 to nucleotide 2467;

(c) a polynucleotide comprising the nucleotide sequence of the full-length protein coding sequence of clone ca106_19x deposited under accession number ATCC 98835;

(d) a polynucleotide encoding the full-length protein encoded by the cDNA insert of clone ca106_19x deposited under accession number ATCC 98835;

(e) a polynucleotide comprising the nucleotide sequence of a mature protein coding sequence of clone ca106_19x deposited under accession number ATCC 98835;

(f) a polynucleotide encoding a mature protein encoded by the cDNA insert of clone ca106_19x deposited under accession number ATCC 98835;

(g) a polynucleotide encoding a protein comprising the amino acid sequence of SEQ ID NO:20;

(h) a polynucleotide encoding a protein comprising a fragment of the amino acid sequence of SEQ ID NO:20 having biological activity, the fragment comprising eight contiguous amino acids of SEQ ID NO:20;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:19.

Preferably, such polynucleotide comprises the nucleotide sequence of SEQ ID NO:19 from nucleotide 509 to nucleotide 2467; the nucleotide sequence of the full-length protein coding sequence of clone ca106_19x deposited under accession number ATCC 98835; or the nucleotide sequence of a mature protein coding sequence of clone ca106_19x deposited under accession number ATCC 98835. In other preferred embodiments, the polynucleotide encodes the full-length or a mature protein encoded by the cDNA insert of clone ca106_19x deposited under accession number ATCC 98835. In further preferred embodiments, the present invention provides a polynucleotide encoding a protein comprising a fragment of the amino acid sequence of SEQ ID NO:20 having biological activity, the fragment preferably comprising eight (more preferably twenty, most preferably thirty) contiguous amino acids of SEQ ID NO:20, or a polynucleotide encoding a protein comprising a fragment of the amino acid sequence of SEQ ID NO:20 having biological activity, the fragment comprising the amino acid sequence from amino acid 321 to amino acid 330 of SEQ ID NO:20.

Other embodiments provide the gene corresponding to the cDNA sequence of SEQ ID NO:19.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:19, but excluding the poly(A) tail at the 3' end of SEQ ID NO:19; and (ab) the nucleotide sequence of the cDNA insert of clone ca106_19x deposited under accession number ATCC 98835;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:19, but excluding the poly(A) tail at the 3' end of SEQ ID NO:19; and (bb) the nucleotide sequence of the cDNA insert of clone ca106_19x deposited under accession number ATCC 98835;

(ii) hybridizing said primer(s) to human genomic DNA in conditions at least as stringent as 4×SSC at 50 degrees C.;

(iii) amplifying human DNA sequences; and (iv) isolating the polynucleotide products of step (b)(iii).

Preferably the polynucleotide isolated according to the above process comprises a nucleotide sequence corresponding to the cDNA sequence of SEQ ID NO:19, and extending contiguously from a nucleotide sequence corresponding to the 5' end of SEQ ID NO:19 to a nucleotide sequence corresponding to the 3' end of SEQ ID NO:19, but excluding the poly(A) tail at the 3' end of SEQ ID NO:19. Also preferably the polynucleotide isolated according to the above process comprises a nucleotide sequence corresponding to the cDNA sequence of SEQ ID NO:19 from nucleotide 509 to nucleotide 2467, and extending contiguously from a nucleotide sequence corresponding to the 5' end of said sequence of SEQ ID NO:19 from nucleotide 509 to nucleotide 2467, to a nucleotide sequence corresponding to the 3' end of said sequence of SEQ ID NO:19 from nucleotide 509 to nucleotide 2467.

In other embodiments, the present invention provides a composition comprising a protein, wherein said protein comprises an amino acid sequence selected from the group consisting of:

(a) the amino acid sequence of SEQ ID NO:20;

(b) a fragment of the amino acid sequence of SEQ ID NO:20, the fragment comprising eight contiguous amino acids of SEQ ID NO:20; and (c) the amino acid sequence encoded by the cDNA insert of clone ca106_19x deposited under accession number ATCC 98835;

the protein being substantially free from other mammalian proteins. Preferably such protein comprises the amino acid sequence of SEQ ID NO:20. In further preferred embodiments, the present invention provides a protein comprising a fragment of the amino acid sequence of SEQ ID NO:20 having biological activity, the fragment preferably comprising eight (more preferably twenty, most preferably thirty) contiguous amino acids of SEQ ID NO:20, or a protein comprising a fragment of the amino acid sequence of SEQ ID NO:20 having biological activity, the fragment comprising the amino acid sequence from amino acid 321 to amino acid 330 of SEQ ID NO:20.

In one embodiment, the present invention provides a composition comprising an isolated polynucleotide selected from the group consisting of:

(a) a polynucleotide comprising the nucleotide sequence of SEQ ID NO:21;

(b) a polynucleotide comprising the nucleotide sequence of SEQ ID NO:21 from nucleotide 179 to nucleotide 802;

(c) a polynucleotide comprising the nucleotide sequence of SEQ ID NO:21 from nucleotide 242 to nucleotide 802;

(d) a polynucleotide comprising the nucleotide sequence of the full-length protein coding sequence of clone ci52_2 deposited under accession number ATCC 98835;

(e) a polynucleotide encoding the full-length protein encoded by the cDNA insert of clone ci52_2 deposited under accession number ATCC 98835;

(f) a polynucleotide comprising the nucleotide sequence of a mature protein coding sequence of clone ci52_2 deposited under accession number ATCC 98835;

(g) a polynucleotide encoding a mature protein encoded by the cDNA insert of clone ci52_2 deposited under accession number ATCC 98835;

(h) a polynucleotide encoding a protein comprising the amino acid sequence of SEQ ID NO:22;

(i) a polynucleotide encoding a protein comprising a fragment of the amino acid sequence of SEQ ID NO:22 having biological activity, the fragment comprising eight contiguous amino acids of SEQ ID NO:22;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:21.

Preferably, such polynucleotide comprises the nucleotide sequence of SEQ ID NO:21 from nucleotide 179 to nucleotide 802; the nucleotide sequence of SEQ ID NO:21 from nucleotide 242 to nucleotide 802; the nucleotide sequence of the full-length protein coding sequence of clone ci52_2 deposited under accession number ATCC 98835; or the nucleotide sequence of a mature protein coding sequence of clone ci52_2 deposited under accession number ATCC 98835. In other preferred embodiments, the polynucleotide encodes the full-length or a mature protein encoded by the cDNA insert of clone ci52_2 deposited under accession number ATCC 98835. In further preferred embodiments, the present invention provides a polynucleotide encoding a protein comprising a fragment of the amino acid sequence of SEQ ID NO:22 having biological activity, the fragment preferably comprising eight (more preferably twenty, most preferably thirty) contiguous amino acids of SEQ ID NO:22, or a polynucleotide encoding a protein comprising a fragment of the amino acid sequence of SEQ ID NO:22 having biological activity, the fragment comprising the amino acid sequence from amino acid 99 to amino acid 108 of SEQ ID NO:22.

Other embodiments provide the gene corresponding to the cDNA sequence of SEQ ID NO:21.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:21, but excluding the poly(A) tail at the 3' end of SEQ ID NO:21; and (ab) the nucleotide sequence of the cDNA insert of clone ci52_2 deposited under accession number ATCC 98835;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:21, but excluding the poly(A) tail at the 3' end of SEQ ID NO:21; and (bb) the nucleotide sequence of the cDNA insert of clone ci52_2 deposited under accession number ATCC 98835;

(ii) hybridizing said primer(s) to human genomic DNA in conditions at least as stringent as 4×SSC at 50 degrees C.;

(iii) amplifying human DNA sequences; and (iv) isolating the polynucleotide products of step (b)(iii).

Preferably the polynucleotide isolated according to the above process comprises a nucleotide sequence corresponding to the cDNA sequence of SEQ ID NO:21, and extending contiguously from a nucleotide sequence corresponding to the 5' end of SEQ ID NO:21 to a nucleotide sequence corresponding to the 3' end of SEQ ID NO:21, but excluding the poly(A) tail at the 3' end of SEQ ID NO:21. Also preferably the polynucleotide isolated according to the above process comprises a nucleotide sequence corresponding to the cDNA sequence of SEQ ID NO:21 from nucleotide 179 to nucleotide 802, and extending contiguously from a nucleotide sequence corresponding to the 5' end of said sequence of SEQ ID NO:21 from nucleotide 179 to nucleotide 802, to a nucleotide sequence corresponding to the 3' end of said sequence of SEQ ID NO:21 from nucleotide 179 to nucleotide 802. Also preferably the polynucleotide isolated according to the above process comprises a nucleotide sequence corresponding to the cDNA sequence of SEQ ID NO:21 from nucleotide 242 to nucleotide 802, and extending contiguously from a nucleotide sequence corresponding to the 5' end of said sequence of SEQ ID NO:21 from nucleotide 242 to nucleotide 802, to a nucleotide sequence corresponding to the 3' end of said sequence of SEQ ID NO:21 from nucleotide 242 to nucleotide 802.

In other embodiments, the present invention provides a composition comprising a protein, wherein said protein comprises an amino acid sequence selected from the group consisting of:

(a) the amino acid sequence of SEQ ID NO:22;

(b) a fragment of the amino acid sequence of SEQ ID NO:22, the fragment comprising eight contiguous amino acids of SEQ ID NO:22; and (c) the amino acid sequence encoded by the cDNA insert of clone ci52_2 deposited under accession number ATCC 98835;

the protein being substantially free from other mammalian proteins. Preferably such protein comprises the amino acid sequence of SEQ ID NO:22. In further preferred embodiments, the present invention provides a protein comprising a fragment of the amino acid sequence of SEQ ID NO:22 having biological activity, the fragment preferably comprising eight (more preferably twenty, most preferably thirty) contiguous amino acids of SEQ ID NO:22, or a protein comprising a fragment of the amino acid sequence of SEQ ID NO:22 having biological activity, the fragment comprising the amino acid sequence from amino acid 99 to amino acid 108 of SEQ ID NO:22.

In one embodiment, the present invention provides a composition comprising an isolated polynucleotide selected from the group consisting of:

(a) a polynucleotide comprising the nucleotide sequence of SEQ ID NO:23;

(b) a polynucleotide comprising the nucleotide sequence of SEQ ID NO:23 from nucleotide 46 to nucleotide 714;

(c) a polynucleotide comprising the nucleotide sequence of SEQ ID NO:23 from nucleotide 538 to nucleotide 714;

(d) a polynucleotide comprising the nucleotide sequence of the full-length protein coding sequence of clone md124__16 deposited under accession number ATCC 98835;

(e) a polynucleotide encoding the full-length protein encoded by the cDNA insert of clone md124__16 deposited under accession number ATCC 98835;

(f) a polynucleotide comprising the nucleotide sequence of a mature protein coding sequence of clone md124__16 deposited under accession number ATCC 98835;

(g) a polynucleotide encoding a mature protein encoded by the cDNA insert of clone md124__16 deposited under accession number ATCC 98835;

(h) a polynucleotide encoding a protein comprising the amino acid sequence of SEQ ID NO:24;

(i) a polynucleotide encoding a protein comprising a fragment of the amino acid sequence of SEQ ID NO:24 having biological activity, the fragment comprising eight contiguous amino acids of SEQ ID NO:24;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:23.

Preferably, such polynucleotide comprises the nucleotide sequence of SEQ ID NO:23 from nucleotide 46 to nucleotide 714; the nucleotide sequence of SEQ ID NO:23 from nucleotide 538 to nucleotide 714; the nucleotide sequence of the full-length protein coding sequence of clone md124__16 deposited under accession number ATCC 98835; or the nucleotide sequence of a mature protein coding sequence of clone md124__16 deposited under accession number ATCC 98835. In other preferred embodiments, the polynucleotide encodes the full-length or a mature protein encoded by the cDNA insert of clone md124__16 deposited under accession number ATCC 98835. In further preferred embodiments, the present invention provides a polynucleotide encoding a protein comprising a fragment of the amino acid sequence of SEQ ID NO:24 having biological activity, the fragment preferably comprising eight (more preferably twenty, most preferably thirty) contiguous amino acids of SEQ ID NO:24, or a polynucleotide encoding a protein comprising a fragment of the amino acid sequence of SEQ ID NO:24 having biological activity, the fragment comprising the amino acid sequence from amino acid 106 to amino acid 115 of SEQ ID NO:24.

Other embodiments provide the gene corresponding to the cDNA sequence of SEQ ID NO:23.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:23, but excluding the poly(A) tail at the 3' end of SEQ ID NO:23; and (ab) the nucleotide sequence of the cDNA insert of clone md124__16 deposited under accession number ATCC 98835;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:23, but excluding the poly(A) tail at the 3' end of SEQ ID NO:23; and (bb) the nucleotide sequence of the cDNA insert of clone md124__16 deposited under accession number ATCC 98835;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:23, and extending contiguously from a nucleotide sequence corresponding to the 5' end of SEQ ID NO:23 to a nucleotide sequence corresponding to the 3' end of SEQ ID NO:23, but excluding the poly(A) tail at the 3' end of SEQ ID NO:23. Also preferably the polynucleotide isolated according to the above process comprises a nucleotide sequence corresponding to the cDNA sequence of SEQ ID NO:23 from nucleotide 46 to nucleotide 714, and extending contiguously from a nucleotide sequence corresponding to the 5' end of said sequence of SEQ ID NO:23 from nucleotide 46 to nucleotide 714, to a nucleotide sequence corresponding to the 3' end of said sequence of SEQ ID NO:23 from nucleotide 46 to nucleotide 714. Also preferably the polynucleotide isolated according to the above process comprises a nucleotide sequence corresponding to the cDNA sequence of SEQ ID NO:23 from nucleotide 538 to nucleotide 714, and extending contiguously from a nucleotide sequence corresponding to the 5' end of said sequence of SEQ ID NO:23 from nucleotide 538 to nucleotide 714, to a nucleotide sequence corresponding to the 3' end of said sequence of SEQ ID NO:23 from nucleotide 538 to nucleotide 714.

In other embodiments, the present invention provides a composition comprising a protein, wherein said protein comprises an amino acid sequence selected from the group consisting of:

(a) the amino acid sequence of SEQ ID NO:24;

(b) a fragment of the amino acid sequence of SEQ ID NO:24, the fragment comprising eight contiguous amino acids of SEQ ID NO:24; and (c) the amino acid sequence encoded by the cDNA insert of clone md124_16 deposited under accession number ATCC 98835;

the protein being substantially free from other mammalian proteins. Preferably such protein comprises the amino acid sequence of SEQ ID NO:24. In further preferred embodiments, the present invention provides a protein comprising a fragment of the amino acid sequence of SEQ ID NO:24 having biological activity, the fragment preferably comprising eight (more preferably twenty, most preferably thirty) contiguous amino acids of SEQ ID NO:24, or a protein comprising a fragment of the amino acid sequence of SEQ ID NO:24 having biological activity, the fragment comprising the amino acid sequence from amino acid 106 to amino acid 115 of SEQ ID NO:24.

In one embodiment, the present invention provides a composition comprising an isolated polynucleotide selected from the group consisting of:

(a) a polynucleotide comprising the nucleotide sequence of SEQ ID NO:25;

(b) a polynucleotide comprising the nucleotide sequence of SEQ ID NO:25 from nucleotide 92 to nucleotide 1726;

(c) a polynucleotide comprising the nucleotide sequence of SEQ ID NO:25 from nucleotide $^{1211}$ to nucleotide 1726;

(d) a polynucleotide comprising the nucleotide sequence of the full-length protein coding sequence of clone pk366_7 deposited under accession number ATCC 98835;

(e) a polynucleotide encoding the full-length protein encoded by the cDNA insert of clone pk366_7 deposited under accession number ATCC 98835;

(f) a polynucleotide comprising the nucleotide sequence of a mature protein coding sequence of clone pk366_7 deposited under accession number ATCC 98835;

(g) a polynucleotide encoding a mature protein encoded by the cDNA insert of clone pk366_7 deposited under accession number ATCC 98835;

(h) a polynucleotide encoding a protein comprising the amino acid sequence of SEQ ID NO:26;

(i) a polynucleotide encoding a protein comprising a fragment of the amino acid sequence of SEQ ID NO:26 having biological activity, the fragment comprising eight contiguous amino acids of SEQ ID NO:26;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:25.

Preferably, such polynucleotide comprises the nucleotide sequence of SEQ ID NO:25 from nucleotide 92 to nucleotide 1726; the nucleotide sequence of SEQ ID NO:25 from nucleotide $^{1211}$ to nucleotide 1726; the nucleotide sequence of the full-length protein coding sequence of clone pk366_7 deposited under accession number ATCC 98835; or the nucleotide sequence of a mature protein coding sequence of clone pk366_7 deposited under accession number ATCC 98835. In other preferred embodiments, the polynucleotide encodes the full-length or a mature protein encoded by the cDNA insert of clone pk366_7 deposited under accession number ATCC 98835. In further preferred embodiments, the present invention provides a polynucleotide encoding a protein comprising a fragment of the amino acid sequence of SEQ ID NO:26 having biological activity, the fragment preferably comprising eight (more preferably twenty, most preferably thirty) contiguous amino acids of SEQ ID NO:26, or a polynucleotide encoding a protein comprising a fragment of the amino acid sequence of SEQ ID NO:26 having biological activity, the fragment comprising the amino acid sequence from amino acid 267 to amino acid 276 of SEQ ID NO:26.

Other embodiments provide the gene corresponding to the cDNA sequence of SEQ ID NO:25.

Further embodiments of the invention provide isolated polynucleotides produced according to a process selected from the group consisting of:

(a) a process comprising the steps of:
 (i) preparing one or more polynucleotide probes that hybridize in 6×SSC at 65 degrees C. to a nucleotide sequence selected from the group consisting of:
  (aa) SEQ ID NO:25, but excluding the poly(A) tail at the 3' end of SEQ ID NO:25; and
  (ab) the nucleotide sequence of the cDNA insert of clone pk366_7 deposited under accession number ATCC 98835;
 (ii) hybridizing said probe(s) to human genomic DNA in conditions at least as stringent as 4×SSC at 50 degrees C.; and
 (iii) isolating the DNA polynucleotides detected with the probe(s); and (b) a process comprising the steps of:
 (i) preparing one or more polynucleotide primers that hybridize in 6×SSC at 65 degrees C. to a nucleotide sequence selected from the group consisting of:
  (ba) SEQ ID NO:25, but excluding the poly(A) tail at the 3' end of SEQ ID NO:25; and
  (bb) the nucleotide sequence of the cDNA insert of clone pk366_7 deposited under accession number ATCC 98835;
 (ii) hybridizing said primer(s) to human genomic DNA in conditions at least as stringent as 4×SSC at 50 degrees C.;
 (iii) amplifying human DNA sequences; and
 (iv) isolating the polynucleotide products of step (b) (iii).

Preferably the polynucleotide isolated according to the above process comprises a nucleotide sequence corresponding to the cDNA sequence of SEQ ID NO:25, and extending contiguously from a nucleotide sequence corresponding to the 5' end of SEQ ID NO:25 to a nucleotide sequence corresponding to the 3' end of SEQ ID NO:25, but excluding the poly(A) tail at the 3' end of SEQ ID NO:25. Also preferably the polynucleotide isolated according to the above process comprises a nucleotide sequence corresponding to the cDNA sequence of SEQ ID NO:25 from nucleotide 92 to nucleotide 1726, and extending contiguously from a nucleotide sequence corresponding to the 5' end of said sequence of SEQ ID NO:25 from nucleotide 92 to nucleotide 1726, to a nucleotide sequence corresponding to the 3' end of said sequence of SEQ ID NO:25 from nucleotide 92 to nucleotide 1726. Also preferably the polynucleotide isolated according to the above process comprises a nucleotide sequence corresponding to the cDNA sequence of SEQ ID NO:25 from nucleotide 1211 to nucleotide 1726, and extending contiguously from a nucleotide sequence corresponding to the 5' end of said sequence of SEQ ID NO:25 from nucleotide 1211 to nucleotide 1726, to a nucleotide sequence corresponding to the 3' end of said sequence of SEQ ID NO:25 from nucleotide 1211 to nucleotide 1726.

In other embodiments, the present invention provides a composition comprising a protein, wherein said protein comprises an amino acid sequence selected from the group consisting of:

(a) the amino acid sequence of SEQ ID NO:26;

(b) a fragment of the amino acid sequence of SEQ ID NO:26, the fragment comprising eight contiguous amino acids of SEQ ID NO:26; and (c) the amino acid sequence encoded by the cDNA insert of clone pk366_7 deposited under accession number ATCC 98835;

the protein being substantially free from other mammalian proteins. Preferably such protein comprises the amino acid sequence of SEQ ID NO:26. In further preferred embodiments, the present invention provides a protein comprising a fragment of the amino acid sequence of SEQ ID NO:26 having biological activity, the fragment preferably comprising eight (more preferably twenty, most preferably thirty) contiguous amino acids of SEQ ID NO:26, or a protein comprising a fragment of the amino acid sequence of SEQ ID NO:26 having biological activity, the fragment comprising the amino acid sequence from amino acid 267 to amino acid 276 of SEQ ID NO:26.

In one embodiment, the present invention provides a composition comprising an isolated polynucleotide selected from the group consisting of:

(a) a polynucleotide comprising the nucleotide sequence of SEQ ID NO:27;

(b) a polynucleotide comprising the nucleotide sequence of SEQ ID NO:27 from nucleotide 16 to nucleotide 1788;

(c) a polynucleotide comprising the nucleotide sequence of SEQ ID NO:27 from nucleotide 61 to nucleotide 1788;

(d) a polynucleotide comprising the nucleotide sequence of the full-length protein coding sequence of clone pl741_5 deposited under accession number ATCC 98835;

(e) a polynucleotide encoding the full-length protein encoded by the cDNA insert of clone pl741_5 deposited under accession number ATCC 98835;

(f) a polynucleotide comprising the nucleotide sequence of a mature protein coding sequence of clone pl741_5 deposited under accession number ATCC 98835;

(g) a polynucleotide encoding a mature protein encoded by the cDNA insert of clone pl741_5 deposited under accession number ATCC 98835;

(h) a polynucleotide encoding a protein comprising the amino acid sequence of SEQ ID NO:28;

(i) a polynucleotide encoding a protein comprising a fragment of the amino acid sequence of SEQ ID NO:28 having biological activity, the fragment comprising eight contiguous amino acids of SEQ ID NO:28;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:27.

Preferably, such polynucleotide comprises the nucleotide sequence of SEQ ID NO:27 from nucleotide 16 to nucleotide 1788; the nucleotide sequence of SEQ ID NO:27 from nucleotide 61 to nucleotide 1788; the nucleotide sequence of the full-length protein coding sequence of clone pl741_5 deposited under accession number ATCC 98835; or the nucleotide sequence of a mature protein coding sequence of clone pl741_5 deposited under accession number ATCC 98835. In other preferred embodiments, the polynucleotide encodes the full-length or a mature protein encoded by the cDNA insert of clone pl741_5 deposited under accession number ATCC 98835. In further preferred embodiments, the present invention provides a polynucleotide encoding a protein comprising a fragment of the amino acid sequence of SEQ ID NO:28 having biological activity, the fragment preferably comprising eight (more preferably twenty, most preferably thirty) contiguous amino acids of SEQ ID NO:28, or a polynucleotide encoding a protein comprising a fragment of the amino acid sequence of SEQ ID NO:28 having biological activity, the fragment comprising the amino acid sequence from amino acid 290 to amino acid 299 of SEQ ID NO:28.

Other embodiments provide the gene corresponding to the cDNA sequence of SEQ ID NO:27.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:27, but excluding the poly(A) tail at the 3' end of SEQ ID NO:27; and
    (ab) the nucleotide sequence of the cDNA insert of clone pl741_5 deposited under accession number ATCC 98835;
  (ii) hybridizing said probe(s) to human genomic DNA in conditions at least as stringent as 4×SSC at 50 degrees C.; and
  (iii) isolating the DNA polynucleotides detected with the probe(s); and (b) a process comprising the steps of:
  (i) preparing one or more polynucleotide primers that hybridize in 6×SSC at 65 degrees C. to a nucleotide sequence selected from the group consisting of:
    (ba) SEQ ID NO:27, but excluding the poly(A) tail at the 3' end of SEQ ID NO:27; and
    (bb) the nucleotide sequence of the cDNA insert of clone pl741_5 deposited under accession number ATCC 98835;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:27, and extending contiguously from a nucleotide sequence corresponding to the 5' end of SEQ ID NO:27 to a nucleotide sequence corresponding to the 3' end of SEQ ID NO:27, but excluding the poly(A) tail at the 3' end of SEQ ID NO:27. Also preferably the polynucleotide isolated according to the above process comprises a nucleotide sequence corresponding to the cDNA sequence of SEQ ID NO:27 from nucleotide 16 to nucleotide 1788, and extending contiguously from a nucleotide sequence corresponding to the 5' end of said sequence of SEQ ID NO:27 from nucleotide 16 to nucleotide 1788, to a nucleotide sequence corresponding to the 3' end of said sequence of SEQ ID NO:27 from nucleotide 16 to nucleotide 1788. Also preferably the polynucleotide isolated according to the above process comprises a nucleotide sequence corresponding to the cDNA sequence of SEQ ID NO:27 from nucleotide 61 to nucleotide 1788, and extending contiguously from a nucleotide sequence corresponding to the 5' end of said sequence of SEQ ID NO:27 from nucleotide 61 to nucleotide 1788, to a nucleotide sequence corresponding to the 3' end of said sequence of SEQ ID NO:27 from nucleotide 61 to nucleotide 1788.

In other embodiments, the present invention provides a composition comprising a protein, wherein said protein comprises an amino acid sequence selected from the group consisting of:

(a) the amino acid sequence of SEQ ID NO:28;

(b) a fragment of the amino acid sequence of SEQ ID NO:28, the fragment comprising eight contiguous amino acids of SEQ ID NO:28; and (c) the amino acid sequence encoded by the cDNA insert of clone pl741__5 deposited under accession number ATCC 98835;

the protein being substantially free from other mammalian proteins. Preferably such protein comprises the amino acid sequence of SEQ ID NO:28. In further preferred embodiments, the present invention provides a protein comprising a fragment of the amino acid sequence of SEQ ID NO:28 having biological activity, the fragment preferably comprising eight (more preferably twenty, most preferably thirty) contiguous amino adds of SEQ ID NO:28, or a protein comprising a fragment of the amino acid sequence of SEQ ID NO:28 having biological activity, the fragment comprising the amino acid sequence from amino acid 290 to amino acid 299 of SEQ ID NO:28.

In one embodiment, the present invention provides a composition comprising an isolated polynucleotide selected from the group consisting of:

(a) a polynucleotide comprising the nucleotide sequence of SEQ ID NO:29;

(b) a polynucleotide comprising the nucleotide sequence of SEQ ID NO:29 from nucleotide 629 to nucleotide 2338;

(c) a polynucleotide comprising the nucleotide sequence of the full-length protein coding sequence of clone pp314__19 deposited under accession number ATCC 98835;

(d) a polynucleotide encoding the full-length protein encoded by the cDNA insert of clone pp314__19 deposited under accession number ATCC 98835;

(e) a polynucleotide comprising the nucleotide sequence of a mature protein coding sequence of clone pp314__19 deposited under accession number ATCC 98835;

(f) a polynucleotide encoding a mature protein encoded by the cDNA insert of clone pp314__19 deposited under accession number ATCC 98835;

(g) a polynucleotide encoding a protein comprising the amino acid sequence of SEQ ID NO:30;

(h) a polynucleotide encoding a protein comprising a fragment of the amino acid sequence of SEQ ID NO:30 having biological activity, the fragment comprising eight contiguous amino acids of SEQ ID NO:30;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:29.

Preferably, such polynucleotide comprises the nucleotide sequence of SEQ ID NO:29 from nucleotide 629 to nucleotide 2338; the nucleotide sequence of the full-length protein coding sequence of clone pp314__19 deposited under accession number ATCC 98835; or the nucleotide sequence of a mature protein coding sequence of clone pp314__19 deposited under accession number ATCC 98835. In other preferred embodiments, the polynucleotide encodes the full-length or a mature protein encoded by the cDNA insert of clone pp314__19 deposited under accession number ATCC 98835. In further preferred embodiments, the present invention provides a polynucleotide encoding a protein comprising a fragment of the amino acid sequence of SEQ ID NO:30 having biological activity, the fragment preferably comprising eight (more preferably twenty, most preferably thirty) contiguous amino acids of SEQ ID NO:30, or a polynucleotide encoding a protein comprising a fragment of the amino acid sequence of SEQ ID NO:30 having biological activity, the fragment comprising the amino acid sequence from amino acid 280 to amino acid 289 of SEQ ID NO:30.

Other embodiments provide the gene corresponding to the cDNA sequence of SEQ ID NO:29.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:29, but excluding the poly(A) tail at the 3' end of SEQ ID NO:29; and (ab) the nucleotide sequence of the cDNA insert of clone pp314__19 deposited under accession number ATCC 98835;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:29, but excluding the poly(A) tail at the 3' end of SEQ ID NO:29; and (bb) the nucleotide sequence of the cDNA insert of clone pp314_19 deposited under accession number ATCC 98835;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:29, and extending contiguously from a nucleotide sequence corresponding to the 5' end of SEQ ID NO:29 to a nucleotide sequence corresponding to the 3' end of SEQ ID NO:29, but excluding the poly(A) tail at the 3' end of SEQ ID NO:29. Also preferably the polynucleotide isolated according to the above process comprises a nucleotide sequence corresponding to the cDNA sequence of SEQ ID NO:29 from nucleotide 629 to nucleotide 2338, and extending contiguously from a nucleotide sequence corresponding to the 5' end of said sequence of SEQ ID NO:29 from nucleotide 629 to nucleotide 2338, to a nucleotide sequence corresponding to the 3' end of said sequence of SEQ ID NO:29 from nucleotide 629 to nucleotide 2338.

In other embodiments, the present invention provides a composition comprising a protein, wherein said protein comprises an amino acid sequence selected from the group consisting of:

(a) the amino acid sequence of SEQ ID NO:30;

(b) a fragment of the amino add sequence of SEQ ID NO:30, the fragment comprising eight contiguous amino acids of SEQ ID NO:30; and (c) the amino acid sequence encoded by the cDNA insert of clone pp314_19 deposited under accession number ATCC 98835;

the protein being substantially free from other mammalian proteins. Preferably such protein comprises the amino acid sequence of SEQ ID NO:30. In further preferred embodiments, the present invention provides a protein comprising a fragment of the amino acid sequence of SEQ ID NO:30 having biological activity, the fragment preferably comprising eight (more preferably twenty, most preferably thirty) contiguous amino acids of SEQ ID NO:30, or a protein comprising a fragment of the amino acid sequence of SEQ ID NO:30 having biological activity, the fragment comprising the amino acid sequence from amino acid 280 to amino acid 289 of SEQ ID NO:30.

In one embodiment, the present invention provides a composition comprising an isolated polynucleotide selected from the group consisting of:

(a) a polynucleotide comprising the nucleotide sequence of SEQ ID NO:31;

(b) a polynucleotide comprising the nucleotide sequence of SEQ ID NO:31 from nucleotide 158 to nucleotide 1102;

(c) a polynucleotide comprising the nucleotide sequence of the full-length protein coding sequence of clone pv35_1 deposited under accession number ATCC 98835;

(d) a polynucleotide encoding the full-length protein encoded by the cDNA insert of clone pv35_1 deposited under accession number ATCC 98835;

(e) a polynucleotide comprising the nucleotide sequence of a mature protein coding sequence of clone pv35_1 deposited under accession number ATCC 98835;

(f) a polynucleotide encoding a mature protein encoded by the cDNA insert of clone pv35_1 deposited under accession number ATCC 98835;

(g) a polynucleotide encoding a protein comprising the amino acid sequence of SEQ ID NO:32;

(h) a polynucleotide encoding a protein comprising a fragment of the amino acid sequence of SEQ ID NO:32 having biological activity, the fragment comprising eight contiguous amino acids of SEQ ID NO:32;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:31.

Preferably, such polynucleotide comprises the nucleotide sequence of SEQ ID NO:31 from nucleotide 158 to nucleotide 1102; the nucleotide sequence of the fun-length protein coding sequence of clone pv35_1 deposited under accession number ATCC 98835; or the nucleotide sequence of a mature protein coding sequence of clone pv35_1 deposited under accession number ATCC 98835. In other preferred embodiments, the polynucleotide encodes the full-length or a mature protein encoded by the cDNA insert of clone pv35_1 deposited under accession number ATCC 98835. In further preferred embodiments, the present invention provides a polynucleotide encoding a protein comprising a fragment of the amino acid sequence of SEQ ID NO:32 having biological activity, the fragment preferably comprising eight (more preferably twenty, most preferably thirty) contiguous amino acids of SEQ ID NO:32, or a polynucleotide encoding a protein comprising a fragment of the amino acid sequence of SEQ ID NO:32 having biological activity, the fragment comprising the amino acid sequence from amino acid 152 to amino acid 161 of SEQ ID NO:32.

Other embodiments provide the gene corresponding to the cDNA sequence of SEQ ID NO:31.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:31, but excluding the poly(A) tail at the 3' end of SEQ ID NO:31; and (ab) the nucleotide sequence of the cDNA insert of clone pv35_1 deposited under accession number ATCC 98835;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:31, but excluding the poly(A) tail at the 3' end of SEQ ID NO:31; and (bb) the nucleotide sequence of the cDNA insert of clone pv35_1 deposited under accession number ATCC 98835;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:31, and extending contiguously from a nucleotide sequence corresponding to the 5' end of SEQ ID NO:31 to a nucleotide sequence corresponding to the 3' end of SEQ ID NO:31, but excluding the poly(A) tail at the 3' end of SEQ ID NO:31. Also preferably the polynucleotide isolated according to the above process comprises a nucleotide sequence corresponding to the cDNA sequence of SEQ ID NO:31 from nucleotide 158 to nucleotide 1102, and extending contiguously from a nucleotide sequence corresponding to the 5' end of said sequence of SEQ ID NO:31 from nucleotide 158 to nucleotide 1102, to a nucleotide sequence corresponding to the 3' end of said sequence of SEQ ID NO:31 from nucleotide 158 to nucleotide 1102.

In other embodiments, the present invention provides a composition comprising a protein, wherein said protein comprises an amino acid sequence selected from the group consisting of:

(a) the amino acid sequence of SEQ ID NO:32;

(b) a fragment of the amino acid sequence of SEQ ID NO:32, the fragment comprising eight contiguous amino acids of SEQ ID NO:32; and (c) the amino acid sequence encoded by the cDNA insert of clone pv35_1 deposited under accession number ATCC 98835;

the protein being substantially free from other mammalian proteins. Preferably such protein comprises the amino acid sequence of SEQ ID NO:32. In further preferred embodiments, the present invention provides a protein comprising a fragment of the amino add sequence of SEQ ID NO:32 having biological activity, the fragment preferably comprising eight (more preferably twenty, most preferably thirty) contiguous amino acids of SEQ ID NO:32, or a protein comprising a fragment of the amino acid sequence of SEQ ID NO:32 having biological activity, the fragment comprising the amino acid sequence from amino acid 152 to amino acid 161 of SEQ ID NO:32.

In one embodiment, the present invention provides a composition comprising an isolated polynucleotide selected from the group consisting of:

(a) a polynucleotide comprising the nucleotide sequence of SEQ ID NO:33;

(b) a polynucleotide comprising the nucleotide sequence of SEQ ID NO:33 from nucleotide 413 to nucleotide 733;

(c) a polynucleotide comprising the nucleotide sequence of the full-length protein coding sequence of clone pw337_6 deposited under accession number ATCC 98835;

(d) a polynucleotide encoding the full-length protein encoded by the cDNA insert of clone pw337_6 deposited under accession number ATCC 98835;

(e) a polynucleotide comprising the nucleotide sequence of a mature protein coding sequence of clone pw337_6 deposited under accession number ATCC 98835;

(f) a polynucleotide encoding a mature protein encoded by the cDNA insert of clone pw337_6 deposited under accession number ATCC 98835;

(g) a polynucleotide encoding a protein comprising the amino acid sequence of SEQ ID NO:34;

(h) a polynucleotide encoding a protein comprising a fragment of the amino acid sequence of SEQ ID NO:34 having biological activity, the fragment comprising eight contiguous amino acids of SEQ ID NO:34;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:33.

Preferably, such polynucleotide comprises the nucleotide sequence of SEQ ID NO:33 from nucleotide 413 to nucleotide 733; the nucleotide sequence of the full-length protein coding sequence of clone pw337_6 deposited under accession number ATCC 98835; or the nucleotide sequence of a mature protein coding sequence of clone pw337_6 deposited under accession number ATCC 98835. In other preferred embodiments, the polynucleotide encodes the full-length or a mature protein encoded by the cDNA insert of clone pw337_6 deposited under accession number ATCC 98835. In further preferred embodiments, the present invention provides a polynucleotide encoding a protein comprising a fragment of the amino acid sequence of SEQ ID NO:34 having biological activity, the fragment preferably comprising eight (more preferably twenty, most preferably thirty) contiguous amino acids of SEQ ID NO:34, or a polynucleotide encoding a protein comprising a fragment of the amino acid sequence of SEQ ID NO:34 having biological activity, the fragment comprising the amino acid sequence from amino acid 48 to amino acid 57 of SEQ ID NO:34.

Other embodiments provide the gene corresponding to the cDNA sequence of SEQ ID NO:33.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:33, but excluding the poly(A) tail at the 3' end of SEQ ID NO:33; and (ab) the nucleotide sequence of the cDNA insert of clone pw337_6 deposited under accession number ATCC 98835;

(ii) hybridizing said probe(s) to human genomic DNA in conditions at least as stringent as 4×SSC at 50 degrees C.; and (ii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:33, but excluding the poly(A) tail at the 3' end of SEQ ID NO:33; and (bb) the nucleotide sequence of the cDNA insert of clone pw337_6 deposited under accession number ATCC 98835;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:33, and extending contiguously from a nucleotide sequence corresponding to the 5' end of SEQ ID NO:33 to a nucleotide sequence corresponding to the 3' end of SEQ ID NO:33, but excluding the poly(A) tail at the 3' end of SEQ ID NO:33. Also preferably the polynucleotide isolated according to the above process comprises a nucleotide sequence corresponding to the cDNA sequence of SEQ ID NO:33 from nucleotide 413 to nucleotide 733, and extending contiguously from a nucleotide sequence corresponding to the 5' end of said sequence of SEQ ID NO:33 from nucleotide 413 to nucleotide 733, to a nucleotide sequence corresponding to the 3' end of said sequence of SEQ ID NO:33 from nucleotide 413 to nucleotide 733.

In other embodiments, the present invention provides a composition comprising a protein, wherein said protein comprises an amino acid sequence selected from the group consisting of:

(a) the amino acid sequence of SEQ ID NO:34;

(b) a fragment of the amino acid sequence of SEQ ID NO:34, the fragment comprising eight contiguous amino acids of SEQ ID NO:34; and (c) the amino acid sequence encoded by the cDNA insert of clone pw337_6 deposited under accession number ATCC 98835;

the protein being substantially free from other mammalian proteins. Preferably such protein comprises the amino acid sequence of SEQ ID NO:34. In further preferred embodiments, the present invention provides a protein comprising a fragment of the amino acid sequence of SEQ ID NO:34 having biological activity, the fragment preferably comprising eight (more preferably twenty, most preferably thirty) contiguous amino adds of SEQ ID NO:34, or a protein comprising a fragment of the amino acid sequence of SEQ ID NO:34 having biological activity, the fragment comprising the amino add sequence from amino acid 48 to amino acid 57 of SEQ ID NO:34.

In one embodiment, the present invention provides a composition comprising an isolated polynucleotide selected from the group consisting of:

(a) a polynucleotide comprising the nucleotide sequence of SEQ ID NO:35;

(b) a polynucleotide comprising the nucleotide sequence of SEQ ID NO:35 from nucleotide 678 to nucleotide 938;

(c) a polynucleotide comprising the nucleotide sequence of the full-length protein coding sequence of clone rd610_1 deposited under accession number ATCC 98835;

(d) a polynucleotide encoding the full-length protein encoded by the cDNA insert of clone rd610_1 deposited under accession number ATCC 98835;

(e) a polynucleotide comprising the nucleotide sequence of a mature protein coding sequence of clone rd610_1 deposited under accession number ATCC 98835;

(f) a polynucleotide encoding a mature protein encoded by the cDNA insert of clone rd610_1 deposited under accession number ATCC 98835;

(g) a polynucleotide encoding a protein comprising the amino acid sequence of SEQ ID NO:36;

(h) a polynucleotide encoding a protein comprising a fragment of the amino acid sequence of SEQ ID NO:36 having biological activity, the fragment comprising eight contiguous amino acids of SEQ ID NO:36;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:35.

Preferably, such polynucleotide comprises the nucleotide sequence of SEQ ID NO:35 from nucleotide 678 to nucleotide 938; the nucleotide sequence of the full-length protein coding sequence of clone rd610_1 deposited under accession number ATCC 98835; or the nucleotide sequence of a mature protein coding sequence of clone rd610_1 deposited under accession number ATCC 98835. In other preferred embodiments, the polynucleotide encodes the full-length or a mature protein encoded by the cDNA insert of clone rd610_1 deposited under accession number ATCC 98835. In further preferred embodiments, the present invention provides a polynucleotide encoding a protein comprising a fragment of the amino acid sequence of SEQ ID NO:36 having biological activity, the fragment preferably comprising eight (more preferably twenty, most preferably thirty) contiguous amino acids of SEQ ID NO:36, or a polynucleotide encoding a protein comprising a fragment of the amino acid sequence of SEQ ID NO:36 having biological activity, the fragment comprising the amino acid sequence from amino acid 38 to amino acid 47 of SEQ ID NO:36.

Other embodiments provide the gene corresponding to the cDNA sequence of SEQ ID NO:35.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:35, but excluding the poly(A) tail at the 3' end of SEQ ID NO:35; and (ab) the nucleotide sequence of the cDNA insert of clone rd610_1 deposited under accession number ATCC 98835;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:35, but excluding the poly(A) tail at the 3' end of SEQ ID NO:35; and (bb) the nucleotide sequence of the cDNA insert of clone rd610_1 deposited under accession number ATCC 98835;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:35, and extending contiguously from a nucleotide sequence corresponding to the 5' end of SEQ ID NO:35 to a nucleotide sequence corresponding to the 3' end of SEQ ID NO:35, but excluding the poly(A) tail at the 3' end of SEQ ID NO:35. Also preferably the polynucleotide isolated according to the above process comprises a nucleotide sequence corresponding to the cDNA sequence of SEQ ID NO:35 from nucleotide 678 to nucleotide 938, and extending contiguously from a nucleotide sequence corresponding to the 5' end of said sequence of SEQ ID NO:35 from nucleotide 678 to nucleotide 938, to a nucleotide sequence corresponding to the 3' end of said sequence of SEQ ID NO:35 from nucleotide 678 to nucleotide 938.

In other embodiments, the present invention provides a composition comprising a protein, wherein said protein comprises an amino acid sequence selected from the group consisting of:

(a) the amino acid sequence of SEQ ID NO:36;

(b) a fragment of the amino acid sequence of SEQ ID NO:36, the fragment comprising eight contiguous amino acids of SEQ ID NO:36; and (c) the amino acid sequence encoded by the cDNA insert of clone rd610_1 deposited under accession number ATCC 98835;

the protein being substantially free from other mammalian proteins. Preferably such protein comprises the amino acid sequence of SEQ ID NO:36. In further preferred embodiments, the present invention provides a protein comprising a fragment of the amino add sequence of SEQ ID NO:36 having biological activity, the fragment preferably comprising eight (more preferably twenty, most preferably thirty) contiguous amino adds of SEQ ID NO:36, or a protein comprising a fragment of the amino acid sequence of SEQ ID NO:36 having biological activity, the fragment comprising the amino acid sequence from amino acid 38 to amino acid 47 of SEQ ID NO:36.

In one embodiment, the present invention provides a composition comprising an isolated polynucleotide selected from the group consisting of:

(a) a polynucleotide comprising the nucleotide sequence of SEQ ID NO:37;

(b) a polynucleotide comprising the nucleotide sequence of SEQ ID NO:37 from nucleotide 75 to nucleotide 494;

(c) a polynucleotide comprising the nucleotide sequence of SEQ ID NO:37 from nucleotide 447 to nucleotide 494;

(d) a polynucleotide comprising the nucleotide sequence of the full-length protein coding sequence of clone rd810_6 deposited under accession number ATCC 98835;

(e) a polynucleotide encoding the full-length protein encoded by the cDNA insert of clone rd810_6 deposited under accession number ATCC 98835;

(f) a polynucleotide comprising the nucleotide sequence of a mature protein coding sequence of clone rd810_6 deposited under accession number ATCC 98835;

(g) a polynucleotide encoding a mature protein encoded by the cDNA insert of clone rd810_6 deposited under accession number ATCC 98835;

(h) a polynucleotide encoding a protein comprising the amino acid sequence of SEQ ID NO:38;

(i) a polynucleotide encoding a protein comprising a fragment of the amino acid sequence of SEQ ID NO:38 having biological activity, the fragment comprising eight contiguous amino acids of SEQ ID NO:38;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:37.

Preferably, such polynucleotide comprises the nucleotide sequence of SEQ ID NO:37 from nucleotide 75 to nucleotide 494; the nucleotide sequence of SEQ ID NO:37 from nucleotide 447 to nucleotide 494; the nucleotide sequence of the full-length protein coding sequence of clone rd810_6 deposited under accession number ATCC 98835; or the nucleotide sequence of a mature protein coding sequence of clone rd810_6 deposited under accession number ATCC 98835. In other preferred embodiments, the polynucleotide encodes the full-length or a mature protein encoded by the cDNA insert of clone rd810_6 deposited under accession number ATCC 98835. In further preferred embodiments, the present invention provides a polynucleotide encoding a protein comprising a fragment of the amino acid sequence of SEQ ID NO:38 having biological activity, the fragment preferably comprising eight (more preferably twenty, most preferably thirty) contiguous amino acids of SEQ ID NO:38, or a polynucleotide encoding a protein comprising a fragment of the amino acid sequence of SEQ ID NO:38 having biological activity, the fragment comprising the amino acid sequence from amino acid 65 to amino acid 74 of SEQ ID NO:38.

Other embodiments provide the gene corresponding to the cDNA sequence of SEQ ID NO:37.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:37, but excluding the poly(A) tail at the 3' end of SEQ ID NO:37; and (ab) the nucleotide sequence of the cDNA insert of clone rd810_6 deposited under accession number ATCC 98835;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:37, but excluding the poly(A) tail at the 3' end of SEQ ID NO:37; and (bb) the nucleotide sequence of the cDNA insert of clone rd810_6 deposited under accession number ATCC 98835;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:37, and extending contiguously from a nucleotide sequence corresponding to the 5' end of SEQ ID NO:37 to a nucleotide sequence corresponding to the 3' end of SEQ ID NO:37, but excluding the poly(A) tail at the 3' end of SEQ ID NO:37. Also preferably the polynucleotide isolated according to the above process comprises a nucleotide sequence corresponding to the cDNA sequence of SEQ ID NO:37 from nucleotide 75 to nucleotide 494, and extending contiguously from a nucleotide sequence corresponding to the 5' end of said sequence of SEQ ID NO:37 from nucleotide 75 to nucleotide 494, to a nucleotide sequence corresponding to the 3' end of said sequence of SEQ ID NO:37 from nucleotide 75 to nucleotide 494. Also preferably the polynucleotide isolated according to the above process comprises a nucleotide sequence corresponding to the cDNA sequence of SEQ ID NO:37 from nucleotide 447 to nucleotide 494, and extending contiguously from a nucleotide sequence corresponding to the 5' end of said sequence of SEQ ID NO:37 from nucleotide 447 to nucleotide 494, to a nucleotide sequence corresponding to the 3' end of said sequence of SEQ ID NO:37 from nucleotide 447 to nucleotide 494.

In other embodiments, the present invention provides a composition comprising a protein, wherein said protein comprises an amino acid sequence selected from the group consisting of:

(a) the amino acid sequence of SEQ ID NO:38;

(b) a fragment of the amino acid sequence of SEQ ID NO:38, the fragment comprising eight contiguous amino acids of SEQ ID NO:38; and (c) the amino acid sequence encoded by the cDNA insert of clone rd810_6 deposited under accession number ATCC 98835;

the protein being substantially free from other mammalian proteins. Preferably such protein comprises the amino acid sequence of SEQ ID NO:38. In further preferred embodiments, the present invention provides a protein comprising a fragment of the amino acid sequence of SEQ ID NO:38 having biological activity, the fragment preferably comprising eight (more preferably twenty, most preferably thirty) contiguous amino acids of SEQ ID NO:38, or a protein comprising a fragment of the amino acid sequence of SEQ ID NO:38 having biological activity, the fragment comprising the amino acid sequence from amino acid 65 to amino acid 74 of SEQ ID NO:38.

In one embodiment, the present invention provides a composition comprising an isolated polynucleotide selected from the group consisting of:

(a) a polynucleotide comprising the nucleotide sequence of SEQ ID NO:39;

(b) a polynucleotide comprising the nucleotide sequence of SEQ ID NO:39 from nucleotide 181 to nucleotide 1080;

(c) a polynucleotide comprising the nucleotide sequence of the full-length protein coding sequence of clone cf85_1 deposited under accession number ATCC 98850;

(d) a polynucleotide encoding the full-length protein encoded by the cDNA insert of clone cf85_1 deposited under accession number ATCC 98850;

(e) a polynucleotide comprising the nucleotide sequence of a mature protein coding sequence of clone cf85_1 deposited under accession number ATCC 98850;

(f) a polynucleotide encoding a mature protein encoded by the cDNA insert of clone cf85_1 deposited under accession number ATCC 98850;

(g) a polynucleotide encoding a protein comprising the amino acid sequence of SEQ ID NO:40;

(h) a polynucleotide encoding a protein comprising a fragment of the amino acid sequence of SEQ ID NO:40 having biological activity, the fragment comprising eight contiguous amino acids of SEQ ID NO:40;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:39.

Preferably, such polynucleotide comprises the nucleotide sequence of SEQ ID NO:39 from nucleotide 181 to nucleotide 1080; the nucleotide sequence of the full-length protein coding sequence of clone cf85_1 deposited under accession number ATCC 98850; or the nucleotide sequence of a mature protein coding sequence of clone cf85_1 deposited under accession number ATCC 98850. In other preferred embodiments, the polynucleotide encodes the full-length or a mature protein encoded by the cDNA insert of clone cf85_1 deposited under accession number ATCC 98850. In further preferred embodiments, the present invention provides a polynucleotide encoding a protein comprising a fragment of the amino acid sequence of SEQ ID NO:40 having biological activity, the fragment preferably comprising eight (more preferably twenty, most preferably thirty) contiguous amino acids of SEQ ID NO:40, or a polynucleotide encoding a protein comprising a fragment of the amino acid sequence of SEQ ID NO:40 having biological activity, the fragment comprising the amino acid sequence from amino acid 145 to amino acid 154 of SEQ ID NO:40.

Other embodiments provide the gene corresponding to the cDNA sequence of SEQ ID NO:39.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:39, but excluding the poly(A) tail at the 3' end of SEQ ID NO:39; and (ab) the nucleotide sequence of the cDNA insert of clone cf85_1 deposited under accession number ATCC 98850;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:39, but excluding the poly(A) tail at the 3' end of SEQ ID NO:39; and (bb) the nucleotide sequence of the cDNA insert of clone cf85_1 deposited under accession number ATCC 98850;

(ii) hybridizing said primer(s) to human genomic DNA in conditions at least as stringent as 4×SSC at 50 degrees C;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:39, and extending contiguously from a nucleotide sequence corresponding to the 5' end of SEQ ID NO:39 to a nucleotide sequence corresponding to the 3' end of SEQ ID NO:39, but excluding the poly(A) tail at the 3' end of SEQ ID NO:39. Also preferably the polynucleotide isolated according to the above process comprises a nucleotide sequence corresponding to the cDNA sequence of SEQ ID NO:39 from nucleotide 181 to nucleotide 1080, and extending contiguously from a nucleotide sequence corresponding to the 5' end of said sequence of SEQ ID NO:39 from nucleotide 181 to nucleotide 1080, to a nucleotide sequence corresponding to the 3' end of said sequence of SEQ ID NO:39 from nucleotide 181 to nucleotide 1080.

In other embodiments, the present invention provides a composition comprising a protein, wherein said protein comprises an amino acid sequence selected from the group consisting of:

(a) the amino acid sequence of SEQ ID NO:40;

(b) a fragment of the amino acid sequence of SEQ ID NO:40, the fragment comprising eight contiguous amino acids of SEQ ID NO:40; and (c) the amino acid sequence encoded by the cDNA insert of clone cf85_1 deposited under accession number ATCC 98850;

the protein being substantially free from other mammalian proteins. Preferably such protein comprises the amino acid sequence of SEQ ID NO:40. In further preferred embodiments, the present invention provides a protein comprising a fragment of the amino acid sequence of SEQ ID NO:40 having biological activity, the fragment preferably comprising eight (more preferably twenty, most preferably thirty) contiguous amino adds of SEQ ID NO:40, or a protein comprising a fragment of the amino acid sequence of SEQ ID NO:40 having biological activity, the fragment comprising the amino acid sequence from amino acid 145 to amino acid 154 of SEQ ID NO:40.

In one embodiment, the present invention provides a composition comprising an isolated polynucleotide selected from the group consisting of:

(a) a polynucleotide comprising the nucleotide sequence of SEQ ID NO:41;

(b) a polynucleotide comprising the nucleotide sequence of SEQ ID NO:41 from nucleotide 161 to nucleotide 1348;

(c) a polynucleotide comprising the nucleotide sequence of SEQ ID NO:41 from nucleotide 599 to nucleotide 1348;

(d) a polynucleotide comprising the nucleotide sequence of the full-length protein coding sequence of clone dd504_18 deposited under accession number ATCC 98850;

(e) a polynucleotide encoding the full-length protein encoded by the cDNA insert of clone dd504_18 deposited under accession number ATCC 98850;

(f) a polynucleotide comprising the nucleotide sequence of a mature protein coding sequence of clone dd504_18 deposited under accession number ATCC 98850;

(g) a polynucleotide encoding a mature protein encoded by the cDNA insert of clone dd504_18 deposited under accession number ATCC 98850;

(h) a polynucleotide encoding a protein comprising the amino acid sequence of SEQ ID NO:42;

(i) a polynucleotide encoding a protein comprising a fragment of the amino acid sequence of SEQ ID NO:42 having biological activity, the fragment comprising eight contiguous amino acids of SEQ ID NO:42;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:41.

Preferably, such polynucleotide comprises the nucleotide sequence of SEQ ID NO:41 from nucleotide 161 to nucleotide 1348; the nucleotide sequence of SEQ ID NO:41 from nucleotide 599 to nucleotide 1348; the nucleotide sequence of the full-length protein coding sequence of clone dd504_18 deposited under accession number ATCC 98850; or the nucleotide sequence of a mature protein coding sequence of clone dd504_18 deposited under accession number ATCC 98850. In other preferred embodiments, the polynucleotide encodes the full-length or a mature protein encoded by the cDNA insert of clone dd504_18 deposited under accession number ATCC 98850. In further preferred embodiments, the present invention provides a polynucleotide encoding a protein comprising a fragment of the amino acid sequence of SEQ ID NO:42 having biological activity, the fragment preferably comprising eight (more preferably twenty, most preferably thirty) contiguous amino acids of SEQ ID NO:42, or a polynucleotide encoding a protein comprising a fragment of the amino acid sequence of SEQ ID NO:42 having biological activity, the fragment comprising the amino acid sequence from amino acid 193 to amino acid 202 of SEQ ID NO:42.

Other embodiments provide the gene corresponding to the cDNA sequence of SEQ ID NO:41.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:41, but excluding the poly(A) tail at the 3' end of SEQ ID NO:41; and
    (ab) the nucleotide sequence of the cDNA insert of clone dd504_18 deposited under accession number ATCC 98850;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:41, but excluding the poly(A) tail at the 3' end of SEQ ID NO:41; and
    (bb) the nucleotide sequence of the cDNA insert of clone dd504_18 deposited under accession number ATCC 98850;
  (ii) hybridizing said primer(s) to human genomic DNA in conditions at least as stringent as 4×SSC at 50 degrees C.;
  (ii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:41, and extending contiguously from a nucleotide sequence corresponding to the 5' end of SEQ ID NO:41 to a nucleotide sequence corresponding to the 3' end of SEQ ID NO:41, but excluding the poly(A) tail at the 3' end of SEQ ID NO:41. Also preferably the polynucleotide isolated according to the above process comprises a nucleotide sequence corresponding to the cDNA sequence of SEQ ID NO:41 from nucleotide 161 to nucleotide 1348, and extending contiguously from a nucleotide sequence corresponding to the 5' end of said sequence of SEQ ID NO:41 from nucleotide 161 to nucleotide 1348, to a nucleotide sequence corresponding to the 3' end of said sequence of SEQ ID NO:41 from nucleotide 161 to nucleotide 1348. Also preferably the polynucleotide isolated according to the above process comprises a nucleotide sequence corresponding to the cDNA sequence of SEQ ID NO:41 from nucleotide 599 to nucleotide 1348, and extending contiguously from a nucleotide sequence corresponding to the 5' end of said sequence of SEQ ID NO:41 from nucleotide 599 to nucleotide 1348, to a nucleotide sequence corresponding to the 3' end of said sequence of SEQ ID NO:41 from nucleotide 599 to nucleotide 1348.

In other embodiments, the present invention provides a composition comprising a protein, wherein said protein comprises an amino acid sequence selected from the group consisting of:

(a) the amino acid sequence of SEQ ID NO:42;
(b) a fragment of the amino acid sequence of SEQ ID NO:42, the fragment comprising eight contiguous amino acids of SEQ ID NO:42; and
(c) the amino acid sequence encoded by the cDNA insert of clone dd504_18 deposited under accession number ATCC 98850;

the protein being substantially free from other mammalian proteins. Preferably such protein comprises the amino acid sequence of SEQ ID NO:42. In further preferred embodiments, the present invention provides a protein comprising a fragment of the amino acid sequence of SEQ ID NO:42 having biological activity, the fragment preferably comprising eight (more preferably twenty, most preferably thirty) contiguous amino acids of SEQ ID NO:42, or a protein comprising a fragment of the amino acid sequence of SEQ ID NO:42 having biological activity, the fragment comprising the amino acid sequence from amino acid 193 to amino acid 202 of SEQ ID NO:42.

In one embodiment, the present invention provides a composition comprising an isolated polynucleotide selected from the group consisting of:

(a) a polynucleotide comprising the nucleotide sequence of SEQ ID NO:43;
(b) a polynucleotide comprising the nucleotide sequence of SEQ ID NO:43 from nucleotide 70 to nucleotide 1386;
(c) a polynucleotide comprising the nucleotide sequence of the full-length protein coding sequence of clone np26_3 deposited under accession number ATCC 98850;
(d) a polynucleotide encoding the full-length protein encoded by the cDNA insert of clone np26_3 deposited under accession number ATCC 98850;
(e) a polynucleotide comprising the nucleotide sequence of a mature protein coding sequence of clone np26_3 deposited under accession number ATCC 98850;
(f) a polynucleotide encoding a mature protein encoded by the cDNA insert of clone np26_3 deposited under accession number ATCC 98850;
(g) a polynucleotide encoding a protein comprising the amino acid sequence of SEQ ID NO:44;
(h) a polynucleotide encoding a protein comprising a fragment of the amino acid sequence of SEQ ID NO:44 having biological activity, the fragment comprising eight contiguous amino acids of SEQ ID NO:44;
(i) a polynucleotide which is an allelic variant of a polynucleotide of (a)-(f) above;
(j) a polynucleotide which encodes a species homologue of the protein of (g) or (h) above;
(k) a polynucleotide that hybridizes under stringent conditions to any one of the polynucleotides specified in (a)-(h); and
(l) a polynucleotide that hybridizes under stringent conditions to any one of the polynucleotides specified in (a)-(h) and that has a length that is at least 25% of the length of SEQ ID NO:43.

Preferably, such polynucleotide comprises the nucleotide sequence of SEQ ID NO:43 from nucleotide 70 to nucleotide 1386; the nucleotide sequence of the full-length protein coding sequence of clone np26_3 deposited under accession number ATCC 98850; or the nucleotide sequence of a mature protein coding sequence of clone np26_3 deposited under accession number ATCC 98850. In other preferred embodiments, the polynucleotide encodes the full-length or a mature protein encoded by the cDNA insert of clone np26_3 deposited under accession number ATCC 98850. In further preferred embodiments, the present invention provides a polynucleotide encoding a protein comprising a fragment of the amino acid sequence of SEQ ID NO:44 having biological activity, the fragment preferably comprising eight (more preferably twenty, most preferably thirty) contiguous amino acids of SEQ ID NO:44, or a polynucleotide encoding a protein comprising a fragment of the amino acid sequence of SEQ ID NO:44 having biological activity, the fragment comprising the amino acid sequence from amino acid 214 to amino acid 223 of SEQ ID NO:44.

Other embodiments provide the gene corresponding to the cDNA sequence of SEQ ID NO:43.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:43, but excluding the poly(A) tail at the 3' end of SEQ ID NO:43; and
    (ab) the nucleotide sequence of the cDNA insert of clone np26_3 deposited under accession number ATCC 98850;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:43, but excluding the poly(A) tail at the 3' end of SEQ ID NO:43; and
    (bb) the nucleotide sequence of the cDNA insert of clone np26_3 deposited under accession number ATCC 98850;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:43, and extending contiguously from a nucleotide sequence corresponding to the 5' end of SEQ ID NO:43 to a nucleotide sequence corresponding to the 3' end of SEQ ID NO:43, but excluding the poly(A) tail at the 3' end of SEQ ID NO:43. Also preferably the polynucleotide isolated according to the above process comprises a nucleotide sequence corresponding to the cDNA sequence of SEQ ID NO:43 from nucleotide 70 to nucleotide 1386, and extending contiguously from a nucleotide sequence corresponding to the 5' end of said sequence of SEQ ID NO:43 from nucleotide 70 to nucleotide 1386, to a nucleotide sequence corresponding to the 3' end of said sequence of SEQ ID NO:43 from nucleotide 70 to nucleotide 1386.

In other embodiments, the present invention provides a composition comprising a protein, wherein said protein comprises an amino acid sequence selected from the group consisting of:

(a) the amino acid sequence of SEQ ID NO:44;
(b) a fragment of the amino acid sequence of SEQ ID NO:44, the fragment comprising eight contiguous amino acids of SEQ ID NO:44; and
(c) the amino acid sequence encoded by the cDNA insert of clone np26_3 deposited under accession number ATCC 98850;

the protein being substantially free from other mammalian proteins. Preferably such protein comprises the amino acid sequence of SEQ ID NO:44. In further preferred embodiments, the present invention provides a protein comprising a fragment of the amino acid sequence of SEQ ID NO:44 having biological activity, the fragment preferably comprising eight (more preferably twenty, most preferably thirty) contiguous amino acids of SEQ ID NO:44, or a protein comprising a fragment of the amino acid sequence of SEQ ID NO:44 having biological activity, the fragment comprising the amino acid sequence from amino acid 214 to amino acid 223 of SEQ ID NO:44.

In one embodiment, the present invention provides a composition comprising an isolated polynucleotide selected from the group consisting of:

(a) a polynucleotide comprising the nucleotide sequence of SEQ ID NO:45;
(b) a polynucleotide comprising the nucleotide sequence of SEQ ID NO:45 from nucleotide 60 to nucleotide 3515;
(c) a polynucleotide comprising the nucleotide sequence of the full-length protein coding sequence of clone pm412_12 deposited under accession number ATCC 98850;
(d) a polynucleotide encoding the full-length protein encoded by the cDNA insert of clone pm412_12 deposited under accession number ATCC 98850;
(e) a polynucleotide comprising the nucleotide sequence of a mature protein coding sequence of clone pm412_12 deposited under accession number ATCC 98850;
(f) a polynucleotide encoding a mature protein encoded by the cDNA insert of clone pm412_12 deposited under accession number ATCC 98850;
(g) a polynucleotide encoding a protein comprising the amino acid sequence of SEQ ID NO:46;
(h) a polynucleotide encoding a protein comprising a fragment of the amino acid sequence of SEQ ID NO:46 having biological activity, the fragment comprising eight contiguous amino acids of SEQ ID NO:46;
(i) a polynucleotide which is an allelic variant of a polynucleotide of (a)-(f) above;
(j) a polynucleotide which encodes a species homologue of the protein of (g) or (h) above;
(k) a polynucleotide that hybridizes under stringent conditions to any one of the polynucleotides specified in (a)-(h); and
(l) a polynucleotide that hybridizes under stringent conditions to any one of the polynucleotides specified in (a)-(h) and that has a length that is at least 25% of the length of SEQ ID NO:45.

Preferably, such polynucleotide comprises the nucleotide sequence of SEQ ID NO:45 from nucleotide 60 to nucleotide 3515; the nucleotide sequence of the full-length protein coding sequence of clone pm412_12 deposited under accession number ATCC 98850; or the nucleotide sequence of a mature protein coding sequence of clone pm412_12 deposited under accession number ATCC 98850. In other preferred embodiments, the polynucleotide encodes the full-length or a mature protein encoded by the cDNA insert of clone pm412_12 deposited under accession number ATCC 98850. In further preferred embodiments, the present invention provides a polynucleotide encoding a protein comprising a fragment of the amino acid sequence of SEQ ID NO:46 having biological activity, the fragment preferably comprising eight (more preferably twenty, most preferably thirty) contiguous amino acids of SEQ ID NO:46, or a polynucleotide encoding a protein comprising a fragment of the amino acid sequence of SEQ ID NO:46 having biological activity, the fragment comprising the amino acid sequence from amino acid 571 to amino acid 580 of SEQ ID NO:46.

Other embodiments provide the gene corresponding to the cDNA sequence of SEQ ID NO:45.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:45, but excluding the poly(A) tail at the 3' end of SEQ ID NO:45; and
    (ab) the nucleotide sequence of the cDNA insert of clone pm412_12 deposited under accession number ATCC 98850;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:45, but excluding the poly(A) tail at the 3' end of SEQ ID NO:45; and
    (bb) the nucleotide sequence of the cDNA insert of clone pm412_12 deposited under accession number ATCC 98850;
  (ii) hybridizing said primer(s) to human genomic DNA in conditions at least as stringent as 4×SSC at 50 degrees C.;
  (ii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:45, and extending contiguously from a nucleotide sequence corresponding to the 5' end of SEQ ID NO:45 to a nucleotide sequence corresponding to the 3' end of SEQ ID NO:45, but excluding the poly(A) tail at the 3' end of SEQ ID NO:45. Also preferably the polynucleotide isolated according to the above process comprises a nucleotide sequence corresponding to the cDNA sequence of SEQ ID NO:45 from nucleotide 60 to nucleotide 3515, and extending contiguously from a nucleotide sequence corresponding to the 5' end of said sequence of SEQ ID NO:45 from nucleotide 60 to nucleotide 3515, to a nucleotide sequence corresponding to the 3' end of said sequence of SEQ ID NO:45 from nucleotide 60 to nucleotide 3515.

In other embodiments, the present invention provides a composition comprising a protein, wherein said protein comprises an amino acid sequence selected from the group consisting of:

(a) the amino acid sequence of SEQ ID NO:46;
(b) a fragment of the amino acid sequence of SEQ ID NO:46, the fragment comprising eight contiguous amino acids of SEQ ID NO:46; and
(c) the amino acid sequence encoded by the cDNA insert of clone pm412_12 deposited under accession number ATCC 98850;

the protein being substantially free from other mammalian proteins. Preferably such protein comprises the amino acid sequence of SEQ ID NO:46. In further preferred embodiments, the present invention provides a protein comprising a fragment of the amino acid sequence of SEQ ID NO:46 having biological activity, the fragment preferably comprising eight (more preferably twenty, most preferably thirty) contiguous amino acids of SEQ ID NO:46, or a protein comprising a fragment of the amino acid sequence of SEQ ID NO:46 having biological activity, the fragment comprising the amino acid sequence from amino acid 571 to amino acid 580 of SEQ ID NO:46.

In one embodiment, the present invention provides a composition comprising an isolated polynucleotide selected from the group consisting of:

(a) a polynucleotide comprising the nucleotide sequence of SEQ ID NO:47;
(b) a polynucleotide comprising the nucleotide sequence of SEQ ID NO:47 from nucleotide 1490 to nucleotide 1780;
(c) a polynucleotide comprising the nucleotide sequence of SEQ ID NO:47 from nucleotide 1556 to nucleotide 1780;
(d) a polynucleotide comprising the nucleotide sequence of the full-length protein coding sequence of clone pm421_3 deposited under accession number ATCC 98850;
(e) a polynucleotide encoding the full-length protein encoded by the cDNA insert of clone pm421_3 deposited under accession number ATCC 98850;
(f) a polynucleotide comprising the nucleotide sequence of a mature protein coding sequence of clone pm421_3 deposited under accession number ATCC 98850;
(g) a polynucleotide encoding a mature protein encoded by the cDNA insert of clone pm421_3 deposited under accession number ATCC 98850;
(h) a polynucleotide encoding a protein comprising the amino acid sequence of SEQ ID NO:48;
(i) a polynucleotide encoding a protein comprising a fragment of the amino acid sequence of SEQ ID NO:48 having biological activity, the fragment comprising eight contiguous amino acids of SEQ ID NO:48;
(j) a polynucleotide which is an allelic variant of a polynucleotide of (a)-(g) above;
(k) a polynucleotide which encodes a species homologue of the protein of (h) or (i) above;
(l) a polynucleotide that hybridizes under stringent conditions to any one of the polynucleotides specified in (a)-(i); and
(m) a polynucleotide that hybridizes under stringent conditions to any one of the polynucleotides specified in (a)-(i) and that has a length that is at least 25% of the length of SEQ ID NO:47.

Preferably, such polynucleotide comprises the nucleotide sequence of SEQ ID NO:47 from nucleotide 1490 to nucleotide 1780; the nucleotide sequence of SEQ ID NO:47 from nucleotide 1556 to nucleotide 1780; the nucleotide sequence of the full-length protein coding sequence of clone pm421_3 deposited under accession number ATCC 98850; or the nucleotide sequence of a mature protein coding sequence of clone pm421_3 deposited under accession number ATCC 98850. In other preferred embodiments, the polynucleotide encodes the full-length or a mature protein encoded by the cDNA insert of clone pm421_3 deposited under accession number ATCC 98850. In further preferred embodiments, the present invention provides a polynucleotide encoding a protein comprising a fragment of the amino acid sequence of SEQ ID NO:48 having biological activity, the fragment preferably comprising eight (more preferably twenty, most preferably thirty) contiguous amino acids of SEQ ID NO:48, or a polynucleotide encoding a protein comprising a fragment of the amino acid sequence of SEQ ID NO:48 having biological activity, the fragment comprising the amino acid sequence from amino acid 43 to amino acid 52 of SEQ ID NO:48.

Other embodiments provide the gene corresponding to the cDNA sequence of SEQ ID NO:47.

Further embodiments of the invention provide isolated polynucleotides produced according to a process selected from the group consisting of:

- (a) a process comprising the steps of:
  - (i) preparing one or more polynucleotide probes that hybridize in 6×SSC at 65 degrees C. to a nucleotide sequence selected from the group consisting of:
    - (aa) SEQ ID NO:47, but excluding the poly(A) tail at the 3' end of SEQ ID NO:47; and
    - (ab) the nucleotide sequence of the cDNA insert of clone pm421_3 deposited under accession number ATCC 98850;
  - (ii) hybridizing said probe(s) to human genomic DNA in conditions at least as stringent as 4×SSC at 50 degrees C.; and
  - (iii) isolating the DNA polynucleotides detected with the probe(s); and
- (b) a process comprising the steps of:
  - (i) preparing one or more polynucleotide primers that hybridize in 6×SSC at 65 degrees C. to a nucleotide sequence selected from the group consisting of:
    - (ba) SEQ ID NO:47, but excluding the poly(A) tail at the 3' end of SEQ ID NO:47; and
    - (bb) the nucleotide sequence of the cDNA insert of clone pm421_3 deposited under accession number ATCC 98850;
  - (ii) hybridizing said primer(s) to human genomic DNA in conditions at least as stringent as 4×SSC at 50 degrees C.;
  - (iii) amplifying human DNA sequences; and
  - (iv) isolating the polynucleotide products of step (b)(iii).

Preferably the polynucleotide isolated according to the above process comprises a nucleotide sequence corresponding to the cDNA sequence of SEQ ID NO:47, and extending contiguously from a nucleotide sequence corresponding to the 5' end of SEQ ID NO:47 to a nucleotide sequence corresponding to the 3' end of SEQ ID NO:47, but excluding the poly(A) tail at the 3' end of SEQ ID NO:47. Also preferably the polynucleotide isolated according to the above process comprises a nucleotide sequence corresponding to the cDNA sequence of SEQ ID NO:47 from nucleotide 1490 to nucleotide 1780, and extending contiguously from a nucleotide sequence corresponding to the 5' end of said sequence of SEQ ID NO:47 from nucleotide 1490 to nucleotide 1780, to a nucleotide sequence corresponding to the 3' end of said sequence of SEQ ID NO:47 from nucleotide 1490 to nucleotide 1780. Also preferably the polynucleotide isolated according to the above process comprises a nucleotide sequence corresponding to the cDNA sequence of SEQ ID NO:47 from nucleotide 1556 to nucleotide 1780, and extending contiguously from a nucleotide sequence corresponding to the 5' end of said sequence of SEQ ID NO:47 from nucleotide 1556 to nucleotide 1780, to a nucleotide sequence corresponding to the 3' end of said sequence of SEQ ID NO:47 from nucleotide 1556 to nucleotide 1780.

In other embodiments, the present invention provides a composition comprising a protein, wherein said protein comprises an amino acid sequence selected from the group consisting of:

- (a) the amino acid sequence of SEQ ID NO:48;
- (b) a fragment of the amino acid sequence of SEQ ID NO:48, the fragment comprising eight contiguous amino acids of SEQ ID NO:48; and
- (c) the amino acid sequence encoded by the cDNA insert of clone pm421_3 deposited under accession number ATCC 98850;

the protein being substantially free from other mammalian proteins. Preferably such protein comprises the amino acid sequence of SEQ ID NO:48. In further preferred embodiments, the present invention provides a protein comprising a fragment of the amino acid sequence of SEQ ID NO:48 having biological activity, the fragment preferably comprising eight (more preferably twenty, most preferably thirty) contiguous amino acids of SEQ ID NO:48, or a protein comprising a fragment of the amino acid sequence of SEQ ID NO:48 having biological activity, the fragment comprising the amino acid sequence from amino acid 43 to amino acid 52 of SEQ ID NO:48.

In one embodiment, the present invention provides a composition comprising an isolated polynucleotide selected from the group consisting of:

- (a) a polynucleotide comprising the nucleotide sequence of SEQ ID NO:49;
- (b) a polynucleotide comprising the nucleotide sequence of SEQ ID NO:49 from nucleotide 64 to nucleotide 486;
- (c) a polynucleotide comprising the nucleotide sequence of SEQ ID NO:49 from nucleotide 217 to nucleotide 486;
- (d) a polynucleotide comprising the nucleotide sequence of the full-length protein coding sequence of clone pv6_1 deposited under accession number ATCC 98850;
- (e) a polynucleotide encoding the full-length protein encoded by the cDNA insert of clone pv6_1 deposited under accession number ATCC 98850;
- (f) a polynucleotide comprising the nucleotide sequence of a mature protein coding sequence of clone pv6_1 deposited under accession number ATCC 98850;
- (g) a polynucleotide encoding a mature protein encoded by the cDNA insert of clone pv6_1 deposited under accession number ATCC 98850;
- (h) a polynucleotide encoding a protein comprising the amino acid sequence of SEQ ID NO:50;
- (i) a polynucleotide encoding a protein comprising a fragment of the amino acid sequence of SEQ ID NO:50 having biological activity, the fragment comprising eight contiguous amino acids of SEQ ID NO:50;
- (j) a polynucleotide which is an allelic variant of a polynucleotide of (a)-(g) above;
- (k) a polynucleotide which encodes a species homologue of the protein of (h) or (i) above;
- (l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:49.

Preferably, such polynucleotide comprises the nucleotide sequence of SEQ ID NO:49 from nucleotide 64 to nucleotide 486; the nucleotide sequence of SEQ ID NO:49 from nucleotide 217 to nucleotide 486; the nucleotide sequence of the full-length protein coding sequence of clone pv6_1 deposited under accession number ATCC 98850; or the nucleotide sequence of a mature protein coding sequence of clone pv6_1 deposited under accession number ATCC 98850. In other preferred embodiments, the polynucleotide encodes the full-length or a mature protein encoded by the cDNA insert of clone pv6_1 deposited under accession number ATCC 98850. In further preferred embodiments, the present invention provides a polynucleotide encoding a protein comprising a fragment of the amino acid sequence of SEQ ID NO:50 having biological activity, the fragment preferably comprising eight (more preferably twenty, most preferably thirty) contiguous amino acids of SEQ ID NO:50, or a polynucleotide encoding a protein comprising a fragment of the amino acid sequence of SEQ ID NO:50 having biological activity, the fragment comprising the amino acid sequence from amino acid 65 to amino acid 74 of SEQ ID NO:50.

Other embodiments provide the gene corresponding to the cDNA sequence of SEQ ID NO:49.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:49, but excluding the poly(A) tail at the 3' end of SEQ ID NO:49; and
    (ab) the nucleotide sequence of the cDNA insert of clone pv6_1 deposited under accession number ATCC 98850;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:49, but excluding the poly(A) tail at the 3' end of SEQ ID NO:49; and
    (bb) the nucleotide sequence of the cDNA insert of clone pv6_1 deposited under accession number ATCC 98850;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:49, and extending contiguously from a nucleotide sequence corresponding to the 5' end of SEQ ID NO:49 to a nucleotide sequence corresponding to the 3' end of SEQ ID NO:49, but excluding the poly(A) tail at the 3' end of SEQ ID NO:49. Also preferably the polynucleotide isolated according to the above process comprises a nucleotide sequence corresponding to the cDNA sequence of SEQ ID NO:49 from nucleotide 64 to nucleotide 486, and extending contiguously from a nucleotide sequence corresponding to the 5' end of said sequence of SEQ ID NO:49 from nucleotide 64 to nucleotide 486, to a nucleotide sequence corresponding to the 3' end of said sequence of SEQ ID NO:49 from nucleotide 64 to nucleotide 486. Also preferably the polynucleotide isolated according to the above process comprises a nucleotide sequence corresponding to the cDNA sequence of SEQ ID NO:49 from nucleotide 217 to nucleotide 486, and extending contiguously from a nucleotide sequence corresponding to the 5' end of said sequence of SEQ ID NO:49 from nucleotide 217 to nucleotide 486, to a nucleotide sequence corresponding to the 3' end of said sequence of SEQ ID NO:49 from nucleotide 217 to nucleotide 486.

In other embodiments, the present invention provides a composition comprising a protein, wherein said protein comprises an amino acid sequence selected from the group consisting of:

(a) the amino acid sequence of SEQ ID NO:50;
(b) a fragment of the amino acid sequence of SEQ ID NO:50, the fragment comprising eight contiguous amino acids of SEQ ID NO:50; and
(c) the amino acid sequence encoded by the cDNA insert of clone pv6_1 deposited under accession number ATCC 98850;

the protein being substantially free from other mammalian proteins. Preferably such protein comprises the amino acid sequence of SEQ ID NO:50. In further preferred embodiments, the present invention provides a protein comprising a fragment of the amino acid sequence of SEQ ID NO:50 having biological activity, the fragment preferably comprising eight (more preferably twenty, most preferably thirty) contiguous amino acids of SEQ ID NO:50, or a protein comprising a fragment of the amino acid sequence of SEQ ID NO:50 having biological activity, the fragment comprising the amino acid sequence from amino acid 65 to amino acid 74 of SEQ ID NO:50.

In one embodiment, the present invention provides a composition comprising an isolated polynucleotide selected from the group consisting of:

(a) a polynucleotide comprising the nucleotide sequence of SEQ ID NO:51;
(b) a polynucleotide comprising the nucleotide sequence of SEQ ID NO:51 from nucleotide 379 to nucleotide 3783;
(c) a polynucleotide comprising the nucleotide sequence of SEQ ID NO:51 from nucleotide 460 to nucleotide 3783;
(d) a polynucleotide comprising the nucleotide sequence of SEQ ID NO:51 from nucleotide 1983 to nucleotide 3938;
(e) a polynucleotide comprising the nucleotide sequence of the full-length protein coding sequence of clone qs14_3 deposited under accession number ATCC 98850;
(f) a polynucleotide encoding the full-length protein encoded by the cDNA insert of clone qs14_3 deposited under accession number ATCC 98850;
(g) a polynucleotide comprising the nucleotide sequence of a mature protein coding sequence of clone qs14_3 deposited under accession number ATCC 98850;

(h) a polynucleotide encoding a mature protein encoded by the cDNA insert of clone qs14_3 deposited under accession number ATCC 98850;

(i) a polynucleotide encoding a protein comprising the amino acid sequence of SEQ ID NO:52;

(j) a polynucleotide encoding a protein comprising a fragment of the amino acid sequence of SEQ ID NO:52 having biological activity, the fragment comprising eight contiguous amino acids of SEQ ID NO:52;

(k) a polynucleotide which is an allelic variant of a polynucleotide of (a)-(h) above;

(l) a polynucleotide which encodes a species homologue of the protein of (i) or (j) above;

(m) a polynucleotide that hybridizes under stringent conditions to any one of the polynucleotides specified in (a)-(j); and (n) a polynucleotide that hybridizes under stringent conditions to any one of the polynucleotides specified in (a)-(j) and that has a length that is at least 25% of the length of SEQ ID NO:51.

Preferably, such polynucleotide comprises the nucleotide sequence of SEQ ID NO:51 from nucleotide 379 to nucleotide 3783; the nucleotide sequence of SEQ ID NO:51 from nucleotide 460 to nucleotide 3783; the nucleotide sequence of SEQ ID NO:51 from nucleotide 1983 to nucleotide 3938; the nucleotide sequence of the full-length protein coding sequence of clone qs14_3 deposited under accession number ATCC 98850; or the nucleotide sequence of a mature protein coding sequence of clone qs14_3 deposited under accession number ATCC 98850. In other preferred embodiments, the polynucleotide encodes the full-length or a mature protein encoded by the cDNA insert of clone qs14_3 deposited under accession number ATCC 98850. In yet other preferred embodiments, the present invention provides a polynucleotide encoding a protein comprising the amino acid sequence of SEQ ID NO:52 from amino acid 536 to amino acid 1135. In further preferred embodiments, the present invention provides a polynucleotide encoding a protein comprising a fragment of the amino acid sequence of SEQ ID NO:52 having biological activity, the fragment preferably comprising eight (more preferably twenty, most preferably thirty) contiguous amino acids of SEQ ID NO:52, or a polynucleotide encoding a protein comprising a fragment of the amino acid sequence of SEQ ID NO:52 having biological activity, the fragment comprising the amino acid sequence from amino acid 562 to amino acid 571 of SEQ ID NO:52.

Other embodiments provide the gene corresponding to the cDNA sequence of SEQ ID NO:51.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:51, but excluding the poly(A) tail at the 3' end of SEQ ID NO:51; and (ab) the nucleotide sequence of the cDNA insert of clone qs14_3 deposited under accession number ATCC 98850;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:51, but excluding the poly(A) tail at the 3' end of SEQ ID NO:51; and (bb) the nucleotide sequence of the cDNA insert of clone qs14_3 deposited under accession number ATCC 98850;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:51, and extending contiguously from a nucleotide sequence corresponding to the 5' end of SEQ ID NO:51 to a nucleotide sequence corresponding to the 3' end of SEQ ID NO:51, but excluding the poly(A) tail at the 3' end of SEQ ID NO:51. Also preferably the polynucleotide isolated according to the above process comprises a nucleotide sequence corresponding to the cDNA sequence of SEQ ID NO:51 from nucleotide 379 to nucleotide 3783, and extending contiguously from a nucleotide sequence corresponding to the 5' end of said sequence of SEQ ID NO:51 from nucleotide 379 to nucleotide 3783, to a nucleotide sequence corresponding to the 3' end of said sequence of SEQ ID NO:51 from nucleotide 379 to nucleotide 3783. Also preferably the polynucleotide isolated according to the above process comprises a nucleotide sequence corresponding to the cDNA sequence of SEQ ID NO:51 from nucleotide 460 to nucleotide 3783, and extending contiguously from a nucleotide sequence corresponding to the 5' end of said sequence of SEQ ID NO:51 from nucleotide 460 to nucleotide 3783, to a nucleotide sequence corresponding to the 3' end of said sequence of SEQ ID NO:51 from nucleotide 460 to nucleotide 3783. Also preferably the polynucleotide isolated according to the above process comprises a nucleotide sequence corresponding to the cDNA sequence of SEQ ID NO:51 from nucleotide 1983 to nucleotide 3938, and extending contiguously from a nucleotide sequence corresponding to the 5' end of said sequence of SEQ ID NO:51 from nucleotide 1983 to nucleotide 3938, to a nucleotide sequence corresponding to the 3' end of said sequence of SEQ ID NO:51 from nucleotide 1983 to nucleotide 3938.

In other embodiments, the present invention provides a composition comprising a protein, wherein said protein comprises an amino acid sequence selected from the group consisting of:

(a) the amino acid sequence of SEQ ID NO:52;

(b) the amino acid sequence of SEQ ID NO:52 from amino acid 536 to amino acid 1135;

(c) a fragment of the amino acid sequence of SEQ ID NO:52, the fragment comprising eight contiguous amino acids of SEQ ID NO:52; and (d) the amino acid sequence encoded by the cDNA insert of clone qs14_3 deposited under accession number ATCC 98850;

the protein being substantially free from other mammalian proteins. Preferably such protein comprises the amino acid sequence of SEQ ID NO:52 or the amino acid sequence of SEQ ID NO:52 from amino acid 536 to amino acid 1135. In further preferred embodiments, the present invention provides a protein comprising a fragment of the amino acid sequence of SEQ ID NO:52 having biological activity, the fragment preferably comprising eight (more preferably twenty, most preferably thirty) contiguous amino acids of SEQ ID NO:52, or a protein comprising a fragment of the amino acid sequence of SEQ ID NO:52 having biological activity, the fragment comprising the amino acid sequence from amino acid 562 to amino acid 571 of SEQ ID NO:52.

In one embodiment, the present invention provides a composition comprising an isolated polynucleotide selected from the group consisting of:

(a) a polynucleotide comprising the nucleotide sequence of SEQ ID NO:53;

(b) a polynucleotide comprising the nucleotide sequence of SEQ ID NO:53 from nucleotide 1 to nucleotide 843;

(c) a polynucleotide comprising the nucleotide sequence of SEQ ID NO:53 from nucleotide 469 to nucleotide 843;

(d) a polynucleotide comprising the nucleotide sequence of the full length protein coding sequence of clone qy338_9 deposited under accession number ATCC 98850;

(e) a polynucleotide encoding the full-length protein encoded by the cDNA insert of clone qy338_9 deposited under accession number ATCC 98850;

(f) a polynucleotide comprising the nucleotide sequence of a mature protein coding sequence of clone qy338_9 deposited under accession number ATCC 98850;

(g) a polynucleotide encoding a mature protein encoded by the cDNA insert of clone qy338_9 deposited under accession number ATCC 98850;

(h) a polynucleotide encoding a protein comprising the amino acid sequence of SEQ ID NO:54;

(i) a polynucleotide encoding a protein comprising a fragment of the amino acid sequence of SEQ ID NO:54 having biological activity, the fragment comprising eight contiguous amino acids of SEQ ID NO:54;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:53.

Preferably, such polynucleotide comprises the nucleotide sequence of SEQ ID NO:53 from nucleotide 1 to nucleotide 843; the nucleotide sequence of SEQ ID NO:53 from nucleotide 469 to nucleotide 843; the nucleotide sequence of the full-length protein coding sequence of clone qy338_9 deposited under accession number ATCC 98850; or the nucleotide sequence of a mature protein coding sequence of clone qy338_9 deposited under accession number ATCC 98850. In other preferred embodiments, the polynucleotide encodes the full-length or a mature protein encoded by the cDNA insert of clone qy338_9 deposited under accession number ATCC 98850. In further preferred embodiments, the present invention provides a polynucleotide encoding a protein comprising a fragment of the amino acid sequence of SEQ ID NO:54 having biological activity, the fragment preferably comprising eight (more preferably twenty, most preferably thirty) contiguous amino acids of SEQ ID NO:54, or a polynucleotide encoding a protein comprising a fragment of the amino acid sequence of SEQ ID NO:54 having biological activity, the fragment comprising the amino acid sequence from amino acid 135 to amino acid 144 of SEQ ID NO:54.

Other embodiments provide the gene corresponding to the cDNA sequence of SEQ ID NO:53.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:53, but excluding the poly(A) tail at the 3' end of SEQ ID NO:53; and (ab) the nucleotide sequence of the cDNA insert of clone qy338_9 deposited under accession number ATCC 98850;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:53, but excluding the poly(A) tail at the 3' end of SEQ ID NO:53; and (bb) the nucleotide sequence of the cDNA insert of clone qy338_9 deposited under accession number ATCC 98850;

(ii) hybridizing said primer(s) to human genomic DNA in conditions at least as stringent as 4×SSC at 50 degrees C.;

(iii) amplifying human DNA sequences; and (iv) isolating the polynucleotide products of step (b)(iii).

Preferably the polynucleotide isolated according to the above process comprises a nucleotide sequence corresponding to the cDNA sequence of SEQ ID NO:53, and extending contiguously from a nucleotide sequence corresponding to the 5' end of SEQ ID NO:53 to a nucleotide sequence corresponding to the 3' end of SEQ ID NO:53, but excluding the poly(A) tail at the 3' end of SEQ ID NO:53. Also preferably the polynucleotide isolated according to the above process comprises a nucleotide sequence corresponding to the cDNA sequence of SEQ ID NO:53 from nucleotide 1 to nucleotide 843, and extending contiguously from a nucleotide sequence corresponding to the 5' end of said sequence of SEQ ID NO:53 from nucleotide 1 to nucleotide 843, to a nucleotide sequence corresponding to the 3' end of said sequence of SEQ ID NO:53 from nucleotide 1 to nucleotide 843. Also preferably the polynucleotide isolated according to the above process comprises a nucleotide sequence corresponding to the cDNA sequence of SEQ ID NO:53 from nucleotide 469 to nucleotide 843, and extending contiguously from a nucleotide sequence corresponding to the 5' end of said sequence of SEQ ID NO:53 from nucleotide 469 to nucleotide 843, to a nucleotide sequence corresponding to the 3' end of said sequence of SEQ ID NO:53 from nucleotide 469 to nucleotide 843.

In other embodiments, the present invention provides a composition comprising a protein, wherein said protein comprises an amino acid sequence selected from the group consisting of:

(a) the amino acid sequence of SEQ ID NO:54;

(b) a fragment of the amino acid sequence of SEQ ID NO:54, the fragment comprising eight contiguous amino acids of SEQ ID NO:54; and (c) the amino acid sequence encoded by the cDNA insert of clone qy338_9 deposited under accession number ATCC 98850;

the protein being substantially free from other mammalian proteins. Preferably such protein comprises the amino acid sequence of SEQ ID NO:54. In further preferred embodiments, the present invention provides a protein comprising a fragment of the amino acid sequence of SEQ ID NO:54 having biological activity, the fragment preferably comprising eight (more preferably twenty, most preferably thirty) contiguous amino acids of SEQ ID NO:54, or a protein comprising a fragment of the amino acid sequence of SEQ ID NO:54 having biological activity, the fragment comprising the amino acid sequence from amino acid 135 to amino acid 144 of SEQ ID NO:54.

In one embodiment, the present invention provides a composition comprising an isolated polynucleotide selected from the group consisting of:

(a) a polynucleotide comprising the nucleotide sequence of SEQ ID NO:55;

(b) a polynucleotide comprising the nucleotide sequence of SEQ ID NO:55 from nucleotide 283 to nucleotide 906;

(c) a polynucleotide comprising the nucleotide sequence of SEQ ID NO:55 from nucleotide 325 to nucleotide 906;

(d) a polynucleotide comprising the nucleotide sequence of the full-length protein coding sequence of clone rc58_1 deposited under accession number ATCC 98850;

(e) a polynucleotide encoding the full-length protein encoded by the cDNA insert of clone rc58_1 deposited under accession number ATCC 98850;

(f) a polynucleotide comprising the nucleotide sequence of a mature protein coding sequence of clone rc58_1 deposited under accession number ATCC 98850;

(g) a polynucleotide encoding a mature protein encoded by the cDNA insert of clone rc58_1 deposited under accession number ATCC 98850;

(h) a polynucleotide encoding a protein comprising the amino acid sequence of SEQ ID NO:56;

(i) a polynucleotide encoding a protein comprising a fragment of the amino acid sequence of SEQ ID NO:56 having biological activity, the fragment comprising eight contiguous amino acids of SEQ ID NO:56;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:55.

Preferably, such polynucleotide comprises the nucleotide sequence of SEQ ID NO:55 from nucleotide 283 to nucleotide 906; the nucleotide sequence of SEQ ID NO:55 from nucleotide 325 to nucleotide 906; the nucleotide sequence of the full-length protein coding sequence of clone rc58_1 deposited under accession number ATCC 98850; or the nucleotide sequence of a mature protein coding sequence of clone rc58_1 deposited under accession number ATCC 98850. In other preferred embodiments, the polynucleotide encodes the full-length or a mature protein encoded by the cDNA insert of clone rc58_1 deposited under accession number ATCC 98850. In further preferred embodiments, the present invention provides a polynucleotide encoding a protein comprising a fragment of the amino acid sequence of SEQ ID NO:56 having biological activity, the fragment preferably comprising eight (more preferably twenty, most preferably thirty) contiguous amino acids of SEQ ID NO:56, or a polynucleotide encoding a protein comprising a fragment of the amino acid sequence of SEQ ID NO:56 having biological activity, the fragment comprising the amino acid sequence from amino acid 99 to amino acid 108 of SEQ ID NO:56.

Other embodiments provide the gene corresponding to the cDNA sequence of SEQ ID NO:55.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:55, but excluding the poly(A) tail at the 3' end of SEQ ID NO:55; and (ab) the nucleotide sequence of the cDNA insert of clone rc58_1 deposited under accession number ATCC 98850;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:55, but excluding the poly(A) tail at the 3' end of SEQ ID NO:55; and (bb) the nucleotide sequence of the cDNA insert of clone rc58_1 deposited under accession number ATCC 98850;

(ii) hybridizing said primer(s) to human genomic DNA in conditions at least as stringent as 4×SSC at 50 degrees C.;

(iii) amplifying human DNA sequences; and (iv) isolating the polynucleotide products of step (b)(iii).

Preferably the polynucleotide isolated according to the above process comprises a nucleotide sequence corresponding to the cDNA sequence of SEQ ID NO:55, and extending contiguously from a nucleotide sequence corresponding to the 5' end of SEQ ID NO:55 to a nucleotide sequence corresponding to the 3' end of SEQ ID NO:55, but excluding the poly(A) tail at the 3' end of SEQ ID NO:55. Also preferably the polynucleotide isolated according to the above process comprises a nucleotide sequence corresponding to the cDNA sequence of SEQ ID NO:55 from nucleotide 283 to nucleotide 906, and extending contiguously from a nucleotide sequence corresponding to the 5' end of said sequence of SEQ ID NO:55 from nucleotide 283 to nucleotide 906, to a nucleotide sequence corresponding to the 3' end of said sequence of SEQ ID NO:55 from nucleotide 283 to nucleotide 906. Also preferably the polynucleotide isolated according to the above process comprises a nucleotide sequence corresponding to the cDNA sequence of SEQ ID NO:55 from nucleotide 325 to nucleotide 906, and extending contiguously from a nucleotide sequence corresponding to the 5' end of said sequence of SEQ ID NO:55 from nucleotide 325 to nucleotide 906, to a nucleotide sequence corresponding to the 3' end of said sequence of SEQ ID NO:55 from nucleotide 325 to nucleotide 906.

In other embodiments, the present invention provides a composition comprising a protein, wherein said protein comprises an amino acid sequence selected from the group consisting of:

(a) the amino acid sequence of SEQ ID NO:56;

(b) a fragment of the amino acid sequence of SEQ ID NO:56, the fragment comprising eight contiguous amino acids of SEQ ID NO:56; and (c) the amino acid sequence encoded by the cDNA insert of clone rc58_1 deposited under accession number ATCC 98850;

the protein being substantially free from other mammalian proteins. Preferably such protein comprises the amino acid sequence of SEQ ID NO:56. In further preferred embodiments, the present invention provides a protein comprising a fragment of the amino acid sequence of SEQ ID NO:56 having biological activity, the fragment preferably comprising eight (more preferably twenty, most preferably thirty) contiguous amino acids of SEQ ID NO:56, or a protein comprising a fragment of the amino acid sequence of SEQ ID NO:56 having biological activity, the fragment comprising the amino acid sequence from amino acid 99 to amino acid 108 of SEQ ID NO:56.

In one embodiment, the present invention provides a composition comprising an isolated polynucleotide selected from the group consisting of:

(a) a polynucleotide comprising the nucleotide sequence of SEQ ID NO:57;

(b) a polynucleotide comprising the nucleotide sequence of SEQ ID NO:57 from nucleotide 56 to nucleotide 973;

(c) a polynucleotide comprising the nucleotide sequence of the full-length protein coding sequence of clone rd232_5 deposited under accession number ATCC 98850;

(d) a polynucleotide encoding the full-length protein encoded by the cDNA insert of clone rd232_5 deposited under accession number ATCC 98850;

(e) a polynucleotide comprising the nucleotide sequence of a mature protein coding sequence of clone rd232_5 deposited under accession number ATCC 98850;

(f) a polynucleotide encoding a mature protein encoded by the cDNA insert of clone rd232_5 deposited under accession number ATCC 98850;

(g) a polynucleotide encoding a protein comprising the amino acid sequence of SEQ ID NO:58;

(h) a polynucleotide encoding a protein comprising a fragment of the amino acid sequence of SEQ ID NO:58 having biological activity, the fragment comprising eight contiguous amino acids of SEQ ID NO:58;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:57.

Preferably, such polynucleotide comprises the nucleotide sequence of SEQ ID NO:57 from nucleotide 56 to nucleotide 973; the nucleotide sequence of the full-length protein coding sequence of clone rd232_5 deposited under accession number ATCC 98850; or the nucleotide sequence of a mature protein coding sequence of clone rd232_5 deposited under accession number ATCC 98850. In other preferred embodiments, the polynucleotide encodes the full-length or a mature protein encoded by the cDNA insert of clone rd232_5 deposited under accession number ATCC 98850. In further preferred embodiments, the present invention provides a polynucleotide encoding a protein comprising a fragment of the amino acid sequence of SEQ ID NO:58 having biological activity, the fragment preferably comprising eight (more preferably twenty, most preferably thirty) contiguous amino acids of SEQ ID NO:58, or a polynucleotide encoding a protein comprising a fragment of the amino acid sequence of SEQ ID NO:58 having biological activity, the fragment comprising the amino acid sequence from amino acid 148 to amino acid 157 of SEQ ID NO:58.

Other embodiments provide the gene corresponding to the cDNA sequence of SEQ ID NO:57.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:57, but excluding the poly(A) tail at the 3' end of SEQ ID NO:57; and
    (ab) the nucleotide sequence of the cDNA insert of clone rd232_5 deposited under accession number ATCC 98850;
  (ii) hybridizing said probe(s) to human genomic DNA in conditions at least as stringent as 4×SSC at 50 degrees C.; and
  (iii) isolating the DNA polynucleotides detected with the probe(s); and (b) a process comprising the steps of:
  (i) preparing one or more polynucleotide primers that hybridize in 6×SSC at 65 degrees C. to a nucleotide sequence selected from the group consisting of:
    (ba) SEQ ID NO:57, but excluding the poly(A) tail at the 3' end of SEQ ID NO:57; and
    (bb) the nucleotide sequence of the cDNA insert of clone rd232_5 deposited under accession number ATCC 98850;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:57, and extending contiguously from a nucleotide sequence corresponding to the 5' end of SEQ ID NO:57 to a nucleotide sequence corresponding to the 3' end of SEQ ID NO:57, but excluding the poly(A) tail at the 3' end of SEQ ID NO:57. Also preferably the polynucleotide isolated according to the above process comprises a nucleotide sequence corresponding to the cDNA sequence of SEQ ID NO:57 from nucleotide 56 to nucleotide 973, and extending contiguously from a nucleotide sequence corresponding to the 5' end of said sequence of SEQ ID NO:57 from nucleotide 56 to nucleotide 973, to a nucleotide sequence corresponding to the 3' end of said sequence of SEQ ID NO:57 from nucleotide 56 to nucleotide 973.

In other embodiments, the present invention provides a composition comprising a protein, wherein said protein comprises an amino acid sequence selected from the group consisting of:

(a) the amino acid sequence of SEQ ID NO:58;

(b) a fragment of the amino acid sequence of SEQ ID NO:58, the fragment comprising eight contiguous amino acids of SEQ ID NO:58; and (c) the amino acid sequence encoded by the cDNA insert of clone rd232_5 deposited under accession number ATCC 98850;

the protein being substantially free from other mammalian proteins. Preferably such protein comprises the amino acid sequence of SEQ ID NO:58. In further preferred embodiments, the present invention provides a protein comprising a fragment of the amino acid sequence of SEQ ID NO:58 having biological activity, the fragment preferably comprising eight (more preferably twenty, most preferably thirty) contiguous amino acids of SEQ ID NO:58, or a protein comprising a fragment of the amino acid sequence of SEQ ID NO:58 having biological activity, the fragment comprising the amino acid sequence from amino acid 148 to amino acid 157 of SEQ ID NO:58.

In one embodiment, the present invention provides a composition comprising an isolated polynucleotide selected from the group consisting of:

(a) a polynucleotide comprising the nucleotide sequence of SEQ ID NO:59;

(b) a polynucleotide comprising the nucleotide sequence of SEQ ID NO:59 from nucleotide 893 to nucleotide 2596;

(c) a polynucleotide comprising the nucleotide sequence of the full-length protein coding sequence of clone ck213_12 deposited under accession number ATCC 98918;

(d) a polynucleotide encoding the full-length protein encoded by the cDNA insert of clone ck213_12 deposited under accession number ATCC 98918;

(e) a polynucleotide comprising the nucleotide sequence of a mature protein coding sequence of clone ck213_12 deposited under accession number ATCC 98918;

(f) a polynucleotide encoding a mature protein encoded by the cDNA insert of clone ck213_12 deposited under accession number ATCC 98918;

(g) a polynucleotide encoding a protein comprising the amino acid sequence of SEQ ID NO:60;

(h) a polynucleotide encoding a protein comprising a fragment of the amino acid sequence of SEQ ID NO:60 having biological activity, the fragment comprising eight contiguous amino acids of SEQ ID NO:60;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:59.

Preferably, such polynucleotide comprises the nucleotide sequence of SEQ ID NO:59 from nucleotide 893 to nucleotide 2596; the nucleotide sequence of the full-length protein coding sequence of clone ck213_12 deposited under accession number ATCC 98918; or the nucleotide sequence of a mature protein coding sequence of clone ck213_12 deposited under accession number ATCC 98918. In other preferred embodiments, the polynucleotide encodes the full-length or a mature protein encoded by the cDNA insert of clone ck213_12 deposited under accession number ATCC 98918. In further preferred embodiments, the present invention provides a polynucleotide encoding a protein comprising a fragment of the amino acid sequence of SEQ ID NO:60 having biological activity, the fragment preferably comprising eight (more preferably twenty, most preferably thirty) contiguous amino acids of SEQ ID NO:60, or a polynucleotide encoding a protein comprising a fragment of the amino acid sequence of SEQ ID NO:60 having biological activity, the fragment comprising the amino acid sequence from amino acid 279 to amino acid 288 of SEQ ID NO:60.

Other embodiments provide the gene corresponding to the cDNA sequence of SEQ ID NO:59.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:59, but excluding the poly(A) tail at the 3' end of SEQ ID NO:59; and (ab) the nucleotide sequence of the cDNA insert of clone ck213_12 deposited under accession number ATCC 98918;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:59, but excluding the poly(A) tail at the 3' end of SEQ ID NO:59; and (bb) the nucleotide sequence of the cDNA insert of clone ck213_12 deposited under accession number ATCC 98918;

(ii) hybridizing said primer(s) to human genomic DNA in conditions at least as stringent as 4×SSC at 50 degrees C.;

(iii) amplifying human DNA sequences; and (iv) isolating the polynucleotide products of step (b)(iii).

Preferably the polynucleotide isolated according to the above process comprises a nucleotide sequence corresponding to the cDNA sequence of SEQ ID NO:59, and extending contiguously from a nucleotide sequence corresponding to the 5' end of SEQ ID NO:59 to a nucleotide sequence corresponding to the 3' end of SEQ ID NO:59, but excluding the poly(A) tail at the 3' end of SEQ ID NO:59. Also preferably the polynucleotide isolated according to the above process comprises a nucleotide sequence corresponding to the cDNA sequence of SEQ ID NO:59 from nucleotide 893 to nucleotide 2596, and extending contiguously from a nucleotide sequence corresponding to the 5' end of said sequence of SEQ ID NO:59 from nucleotide 893 to nucleotide 2596, to a nucleotide sequence corresponding to the 3' end of said sequence of SEQ ID NO:59 from nucleotide 893 to nucleotide 2596.

In other embodiments, the present invention provides a composition comprising a protein, wherein said protein comprises an amino acid sequence selected from the group consisting of:

(a) the amino acid sequence of SEQ ID NO:60;

(b) a fragment of the amino acid sequence of SEQ ID NO:60, the fragment comprising eight contiguous amino acids of SEQ ID NO:60; and (c) the amino acid sequence encoded by the cDNA insert of clone ck213_12 deposited under accession number ATCC 98918;

the protein being substantially free from other mammalian proteins. Preferably such protein comprises the amino acid sequence of SEQ ID NO:60. In further preferred embodiments, the present invention provides a protein comprising a fragment of the amino acid sequence of SEQ ID NO:60 having biological activity, the fragment preferably comprising eight (more preferably twenty, most preferably thirty) contiguous amino acids of SEQ ID NO:60, or a protein comprising a fragment of the amino acid sequence of SEQ ID NO:60 having biological activity, the fragment comprising the amino acid sequence from amino acid 279 to amino acid 288 of SEQ ID NO:60.

In one embodiment, the present invention provides a composition comprising an isolated polynucleotide selected from the group consisting of:

(a) a polynucleotide comprising the nucleotide sequence of SEQ ID NO:61;

(b) a polynucleotide comprising the nucleotide sequence of SEQ ID NO:61 from nucleotide 29 to nucleotide 1750;

(c) a polynucleotide comprising the nucleotide sequence of the full-length protein coding sequence of clone pg195_1 deposited under accession number ATCC 98918;

(d) a polynucleotide encoding the full-length protein encoded by the cDNA insert of clone pg195_1 deposited under accession number ATCC 98918;

(e) a polynucleotide comprising the nucleotide sequence of a mature protein coding sequence of clone pg195_1 deposited under accession number ATCC 98918;

(f) a polynucleotide encoding a mature protein encoded by the cDNA insert of clone pg195_1 deposited under accession number ATCC 98918;

(g) a polynucleotide encoding a protein comprising the amino acid sequence of SEQ ID NO:62;

(h) a polynucleotide encoding a protein comprising a fragment of the amino acid sequence of SEQ ID NO:62 having biological activity, the fragment comprising eight contiguous amino acids of SEQ ID NO:62;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:61.

Preferably, such polynucleotide comprises the nucleotide sequence of SEQ ID NO:61 from nucleotide 29 to nucleotide 1750; the nucleotide sequence of the full-length protein coding sequence of clone pg195_1 deposited under accession number ATCC 98918; or the nucleotide sequence of a mature protein coding sequence of clone pg195_1 deposited under accession number ATCC 98918. In other preferred embodiments, the polynucleotide encodes the full-length or a mature protein encoded by the cDNA insert of clone pg195_1 deposited under accession number ATCC 98918. In further preferred embodiments, the present invention provides a polynucleotide encoding a protein comprising a fragment of the amino acid sequence of SEQ ID NO:62 having biological activity, the fragment preferably comprising eight (more preferably twenty, most preferably thirty) contiguous amino acids of SEQ ID NO:62, or a polynucleotide encoding a protein comprising a fragment of the amino acid sequence of SEQ ID NO:62 having biological activity, the fragment comprising the amino acid sequence from amino acid 282 to amino acid 291 of SEQ ID NO:62.

Other embodiments provide the gene corresponding to the cDNA sequence of SEQ ID NO:61.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:61, but excluding the poly(A) tail at the 3' end of SEQ ID NO:61; and
    (ab) the nucleotide sequence of the cDNA insert of clone pg195_1 deposited under accession number ATCC 98918;
  (ii) hybridizing said probe(s) to human genomic DNA in conditions at least as stringent as 4×SSC at 50 degrees C.; and
  (iii) isolating the DNA polynucleotides detected with the probe(s); and (b) a process comprising the steps of:
  (i) preparing one or more polynucleotide primers that hybridize in 6×SSC at 65 degrees C. to a nucleotide sequence selected from the group consisting of:
    (ba) SEQ ID NO:61, but excluding the poly(A) tail at the 3' end of SEQ ID NO:61; and
    (bb) the nucleotide sequence of the cDNA insert of clone pg195_1 deposited under accession number ATCC 98918;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:61, and extending contiguously from a nucleotide sequence corresponding to the 5' end of SEQ ID NO:61 to a nucleotide sequence corresponding to the 3' end of SEQ ID NO:61, but excluding the poly(A) tail at the 3' end of SEQ ID NO:61. Also preferably the polynucleotide isolated according to the above process comprises a nucleotide sequence corresponding to the cDNA sequence of SEQ ID NO:61 from nucleotide 29 to nucleotide 1750, and extending contiguously from a nucleotide sequence corresponding to the 5' end of said sequence of SEQ ID NO:61 from nucleotide 29 to nucleotide 1750, to a nucleotide sequence corresponding to the 3' end of said sequence of SEQ ID NO:61 from nucleotide 29 to nucleotide 1750.

In other embodiments, the present invention provides a composition comprising a protein, wherein said protein comprises an amino acid sequence selected from the group consisting of:

(a) the amino acid sequence of SEQ ID NO:62;

(b) a fragment of the amino acid sequence of SEQ ID NO:62, the fragment comprising eight contiguous amino acids of SEQ ID NO:62; and (c) the amino acid sequence encoded by the cDNA insert of clone pg195_1 deposited under accession number ATCC 98918;

the protein being substantially free from other mammalian proteins. Preferably such protein comprises the amino acid sequence of SEQ ID NO:62. In further preferred embodiments, the present invention provides a protein comprising a fragment of the amino acid sequence of SEQ ID NO:62 having biological activity, the fragment preferably comprising eight (more preferably twenty, most preferably thirty) contiguous amino acids of SEQ ID NO:62, or a protein comprising a fragment of the amino acid sequence of SEQ ID NO:62 having biological activity, the fragment comprising the amino add sequence from amino acid 282 to amino acid 291 of SEQ ID NO:62.

In one embodiment, the present invention provides a composition comprising an isolated polynucleotide selected from the group consisting of:

(a) a polynucleotide comprising the nucleotide sequence of SEQ ID NO:63;

(b) a polynucleotide comprising the nucleotide sequence of SEQ ID NO:63 from nucleotide 1147 to nucleotide 1440;

(c) a polynucleotide comprising the nucleotide sequence of SEQ ID NO:63 from nucleotide 1234 to nucleotide 1440;

(d) a polynucleotide comprising the nucleotide sequence of the full-length protein coding sequence of clone pw460_5 deposited under accession number ATCC 98918;

(e) a polynucleotide encoding the full-length protein encoded by the cDNA insert of clone pw460_5 deposited under accession number ATCC 98918;

(f) a polynucleotide comprising the nucleotide sequence of a mature protein coding sequence of clone pw460_5 deposited under accession number ATCC 98918;

(g) a polynucleotide encoding a mature protein encoded by the cDNA insert of clone pw460_5 deposited under accession number ATCC 98918;

(h) a polynucleotide encoding a protein comprising the amino acid sequence of SEQ ID NO:64;

(i) a polynucleotide encoding a protein comprising a fragment of the amino acid sequence of SEQ ID NO:64 having biological activity, the fragment comprising eight contiguous amino acids of SEQ ID NO:64;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:63.

Preferably, such polynucleotide comprises the nucleotide sequence of SEQ ID NO:63 from nucleotide 1147 to nucleotide 1440; the nucleotide sequence of SEQ ID NO:63 from nucleotide 1234 to nucleotide 1440; the nucleotide sequence of the full-length protein coding sequence of clone pw460_5 deposited under accession number ATCC 98918; or the nucleotide sequence of a mature protein coding sequence of clone pw460_5 deposited under accession number ATCC 98918. In other preferred embodiments, the polynucleotide encodes the full-length or a mature protein encoded by the cDNA insert of clone pw460_5 deposited under accession number ATCC 98918. In further preferred embodiments, the present invention provides a polynucleotide encoding a protein comprising a fragment of the amino acid sequence of SEQ ID NO:64 having biological activity, the fragment preferably comprising eight (more preferably twenty, most preferably thirty) contiguous amino acids of SEQ ID NO:64, or a polynucleotide encoding a protein comprising a fragment of the amino acid sequence of SEQ ID NO:64 having biological activity, the fragment comprising the amino acid sequence from amino acid 44 to amino acid 53 of SEQ ID NO:64.

Other embodiments provide the gene corresponding to the cDNA sequence of SEQ ID NO:63.

Further embodiments of the invention provide isolated polynucleotides produced according to a process selected from the group consisting of:

(a) a process comprising the steps of:
   (i) preparing one or more polynucleotide probes that hybridize in 6×SSC at 65 degrees C. to a nucleotide sequence selected from the group consisting of:
      (aa) SEQ ID NO:63, but excluding the poly(A) tail at the 3' end of SEQ ID NO:63; and
      (ab) the nucleotide sequence of the cDNA insert of clone pw460_5 deposited under accession number ATCC 98918;
   (ii) hybridizing said probe(s) to human genomic DNA in conditions at least as stringent as 4×SSC at 50 degrees C.; and
   (iii) isolating the DNA polynucleotides detected with the probe(s); and (b) a process comprising the steps of:
   (i) preparing one or more polynucleotide primers that hybridize in 6×SSC at 65 degrees C. to a nucleotide sequence selected from the group consisting of:
      (ba) SEQ ID NO:63, but excluding the poly(A) tail at the 3' end of SEQ ID NO:63; and
      (bb) the nucleotide sequence of the cDNA insert of clone pw460_5 deposited under accession number ATCC 98918;
   (ii) hybridizing said primer(s) to human genomic DNA in conditions at least as stringent as 4×SSC at 50 degrees C.;
   (iii) amplifying human DNA sequences; and
   (iv) isolating the polynucleotide products of step (b) (iii).

Preferably the polynucleotide isolated according to the above process comprises a nucleotide sequence corresponding to the cDNA sequence of SEQ ID NO:63, and extending contiguously from a nucleotide sequence corresponding to the 5' end of SEQ ID NO:63 to a nucleotide sequence corresponding to the 3' end of SEQ ID NO:63, but excluding the poly(A) tail at the 3' end of SEQ ID NO:63. Also preferably the polynucleotide isolated according to the above process comprises a nucleotide sequence corresponding to the cDNA sequence of SEQ ID NO:63 from nucleotide 1147 to nucleotide 1440, and extending contiguously from a nucleotide sequence corresponding to the 5' end of said sequence of SEQ ID NO:63 from nucleotide 1147 to nucleotide 1440, to a nucleotide sequence corresponding to the 3' end of said sequence of SEQ ID NO:63 from nucleotide 1147 to nucleotide 1440. Also preferably the polynucleotide isolated according to the above process comprises a nucleotide sequence corresponding to the cDNA sequence of SEQ ID NO:63 from nucleotide 1234 to nucleotide 1440, and extending contiguously from a nucleotide sequence corresponding to the 5' end of said sequence of SEQ ID NO:63 from nucleotide 1234 to nucleotide 1440, to a nucleotide sequence corresponding to the 3' end of said sequence of SEQ ID NO:63 from nucleotide 1234 to nucleotide 1440.

In other embodiments, the present invention provides a composition comprising a protein, wherein said protein comprises an amino acid sequence selected from the group consisting of:

(a) the amino acid sequence of SEQ ID NO:64;

(b) a fragment of the amino acid sequence of SEQ ID NO:64, the fragment comprising eight contiguous amino acids of SEQ ID NO:64; and (c) the amino acid sequence encoded by the cDNA insert of clone pw460_5 deposited under accession number ATCC 98918;

the protein being substantially free from other mammalian proteins. Preferably such protein comprises the amino acid sequence of SEQ ID NO:64. In further preferred embodiments, the present invention provides a protein comprising a fragment of the amino acid sequence of SEQ ID NO:64 having biological activity, the fragment preferably comprising eight (more preferably twenty, most preferably thirty) contiguous amino acids of SEQ ID NO:64, or a protein comprising a fragment of the amino acid sequence of SEQ ID NO:64 having biological activity, the fragment comprising the amino acid sequence from amino acid 44 to amino acid 53 of SEQ ID NO:64.

In one embodiment, the present invention provides a composition comprising an isolated polynucleotide selected from the group consisting of:

(a) a polynucleotide comprising the nucleotide sequence of SEQ ID NO:65;

(b) a polynucleotide comprising the nucleotide sequence of SEQ ID NO:65 from nucleotide 46 to nucleotide 1356;

(c) a polynucleotide comprising the nucleotide sequence of SEQ ID NO:65 from nucleotide 127 to nucleotide 1356;

(d) a polynucleotide comprising the nucleotide sequence of the full-length protein coding sequence of clone qa136_1 deposited under accession number ATCC 98918;

(e) a polynucleotide encoding the full-length protein encoded by the cDNA insert of clone qa136_1 deposited under accession number ATCC 98918;

(f) a polynucleotide comprising the nucleotide sequence of a mature protein coding sequence of clone qa136_1 deposited under accession number ATCC 98918;

(g) a polynucleotide encoding a mature protein encoded by the cDNA insert of clone qa136_1 deposited under accession number ATCC 98918;

(h) a polynucleotide encoding a protein comprising the amino acid sequence of SEQ ID NO:66;

(i) a polynucleotide encoding a protein comprising a fragment of the amino acid sequence of SEQ ID NO:66 having biological activity, the fragment comprising eight contiguous amino acids of SEQ ID NO:66;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:65.

Preferably, such polynucleotide comprises the nucleotide sequence of SEQ ID NO:65 from nucleotide 46 to nucleotide 1356; the nucleotide sequence of SEQ ID NO:65 from nucleotide 127 to nucleotide 1356; the nucleotide sequence of the full-length protein coding sequence of clone qa136_1 deposited under accession number ATCC 98918; or the nucleotide sequence of a mature protein coding sequence of clone qa136_1 deposited under accession number ATCC 98918. In other preferred embodiments, the polynucleotide encodes the full-length or a mature protein encoded by the cDNA insert of clone qa136_1 deposited under accession number ATCC 98918. In further preferred embodiments, the present invention provides a polynucleotide encoding a protein comprising a fragment of the amino acid sequence of SEQ ID NO:66 having biological activity, the fragment preferably comprising eight (more preferably twenty, most preferably thirty) contiguous amino acids of SEQ ID NO:66, or a polynucleotide encoding a protein comprising a fragment of the amino acid sequence of SEQ ID NO:66 having biological activity, the fragment comprising the amino acid sequence from amino acid 213 to amino acid 222 of SEQ ID NO:66.

Other embodiments provide the gene corresponding to the cDNA sequence of SEQ ID NO:65.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:65; and (ab) the nucleotide sequence of the cDNA insert of clone qa136_1 deposited under accession number ATCC 98918;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:65; and (bb) the nucleotide sequence of the cDNA insert of clone qa136__1 deposited under accession number ATCC 98918;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:65, and extending contiguously from a nucleotide sequence corresponding to the 5' end of SEQ ID NO:65 to a nucleotide sequence corresponding to the 3' end of SEQ ID NO:65. Also preferably the polynucleotide isolated according to the above process comprises a nucleotide sequence corresponding to the cDNA sequence of SEQ ID NO:65 from nucleotide 46 to nucleotide 1356, and extending contiguously from a nucleotide sequence corresponding to the 5' end of said sequence of SEQ ID NO:65 from nucleotide 46 to nucleotide 1356, to a nucleotide sequence corresponding to the 3' end of said sequence of SEQ ID NO:65 from nucleotide 46 to nucleotide 1356. Also preferably the polynucleotide isolated according to the above process comprises a nucleotide sequence corresponding to the cDNA sequence of SEQ ID NO:65 from nucleotide 127 to nucleotide 1356, and extending contiguously from a nucleotide sequence corresponding to the 5' end of said sequence of SEQ ID NO:65 from nucleotide 127 to nucleotide 1356, to a nucleotide sequence corresponding to the 3' end of said sequence of SEQ ID NO:65 from nucleotide 127 to nucleotide 1356.

In other embodiments, the present invention provides a composition comprising a protein, wherein said protein comprises an amino acid sequence selected from the group consisting of:

(a) the amino acid sequence of SEQ ID NO:66;

(b) a fragment of the amino acid sequence of SEQ ID NO:66, the fragment comprising eight contiguous amino acids of SEQ ID NO:66; and (c) the amino acid sequence encoded by the cDNA insert of clone qa136__1 deposited under accession number ATCC 98918;

the protein being substantially free from other mammalian proteins. Preferably such protein comprises the amino acid sequence of SEQ ID NO:66. In further preferred embodiments, the present invention provides a protein comprising a fragment of the amino acid sequence of SEQ ID NO:66 having biological activity, the fragment preferably comprising eight (more preferably twenty, most preferably thirty) contiguous amino acids of SEQ ID NO:66, or a protein comprising a fragment of the amino acid sequence of SEQ ID NO:66 having biological activity, the fragment comprising the amino acid sequence from amino acid 213 to amino acid 222 of SEQ ID NO:66.

In one embodiment, the present invention provides a composition comprising an isolated polynucleotide selected from the group consisting of:

(a) a polynucleotide comprising the nucleotide sequence of SEQ ID NO:67;

(b) a polynucleotide comprising the nucleotide sequence of SEQ ID NO:67 from nucleotide 206 to nucleotide 1624;

(c) a polynucleotide comprising the nucleotide sequence of SEQ ID NO:67 from nucleotide 542 to nucleotide 1624;

(d) a polynucleotide comprising the nucleotide sequence of the full-length protein coding sequence of clone qy1261__2 deposited under accession number ATCC 98918;

(e) a polynucleotide encoding the full-length protein encoded by the cDNA insert of clone qy1261__2 deposited under accession number ATCC 98918;

(f) a polynucleotide comprising the nucleotide sequence of a mature protein coding sequence of clone qy1261__2 deposited under accession number ATCC 98918;

(g) a polynucleotide encoding a mature protein encoded by the cDNA insert of clone qy1261__2 deposited under accession number ATCC 98918;

(h) a polynucleotide encoding a protein comprising the amino acid sequence of SEQ ID NO:68;

(i) a polynucleotide encoding a protein comprising a fragment of the amino acid sequence of SEQ ID NO:68 having biological activity, the fragment comprising eight contiguous amino acids of SEQ ID NO:68;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:67.

Preferably, such polynucleotide comprises the nucleotide sequence of SEQ ID NO:67 from nucleotide 206 to nucleotide 1624; the nucleotide sequence of SEQ ID NO:67 from nucleotide 542 to nucleotide 1624; the nucleotide sequence of the full-length protein coding sequence of clone qy1261__2 deposited under accession number ATCC 98918; or the nucleotide sequence of a mature protein coding sequence of clone qy1261__2 deposited under accession number ATCC 98918. In other preferred embodiments, the polynucleotide encodes the full-length or a mature protein encoded by the cDNA insert of clone qy1261__2 deposited under accession number ATCC 98918. In further preferred embodiments, the present invention provides a polynucleotide encoding a protein comprising a fragment of the amino acid sequence of SEQ ID NO:68 having biological activity, the fragment preferably comprising eight (more preferably twenty, most preferably thirty) contiguous amino acids of SEQ ID NO:68, or a polynucleotide encoding a protein comprising a fragment of the amino acid sequence of SEQ ID NO:68 having biological activity, the fragment comprising the amino acid sequence from amino acid 231 to amino acid 240 of SEQ ID NO:68.

Other embodiments provide the gene corresponding to the cDNA sequence of SEQ ID NO:67.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:67, but excluding the poly(A) tail at the 3' end of SEQ ID NO:67; and (ab) the nucleotide sequence of the cDNA insert of clone qy1261__2 deposited under accession number ATCC 98918;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:67, but excluding the poly(A) tail at the 3' end of SEQ ID NO:67; and (bb) the nucleotide sequence of the cDNA insert of clone qy1261_2 deposited under accession number ATCC 98918;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:67, and extending contiguously from a nucleotide sequence corresponding to the 5' end of SEQ ID NO:67 to a nucleotide sequence corresponding to the 3' end of SEQ ID NO:67, but excluding the poly(A) tail at the 3' end of SEQ ID NO:67. Also preferably the polynucleotide isolated according to the above process comprises a nucleotide sequence corresponding to the cDNA sequence of SEQ ID NO:67 from nucleotide 206 to nucleotide 1624, and extending contiguously from a nucleotide sequence corresponding to the 5' end of said sequence of SEQ ID NO:67 from nucleotide 206 to nucleotide 1624, to a nucleotide sequence corresponding to the 3' end of said sequence of SEQ ID NO:67 from nucleotide 206 to nucleotide 1624. Also preferably the polynucleotide isolated according to the above process comprises a nucleotide sequence corresponding to the cDNA sequence of SEQ ID NO:67 from nucleotide 542 to nucleotide 1624, and extending contiguously from a nucleotide sequence corresponding to the 5' end of said sequence of SEQ ID NO:67 from nucleotide 542 to nucleotide 1624, to a nucleotide sequence corresponding to the 3' end of said sequence of SEQ ID NO:67 from nucleotide 542 to nucleotide 1624.

In other embodiments, the present invention provides a composition comprising a protein, wherein said protein comprises an amino add sequence selected from the group consisting of:

(a) the amino acid sequence of SEQ ID NO:68;

(b) a fragment of the amino acid sequence of SEQ ID NO:68, the fragment comprising eight contiguous amino acids of SEQ ID NO:68; and (c) the amino acid sequence encoded by the cDNA insert of clone qy1261_2 deposited under accession number ATCC 98918;

the protein being substantially free from other mammalian proteins. Preferably such protein comprises the amino acid sequence of SEQ ID NO:68. In further preferred embodiments, the present invention provides a protein comprising a fragment of the amino acid sequence of SEQ ID NO:68 having biological activity, the fragment preferably comprising eight (more preferably twenty, most preferably thirty) contiguous amino acids of SEQ ID NO:68, or a protein comprising a fragment of the amino acid sequence of SEQ ID NO:68 having biological activity, the fragment comprising the amino acid sequence from amino acid 231 to amino acid 240 of SEQ ID NO:68.

In one embodiment, the present invention provides a composition comprising an isolated polynucleotide selected from the group consisting of:

(a) a polynucleotide comprising the nucleotide sequence of SEQ ID NO:69;

(b) a polynucleotide comprising the nucleotide sequence of SEQ ID NO:69 from nucleotide 1359 to nucleotide 1817;

(c) a polynucleotide comprising the nucleotide sequence of the full-length protein coding sequence of clone rd432_4 deposited under accession number ATCC 98918;

(d) a polynucleotide encoding the full-length protein encoded by the cDNA insert of clone rd432_4 deposited under accession number ATCC 98918;

(e) a polynucleotide comprising the nucleotide sequence of a mature protein coding sequence of clone rd432_4 deposited under accession number ATCC 98918;

(f) a polynucleotide encoding a mature protein encoded by the cDNA insert of clone rd432_4 deposited under accession number ATCC 98918;

(g) a polynucleotide encoding a protein comprising the amino acid sequence of SEQ ID NO:70;

(h) a polynucleotide encoding a protein comprising a fragment of the amino acid sequence of SEQ ID NO:70 having biological activity, the fragment comprising eight contiguous amino acids of SEQ ID NO:70;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:69.

Preferably, such polynucleotide comprises the nucleotide sequence of SEQ ID NO:69 from nucleotide 1359 to nucleotide 1817; the nucleotide sequence of the full-length protein coding sequence of clone rd432_4 deposited under accession number ATCC 98918; or the nucleotide sequence of a mature protein coding sequence of clone rd432_4 deposited under accession number ATCC 98918. In other preferred embodiments, the polynucleotide encodes the full-length or a mature protein encoded by the cDNA insert of clone rd432_4 deposited under accession number ATCC 98918. In further preferred embodiments, the present invention provides a polynucleotide encoding a protein comprising a fragment of the amino acid sequence of SEQ ID NO:70 having biological activity, the fragment preferably comprising eight (more preferably twenty, most preferably thirty) contiguous amino acids of SEQ ID NO:70, or a polynucleotide encoding a protein comprising a fragment of the amino acid sequence of SEQ ID NO:70 having biological activity, the fragment comprising the amino acid sequence from amino acid 71 to amino acid 80 of SEQ ID NO:70.

Other embodiments provide the gene corresponding to the cDNA sequence of SEQ ID NO:69.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:69, but excluding the poly(A) tail at the 3' end of SEQ ID NO:69; and (ab) the nucleotide sequence of the cDNA insert of clone rd432_4 deposited under accession number ATCC 98918;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:69, but excluding the poly(A) tail at the 3' end of SEQ ID NO:69; and (bb) the nucleotide sequence of the cDNA insert of clone rd432_4 deposited under accession number ATCC 98918;

(ii) hybridizing said primer(s) to human genomic DNA in conditions at least as stringent as 4×SSC at 50 degrees C.;

(iii) amplifying human DNA sequences; and (iv) isolating the polynucleotide products of step (b)(iii).

Preferably the polynucleotide isolated according to the above process comprises a nucleotide sequence corresponding to the cDNA sequence of SEQ ID NO:69, and extending contiguously from a nucleotide sequence corresponding to the 5' end of SEQ ID NO:69 to a nucleotide sequence corresponding to the 3' end of SEQ ID NO:69, but excluding the poly(A) tail at the 3' end of SEQ ID NO:69. Also preferably the polynucleotide isolated according to the above process comprises a nucleotide sequence corresponding to the cDNA sequence of SEQ ID NO:69 from nucleotide 1359 to nucleotide 1817, and extending contiguously from a nucleotide sequence corresponding to the 5' end of said sequence of SEQ ID NO:69 from nucleotide 1359 to nucleotide 1817, to a nucleotide sequence corresponding to the 3' end of said sequence of SEQ ID NO:69 from nucleotide 1359 to nucleotide 1817.

In other embodiments, the present invention provides a composition comprising a protein, wherein said protein comprises an amino acid sequence selected from the group consisting of:

(a) the amino acid sequence of SEQ ID NO:70;

(b) a fragment of the amino acid sequence of SEQ ID NO:70, the fragment comprising eight contiguous amino acids of SEQ ID NO:70; and (c) the amino acid sequence encoded by the cDNA insert of clone rd432_4 deposited under accession number ATCC 98918;

the protein being substantially free from other mammalian proteins. Preferably such protein comprises the amino acid sequence of SEQ ID NO:70. In further preferred embodiments, the present invention provides a protein comprising a fragment of the amino acid sequence of SEQ ID NO:70 having biological activity, the fragment preferably comprising eight (more preferably twenty, most preferably thirty) contiguous amino acids of SEQ ID NO:70, or a protein comprising a fragment of the amino acid sequence of SEQ ID NO:70 having biological activity, the fragment comprising the amino acid sequence from amino acid 71 to amino acid 80 of SEQ ID NO:70.

In one embodiment, the present invention provides a composition comprising an isolated polynucleotide selected from the group consisting of:

(a) a polynucleotide comprising the nucleotide sequence of SEQ ID NO:71;

(b) a polynucleotide comprising the nucleotide sequence of SEQ ID NO:71 from nucleotide 884 to nucleotide 1195;

(c) a polynucleotide comprising the nucleotide sequence of SEQ ID NO:71 from nucleotide 947 to nucleotide 1195;

(d) a polynucleotide comprising the nucleotide sequence of the full-length protein coding sequence of clone rb789_14 deposited under accession number ATCC 207004;

(e) a polynucleotide encoding the full-length protein encoded by the cDNA insert of clone rb789_14 deposited under accession number ATCC 207004;

(f) a polynucleotide comprising the nucleotide sequence of a mature protein coding sequence of clone rb789_14 deposited under accession number ATCC 207004;

(g) a polynucleotide encoding a mature protein encoded by the cDNA insert of clone rb789_14 deposited under accession number ATCC 207004;

(h) a polynucleotide encoding a protein comprising the amino acid sequence of SEQ ID NO:72;

(i) a polynucleotide encoding a protein comprising a fragment of the amino acid sequence of SEQ ID NO:72 having biological activity, the fragment comprising eight contiguous amino acids of SEQ ID NO:72;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:71.

Preferably, such polynucleotide comprises the nucleotide sequence of SEQ ID NO:71 from nucleotide 884 to nucleotide 1195; the nucleotide sequence of SEQ ID NO:71 from nucleotide 947 to nucleotide 1195; the nucleotide sequence of the full-length protein coding sequence of clone rb789_14 deposited under accession number ATCC 207004; or the nucleotide sequence of a mature protein coding sequence of clone rb789_14 deposited under accession number ATCC 207004. In other preferred embodiments, the polynucleotide encodes the full-length or a mature protein encoded by the cDNA insert of clone rb789_14 deposited under accession number ATCC 207004. In further preferred embodiments, the present invention provides a polynucleotide encoding a protein comprising a fragment of the amino acid sequence of SEQ ID NO:72 having biological activity, the fragment preferably comprising eight (more preferably twenty, most preferably thirty) contiguous amino acids of SEQ ID NO:72, or a polynucleotide encoding a protein comprising a fragment of the amino acid sequence of SEQ ID NO:72 having biological activity, the fragment comprising the amino acid sequence from amino acid 47 to amino acid 56 of SEQ ID NO:72.

Other embodiments provide the gene corresponding to the cDNA sequence of SEQ ID NO:71.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:71, but excluding the poly(A) tail at the 3' end of SEQ ID NO:71; and
    (ab) the nucleotide sequence of the cDNA insert of clone rb789 14 deposited under accession number ATCC 207004;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:71, but excluding the poly(A) tail at the 3' end of SEQ ID NO:71; and
    (bb) the nucleotide sequence of the cDNA insert of clone rb789_14 deposited under accession number ATCC 207004;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:71, and extending contiguously from a nucleotide sequence corresponding to the 5' end of SEQ ID NO:71 to a nucleotide sequence corresponding to the 3' end of SEQ ID NO:71, but excluding the poly(A) tail at the 3' end of SEQ ID NO:71. Also preferably the polynucleotide isolated according to the above process comprises a nucleotide sequence corresponding to the cDNA sequence of SEQ ID NO:71 from nucleotide 884 to nucleotide 1195, and extending contiguously from a nucleotide sequence corresponding to the 5' end of said sequence of SEQ ID NO:71 from nucleotide 884 to nucleotide 1195, to a nucleotide sequence corresponding to the 3' end of said sequence of SEQ ID NO:71 from nucleotide 884 to nucleotide 1195. Also preferably the polynucleotide isolated according to the above process comprises a nucleotide sequence corresponding to the cDNA sequence of SEQ ID NO:71 from nucleotide 947 to nucleotide 1195, and extending contiguously from a nucleotide sequence corresponding to the 5' end of said sequence of SEQ ID NO:71 from nucleotide 947 to nucleotide 1195, to a nucleotide sequence corresponding to the 3' end of said sequence of SEQ ID NO:71 from nucleotide 947 to nucleotide 1195.

In other embodiments, the present invention provides a composition comprising a protein, wherein said protein comprises an amino acid sequence selected from the group consisting of:

(a) the amino acid sequence of SEQ ID NO:72;
(b) a fragment of the amino acid sequence of SEQ ID NO:72, the fragment comprising eight contiguous amino acids of SEQ ID NO:72; and
(c) the amino acid sequence encoded by the cDNA insert of clone rb789_14 deposited under accession number ATCC 207004;

the protein being substantially free from other mammalian proteins. Preferably such protein comprises the amino acid sequence of SEQ ID NO:72. In further preferred embodiments, the present invention provides a protein comprising a fragment of the amino acid sequence of SEQ ID NO:72 having biological activity, the fragment preferably comprising eight (more preferably twenty, most preferably thirty) contiguous amino adds of SEQ ID NO:72, or a protein comprising a fragment of the amino acid sequence of SEQ ID NO:72 having biological activity, the fragment comprising the amino acid sequence from amino acid 47 to amino acid 56 of SEQ ID NO:72.

In one embodiment, the present invention provides a composition comprising an isolated polynucleotide selected from the group consisting of:

(a) a polynucleotide comprising the nucleotide sequence of SEQ ID NO:73;
(b) a polynucleotide comprising the nucleotide sequence of SEQ ID NO:73 from nucleotide 69 to nucleotide 374;
(c) a polynucleotide comprising the nucleotide sequence of SEQ ID NO:73 from nucleotide 186 to nucleotide 374;
(d) a polynucleotide comprising the nucleotide sequence of the full-length protein coding sequence of clone yd137_1 deposited under accession number ATCC 207004;
(e) a polynucleotide encoding the full-length protein encoded by the cDNA insert of clone yd137_1 deposited under accession number ATCC 207004;
(f) a polynucleotide comprising the nucleotide sequence of a mature protein coding sequence of clone yd137_1 deposited under accession number ATCC 207004;
(g) a polynucleotide encoding a mature protein encoded by the cDNA insert of clone yd137_1 deposited under accession number ATCC 207004;
(h) a polynucleotide encoding a protein comprising the amino add sequence of SEQ ID NO:74;
(i) a polynucleotide encoding a protein comprising a fragment of the amino acid sequence of SEQ ID NO:74 having biological activity, the fragment comprising eight contiguous amino acids of SEQ ID NO:74;
(j) a polynucleotide which is an allelic variant of a polynucleotide of (a)-(g) above;
(k) a polynucleotide which encodes a species homologue of the protein of (h) or (i) above;
(l) a polynucleotide that hybridizes under stringent conditions to any one of the polynucleotides specified in (a)-(i); and
(m) a polynucleotide that hybridizes under stringent conditions to any one of the polynucleotides specified in (a)-(i) and that has a length that is at least 25% of the length of SEQ ID NO:73.

Preferably, such polynucleotide comprises the nucleotide sequence of SEQ ID NO:73 from nucleotide 69 to nucleotide 374; the nucleotide sequence of SEQ ID NO:73 from nucleotide 186 to nucleotide 374; the nucleotide sequence of the full-length protein coding sequence of clone yd137_1 deposited under accession number ATCC 207004; or the nucleotide sequence of a mature protein coding sequence of clone yd137_1 deposited under accession number ATCC 207004. In other preferred embodiments, the polynucleotide encodes the full-length or a mature protein encoded by the cDNA insert of clone yd137_1 deposited under accession number ATCC 207004. In further preferred embodiments, the present invention provides a polynucleotide encoding a protein comprising a fragment of the amino acid sequence of SEQ ID NO:74 having biological activity, the fragment preferably comprising eight (more preferably twenty, most preferably thirty) contiguous amino adds of SEQ ID NO:74, or a polynucleotide encoding a protein comprising a fragment of the amino acid sequence of SEQ ID NO:74 having biological activity, the fragment comprising the amino acid sequence from amino acid 46 to amino acid 55 of SEQ ID NO:74.

Other embodiments provide the gene corresponding to the cDNA sequence of SEQ ID NO:73.

Further embodiments of the invention provide isolated polynucleotides produced according to a process selected from the group consisting of:

- (a) a process comprising the steps of:
  - (i) preparing one or more polynucleotide probes that hybridize in 6×SSC at 65 degrees C. to a nucleotide sequence selected from the group consisting of:
    - (aa) SEQ ID NO:73, but excluding the poly(A) tail at the 3' end of SEQ ID NO:73; and
    - (ab) the nucleotide sequence of the cDNA insert of clone yd137_1 deposited under accession number ATCC 207004;
  - (ii) hybridizing said probe(s) to human genomic DNA in conditions at least as stringent as 4×SSC at 50 degrees C.; and
  - (iii) isolating the DNA polynucleotides detected with the probe(s); and
- (b) a process comprising the steps of:
  - (i) preparing one or more polynucleotide primers that hybridize in 6×SSC at 65 degrees C. to a nucleotide sequence selected from the group consisting of:
    - (ba) SEQ ID NO:73, but excluding the poly(A) tail at the 3' end of SEQ ID NO:73; and
    - (bb) the nucleotide sequence of the cDNA insert of clone yd137_1 deposited under accession number ATCC 207004;
  - (ii) hybridizing said primer(s) to human genomic DNA in conditions at least as stringent as 4×SSC at 50 degrees C.;
  - (iii) amplifying human DNA sequences; and
  - (iv) isolating the polynucleotide products of step (b) (iii).

Preferably the polynucleotide isolated according to the above process comprises a nucleotide sequence corresponding to the cDNA sequence of SEQ ID NO:73, and extending contiguously from a nucleotide sequence corresponding to the 5' end of SEQ ID NO:73 to a nucleotide sequence corresponding to the 3' end of SEQ ID NO:73, but excluding the poly(A) tail at the 3' end of SEQ ID NO:73. Also preferably the polynucleotide isolated according to the above process comprises a nucleotide sequence corresponding to the cDNA sequence of SEQ ID NO:73 from nucleotide 69 to nucleotide 374, and extending contiguously from a nucleotide sequence corresponding to the 5' end of said sequence of SEQ ID NO:73 from nucleotide 69 to nucleotide 374, to a nucleotide sequence corresponding to the 3' end of said sequence of SEQ ID NO:73 from nucleotide 69 to nucleotide 374. Also preferably the polynucleotide isolated according to the above process comprises a nucleotide sequence corresponding to the cDNA sequence of SEQ ID NO:73 from nucleotide 186 to nucleotide 374, and extending contiguously from a nucleotide sequence corresponding to the 5' end of said sequence of SEQ ID NO:73 from nucleotide 186 to nucleotide 374, to a nucleotide sequence corresponding to the 3' end of said sequence of SEQ ID NO:73 from nucleotide 186 to nucleotide 374.

In other embodiments, the present invention provides a composition comprising a protein, wherein said protein comprises an amino acid sequence selected from the group consisting of:

- (a) the amino acid sequence of SEQ ID NO:74;
- (b) a fragment of the amino acid sequence of SEQ ID NO:74, the fragment comprising eight contiguous amino acids of SEQ ID NO:74; and
- (c) the amino acid sequence encoded by the cDNA insert of clone yd137_1 deposited under accession number ATCC 207004;

the protein being substantially free from other mammalian proteins. Preferably such protein comprises the amino acid sequence of SEQ ID NO:74. In further preferred embodiments, the present invention provides a protein comprising a fragment of the amino acid sequence of SEQ ID NO:74 having biological activity, the fragment preferably comprising eight (more preferably twenty, most preferably thirty) contiguous amino acids of SEQ ID NO:74, or a protein comprising a fragment of the amino acid sequence of SEQ ID NO:74 having biological activity, the fragment comprising the amino acid sequence from amino acid 46 to amino acid 55 of SEQ ID NO:74.

In one embodiment, the present invention provides a composition comprising an isolated polynucleotide selected from the group consisting of:

- (a) a polynucleotide comprising the nucleotide sequence of SEQ ID NO:75;
- (b) a polynucleotide comprising the nucleotide sequence of SEQ ID NO:75 from nucleotide 8 to nucleotide 343;
- (c) a polynucleotide comprising the nucleotide sequence of SEQ ID NO:75 from nucleotide 50 to nucleotide 343;
- (d) a polynucleotide comprising the nucleotide sequence of the full-length protein coding sequence of clone yd218_1 deposited under accession number ATCC 207004;
- (e) a polynucleotide encoding the full-length protein encoded by the cDNA insert of clone yd218_1 deposited under accession number ATCC 207004;
- (f) a polynucleotide comprising the nucleotide sequence of a mature protein coding sequence of clone yd218_1 deposited under accession number ATCC 207004;
- (g) a polynucleotide encoding a mature protein encoded by the cDNA insert of clone yd218_1 deposited under accession number ATCC 207004;
- (h) a polynucleotide encoding a protein comprising the amino acid sequence of SEQ ID NO:76;
- (i) a polynucleotide encoding a protein comprising a fragment of the amino acid sequence of SEQ ID NO:76 having biological activity, the fragment comprising eight contiguous amino acids of SEQ ID NO:76;
- (j) a polynucleotide which is an allelic variant of a polynucleotide of (a)-(g) above;
- (k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:75.

Preferably, such polynucleotide comprises the nucleotide sequence of SEQ ID NO:75 from nucleotide 8 to nucleotide 343; the nucleotide sequence of SEQ ID NO:75 from nucleotide 50 to nucleotide 343; the nucleotide sequence of the full-length protein coding sequence of clone yd218_1 deposited under accession number ATCC 207004; or the nucleotide sequence of a mature protein coding sequence of clone yd218_1 deposited under accession number ATCC 207004. In other preferred embodiments, the polynucleotide encodes the full-length or a mature protein encoded by the cDNA insert of clone yd218_1 deposited under accession number ATCC 207004. In further preferred embodiments, the present invention provides a polynucleotide encoding a protein comprising a fragment of the amino acid sequence of SEQ ID NO:76 having biological activity, the fragment preferably comprising eight (more preferably twenty, most preferably thirty) contiguous amino acids of SEQ ID NO:76, or a polynucleotide encoding a protein comprising a fragment of the amino acid sequence of SEQ ID NO:76 having biological activity, the fragment comprising the amino acid sequence from amino acid 51 to amino acid 60 of SEQ ID NO:76.

Other embodiments provide the gene corresponding to the cDNA sequence of SEQ ID NO:75.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:75, but excluding the poly(A) tail at the 3' end of SEQ ID NO:75; and
    (ab) the nucleotide sequence of the cDNA insert of clone yd218_1 deposited under accession number ATCC 207004;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:75, but excluding the poly(A) tail at the 3' end of SEQ ID NO:75; and
    (bb) the nucleotide sequence of the cDNA insert of clone yd218_1 deposited under accession number ATCC 207004;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:75, and extending contiguously from a nucleotide sequence corresponding to the 5' end of SEQ ID NO:75 to a nucleotide sequence corresponding to the 3' end of SEQ ID NO:75, but excluding the poly(A) tail at the 3' end of SEQ ID NO:75. Also preferably the polynucleotide isolated according to the above process comprises a nucleotide sequence corresponding to the cDNA sequence of SEQ ID NO:75 from nucleotide 8 to nucleotide 343, and extending contiguously from a nucleotide sequence corresponding to the 5' end of said sequence of SEQ ID NO:75 from nucleotide 8 to nucleotide 343, to a nucleotide sequence corresponding to the 3' end of said sequence of SEQ ID NO:75 from nucleotide 8 to nucleotide 343. Also preferably the polynucleotide isolated according to the above process comprises a nucleotide sequence corresponding to the cDNA sequence of SEQ ID NO:75 from nucleotide 50 to nucleotide 343, and extending contiguously from a nucleotide sequence corresponding to the 5' end of said sequence of SEQ ID NO:75 from nucleotide 50 to nucleotide 343, to a nucleotide sequence corresponding to the 3' end of said sequence of SEQ ID NO:75 from nucleotide 50 to nucleotide 343.

In other embodiments, the present invention provides a composition comprising a protein, wherein said protein comprises an amino acid sequence selected from the group consisting of:

(a) the amino acid sequence of SEQ ID NO:76;
(b) a fragment of the amino acid sequence of SEQ ID NO:76, the fragment comprising eight contiguous amino acids of SEQ ID NO:76; and
(c) the amino acid sequence encoded by the cDNA insert of clone yd218_1 deposited under accession number ATCC 207004;

the protein being substantially free from other mammalian proteins. Preferably such protein comprises the amino acid sequence of SEQ ID NO:76. In further preferred embodiments, the present invention provides a protein comprising a fragment of the amino acid sequence of SEQ ID NO:76 having biological activity, the fragment preferably comprising eight (more preferably twenty, most preferably thirty) contiguous amino acids of SEQ ID NO:76, or a protein comprising a fragment of the amino acid sequence of SEQ ID NO:76 having biological activity, the fragment comprising the amino acid sequence from amino acid 51 to amino acid 60 of SEQ ID NO:76.

In one embodiment, the present invention provides a composition comprising an isolated polynucleotide selected from the group consisting of:

(a) a polynucleotide comprising the nucleotide sequence of SEQ ID NO:77;
(b) a polynucleotide comprising the nucleotide sequence of SEQ ID NO:77 from nucleotide 84 to nucleotide 1679;
(c) a polynucleotide comprising the nucleotide sequence of the full-length protein coding sequence of clone ye11_1 deposited under accession number ATCC 207004;
(d) a polynucleotide encoding the full-length protein encoded by the cDNA insert of clone ye11_1 deposited under accession number ATCC 207004;
(e) a polynucleotide comprising the nucleotide sequence of a mature protein coding sequence of clone ye11_1 deposited under accession number ATCC 207004;
(f) a polynucleotide encoding a mature protein encoded by the cDNA insert of clone ye11_1 deposited under accession number ATCC 207004;
(g) a polynucleotide encoding a protein comprising the amino acid sequence of SEQ ID NO:78;

(h) a polynucleotide encoding a protein comprising a fragment of the amino acid sequence of SEQ ID NO:78 having biological activity, the fragment comprising eight contiguous amino acids of SEQ ID NO:78;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:77.

Preferably, such polynucleotide comprises the nucleotide sequence of SEQ ID NO:77 from nucleotide 84 to nucleotide 1679; the nucleotide sequence of the full-length protein coding sequence of clone ye11_1 deposited under accession number ATCC 207004; or the nucleotide sequence of a mature protein coding sequence of clone ye11_1 deposited under accession number ATCC 207004. In other preferred embodiments, the polynucleotide encodes the full-length or a mature protein encoded by the cDNA insert of clone ye11_1 deposited under accession number ATCC 207004. In further preferred embodiments, the present invention provides a polynucleotide encoding a protein comprising a fragment of the amino acid sequence of SEQ ID NO:78 having biological activity, the fragment preferably comprising eight (more preferably twenty, most preferably thirty) contiguous amino acids of SEQ ID NO:78, or a polynucleotide encoding a protein comprising a fragment of the ammo acid sequence of SEQ ID NO:78 having biological activity, the fragment comprising the amino acid sequence from amino acid 261 to amino acid 270 of SEQ ID NO:78.

Other embodiments provide the gene corresponding to the cDNA sequence of SEQ ID NO:77.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:77, but excluding the poly(A) tail at the 3' end of SEQ ID NO:77; and
    (ab) the nucleotide sequence of the cDNA insert of clone ye11_1 deposited under accession number ATCC 207004;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:77, but excluding the poly(A) tail at the 3' end of SEQ ID NO:77; and
    (bb) the nucleotide sequence of the cDNA insert of clone ye11_1 deposited under accession number ATCC 207004;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:77, and extending contiguously from a nucleotide sequence corresponding to the 5' end of SEQ ID NO:77 to a nucleotide sequence corresponding to the 3' end of SEQ ID NO:77, but excluding the poly(A) tail at the 3' end of SEQ ID NO:77. Also preferably the polynucleotide isolated according to the above process comprises a nucleotide sequence corresponding to the cDNA sequence of SEQ ID NO:77 from nucleotide 84 to nucleotide 1679, and extending contiguously from a nucleotide sequence corresponding to the 5' end of said sequence of SEQ ID NO:77 from nucleotide 84 to nucleotide 1679, to a nucleotide sequence corresponding to the 3' end of said sequence of SEQ ID NO:77 from nucleotide 84 to nucleotide 1679.

In other embodiments, the present invention provides a composition comprising a protein, wherein said protein comprises an amino acid sequence selected from the group consisting of:

(a) the amino acid sequence of SEQ ID NO:78;

(b) a fragment of the amino acid sequence of SEQ ID NO:78, the fragment comprising eight contiguous amino acids of SEQ ID NO:78; and (c) the amino acid sequence encoded by the cDNA insert of clone ye11_1 deposited under accession number ATCC 207004;

the protein being substantially free from other mammalian proteins. Preferably such protein comprises the amino acid sequence of SEQ ID NO:78. In further preferred embodiments, the present invention provides a protein comprising a fragment of the amino acid sequence of SEQ ID NO:78 having biological activity, the fragment preferably comprising eight (more preferably twenty, most preferably thirty) contiguous amino acids of SEQ ID NO:78, or a protein comprising a fragment of the amino acid sequence of SEQ ID NO:78 having biological activity, the fragment comprising the amino acid sequence from amino acid 261 to amino acid 270 of SEQ ID NO:78.

In one embodiment, the present invention provides a composition comprising an isolated polynucleotide selected from the group consisting of:

(a) a polynucleotide comprising the nucleotide sequence of SEQ ID NO:79;

(b) a polynucleotide comprising the nucleotide sequence of SEQ ID NO:79 from nucleotide 72 to nucleotide 1646;

(c) a polynucleotide comprising the nucleotide sequence of SEQ ID NO:79 from nucleotide 180 to nucleotide 1646;

(d) a polynucleotide comprising the nucleotide sequence of the full-length protein coding sequence of clone ye72_1 deposited under accession number ATCC 207004;

(e) a polynucleotide encoding the full-length protein encoded by the cDNA insert of clone ye72_1 deposited under accession number ATCC 207004;

(f) a polynucleotide comprising the nucleotide sequence of a mature protein coding sequence of clone ye72_1 deposited under accession number ATCC 207004;

(g) a polynucleotide encoding a mature protein encoded by the cDNA insert of clone ye72_1 deposited under accession number ATCC 207004;

(h) a polynucleotide encoding a protein comprising the amino acid sequence of SEQ ID NO:80;

(i) a polynucleotide encoding a protein comprising a fragment of the amino acid sequence of SEQ ID NO:80 having biological activity, the fragment comprising eight contiguous amino acids of SEQ ID NO:80;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:79.

Preferably, such polynucleotide comprises the nucleotide sequence of SEQ ID NO:79 from nucleotide 72 to nucleotide 1646; the nucleotide sequence of SEQ ID NO:79 from nucleotide 180 to nucleotide 1646; the nucleotide sequence of the full-length protein coding sequence of clone ye72_1 deposited under accession number ATCC 207004; or the nucleotide sequence of a mature protein coding sequence of clone ye72_1 deposited under accession number ATCC 207004. In other preferred embodiments, the polynucleotide encodes the full-length or a mature protein encoded by the cDNA insert of clone ye72_1 deposited under accession number ATCC 207004. In further preferred embodiments, the present invention provides a polynucleotide encoding a protein comprising a fragment of the amino acid sequence of SEQ ID NO:80 having biological activity, the fragment preferably comprising eight (more preferably twenty, most preferably thirty) contiguous amino acids of SEQ ID NO:80, or a polynucleotide encoding a protein comprising a fragment of the amino acid sequence of SEQ ID NO:80 having biological activity, the fragment comprising the amino acid sequence from amino acid 257 to amino acid 266 of SEQ ID NO:80.

Other embodiments provide the gene corresponding to the cDNA sequence of SEQ ID NO:79.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:79, but excluding the poly(A) tail at the 3' end of SEQ ID NO:79; and (ab) the nucleotide sequence of the cDNA insert of clone ye72_1 deposited under accession number ATCC 207004;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:79, but excluding the poly(A) tail at the 3' end of SEQ ID NO:79; and (bb) the nucleotide sequence of the cDNA insert of clone ye72_1 deposited under accession number ATCC 207004;

(ii) hybridizing said primer(s) to human genomic DNA in conditions at least as stringent as 4×SSC at 50 degrees C.;

(iii) amplifying human DNA sequences; and (iv) isolating the polynucleotide products of step (b)(iii).

Preferably the polynucleotide isolated according to the above process comprises a nucleotide sequence corresponding to the cDNA sequence of SEQ ID NO:79, and extending contiguously from a nucleotide sequence corresponding to the 5' end of SEQ ID NO:79 to a nucleotide sequence corresponding to the 3' end of SEQ ID NO:79, but excluding the poly(A) tail at the 3' end of SEQ ID NO:79. Also preferably the polynucleotide isolated according to the above process comprises a nucleotide sequence corresponding to the cDNA sequence of SEQ ID NO:79 from nucleotide 72 to nucleotide 1646, and extending contiguously from a nucleotide sequence corresponding to the 5' end of said sequence of SEQ ID NO:79 from nucleotide 72 to nucleotide 1646, to a nucleotide sequence corresponding to the 3' end of said sequence of SEQ ID NO:79 from nucleotide 72 to nucleotide 1646. Also preferably the polynucleotide isolated according to the above process comprises a nucleotide sequence corresponding to the cDNA sequence of SEQ ID NO:79 from nucleotide 180 to nucleotide 1646, and extending contiguously from a nucleotide sequence corresponding to the 5' end of said sequence of SEQ ID NO:79 from nucleotide 180 to nucleotide 1646, to a nucleotide sequence corresponding to the 3' end of said sequence of SEQ ID NO:79 from nucleotide 180 to nucleotide 1646.

In other embodiments, the present invention provides a composition comprising a protein, wherein said protein comprises an amino acid sequence selected from the group consisting of:

(a) the amino acid sequence of SEQ ID NO:80;

(b) a fragment of the amino acid sequence of SEQ ID NO:80, the fragment comprising eight contiguous amino acids of SEQ ID NO:80; and (c) the amino acid sequence encoded by the cDNA insert of clone ye72_1 deposited under accession number ATCC 207004;

the protein being substantially free from other mammalian proteins. Preferably such protein comprises the amino acid sequence of SEQ ID NO:80. In further preferred embodiments, the present invention provides a protein comprising a fragment of the ammo acid sequence of SEQ ID NO:80 having biological activity, the fragment preferably comprising eight (more preferably twenty, most preferably thirty) contiguous amino acids of SEQ ID NO:80, or a protein comprising a fragment of the amino acid sequence of SEQ ID NO:80 having biological activity, the fragment comprising the amino acid sequence from amino acid 257 to amino acid 266 of SEQ ID NO:80.

In one embodiment, the present invention provides a composition comprising an isolated polynucleotide selected from the group consisting of:

(a) a polynucleotide comprising the nucleotide sequence of SEQ ID NO:81;

(b) a polynucleotide comprising the nucleotide sequence of SEQ ID NO:81 from nucleotide 954 to nucleotide 2423;

(c) a polynucleotide comprising the nucleotide sequence of SEQ ID NO:81 from nucleotide 1224 to nucleotide 2423;

(d) a polynucleotide comprising the nucleotide sequence of the full-length protein coding sequence of clone ye78_1 deposited under accession number ATCC 207004;

(e) a polynucleotide encoding the full-length protein encoded by the cDNA insert of clone ye78_1 deposited under accession number ATCC 207004;

(f) a polynucleotide comprising the nucleotide sequence of a mature protein coding sequence of clone ye78_1 deposited under accession number ATCC 207004;

(g) a polynucleotide encoding a mature protein encoded by the cDNA insert of clone ye78_1 deposited under accession number ATCC 207004;

(h) a polynucleotide encoding a protein comprising the amino acid sequence of SEQ ID NO:82;

(i) a polynucleotide encoding a protein comprising a fragment of the amino acid sequence of SEQ ID NO:82 having biological activity, the fragment comprising eight contiguous amino acids of SEQ ID NO:82;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:81.

Preferably, such polynucleotide comprises the nucleotide sequence of SEQ ID NO:81 from nucleotide 954 to nucleotide 2423; the nucleotide sequence of SEQ ID NO:81 from nucleotide 1224 to nucleotide 2423; the nucleotide sequence of the full-length protein coding sequence of clone ye78_1 deposited under accession number ATCC 207004; or the nucleotide sequence of a mature protein coding sequence of clone ye78_1 deposited under accession number ATCC 207004. In other preferred embodiments, the polynucleotide encodes the full-length or a mature protein encoded by the cDNA insert of clone ye78_1 deposited under accession number ATCC 207004. In further preferred embodiments, the present invention provides a polynucleotide encoding a protein comprising a fragment of the amino add sequence of SEQ ID NO:82 having biological activity, the fragment preferably comprising eight (more preferably twenty, most preferably thirty) contiguous amino acids of SEQ ID NO:82, or a polynucleotide encoding a protein comprising a fragment of the amino acid sequence of SEQ ID NO:82 having biological activity, the fragment comprising the amino acid sequence from amino acid 240 to amino acid 249 of SEQ ID NO:82.

Other embodiments provide the gene corresponding to the cDNA sequence of SEQ ID NO:81.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:81, but excluding the poly(A) tail at the 3' end of SEQ ID NO:81; and (ab) the nucleotide sequence of the cDNA insert of clone ye78_1 deposited under accession number ATCC 207004;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:81, but excluding the poly(A) tail at the 3' end of SEQ ID NO:81; and (bb) the nucleotide sequence of the cDNA insert of clone ye78_1 deposited under accession number ATCC 207004;

(ii) hybridizing said primer(s) to human genomic DNA in conditions at least as stringent as 4×SSC at 50 degrees C.;

(ii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:81, and extending contiguously from a nucleotide sequence corresponding to the 5' end of SEQ ID NO:81 to a nucleotide sequence corresponding to the 3' end of SEQ ID NO:81, but excluding the poly(A) tail at the 3' end of SEQ ID NO:81. Also preferably the polynucleotide isolated according to the above process comprises a nucleotide sequence corresponding to the cDNA sequence of SEQ ID NO:81 from nucleotide 954 to nucleotide 2423, and extending contiguously from a nucleotide sequence corresponding to the 5' end of said sequence of SEQ ID NO:81 from nucleotide 954 to nucleotide 2423, to a nucleotide sequence corresponding to the 3' end of said sequence of SEQ ID NO:81 from nucleotide 954 to nucleotide 2423. Also preferably the polynucleotide isolated according to the above process comprises a nucleotide sequence corresponding to the cDNA sequence of SEQ ID NO:81 from nucleotide 1224 to nucleotide 2423, and extending contiguously from a nucleotide sequence corresponding to the 5' end of said sequence of SEQ ID NO:81 from nucleotide 1224 to nucleotide 2423, to a nucleotide sequence corresponding to the 3' end of said sequence of SEQ ID NO:81 from nucleotide 1224 to nucleotide 2423.

In other embodiments, the present invention provides a composition comprising a protein, wherein said protein comprises an amino acid sequence selected from the group consisting of:

(a) the amino acid sequence of SEQ ID NO:82;

(b) a fragment of the amino acid sequence of SEQ ID NO:82, the fragment comprising eight contiguous amino acids of SEQ ID NO:82; and (c) the amino acid sequence encoded by the cDNA insert of clone ye78_1 deposited under accession number ATCC 207004;

the protein being substantially free from other mammalian proteins. Preferably such protein comprises the amino acid sequence of SEQ ID NO:82. In further preferred embodiments, the present invention provides a protein comprising a fragment of the amino acid sequence of SEQ ID NO:82 having biological activity, the fragment preferably comprising eight (more preferably twenty, most preferably thirty) contiguous amino acids of SEQ ID NO:82, or a protein comprising a fragment of the amino acid sequence of SEQ ID NO:82 having biological activity, the fragment comprising the amino acid sequence from amino acid 240 to amino acid 249 of SEQ ID NO:82.

In one embodiment, the present invention provides a composition comprising an isolated polynucleotide selected from the group consisting of:

(a) a polynucleotide comprising the nucleotide sequence of SEQ ID NO:83;

(b) a polynucleotide comprising the nucleotide sequence of SEQ ID NO:83 from nucleotide 176 to nucleotide 1321;

(c) a polynucleotide comprising the nucleotide sequence of SEQ ID NO:83 from nucleotide 233 to nucleotide 1321;

(d) a polynucleotide comprising the nucleotide sequence of the full-length protein coding sequence of clone ye90_1 deposited under accession number ATCC 207004;

(e) a polynucleotide encoding the full-length protein encoded by the cDNA insert of clone ye90_1 deposited under accession number ATCC 207004;

(f) a polynucleotide comprising the nucleotide sequence of a mature protein coding sequence of clone ye90_1 deposited under accession number ATCC 207004;

(g) a polynucleotide encoding a mature protein encoded by the cDNA insert of clone ye90_1 deposited under accession number ATCC 207004;

(h) a polynucleotide encoding a protein comprising the amino acid sequence of SEQ ID NO:84;

(i) a polynucleotide encoding a protein comprising a fragment of the amino acid sequence of SEQ ID NO:84 having biological activity, the fragment comprising eight contiguous amino acids of SEQ ID NO:84;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:83.

Preferably, such polynucleotide comprises the nucleotide sequence of SEQ ID NO:83 from nucleotide 176 to nucleotide 1321; the nucleotide sequence of SEQ ID NO:83 from nucleotide 233 to nucleotide 1321; the nucleotide sequence of the full-length protein coding sequence of clone ye90_1 deposited under accession number ATCC 207004; or the nucleotide sequence of a mature protein coding sequence of clone ye90_1 deposited under accession number ATCC 207004. In other preferred embodiments, the polynucleotide encodes the full-length or a mature protein encoded by the cDNA insert of clone ye90_1 deposited under accession number ATCC 207004. In further preferred embodiments, the present invention provides a polynucleotide encoding a protein comprising a fragment of the amino acid sequence of SEQ ID NO:84 having biological activity, the fragment preferably comprising eight (more preferably twenty, most preferably thirty) contiguous amino acids of SEQ ID NO:84, or a polynucleotide encoding a protein comprising a fragment of the amino acid sequence of SEQ ID NO:84 having biological activity, the fragment comprising the amino acid sequence from amino acid 186 to amino acid 195 of SEQ ID NO:84.

Other embodiments provide the gene corresponding to the cDNA sequence of SEQ ID NO:83.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:83, but excluding the poly(A) tail at the 3' end of SEQ ID NO:83; and (ab) the nucleotide sequence of the cDNA insert of clone ye90_1 deposited under accession number ATCC 207004;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:83, but excluding the poly(A) tail at the 3' end of SEQ ID NO:83; and (bb) the nucleotide sequence of the cDNA insert of clone ye90_1 deposited under accession number ATCC 207004;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:83, and extending contiguously from a nucleotide sequence corresponding to the 5' end of SEQ ID NO:83 to a nucleotide sequence corresponding to the 3' end of SEQ ID NO:83, but excluding the poly(A) tail at the 3' end of SEQ ID NO:83. Also preferably the polynucleotide isolated according to the above process comprises a nucleotide sequence corresponding to the cDNA sequence of SEQ ID NO:83 from nucleotide 176 to nucleotide 1321, and extending contiguously from a nucleotide sequence corresponding to the 5' end of said sequence of SEQ ID NO:83 from nucleotide 176 to nucleotide 1321, to a nucleotide sequence corresponding to the 3' end of said sequence of SEQ ID NO:83 from nucleotide 176 to nucleotide 1321. Also preferably the polynucleotide isolated according to the above process comprises a nucleotide sequence corresponding to the cDNA sequence of SEQ ID NO:83 from nucleotide 233 to nucleotide 1321, and extending contiguously from a nucleotide sequence corresponding to the 5' end of said sequence of SEQ ID NO:83 from nucleotide 233 to nucleotide 1321, to a nucleotide sequence corresponding to the 3' end of said sequence of SEQ ID NO:83 from nucleotide 233 to nucleotide 1321.

In other embodiments, the present invention provides a composition comprising a protein, wherein said protein comprises an amino acid sequence selected from the group consisting of:

(a) the amino acid sequence of SEQ ID NO:84;

(b) a fragment of the amino acid sequence of SEQ ID NO:84, the fragment comprising eight contiguous amino acids of SEQ ID NO:84; and (c) the amino acid sequence encoded by the cDNA insert of clone ye90_1 deposited under accession number ATCC 207004;

the protein being substantially free from other mammalian proteins. Preferably such protein comprises the amino acid sequence of SEQ ID NO:84. In further preferred embodiments, the present invention provides a protein comprising a fragment of the amino acid sequence of SEQ ID NO:84 having biological activity, the fragment preferably comprising eight (more preferably twenty, most preferably thirty) contiguous amino acids of SEQ ID NO:84, or a protein comprising a fragment of the amino acid sequence of SEQ ID NO:84 having biological activity, the fragment comprising the amino acid sequence from amino acid 186 to amino acid 195 of SEQ ID NO:84.

In one embodiment, the present invention provides a composition comprising an isolated polynucleotide selected from the group consisting of:

(a) a polynucleotide comprising the nucleotide sequence of SEQ ID NO:85;

(b) a polynucleotide comprising the nucleotide sequence of SEQ ID NO:85 from nucleotide 105 to nucleotide 605;

(c) a polynucleotide comprising the nucleotide sequence of the full-length protein coding sequence of clone yi62_1 deposited under accession number ATCC 207004;

(d) a polynucleotide encoding the full-length protein encoded by the cDNA insert of clone yi62_1 deposited under accession number ATCC 207004;

(e) a polynucleotide comprising the nucleotide sequence of a mature protein coding sequence of clone yi62_1 deposited under accession number ATCC 207004;

(f) a polynucleotide encoding a mature protein encoded by the cDNA insert of clone yi62_1 deposited under accession number ATCC 207004;

(g) a polynucleotide encoding a protein comprising the amino acid sequence of SEQ ID NO:86;

(h) a polynucleotide encoding a protein comprising a fragment of the amino acid sequence of SEQ ID NO:86 having biological activity, the fragment comprising eight contiguous amino acids of SEQ ID NO:86;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:85.

Preferably, such polynucleotide comprises the nucleotide sequence of SEQ ID NO:85 from nucleotide 105 to nucleotide 605; the nucleotide sequence of the full-length protein coding sequence of clone yi62_1 deposited under accession number ATCC 207004; or the nucleotide sequence of a mature protein coding sequence of clone yi62_1 deposited under accession number ATCC 207004. In other preferred embodiments, the polynucleotide encodes the full-length or a mature protein encoded by the cDNA insert of clone yi62_1 deposited under accession number ATCC 207004. In further preferred embodiments, the present invention provides a polynucleotide encoding a protein comprising a fragment of the amino acid sequence of SEQ ID NO:86 having biological activity, the fragment preferably comprising eight (more preferably twenty, most preferably thirty) contiguous amino acids of SEQ ID NO:86, or a polynucleotide encoding a protein comprising a fragment of the amino acid sequence of SEQ ID NO:86 having biological activity, the fragment comprising the amino acid sequence from amino acid 78 to amino acid 87 of SEQ ID NO:86.

Other embodiments provide the gene corresponding to the cDNA sequence of SEQ ID NO:85.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:85, but excluding the poly(A) tail at the 3' end of SEQ ID NO:85; and (ab) the nucleotide sequence of the cDNA insert of clone yi62_1 deposited under accession number ATCC 207004;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:85, but excluding the poly(A) tail at the 3' end of SEQ ID NO:85; and (bb) the nucleotide sequence of the cDNA insert of clone yi62_1 deposited under accession number ATCC 207004;

(ii) hybridizing said primer(s) to human genomic DNA in conditions at least as stringent as 4×SSC at 50 degrees C.;

(iii) amplifying human DNA sequences; and (iv) isolating the polynucleotide products of step (b)(iii).

Preferably the polynucleotide isolated according to the above process comprises a nucleotide sequence corresponding to the cDNA sequence of SEQ ID NO:85, and extending contiguously from a nucleotide sequence corresponding to the 5' end of SEQ ID NO:85 to a nucleotide sequence corresponding to the 3' end of SEQ ID NO:85, but excluding the poly(A) tail at the 3' end of SEQ ID NO:85. Also preferably the polynucleotide isolated according to the above process comprises a nucleotide sequence corresponding to the cDNA sequence of SEQ ID NO:85 from nucleotide 105 to nucleotide 605, and extending contiguously from a nucleotide sequence corresponding to the 5' end of said sequence of SEQ ID NO:85 from nucleotide 105 to nucleotide 605, to a nucleotide sequence corresponding to the 3' end of said sequence of SEQ ID NO:85 from nucleotide 105 to nucleotide 605.

In other embodiments, the present invention provides a composition comprising a protein, wherein said protein comprises an amino acid sequence selected from the group consisting of:

(a) the amino acid sequence of SEQ ID NO:86;

(b) a fragment of the amino acid sequence of SEQ ID NO:86, the fragment comprising eight contiguous amino acids of SEQ ID NO:86; and (c) the amino acid sequence encoded by the cDNA insert of clone yi62_1 deposited under accession number ATCC 207004;

the protein being substantially free from other mammalian proteins. Preferably such protein comprises the amino acid sequence of SEQ ID NO:86. In further preferred embodiments, the present invention provides a protein comprising a fragment of the amino acid sequence of SEQ ID NO:86 having biological activity, the fragment preferably comprising eight (more preferably twenty, most preferably thirty) contiguous amino acids of SEQ ID NO:86, or a protein comprising a fragment of the amino acid sequence of SEQ ID NO:86 having biological activity, the fragment comprising the amino acid sequence from amino acid 78 to amino acid 87 of SEQ ID NO:86.

In one embodiment, the present invention provides a composition comprising an isolated polynucleotide selected from the group consisting of:

(a) a polynucleotide comprising the nucleotide sequence of SEQ ID NO:87;

(b) a polynucleotide comprising the nucleotide sequence of SEQ ID NO:87 from nucleotide 223 to nucleotide 798;

(c) a polynucleotide comprising the nucleotide sequence of SEQ ID NO:87 from nucleotide 430 to nucleotide 798;

(d) a polynucleotide comprising the nucleotide sequence of the full-length protein coding sequence of clone yk78_1 deposited under accession number ATCC 207004;

(e) a polynucleotide encoding the full-length protein encoded by the cDNA insert of clone yk78_1 deposited under accession number ATCC 207004;

(f) a polynucleotide comprising the nucleotide sequence of a mature protein coding sequence of clone yk78_1 deposited under accession number ATCC 207004;

(g) a polynucleotide encoding a mature protein encoded by the cDNA insert of clone yk78_1 deposited under accession number ATCC 207004;

(h) a polynucleotide encoding a protein comprising the amino acid sequence of SEQ ID NO:88;

(i) a polynucleotide encoding a protein comprising a fragment of the amino acid sequence of SEQ ID NO:88 having biological activity, the fragment comprising eight contiguous amino acids of SEQ ID NO:88;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:87.

Preferably, such polynucleotide comprises the nucleotide sequence of SEQ ID NO:87 from nucleotide 223 to nucleotide 798; the nucleotide sequence of SEQ ID NO:87 from nucleotide 430 to nucleotide 798; the nucleotide sequence of the full-length protein coding sequence of clone yk78_1 deposited under accession number ATCC 207004; or the nucleotide sequence of a mature protein coding sequence of clone yk78_1 deposited under accession number ATCC 207004. In other preferred embodiments, the polynucleotide encodes the full-length or a mature protein encoded by the cDNA insert of clone yk78_1 deposited under accession number ATCC 207004. In further preferred embodiments, the present invention provides a polynucleotide encoding a protein comprising a fragment of the amino add sequence of SEQ ID NO:88 having biological activity, the fragment preferably comprising eight (more preferably twenty, most preferably thirty) contiguous amino acids of SEQ ID NO:88, or a polynucleotide encoding a protein comprising a fragment of the amino acid sequence of SEQ ID NO:88 having biological activity, the fragment comprising the amino acid sequence from amino acid 91 to amino acid 100 of SEQ ID NO:88.

Other embodiments provide the gene corresponding to the cDNA sequence of SEQ ID NO:87.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:87, but excluding the poly(A) tail at the 3' end of SEQ ID NO:87; and (ab) the nucleotide sequence of the cDNA insert of clone yk78_1 deposited under accession number ATCC 207004;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:87, but excluding the poly(A) tail at the 3' end of SEQ ID NO:87; and (bb) the nucleotide sequence of the cDNA insert of clone yk78_1 deposited under accession number ATCC 207004;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:87, and extending contiguously from a nucleotide sequence corresponding to the 5' end of SEQ ID NO:87 to a nucleotide sequence corresponding to the 3' end of SEQ ID NO:87, but excluding the poly(A) tail at the 3' end of SEQ ID NO:87. Also preferably the polynucleotide isolated according to the above process comprises a nucleotide sequence corresponding to the cDNA sequence of SEQ ID NO:87 from nucleotide 223 to nucleotide 798, and extending contiguously from a nucleotide sequence corresponding to the 5' end of said sequence of SEQ ID NO:87 from nucleotide 223 to nucleotide 798, to a nucleotide sequence corresponding to the 3' end of said sequence of SEQ ID NO:87 from nucleotide 223 to nucleotide 798. Also preferably the polynucleotide isolated according to the above process comprises a nucleotide sequence corresponding to the cDNA sequence of SEQ ID NO:87 from nucleotide 430 to nucleotide 798, and extending contiguously from a nucleotide sequence corresponding to the 5' end of said sequence of SEQ ID NO:87 from nucleotide 430 to nucleotide 798, to a nucleotide sequence corresponding to the 3' end of said sequence of SEQ ID NO:87 from nucleotide 430 to nucleotide 798.

In other embodiments, the present invention provides a composition comprising a protein, wherein said protein comprises an amino add sequence selected from the group consisting of:

(a) the amino acid sequence of SEQ ID NO:88;

(b) a fragment of the amino acid sequence of SEQ ID NO:88, the fragment comprising eight contiguous amino acids of SEQ ID NO:88; and (c) the amino acid sequence encoded by the cDNA insert of clone yk78__1 deposited under accession number ATCC 207004;

the protein being substantially free from other mammalian proteins. Preferably such protein comprises the amino acid sequence of SEQ ID NO:88. In further preferred embodiments, the present invention provides a protein comprising a fragment of the amino acid sequence of SEQ ID NO:88 having biological activity, the fragment preferably comprising eight (more preferably twenty, most preferably thirty) contiguous amino acids of SEQ ID NO:88, or a protein comprising a fragment of the amino acid sequence of SEQ ID NO:88 having biological activity, the fragment comprising the amino acid sequence from amino acid 91 to amino acid 100 of SEQ ID NO:88.

In one embodiment, the present invention provides a composition comprising an isolated polynucleotide selected from the group consisting of:

(a) a polynucleotide comprising the nucleotide sequence of SEQ ID NO:89;

(b) a polynucleotide comprising the nucleotide sequence of SEQ ID NO:89 from nucleotide 211 to nucleotide 942;

(c) a polynucleotide comprising the nucleotide sequence of SEQ ID NO:89 from nucleotide 298 to nucleotide 942;

(d) a polynucleotide comprising the nucleotide sequence of the full-length protein coding sequence of clone yk251__1 deposited under accession number ATCC 207004;

(e) a polynucleotide encoding the full-length protein encoded by the cDNA insert of clone yk251__1 deposited under accession number ATCC 207004;

(f) a polynucleotide comprising the nucleotide sequence of a mature protein coding sequence of clone yk251__1 deposited under accession number ATCC 207004;

(g) a polynucleotide encoding a mature protein encoded by the cDNA insert of clone yk251__1 deposited under accession number ATCC 207004;

(h) a polynucleotide encoding a protein comprising the amino acid sequence of SEQ ID NO:90;

(i) a polynucleotide encoding a protein comprising a fragment of the amino acid sequence of SEQ ID NO:90 having biological activity, the fragment comprising eight contiguous amino acids of SEQ ID NO:90;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:89.

Preferably, such polynucleotide comprises the nucleotide sequence of SEQ ID NO:89 from nucleotide 211 to nucleotide 942; the nucleotide sequence of SEQ ID NO:89 from nucleotide 298 to nucleotide 942; the nucleotide sequence of the full-length protein coding sequence of clone yk251__1 deposited under accession number ATCC 207004; or the nucleotide sequence of a mature protein coding sequence of clone yk251__1 deposited under accession number ATCC 207004. In other preferred embodiments, the polynucleotide encodes the full-length or a mature protein encoded by the cDNA insert of clone yk251__1 deposited under accession number ATCC 207004. In further preferred embodiments, the present invention provides a polynucleotide encoding a protein comprising a fragment of the amino acid sequence of SEQ ID NO:90 having biological activity, the fragment preferably comprising eight (more preferably twenty, most preferably thirty) contiguous amino acids of SEQ ID NO:90, or a polynucleotide encoding a protein comprising a fragment of the amino acid sequence of SEQ ID NO:90 having biological activity, the fragment comprising the amino acid sequence from amino acid 117 to amino acid 126 of SEQ ID NO:90.

Other embodiments provide the gene corresponding to the cDNA sequence of SEQ ID NO:89.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:89, but excluding the poly(A) tail at the 3' end of SEQ ID NO:89; and (ab) the nucleotide sequence of the cDNA insert of clone yk251__1 deposited under accession number ATCC 207004;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:89, but excluding the poly(A) tail at the 3' end of SEQ ID NO:89; and (bb) the nucleotide sequence of the cDNA insert of clone yk251__1 deposited under accession number ATCC 207004;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:89, and extending contiguously from a nucleotide sequence corresponding to the 5' end of SEQ ID NO:89 to a nucleotide sequence corresponding to the 3' end of SEQ ID NO:89, but excluding the poly(A) tail at the 3' end of SEQ ID NO:89. Also preferably the polynucleotide isolated according to the above process comprises a nucleotide sequence corresponding to the cDNA sequence of SEQ ID NO:89 from nucleotide 211 to nucleotide 942, and extending contiguously from a nucleotide sequence corresponding to the 5' end of said sequence of SEQ ID NO:89 from nucleotide 211 to nucleotide 942, to a nucleotide sequence corresponding to the 3' end of said sequence of SEQ ID NO:89 from nucleotide 211 to nucleotide 942. Also preferably the polynucleotide isolated according to the above process comprises a nucleotide sequence corresponding to the cDNA sequence of SEQ ID NO:89 from nucleotide 298 to nucleotide 942, and extending contiguously from a nucleotide sequence corresponding to the 5' end of said sequence of SEQ ID NO:89 from nucleotide 298 to nucleotide 942, to a nucleotide sequence corresponding to the 3' end of said sequence of SEQ ID NO:89 from nucleotide 298 to nucleotide 942.

In other embodiments, the present invention provides a composition comprising a protein, wherein said protein comprises an amino acid sequence selected from the group consisting of:

(a) the amino acid sequence of SEQ ID NO:90;

(b) a fragment of the amino acid sequence of SEQ ID NO:90, the fragment comprising eight contiguous amino acids of SEQ ID NO:90; and (c) the amino acid sequence encoded by the cDNA insert of clone yk251_1 deposited under accession number ATCC 207004;

the protein being substantially free from other mammalian proteins. Preferably such protein comprises the amino acid sequence of SEQ ID NO:90. In further preferred embodiments, the present invention provides a protein comprising a fragment of the amino acid sequence of SEQ ID NO:90 having biological activity, the fragment preferably comprising eight (more preferably twenty, most preferably thirty) contiguous amino acids of SEQ ID NO:90, or a protein comprising a fragment of the amino acid sequence of SEQ ID NO:90 having biological activity, the fragment comprising the amino acid sequence from amino acid 117 to amino acid 126 of SEQ ID NO:90.

In one embodiment, the present invention provides a composition comprising an isolated polynucleotide selected from the group consisting of:

(a) a polynucleotide comprising the nucleotide sequence of SEQ ID NO:91;

(b) a polynucleotide comprising the nucleotide sequence of SEQ ID NO:91 from nucleotide 149 to nucleotide 784;

(c) a polynucleotide comprising the nucleotide sequence of the full-length protein coding sequence of clone yt14_1 deposited under accession number ATCC 207004;

(d) a polynucleotide encoding the full-length protein encoded by the cDNA insert of clone yt14_1 deposited under accession number ATCC 207004;

(e) a polynucleotide comprising the nucleotide sequence of a mature protein coding sequence of clone yt14_1 deposited under accession number ATCC 207004;

(f) a polynucleotide encoding a mature protein encoded by the cDNA insert of clone yt14_1 deposited under accession number ATCC 207004;

(g) a polynucleotide encoding a protein comprising the amino acid sequence of SEQ ID NO:92;

(h) a polynucleotide encoding a protein comprising a fragment of the amino acid sequence of SEQ ID NO:92 having biological activity, the fragment comprising eight contiguous amino acids of SEQ ID NO:92;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:91.

Preferably, such polynucleotide comprises the nucleotide sequence of SEQ ID NO:91 from nucleotide 149 to nucleotide 784; the nucleotide sequence of the full-length protein coding sequence of clone yt14_1 deposited under accession number ATCC 207004; or the nucleotide sequence of a mature protein coding sequence of clone yt14_1 deposited under accession number ATCC 207004. In other preferred embodiments, the polynucleotide encodes the full-length or a mature protein encoded by the cDNA insert of clone yt14_1 deposited under accession number ATCC 207004. In further preferred embodiments, the present invention provides a polynucleotide encoding a protein comprising a fragment of the amino acid sequence of SEQ ID NO:92 having biological activity, the fragment preferably comprising eight (more preferably twenty, most preferably thirty) contiguous amino acids of SEQ ID NO:92, or a polynucleotide encoding a protein comprising a fragment of the amino acid sequence of SEQ ID NO:92 having biological activity, the fragment comprising the amino acid sequence from amino acid 101 to amino acid 110 of SEQ ID NO:92.

Other embodiments provide the gene corresponding to the cDNA sequence of SEQ ID NO:91.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:91, but excluding the poly(A) tail at the 3' end of SEQ ID NO:91; and
    (ab) the nucleotide sequence of the cDNA insert of clone yt14_1 deposited under accession number ATCC 207004;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:91, but excluding the poly(A) tail at the 3' end of SEQ ID NO:91; and
    (bb) the nucleotide sequence of the cDNA insert of clone yt14_1 deposited under accession number ATCC 207004;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:91, and extending contiguously from a nucleotide sequence corresponding to the 5' end of SEQ ID NO:91 to a nucleotide sequence corresponding to the 3' end of SEQ ID NO:91, but excluding the poly(A) tail at the 3' end of SEQ ID NO:91. Also preferably the polynucleotide isolated according to the above process comprises a nucleotide sequence corresponding to the cDNA sequence of SEQ ID NO:91 from nucleotide 149 to nucleotide 784, and extending contiguously from a nucleotide sequence corresponding to the 5' end of said sequence of SEQ ID NO:91 from nucleotide 149 to nucleotide 784, to a nucleotide sequence corresponding to the 3' end of said sequence of SEQ ID NO:91 from nucleotide 149 to nucleotide 784.

In other embodiments, the present invention provides a composition comprising a protein, wherein said protein comprises an amino acid sequence selected from the group consisting of:

(a) the amino acid sequence of SEQ ID NO:92;

(b) a fragment of the amino acid sequence of SEQ ID NO:92, the fragment comprising eight contiguous amino acids of SEQ ID NO:92; and (c) the amino acid sequence encoded by the cDNA insert of clone yt14__1 deposited under accession number ATCC 207004;

the protein being substantially free from other mammalian proteins. Preferably such protein comprises the amino acid sequence of SEQ ID NO:92. In further preferred embodiments, the present invention provides a protein comprising a fragment of the amino acid sequence of SEQ ID NO:92 having biological activity, the fragment preferably comprising eight (more preferably twenty, most preferably thirty) contiguous amino acids of SEQ ID NO:92, or a protein comprising a fragment of the amino acid sequence of SEQ ID NO:92 having biological activity, the fragment comprising the amino acid sequence from amino acid 101 to amino acid 110 of SEQ ID NO:92.

In one embodiment, the present invention provides a composition comprising an isolated polynucleotide selected from the group consisting of:

(a) a polynucleotide comprising the nucleotide sequence of SEQ ID NO:93;

(b) a polynucleotide comprising the nucleotide sequence of SEQ ID NO:93 from nucleotide 89 to nucleotide 1441;

(c) a polynucleotide comprising the nucleotide sequence of the full-length protein coding sequence of clone bf157__16 deposited under accession number ATCC 207088;

(d) a polynucleotide encoding the full-length protein encoded by the cDNA insert of clone bf157__16 deposited under accession number ATCC 207088;

(e) a polynucleotide comprising the nucleotide sequence of a mature protein coding sequence of clone bf157__16 deposited under accession number ATCC 207088;

(f) a polynucleotide encoding a mature protein encoded by the cDNA insert of clone bf157__16 deposited under accession number ATCC 207088;

(g) a polynucleotide encoding a protein comprising the amino acid sequence of SEQ ID NO:94;

(h) a polynucleotide encoding a protein comprising a fragment of the amino acid sequence of SEQ ID NO:94 having biological activity, the fragment comprising eight contiguous amino acids of SEQ ID NO:94;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:93.

Preferably, such polynucleotide comprises the nucleotide sequence of SEQ ID NO:93 from nucleotide 89 to nucleotide 1441; the nucleotide sequence of the full-length protein coding sequence of clone bf157__16 deposited under accession number ATCC 207088; or the nucleotide sequence of a mature protein coding sequence of clone bf157__16 deposited under accession number ATCC 207088. In other preferred embodiments, the polynucleotide encodes the full-length or a nature protein encoded by the cDNA insert of clone bf157__16 deposited under accession number ATCC 207088. In further preferred embodiments, the present invention provides a polynucleotide encoding a protein comprising a fragment of the amino acid sequence of SEQ ID. NO:94 having biological activity, the fragment preferably comprising eight (more preferably twenty, most preferably thirty) contiguous amino acids of SEQ ID NO:94, or a polynucleotide encoding a protein comprising a fragment of the amino acid sequence of SEQ ID NO:94 having biological activity, the fragment comprising the amino acid sequence from amino acid 220 to amino acid 229 of SEQ ID NO:94.

Other embodiments provide the gene corresponding to the cDNA sequence of SEQ ID NO:93.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:93, but excluding the poly(A) tail at the 3' end of SEQ ID NO:93; and (ab) the nucleotide sequence of the cDNA insert of clone bf157__16 deposited under accession number ATCC 207088;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:93, but excluding the poly(A) tail at the 3' end of SEQ ID NO:93; and (bb) the nucleotide sequence of the cDNA insert of clone bf157__16 deposited under accession number ATCC 207088;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:93, and extending contiguously from a nucleotide sequence corresponding to the 5' end of SEQ ID NO:93 to a nucleotide sequence corresponding to the 3' end of SEQ ID NO:93, but excluding the poly(A) tail at the 3' end of SEQ ID NO:93. Also preferably the polynucleotide isolated according to the above process comprises a nucleotide sequence corresponding to the cDNA sequence of SEQ ID NO:93 from nucleotide 89 to nucleotide 1441, and extending contiguously from a nucleotide sequence corresponding to the 5' end of said sequence of SEQ ID NO:93 from nucleotide 89 to nucleotide 1441, to a nucleotide sequence corresponding to the 3' end of said sequence of SEQ ID NO:93 from nucleotide 89 to nucleotide 1441.

In other embodiments, the present invention provides a composition comprising a protein, wherein said protein comprises an amino acid sequence selected from the group consisting of:

(a) the amino acid sequence of SEQ ID NO:94;

(b) a fragment of the amino acid sequence of SEQ ID NO:94, the fragment comprising eight contiguous amino acids of SEQ ID NO:94; and (c) the amino acid sequence encoded by the cDNA insert of clone bf157_16 deposited under accession number ATCC 207088;

the protein being substantially free from other mammalian proteins. Preferably such protein comprises the amino acid sequence of SEQ ID NO:94. In further preferred embodiments, the present invention provides a protein comprising a fragment of the amino acid sequence of SEQ ID NO:94 having biological activity, the fragment preferably comprising eight (more preferably twenty, most preferably thirty) contiguous amino adds of SEQ ID NO:94, or a protein comprising a fragment of the amino acid sequence of SEQ ID NO:94 having biological activity, the fragment comprising the amino acid sequence from amino acid 220 to amino acid 229 of SEQ ID NO:94.

In one embodiment, the present invention provides a composition comprising an isolated polynucleotide selected from the group consisting of:

(a) a polynucleotide comprising the nucleotide sequence of SEQ ID NO:95;

(b) a polynucleotide comprising the nucleotide sequence of SEQ ID NO:95 from nucleotide 219 to nucleotide 629;

(c) a polynucleotide comprising the nucleotide sequence of the full-length protein coding sequence of clone bk343_2 deposited under accession number ATCC 207088;

(d) a polynucleotide encoding the full-length protein encoded by the cDNA insert of clone bk343_2 deposited under accession number ATCC 207088;

(e) a polynucleotide comprising the nucleotide sequence of a mature protein coding sequence of clone bk343_2 deposited under accession number ATCC 207088;

(f) a polynucleotide encoding a mature protein encoded by the cDNA insert of clone bk343_2 deposited under accession number ATCC 207088;

(g) a polynucleotide encoding a protein comprising the amino acid sequence of SEQ ID NO:96;

(h) a polynucleotide encoding a protein comprising a fragment of the amino acid sequence of SEQ ID NO:96 having biological activity, the fragment comprising eight contiguous amino acids of SEQ ID NO:96;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:95.

Preferably, such polynucleotide comprises the nucleotide sequence of SEQ ID NO:95 from nucleotide 219 to nucleotide 629; the nucleotide sequence of the full-length protein coding sequence of clone bk343_2 deposited under accession number ATCC 207088; or the nucleotide sequence of a mature protein coding sequence of clone bk343_2 deposited under accession number ATCC 207088. In other preferred embodiments, the polynucleotide encodes the full-length or a mature protein encoded by the cDNA insert of clone bk343_2 deposited under accession number ATCC 207088. In further preferred embodiments, the present invention provides a polynucleotide encoding a protein comprising a fragment of the amino acid sequence of SEQ ID NO:96 having biological activity, the fragment preferably comprising eight (more preferably twenty, most preferably thirty) contiguous amino acids of SEQ ID NO:96, or a polynucleotide encoding a protein comprising a fragment of the amino acid sequence of SEQ ID NO:96 having biological activity, the fragment comprising the amino acid sequence from amino acid 63 to amino acid 72 of SEQ ID NO:96.

Other embodiments provide the gene corresponding to the cDNA sequence of SEQ ID NO:95.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:95, but excluding the poly(A) tail at the 3' end of SEQ ID NO:95; and (ab) the nucleotide sequence of the cDNA insert of clone bk343_2 deposited under accession number ATCC 207088;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:95, but excluding the poly(A) tail at the 3' end of SEQ ID NO:95; and (bb) the nucleotide sequence of the cDNA insert of clone bk343 2 deposited under accession number ATCC 207088;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:95, and extending contiguously from a nucleotide sequence corresponding to the 5' end of SEQ ID NO:95 to a nucleotide sequence corresponding to the 3' end of SEQ ID NO:95, but excluding the poly(A) tail at the 3' end of SEQ ID NO:95. Also preferably the polynucleotide isolated according to the above process comprises a nucleotide sequence corresponding to the cDNA sequence of SEQ ID NO:95 from nucleotide 219 to nucleotide 629, and extending contiguously from a nucleotide sequence corresponding to the 5' end of said sequence of SEQ ID NO:95 from nucleotide 219 to nucleotide 629, to a nucleotide sequence corresponding to the 3' end of said sequence of SEQ ID NO:95 from nucleotide 219 to nucleotide 629.

In other embodiments, the present invention provides a composition comprising a protein, wherein said protein comprises an amino acid sequence selected from the group consisting of:

(a) the amino acid sequence of SEQ ID NO:96;

(b) a fragment of the amino acid sequence of SEQ ID NO:96, the fragment comprising eight contiguous amino acids of SEQ ID NO:96; and (c) the amino acid sequence encoded by the cDNA insert of clone bk343__2 deposited under accession number ATCC 207088;

the protein being substantially free from other mammalian proteins. Preferably such protein comprises the amino acid sequence of SEQ ID NO:96. In further preferred embodiments, the present invention provides a protein comprising a fragment of the amino acid sequence of SEQ ID NO:96 having biological activity, the fragment preferably comprising eight (more preferably twenty, most preferably thirty) contiguous amino acids of SEQ ID NO:96, or a protein comprising a fragment of the amino add sequence of SEQ ID NO:96 having biological activity, the fragment comprising the amino acid sequence from amino acid 63 to amino acid 72 of SEQ ID NO:96.

In one embodiment, the present invention provides a composition comprising an isolated polynucleotide selected from the group consisting of:

(a) a polynucleotide comprising the nucleotide sequence of SEQ ID NO:97;

(b) a polynucleotide comprising the nucleotide sequence of SEQ ID NO:97 from nucleotide 556 to nucleotide 951;

(c) a polynucleotide comprising the nucleotide sequence of SEQ ID NO:97 from nucleotide 868 to nucleotide 951;

(d) a polynucleotide comprising the nucleotide sequence of SEQ ID NO:97 from nucleotide 9 to nucleotide 1295;

(e) a polynucleotide comprising the nucleotide sequence of the full-length protein coding sequence of clone cd205__2 deposited under accession number ATCC 207088;

(f) a polynucleotide encoding the full-length protein encoded by the cDNA insert of clone cd205__2 deposited under accession number ATCC 207088;

(g) a polynucleotide comprising the nucleotide sequence of a mature protein coding sequence of clone cd205__2 deposited under accession number ATCC 207088;

(h) a polynucleotide encoding a mature protein encoded by the cDNA insert of clone cd205__2 deposited under accession number ATCC 207088;

(i) a polynucleotide encoding a protein comprising the amino acid sequence of SEQ ID NO:98;

(j) a polynucleotide encoding a protein comprising a fragment of the amino acid sequence of SEQ ID NO:98 having biological activity, the fragment comprising eight contiguous amino acids of SEQ ID NO:98;

(k) a polynucleotide which is an allelic variant of a polynucleotide of (a)-(h) above;

(l) a polynucleotide which encodes a species homologue of the protein of (i) or (j) above;

(m) a polynucleotide that hybridizes under stringent conditions to any one of the polynucleotides specified in (a)-(j); and (n) a polynucleotide that hybridizes under stringent conditions to any one of the polynucleotides specified in (a)-(j) and that has a length that is at least 25% of the length of SEQ ID NO:97.

Preferably, such polynucleotide comprises the nucleotide sequence of SEQ ID NO:97 from nucleotide 556 to nucleotide 951; the nucleotide sequence of SEQ ID NO:97 from nucleotide 868 to nucleotide 951; the nucleotide sequence of SEQ ID NO:97 from nucleotide 9 to nucleotide 1295; the nucleotide sequence of the full-length protein coding sequence of clone cd205__2 deposited under accession number ATCC 207088; or the nucleotide sequence of a mature protein coding sequence of clone cd205__2 deposited under accession number ATCC 207088. In other preferred embodiments, the polynucleotide encodes the full-length or a mature protein encoded by the cDNA insert of clone cd205__2 deposited under accession number ATCC 207088. In further preferred embodiments, the present invention provides a polynucleotide encoding a protein comprising a fragment of the amino acid sequence of SEQ ID NO:98 having biological activity, the fragment preferably comprising eight (more preferably twenty, most preferably thirty) contiguous amino acids of SEQ ID NO:98, or a polynucleotide encoding a protein comprising a fragment of the amino acid sequence of SEQ ID NO:98 having biological activity, the fragment comprising the amino acid sequence from amino acid 61 to amino acid 70 of SEQ ID NO:98.

Other embodiments provide the gene corresponding to the cDNA sequence of SEQ ID NO:97.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:97, but excluding the poly(A) tail at the 3' end of SEQ ID NO:97; and (ab) the nucleotide sequence of the cDNA insert of clone cd205__2 deposited under accession number ATCC 207088;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:97, but excluding the poly(A) tail at the 3' end of SEQ ID NO:97; and (bb) the nucleotide sequence of the cDNA insert of clone cd205_2 deposited under accession number ATCC 207088;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:97, and extending contiguously from a nucleotide sequence corresponding to the 5' end of SEQ ID NO:97 to a nucleotide sequence corresponding to the 3' end of SEQ ID NO:97, but excluding the poly(A) tail at the 3' end of SEQ ID NO:97. Also preferably the polynucleotide isolated according to the above process comprises a nucleotide sequence corresponding to the cDNA sequence of SEQ ID NO:97 from nucleotide 556 to nucleotide 951, and extending contiguously from a nucleotide sequence corresponding to the 5' end of said sequence of SEQ ID NO:97 from nucleotide 556 to nucleotide 951, to a nucleotide sequence corresponding to the 3' end of said sequence of SEQ ID NO:97 from nucleotide 556 to nucleotide 951. Also preferably the polynucleotide isolated according to the above process comprises a nucleotide sequence corresponding to the cDNA sequence of SEQ ID NO:97 from nucleotide 868 to nucleotide 951, and extending contiguously from a nucleotide sequence corresponding to the 5' end of said sequence of SEQ ID NO:97 from nucleotide 868 to nucleotide 951, to a nucleotide sequence corresponding to the 3' end of said sequence of SEQ ID NO:97 from nucleotide 868 to nucleotide 951. Also preferably the polynucleotide isolated according to the above process comprises a nucleotide sequence corresponding to the cDNA sequence of SEQ ID NO:97 from nucleotide 9 to nucleotide 1295, and extending contiguously from a nucleotide sequence corresponding to the 5' end of said sequence of SEQ ID NO:97 from nucleotide 9 to nucleotide 1295, to a nucleotide sequence corresponding to the 3' end of said sequence of SEQ ID NO:97 from nucleotide 9 to nucleotide 1295.

In other embodiments, the present invention provides a composition comprising a protein, wherein said protein comprises an amino acid sequence selected from the group consisting of:

(a) the amino acid sequence of SEQ ID NO:98;

(b) a fragment of the amino acid sequence of SEQ ID NO:98, the fragment comprising eight contiguous amino acids of SEQ ID NO:98; and (c) the amino acid sequence encoded by the cDNA insert of clone cd205_2 deposited under accession number ATCC 207088;

the protein being substantially free from other mammalian proteins. Preferably such protein comprises the amino acid sequence of SEQ ID NO:98. In further preferred embodiments, the present invention provides a protein comprising a fragment of the amino acid sequence of SEQ ID NO:98 having biological activity, the fragment preferably comprising eight (more preferably twenty, most preferably thirty) contiguous amino acids of SEQ ID NO:98, or a protein comprising a fragment of the amino acid sequence of SEQ ID NO:98 having biological activity, the fragment comprising the amino acid sequence from amino acid 61 to amino acid 70 of SEQ ID NO:98.

In one embodiment, the present invention provides a composition comprising an isolated polynucleotide selected from the group consisting of:

(a) a polynucleotide comprising the nucleotide sequence of SEQ ID NO:99;

(b) a polynucleotide comprising the nucleotide sequence of SEQ ID NO:99 from nucleotide 216 to nucleotide 443;

(c) a polynucleotide comprising the nucleotide sequence of SEQ ID NO:99 from nucleotide 306 to nucleotide 443;

(d) a polynucleotide comprising the nucleotide sequence of the full-length protein coding sequence of clone cw1292_8 deposited under accession number ATCC 207088;

(e) a polynucleotide encoding the full-length protein encoded by the cDNA insert of clone cw1292_8 deposited under accession number ATCC 207088;

(f) a polynucleotide comprising the nucleotide sequence of a mature protein coding sequence of clone cw1292_8 deposited under accession number ATCC 207088;

(g) a polynucleotide encoding a mature protein encoded by the cDNA insert of clone cw1292_8 deposited under accession number ATCC 207088;

(h) a polynucleotide encoding a protein comprising the amino acid sequence of SEQ ID NO:100;

(i) a polynucleotide encoding a protein comprising a fragment of the amino acid sequence of SEQ ID NO:100 having biological activity, the fragment comprising eight contiguous amino acids of SEQ ID NO:100;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:99.

Preferably, such polynucleotide comprises the nucleotide sequence of SEQ ID NO:99 from nucleotide 216 to nucleotide 443; the nucleotide sequence of SEQ ID NO:99 from nucleotide 306 to nucleotide 443; the nucleotide sequence of the full-length protein coding sequence of clone cw1292_8 deposited under accession number ATCC 207088; or the nucleotide sequence of a mature protein coding sequence of clone cw1292_8 deposited under accession number ATCC 207088. In other preferred embodiments, the polynucleotide encodes the full-length or a mature protein encoded by the cDNA insert of clone cw1292_8 deposited under accession number ATCC 207088. In further preferred embodiments, the present invention provides a polynucleotide encoding a protein comprising a fragment of the amino acid sequence of SEQ ID NO:100 having biological activity, the fragment preferably comprising eight (more preferably twenty, most preferably thirty) contiguous amino acids of SEQ ID NO:100, or a polynucleotide encoding a protein comprising a fragment of the amino acid sequence of SEQ ID NO:100 having biological activity, the fragment comprising the amino acid sequence from amino acid 33 to amino acid 42 of SEQ ID NO:100.

Other embodiments provide the gene corresponding to the cDNA sequence of SEQ ID NO:99.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:99, but excluding the poly(A) tail at the 3' end of SEQ ID NO:99; and (ab) the nucleotide sequence of the cDNA insert of clone cw1292_8 deposited under accession number ATCC 207088;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:99, but excluding the poly(A) tail at the 3' end of SEQ ID NO:99; and (bb) the nucleotide sequence of the cDNA insert of clone cw1292_8 deposited under accession number ATCC 207088;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:99, and extending contiguously from a nucleotide sequence corresponding to the 5' end of SEQ ID NO:99 to a nucleotide sequence corresponding to the 3' end of SEQ ID NO:99, but excluding the poly(A) tail at the 3' end of SEQ ID NO:99. Also preferably the polynucleotide isolated according to the above process comprises a nucleotide sequence corresponding to the cDNA sequence of SEQ ID NO:99 from nucleotide 216 to nucleotide 443, and extending contiguously from a nucleotide sequence corresponding to the 5' end of said sequence of SEQ ID NO:99 from nucleotide 216 to nucleotide 443, to a nucleotide sequence corresponding to the 3' end of said sequence of SEQ ID NO:99 from nucleotide 216 to nucleotide 443. Also preferably the polynucleotide isolated according to the above process comprises a nucleotide sequence corresponding to the cDNA sequence of SEQ ID NO:99 from nucleotide 306 to nucleotide 443, and extending contiguously from a nucleotide sequence corresponding to the 5' end of said sequence of SEQ ID NO:99 from nucleotide 306 to nucleotide 443, to a nucleotide sequence corresponding to the 3' end of said sequence of SEQ ID NO:99 from nucleotide 306 to nucleotide 443.

In other embodiments, the present invention provides a composition comprising a protein, wherein said protein comprises an amino acid sequence selected from the group consisting of:

(a) the amino acid sequence of SEQ ID NO:100;

(b) a fragment of the amino acid sequence of SEQ ID NO:100, the fragment comprising eight contiguous amino acids of SEQ ID NO:100; and (c) the amino acid sequence encoded by the cDNA insert of clone cw1292_8 deposited under accession number ATCC 207088;

the protein being substantially free from other mammalian proteins. Preferably such protein comprises the amino acid sequence of SEQ ID NO:100. In further preferred embodiments, the present invention provides a protein comprising a fragment of the amino acid sequence of SEQ ID NO:100 having biological activity, the fragment preferably comprising eight (more preferably twenty, most preferably thirty) contiguous amino acids of SEQ ID NO:100, or a protein comprising a fragment of the amino acid sequence of SEQ ID NO:100 having biological activity, the fragment comprising the amino acid sequence from amino acid 33 to amino acid 42 of SEQ ID NO:100.

In one embodiment, the present invention provides a composition comprising an isolated polynucleotide selected from the group consisting of:

(a) a polynucleotide comprising the nucleotide sequence of SEQ ID NO:101;

(b) a polynucleotide comprising the nucleotide sequence of SEQ ID NO:101 from nucleotide 2136 to nucleotide 2447;

(c) a polynucleotide comprising the nucleotide sequence of the full-length protein coding sequence of clone cw1475_2 deposited under accession number ATCC 207088;

(d) a polynucleotide encoding the full-length protein encoded by the cDNA insert of clone cw1475_2 deposited under accession number ATCC 207088;

(e) a polynucleotide comprising the nucleotide sequence of a mature protein coding sequence of clone cw1475_2 deposited under accession number ATCC 207088;

(f) a polynucleotide encoding a mature protein encoded by the cDNA insert of clone cw1475_2 deposited under accession number ATCC 207088;

(g) a polynucleotide encoding a protein comprising the amino acid sequence of SEQ ID NO:102;

(h) a polynucleotide encoding a protein comprising a fragment of the amino acid sequence of SEQ ID NO:102 having biological activity, the fragment comprising eight contiguous amino acids of SEQ ID NO:102;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:101.

Preferably, such polynucleotide comprises the nucleotide sequence of SEQ ID NO:101 from nucleotide 2136 to nucleotide 2447; the nucleotide sequence of the full-length protein coding sequence of clone cw1475_2 deposited under accession number ATCC 207088; or the nucleotide sequence of a mature protein coding sequence of clone cw1475_2 deposited under accession number ATCC 207088. In other preferred embodiments, the polynucleotide encodes the full-length or a mature protein encoded by the cDNA insert of clone cw1475_2 deposited under accession number ATCC 207088.

In further preferred embodiments, the present invention provides a polynucleotide encoding a protein comprising a fragment of the amino acid sequence of SEQ ID NO:102 having biological activity, the fragment preferably comprising eight (more preferably twenty, most preferably thirty) contiguous amino acids of SEQ ID NO:102, or a polynucleotide encoding a protein comprising a fragment of the amino acid sequence of SEQ ID NO:102 having biological activity, the fragment comprising the amino acid sequence from amino acid 47 to amino acid 56 of SEQ ID NO:102.

Other embodiments provide the gene corresponding to the cDNA sequence of SEQ ID NO:101.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:101, but excluding the poly(A) tail at the 3' end of SEQ ID NO:101; and
    (ab) the nucleotide sequence of the cDNA insert of clone cw1475_2 deposited under accession number ATCC 207088;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:101, but excluding the poly(A) tail at the 3' end of SEQ ID NO:101; and
    (bb) the nucleotide sequence of the cDNA insert of clone cw1475_2 deposited under accession number ATCC 207088;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:101, and extending contiguously from a nucleotide sequence corresponding to the 5' end of SEQ ID NO:101 to a nucleotide sequence corresponding to the 3' end of SEQ ID NO:101, but excluding the poly(A) tail at the 3' end of SEQ ID NO:101. Also preferably the polynucleotide isolated according to the above process comprises a nucleotide sequence corresponding to the cDNA sequence of SEQ ID NO:101 from nucleotide 2136 to nucleotide 2447, and extending contiguously from a nucleotide sequence corresponding to the 5' end of said sequence of SEQ ID NO:101 from nucleotide 2136 to nucleotide 2447, to a nucleotide sequence corresponding to the 3' end of said sequence of SEQ ID NO:101 from nucleotide 2136 to nucleotide 2447.

In other embodiments, the present invention provides a composition comprising a protein, wherein said protein comprises an amino acid sequence selected from the group consisting of:

(a) the amino acid sequence of SEQ ID NO:102;
(b) a fragment of the amino acid sequence of SEQ ID NO:102, the fragment comprising eight contiguous amino acids of SEQ ID NO:102; and
(c) the amino acid sequence encoded by the cDNA insert of clone cw1475_2 deposited under accession number ATCC 207088;

the protein being substantially free from other mammalian proteins. Preferably such protein comprises the amino acid sequence of SEQ ID NO:102. In further preferred embodiments, the present invention provides a protein comprising a fragment of the amino acid sequence of SEQ ID NO:102 having biological activity, the fragment preferably comprising eight (more preferably twenty, most preferably thirty) contiguous amino acids of SEQ ID NO:102, or a protein comprising a fragment of the amino acid sequence of SEQ ID NO:102 having biological activity, the fragment comprising the amino acid sequence from amino acid 47 to amino acid 56 of SEQ ID NO:102.

In one embodiment, the present invention provides a composition comprising an isolated polynucleotide selected from the group consisting of:

(a) a polynucleotide comprising the nucleotide sequence of SEQ ID NO:103;
(b) a polynucleotide comprising the nucleotide sequence of SEQ ID NO:103 from nucleotide 310 to nucleotide 954;
(c) a polynucleotide comprising the nucleotide sequence of the full-length protein coding sequence of clone dd428_4 deposited under accession number ATCC 207088;
(d) a polynucleotide encoding the full-length protein encoded by the cDNA insert of clone dd428_4 deposited under accession number ATCC 207088;
(e) a polynucleotide comprising the nucleotide sequence of a mature protein coding sequence of clone dd428_4 deposited under accession number ATCC 207088;
(f) a polynucleotide encoding a mature protein encoded by the cDNA insert of clone dd428_4 deposited under accession number ATCC 207088;
(g) a polynucleotide encoding a protein comprising the amino acid sequence of SEQ ID NO:104;
(h) a polynucleotide encoding a protein comprising a fragment of the amino acid sequence of SEQ ID NO:104 having biological activity, the fragment comprising eight contiguous amino acids of SEQ ID NO:104;
(i) a polynucleotide which is an allelic variant of a polynucleotide of (a)-(f) above;
(j) a polynucleotide which encodes a species homologue of the protein of (g) or (h) above;
(k) a polynucleotide that hybridizes under stringent conditions to any one of the polynucleotides specified in (a)-(h); and
(l) a polynucleotide that hybridizes under stringent conditions to any one of the polynucleotides specified in (a)-(h) and that has a length that is at least 25% of the length of SEQ ID NO:103.

Preferably, such polynucleotide comprises the nucleotide sequence of SEQ ID NO:103 from nucleotide 310 to nucleotide 954; the nucleotide sequence of the full-length protein coding sequence of clone dd428_4 deposited under accession number ATCC 207088; or the nucleotide sequence of a mature protein coding sequence of clone dd428_4 deposited under accession number ATCC 207088. In other preferred embodiments, the polynucleotide encodes the full-length or a mature protein encoded by the cDNA insert of clone dd428_4 deposited under accession number ATCC 207088. In further preferred embodiments, the present invention provides a polynucleotide encoding a protein comprising a fragment of the amino acid sequence of SEQ ID NO:104 having biological activity, the fragment preferably comprising eight (more preferably twenty, most preferably thirty) contiguous amino acids of SEQ ID NO:104, or a polynucleotide encoding a protein comprising a fragment of the amino acid sequence of SEQ ID NO:104 having biological activity, the fragment comprising the amino acid sequence from amino acid 102 to amino acid 111 of SEQ ID NO:104.

Other embodiments provide the gene corresponding to the cDNA sequence of SEQ ID NO:103.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:103, but excluding the poly(A) tail at the 3' end of SEQ ID NO:103; and
    (ab) the nucleotide sequence of the cDNA insert of clone dd428_4 deposited under accession number ATCC 207088;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:103, but excluding the poly(A) tail at the 3' end of SEQ ID NO:103; and
    (bb) the nucleotide sequence of the cDNA insert of clone dd428_4 deposited under accession number ATCC 207088;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:103, and extending contiguously from a nucleotide sequence corresponding to the 5' end of SEQ ID NO:103 to a nucleotide sequence corresponding to the 3' end of SEQ ID NO:103, but excluding the poly(A) tail at the 3' end of SEQ ID NO:103. Also preferably the polynucleotide isolated according to the above process comprises a nucleotide sequence corresponding to the cDNA sequence of SEQ ID NO:103 from nucleotide 310 to nucleotide 954, and extending contiguously from a nucleotide sequence corresponding to the 5' end of said sequence of SEQ ID NO:103 from nucleotide 310 to nucleotide 954, to a nucleotide sequence corresponding to the 3' end of said sequence of SEQ ID NO: 103 from nucleotide 310 to nucleotide 954.

In other embodiments, the present invention provides a composition comprising a protein, wherein said protein comprises an amino acid sequence selected from the group consisting of:

(a) the amino acid sequence of SEQ ID NO:104;
(b) a fragment of the amino acid sequence of SEQ ID NO:104, the fragment comprising eight contiguous amino acids of SEQ ID NO:104; and
(c) the amino acid sequence encoded by the cDNA insert of clone dd428_4 deposited under accession number ATCC 207088;

the protein being substantially free from other mammalian proteins. Preferably such protein comprises the amino acid sequence of SEQ ID NO:104. In further preferred embodiments, the present invention provides a protein comprising a fragment of the amino acid sequence of SEQ ID NO:104 having biological activity, the fragment preferably comprising eight (more preferably twenty, most preferably thirty) contiguous amino acids of SEQ ID NO:104, or a protein comprising a fragment of the amino acid sequence of SEQ ID NO:104 having biological activity, the fragment comprising the amino acid sequence from amino acid 102 to amino acid 111 of SEQ ID NO:104.

In one embodiment, the present invention provides a composition comprising an isolated polynucleotide selected from the group consisting of:

(a) a polynucleotide comprising the nucleotide sequence of SEQ ID NO:105;
(b) a polynucleotide comprising the nucleotide sequence of SEQ ID NO:105 from nucleotide 1698 to nucleotide 1895;
(c) a polynucleotide comprising the nucleotide sequence of the full-length protein coding sequence of clone dh1073_12 deposited under accession number ATCC 207088;
(d) a polynucleotide encoding the full-length protein encoded by the cDNA insert of clone dh1073_12 deposited under accession number ATCC 207088;
(e) a polynucleotide comprising the nucleotide sequence of a mature protein coding sequence of clone dh1073_12 deposited under accession number ATCC 207088;
(f) a polynucleotide encoding a mature protein encoded by the cDNA insert of clone dh1073_12 deposited under accession number ATCC 207088;
(g) a polynucleotide encoding a protein comprising the amino acid sequence of SEQ ID NO:106;
(h) a polynucleotide encoding a protein comprising a fragment of the amino acid sequence of SEQ ID NO:106 having biological activity, the fragment comprising eight contiguous amino acids of SEQ ID NO:106;
(i) a polynucleotide which is an allelic variant of a polynucleotide of (a)-(f) above;
(j) a polynucleotide which encodes a species homologue of the protein of (g) or (h) above;
(k) a polynucleotide that hybridizes under stringent conditions to any one of the polynucleotides specified in (a)-(h); and
(l) a polynucleotide that hybridizes under stringent conditions to any one of the polynucleotides specified in (a)-(h) and that has a length that is at least 25% of the length of SEQ ID NO:105.

Preferably, such polynucleotide comprises the nucleotide sequence of SEQ ID NO:105 from nucleotide 1698 to nucleotide 1895; the nucleotide sequence of the full-length protein coding sequence of clone dh1073_12 deposited under accession number ATCC 207088; or the nucleotide sequence of a mature protein coding sequence of clone dh1073__12 deposited under accession number ATCC 207088. In other preferred embodiments, the polynucleotide encodes the full-length or a mature protein encoded by the cDNA insert of clone dh1073__12 deposited under accession number ATCC 207088.

In further preferred embodiments, the present invention provides a polynucleotide encoding a protein comprising a fragment of the amino acid sequence of SEQ ID NO:106 having biological activity, the fragment preferably comprising eight (more preferably twenty, most preferably thirty) contiguous amino acids of SEQ ID NO:106, or a polynucleotide encoding a protein comprising a fragment of the amino acid sequence of SEQ ID NO:106 having biological activity, the fragment comprising the amino acid sequence from amino acid 28 to amino acid 37 of SEQ ID NO:106.

Other embodiments provide the gene corresponding to the cDNA sequence of SEQ ID NO:105.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:105, but excluding the poly(A) tail at the 3' end of SEQ ID NO:105; and
    (ab) the nucleotide sequence of the cDNA insert of clone dh1073__12 deposited under accession number ATCC 207088;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:105, but excluding the poly(A) tail at the 3' end of SEQ ID NO:105; and
    (bb) the nucleotide sequence of the cDNA insert of clone dh1073__12 deposited under accession number ATCC 207088;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:105, and extending contiguously from a nucleotide sequence corresponding to the 5' end of SEQ ID NO:105 to a nucleotide sequence corresponding to the 3' end of SEQ ID NO:105, but excluding the poly(A) tail at the 3' end of SEQ ID NO:105. Also preferably the polynucleotide isolated according to the above process comprises a nucleotide sequence corresponding to the cDNA sequence of SEQ ID NO:105 from nucleotide 1698 to nucleotide 1895, and extending contiguously from a nucleotide sequence corresponding to the 5' end of said sequence of SEQ ID NO:105 from nucleotide 1698 to nucleotide 1895, to a nucleotide sequence corresponding to the 3' end of said sequence of SEQ ID NO:105 from nucleotide 1698 to nucleotide 1895.

In other embodiments, the present invention provides a composition comprising a protein, wherein said protein comprises an amino acid sequence selected from the group consisting of:

(a) the amino acid sequence of SEQ ID NO:106;
(b) a fragment of the amino acid sequence of SEQ ID NO:106, the fragment comprising eight contiguous amino acids of SEQ ID NO:106; and
(c) the amino acid sequence encoded by the cDNA insert of clone dh1073__12 deposited under accession number ATCC 207088;

the protein being substantially free from other mammalian proteins. Preferably such protein comprises the amino acid sequence of SEQ ID NO:106. In further preferred embodiments, the present invention provides a protein comprising a fragment of the amino acid sequence of SEQ ID NO:106 having biological activity, the fragment preferably comprising eight (more preferably twenty, most preferably thirty) contiguous amino acids of SEQ ID NO:106, or a protein comprising a fragment of the amino acid sequence of SEQ ID NO:106 having biological activity, the fragment comprising the amino acid sequence from amino acid 28 to amino acid 37 of SEQ ID NO:106.

In one embodiment, the present invention provides a composition comprising an isolated polynucleotide selected from the group consisting of:

(a) a polynucleotide comprising the nucleotide sequence of SEQ ID NO:107;
(b) a polynucleotide comprising the nucleotide sequence of SEQ ID NO:107 from nucleotide 423 to nucleotide 791;
(c) a polynucleotide comprising the nucleotide sequence of the full-length protein coding sequence of clone dw78__1 deposited under accession number ATCC 207088;
(d) a polynucleotide encoding the full-length protein encoded by the cDNA insert of clone dw78__1 deposited under accession number ATCC 207088;
(e) a polynucleotide comprising the nucleotide sequence of a mature protein coding sequence of clone dw78__1 deposited under accession number ATCC 207088;
(f) a polynucleotide encoding a mature protein encoded by the cDNA insert of clone dw78__1 deposited under accession number ATCC 207088;
(g) a polynucleotide encoding a protein comprising the amino acid sequence of SEQ ID NO:108;
(h) a polynucleotide encoding a protein comprising a fragment of the amino acid sequence of SEQ ID NO:108 having biological activity, the fragment comprising eight contiguous amino acids of SEQ ID NO:108;
(i) a polynucleotide which is an allelic variant of a polynucleotide of (a)-(f) above;
(j) a polynucleotide which encodes a species homologue of the protein of (g) or (h) above;
(k) a polynucleotide that hybridizes under stringent conditions to any one of the polynucleotides specified in (a)-(h); and
(l) a polynucleotide that hybridizes under stringent conditions to any one of the polynucleotides specified in (a)-(h) and that has a length that is at least 25% of the length of SEQ ID NO:107.

Preferably, such polynucleotide comprises the nucleotide sequence of SEQ ID NO:107 from nucleotide 423 to nucleotide 791; the nucleotide sequence of the full-length protein coding sequence of clone dw78_1 deposited under accession number ATCC 207088; or the nucleotide sequence of a mature protein coding sequence of clone dw78_1 deposited under accession number ATCC 207088. In other preferred embodiments, the polynucleotide encodes the full-length or a mature protein encoded by the cDNA insert of clone dw78_1 deposited under accession number ATCC 207088. In further preferred embodiments, the present invention provides a polynucleotide encoding a protein comprising a fragment of the amino acid sequence of SEQ ID NO:108 having biological activity, the fragment preferably comprising eight (more preferably twenty, most preferably thirty) contiguous amino acids of SEQ ID NO:108, or a polynucleotide encoding a protein comprising a fragment of the amino acid sequence of SEQ ID NO:108 having biological activity, the fragment comprising the amino acid sequence from amino acid 56 to amino acid 65 of SEQ ID NO:108.

Other embodiments provide the gene corresponding to the cDNA sequence of SEQ ID NO:107.

Further embodiments of the invention provide isolated polynucleotides produced according to a process selected from the group consisting of:

- (a) a process comprising the steps of:
  - (i) preparing one or more polynucleotide probes that hybridize in 6×SSC at 65 degrees C. to a nucleotide sequence selected from the group consisting of:
    - (aa) SEQ ID NO:107, but excluding the poly(A) tail at the 3' end of SEQ ID NO:107; and
    - (ab) the nucleotide sequence of the cDNA insert of clone dw78_1 deposited under accession number ATCC 207088;
  - (ii) hybridizing said probe(s) to human genomic DNA in conditions at least as stringent as 4×SSC at 50 degrees C.; and
  - (iii) isolating the DNA polynucleotides detected with the probe(s); and
- (b) a process comprising the steps of:
  - (i) preparing one or more polynucleotide primers that hybridize in 6×SSC at 65 degrees C. to a nucleotide sequence selected from the group consisting of:
    - (ba) SEQ ID NO:107, but excluding the poly(A) tail at the 3' end of SEQ ID NO:107; and
    - (bb) the nucleotide sequence of the cDNA insert of clone dw78_1 deposited under accession number ATCC 207088;
  - (ii) hybridizing said primer(s) to human genomic DNA in conditions at least as stringent as 4×SSC at 50 degrees C.;
  - (iii) amplifying human DNA sequences; and
  - (iv) isolating the polynucleotide products of step (b) (iii).

Preferably the polynucleotide isolated according to the above process comprises a nucleotide sequence corresponding to the cDNA sequence of SEQ ID NO:107, and extending contiguously from a nucleotide sequence corresponding to the 5' end of SEQ ID NO:107 to a nucleotide sequence corresponding to the 3' end of SEQ ID NO:107, but excluding the poly(A) tail at the 3' end of SEQ ID NO:107. Also preferably the polynucleotide isolated according to the above process comprises a nucleotide sequence corresponding to the cDNA sequence of SEQ ID NO:107 from nucleotide 423 to nucleotide 791, and extending contiguously from a nucleotide sequence corresponding to the 5' end of said sequence of SEQ ID NO:107 from nucleotide 423 to nucleotide 791, to a nucleotide sequence corresponding to the 3' end of said sequence of SEQ ID NO:107 from nucleotide 423 to nucleotide 791.

In other embodiments, the present invention provides a composition comprising a protein, wherein said protein comprises an amino acid sequence selected from the group consisting of:

- (a) the amino acid sequence of SEQ ID NO:108;
- (b) a fragment of the amino acid sequence of SEQ ID NO:108, the fragment comprising eight contiguous amino acids of SEQ ID NO:108; and
- (c) the amino acid sequence encoded by the cDNA insert of clone dw78_1 deposited under accession number ATCC 207088;

the protein being substantially free from other mammalian proteins. Preferably such protein comprises the amino acid sequence of SEQ ID NO:108. In further preferred embodiments, the present invention provides a protein comprising a fragment of the amino acid sequence of SEQ ID NO:108 having biological activity, the fragment preferably comprising eight (more preferably twenty, most preferably thirty) contiguous amino adds of SEQ ID NO:108, or a protein comprising a fragment of the amino acid sequence of SEQ ID NO:108 having biological activity, the fragment comprising the amino acid sequence from amino acid 56 to amino acid 65 of SEQ ID NO:108.

In one embodiment, the present invention provides a composition comprising an isolated polynucleotide selected from the group consisting of:

- (a) a polynucleotide comprising the nucleotide sequence of SEQ ID NO:109;
- (b) a polynucleotide comprising the nucleotide sequence of SEQ ID NO:109 from nucleotide 96 to nucleotide 944;
- (c) a polynucleotide comprising the nucleotide sequence of the full-length protein coding sequence of clone fh116_11 deposited under accession number ATCC 207088;
- (d) a polynucleotide encoding the full-length protein encoded by the cDNA insert of clone fh116_11 deposited under accession number ATCC 207088;
- (e) a polynucleotide comprising the nucleotide sequence of a mature protein coding sequence of clone fh116_11 deposited under accession number ATCC 207088;
- (f) a polynucleotide encoding a mature protein encoded by the cDNA insert of clone fh116_11 deposited under accession number ATCC 207088;
- (g) a polynucleotide encoding a protein comprising the amino acid sequence of SEQ ID NO:110;
- (h) a polynucleotide encoding a protein comprising a fragment of the amino acid sequence of SEQ ID NO:110 having biological activity, the fragment comprising eight contiguous amino acids of SEQ ID NO:110;
- (i) a polynucleotide which is an allelic variant of a polynucleotide of (a)-(f) above;
- (j) a polynucleotide which encodes a species homologue of the protein of (g) or (h) above;
- (k) a polynucleotide that hybridizes under stringent conditions to any one of the polynucleotides specified in (a)-(h); and
- (l) a polynucleotide that hybridizes under stringent conditions to any one of the polynucleotides specified in (a)-(h) and that has a length that is at least 25% of the length of SEQ ID NO:109.

Preferably, such polynucleotide comprises the nucleotide sequence of SEQ ID NO:109 from nucleotide 96 to nucleotide 944; the nucleotide sequence of the full-length protein coding sequence of clone fh116_11 deposited under accession number ATCC 207088; or the nucleotide sequence of a mature protein coding sequence of clone fh116_11 deposited under accession number ATCC 207088. In other preferred embodiments, the polynucleotide encodes the full-length or a mature protein encoded by the cDNA insert of clone fh116_11 deposited under accession number ATCC 207088. In further preferred embodiments, the present invention provides a polynucleotide encoding a protein comprising a fragment of the amino acid sequence of SEQ ID NO:110 having biological activity, the fragment preferably comprising eight (more preferably twenty, most preferably thirty) contiguous amino acids of SEQ ID NO:110, or a polynucleotide encoding a protein comprising a fragment of the amino acid sequence of SEQ ID NO:110 having biological activity, the fragment comprising the amino acid sequence from amino acid 136 to amino acid 145 of SEQ ID NO:110.

Other embodiments provide the gene corresponding to the cDNA sequence of SEQ ID NO:109.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:109, but excluding the poly(A) tail at the 3' end of SEQ ID NO:109; and
    (ab) the nucleotide sequence of the cDNA insert of clone fh116_11 deposited under accession number ATCC 207088;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:109, but excluding the poly(A) tail at the 3' end of SEQ ID NO:109; and
    (bb) the nucleotide sequence of the cDNA insert of clone fh116_11 deposited under accession number ATCC 207088;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:109, and extending contiguously from a nucleotide sequence corresponding to the 5' end of SEQ ID NO:109 to a nucleotide sequence corresponding to the 3' end of SEQ ID NO:109, but excluding the poly(A) tail at the 3' end of SEQ ID NO:109. Also preferably the polynucleotide isolated according to the above process comprises a nucleotide sequence corresponding to the cDNA sequence of SEQ ID NO:109 from nucleotide 96 to nucleotide 944, and extending contiguously from a nucleotide sequence corresponding to the 5' end of said sequence of SEQ ID NO:109 from nucleotide 96 to nucleotide 944, to a nucleotide sequence corresponding to the 3' end of said sequence of SEQ ID NO:109 from nucleotide 96 to nucleotide 944.

In other embodiments, the present invention provides a composition comprising a protein, wherein said protein comprises an amino acid sequence selected from the group consisting of:

(a) the amino acid sequence of SEQ ID NO:110;
(b) a fragment of the amino acid sequence of SEQ ID NO:110, the fragment comprising eight contiguous amino acids of SEQ ID NO:110; and
(c) the amino acid sequence encoded by the cDNA insert of clone fh116_11 deposited under accession number ATCC 207088;

the protein being substantially free from other mammalian proteins. Preferably such protein comprises the amino acid sequence of SEQ ID NO:110. In further preferred embodiments, the present invention provides a protein comprising a fragment of the amino acid sequence of SEQ ID NO:110 having biological activity, the fragment preferably comprising eight (more preferably twenty, most preferably thirty) contiguous amino acids of SEQ ID NO:110, or a protein comprising a fragment of the amino acid sequence of: SEQ ID NO:110 having biological activity, the fragment comprising the amino acid sequence from amino acid 136 to amino acid 145 of SEQ ID NO:110.

In one embodiment, the present invention provides a composition comprising an isolated polynucleotide selected from the group consisting of:

(a) a polynucleotide comprising the nucleotide sequence of SEQ ID NO:111;
(b) a polynucleotide comprising the nucleotide sequence of SEQ ID NO:111 from nucleotide 150 to nucleotide 1610;
(c) a polynucleotide comprising the nucleotide sequence of the full-length protein coding sequence of clone fy356_14 deposited under accession number ATCC 207088;
(d) a polynucleotide encoding the full-length protein encoded by the cDNA insert of clone fy356_14 deposited under accession number ATCC 207088;
(e) a polynucleotide comprising the nucleotide sequence of a mature protein coding sequence of clone fy356_14 deposited under accession number ATCC 207088;
(f) a polynucleotide encoding a mature protein encoded by the cDNA insert of clone fy356_14 deposited under accession number ATCC 207088;
(g) a polynucleotide encoding a protein comprising the amino acid sequence of SEQ ID NO:112;
(h) a polynucleotide encoding a protein comprising a fragment of the amino acid sequence of SEQ ID NO:112 having biological activity, the fragment comprising eight contiguous amino acids of SEQ ID NO:112;
(i) a polynucleotide which is an allelic variant of a polynucleotide of (a)-(f) above;
(j) a polynucleotide which encodes a species homologue of the protein of (g) or (h) above;
(k) a polynucleotide that hybridizes under stringent conditions to any one of the polynucleotides specified in (a)-(h); and
(l) a polynucleotide that hybridizes under stringent conditions to any one of the polynucleotides specified in (a)-(h) and that has a length that is at least 25% of the length of SEQ ID NO:111.

Preferably, such polynucleotide comprises the nucleotide sequence of SEQ ID NO:111 from nucleotide 150 to nucleotide 1610; the nucleotide sequence of the full-length protein coding sequence of clone fy356_14 deposited under accession number ATCC 207088; or the nucleotide sequence of a mature protein coding sequence of clone fy356_14 deposited under accession number ATCC 207088. In other preferred embodiments, the polynucleotide encodes the full-length or a mature protein encoded by the cDNA insert of clone fy356_14 deposited under accession number ATCC 207088. In further preferred embodiments, the present invention provides a polynucleotide encoding a protein comprising a fragment of the amino acid sequence of SEQ ID NO:112 having biological activity, the fragment preferably comprising eight (more preferably twenty, most preferably thirty) contiguous amino acids of SEQ ID NO:112, or a polynucleotide encoding a protein comprising a fragment of the amino acid sequence of SEQ ID NO:112 having biological activity, the fragment comprising the amino acid sequence from amino acid 238 to amino acid 247 of SEQ ID NO:112.

Other embodiments provide the gene corresponding to the cDNA sequence of SEQ ID NO:111.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:111, but excluding the poly(A) tail at the 3' end of SEQ ID NO:111; and
    (ab) the nucleotide sequence of the cDNA insert of clone fy356_14 deposited under accession number ATCC 207088;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:111, but excluding the poly(A) tail at the 3' end of SEQ ID NO:111; and
    (bb) the nucleotide sequence of the cDNA insert of clone fy356_14 deposited under accession number ATCC 207088;
  (ii) hybridizing said primer(s) to human genomic DNA in conditions at least as stringent as 4×SSC at 50 degrees C.;
  (ii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:111, and extending contiguously from a nucleotide sequence corresponding to the 5' end of SEQ ID NO:111 to a nucleotide sequence corresponding to the 3' end of SEQ ID NO:111, but excluding the poly(A) tail at the 3' end of SEQ ID NO:111. Also preferably the polynucleotide isolated according to the above process comprises a nucleotide sequence corresponding to the cDNA sequence of SEQ ID NO:111 from nucleotide 150 to nucleotide 1610, and extending contiguously from a nucleotide sequence corresponding to the 5' end of said sequence of SEQ ID NO:111 from nucleotide 150 to nucleotide 1610, to a nucleotide sequence corresponding to the 3' end of said sequence of SEQ ID NO:111 from nucleotide 150 to nucleotide 1610.

In other embodiments, the present invention provides a composition comprising a protein, wherein said protein comprises an amino acid sequence selected from the group consisting of:

(a) the amino acid sequence of SEQ ID NO:112;
(b) a fragment of the amino acid sequence of SEQ ID NO:112, the fragment comprising eight contiguous amino acids of SEQ ID NO:112; and
(c) the amino acid sequence encoded by the cDNA insert of clone fy356_14 deposited under accession number ATCC 207088;

the protein being substantially free from other mammalian proteins. Preferably such protein comprises the amino acid sequence of SEQ ID NO:112. In further preferred embodiments, the present invention provides a protein comprising a fragment of the amino acid sequence of SEQ ID NO:112 having biological activity, the fragment preferably comprising eight (more preferably twenty, most preferably thirty) contiguous amino acids of SEQ ID NO:112, or a protein comprising a fragment of the amino acid sequence of SEQ ID NO:112 having biological activity, the fragment comprising the amino acid sequence from amino acid 238 to amino acid 247 of SEQ ID NO:112.

In one embodiment, the present invention provides a composition comprising an isolated polynucleotide selected from the group consisting of:

(a) a polynucleotide comprising the nucleotide sequence of SEQ ID NO:113;
(b) a polynucleotide comprising the nucleotide sequence of SEQ ID NO:113 from nucleotide 49 to nucleotide 669;
(c) a polynucleotide comprising the nucleotide sequence of SEQ ID NO:113 from nucleotide 112 to nucleotide 669;
(d) a polynucleotide comprising the nucleotide sequence of the full-length protein coding sequence of clone iw66_1 deposited under accession number ATCC 207088;
(e) a polynucleotide encoding the full-length protein encoded by the cDNA insert of clone iw66_1 deposited under accession number ATCC 207088;
(f) a polynucleotide comprising the nucleotide sequence of a mature protein coding sequence of clone iw66_1 deposited under accession number ATCC 207088;
(g) a polynucleotide encoding a mature protein encoded by the cDNA insert of clone iw66_1 deposited under accession number ATCC 207088;
(h) a polynucleotide encoding a protein comprising the amino acid sequence of SEQ ID NO:114;
(i) a polynucleotide encoding a protein comprising a fragment of the amino acid sequence of SEQ ID NO:114 having biological activity, the fragment comprising eight contiguous amino acids of SEQ ID NO:114;
(j) a polynucleotide which is an allelic variant of a polynucleotide of (a)-(g) above;
(k) a polynucleotide which encodes a species homologue of the protein of (h) or (i) above;
(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:113.

Preferably, such polynucleotide comprises the nucleotide sequence of SEQ ID NO:113 from nucleotide 49 to nucleotide 669; the nucleotide sequence of SEQ ID NO:113 from nucleotide 112 to nucleotide 669; the nucleotide sequence of the full-length protein coding sequence of clone iw66_1 deposited under accession number ATCC 207088; or the nucleotide sequence of a mature protein coding sequence of clone iw66_1 deposited under accession number ATCC 207088. In other preferred embodiments, the polynucleotide encodes the full-length or a mature protein encoded by the cDNA insert of clone iw66_1 deposited under accession number ATCC 207088. In further preferred embodiments, the present invention provides a polynucleotide encoding a protein comprising a fragment of the amino acid sequence of SEQ ID NO:114 having biological activity, the fragment preferably comprising eight (more preferably twenty, most preferably thirty) contiguous amino acids of SEQ ID NO:114, or a polynucleotide encoding a protein comprising a fragment of the amino acid sequence of SEQ ID NO:114 having biological activity, the fragment comprising the amino acid sequence from amino acid 98 to amino acid 107 of SEQ ID NO:114.

Other embodiments provide the gene corresponding to the cDNA sequence of SEQ ID NO:113.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:113, but excluding the poly(A) tail at the 3' end of SEQ ID NO:113; and
    (ab) the nucleotide sequence of the cDNA insert of clone iw66_1 deposited under accession number ATCC 207088;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:113, but excluding the poly(A) tail at the 3' end of SEQ ID NO:113; and
    (bb) the nucleotide sequence of the cDNA insert of clone iw66_1 deposited under accession number ATCC 207088;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:113, and extending contiguously from a nucleotide sequence corresponding to the 5' end of SEQ ID NO:113 to a nucleotide sequence corresponding to the 3' end of SEQ ID NO:113, but excluding the poly(A) tail at the 3' end of SEQ ID NO:113. Also preferably the polynucleotide isolated according to the above process comprises a nucleotide sequence corresponding to the cDNA sequence of SEQ ID NO:113 from nucleotide 49 to nucleotide 669, and extending contiguously from a nucleotide sequence corresponding to the 5' end of said sequence of SEQ ID NO:113 from nucleotide 49 to nucleotide 669, to a nucleotide sequence corresponding to the 3' end of said sequence of SEQ ID NO:113 from nucleotide 49 to nucleotide 669. Also preferably the polynucleotide isolated according to the above process comprises a nucleotide sequence corresponding to the cDNA sequence of SEQ ID NO:113 from nucleotide 112 to nucleotide 669, and extending contiguously from a nucleotide sequence corresponding to the 5' end of said sequence of SEQ ID NO:113 from nucleotide 112 to nucleotide 669, to a nucleotide sequence corresponding to the 3' end of said sequence of SEQ ID NO:113 from nucleotide 112 to nucleotide 669.

In other embodiments, the present invention provides a composition comprising a protein, wherein said protein comprises an amino acid sequence selected from the group consisting of:

(a) the amino acid sequence of SEQ ID NO:114;
(b) a fragment of the amino acid sequence of SEQ ID NO:114, the fragment comprising eight contiguous amino acids of SEQ ID NO:114; and
(c) the amino acid sequence encoded by the cDNA insert of clone iw66_1 deposited under accession number ATCC 207088;

the protein being substantially free from other mammalian proteins. Preferably such protein comprises the amino acid sequence of SEQ ID NO:114. In further preferred embodiments, the present invention provides a protein comprising a fragment of the amino acid sequence of SEQ ID NO:114 having biological activity, the fragment preferably comprising eight (more preferably twenty, most preferably thirty) contiguous amino acids of SEQ ID NO:114, or a protein comprising a fragment of the amino acid sequence of SEQ ID NO:114 having biological activity, the fragment comprising the amino acid sequence from amino acid 98 to amino acid 107 of SEQ ID NO:114.

In one embodiment, the present invention provides a composition comprising an isolated polynucleotide selected from the group consisting of:

(a) a polynucleotide comprising the nucleotide sequence of SEQ ID NO:115;
(b) a polynucleotide comprising the nucleotide sequence of SEQ ID NO:115 from nucleotide 165 to nucleotide 416;
(c) a polynucleotide comprising the nucleotide sequence of the full-length protein coding sequence of clone kh13_4 deposited under accession number ATCC 207089;
(d) a polynucleotide encoding the full-length protein encoded by the cDNA insert of clone kh13_4 deposited under accession number ATCC 207089;
(e) a polynucleotide comprising the nucleotide sequence of a mature protein coding sequence of clone kh13_4 deposited under accession number ATCC 207089;
(f) a polynucleotide encoding a mature protein encoded by the cDNA insert of clone kh13_4 deposited under accession number ATCC 207089;
(g) a polynucleotide encoding a protein comprising the amino acid sequence of SEQ ID NO:116;
(h) a polynucleotide encoding a protein comprising a fragment of the amino acid sequence of SEQ ID NO:116 having biological activity, the fragment comprising eight contiguous amino acids of SEQ ID NO:116;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:115.

Preferably, such polynucleotide comprises the nucleotide sequence of SEQ ID NO:115 from nucleotide 165 to nucleotide 416; the nucleotide sequence of the full-length protein coding sequence of clone kh13_4 deposited under accession number ATCC 207089; or the nucleotide sequence of a mature protein coding sequence of clone kh13_4 deposited under accession number ATCC 207089. In other preferred embodiments, the polynucleotide encodes the full-length or a mature protein encoded by the cDNA insert of clone kh13_4 deposited under accession number ATCC 207089. In further preferred embodiments, the present invention provides a polynucleotide encoding a protein comprising a fragment of the amino acid sequence of SEQ ID NO:116 having biological activity, the fragment preferably comprising eight (more preferably twenty, most preferably thirty) contiguous amino acids of SEQ ID NO:116, or a polynucleotide encoding a protein comprising a fragment of the amino acid sequence of SEQ ID NO:116 having biological activity, the fragment comprising the amino acid sequence from amino acid 37 to amino acid 46 of SEQ ID NO:116.

Other embodiments provide the gene corresponding to the cDNA sequence of SEQ ID NO:115.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:115, but excluding the poly(A) tail at the 3' end of SEQ ID NO:115; and
    (ab) the nucleotide sequence of the cDNA insert of clone kh13_4 deposited under accession number ATCC 207089;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:115, but excluding the poly(A) tail at the 3' end of SEQ ID NO:115; and
    (bb) the nucleotide sequence of the cDNA insert of clone kh13_4 deposited under accession number ATCC 207089;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:115, and extending contiguously from a nucleotide sequence corresponding to the 5' end of SEQ ID NO:115 to a nucleotide sequence corresponding to the 3' end of SEQ ID NO:115, but excluding the poly(A) tail at the 3' end of SEQ ID NO:115. Also preferably the polynucleotide isolated according to the above process comprises a nucleotide sequence corresponding to the cDNA sequence of SEQ ID NO:115 from nucleotide 165 to nucleotide 416, and extending contiguously from a nucleotide sequence corresponding to the 5' end of said sequence of SEQ ID NO:115 from nucleotide 165 to nucleotide 416, to a nucleotide sequence corresponding to the 3' end of said sequence of SEQ ID NO:115 from nucleotide 165 to nucleotide 416.

In other embodiments, the present invention provides a composition comprising a protein, wherein said protein comprises an amino acid sequence selected from the group consisting of:

(a) the amino acid sequence of SEQ ID NO:116;

(b) a fragment of the amino acid sequence of SEQ ID NO:116, the fragment comprising eight contiguous amino acids of SEQ ID NO:116; and (c) the amino acid sequence encoded by the cDNA insert of clone kh13_4 deposited under accession number ATCC 207089;

the protein being substantially free from other mammalian proteins. Preferably such protein comprises the amino acid sequence of SEQ ID NO:116. In further preferred embodiments, the present invention provides a protein comprising a fragment of the amino acid sequence of SEQ ID NO:116 having biological activity, the fragment preferably comprising eight (more preferably twenty, most preferably thirty) contiguous amino acids of SEQ ID NO:116, or a protein comprising a fragment of the amino acid sequence of SEQ ID NO:116 having biological activity, the fragment comprising the amino acid sequence from amino acid 37 to amino acid 46 of SEQ ID NO:116.

In one embodiment, the present invention provides a composition comprising an isolated polynucleotide selected from the group consisting of:

(a) a polynucleotide comprising the nucleotide sequence of SEQ ID NO:117;

(b) a polynucleotide comprising the nucleotide sequence of SEQ ID NO:117 from nucleotide 204 to nucleotide 602;

(c) a polynucleotide comprising the nucleotide sequence of the full-length protein coding sequence of clone ko258_4 deposited under accession number ATCC 207089;

(d) a polynucleotide encoding the full-length protein encoded by the cDNA insert of clone ko258_4 deposited under accession number ATCC 207089;

(e) a polynucleotide comprising the nucleotide sequence of a mature protein coding sequence of clone ko258_4 deposited under accession number ATCC 207089;

(f) a polynucleotide encoding a mature protein encoded by the cDNA insert of clone ko258_4 deposited under accession number ATCC 207089;

(g) a polynucleotide encoding a protein comprising the amino acid sequence of SEQ ID NO:118;

(h) a polynucleotide encoding a protein comprising a fragment of the amino acid sequence of SEQ ID NO:118 having biological activity, the fragment comprising eight contiguous amino acids of SEQ ID NO:118;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:117.

Preferably, such polynucleotide comprises the nucleotide sequence of SEQ ID NO:117 from nucleotide 204 to nucleotide 602; the nucleotide sequence of the full-length protein coding sequence of clone ko258_4 deposited under accession number ATCC 207089; or the nucleotide sequence of a mature protein coding sequence of clone ko258_4 deposited under accession number ATCC 207089. In other preferred embodiments, the polynucleotide encodes the full-length or a mature protein encoded by the cDNA insert of clone ko258_4 deposited under accession number ATCC 207089. In further preferred embodiments, the present invention provides a polynucleotide encoding a protein comprising a fragment of the amino acid sequence of SEQ ID NO:118 having biological activity, the fragment preferably comprising eight (more preferably twenty, most preferably thirty) contiguous amino acids of SEQ ID NO:118, or a polynucleotide encoding a protein comprising a fragment of the amino acid sequence of SEQ ID NO:118 having biological activity, the fragment comprising the amino acid sequence from amino acid 61 to amino acid 70 of SEQ ID NO:118.

Other embodiments provide the gene corresponding to the cDNA sequence of SEQ ID NO:117.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:117, but excluding the poly(A) tail at the 3' end of SEQ ID NO:117; and
    (ab) the nucleotide sequence of the cDNA insert of clone ko258_4 deposited under accession number ATCC 207089;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:117, but excluding the poly(A) tail at the 3' end of SEQ ID NO:117; and
    (bb) the nucleotide sequence of the cDNA insert of clone ko258_4 deposited under accession number ATCC 207089;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:117, and extending contiguously from a nucleotide sequence corresponding to the 5' end of SEQ ID NO:117 to a nucleotide sequence corresponding to the 3' end of SEQ ID NO:117, but excluding the poly(A) tail at the 3' end of SEQ ID NO:117. Also preferably the polynucleotide isolated according to the above process comprises a nucleotide sequence corresponding to the cDNA sequence of SEQ ID NO:117 from nucleotide 204 to nucleotide 602, and extending contiguously from a nucleotide sequence corresponding to the 5' end of said sequence of SEQ ID NO:117 from nucleotide 204 to nucleotide 602, to a nucleotide sequence corresponding to the 3' end of said sequence of SEQ ID NO:117 from nucleotide 204 to nucleotide 602.

In other embodiments, the present invention provides a composition comprising a protein, wherein said protein comprises an amino acid sequence selected from the group consisting of:

(a) the amino acid sequence of SEQ ID NO:118;

(b) a fragment of the amino acid sequence of SEQ ID NO:118, the fragment comprising eight contiguous amino acids of SEQ ID NO:118; and (c) the amino acid sequence encoded by the cDNA insert of clone ko258_4 deposited under accession number ATCC 207089;

the protein being substantially free from other mammalian proteins. Preferably such protein comprises the amino acid sequence of SEQ ID NO:118. In further preferred embodiments, the present invention provides a protein comprising a fragment of the amino acid sequence of SEQ ID NO:118 having biological activity, the fragment preferably comprising eight (more preferably twenty, most preferably thirty) contiguous amino acids of SEQ ID NO:118, or a protein comprising a fragment of the amino acid sequence of SEQ ID NO:118 having biological activity, the fragment comprising the amino add sequence from amino acid 61 to amino acid 70 of SEQ ID NO:118.

In one embodiment, the present invention provides a composition comprising an isolated polynucleotide selected from the group consisting of:

(a) a polynucleotide comprising the nucleotide sequence of SEQ ID NO:119;

(b) a polynucleotide comprising the nucleotide sequence of SEQ ID NO:119 from nucleotide 434 to nucleotide 739;

(c) a polynucleotide comprising the nucleotide sequence of the full-length protein coding sequence of clone kv10_8 deposited under accession number ATCC 207089;

(d) a polynucleotide encoding the full-length protein encoded by the cDNA insert of clone kv10_8 deposited under accession number ATCC 207089;

(e) a polynucleotide comprising the nucleotide sequence of a mature protein coding sequence of clone kv10_8 deposited under accession number ATCC 207089;

(f) a polynucleotide encoding a mature protein encoded by the cDNA insert of clone kv10_8 deposited under accession number ATCC 207089;

(g) a polynucleotide encoding a protein comprising the amino acid sequence of SEQ ID NO:120;

(h) a polynucleotide encoding a protein comprising a fragment of the amino acid sequence of SEQ ID NO:120 having biological activity, the fragment comprising eight contiguous amino acids of SEQ ID NO:120;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:119.

Preferably, such polynucleotide comprises the nucleotide sequence of SEQ ID NO:119 from nucleotide 434 to nucleotide 739; the nucleotide sequence of the full-length protein coding sequence of clone kv10_8 deposited under accession number ATCC 207089; or the nucleotide sequence of a mature protein coding sequence of clone kv10_8 deposited under accession number ATCC 207089. In other preferred embodiments, the polynucleotide encodes the full-length or a mature protein encoded by the cDNA insert of clone kv10_8 deposited under accession number ATCC 207089. In further preferred embodiments, the present invention provides a polynucleotide encoding a protein comprising a fragment of the amino acid sequence of SEQ ID NO:120 having biological activity, the fragment preferably comprising eight (more preferably twenty, most preferably thirty) contiguous amino acids of SEQ ID NO:120, or a polynucleotide encoding a protein comprising a fragment of the amino acid sequence of SEQ ID NO:120 having biological activity, the fragment comprising the amino acid sequence from amino acid 46 to amino acid 55 of SEQ ID NO:120.

Other embodiments provide the gene corresponding to the cDNA sequence of SEQ ID NO:119.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:119, but excluding the poly(A) tail at the 3' end of SEQ ID NO:119; and
    (ab) the nucleotide sequence of the cDNA insert of clone kv10_8 deposited under accession number ATCC 207089;
  (ii) hybridizing said probe(s) to human genomic DNA in conditions at least as stringent as 4×SSC at 50 degrees C.; and
  (iii) isolating the DNA polynucleotides detected with the probe(s); and (b) a process comprising the steps of:
  (i) preparing one or more polynucleotide primers that hybridize in 6×SSC at 65 degrees C. to a nucleotide sequence selected from the group consisting of:
    (ba) SEQ ID NO:119, but excluding the poly(A) tail at the 3' end of SEQ ID NO:119; and
    (bb) the nucleotide sequence of the cDNA insert of clone kv10_8 deposited under accession number ATCC 207089;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:119, and extending contiguously from a nucleotide sequence corresponding to the 5' end of SEQ ID NO:119 to a nucleotide sequence corresponding to the 3' end of SEQ ID NO:119, but excluding the poly(A) tail at the 3' end of SEQ ID NO:119. Also preferably the polynucleotide isolated according to the above process comprises a nucleotide sequence corresponding to the cDNA sequence of SEQ ID NO:119 from nucleotide 434 to nucleotide 739, and extending contiguously from a nucleotide sequence corresponding to the 5' end of said sequence of SEQ ID NO:119 from nucleotide 434 to nucleotide 739, to a nucleotide sequence corresponding to the 3' end of said sequence of SEQ ID NO:119 from nucleotide 434 to nucleotide 739.

In other embodiments, the present invention provides a composition comprising a protein, wherein said protein comprises an amino acid sequence selected from the group consisting of:

(a) the amino acid sequence of SEQ ID NO:120;

(b) a fragment of the amino acid sequence of SEQ ID NO:120, the fragment comprising eight contiguous amino acids of SEQ ID NO:120; and (c) the amino acid sequence encoded by the cDNA insert of clone kv10_8 deposited under accession number ATCC 207089;

the protein being substantially free from other mammalian proteins. Preferably such protein comprises the amino acid sequence of SEQ ID NO:120. In further preferred embodiments, the present invention provides a protein comprising a fragment of the amino acid sequence of SEQ ID NO:120 having biological activity, the fragment preferably comprising eight (more preferably twenty, most preferably thirty) contiguous amino acids of SEQ ID NO:120, or a protein comprising a fragment of the amino acid sequence of SEQ ID NO:120 having biological activity, the fragment comprising the amino acid sequence from amino acid 46 to amino acid 55 of SEQ ID NO:120.

In one embodiment, the present invention provides a composition comprising an isolated polynucleotide selected from the group consisting of:

(a) a polynucleotide comprising the nucleotide sequence of SEQ ID NO:121;

(b) a polynucleotide comprising the nucleotide sequence of SEQ ID NO:121 from nucleotide 149 to nucleotide 310;

(c) a polynucleotide comprising the nucleotide sequence of the full-length protein coding sequence of clone LL89_3 deposited under accession number ATCC 207089;

(d) a polynucleotide encoding the full-length protein encoded by the cDNA insert of clone LL89_3 deposited under accession number ATCC 207089;

(e) a polynucleotide comprising the nucleotide sequence of a mature protein coding sequence of clone LL89_3 deposited under accession number ATCC 207089;

(f) a polynucleotide encoding a mature protein encoded by the cDNA insert of clone LL89_3 deposited under accession number ATCC 207089;

(g) a polynucleotide encoding a protein comprising the amino acid sequence of SEQ ID NO:122;

(h) a polynucleotide encoding a protein comprising a fragment of the amino acid sequence of SEQ ID NO:122 having biological activity, the fragment comprising eight contiguous amino acids of SEQ ID NO:122;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:121.

Preferably, such polynucleotide comprises the nucleotide sequence of SEQ ID NO:121 from nucleotide 149 to nucleotide 310; the nucleotide sequence of the full-length protein coding sequence of clone LL89_3 deposited under accession number ATCC 207089; or the nucleotide sequence of a mature protein coding sequence of clone LL89_3 deposited under accession number ATCC 207089. In other preferred embodiments, the polynucleotide encodes the full-length or a mature protein encoded by the cDNA insert of clone LL89_3 deposited under accession number ATCC 207089. In further preferred embodiments, the present invention provides a polynucleotide encoding a protein comprising a fragment of the amino acid sequence of SEQ ID NO:122 having biological activity, the fragment preferably comprising eight (more preferably twenty, most preferably thirty contiguous amino acids of SEQ ID NO:122, or a polynucleotide encoding a protein comprising a fragment of the amino acid sequence of SEQ ID NO:122 having biological activity, the fragment comprising the amino acid sequence from amino acid 22 to amino acid 31 of SEQ ID NO:122.

Other embodiments provide the gene corresponding to the cDNA sequence of SEQ ID NO:121.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:121, but excluding the poly(A) tail at the 3' end of SEQ ID NO:121; and
    (ab) the nucleotide sequence of the cDNA insert of clone LL89_3 deposited under accession number ATCC 207089;
  (ii) hybridizing said probe(s) to human genomic DNA in conditions at least as stringent as 4×SSC at 50 degrees C.; and
  (iii) isolating the DNA polynucleotides, detected with the probe(s); and (b) a process comprising the steps of:
  (i) preparing one or more polynucleotide primers that hybridize in 6×SSC at 65 degrees C. to a nucleotide sequence selected from the group consisting of:
    (ba) SEQ ID NO:121, but excluding the poly(A) tail at the 3' end of SEQ ID NO:121; and
    (bb) the nucleotide sequence of the cDNA insert of clone LL89_3 deposited under accession number ATCC 207089;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:121, and extending contiguously from a nucleotide sequence corresponding to the 5' end of SEQ ID NO:121 to a nucleotide sequence corresponding to the 3' end of SEQ ID NO:121, but excluding the poly(A) tail at the 3' end of SEQ ID NO:121. Also preferably the polynucleotide isolated according to the above process comprises a nucleotide sequence corresponding to the cDNA sequence of SEQ ID NO:121 from nucleotide 149 to nucleotide 310, and extending contiguously from a nucleotide sequence corresponding to the 5' end of said sequence of SEQ ID NO:121 from nucleotide 149 to nucleotide 310, to a nucleotide sequence corresponding to the 3' end of said sequence of SEQ ID NO:121 from nucleotide 149 to nucleotide 310.

In other embodiments, the present invention provides a composition comprising a protein, wherein said protein comprises an amino acid sequence selected from the group consisting of:

(a) the amino acid sequence of SEQ ID NO:122;

(b) a fragment of the amino acid sequence of SEQ ID NO:122, the fragment comprising eight contiguous amino acids of SEQ ID NO:122; and (c) the amino acid sequence encoded by the cDNA insert of clone LL89_3 deposited under accession number ATCC 207089;

the protein being substantially free from other mammalian proteins. Preferably such protein comprises the amino acid sequence of SEQ ID NO:122. In further preferred embodiments, the present invention provides a protein comprising a fragment of the amino acid sequence of SEQ ID NO:122 having biological activity, the fragment preferably comprising eight (more preferably twenty, most preferably thirty) contiguous amino acids of SEQ ID NO:122, or a protein comprising a fragment of the amino acid sequence of SEQ ID NO:122 having biological activity, the fragment comprising the amino acid sequence from amino acid 22 to amino acid 31 of SEQ ID NO:122.

In one embodiment, the present invention provides a composition comprising an isolated polynucleotide selected from the group consisting of:

(a) a polynucleotide comprising the nucleotide sequence of SEQ ID NO:123;

(b) a polynucleotide comprising the nucleotide sequence of SEQ ID NO:123 from nucleotide 22 to nucleotide 288;

(c) a polynucleotide comprising the nucleotide sequence of the full-length protein coding sequence of clone mc300_1 deposited under accession number ATCC 207089;

(d) a polynucleotide encoding the full-length protein encoded by the cDNA insert of clone mc300_1 deposited under accession number ATCC 207089;

(e) a polynucleotide comprising the nucleotide sequence of a mature protein coding sequence of clone mc300_1 deposited under accession number ATCC 207089;

(f) a polynucleotide encoding a mature protein encoded by the cDNA insert of clone mc300_1 deposited under accession number ATCC 207089;

(g) a polynucleotide encoding a protein comprising the amino acid sequence of SEQ ID NO:124;

(h) a polynucleotide encoding a protein comprising a fragment of the amino acid sequence of SEQ ID NO:124 having biological activity, the fragment comprising eight contiguous amino acids of SEQ ID NO:124;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:123.

Preferably, such polynucleotide comprises the nucleotide sequence of SEQ ID NO:123 from nucleotide 22 to nucleotide 288; the nucleotide sequence of the full-length protein coding sequence of clone mc300_1 deposited under accession number ATCC 207089; or the nucleotide sequence of a mature protein coding sequence of clone mc300_1 deposited under accession number ATCC 207089. In other preferred embodiments, the polynucleotide encodes the full-length or a mature protein encoded by the cDNA insert of clone mc300_1 deposited under accession number ATCC 207089. In further preferred embodiments, the present invention provides a polynucleotide encoding a protein comprising a fragment of the amino acid sequence of SEQ ID NO:124 having biological activity, the fragment preferably comprising eight (more preferably twenty, most preferably thirty) contiguous amino acids of SEQ ID NO:124, or a polynucleotide encoding a protein comprising a fragment of the amino acid sequence of SEQ ID NO:124 having biological activity, the fragment comprising the amino acid sequence from amino acid 39 to amino acid 48 of SEQ ID NO:124.

Other embodiments provide the gene corresponding to the cDNA sequence of SEQ ID NO:123.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:123, but excluding the poly(A) tail at the 3' end of SEQ ID NO:123; and
    (ab) the nucleotide sequence of the cDNA insert of clone mc300_1 deposited under accession number ATCC 207089;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:123, but excluding the poly(A) tail at the 3' end of SEQ ID NO:123; and
    (bb) the nucleotide sequence of the cDNA insert of clone mc300_1 deposited under accession number ATCC 207089;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:123, and extending contiguously from a nucleotide sequence corresponding to the 5' end of SEQ ID NO:123 to a nucleotide sequence corresponding to the 3' end of SEQ ID NO:123, but excluding the poly(A) tail at the 3' end of SEQ ID NO:123. Also preferably the polynucleotide isolated according to the above process comprises a nucleotide sequence corresponding to the cDNA sequence of SEQ ID NO:123 from nucleotide 22 to nucleotide 288, and extending contiguously from a nucleotide sequence corresponding to the 5' end of said sequence of SEQ ID NO:123 from nucleotide 22 to nucleotide 288, to a nucleotide sequence corresponding to the 3' end of said sequence of SEQ ID NO:123 from nucleotide 22 to nucleotide 288.

In other embodiments, the present invention provides a composition comprising a protein, wherein said protein comprises an amino acid sequence selected from the group consisting of:

(a) the amino acid sequence of SEQ ID NO:124;

(b) a fragment of the amino acid sequence of SEQ ID NO:124, the fragment comprising eight contiguous amino acids of SEQ ID NO:124; and (c) the amino acid sequence encoded by the cDNA insert of clone mc300_1 deposited under accession number ATCC 207089;

the protein being substantially free from other mammalian proteins. Preferably such protein comprises the amino acid sequence of SEQ ID NO:124. In further preferred embodiments, the present invention provides a protein comprising a fragment of the amino add sequence of SEQ ID NO:124 having biological activity, the fragment preferably comprising eight (more preferably twenty, most preferably thirty) contiguous amino acids of SEQ ID NO:124, or a protein comprising a fragment of the amino add sequence of SEQ ID NO:124 having biological activity, the fragment comprising the amino acid sequence from amino acid 39 to amino acid 48 of SEQ ID NO:124.

In one embodiment, the present invention provides a composition comprising an isolated polynucleotide selected from the group consisting of:

(a) a polynucleotide comprising the nucleotide sequence of SEQ ID NO:125;

(b) a polynucleotide comprising the nucleotide sequence of SEQ ID NO:125 from nucleotide 200 to nucleotide 2449;

(c) a polynucleotide comprising the nucleotide sequence of the full-length protein coding sequence of clone ml227_1 deposited under accession number ATCC 207089;

(d) a polynucleotide encoding the full-length protein encoded by the cDNA insert of clone ml227_1 deposited under accession number ATCC 207089;

(e) a polynucleotide comprising the nucleotide sequence of a mature protein coding sequence of clone ml227_1 deposited under accession number ATCC 207089;

(f) a polynucleotide encoding a mature protein encoded by the cDNA insert of clone ml227_1 deposited under accession number ATCC 207089;

(g) a polynucleotide encoding a protein comprising the amino acid sequence of SEQ ID NO:126;

(h) a polynucleotide encoding a protein comprising a fragment of the amino acid sequence of SEQ ID NO:126 having biological activity, the fragment comprising eight contiguous amino acids of SEQ ID NO:126;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:125.

Preferably, such polynucleotide comprises the nucleotide sequence of SEQ ID NO:125 from nucleotide 200 to nucleotide 2449; the nucleotide sequence of the full-length protein coding sequence of clone ml227__1 deposited under accession number ATCC 207089; or the nucleotide sequence of a mature protein coding sequence of clone ml227__1 deposited under accession number ATCC 207089. In other preferred embodiments, the polynucleotide encodes the full-length or a mature protein encoded by the cDNA insert of clone ml227__1 deposited under accession number ATCC 207089. In further preferred embodiments, the present invention provides a polynucleotide encoding a protein comprising a fragment of the amino acid sequence of SEQ ID NO:126 having biological activity, the fragment preferably comprising eight (more preferably twenty, most preferably thirty) contiguous amino acids of SEQ ID NO:126, or a polynucleotide encoding a protein comprising a fragment of the amino acid sequence of SEQ ID NO:126 having biological activity, the fragment comprising the amino acid sequence from amino acid 370 to amino acid 379 of SEQ ID NO:126.

Other embodiments provide the gene corresponding to the cDNA sequence of SEQ ID NO:125.

Further embodiments of the invention provide isolated polynucleotides produced according to a process selected from the group consisting of:

(a) a process comprising the steps of:
- (i) preparing one or more polynucleotide probes that hybridize in 6×SSC at 65 degrees C. to a nucleotide sequence selected from the group consisting of:
  - (aa) SEQ ID NO:125, but excluding the poly(A) tail at the 3' end of SEQ ID NO:125; and
  - (ab) the nucleotide sequence of the cDNA insert of clone ml227__1 deposited under accession number ATCC 207089;
- (ii) hybridizing said probe(s) to human genomic DNA in conditions at least as stringent as 4×SSC at 50 degrees C.; and
- (iii) isolating the DNA polynucleotides detected with the probe(s); and (b) a process comprising the steps of:
- (i) preparing one or more polynucleotide primers that hybridize in 6×SSC at 65 degrees C. to a nucleotide sequence selected from the group consisting of:
  - (ba) SEQ ID NO:125, but excluding the poly(A) tail at the 3' end of SEQ ID NO:125; and
  - (bb) the nucleotide sequence of the cDNA insert of clone ml227__1 deposited under accession number ATCC 207089;
- (ii) hybridizing said primer(s) to human genomic DNA in conditions at least as stringent as 4×SSC at 50 degrees C.;
- (iii) amplifying human DNA sequences; and
- (iv) isolating the polynucleotide products of step (b)(iii).

Preferably the polynucleotide isolated according to the above process comprises a nucleotide sequence corresponding to the cDNA sequence of SEQ ID NO:125, and extending contiguously from a nucleotide sequence corresponding to the 5' end of SEQ ID NO:125 to a nucleotide sequence corresponding to the 3' end of SEQ ID NO:125, but excluding the poly(A) tail at the 3' end of SEQ ID NO:125. Also preferably the polynucleotide isolated according to the above process comprises a nucleotide sequence corresponding to the cDNA sequence of SEQ ID NO:125 from nucleotide 200 to nucleotide 2449, and extending contiguously from a nucleotide sequence corresponding to the 5' end of said sequence of SEQ ID NO:125 from nucleotide 200 to nucleotide 2449, to a nucleotide sequence corresponding to the 3' end of said sequence of SEQ ID NO:125 from nucleotide 200 to nucleotide 2449.

In other embodiments, the present invention provides a composition comprising a protein, wherein said protein comprises an amino acid sequence selected from the group consisting of:

(a) the amino acid sequence of SEQ ID NO:126;

(b) a fragment of the amino acid sequence of SEQ ID NO:126, the fragment comprising eight contiguous amino acids of SEQ ID NO:126; and (c) the amino acid sequence encoded by the cDNA insert of clone ml227__1 deposited under accession number ATCC 207089;

the protein being substantially free from other mammalian proteins. Preferably such protein comprises the amino acid sequence of SEQ ID NO:126. In further preferred embodiments, the present invention provides a protein comprising a fragment of the amino acid sequence of SEQ ID NO:126 having biological activity, the fragment preferably comprising eight (more preferably twenty, most preferably thirty) contiguous amino acids of SEQ ID NO:126, or a protein comprising a fragment of the amino acid sequence of SEQ ID NO:126 having biological activity, the fragment comprising the amino acid sequence from amino acid 370 to amino acid 379 of SEQ ID NO:126.

In one embodiment, the present invention provides a composition comprising an isolated polynucleotide selected from the group consisting of:

(a) a polynucleotide comprising the nucleotide sequence of SEQ ID NO:127;

(b) a polynucleotide comprising the nucleotide sequence of SEQ ID NO:127 from nucleotide 82 to nucleotide 1980;

(c) a polynucleotide comprising the nucleotide sequence of the full-length protein coding sequence of clone mm367__6 deposited under accession number ATCC 207089;

(d) a polynucleotide encoding the full-length protein encoded by the cDNA insert of clone mm367__6 deposited under accession number ATCC 207089;

(e) a polynucleotide comprising the nucleotide sequence of a mature protein coding sequence of clone mm367__6 deposited under accession number ATCC 207089;

(f) a polynucleotide encoding a mature protein encoded by the cDNA insert of clone mm367__6 deposited under accession number ATCC 207089;

(g) a polynucleotide encoding a protein comprising the amino acid sequence of SEQ ID NO:128;

(h) a polynucleotide encoding a protein comprising a fragment of the amino acid sequence of SEQ ID NO:128 having biological activity, the fragment comprising eight contiguous amino acids of SEQ ID NO:128;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:127.

Preferably, such polynucleotide comprises the nucleotide sequence of SEQ ID NO:127 from nucleotide 82 to nucleotide 1980; the nucleotide sequence of the full-length protein coding sequence of clone mm367_6 deposited under accession number ATCC 207089; or the nucleotide sequence of a mature protein coding sequence of clone mm367_6 deposited under accession number ATCC 207089. In other preferred embodiments, the polynucleotide encodes the full-length or a mature protein encoded by the cDNA insert of clone mm367_6 deposited under accession number ATCC 207089. In further preferred embodiments, the present invention provides a polynucleotide encoding a protein comprising a fragment of the amino acid sequence of SEQ ID NO:128 having biological activity, the fragment preferably comprising eight (more preferably twenty, most preferably thirty) contiguous amino acids of SEQ ID NO:128, or a polynucleotide encoding a protein comprising a fragment of the amino acid sequence of SEQ ID NO:128 having biological activity, the fragment comprising the amino acid sequence from amino acid 311 to amino acid 320 of SEQ ID NO:128.

Other embodiments provide the gene corresponding to the cDNA sequence of SEQ ID NO:127.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:127, but excluding the poly(A) tail at the 3' end of SEQ ID NO:127; and
    (ab) the nucleotide sequence of the cDNA insert of clone mm367_6 deposited under accession number ATCC 207089;
  (ii) hybridizing said probe(s) to human genomic DNA in conditions at least as stringent as 4×SSC at 50 degrees C.; and
  (iii) isolating the DNA polynucleotides detected with the probe(s); and (b) a process comprising the steps of:
  (i) preparing one or more polynucleotide primers that hybridize in 6×SSC at 65 degrees C. to a nucleotide sequence selected from the group consisting of:
    (ba) SEQ ID NO:127, but excluding the poly(A) tail at the 3' end of SEQ ID NO:127; and
    (bb) the nucleotide sequence of the cDNA insert of clone mm367_6 deposited under accession number ATCC 207089;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:127, and extending contiguously from a nucleotide sequence corresponding to the 5' end of SEQ ID NO:127 to a nucleotide sequence corresponding to the 3' end of SEQ ID NO:127, but excluding the poly(A) tail at the 3' end of SEQ ID NO:127. Also preferably the polynucleotide isolated according to the above process comprises a nucleotide sequence corresponding to the cDNA sequence of SEQ ID NO:127 from nucleotide 82 to nucleotide 1980, and extending contiguously from a nucleotide sequence corresponding to the 5' end of said sequence of SEQ ID NO:127 from nucleotide 82 to nucleotide 1980, to a nucleotide sequence corresponding to the 3' end of said sequence of SEQ ID NO:127 from nucleotide 82 to nucleotide 1980.

In other embodiments, the present invention provides a composition comprising a protein, wherein said protein comprises an amino acid sequence selected from the group consisting of:

(a) the amino acid sequence of SEQ ID NO:128;

(b) a fragment of the amino acid sequence of SEQ ID NO:128, the fragment comprising eight contiguous amino acids of SEQ ID NO:128; and (c) the amino acid sequence encoded by the cDNA insert of clone mm367_6 deposited under accession number ATCC 207089;

the protein being substantially free from other mammalian proteins. Preferably such protein comprises the amino acid sequence of SEQ ID NO:128. In further preferred embodiments, the present invention provides a protein comprising a fragment of the amino acid sequence of SEQ ID NO:128 having biological activity, the fragment preferably comprising eight (more preferably twenty, most preferably thirty) contiguous amino acids of SEQ ID NO:128, or a protein comprising a fragment of the amino acid sequence of SEQ ID NO:128 having biological activity, the fragment comprising the amino acid sequence from amino acid 311 to amino acid 320 of SEQ ID NO:128.

In one embodiment, the present invention provides a composition comprising an isolated polynucleotide selected from the group consisting of:

(a) a polynucleotide comprising the nucleotide sequence of SEQ ID NO:129;

(b) a polynucleotide comprising the nucleotide sequence of SEQ ID NO:129 from nucleotide 125 to nucleotide 856;

(c) a polynucleotide comprising the nucleotide sequence of the full-length protein coding sequence of clone mt124_3 deposited under accession number ATCC 207089;

(d) a polynucleotide encoding the full-length protein encoded by the cDNA insert of clone mt124_3 deposited under accession number ATCC 207089;

(e) a polynucleotide comprising the nucleotide sequence of a mature protein coding sequence of clone mt124_3 deposited under accession number ATCC 207089;

(f) a polynucleotide encoding a mature protein encoded by the cDNA insert of clone mt124_3 deposited under accession number ATCC 207089;

(g) a polynucleotide encoding a protein comprising the amino acid sequence of SEQ ID NO:130;

(h) a polynucleotide encoding a protein comprising a fragment of the amino acid sequence of SEQ ID NO:130 having biological activity, the fragment comprising eight contiguous amino acids of SEQ ID NO:130;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:129.

Preferably, such polynucleotide comprises the nucleotide sequence of SEQ ID NO:129 from nucleotide 125 to nucleotide 856; the nucleotide sequence of the full-length protein coding sequence of clone mt124_3 deposited under accession number ATCC 207089; or the nucleotide sequence of a mature protein coding sequence of clone mt124_3 deposited under accession number ATCC 207089. In other preferred embodiments, the polynucleotide encodes the full-length or a mature protein encoded by the cDNA insert of clone mt124_3 deposited under accession number ATCC 207089. In further preferred embodiments, the present invention provides a polynucleotide encoding a protein comprising a fragment of the amino acid sequence of SEQ ID NO:130 having biological activity, the fragment preferably comprising eight (more preferably twenty, most preferably thirty) contiguous amino acids of SEQ ID NO:130, or a polynucleotide encoding a protein comprising a fragment of the amino acid sequence of SEQ ID NO:130 having biological activity, the fragment comprising the amino acid sequence from amino acid 117 to amino acid 126 of SEQ ID NO:130.

Other embodiments provide the gene corresponding to the cDNA sequence of SEQ ID NO:129.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:129, but excluding the poly(A) tail at the 3' end of SEQ ID NO:129; and
    (ab) the nucleotide sequence of the cDNA insert of clone mt124_3 deposited under accession number ATCC 207089;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:129, but excluding the poly(A) tail at the 3' end of SEQ ID NO:129; and
    (bb) the nucleotide sequence of the cDNA insert of clone mt124_3 deposited under accession number ATCC 207089;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:129, and extending contiguously from a nucleotide sequence corresponding to the 5' end of SEQ ID NO:129 to a nucleotide sequence corresponding to the 3' end of SEQ ID NO:129, but excluding the poly(A) tail at the 3' end of SEQ ID NO:129. Also preferably the polynucleotide isolated according to the above process comprises a nucleotide sequence corresponding to the cDNA sequence of SEQ ID NO:129 from nucleotide 125 to nucleotide 856, and extending contiguously from a nucleotide sequence corresponding to the 5' end of said sequence of SEQ ID NO:129 from nucleotide 125 to nucleotide 856, to a nucleotide sequence corresponding to the 3' end of said sequence of SEQ ID NO:129 from nucleotide 125 to nucleotide 856.

In other embodiments, the present invention provides a composition comprising a protein, wherein said protein comprises an amino acid sequence selected from the group consisting of:

(a) the amino acid sequence of SEQ ID NO:130;

(b) a fragment of the amino acid sequence of SEQ ID NO:130, the fragment comprising eight contiguous amino acids of SEQ ID NO:130; and (c) the amino acid sequence encoded by the cDNA insert of clone mt124_3 deposited under accession number ATCC 207089;

the protein being substantially free from other mammalian proteins. Preferably such protein comprises the amino acid sequence of SEQ ID NO:130. In further preferred embodiments, the present invention provides a protein comprising a fragment of the amino acid sequence of SEQ ID NO 130 having biological activity, the fragment preferably comprising eight (more preferably twenty, most preferably thirty) contiguous amino acids of SEQ ID NO:130, or a protein comprising a fragment of the amino acid sequence of SEQ ID NO:130 having biological activity, the fragment comprising the amino acid sequence from amino acid 117 to amino acid 126 of SEQ ID NO:130.

In one embodiment, the present invention provides a composition comprising an isolated polynucleotide selected from the group consisting of:

(a) a polynucleotide comprising the nucleotide sequence of SEQ ID NO:131;

(b) a polynucleotide comprising the nucleotide sequence of SEQ ID NO:131 from nucleotide 856 to nucleotide 2940;

(c) a polynucleotide comprising the nucleotide sequence of SEQ ID NO:131 from nucleotide 901 to nucleotide 2940;

(d) a polynucleotide comprising the nucleotide sequence of the full-length protein coding sequence of clone nf56_3 deposited under accession number ATCC 207089;

(e) a polynucleotide encoding the full-length protein encoded by the cDNA insert of clone nf56_3 deposited under accession number ATCC 207089;

(f) a polynucleotide comprising the nucleotide sequence of a mature protein coding sequence of clone nf56_3 deposited under accession number ATCC 207089;

(g) a polynucleotide encoding a mature protein encoded by the cDNA insert of clone nf56_3 deposited under accession number ATCC 207089;

(h) a polynucleotide encoding a protein comprising the amino acid sequence of SEQ ID NO:132;

(i) a polynucleotide encoding a protein comprising a fragment of the amino acid sequence of SEQ ID NO:132 having biological activity, the fragment comprising eight contiguous amino acids of SEQ ID NO:132;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:131.

Preferably, such polynucleotide comprises the nucleotide sequence of SEQ ID NO:131 from nucleotide 856 to nucleotide 2940; the nucleotide sequence of SEQ ID NO:131 from nucleotide 901 to nucleotide 2940; the nucleotide sequence of the full-length protein coding sequence of clone nf56_3 deposited under accession number ATCC 207089; or the nucleotide sequence of a mature protein coding sequence of clone nf56_3 deposited under accession number ATCC 207089. In other preferred embodiments, the polynucleotide encodes the full-length or a mature protein encoded by the cDNA insert of clone nf56_3 deposited under accession number ATCC 207089. In further preferred embodiments, the present invention provides a polynucleotide encoding a protein comprising a fragment of the amino acid sequence of SEQ ID NO:132 having biological activity, the fragment preferably comprising eight (more preferably twenty, most preferably thirty) contiguous amino acids of SEQ ID NO:132, or a polynucleotide encoding a protein comprising a fragment of the amino acid sequence of SEQ ID NO:132 having biological activity, the fragment comprising the amino acid sequence from amino acid 342 to amino acid 351 of SEQ ID NO:132.

Other embodiments provide the gene corresponding to the cDNA sequence of SEQ ID NO:131.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:131, but excluding the poly(A) tail at the 3' end of SEQ ID NO:131; and (ab) the nucleotide sequence of the cDNA insert of clone nf56_3 deposited under accession number ATCC 207089;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:131, but excluding the poly(A) tail at the 3' end of SEQ ID NO:131; and (bb) the nucleotide sequence of the cDNA insert of clone nf56_3 deposited under accession number ATCC 207089;

(ii) hybridizing said primer(s) to human genomic DNA in conditions at least as stringent as 4×SSC at 50 degrees C.;

(iii) amplifying human DNA sequences; and (iv) isolating the polynucleotide products of step (b)(iii).

Preferably the polynucleotide isolated according to the above process comprises a nucleotide sequence corresponding to the cDNA sequence of SEQ ID NO:131, and extending contiguously from a nucleotide sequence corresponding to the 5' end of SEQ ID NO:131 to a nucleotide sequence corresponding to the 3' end of SEQ ID NO:131, but excluding the poly(A) tail at the 3' end of SEQ ID NO:131. Also preferably the polynucleotide isolated according to the above process comprises a nucleotide sequence corresponding to the cDNA sequence of SEQ ID NO:131 from nucleotide 856 to nucleotide 2940, and extending contiguously from a nucleotide sequence corresponding to the 5' end of said sequence of SEQ ID NO:131 from nucleotide 856 to nucleotide 2940, to a nucleotide sequence corresponding to the 3' end of said sequence of SEQ ID NO:131 from nucleotide 856 to nucleotide 2940. Also preferably the polynucleotide isolated according to the above process comprises a nucleotide sequence corresponding to the cDNA sequence of SEQ ID NO:131 from nucleotide 901 to nucleotide 2940, and extending contiguously from a nucleotide sequence corresponding to the 5' end of said sequence of SEQ ID NO:131 from nucleotide 901 to nucleotide 2940, to a nucleotide sequence corresponding to the 3' end of said sequence of SEQ ID NO:131 from nucleotide 901 to nucleotide 2940.

In other embodiments, the present invention provides a composition comprising a protein, wherein said protein comprises an amino add sequence selected from the group consisting of:

(a) the amino acid sequence of SEQ ID NO:132;

(b) a fragment of the amino acid sequence of SEQ ID NO:132, the fragment comprising eight contiguous amino acids of SEQ ID NO:132; and (c) the amino acid sequence encoded by the cDNA insert of clone nf56_3 deposited under accession number ATCC 207089;

the protein being substantially free from other mammalian proteins. Preferably such protein comprises the amino acid sequence of SEQ ID NO:132. In further preferred embodiments, the present invention provides a protein comprising a fragment of the amino acid sequence of SEQ ID NO:132 having biological activity, the fragment preferably comprising eight (more preferably twenty, most preferably thirty) contiguous amino acids of SEQ ID NO:132, or a protein comprising a fragment of the amino acid sequence of SEQ ID NO:132 having biological activity, the fragment comprising the amino acid sequence from amino acid 342 to amino acid 351 of SEQ ID NO:132.

In one embodiment, the present invention provides a composition comprising an isolated polynucleotide selected from the group consisting of:

(a) a polynucleotide comprising the nucleotide sequence of SEQ ID NO:133;

(b) a polynucleotide comprising the nucleotide sequence of SEQ ID NO:133 from nucleotide 122 to nucleotide 448;

(c) a polynucleotide comprising the nucleotide sequence of SEQ ID NO:133 from nucleotide 167 to nucleotide 448;

(d) a polynucleotide comprising the nucleotide sequence of the full-length protein coding sequence of clone qy442_2 deposited under accession number ATCC 207089;

(e) a polynucleotide encoding the full-length protein encoded by the cDNA insert of clone qy442_2 deposited under accession number ATCC 207089;

(f) a polynucleotide comprising the nucleotide sequence of a mature protein coding sequence of clone qy442_2 deposited under accession number ATCC 207089;

(g) a polynucleotide encoding a mature protein encoded by the cDNA insert of clone qy442_2 deposited under accession number ATCC 207089;

(h) a polynucleotide encoding a protein comprising the amino acid sequence of SEQ ID NO:134;

(i) a polynucleotide encoding a protein comprising a fragment of the amino acid sequence of SEQ ID NO:134 having biological activity, the fragment comprising eight contiguous amino acids of SEQ ID NO:134;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:133.

Preferably, such polynucleotide comprises the nucleotide sequence of SEQ ID NO:133 from nucleotide 122 to nucleotide 448; the nucleotide sequence of SEQ ID NO:133 from nucleotide 167 to nucleotide 448; the nucleotide sequence of the full-length protein coding sequence of clone qy442_2 deposited under accession number ATCC 207089; or the nucleotide sequence of a mature protein coding sequence of clone qy442_2 deposited under accession number ATCC 207089. In other preferred embodiments, the polynucleotide encodes the full-length or a mature protein encoded by the cDNA insert of clone qy442_2 deposited under accession number ATCC 207089. In further preferred embodiments, the present invention provides a polynucleotide encoding a protein comprising a fragment of the amino acid sequence of SEQ ID NO:134 having biological activity, the fragment preferably comprising eight (more preferably twenty, most preferably thirty) contiguous amino acids of SEQ ID NO:134, or a polynucleotide encoding a protein comprising a fragment of the amino acid sequence of SEQ ID NO:134 having biological activity, the fragment comprising the amino acid sequence from amino acid 49 to amino acid 58 of SEQ ID NO:134.

Other embodiments provide the gene corresponding to the cDNA sequence of SEQ ID NO:133.

Further embodiments of the invention provide isolated polynucleotides produced according to a process selected from the group consisting of:

(a) a process comprising the steps of:
- (i) preparing one or more polynucleotide probes that hybridize in 6×SSC at 65 degrees C. to a nucleotide sequence selected from the group consisting of:
  - (aa) SEQ ID NO:133, but excluding the poly(A) tail at the 3' end of SEQ ID NO:133; and
  - (ab) the nucleotide sequence of the cDNA insert of clone qy442_2 deposited under accession number ATCC 207089;
- (ii) hybridizing said probe(s) to human genomic DNA in conditions at least as stringent as 4×SSC at 50 degrees C.; and
- (iii) isolating the DNA polynucleotides detected with the probe(s); and (b) a process comprising the steps of:
- (i) preparing one or more polynucleotide primers that hybridize in 6×SSC at 65 degrees C. to a nucleotide sequence selected from the group consisting of:
  - (ba) SEQ ID NO:133, but excluding the poly(A) tail at the 3' end of SEQ ID NO:133; and
  - (bb) the nucleotide sequence of the cDNA insert of clone qy442_2 deposited under accession number ATCC 207089;
- (ii) hybridizing said primer(s) to human genomic DNA in conditions at least as stringent as 4×SSC at 50 degrees C.;
- (iii) amplifying human DNA sequences; and
- (iv) isolating the polynucleotide products of step (b) (iii).

Preferably the polynucleotide isolated according to the above process comprises a nucleotide sequence corresponding to the cDNA sequence of SEQ ID NO:133, and extending contiguously from a nucleotide sequence corresponding to the 5' end of SEQ ID NO:133 to a nucleotide sequence corresponding to the 3' end of SEQ ID NO:133, but excluding the poly(A) tail at the 3' end of SEQ ID NO:133. Also preferably the polynucleotide isolated according to the above process comprises a nucleotide sequence corresponding to the cDNA sequence of SEQ ID NO:133 from nucleotide 122 to nucleotide 448, and extending contiguously from a nucleotide sequence corresponding to the 5' end of said sequence of SEQ ID NO:133 from nucleotide 122 to nucleotide 448, to a nucleotide sequence corresponding to the 3' end of said sequence of SEQ ID NO:133 from nucleotide 122 to nucleotide 448. Also preferably the polynucleotide isolated according to the above process comprises a nucleotide sequence corresponding to the cDNA sequence of SEQ ID NO:133 from nucleotide 167 to nucleotide 448, and extending contiguously from a nucleotide sequence corresponding to the 5' end of said sequence of SEQ ID NO:133 from nucleotide 167 to nucleotide 448, to a nucleotide sequence corresponding to the 3' end of said sequence of SEQ ID NO:133 from nucleotide 167 to nucleotide 448.

In other embodiments, the present invention provides a composition comprising a protein, wherein said protein comprises an amino acid sequence selected from the group consisting of:

(a) the amino acid sequence of SEQ ID NO:134;

(b) a fragment of the amino acid sequence of SEQ ID NO:134, the fragment comprising eight contiguous amino acids of SEQ ID NO:134; and (c) the amino acid sequence encoded by the cDNA insert of clone qy442_2 deposited under accession number ATCC 207089;

the protein being substantially free from other mammalian proteins. Preferably such protein comprises the amino acid sequence of SEQ ID NO:134. In further preferred embodiments, the present invention provides a protein comprising a fragment of the amino acid sequence of SEQ ID NO:134 having biological activity, the fragment preferably comprising eight (more preferably twenty, most preferably thirty) contiguous amino acids of SEQ ID NO:134, or a protein comprising a fragment of the amino acid sequence of SEQ ID NO:134 having biological activity, the fragment comprising the amino acid sequence from amino acid 49 to amino acid 58 of SEQ ID NO:134.

In one embodiment, the present invention provides a composition comprising an isolated polynucleotide selected from the group consisting of:

(a) a polynucleotide comprising the nucleotide sequence of SEQ ID NO:135;

(b) a polynucleotide comprising the nucleotide sequence of SEQ ID NO:135 from nucleotide 28 to nucleotide 777; (c) a polynucleotide comprising the nucleotide sequence of SEQ ID NO:135 from nucleotide 73 to nucleotide 777;

(d) a polynucleotide comprising the nucleotide sequence of the full-length protein coding sequence of clone rj214_14 deposited under accession number ATCC 207089;

(e) a polynucleotide encoding the full-length protein encoded by the cDNA insert of clone rj214_14 deposited under accession number ATCC 207089;

(f) a polynucleotide comprising the nucleotide sequence of a mature protein coding sequence of clone rj214_14 deposited under accession number ATCC 207089;

(g) a polynucleotide encoding a mature protein encoded by the cDNA insert of clone rj214_14 deposited under accession number ATCC 207089;

(h) a polynucleotide encoding a protein comprising the amino acid sequence of SEQ ID NO:136;

(i) a polynucleotide encoding a protein comprising a fragment of the amino acid sequence of SEQ ID NO:136 having biological activity, the fragment comprising eight contiguous amino acids of SEQ ID NO:136;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:135.

Preferably, such polynucleotide comprises the nucleotide sequence of SEQ ID NO:135 from nucleotide 28 to nucleotide 777; the nucleotide sequence of SEQ ID NO:135 from nucleotide 73 to nucleotide 777; the nucleotide sequence of the full-length protein coding sequence of clone rj214_14 deposited under accession number ATCC 207089; or the nucleotide sequence of a mature protein coding sequence of clone rj214_14 deposited under accession number ATCC 207089. In other preferred embodiments, the polynucleotide encodes the full-length or a mature protein encoded by the cDNA insert of clone rj214_14 deposited under accession number ATCC 207089. In further preferred embodiments, the present invention provides a polynucleotide encoding a protein comprising a fragment of the amino add sequence of SEQ ID NO:136 having biological activity, the fragment preferably comprising eight (more preferably twenty, most preferably thirty) contiguous amino acids of SEQ ID NO:136, or a polynucleotide encoding a protein comprising a fragment of the amino acid sequence of SEQ ID NO:136 having biological activity, the fragment comprising the amino add sequence from amino acid 120 to amino acid 129 of SEQ ID NO:136.

Other embodiments provide the gene corresponding to the cDNA sequence of SEQ ID NO:135.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:135, but excluding the poly(A) tail at the 3' end of SEQ ID NO:135; and (ab) the nucleotide sequence of the cDNA insert of clone rj214_14 deposited under accession number ATCC 207089;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:135, but excluding the poly(A) tail at the 3' end of SEQ ID NO:135; and (bb) the nucleotide sequence of the cDNA insert of clone rj214_14 deposited under accession number ATCC 207089;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:135, and extending contiguously from a nucleotide sequence corresponding to the 5' end of SEQ ID NO:135 to a nucleotide sequence corresponding to the 3' end of SEQ ID NO:135, but excluding the poly(A) tail at the 3' end of SEQ ID NO:135. Also preferably the polynucleotide isolated according to the above process comprises a nucleotide sequence corresponding to the cDNA sequence of SEQ ID NO:135 from nucleotide 28 to nucleotide 777, and extending contiguously from a nucleotide sequence corresponding to the 5' end of said sequence of SEQ ID NO:135 from nucleotide 28 to nucleotide 777, to a nucleotide sequence corresponding to the 3' end of said sequence of SEQ ID NO:135 from nucleotide 28 to nucleotide 777. Also preferably the polynucleotide isolated according to the above process comprises a nucleotide sequence corresponding to the cDNA sequence of SEQ ID NO:135 from nucleotide 73 to nucleotide 777, and extending contiguously from a nucleotide sequence corresponding to the 5' end of said sequence of SEQ ID NO:135 from nucleotide 73 to nucleotide 777, to a nucleotide sequence corresponding to the 3' end of said sequence of SEQ ID NO:135 from nucleotide 73 to nucleotide 777.

In other embodiments, the present invention provides a composition comprising a protein, wherein said protein comprises an amino acid sequence selected from the group consisting of:

(a) the amino acid sequence of SEQ ID NO:136;
(b) a fragment of the amino acid sequence of SEQ ID NO:136, the fragment comprising eight contiguous amino acids of SEQ ID NO:136; and
(c) the amino acid sequence encoded by the cDNA insert of clone rj214_14 deposited under accession number ATCC 207089;

the protein being substantially free from other mammalian proteins. Preferably such protein comprises the amino acid sequence of SEQ ID NO:136. In further preferred embodiments, the present invention provides a protein comprising a fragment of the amino acid sequence of SEQ ID NO:136 having biological activity, the fragment preferably comprising eight (more preferably twenty, most preferably thirty) contiguous amino acids of SEQ ID NO:136, or a protein comprising a fragment of the amino acid sequence of SEQ ID NO:136 having biological activity, the fragment comprising the amino acid sequence from amino acid 120 to amino acid 129 of SEQ ID NO:136.

In one embodiment, the present invention provides a composition comprising an isolated polynucleotide selected from the group consisting of:

(a) a polynucleotide comprising the nucleotide sequence of SEQ ID NO:137;
(b) a polynucleotide comprising the nucleotide sequence of SEQ ID NO:137 from nucleotide 179 to nucleotide 745;
(c) a polynucleotide comprising the nucleotide sequence of SEQ ID NO:137 from nucleotide 233 to nucleotide 745;
(d) a polynucleotide comprising the nucleotide sequence of the full-length protein coding sequence of clone rk80_3 deposited under accession number ATCC 207089;
(e) a polynucleotide encoding the full-length protein encoded by the cDNA insert of clone rk80_3 deposited under accession number ATCC 207089;
(f) a polynucleotide comprising the nucleotide sequence of a mature protein coding sequence of clone rk8O_3 deposited under accession number ATCC 207089;
(g) a polynucleotide encoding a mature protein encoded by the cDNA insert of clone rk80_3 deposited under accession number ATCC 207089;
(h) a polynucleotide encoding a protein comprising the amino acid sequence of SEQ ID NO:138;
(i) a polynucleotide encoding a protein comprising a fragment of the amino acid sequence of SEQ ID NO:138 having biological activity, the fragment comprising eight contiguous amino acids of SEQ ID NO:138;
(j) a polynucleotide which is an allelic variant of a polynucleotide of (a)-(g) above;
(k) a polynucleotide which encodes a species homologue of the protein of (h) or (i) above;
(l) a polynucleotide that hybridizes under stringent conditions to any one of the polynucleotides specified in (a)-(i); and
(m) a polynucleotide that hybridizes under stringent conditions to any one of the polynucleotides specified in (a)-(i) and that has a length that is at least 25% of the length of SEQ ID NO:137.

Preferably, such polynucleotide comprises the nucleotide sequence of SEQ ID NO:137 from nucleotide 179 to nucleotide 745; the nucleotide sequence of SEQ ID NO:137 from nucleotide 233 to nucleotide 745; the nucleotide sequence of the full-length protein coding sequence of clone rk80_3 deposited under accession number ATCC 207089; or the nucleotide sequence of a mature protein coding sequence of clone rk80_3 deposited under accession number ATCC 207089. In other preferred embodiments, the polynucleotide encodes the full-length or a mature protein encoded by the cDNA insert of clone rk80_3 deposited under accession number ATCC 207089. In further preferred embodiments, the present invention provides a polynucleotide encoding a protein comprising a fragment of the amino acid sequence of SEQ ID NO:138 having biological activity, the fragment preferably comprising eight (more preferably twenty, most preferably thirty) contiguous amino acids of SEQ ID NO:138, or a polynucleotide encoding a protein comprising a fragment of the amino acid sequence of SEQ ID NO:138 having biological activity, the fragment comprising the amino acid sequence from amino acid 89 to amino acid 98 of SEQ ID NO:138.

Other embodiments provide the gene corresponding to the cDNA sequence of SEQ ID NO:137.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:137, but excluding the poly(A) tail at the 3' end of SEQ ID NO:137; and
    (ab) the nucleotide sequence of the cDNA insert of clone rk80_3 deposited under accession number ATCC 207089;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:137, but excluding the poly(A) tail at the 3' end of SEQ ID NO:137; and
    (bb) the nucleotide sequence of the cDNA insert of clone rk80_3 deposited under accession number ATCC 207089;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:137, and extending contiguously from a nucleotide sequence corresponding to the 5' end of SEQ ID NO:137 to a nucleotide sequence corresponding to the 3' end of SEQ ID NO:137, but excluding the poly(A) tail at the 3' end of SEQ ID NO:137. Also preferably the polynucleotide isolated according to the above process comprises a nucleotide sequence corresponding to the cDNA sequence of SEQ ID NO:137 from nucleotide 179 to nucleotide 745, and extending contiguously from a nucleotide sequence corresponding to the 5' end of said sequence of SEQ ID NO:137 from nucleotide 179 to nucleotide 745, to a nucleotide sequence corresponding to the 3' end of said sequence of SEQ ID NO:137 from nucleotide 179 to nucleotide 745. Also preferably the polynucleotide isolated according to the above process comprises a nucleotide sequence corresponding to the cDNA sequence of SEQ ID NO:137 from nucleotide 233 to nucleotide 745, and extending contiguously from a nucleotide sequence corresponding to the 5' end of said sequence of SEQ ID NO:137 from nucleotide 233 to nucleotide 745, to a nucleotide sequence corresponding to the 3' end of said sequence of SEQ ID NO:137 from nucleotide 233 to nucleotide 745.

In other embodiments, the present invention provides a composition comprising a protein, wherein said protein comprises an amino acid sequence selected from the group consisting of:

(a) the amino acid sequence of SEQ ID NO:138;

(b) a fragment of the amino acid sequence of SEQ ID NO:138, the fragment comprising eight contiguous amino acids of SEQ ID NO:138; and (c) the amino acid sequence encoded by the cDNA insert of clone rk80_3 deposited under accession number ATCC 207089;

the protein being substantially free from other mammalian proteins. Preferably such protein comprises the amino acid sequence of SEQ ID NO:138. In further preferred embodiments, the present invention provides a protein comprising a fragment of the amino acid sequence of SEQ ID NO:138 having biological activity, the fragment preferably comprising eight (more preferably twenty, most preferably thirty) contiguous amino acids of SEQ ID NO:138, or a protein comprising a fragment of the amino acid sequence of SEQ ID NO:138 having biological activity, the fragment comprising the amino acid sequence from amino acid 89 to amino acid 98 of SEQ ID NO:138.

In one embodiment, the present invention provides a composition comprising an isolated polynucleotide selected from the group consisting of:

(a) a polynucleotide comprising the nucleotide sequence of SEQ ID NO:139;

(b) a polynucleotide comprising the nucleotide sequence of SEQ ID NO:139 from nucleotide 1017 to nucleotide 1274;

(c) a polynucleotide comprising the nucleotide sequence of the full-length protein coding sequence of clone au36_42 deposited under accession number ATCC 207187;

(d) a polynucleotide encoding the full-length protein encoded by the cDNA insert of clone au36_42 deposited under accession number ATCC 207187;

(e) a polynucleotide comprising the nucleotide sequence of a mature protein coding sequence of clone au36_42 deposited under accession number ATCC 207187;

(f) a polynucleotide encoding a mature protein encoded by the cDNA insert of clone au36_42 deposited under accession number ATCC 207187;

(g) a polynucleotide encoding a protein comprising the amino acid sequence of SEQ ID NO:140;

(h) a polynucleotide encoding a protein comprising a fragment of the amino acid sequence of SEQ ID NO:140 having biological activity, the fragment comprising eight contiguous amino acids of SEQ ID NO:140;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:139.

Preferably, such polynucleotide comprises the nucleotide sequence of SEQ ID NO:139 from nucleotide 1017 to nucleotide 1274; the nucleotide sequence of the full-length protein coding sequence of clone au36_42 deposited under accession number ATCC 207187; or the nucleotide sequence of a mature protein coding sequence of clone au36_42 deposited under accession number ATCC 207187. In other preferred embodiments, the polynucleotide encodes the full-length or a mature protein encoded by the cDNA insert of clone au36_42 deposited under accession number ATCC 207187. In further preferred embodiments, the present invention provides a polynucleotide encoding a protein comprising a fragment of the amino acid sequence of SEQ ID NO:140 having biological activity, the fragment preferably comprising eight (more preferably twenty, most preferably thirty) contiguous amino acids of SEQ ID NO:140, or a polynucleotide encoding a protein comprising a fragment of the amino acid sequence of SEQ ID NO:140 having biological activity, the fragment comprising the amino acid sequence from amino acid 38 to amino acid 47 of SEQ ID NO:140.

Other embodiments provide the gene corresponding to the cDNA sequence of SEQ ID NO:139.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:139, but excluding the poly(A) tail at the 3' end of SEQ ID NO:139; and (ab) the nucleotide sequence of the cDNA insert of clone au36_42 deposited under accession number ATCC 207187;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:139, but excluding the poly(A) tail at the 3' end of SEQ ID NO:139; and (bb) the nucleotide sequence of the cDNA insert of clone au36_42 deposited under accession number ATCC 207187;

(ii) hybridizing said primer(s) to human genomic DNA in conditions at least as stringent as 4×SSC at 50 degrees C.;

(ii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:139, and extending contiguously from a nucleotide sequence corresponding to the 5' end of SEQ ID NO:139 to a nucleotide sequence corresponding to the 3' end of SEQ ID NO:139, but excluding the poly(A) tail at the 3' end of SEQ ID NO:139. Also preferably the polynucleotide isolated according to the above process comprises a nucleotide sequence corresponding to the cDNA sequence of SEQ ID NO:139 from nucleotide 1017 to nucleotide 1274, and extending contiguously from a nucleotide sequence corresponding to the 5' end of said sequence of SEQ ID NO:139 from nucleotide 1017 to nucleotide 1274, to a nucleotide sequence corresponding to the 3' end of said sequence of SEQ ID NO:139 from nucleotide 1017 to nucleotide 1274.

In other embodiments, the present invention provides a composition comprising a protein, wherein said protein comprises an amino acid sequence selected from the group consisting of:

(a) the amino acid sequence of SEQ ID NO:140;

(b) a fragment of the amino acid sequence of SEQ ID NO:140, the fragment comprising eight contiguous amino acids of SEQ ID NO:140; and (c) the amino acid sequence encoded by the cDNA insert of clone au36_42 deposited under accession number ATCC 207187;

the protein being substantially free from other mammalian proteins. Preferably such protein comprises the amino acid sequence of SEQ ID NO:140. In further preferred embodiments, the present invention provides a protein comprising a fragment of the amino acid sequence of SEQ ID NO:140 having biological activity, the fragment preferably comprising eight (more preferably twenty, most preferably thirty) contiguous amino acids of SEQ ID NO:140, or a protein comprising a fragment of the amino acid sequence of SEQ ID NO:140 having biological activity, the fragment comprising the amino acid sequence from amino acid 38 to amino acid 47 of SEQ ID NO:140.

In one embodiment, the present invention provides a composition comprising an isolated polynucleotide selected from the group consisting of:

(a) a polynucleotide comprising the nucleotide sequence of SEQ ID NO:141;

(b) a polynucleotide comprising the nucleotide sequence of SEQ ID NO:141 from nucleotide 580 to nucleotide 774;

(c) a polynucleotide comprising the nucleotide sequence of the full-length protein coding sequence of clone bo549_13 deposited under accession number ATCC 207187;

(d) a polynucleotide encoding the full-length protein encoded by the cDNA insert of clone bo549_13 deposited under accession number ATCC 207187;

(e) a polynucleotide comprising the nucleotide sequence of a mature protein coding sequence of clone bo549_13 deposited under accession number ATCC 207187;

(f) a polynucleotide encoding a mature protein encoded by the cDNA insert of clone bo549_13 deposited under accession number ATCC 207187;

(g) a polynucleotide encoding a protein comprising the amino acid sequence of SEQ ID NO:142;

(h) a polynucleotide encoding a protein comprising a fragment of the amino acid sequence of SEQ ID NO:142 having biological activity, the fragment comprising eight contiguous amino acids of SEQ ID NO:142;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:141.

Preferably, such polynucleotide comprises the nucleotide sequence of SEQ ID NO:141 from nucleotide 580 to nucleotide 774; the nucleotide sequence of the full-length protein coding sequence of clone bo549_13 deposited under accession number ATCC 207187; or the nucleotide sequence of a mature protein coding sequence of clone bo549_13 deposited under accession number ATCC 207187. In other preferred embodiments, the polynucleotide encodes the full-length or a mature protein encoded by the cDNA insert of clone bo549_13 deposited under accession number ATCC 207187. In further preferred embodiments, the present invention provides a polynucleotide encoding a protein comprising a fragment of the amino acid sequence of SEQ ID NO:142 having biological activity, the fragment preferably comprising eight (more preferably twenty, most preferably thirty) contiguous amino acids of SEQ ID NO:142, or a polynucleotide encoding a protein comprising a fragment of the amino acid sequence of SEQ ID NO:142 having biological activity, the fragment comprising the amino acid sequence from amino acid 27 to amino acid 36 of SEQ ID NO:142.

Other embodiments provide the gene corresponding to the cDNA sequence of SEQ ID NO:141.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:141, but excluding the poly(A) tail at the 3' end of SEQ ID NO:141; and (ab) the nucleotide sequence of the cDNA insert of clone bo549_13 deposited under accession number ATCC 207187;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:141, but excluding the poly(A) tail at the 3' end of SEQ ID NO:141; and (bb) the nucleotide sequence of the cDNA insert of clone bo549_13 deposited under accession number ATCC 207187;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:141, and extending contiguously from a nucleotide sequence corresponding to the 5' end of SEQ ID NO:141 to a nucleotide sequence corresponding to the 3' end of SEQ ID NO:141, but excluding the poly(A) tail at the 3' end of SEQ ID NO:141. Also preferably the polynucleotide isolated according to the above process comprises a nucleotide sequence corresponding to the cDNA sequence of SEQ ID NO:141 from nucleotide 580 to nucleotide 774, and extending contiguously from a nucleotide sequence corresponding to the 5' end of said sequence of SEQ ID NO:141 from nucleotide 580 to nucleotide 774, to a nucleotide sequence corresponding to the 3' end of said sequence of SEQ ID NO:141 from nucleotide 580 to nucleotide 774.

In other embodiments, the present invention provides a composition comprising a protein, wherein said protein comprises an amino acid sequence selected from the group consisting of:

(a) the amino acid sequence of SEQ ID NO:142;

(b) a fragment of the amino acid sequence of SEQ ID NO:142, the fragment comprising eight contiguous amino acids of SEQ ID NO:142; and (c) the amino acid sequence encoded by the cDNA insert of clone bo549_13 deposited under accession number ATCC 207187;

the protein being substantially free from other mammalian proteins. Preferably such protein comprises the amino add sequence of SEQ ID NO:142. In further preferred embodiments, the present invention provides a protein comprising a fragment of the amino acid sequence of SEQ ID NO:142 having biological activity, the fragment preferably comprising eight (more preferably twenty, most preferably thirty) contiguous amino adds of SEQ ID NO:142, or a protein comprising a fragment of the amino acid sequence of SEQ ID NO:142 having biological activity, the fragment comprising the amino acid sequence from amino acid 27 to amino acid 36 of SEQ ID NO:142.

In one embodiment, the present invention provides a composition comprising an isolated polynucleotide selected from the group consisting of:

(a) a polynucleotide comprising the nucleotide sequence of SEQ ID NO:143;

(b) a polynucleotide comprising the nucleotide sequence of SEQ ID NO:143 from nucleotide 172 to nucleotide 969;

(c) a polynucleotide comprising the nucleotide sequence of SEQ ID NO:143 from nucleotide 385 to nucleotide 969;

(d) a polynucleotide comprising the nucleotide sequence of the full-length protein coding sequence of clone da529_3 deposited under accession number ATCC 207187;

(e) a polynucleotide encoding the full-length protein encoded by the cDNA insert of clone da529_3 deposited under accession number ATCC 207187;

(f) a polynucleotide comprising the nucleotide sequence of a mature protein coding sequence of clone da529_3 deposited under accession number ATCC 207187;

(g) a polynucleotide encoding a mature protein encoded by the cDNA insert of clone da529_3 deposited under accession number ATCC 207187;

(h) a polynucleotide encoding a protein comprising the amino acid sequence of SEQ ID NO:144;

(i) a polynucleotide encoding a protein comprising a fragment of the amino acid sequence of SEQ ID NO:144 having biological activity, the fragment comprising eight contiguous amino acids of SEQ ID NO:144;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:143.

Preferably, such polynucleotide comprises the nucleotide sequence of SEQ ID NO:143 from nucleotide 172 to nucleotide 969; the nucleotide sequence of SEQ ID NO:143 from nucleotide 385 to nucleotide 969; the nucleotide sequence of the full-length protein coding sequence of clone da529_3 deposited under accession number ATCC 207187; or the nucleotide sequence of a mature protein coding sequence of clone da529_3 deposited under accession number ATCC 207187. In other preferred embodiments, the polynucleotide encodes the full-length or a mature protein encoded by the cDNA insert of clone da529_3 deposited under accession number ATCC 207187. In further preferred embodiments, the present invention provides a polynucleotide encoding a protein comprising a fragment of the amino acid sequence of SEQ ID NO:144 having biological activity, the fragment preferably comprising eight (more preferably twenty, most preferably thirty) contiguous amino acids of SEQ ID NO:144, or a polynucleotide encoding a protein comprising a fragment of the amino acid sequence of SEQ ID NO:144 having biological activity, the fragment comprising the amino acid sequence from amino acid 128 to amino acid 137 of SEQ ID NO:144.

Other embodiments provide the gene corresponding to the cDNA sequence of SEQ ID NO:143.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:143, but excluding the poly(A) tail at the 3' end of SEQ ID NO:143; and (ab) the nucleotide sequence of the cDNA insert of clone da529_3 deposited under accession number ATCC 207187;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:143, but excluding the poly(A) tail at the 3' end of SEQ ID NO:143; and (bb) the nucleotide sequence of the cDNA insert of clone da529_3 deposited under accession number ATCC 207187;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:143, and extending contiguously from a nucleotide sequence corresponding to the 5' end of SEQ ID NO:143 to a nucleotide sequence corresponding to the 3' end of SEQ ID NO:143, but excluding the poly(A) tail at the 3' end of SEQ ID NO:143. Also preferably the polynucleotide isolated according to the above process comprises a nucleotide sequence corresponding to the cDNA sequence of SEQ ID NO:143 from nucleotide 172 to nucleotide 969, and extending contiguously from a nucleotide sequence corresponding to the 5' end of said sequence of SEQ ID NO:143 from nucleotide 172 to nucleotide 969, to a nucleotide sequence corresponding to the 3' end of said sequence of SEQ ID NO:143 from nucleotide 172 to nucleotide 969. Also preferably the polynucleotide isolated according to the above process comprises a nucleotide sequence corresponding to the cDNA sequence of SEQ ID NO:143 from nucleotide 385 to nucleotide 969, and extending contiguously from a nucleotide sequence corresponding to the 5' end of said sequence of SEQ ID NO:143 from nucleotide 385 to nucleotide 969, to a nucleotide sequence corresponding to the 3' end of said sequence of SEQ ID NO:143 from nucleotide 385 to nucleotide 969.

In other embodiments, the present invention provides a composition comprising a protein, wherein said protein comprises an amino acid sequence selected from the group consisting of:

(a) the amino acid sequence of SEQ ID NO:144;

(b) a fragment of the amino acid sequence of SEQ ID NO:144, the fragment comprising eight contiguous amino acids of SEQ ID NO:144; and (c) the amino acid sequence encoded by the cDNA insert of done da529_3 deposited under accession number ATCC 207187;

the protein being substantially free from other mammalian proteins. Preferably such protein comprises the amino acid sequence of SEQ ID NO:144. In further preferred embodiments, the present invention provides a protein comprising a fragment of the amino acid sequence of SEQ ID NO:144 having biological activity, the fragment preferably comprising eight (more preferably twenty, most preferably thirty) contiguous amino acids of SEQ ID NO 144, or a protein comprising a fragment of the amino acid sequence of SEQ ID NO:144 having biological activity, the fragment comprising the amino acid sequence from amino acid 128 to amino acid 137 of SEQ ID NO:144.

In one embodiment, the present invention provides a composition comprising an isolated polynucleotide selected from the group consisting of:

(a) a polynucleotide comprising the nucleotide sequence of SEQ ID NO:145;

(b) a polynucleotide comprising the nucleotide sequence of SEQ ID NO:145 from nucleotide 329 to nucleotide 667;

(c) a polynucleotide comprising the nucleotide sequence of SEQ ID NO:145 from nucleotide 368 to nucleotide 667;

(d) a polynucleotide comprising the nucleotide sequence of the full-length protein coding sequence of clone dm365_3 deposited under accession number ATCC 207187;

(e) a polynucleotide encoding the full-length protein encoded by the cDNA insert of clone dm365_3 deposited under accession number ATCC 207187;

(f) a polynucleotide comprising the nucleotide sequence of a mature protein coding sequence of clone dm365_3 deposited under accession number ATCC 207187;

(g) a polynucleotide encoding a mature protein encoded by the cDNA insert of clone dm365_3 deposited under accession number ATCC 207187;

(h) a polynucleotide encoding a protein comprising the amino acid sequence of SEQ ID NO:146;

(i) a polynucleotide encoding a protein comprising a fragment of the amino acid sequence of SEQ ID NO:146 having biological activity, the fragment comprising eight contiguous amino acids of SEQ ID NO:146;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:145.

Preferably, such polynucleotide comprises the nucleotide sequence of SEQ ID NO:145 from nucleotide 329 to nucleotide 667; the nucleotide sequence of SEQ ID NO:145 from nucleotide 368 to nucleotide 667; the nucleotide sequence of the full-length protein coding sequence of clone dm365_3 deposited under accession number ATCC 207187; or the nucleotide sequence of a mature protein coding sequence of clone dm365_3 deposited under accession number ATCC 207187. In other preferred embodiments, the polynucleotide encodes the full-length or a mature protein encoded by the cDNA insert of clone dm365_3 deposited under accession number ATCC 207187. In further preferred embodiments, the present invention provides a polynucleotide encoding a protein comprising a fragment of the amino acid sequence of SEQ ID NO:146 having biological activity, the fragment preferably comprising eight (more preferably twenty, most preferably thirty) contiguous amino acids of SEQ ID NO:146, or a polynucleotide encoding a protein comprising a fragment of the amino acid sequence of SEQ ID NO:146 having biological activity, the fragment comprising the amino acid sequence from amino acid 51 to amino acid 60 of SEQ ID NO:146.

Other embodiments provide the gene corresponding to the cDNA sequence of SEQ ID NO:145.

Further embodiments of the invention provide isolated polynucleotides produced according to a process selected from the group consisting of:

(a) a process comprising the steps of:
 (i) preparing one or more polynucleotide probes that hybridize in 6×SSC at 65 degrees C. to a nucleotide sequence selected from the group consisting of:
  (aa) SEQ ID NO:145, but excluding the poly(A) tail at the 3' end of SEQ ID NO:145; and
  (ab) the nucleotide sequence of the cDNA insert of clone dm365_3 deposited under accession number ATCC 207187;
 (ii) hybridizing said probe(s) to human genomic DNA in conditions at least as stringent as 4×SSC at 50 degrees C.; and
 (iii) isolating the DNA polynucleotides detected with the probe(s); and
(b) a process comprising the steps of:
 (i) preparing one or more polynucleotide primers that hybridize in 6×SSC at 65 degrees C. to a nucleotide sequence selected from the group consisting of:
  (ba) SEQ ID NO:145, but excluding the poly(A) tail at the 3' end of SEQ ID NO:145; and
  (bb) the nucleotide sequence of the cDNA insert of clone dm365_3 deposited under accession number ATCC 207187;
 (ii) hybridizing said primer(s) to human genomic DNA in conditions at least as stringent as 4×SSC at 50 degrees C.;
 (iii) amplifying human DNA sequences; and
 (iv) isolating the polynucleotide products of step (b) (iii).

Preferably the polynucleotide isolated according to the above process comprises a nucleotide sequence corresponding to the cDNA sequence of SEQ ID NO:145, and extending contiguously from a nucleotide sequence corresponding to the 5' end of SEQ ID NO:145 to a nucleotide sequence corresponding to the 3' end of SEQ ID NO:145, but excluding the poly(A) tail at the 3' end of SEQ ID NO:145. Also preferably the polynucleotide isolated according to the above process comprises a nucleotide sequence corresponding to the cDNA sequence of SEQ ID NO:145 from nucleotide 329 to nucleotide 667, and extending contiguously from a nucleotide sequence corresponding to the 5' end of said sequence of SEQ ID NO:145 from nucleotide 329 to nucleotide 667, to a nucleotide sequence corresponding to the 3' end of said sequence of SEQ ID NO:145 from nucleotide 329 to nucleotide 667. Also preferably the polynucleotide isolated according to the above process comprises a nucleotide sequence corresponding to the cDNA sequence of SEQ ID NO:145 from nucleotide 368 to nucleotide 667, and extending contiguously from a nucleotide sequence corresponding to the 5' end of said sequence of SEQ ID NO:145 from nucleotide 368 to nucleotide 667, to a nucleotide sequence corresponding to the 3' end of said sequence of SEQ ID NO:145 from nucleotide 368 to nucleotide 667.

In other embodiments, the present invention provides a composition comprising a protein, wherein said protein comprises an amino acid sequence selected from the group consisting of:

(a) the amino acid sequence of SEQ ID NO:146;
(b) a fragment of the amino acid sequence of SEQ ID NO:146, the fragment comprising eight contiguous amino acids of SEQ ID NO:146; and
(c) the amino acid sequence encoded by the cDNA insert of clone dm365_3 deposited under accession number ATCC 207187;

the protein being substantially free from other mammalian proteins. Preferably such protein comprises the amino acid sequence of SEQ ID NO:146. In further preferred embodiments, the present invention provides a protein comprising a fragment of the amino acid sequence of SEQ ID NO:146 having biological activity, the fragment preferably comprising eight (more preferably twenty, most preferably thirty) contiguous amino acids of SEQ ID NO:146, or a protein comprising a fragment of the amino acid sequence of SEQ ID NO:146 having biological activity, the fragment comprising the amino acid sequence from amino acid 51 to amino acid 60 of SEQ ID NO:146.

In one embodiment, the present invention provides a composition comprising an isolated polynucleotide selected from the group consisting of:

(a) a polynucleotide comprising the nucleotide sequence of SEQ ID NO:147;
(b) a polynucleotide comprising the nucleotide sequence of SEQ ID NO:147 from nucleotide 103 to nucleotide 1368;
(c) a polynucleotide comprising the nucleotide sequence of the full-length protein coding sequence of clone fa171_1 deposited under accession number ATCC 207187;
(d) a polynucleotide encoding the full-length protein encoded by the cDNA insert of clone fa171_1 deposited under accession number ATCC 207187;
(e) a polynucleotide comprising the nucleotide sequence of a mature protein coding sequence of clone fa171_1 deposited under accession number ATCC 207187;
(f) a polynucleotide encoding a mature protein encoded by the cDNA insert of clone fa171_1 deposited under accession number ATCC 207187;
(g) a polynucleotide encoding a protein comprising the amino acid sequence of SEQ ID NO:148;
(h) a polynucleotide encoding a protein comprising a fragment of the amino acid sequence of SEQ ID NO:148 having biological activity, the fragment comprising eight contiguous amino acids of SEQ ID NO:148;
(i) a polynucleotide which is an allelic variant of a polynucleotide of (a)-(f) above;
(j) a polynucleotide which encodes a species homologue of the protein of (g) or (h) above;
(k) a polynucleotide that hybridizes under stringent conditions to any one of the polynucleotides specified in (a)-(h); and
(l) a polynucleotide that hybridizes under stringent conditions to any one of the polynucleotides specified in (a)-(h) and that has a length that is at least 25% of the length of SEQ ID NO 147.

Preferably, such polynucleotide comprises the nucleotide sequence of SEQ ID NO:147 from nucleotide 103 to nucleotide 1368, the nucleotide sequence of the full-length protein coding sequence of clone fa171_1 deposited under accession number ATCC 207187; or the nucleotide sequence of a mature protein coding sequence of clone fa171_1 deposited under accession number ATCC 207187. In other preferred embodiments, the polynucleotide encodes the full-length or a mature protein encoded by the cDNA insert of clone fa171_1 deposited under accession number ATCC 207187. In further preferred embodiments, the present invention provides a polynucleotide encoding a protein comprising a fragment of the amino acid sequence of SEQ ID NO:148 having biological activity, the fragment preferably comprising eight (more preferably twenty, most preferably thirty) contiguous amino acids of SEQ ID NO:148, or a polynucleotide encoding a protein comprising a fragment of the amino acid sequence of SEQ ID NO:148 having biological activity, the fragment comprising the amino acid sequence from amino acid 206 to amino acid 215 of SEQ ID NO:148.

Other embodiments provide the gene corresponding to the cDNA sequence of SEQ ID NO:147.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:147, but excluding the poly(A) tail at the 3' end of SEQ ID NO:147; and
    (ab) the nucleotide sequence of the cDNA insert of clone fa171_1 deposited under accession number ATCC 207187;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:147, but excluding the poly(A) tail at the 3' end of SEQ ID NO:147; and
    (bb) the nucleotide sequence of the cDNA insert of clone fa171_1 deposited under accession number ATCC 207187;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:147, and extending contiguously from a nucleotide sequence corresponding to the 5' end of SEQ ID NO:147 to a nucleotide sequence corresponding to the 3' end of SEQ ID NO:147, but excluding the poly(A) tail at the 3' end of SEQ ID NO:147. Also preferably the polynucleotide isolated according to the above process comprises a nucleotide sequence corresponding to the cDNA sequence of SEQ ID NO:147 from nucleotide 103 to nucleotide 1368, and extending contiguously from a nucleotide sequence corresponding to the 5' end of said sequence of SEQ ID NO:147 from nucleotide 103 to nucleotide 1368, to a nucleotide sequence corresponding to the 3' end of said sequence of SEQ ID NO:147 from nucleotide 103 to nucleotide 1368.

In other embodiments, the present invention provides a composition comprising a protein, wherein said protein comprises an amino acid sequence selected from the group consisting of:

(a) the amino acid sequence of SEQ ID NO:148;
(b) a fragment of the amino acid sequence of SEQ ID NO:148, the fragment comprising eight contiguous amino acids of SEQ ID NO:148; and
(c) the amino acid sequence encoded by the cDNA insert of clone fa171_1 deposited under accession number ATCC 207187;

the protein being substantially free from other mammalian proteins. Preferably such protein comprises the amino acid sequence of SEQ ID NO:148. In further preferred embodiments, the present invention provides a protein comprising a fragment of the amino acid sequence of SEQ ID NO:148 having biological activity, the fragment preferably comprising eight (more preferably twenty, most preferably thirty) contiguous amino acids of SEQ ID NO:148, or a protein comprising a fragment of the amino acid sequence of SEQ ID NO:148 having biological activity, the fragment comprising the amino acid sequence from amino acid 206 to amino acid 215 of SEQ ID NO:148.

In one embodiment, the present invention provides a composition comprising an isolated polynucleotide selected from the group consisting of:

(a) a polynucleotide comprising the nucleotide sequence of SEQ ID NO:149;
(b) a polynucleotide comprising the nucleotide sequence of SEQ ID NO:149 from nucleotide 190 to nucleotide 1407;
(c) a polynucleotide comprising the nucleotide sequence of SEQ ID NO:149 from nucleotide 463 to nucleotide 1407;
(d) a polynucleotide comprising the nucleotide sequence of the full-length protein coding sequence of clone lp572_2 deposited under accession number ATCC 207187;
(e) a polynucleotide encoding the full-length protein encoded by the cDNA insert of clone lp572_2 deposited under accession number ATCC 207187;
(f) a polynucleotide comprising the nucleotide sequence of a mature protein coding sequence of clone lp572_2 deposited under accession number ATCC 207187;
(g) a polynucleotide encoding a mature protein encoded by the cDNA insert of clone lp572_2 deposited under accession number ATCC 207187;
(h) a polynucleotide encoding a protein comprising the amino add sequence of SEQ ID NO:150;
(i) a polynucleotide encoding a protein comprising a fragment of the amino acid sequence of SEQ ID NO:150 having biological activity, the fragment comprising eight contiguous amino acids of SEQ ID NO:150;
(j) a polynucleotide which is an allelic variant of a polynucleotide of (a)-(g) above;
(k) a polynucleotide which encodes a species homologue of the protein of (h) or (i) above;
(l) a polynucleotide that hybridizes under stringent conditions to any one of the polynucleotides specified in (a)-(i); and
(m) a polynucleotide that hybridizes under stringent conditions to any one of the polynucleotides specified in (a)-(i) and that has a length that is at least 25% of the length of SEQ ID NO:149.

Preferably, such polynucleotide comprises the nucleotide sequence of SEQ ID NO:149 from nucleotide 190 to nucleotide 1407; the nucleotide sequence of SEQ ID NO:149 from nucleotide 463 to nucleotide 1407; the nucleotide sequence of the full-length protein coding sequence of clone lp572_2 deposited under accession number ATCC 207187;

or the nucleotide sequence of a mature protein coding sequence of clone lp572_2 deposited under accession number ATCC 207187. In other preferred embodiments, the polynucleotide encodes the full-length or a mature protein encoded by the cDNA insert of clone lp572_2 deposited under accession number ATCC 207187. In further preferred embodiments, the present invention provides a polynucleotide encoding a protein comprising a fragment of the amino acid sequence of SEQ ID NO:150 having biological activity, the fragment preferably comprising eight (more preferably twenty, most preferably thirty) contiguous amino acids of SEQ ID NO:150, or a polynucleotide encoding a protein comprising a fragment of the amino acid sequence of SEQ ID NO:150 having biological activity, the fragment comprising the amino acid sequence from amino acid 198 to amino acid 207 of SEQ ID NO:150.

Other embodiments provide the gene corresponding to the cDNA sequence of SEQ ID NO:149.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:149, but excluding the poly(A) tail at the 3' end of SEQ ID NO:149; and
    (ab) the nucleotide sequence of the cDNA insert of clone lp572_2 deposited under accession number ATCC 207187;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:149, but excluding the poly(A) tail at the 3' end of SEQ ID NO:149; and
    (bb) the nucleotide sequence of the cDNA insert of clone lp572_2 deposited under accession number ATCC 207187;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:149, and extending contiguously from a nucleotide sequence corresponding to the 5' end of SEQ ID NO:149 to a nucleotide sequence corresponding to the 3' end of SEQ ID NO:149, but excluding the poly(A) tail at the 3' end of SEQ ID NO:149. Also preferably the polynucleotide isolated according to the above process comprises a nucleotide sequence corresponding to the cDNA sequence of SEQ ID NO:149 from nucleotide 190 to nucleotide 1407, and extending contiguously from a nucleotide sequence corresponding to the 5' end of said sequence of SEQ ID NO:149 from nucleotide 190 to nucleotide 1407, to a nucleotide sequence corresponding to the 3' end of said sequence of SEQ ID NO:149 from nucleotide 190 to nucleotide 1407. Also preferably the polynucleotide isolated according to the above process comprises a nucleotide sequence corresponding to the cDNA sequence of SEQ ID NO:149 from nucleotide 463 to nucleotide 1407, and extending contiguously from a nucleotide sequence corresponding to the 5' end of said sequence of SEQ ID NO:149 from nucleotide 463 to nucleotide 1407, to a nucleotide sequence corresponding to the 3' end of said sequence of SEQ ID NO:149 from nucleotide 463 to nucleotide 1407.

In other embodiments, the present invention provides a composition comprising a protein, wherein said protein comprises an amino acid sequence selected from the group consisting of:

(a) the amino acid sequence of SEQ ID NO:150;
(b) a fragment of the amino acid sequence of SEQ ID NO:150, the fragment comprising eight contiguous amino acids of SEQ ID NO:150; and
(c) the amino acid sequence encoded by the cDNA insert of clone lp572_2 deposited under accession number ATCC 207187;

the protein being substantially free from other mammalian proteins. Preferably such protein comprises the amino acid sequence of SEQ ID NO:150. In further preferred embodiments, the present invention provides a protein comprising a fragment of the amino acid sequence of SEQ ID NO:150 having biological activity, the fragment preferably comprising eight (more preferably twenty, most preferably thirty) contiguous amino acids of SEQ ID NO:150, or a protein comprising a fragment of the amino acid sequence of SEQ ID NO:150 having biological activity, the fragment comprising the amino acid sequence from amino acid 198 to amino acid 207 of SEQ ID NO:150.

In one embodiment, the present invention provides a composition comprising an isolated polynucleotide selected from the group consisting of:

(a) a polynucleotide comprising the nucleotide sequence of SEQ ID NO:151;
(b) a polynucleotide comprising the nucleotide sequence of SEQ ID NO:151 from nucleotide 301 to nucleotide 1035;
(c) a polynucleotide comprising the nucleotide sequence of SEQ ID NO:151 from nucleotide 916 to nucleotide 1035;
(d) a polynucleotide comprising the nucleotide sequence of the full-length protein coding sequence of clone pe246_1 deposited under accession number ATCC 207187;
(e) a polynucleotide encoding the full-length protein encoded by the cDNA insert of clone pe246_1 deposited under accession number ATCC 207187;
(f) a polynucleotide comprising the nucleotide sequence of a mature protein coding sequence of clone pe246_1 deposited under accession number ATCC 207187;
(g) a polynucleotide encoding a mature protein encoded by the cDNA insert of clone pe246_1 deposited under accession number ATCC 207187;
(h) a polynucleotide encoding a protein comprising the amino acid sequence of SEQ ID NO:152;
(i) a polynucleotide encoding a protein comprising a fragment of the amino acid sequence of SEQ ID NO:152 having biological activity, the fragment comprising eight contiguous amino acids of SEQ ID NO:152;
(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a>(i) and that has a length that is at least 25% of the length of SEQ ID NO:151.

Preferably, such polynucleotide comprises the nucleotide sequence of SEQ ID NO:151 from nucleotide 301 to nucleotide 1035; the nucleotide sequence of SEQ ID NO:151 from nucleotide 916 to nucleotide 1035; the nucleotide sequence of the full-length protein coding sequence of clone pe246__1 deposited under accession number ATCC 207187; or the nucleotide sequence of a mature protein coding sequence of clone pe246__1 deposited under accession number ATCC 207187. In other preferred embodiments, the polynucleotide encodes the full-length or a mature protein encoded by the cDNA insert of clone pe246__1 deposited under accession number ATCC 207187. In further preferred embodiments, the present invention provides a polynucleotide encoding a protein comprising a fragment of the amino acid sequence of SEQ ID NO:152 having biological activity, the fragment preferably comprising eight (more preferably twenty, most preferably thirty) contiguous amino acids of SEQ ID NO:152, or a polynucleotide encoding a protein comprising a fragment of the amino acid sequence of SEQ ID NO:152 having biological activity, the fragment comprising the amino acid sequence from amino acid 117 to amino acid 126 of SEQ ID NO 152.

Other embodiments provide the gene corresponding to the cDNA sequence of SEQ ID NO:151.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:151, but excluding the poly(A) tail at the 3' end of SEQ ID NO:151; and
    (ab) the nucleotide sequence of the cDNA insert of clone pe246__1 deposited under accession number ATCC 207187;
  (ii) hybridizing said probe(s) to human genomic DNA in conditions at least as stringent as 4×SSC at 50 degrees C.; and
  (iii) isolating the DNA polynucleotides detected with the probe(s); and (b) a process comprising the steps of:
  (i) preparing one or more polynucleotide primers that hybridize in 6×SSC at 65 degrees C. to a nucleotide sequence selected from the group consisting of:
    (ba) SEQ ID NO:151, but excluding the poly(A) tail at the 3' end of SEQ ID NO:151; and
    (bb) the nucleotide sequence of the cDNA insert of clone pe246__1 deposited under accession number ATCC 207187;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:151, and extending contiguously from a nucleotide sequence corresponding to the 5' end of SEQ ID NO:151 to a nucleotide sequence corresponding to the 3' end of SEQ ID NO:151, but excluding the poly(A) tail at the 3' end of SEQ ID NO:151. Also preferably the polynucleotide isolated according to the above process comprises a nucleotide sequence corresponding to the cDNA sequence of SEQ ID NO:151 from nucleotide 301 to nucleotide 1035, and extending contiguously from a nucleotide sequence corresponding to the 5' end of said sequence of SEQ ID NO:151 from nucleotide 301 to nucleotide 1035, to a nucleotide sequence corresponding to the 3' end of said sequence of SEQ ID NO:151 from nucleotide 301 to nucleotide 1035. Also preferably the polynucleotide isolated according to the above process comprises a nucleotide sequence corresponding to the cDNA sequence of SEQ ID NO:151 from nucleotide 916 to nucleotide 1035, and extending contiguously from a nucleotide sequence corresponding to the 5' end of said sequence of SEQ ID NO:151 from nucleotide 916 to nucleotide 1035, to a nucleotide sequence corresponding to the 3' end of said sequence of SEQ ID NO:151 from nucleotide 916 to nucleotide 1035.

In other embodiments, the present invention provides a composition comprising a protein, wherein said protein comprises an amino acid sequence selected from the group consisting of:

(a) the amino acid sequence of SEQ ID NO:152;

(b) a fragment of the amino acid sequence of SEQ ID NO:152, the fragment comprising eight contiguous amino acids of SEQ ID NO:152; and (c) the amino acid sequence encoded by the cDNA insert of clone pe246__1 deposited under accession number ATCC 207187;

the protein being substantially free from other mammalian proteins. Preferably such protein comprises the amino acid sequence of SEQ ID NO:152. In further preferred embodiments, the present invention provides a protein comprising a fragment of the amino acid sequence of SEQ ID NO:152 having biological activity, the fragment preferably comprising eight (more preferably twenty, most preferably thirty) contiguous amino acids of SEQ ID NO:152, or a protein comprising a fragment of the amino acid sequence of SEQ ID NO:152 having biological activity, the fragment comprising the amino acid sequence from amino acid 117 to amino acid 126 of SEQ ID NO:152.

In one embodiment, the present invention provides a composition comprising an isolated polynucleotide selected from the group consisting of:

(a) a polynucleotide comprising the nucleotide sequence of SEQ ID NO:153;

(b) a polynucleotide comprising the nucleotide sequence of SEQ ID NO:153 from nucleotide 94 to nucleotide 1281;

(c) a polynucleotide comprising the nucleotide sequence of the full-length protein coding sequence of clone qf122__3 deposited under accession number ATCC 207187;

(d) a polynucleotide encoding the full-length protein encoded by the cDNA insert of clone qf122__3 deposited under accession number ATCC 207187;

(e) a polynucleotide comprising the nucleotide sequence of a mature protein coding sequence of clone qf122__3 deposited under accession number ATCC 207187;

(f) a polynucleotide encoding a mature protein encoded by the cDNA insert of clone qf122_3 deposited under accession number ATCC 207187;

(g) a polynucleotide encoding a protein comprising the amino acid sequence of SEQ ID NO:154;

(h) a polynucleotide encoding a protein comprising a fragment of the amino acid sequence of SEQ ID NO:154 having biological activity, the fragment comprising eight contiguous amino acids of SEQ ID NO:154;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:153.

Preferably, such polynucleotide comprises the nucleotide sequence of SEQ ID NO:153 from nucleotide 94 to nucleotide 1281; the nucleotide sequence of the full-length protein coding sequence of clone qf122_3 deposited under accession number ATCC 207187; or the nucleotide sequence of a mature protein coding sequence of clone qf122_3 deposited under accession number ATCC 207187. In other preferred embodiments, the polynucleotide encodes the full-length or a mature protein encoded by the cDNA insert of clone qf122_3 deposited under accession number ATCC 207187. In further preferred embodiments, the present invention provides a polynucleotide encoding a protein comprising a fragment of the amino acid sequence of SEQ ID NO:154 having biological activity, the fragment preferably comprising eight (more preferably twenty, most preferably thirty) contiguous amino acids of SEQ ID NO:154, or a polynucleotide encoding a protein comprising a fragment of the amino acid sequence of SEQ ID NO:154 having biological activity, the fragment comprising the amino acid sequence from amino acid 193 to amino acid 202 of SEQ ID NO:154.

Other embodiments provide the gene corresponding to the cDNA sequence of SEQ ID NO:153.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:153; and (ab) the nucleotide sequence of the cDNA insert of clone qf122_3 deposited under accession number ATCC 207187;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:153; and (bb) the nucleotide sequence of the cDNA insert of clone qf122_3 deposited under accession number ATCC 207187;

(ii) hybridizing said primer(s) to human genomic DNA in conditions at least as stringent as 4×SSC at 50 degrees C.;

(iii) amplifying human DNA sequences; and (iv) isolating the polynucleotide products of step (b)(iii).

Preferably the polynucleotide isolated according to the above process comprises a nucleotide sequence corresponding to the cDNA sequence of SEQ ID NO:153, and extending contiguously from a nucleotide sequence corresponding to the 5' end of SEQ ID NO:153 to a nucleotide sequence corresponding to the 3' end of SEQ ID NO:153. Also preferably the polynucleotide isolated according to the above process comprises a nucleotide sequence corresponding to the cDNA sequence of SEQ ID NO:153 from nucleotide 94 to nucleotide 1281, and extending contiguously from a nucleotide sequence corresponding to the 5' end of said sequence of SEQ ID NO:153 from nucleotide 94 to nucleotide 1281, to a nucleotide sequence corresponding to the 3' end of said sequence of SEQ ID NO:153 from nucleotide 94 to nucleotide 1281.

In other embodiments, the present invention provides a composition comprising a protein, wherein said protein comprises an amino acid sequence selected from the group consisting of:

(a) the amino acid sequence of SEQ ID NO:154;

(b) a fragment of the amino acid sequence of SEQ ID NO:154, the fragment comprising eight contiguous amino acids of SEQ ID NO:154; and (c) the amino acid sequence encoded by the cDNA insert of clone qf122_3 deposited under accession number ATCC 207187;

the protein being substantially free from other mammalian proteins. Preferably such protein comprises the amino acid sequence of SEQ ID NO:154. In further preferred embodiments, the present invention provides a protein comprising a fragment of the amino acid sequence of SEQ ID NO:154 having biological activity, the fragment preferably comprising eight (more preferably twenty, most preferably thirty) contiguous amino acids of SEQ ID NO:154, or a protein comprising a fragment of the amino acid sequence of SEQ ID NO:154 having biological activity, the fragment comprising the amino acid sequence from amino acid 193 to amino acid 202 of SEQ ID NO:154.

In one embodiment, the present invention provides a composition comprising an isolated polynucleotide selected from the group consisting of:

(a) a polynucleotide comprising the nucleotide sequence of SEQ ID NO:155;

(b) a polynucleotide comprising the nucleotide sequence of SEQ ID NO:155 from nucleotide 110 to nucleotide 742;

(c) a polynucleotide comprising the nucleotide sequence of SEQ ID NO:155 from nucleotide 170 to nucleotide 742;

(d) a polynucleotide comprising the nucleotide sequence of the full-length protein coding sequence of clone qv538_1 deposited under accession number ATCC 207187;

(e) a polynucleotide encoding the full-length protein encoded by the cDNA insert of clone qv538_1 deposited under accession number ATCC 207187;

(f) a polynucleotide comprising the nucleotide sequence of a mature protein coding sequence of clone qv538_1 deposited under accession number ATCC 207187;

(g) a polynucleotide encoding a mature protein encoded by the cDNA insert of clone qv538_1 deposited under accession number ATCC 207187;

(h) a polynucleotide encoding a protein comprising the amino acid sequence of SEQ ID NO:156;

(i) a polynucleotide encoding a protein comprising a fragment of the amino acid sequence of SEQ ID NO:156 having biological activity, the fragment comprising eight contiguous amino acids of SEQ ID NO:156;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:155.

Preferably, such polynucleotide comprises the nucleotide sequence of SEQ ID NO:155 from nucleotide 110 to nucleotide 742; the nucleotide sequence of SEQ ID NO:155 from nucleotide 170 to nucleotide 742; the nucleotide sequence of the full-length protein coding sequence of clone qv538_1 deposited under accession number ATCC 207187; or the nucleotide sequence of a mature protein coding sequence of clone qv538_1 deposited under accession number ATCC 207187. In other preferred embodiments, the polynucleotide encodes the full-length or a mature protein encoded by the cDNA insert of clone qv538_1 deposited under accession number ATCC 207187. In further preferred embodiments, the present invention provides a polynucleotide encoding a protein comprising a fragment of the amino add sequence of SEQ ID NO:156 having biological activity, the fragment preferably comprising eight (more preferably twenty, most preferably thirty) contiguous amino acids of SEQ ID NO:156, or a polynucleotide encoding a protein comprising a fragment of the amino acid sequence of SEQ ID NO:156 having biological activity, the fragment comprising the amino acid sequence from amino acid 100 to amino acid 109 of SEQ ID NO:156.

Other embodiments provide the gene corresponding to the cDNA sequence of SEQ ID NO:155.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:155, but excluding the poly(A) tail at the 3' end of SEQ ID NO:155; and (ab) the nucleotide sequence of the cDNA insert of clone qv538_1 deposited under accession number ATCC 207187;

(ii) hybridizing said probe(s) to human genomic DNA in conditions at least as stringent as 4×SSC at 50 degrees C.; and (iii) isolating the DNA polynucleotides detected with the probe(s); and (b) a process comprising the steps of:

(i) preparing one or more polynucleotide primers that hybridize in 6×SSC at 65 degrees C. to a nucleotide sequence selected from the group consisting of:

(ba) SEQ ID NO:155, but excluding the poly(A) tail at the 3' end of SEQ ID NO:155; and (bb) the nucleotide sequence of the cDNA insert of clone qv538_1 deposited under accession number ATCC 207187;

(ii) hybridizing said primer(s) to human genomic DNA in conditions at least as stringent as 4×SSC at 50 degrees C.;

(ii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:155, and extending contiguously from a nucleotide sequence corresponding to the 5' end of SEQ ID NO:155 to a nucleotide sequence corresponding to the 3' end of SEQ ID NO:155, but excluding the poly(A) tail at the 3' end of SEQ ID NO:155. Also preferably the polynucleotide isolated according to the above process comprises a nucleotide sequence corresponding to the cDNA sequence of SEQ ID NO:155 from nucleotide 110 to nucleotide 742, and extending contiguously from a nucleotide sequence corresponding to the 5' end of said sequence of SEQ ID NO:155 from nucleotide 110 to nucleotide 742, to a nucleotide sequence corresponding to the 3' end of said sequence of SEQ ID NO:155 from nucleotide 110 to nucleotide 742. Also preferably the polynucleotide isolated according to the above process comprises a nucleotide sequence corresponding to the cDNA sequence of SEQ ID NO:155 from nucleotide 170 to nucleotide 742, and extending contiguously from a nucleotide sequence corresponding to the 5' end of said sequence of SEQ ID NO:155 from nucleotide 170 to nucleotide 742, to a nucleotide sequence corresponding to the 3' end of said sequence of SEQ ID NO:155 from nucleotide 170 to nucleotide 742.

In other embodiments, the present invention provides a composition comprising a protein, wherein said protein comprises an amino acid sequence selected from the group consisting of:

(a) the amino acid sequence of SEQ ID NO:156;

(b) a fragment of the amino add sequence of SEQ ID NO:156, the fragment comprising eight contiguous amino acids of SEQ ID NO:156; and (c) the amino acid sequence encoded by the cDNA insert of clone qv538_1 deposited under accession number ATCC 207187;

the protein being substantially free from other mammalian proteins. Preferably such protein comprises the amino acid sequence of SEQ ID NO:156. In further preferred embodiments, the present invention provides a protein comprising a fragment of the amino acid sequence of SEQ ID NO:156 having biological activity, the fragment preferably comprising eight (more preferably twenty, most preferably thirty) contiguous amino acids of SEQ ID NO:156, or a protein comprising a fragment of the amino acid sequence of SEQ ID NO 156 having biological activity, the fragment comprising the amino acid sequence from amino acid 100 to amino acid 109 of SEQ ID NO:156.

In one embodiment, the present invention provides a composition comprising an isolated polynucleotide selected from the group consisting of:

(a) a polynucleotide comprising the nucleotide sequence of SEQ ID NO:157;

(b) a polynucleotide comprising the nucleotide sequence of SEQ ID NO:157 from nucleotide 41 to nucleotide 757;

(c) a polynucleotide comprising the nucleotide sequence of the full-length protein coding sequence of clone ys20_1 deposited under accession number ATCC 207187;

(d) a polynucleotide encoding the full-length protein encoded by the cDNA insert of clone ys20_1 deposited under accession number ATCC 207187;

(e) a polynucleotide comprising the nucleotide sequence of a mature protein coding sequence of clone ys20_1 deposited under accession number ATCC 207187;

(f) a polynucleotide encoding a mature protein encoded by the cDNA insert of clone ys20_1 deposited under accession number ATCC 207187;

(g) a polynucleotide encoding a protein comprising the amino acid sequence of SEQ ID NO:158;

(h) a polynucleotide encoding a protein comprising a fragment of the amino acid sequence of SEQ ID NO:158 having biological activity, the fragment comprising eight contiguous amino acids of SEQ ID NO:158;

(i) a polynucleotide which is an allelic variant of a polynucleotide of (a)-(f) above;

(j) a polynucleotide which encodes a species homologue of the protein of (g) or (h) above;

(k) a polynucleotide that hybridizes under stringent conditions to any one of the polynucleotides specified in (a)-(h); and (l) a polynucleotide that hybridizes under stringent conditions to any one of the polynucleotides specified in (a)-(h) and that has a length that is at least 25% of the length of SEQ ID NO:157.

Preferably, such polynucleotide comprises the nucleotide sequence of SEQ ID NO:157 from nucleotide 41 to nucleotide 757; the nucleotide sequence of the full-length protein coding sequence of clone ys20_1 deposited under accession number ATCC 207187; or the nucleotide sequence of a mature protein coding sequence of clone ys20_1 deposited under accession number ATCC 207187. In other preferred embodiments, the polynucleotide encodes the full-length or a mature protein encoded by the cDNA insert of clone ys20_1 deposited under accession number ATCC 207187. In further preferred embodiments, the present invention provides a polynucleotide encoding a protein comprising a fragment of the amino acid sequence of SEQ ID NO:158 having biological activity, the fragment preferably comprising eight (more preferably twenty, most preferably thirty) contiguous amino acids of SEQ ID NO:158, or a polynucleotide encoding a protein comprising a fragment of the amino acid sequence of SEQ ID NO:158 having biological activity, the fragment comprising the amino acid sequence from amino acid 114 to amino acid 123 of SEQ ID NO:158.

Other embodiments provide the gene corresponding to the cDNA sequence of SEQ ID NO:157.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:157, but excluding the poly(A) tail at the 3' end of SEQ ID NO:157; and
    (ab) the nucleotide sequence of the cDNA insert of clone ys20_1 deposited under accession number ATCC 207187;
  (ii) hybridizing said probe(s) to human genomic DNA in conditions at least as stringent as 4×SSC at 50 degrees C.; and
  (iii) isolating the DNA polynucleotides detected with the probe(s); and (b) a process comprising the steps of:
  (i) preparing one or more polynucleotide primers that hybridize in 6×SSC at 65 degrees C. to a nucleotide sequence selected from the group consisting of:
    (ba) SEQ ID NO:157, but excluding the poly(A) tail at the 3' end of SEQ ID NO:157; and
    (bb) the nucleotide sequence of the cDNA insert of clone ys20_1 deposited under accession number ATCC 207187;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:157, and extending contiguously from a nucleotide sequence corresponding to the 5' end of SEQ ID NO:157 to a nucleotide sequence corresponding to the 3' end of SEQ ID NO:157, but excluding the poly(A) tail at the 3' end of SEQ ID NO:157. Also preferably the polynucleotide isolated according to the above process comprises a nucleotide sequence corresponding to the cDNA sequence of SEQ ID NO:157 from nucleotide 41 to nucleotide 757, and extending contiguously from a nucleotide sequence corresponding to the 5' end of said sequence of SEQ ID NO:157 from nucleotide 41 to nucleotide 757, to a nucleotide sequence corresponding to the 3' end of said sequence of SEQ ID NO:157 from nucleotide 41 to nucleotide 757.

In other embodiments, the present invention provides a composition comprising a protein, wherein said protein comprises an amino acid sequence selected from the group consisting of:

(a) the amino acid sequence of SEQ ID NO:158;

(b) a fragment of the amino acid sequence of SEQ ID NO:158, the fragment comprising eight contiguous amino acids of SEQ ID NO:158; and (c) the amino acid sequence encoded by the cDNA insert of clone ys20_1 deposited under accession number ATCC 207187;

the protein being substantially free from other mammalian proteins. Preferably such protein comprises the amino acid sequence of SEQ ID NO:158. In further preferred embodiments, the present invention provides a protein comprising a fragment of the amino acid sequence of SEQ ID NO:158 having biological activity, the fragment preferably comprising eight (more preferably twenty, most preferably thirty)

contiguous amino acids of SEQ ID NO 158, or a protein comprising a fragment of the amino acid sequence of SEQ ID NO:158 having biological activity, the fragment comprising the amino acid sequence from amino acid 114 to amino acid 123 of SEQ ID NO:158.

In one embodiment, the present invention provides a composition comprising an isolated polynucleotide selected from the group consisting of:

(a) a polynucleotide comprising the nucleotide sequence of SEQ ID NO:159;

(b) a polynucleotide comprising the nucleotide sequence of SEQ ID NO:159 from nucleotide 28 to nucleotide 2253;

(c) a polynucleotide comprising the nucleotide sequence of SEQ ID NO:159 from nucleotide 568 to nucleotide 2253;

(d) a polynucleotide comprising the nucleotide sequence of the full-length protein coding sequence of clone as180_1;

(e) a polynucleotide encoding the full-length protein encoded by the cDNA insert of clone as180_1;

(f) a polynucleotide comprising the nucleotide sequence of a mature protein coding sequence of clone as180_1;

(g) a polynucleotide encoding a mature protein encoded by the cDNA insert of clone as180_1;

(h) a polynucleotide encoding a protein comprising the amino acid sequence of SEQ ID NO:160;

(i) a polynucleotide encoding a protein comprising a fragment of the amino acid sequence of SEQ ID NO:160 having biological activity, the fragment comprising eight contiguous amino acids of SEQ ID NO:160;

(j) a polynucleotide which is an allelic variant of a polynucleotide of (a)-(g) above;

(k) a polynucleotide which encodes a species homologue of the protein of (h) or (i) above;

(l) a polynucleotide that hybridizes under stringent conditions to any one of the polynucleotides specified in (a)-(i); and (m) a polynucleotide that hybridizes under stringent conditions to any one of the polynucleotides specified in (a)-(i) and that has a length that is at least 25% of the length of SEQ ID NO:159.

Preferably, such polynucleotide comprises the nucleotide sequence of SEQ ID NO:159 from nucleotide 28 to nucleotide 2253; the nucleotide sequence of SEQ ID NO:159 from nucleotide 568 to nucleotide 2253; the nucleotide sequence of the full-length protein coding sequence of clone as180_1; or the nucleotide sequence of a mature protein coding sequence of clone as180_1. In other preferred embodiments, the polynucleotide encodes the full-length or a mature protein encoded by the cDNA insert of clone as180_1. In further preferred embodiments, the present invention provides a polynucleotide encoding a protein comprising a fragment of the amino acid sequence of SEQ ID NO:160 having biological activity, the fragment preferably comprising eight (more preferably twenty, most preferably thirty) contiguous amino acids of SEQ ID NO:160, or a polynucleotide encoding a protein comprising a fragment of the amino acid sequence of SEQ ID NO:160 having biological activity, the fragment comprising the amino acid sequence from amino acid 366 to amino acid 375 of SEQ ID NO:160.

Other embodiments provide the gene corresponding to the cDNA sequence of SEQ ID NO:159.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:159; and
    (ab) the nucleotide sequence of the cDNA insert of clone as180_1;
  (ii) hybridizing said probe(s) to human genomic DNA in conditions at least as stringent as 4×SSC at 50 degrees C.; and
  (iii) isolating the DNA polynucleotides detected with the probe(s); and
(b) a process comprising the steps of:
  (i) preparing one or more polynucleotide primers that hybridize in 6×SSC at 65 degrees C. to a nucleotide sequence selected from the group consisting of.
    (ba) SEQ ID NO:159; and
    (bb) the nucleotide sequence of the cDNA insert of clone as180_1;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:159, and extending contiguously from a nucleotide sequence corresponding to the 5' end of SEQ ID NO:159 to a nucleotide sequence corresponding to the 3' end of SEQ ID NO:159. Also preferably the polynucleotide isolated according to the above process comprises a nucleotide sequence corresponding to the cDNA sequence of SEQ ID NO:159 from nucleotide 28 to nucleotide 2253, and extending contiguously from a nucleotide sequence corresponding to the 5' end of said sequence of SEQ ID NO:159 from nucleotide 28 to nucleotide 2253, to a nucleotide sequence corresponding to the 3' end of said sequence of SEQ ID NO:159 from nucleotide 28 to nucleotide 2253. Also preferably the polynucleotide isolated according to the above process comprises a nucleotide sequence corresponding to the cDNA sequence of SEQ ID NO:159 from nucleotide 568 to nucleotide 2253, and extending contiguously from a nucleotide sequence corresponding to the 5' end of said sequence of SEQ ID NO:159 from nucleotide 568 to nucleotide 2253, to a nucleotide sequence corresponding to the 3' end of said sequence of SEQ ID NO:159 from nucleotide 568 to nucleotide 2253.

In other embodiments, the present invention provides a composition comprising a protein, wherein said protein comprises an amino acid sequence selected from the group consisting of:

(a) the amino acid sequence of SEQ ID NO:160;

(b) a fragment of the amino acid sequence of SEQ ID NO:160, the fragment comprising eight contiguous amino acids of SEQ ID NO:160; and (c) the amino acid sequence encoded by the cDNA insert of clone as180_1;

the protein being substantially free from other mammalian proteins. Preferably such protein comprises the amino acid sequence of SEQ ID NO:160. In further preferred embodiments, the present invention provides a protein comprising a fragment of the amino acid sequence of SEQ ID NO:160 having biological activity, the fragment preferably comprising eight (more preferably twenty, most preferably thirty) contiguous amino acids of SEQ ID NO:160, or a protein comprising a fragment of the amino acid sequence of SEQ ID NO:160 having biological activity, the fragment comprising the amino acid sequence from amino acid 366 to amino acid 375 of SEQ ID NO:160.

In certain preferred embodiments, the polynucleotide is operably linked to an expression control sequence. The invention also provides a host cell, including bacterial, yeast, insect and mammalian cells, transformed with such polynucleotide compositions. Also provided by the present invention are organisms that have enhanced, reduced, or modified expression of the gene(s) corresponding to the polynucleotide sequences disclosed herein.

Processes are also provided for producing a protein, which comprise:

(a) growing a culture of the host cell transformed with such polynucleotide compositions in a suitable culture medium; and (b) purifying the protein from the culture.

The protein produced according to such methods is also provided by the present invention.

Protein compositions of the present invention may further comprise a pharmaceutically acceptable carrier. Compositions comprising an antibody which specifically reacts with such protein are also provided by the present invention.

Methods are also provided for preventing, treating or ameliorating a medical condition which comprises administering to a mammalian subject a therapeutically effective amount of a composition comprising a protein of the present invention and a pharmaceutically acceptable carrier.

DETAILED DESCRIPTION

Isolated Proteins and Polynucleotides

Figure 1A:
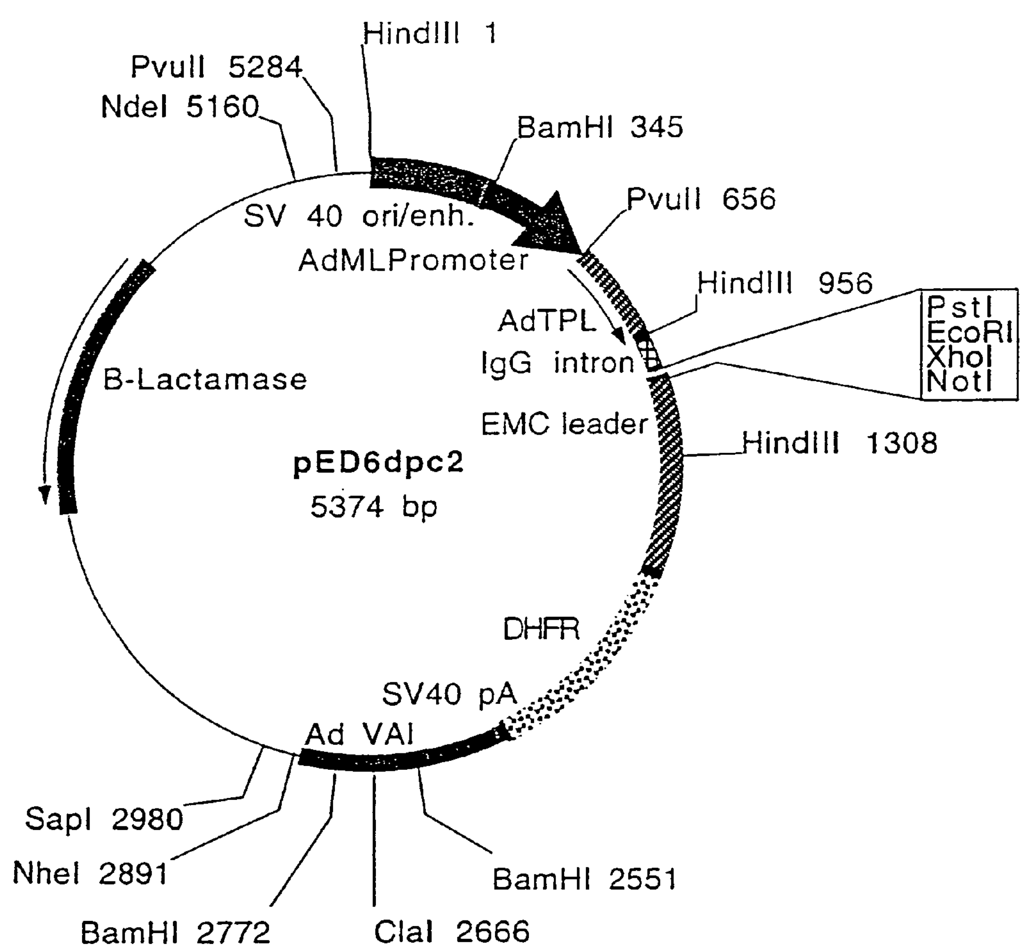
FIGS. 1A and 1B are schematic representations of the pED6 and pNOTs vectors, respectively, used for deposit of clones disclosed herein.

Nucleotide and amino acid sequences, as presently determined, are reported below for each clone and protein disclosed in the present application. The nucleotide sequence of each clone can readily be determined by sequencing of the deposited clone in accordance with known methods. The predicted amino acid sequence (both full-length and mature forms) can then be determined from such nucleotide sequence. The amino acid sequence of the protein encoded by a particular clone can also be determined by expression of the clone in a suitable host cell, collecting the protein and determining its sequence. For each disclosed protein applicants have identified what they have determined to be the reading frame best identifiable with sequence information available at the time of filing.

As used herein a "secreted" protein is one which, when expressed in a suitable host cell, is transported across or through a membrane, including transport as a result of signal sequences in its amino acid sequence. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum.

Clone "co62_12"

A polynucleotide of the present invention has been identified as clone "co62_12". co62_12 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. co62_12 is a full-length clone, including the entire coding sequence of a secreted protein (also referred to herein as "co62_12 protein").

The nucleotide sequence of co62_12 as presently determined is reported in SEQ ID NO:1, and includes a poly(A) tail. What applicants presently believe to be the proper reading frame and the predicted amino acid sequence of the co62_12 protein corresponding to the foregoing nucleotide sequence is reported in SEQ ID NO:2. Amino acids 1 to 11 of SEQ ID NO:2 are a predicted leader/signal sequence, with the predicted mature amino acid sequence beginning at amino acid 12. Due to the hydrophobic nature of the predicted leader/signal sequence, it is likely to act as a transmembrane domain should the predicted leader/signal sequence not be separated from the remainder of the co62_12 protein.

The EcoRI/NotI restriction fragment obtainable from the deposit containing clone co62_12 should be approximately 2200 bp.

The nucleotide sequence disclosed herein for co62_12 was searched against the GenBank and GeneSeq nucleotide sequence databases using BLASTN/BLASTX and FASTA search protocols. co62_12 demonstrated at least some similarity with sequences identified as AA019597 (ze60f10.s1 Soares retina N2b4HR *Homo sapiens* cDNA), AA021678 (mh82c02.r1 Soares mouse placenta 4NbMP13.5 14.5 *Mus*), AA057573 (zf62d10.s1 Soares retina N2b4HR *Homo sapiens* cDNA clone 381523 3' similar to WP T12G3.4 CE06440 STRICTOSIDINE SYNTHASE LIKE, mRNA sequence), AA130982, AA287697 (zs53g02.r1 Soares NbHTGBC *Homo sapiens* cDNA clone 701234 5'), AI042188 (oy37d10.x1 Soares_parathyroid_tumor_NbHPA *Homo sapiens* cDNA clone IMAGE:1668019 3' similar to WP:F57C2.5 CE16156, mRNA sequence), R63905 (yi19b03.s1 *Homo sapiens* cDNA clone 139661 3'), T03538 (IB43 Infant brain, Bento Soares *Homo sapiens* cDNA clone IB43 3 end), T20257 (Human gene signature HUMGS01405), and T23663 (seq294 *Homo sapiens* cDNA clone b4HB3MA-Cot109+103-Bio-24 3'). The predicted amino acid sequence disclosed herein for co62_12 was searched against the GenPept and GeneSeq amino acid sequence databases using the BLASTX search protocol. The predicted co62_12 protein demonstrated at least some similarity to sequences identified as R88502 (Protein sequence for mediating male fertility in plants) and Z83110 (F57C2.5 *[Caenorhabditis elegans]*). Based upon sequence similarity, co62_12 proteins and each similar protein or peptide may share at least some activity.

Clone "lo311_8"

A polynucleotide of the present invention has been identified as clone "lo311_8". lo311_8 was isolated from a human adult thyroid cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. lo311_8 is a full-length clone, including the entire coding sequence of a secreted protein (also referred to herein as "lo311_8 protein").

The nucleotide sequence of lo311_8 as presently determined is reported in SEQ ID NO:3, and includes a poly(A) tail. What applicants presently believe to be the proper reading frame and the predicted amino acid sequence of the lo311_8 protein corresponding to the foregoing nucleotide sequence is reported in SEQ ID NO:4. Amino acids 17 to 29 of SEQ ID NO:4 are a predicted leader/signal sequence, with the predicted mature amino acid sequence beginning at amino acid 30. Due to the hydrophobic nature of the predicted leader/signal sequence, it is likely to act as a transmembrane domain should the predicted leader/signal sequence not be separated from the remainder of the lo311_8 protein.

The EcoRI/NotI restriction fragment obtainable from the deposit containing clone lo311_8 should be approximately 3850 bp.

The nucleotide sequence disclosed herein for lo311_8 was searched against the GenBank and GeneSeq nucleotide sequence databases using BLASTN/BLASTX and FASTA search protocols. lo311_8 demonstrated at least some similarity with sequences identified as AA046836 (zf14b10.r1 Soares fetal heart NbHH19W *Homo sapiens* cDNA clone 376891 5' similar to WP:ZK686.3 CE00457), AA297716 (EST113273 Infant adrenal gland, subtracted (total cDNA) I *Homo sapiens* cDNA 5' end similar to similar to *C. elegans* hypothetical protein, cosmid ZK686_3), AF008554 (*Rattus norvegicus* implantation-associated protein (IAG2) mRNA, partial cds), T68050 (yc39h10.r1 *Homo sapiens* cDNA clone 83107 5' similar to SP ZK686.3 CE00457), and U42349 (Human N33 mRNA, complete cds). The predicted amino acid sequence disclosed herein for lo311_8 was searched against the GenPept and GeneSeq amino acid sequence databases using the BLASTX search protocol. The predicted lo311_8 protein demonstrated at least some similarity to sequences identified as AF008554 (implantation-associated protein [*Rattus norvegicus*]), R85333 (Human prostate/colon tumour suppressor protein form 1) and U42349 (39 kDa encoded by N33 *[Homo sapiens*]). Based upon sequence similarity, lo311_8 proteins and each similar protein or peptide may share at least some activity. The TopPredII computer program predicts five additional potential transmembrane domains within the lo311_8 protein sequence, centered around amino acids 10, 190, 220, 275, and 310 of SEQ ID NO:4, respectively.

Clone "ns197_1"

A polynucleotide of the present invention has been identified as clone "ns197_1". ns197_1 was isolated from a human adult retina (retinoblastoma WERI-Rb1) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. ns197_1 is a full-length clone, including the entire coding sequence of a secreted protein (also referred to herein as "ns197_1 protein").

The nucleotide sequence of ns197_1 as presently determined is reported in SEQ ID NO:5, and includes a poly(A) tail. What applicants presently believe to be the proper reading frame and the predicted amino acid sequence of the ns197_1 protein corresponding to the foregoing nucleotide sequence is reported in SEQ ID NO:6.

The EcoRI/NotI restriction fragment obtainable from the deposit containing clone ns197_1 should be approximately 3650 bp.

The nucleotide sequence disclosed herein for ns197_1 was searched against the GenBank and GeneSeq nucleotide sequence databases using BLASTN/BLASTX and FASTA search protocols. ns197_1 demonstrated at least some similarity with sequences identified as AA495135 (fa03c11.r1 Zebrafish ICRFzfls *Danio rerio* cDNA clone 3K8 5' similar to WP:ZC518.3 CE06603 ALCOHOL DEHYDROGENASE TRANSCRIPTION EFFECTOR LIKE; mRNA sequence). The predicted amino acid sequence disclosed herein for ns197_1 was searched against the GenPept and GeneSeq amino acid sequence databases using the BLASTX search protocol. The predicted ns197_1 protein demonstrated at least some similarity to the sequence identified as Z68753 (ZC518.3 [*Caenorhabditis elegans*]). Based upon sequence similarity, ns197_1 proteins and each similar protein or peptide may share at least some activity. The TopPredII computer program predicts a potential transmembrane domain within the ns197_1 protein sequence centered around amino acid 135 of SEQ ID NO:6. The nucleotide sequence of ns197_1 indicates that it may contain one or more repeat sequences, including primate simple repeat GCC, Alu, and other repetitive elements.

Clone "pj193_5"

A polynucleotide of the present invention has been identified as clone "pj193_5". pj193_5 was isolated from a human fetal carcinoma (NTD2 cells, treated with retinoic acid for 23 days) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. pj193_5 is a full-length clone, including the entire coding sequence of a secreted protein (also referred to herein as "pj193_5 protein"). The nucleotide sequence of pj193_5 as presently determined is reported in SEQ ID NO:7, and includes a poly(A) tail. What applicants presently believe to be the proper reading frame and the predicted amino acid sequence of the pj193_5 protein corresponding to the foregoing nucleotide sequence is reported in SEQ ID NO:8. Amino acids 9 to 21 of SEQ ID NO:8 are a predicted leader/signal sequence, with the predicted mature amino acid sequence beginning at amino acid 22. Due to the hydrophobic nature of the predicted leader/signal sequence, it is likely to act as a transmembrane domain should the predicted leader/signal sequence not be separated from the remainder of the pj193_5 protein.

The EcoRI/NotI restriction fragment obtainable from the deposit containing clone pj193_5 should be approximately 1500 bp.

The nucleotide sequence disclosed herein for pj193_5 was searched against the GenBank and GeneSeq nucleotide sequence databases using BLASTN/BLASTX and FASTA search protocols. pj193_5 demonstrated at least some similarity with sequences identified as AA296889 (EST112653 Cerebellum II *Homo sapiens* cDNA 5' end), AA296961 (EST112514 Adrenal gland tumor *Homo sapiens* cDNA 5' end), AA661635 (nv02g06.s1 NCI_CGAP_Pr22 *Homo sapiens* cDNA clone IMAGE:1219066), and U80744 (*Homo sapiens* CTG4a mRNA, complete cds). The predicted amino acid sequence disclosed herein for pj193_5 was searched against the GenPept and GeneSeq amino acid sequence databases using the BLASTX search protocol. The predicted pj193_5 protein demonstrated at least some similarity to the sequence identified as U80744 (CTG4a [*Homo sapiens*]). Based upon sequence similarity, pj193_5 proteins and each similar protein or peptide may share at least some activity. The nucleotide sequence of pj193_5 indicates that it may contain CAG nucleotide repeats; these repeats may create a "hotspot" for certain types of mutations. "Twelve diseases, most with neuropsychiatric features, arise from trinucleotide repeat expansion mutations. Expansion mutations may also cause a number of other disorders, including several additional forms of spinocerebellar ataxia, bipolar affective disorder, schizophrenia, and autism." (Margolis et al., 1997, *Human Genetics* 100(1): 114-122, which is incorporated by reference herein.) It is possible that the gene corresponding to pj193_5 undergoes a similar etiology.

pj193_5 protein was expressed in a COS cell expression system, and an expressed protein band of approximately 31 kDa was detected in conditioned medium and membrane fractions using SDS polyacrylamide gel electrophoresis.

Clone "pj317_2"

A polynucleotide of the present invention has been identified as clone "pj317_2". pj317_2 was isolated from a human fetal carcinoma (NTD2 cells, treated with retinoic acid for 23 days) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. pj317_2 is a full-length clone, including the entire coding sequence of a secreted protein (also referred to herein as "pj317_2 protein").

The nucleotide sequence of pj317_2 as presently determined is reported in SEQ ID NO:9, and includes a poly(A) tail. What applicants presently believe to be the proper reading frame and the predicted amino acid sequence of the pj317_2 protein corresponding to the foregoing nucleotide sequence is reported in SEQ ID NO:10. The EcoRI/NotI restriction fragment obtainable from the deposit containing clone pj317_2 should be approximately 2300 bp.

The nucleotide sequence disclosed herein for pj317_2 was searched against the GenBank and GeneSeq nucleotide sequence databases using BLASTN/BLASTX and FASTA search protocols. pj317_2 demonstrated at least some similarity with sequences identified as AA305508 (EST176494 Colon carcinoma (Caco-2) cell line II *Homo sapiens* cDNA 5' end, mRNA sequence), AA471379 (PMY1151 KG1a Lambda Zap Express cDNA Library *Homo sapiens* cDNA 5', mRNA sequence), and AA906311 (ok03f08.s1 Soares NFL_T_GBC_S1 *Homo sapiens* cDNA clone IMAGE: 1506759 3', mRNA sequence). The predicted amino acid sequence disclosed herein for pj317_2 was searched against the GenPept and GeneSeq amino acid sequence databases using the BLASTX search protocol.

The predicted pj317_2 protein demonstrated at least some similarity to the sequences identified as U37763 (Per9p [*Pichia angusta*]) and U56965 (*Caenorhabditis elegans* cosmid $C_{15}H_9$). Per9p is a peroxisomal membrane protein, and the predicted pj317_2 protein demonstrated at least some similarity to peroxisomal proteins from other species as well. Based upon sequence similarity, pj317_2 proteins and each similar protein or peptide may share at least some activity. The TopPredII computer program predicts a potential transmembrane domain within the pj317_2 protein sequence centered around amino acid 25 of SEQ ID NO:10. The nucleotide sequence of pj317_2 indicates that it may contain a simple AT and MER repeat region.

Clone "pt332_1"

A polynucleotide of the present invention has been identified as clone "pt332_1". pt332_1 was isolated from a human adult blood (lymphoblastic leukemia MOLT-4) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. pt332_1 is a full-length clone, including the entire coding sequence of a secreted protein (also referred to herein as "pt332_1 protein").

The nucleotide sequence of pt332_1 as presently determined is reported in SEQ ID NO:11, and includes a poly(A) tail. What applicants presently believe to be the proper reading frame and the predicted amino acid sequence of the pt332_1 protein corresponding to the foregoing nucleotide sequence is reported in SEQ ID NO:12. Amino acids 287 to 299 of SEQ ID NO:12 are a predicted leader/signal sequence, with the predicted mature amino acid sequence beginning at amino acid 300. Due to the hydrophobic nature of the predicted leader/signal sequence, it is likely to act as a transmembrane domain should the predicted leader/signal sequence not be separated from the remainder of the pt332_1 protein.

The EcoRI/NotI restriction fragment obtainable from the deposit containing clone pt332_1 should be approximately 3450 bp.

The nucleotide sequence disclosed herein for pt332_1 was searched against the GenBank and GeneSeq nucleotide sequence databases using BLASTN/BLASTX and FASTA search protocols. pt332_1 demonstrated at least some similarity with sequences identified as AA167221 (zp13c09.s1 Stratagene fetal retina 937202 *Homo sapiens* cDNA clone 609328 3'), AA437109 (zv53c07.s1 Soares testis NHT *Homo sapiens* cDNA clone 757356 3'), H14107 (ym62a06.r1 *Homo sapiens* cDNA clone 163474 5'), and U41264 (*C. elegans* cDNA). Based upon sequence similarity, pt332_1 proteins and each similar protein or peptide may share at least some activity. The TopPredII computer program predicts a potential transmembrane domain within the pt332_1 protein sequence centered around amino acid 270 of SEQ ID NO:12.

pt332_1 protein was expressed in a COS cell expression system, and an expressed protein band of approximately 100 kDa was detected in membrane fractions using SDS polyacrylamide gel electrophoresis.

Clone "qc297_15"

A polynucleotide of the present invention has been identified as clone "qc297_15". qc297_15 was isolated from a human adult neural (neuroepithelioma HTB-10 cell line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. qc297_15 is a full-length clone, including the entire coding sequence of a secreted protein (also referred to herein as "qc297_15 protein").

The nucleotide sequence of qc297_15 as presently determined is reported in SEQ ID NO:13, and includes a poly(A) tail. What applicants presently believe to be the proper reading frame and the predicted amino acid sequence of the qc297_15 protein corresponding to the foregoing nucleotide sequence is reported in SEQ ID NO:14.

The EcoRI/NotI restriction fragment obtainable from the deposit containing clone qc297_15 should be approximately 1400 bp.

The nucleotide sequence disclosed herein for qc297_15 was searched against the GenBank and GeneSeq nucleotide sequence databases using BLASTN/BLASTX and FASTA search protocols. qc297_15 demonstrated at least some similarity with sequences identified as AA625537 (af72g07.r1 Soares NhHMPu S1 *Homo sapiens* cDNA clone 1047612 5') and T24537 (EST112 *Homo sapiens* cDNA clone 4H3). Based upon sequence similarity, qc297__15 proteins and each similar protein or peptide may share at least some activity. The TopPredII computer program predicts a potential transmembrane domain within the qc297__15 protein sequence, around amino acid 20 of SEQ ID NO:14. The nucleotide/amino acid sequence of qc297__15 indicates that it may contain an Alu/SVA/MER repeat region.

qc297__15 protein was expressed in a COS cell expression system, and an expressed protein band of approximately 7 kDa was detected in conditioned medium and membrane fractions using SDS polyacrylamide gel electrophoresis.

Clone "qg596__12"

A polynucleotide of the present invention has been identified as clone "qg596__12". qg596__12 was isolated from a human adult neural (neuroepithelioma HTB-10 cell line) cDNA library using methods which are selective for cDNAs encoding secreted proteins (see U.S. Pat No. 5,536,637), or was identified as encoding a secreted or transmembrane protein on the basis of computer analysis of the amino acid sequence of the encoded protein. qg596__12 is a full-length clone, including the entire coding sequence of a secreted protein (also referred to herein as "4g596__12 protein").

The nucleotide sequence of qg596__12 as presently determined is reported in SEQ ID NO:15, and includes a poly(A) tail. What applicants presently believe to be the proper reading frame and the predicted amino acid sequence of the qg596__12 protein corresponding to the foregoing nucleotide sequence is reported in SEQ ID NO:16.

The EcoRI/NotI restriction fragment obtainable from the deposit containing clone qg596__12 should be approximately 2750 bp.

The nucleotide sequence disclosed herein for qg596__12 was searched against the GenBank and GeneSeq nucleotide sequence databases using BLASTN/BLASTX and FASTA search protocols. qg596__12 demonstrated at least some similarity with sequences identified as AA332939 (EST37132 Embryo, 8 week I *Homo sapiens* cDNA 5' end), AA334678 (EST39190 Embryo, 9 week *Homo sapiens* cDNA 5' end), AA362653 (EST72375 Namalwa B cells I *Homo sapiens* cDNA 5' end), and AA829841 (od40d01.s1 NCI_CGAP_GCB1 *Homo sapiens* cDNA clone IMAGE: 1370401 3' similar to WP:F10G7.1 CE02624). The predicted amino acid sequence disclosed herein for qg596__12 was searched against the GenPept and GeneSeq amino acid sequence databases using the BLASTX search protocol. The predicted qg596__12 protein demonstrated at least some similarity to the sequence identified as U40029 (coded for by *C. elegans* cDNA yk16b1.3; coded for by *C. elegans* cDNA yk8g6.5; coded for by *C. elegans* cDNA yk8g6.3; coded for by *C. elegans* cDNA yk6d3.5). Based upon sequence similarity, qg596__12 proteins and each similar protein or peptide may share at least some activity. The TopPredII computer program predicts two potential transmembrane domains within the qg596__12 protein sequence, one centered around amino acid 180 and another around amino acid 660 of SEQ ID NO:16.

qg596__12 protein was expressed in a COS cell expression system, and an expressed protein band of approximately 33 kDa was detected in membrane fractions using SDS polyacrylamide gel electrophoresis.

Clone "rb649__3"

A polynucleotide of the present invention has been identified as clone "rb649__3". rb649__3 was isolated from a human fetal kidney (293 cell line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. rb649__3 is a full-length clone, including the entire coding sequence of a secreted protein (also referred to herein as "rb649__3 protein"). The nucleotide sequence of rb649__3 as presently determined is reported in SEQ ID NO:17, and includes a poly(A) tail. What applicants presently believe to be the proper reading frame and the predicted amino acid sequence of the rb649__3 protein corresponding to the foregoing nucleotide sequence is reported in SEQ ID NO:18. Amino acids 42 to 54 of SEQ ID NO:18 are a predicted leader/signal sequence, with the predicted mature amino acid sequence beginning at amino acid 55. Due to the hydrophobic nature of the predicted leader/signal sequence, it is likely to act as a transmembrane domain should the predicted leader/signal sequence not be separated from the remainder of the rb649__3 protein.

The EcoRI/NotI restriction fragment obtainable from the deposit containing clone rb649__3 should be approximately 2500 bp.

The nucleotide sequence disclosed herein for rb649__3 was searched against the GenBank and GeneSeq nucleotide sequence databases using BLASTN/BLASTX and FASTA search protocols. rb649__3 demonstrated at least some similarity with sequences identified as AA177001 (nc01h02.s1 NCI_CGAP_Pr1 *Homo sapiens* cDNA clone IMAGE 182). The predicted amino acid sequence disclosed herein for rb649__3 was searched against the GenPept and GeneSeq amino acid sequence databases using the BLASTX search protocol. The predicted rb649__3 protein demonstrated at least some similarity to sequences identified as AB002405 (LAK-4p [*Homo sapiens*]), R89470 (Collagen/TGF-beta-1 fusion protein), and U23516 (Undefined [*Caenorhabditis elegans*]). Based upon sequence similarity, rb649__3 proteins and each similar protein or peptide may share at least some activity. The TopPredII computer program predicts eight additional potential transmembrane domains within the rb649__3 protein sequence, centered around amino acids 140, 240, 280, 325, 370, 425, 475, and 540 of SEQ ID NO:18, respectively. The nucleotide sequence of rb649__3 indicates that it may contain a simple GGA repeat region.

Clone "ca106__19x"

A polynucleotide of the present invention has been identified as clone "ca106__19x".

A cDNA clone was first isolated from a mouse embryonic (ES cell embryoid bodies harvested 2-12 days after LIF removed) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. This cDNA clone was then used to isolate ca106__19x from a mixture of human fetal brain and human adult brain cDNA libraries. ca106__19x is a full-length human clone, including the entire coding sequence of a secreted protein (also referred to herein as "ca106__19x protein").

The nucleotide sequence of ca106__19x as presently determined is reported in SEQ ID NO:19, and includes a poly(A) tail. What applicants presently believe to be the proper reading frame and the predicted amino acid sequence of the ca106__19x protein corresponding to the foregoing nucleotide sequence is reported in SEQ ID NO:20.

The EcoRI/NotI restriction fragment obtainable from the deposit containing clone ca106__19x should be approximately 4050 bp.

The nucleotide sequence disclosed herein for ca106_19x was searched against the GenBank and GeneSeq nucleotide sequence databases using BLASTN/BLASTX and FASTA search protocols. ca106_19x demonstrated at least some similarity with sequences identified as AA886998 (oj30g03.s1 NCI_CGAP_Lu5 *Homo sapiens* cDNA clone IMAGE:1499860 3'), F08279 (*H. sapiens* partial cDNA sequence; clone c-zpe 11), F13022 (*H. sapiens* partial cDNA sequence; clone c-3hf07), H38128 (yp46c12.s1 *Homo sapiens* cDNA clone 190486 3'), T77601 (yc91e07.r1 *Homo sapiens* cDNA clone 23192 5'), U93720 (*Homo sapiens* TEX28 mRNA, complete cds), W55512 (ma28h03.r1 Life Tech mouse brain *Mus musculus* cDNA clone 312053 5'), and Z22333 (*H. sapiens* DNA sequence). The predicted amino acid sequence disclosed herein for ca106_19x was searched against the GenPept and GeneSeq amino acid sequence databases using the BLASTX search protocol. The predicted ca106_19x protein demonstrated at least some similarity to sequences identified as U56965 ($C_{15}H_{9.4}$ gene product [*Caenorhabditis elegans*]) and U93720 (TEX28 [*Homo sapiens*]). Based upon sequence similarity, ca106_19x proteins and each similar protein or peptide may share at least some activity. The TopPredII computer program predicts four potential transmembrane domains within the ca106_19x protein sequence, centered around amino acids 170, 430, 590, and 625 of SEQ ID NO:20, respectively. The nucleotide sequence of ca106_19x indicates that it contains at least one repetitive element.

Clone "ci52_2"

A polynucleotide of the present invention has been identified as clone "ci52_2". A cDNA clone was first isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. This cDNA clone was then used to isolate ci52_2 from a human fetal brain cDNA library. ci52_2 is a full-length clone, including the entire coding sequence of a secreted protein (also referred to herein as "ci52_2 protein").

The nucleotide sequence of ci52_2 as presently determined is reported in SEQ ID NO:21, and includes a poly(A) tail. What applicants presently believe to be the proper reading frame and the predicted amino acid sequence of the ci52_2 protein corresponding to the foregoing nucleotide sequence is reported in SEQ ID NO:22. Amino acids 9 to 21 of SEQ ID NO:22 are a predicted leader/signal sequence, with the predicted mature amino acid sequence beginning at amino acid 22. Due to the hydrophobic nature of the predicted leader/signal sequence, it is likely to act as a transmembrane domain should the predicted leader/signal sequence not be separated from the remainder of the ci52_2 protein.

The EcoRI/NotI restriction fragment obtainable from the deposit containing clone ci52_2 should be approximately 1775 bp. The nucleotide sequence disclosed herein for ci52_2 was searched against the GenBank and GeneSeq nucleotide sequence databases using BLASTN/BLASTX and FASTA search protocols. ci52_2 demonstrated at least some similarity with sequences identified as AA083339 (zn31d10.r1 Stratagene endothelial cell 937223 *Homo sapiens* cDNA clone 549043 5'), AA514339 (nf56c10.s1 NCI_CGAP_Co3 *Homo sapiens* cDNA clone 923922), AA628942 (af28f01.s1 Soares total fetus Nb2HF8 9w *Homo sapiens* cDNA clone 1032985 3', mRNA sequence), M78692 (EST00840 *Homo sapiens* cDNA clone HHCMC16), N67265 (yz49d04.s1 *Homo sapiens* cDNA clone 286375 3'), N95514 (yy62d10.r1 *Homo sapiens* cDNA clone 278131 5'), Q60715 (Human brain Expressed Sequence Tag EST00840; standard; cDNA), and R46588 (yg51a12.s1 *Homo sapiens* cDNA clone 35984 3'). The predicted amino acid sequence disclosed herein for ci52_2 was searched against the GenPept and GeneSeq amino acid sequence databases using the BLASTX search protocol. The predicted ci52_2 protein demonstrated at least some similarity to the sequence identified as M68866 (stranded at second [*Drosophila melanogaster*]). Based upon sequence similarity, ci52_2 proteins and each similar protein or peptide may share at least some activity. The TopPredII computer program predicts two additional potential transmembrane domains within the ci52_2 protein sequence, one around amino acid 146 and another around amino acid 177 of SEQ ID NO:22.

Clone "md124_16"

A polynucleotide of the present invention has been identified as clone "md124_16".

A cDNA clone was first isolated from a human fetal kidney cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. This cDNA clone was then used to isolate md124_16 from a human adult kidney cDNA library. md124_16 is a full-length clone, including the entire coding sequence of a secreted protein (also referred to herein as "md124_16 protein").

The nucleotide sequence of md124_16 as presently determined is reported in SEQ ID NO:23, and includes a poly(A) tail. What applicants presently believe to be the proper reading frame and the predicted amino acid sequence of the md124_16 protein corresponding to the foregoing nucleotide sequence is reported in SEQ ID NO:24. Amino acids 152 to 164 of SEQ ID NO:24 are a predicted leader/signal sequence, with the predicted mature amino acid sequence beginning at amino acid 165. Due to the hydrophobic nature of the predicted leader/signal sequence, it is likely to act as a transmembrane domain should the predicted leader/signal sequence not be separated from the remainder of the md124_16 protein.

The EcoRI/NotI restriction fragment obtainable from the deposit containing clone md124_16 should be approximately 2300 bp.

The nucleotide sequence disclosed herein for md124_16 was searched against the GenBank and GeneSeq nucleotide sequence databases using BLASTN/BLASTX and FASTA search protocols. md124_16 demonstrated at least some similarity with sequences identified as AA215643 (zr98d05.s1 NCI_CGAP_GCB1 *Homo sapiens* cDNA clone IMAGE:683721 3'), AA489121 (aa56b07.r1 NCI_CGAP_GCB1 *Homo sapiens* cDNA clone IMAGE:824917 5'), W72865 (zd59e07.s1 Soares fetal heart NbHH19W *Homo sapiens* cDNA clone 344964 3'), and W76100 (zd59e07.r1 Soares fetal heart NbHH19W *Homo sapiens* cDNA clone 344964 5'). Based upon sequence similarity, md124_16 proteins and each similar protein or peptide may share at least some activity. The nucleotide sequence of md124_16 indicates that it may contain at least one MER repeat sequence.

Clone "pk366_7"

A polynucleotide of the present invention has been identified as clone "pk366_7". pk366_7 was isolated from a human fetal kidney (293 cell line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. pk366_7 is a full-length clone, including the entire coding sequence of a secreted protein (also referred to herein as "pk366_7 protein").

The nucleotide sequence of pk366_7 as presently determined is reported in SEQ ID NO:25, and includes a poly(A) tail. What applicants presently believe to be the proper reading frame and the predicted amino acid sequence of the pk366_7 protein corresponding to the foregoing nucleotide sequence is reported in SEQ ID NO:26. Amino acids 361 to 373 of SEQ ID NO:26 are a predicted leader/signal sequence, with the predicted mature amino acid sequence beginning at amino acid 374. Due to the hydrophobic nature of the predicted leader/signal sequence, it is likely to act as a transmembrane domain should the predicted leader/signal sequence not be separated from the remainder of the pk366_7 protein.

The EcoRI/NotI restriction fragment obtainable from the deposit containing clone pk366_7 should be approximately 3300 bp.

The nucleotide sequence disclosed herein for pk366_7 was searched against the GenBank and GeneSeq nucleotide sequence databases using BLASTN/BLASTX and FASTA search protocols. pk366_7 demonstrated at least some similarity with sequences identified as AA057428 (zf57c11.s1 Soares retina N2b4HR *Homo sapiens* cDNA clone 381044 3'), AA457625 (aa89e09.r1 Stratagene fetal retina 937202 *Homo sapiens* cDNA clone 838504 5'), AA601545 (nn87h11.s1 NCI_CGAP_Br2 *Homo sapiens* cDNA clone IMAGE:1098213), T19564 (Human gene signature HUMGS00629; standard; cDNA to mRNA), and U94831 (*Homo sapiens* multispanning membrane protein mRNA, complete cds). The predicted amino acid sequence disclosed herein for pk366_7 was searched against the GenPept and GeneSeq amino acid sequence databases using the BLASTX search protocol. The predicted pk366_7 protein demonstrated at least some similarity to sequences identified as D87444 (endomembrane protein EMP70 precursor isolog [*Arabidopsis thaliana*]), U94831 (multispanning membrane protein [*Homo sapiens*]), and U95973 (endomembrane protein EMP70 precusor isolog [*Arabidopsis thaliana*]). Based upon sequence similarity, pk366_7 proteins and each similar protein or peptide may share at least some activity. The TopPredII computer program predicts nine additional potential transmembrane domains within the pk366_7 protein sequence, centered around amino acids 191, 260, 288, 325, 355, 412, 447, 481, and 517 of SEQ ID NO:26, respectively.

Clone "pl741_5"

A polynucleotide of the present invention has been identified as clone "pl741_5". pl741_5 was isolated from a human fetal kidney (293 cell line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. pl741_5 is a full-length clone, including the entire coding sequence of a secreted protein (also referred to herein as "pl741_5 protein"). The nucleotide sequence of pl741_5 as presently determined is reported in SEQ ID NO:27, and includes a poly(A) tail. What applicants presently believe to be the proper reading frame and the predicted amino acid sequence of the pl741_5 protein corresponding to the foregoing nucleotide sequence is reported in SEQ ID NO:28. Amino acids 3 to 15 of SEQ ID NO:28 are a predicted leader/signal sequence, with the predicted mature amino acid sequence beginning at amino acid 16. Due to the hydrophobic nature of the predicted leader/signal sequence, it is likely to act as a transmembrane domain should the predicted leader/signal sequence not be separated from the remainder of the pl741_5 protein.

The EcoRI/NotI restriction fragment obtainable from the deposit containing clone pl741_5 should be approximately 3000 bp.

The nucleotide sequence disclosed herein for pl741_5 was searched against the GenBank and GeneSeq nucleotide sequence databases using BLASTN/BLASTX and FASTA search protocols. pl741_5 demonstrated at least some similarity with sequences identified as AA283176 (zt17a04.s1 Soares ovary tumor NbHOT *Homo sapiens* cDNA clone 713358 3'), AA204801 (zq61d12.r1 *Stratagene neuroepithelium* (#937231) *Homo sapiens* cDNA clone 646103 5'), and H59410 (yr19g04.r1 *Homo sapiens* cDNA clone 205782 5'). The predicted amino acid sequence disclosed herein for pl741_5 was searched against the GenPept and GeneSeq amino acid sequence databases using the BLASTX search protocol. The predicted pl741_5 protein demonstrated at least some similarity to sequences identified as U00027 (Cdc23p cell cycle protein [*Saccharomyces cerevisiae*]) and U58763 (F10C5.1 [*Caenorhabditis elegans*]). Based upon sequence similarity, pl741_5 proteins and each similar protein or peptide may share at least some activity. Analysis of the amino acid sequence of the predicted pl741_5 protein reveals the presence of four TPR (tetratricopeptide) domains. TPR domains are found in a wide variety of proteins with varying functions and localizations—from the nucleus to the extracellular milieu—and are thought to function as protein-protein interaction domains. The TPR domains are found at amino acid residues 166-194, 328-356, 362-390, and 396-424 of SEQ ID NO:28.

Clone "pp314_19"

A polynucleotide of the present invention has been identified as clone "pp314_19". pp314_19 was isolated from a human adult blood (lymphoblastic leukemia MOLT-4) EDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. pp314_19 is a full-length clone, including the entire coding sequence of a secreted protein (also referred to herein as "pp314_19 protein").

The nucleotide sequence of pp314_19 as presently determined is reported in SEQ ID NO:29, and includes a poly(A) tail. What applicants presently believe to be the proper reading frame and the predicted amino acid sequence of the pp314_19 protein corresponding to the foregoing nucleotide sequence is reported in SEQ ID NO:30. Amino acids 147 to 159 of SEQ ID NO:30 are a possible leader/signal sequence, with the predicted mature amino acid sequence beginning at amino acid 160; amino acids 238 to 250 of SEQ ID NO:30 are also a possible leader/signal sequence, with the predicted mature amino acid sequence beginning at amino acid 251. Due to the hydrophobic nature of these possible leader/signal sequences, each is likely to act as a transmembrane domain should it not be separated from the remainder of the pp314_19 protein.

The EcoRI/NotI restriction fragment obtainable from the deposit containing clone pp314_19 should be approximately 2300 bp.

The nucleotide sequence disclosed herein for pp314_19 was searched against the GenBank and GeneSeq nucleotide sequence databases using BLASTN/BLASTX and FASTA search protocols. pp314_19 demonstrated at least some similarity with sequences identified as AA044042 (zk58g05.r1 Soares pregnant uterus NbHPU *Homo sapiens* cDNA clone 487064 5', mRNA sequence), AA127902 (zl12d01.r1 Soares pregnant uterus NbHPU *Homo sapiens* cDNA clone 501697 5'), AA609481 (af14a12.s1 Soares testis NHT *Homo sapiens* cDNA clone 1031614 3', mRNA sequence), T26699 (Human gene signature HUMGS08949; standard; cDNA to mRNA), and W93399 (zd95b06.s1 Soares fetal heart NbHH19W *Homo sapiens* cDNA clone 357203 3'). The predicted amino add sequence disclosed herein for pp314_19 was searched against the GenPept and GeneSeq amino acid sequence databases using the BLASTX search protocol. The predicted pp314_19 protein demonstrated at least some similarity to sequences identified as AE000857 (chaperonin [*Methanobacterium thermoautotrophicum*]), AJ006549 (ThsA [*Pyrodictium occultum*]), and L34691 (thermophilic factor 56 [*Sulfolobus shibatae*]). Based upon sequence similarity, pp314_19 proteins and each similar protein or peptide may share at least some activity. Analysis of the amino acid sequence of the predicted pp314_19 protein revealed the cpn60_TCP1 signature (at amino acids 29-570 of SEQ ID NO:30) which has some ATPase activity and is indicative of chaperoning. A P-loop motif—a common motif in ATP- and GTP-binding proteins—is found around amino acid 200 of SEQ ID NO:30. The presence of the P-loop is interesting when taken in conjunction with the potential ATPase activity associated with the cpn60_TCP1 signature. The TopPredII computer program predicts three additional potential transmembrane domains within the pp314_19 protein sequence, centered around amino acids 55, 90, and 330 of SEQ ID NO:30, respectively.

pp314_19 protein was expressed in a COS cell expression system, and an expressed protein band of approximately 6 kDa was detected in membrane fractions using SDS polyacrylamide gel electrophoresis.

Clone “pv35_1”

A polynucleotide of the present invention has been identified as clone “pv35_1”. pv35_1 was isolated from a human adult brain (cerebellum) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. pv35_1 is a full-length clone, including the entire coding sequence of a secreted protein (also referred to herein as “pv35_1 protein”).

The nucleotide sequence of pv35_1 as presently determined is reported in SEQ ID NO:31, and includes a poly(A) tail. What applicants presently believe to be the proper reading frame and the predicted amino acid sequence of the pv35_1 protein corresponding to the foregoing nucleotide sequence is reported in SEQ ID NO:32.

The EcoRI/NotI restriction fragment obtainable from the deposit containing clone pv35_1 should be approximately 2300 bp.

The nucleotide sequence disclosed herein for pv35_1 was searched against the GenBank and GeneSeq nucleotide sequence databases using BLASTN/BLASTX and FASTA search protocols. pv35_1 demonstrated at least some similarity with sequences identified as AA335869 (EST40348 Epididymus *Homo sapiens* cDNA 5' end), AA599418 (ag23c03.s1 Jia bone marrow stroma *Homo sapiens* cDNA clone 1071172 3'), and H03595 (yj42e06.r1 *Homo sapiens* cDNA clone 151426 5'). The predicted amino acid sequence disclosed herein for pv35_1 was searched against the GenPept and GeneSeq amino acid sequence databases using the BLASTX search protocol. The predicted pv35_1 protein demonstrated at least some similarity to sequences identified as Z99277 (Y53C12A.3 [*Caenorhabditis elegans*]) Based upon sequence similarity, pv35_1 proteins and each similar protein or peptide may share at least some activity. The TopPredII computer program predicts four potential transmembrane domains within the pv35_1 protein sequence, centered around amino acids 127, 161, 192, and 250 of SEQ ID NO:32, respectively.

Clone “pw337_6”

A polynucleotide of the present invention has been identified as clone “pw337_6”. pw337_6 was isolated from a human adult brain (cerebellum) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. pw337_6 is a full-length clone, including the entire coding sequence of a secreted protein (also referred to herein as “pw337_6 protein”).

The nucleotide sequence of pw337_6 as presently determined is reported in SEQ ID NO:33, and includes a poly(A) tail. What applicants presently believe to be the proper reading frame and the predicted amino acid sequence of the pw337_6 protein corresponding to the foregoing nucleotide sequence is reported in SEQ ID NO:34.

Another potential pw337_6 reading frame and predicted amino acid sequence is encoded by basepairs 648 to 908 of SEQ ID NO:33 and is reported in SEQ ID NO:238. The overlapping reading frames of SEQ ID NO:34 and SEQ ID NO:238 could be joined if a frameshift were introduced into the nucleotide sequence of SEQ ID NO:33 between position 645 and position 736.

The EcoRI/NotI restriction fragment obtainable from the deposit containing clone pw337_6 should be approximately 1000 bp. The nucleotide sequence disclosed herein for pw337_6 was searched against the GenBank and GeneSeq nucleotide sequence databases using BLASTN/BLASTX and FASTA search protocols. pw337_6 demonstrated at least some similarity with sequences identified as AA682471 (zj18c02.s1 Soares fetal liver spleen 1NFLS S1 *Homo sapiens* cDNA clone 450626 3', mRNA sequence), T20708 (Human gene signature HUMGS01925;

standard; cDNA to mRNA), W24658 (zb63b05.r1 Soares fetal lung NbHL19W *Homo sapiens* cDNA clone 308241 5'), and Z82192 (*Homo sapiens* DNA sequence from PAC 186O1 on chromosome 22). The predicted amino acid sequence disclosed herein for pw337_6 was searched against the GenPept and GeneSeq amino acid sequence databases using the BLASTX search protocol. The predicted pw337_6 protein demonstrated at least some similarity to the sequence identified as Z82192 (dJ186O1.1 [*Homo sapiens*]). Based upon sequence similarity, pw337_6 proteins and each similar protein or peptide may share at least some activity. The TopPredII computer program predicts a potential transmembrane domain within the pw337_6 protein sequence centered around amino acid 75 of SEQ ID NO:34. The nucleotide sequence of pw337_6 indicates that it may contain one or more repetitive elements.

pw337_6 protein was expressed in a COS cell expression system, and an expressed protein band of approximately 22 kDa was detected in membrane fractions using SDS polyacrylamide gel electrophoresis.

Clone “rd610_1”

A polynucleotide of the present invention has been identified as clone “rd610_1”. rd610_1 was isolated from a human fetal kidney (293 cell line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. rd610_1 is a full-length clone, including the entire coding sequence of a secreted protein (also referred to herein as "rd610_1 protein").

The nucleotide sequence of rd610_1 as presently determined is reported in SEQ ID NO:35, and includes a poly(A) tail. What applicants presently believe to be the proper reading frame and the predicted amino acid sequence of the rd610_1 protein corresponding to the foregoing nucleotide sequence is reported in SEQ ID NO:36.

The EcoRI/NotI restriction fragment obtainable from the deposit containing clone rd610_1 should be approximately 1800 bp. The nucleotide sequence disclosed herein for rd610_1 was searched against the GenBank and GeneSeq nucleotide sequence databases using BLASTN/BLASTX and FASTA search protocols. rd610_1 demonstrated at least some similarity with sequences identified as AA442056 (zw56f08.r1 Soares total fetus Nb2HF8 9w *Homo sapiens* cDNA clone 774087 5'), AA992905 (ot92b06.s1 Soares_total_fetus_Nb2HF8_9w *Homo sapiens* cDNA clone IMAGE 1624211 3', mRNA sequence), D31767 (Human mRNA for KIAA0058 gene, complete cds), and T40090 (Human Serrate-1 (HJ1) cDNA; standard; cDNA). Based upon sequence similarity, rd610_1 proteins and each similar protein or peptide may share at least some activity. The TopPredII computer program predicts a potential transmembrane domain within the rd610_1 protein sequence centered around amino acid 30 of SEQ ID NO:36; amino acids 23 to 35 of SEQ ID NO:36 are also a possible leader/signal sequence, with the predicted mature amino acid sequence beginning at amino acid 36.

rd610_1 protein was expressed in a COS cell expression system, and an expressed protein band of approximately 7 kDa was detected in conditioned medium using SDS polyacrylamide gel electrophoresis.

Clone "rd810_6"

A polynucleotide of the present invention has been identified as clone "rd810_6". rd810_6 was isolated from a human fetal kidney (293 cell line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. rd810_6 is a full-length clone, including the entire coding sequence of a secreted protein (also referred to herein as "rd810_6 protein").

The nucleotide sequence of rd810_6 as presently determined is reported in SEQ ID NO:37, and includes a poly(A) tail. What applicants presently believe to be the proper reading frame and the predicted amino acid sequence of the rd810_6 protein corresponding to the foregoing nucleotide sequence is reported in SEQ ID NO:38. Amino acids 112 to 124 of SEQ ID NO:38 are a predicted leader/signal sequence, with the predicted mature amino acid sequence beginning at amino acid 125. Due to the hydrophobic nature of the predicted leader/signal sequence, it is likely to act as a transmembrane domain should the predicted leader/signal sequence not be separated from the remainder of the rd810_6 protein.

The EcoRI/NotI restriction fragment obtainable from the deposit containing clone rd810_6 should be approximately 850 bp.

The nucleotide sequence disclosed herein for rd810_6 was searched against the GenBank and GeneSeq nucleotide sequence databases using BLASTN/BLASTX and FASTA search protocols. rd810_6 demonstrated at least some similarity with sequences identified as AA452718 (zx39d04.r1 Soares total fetus Nb2HF8 9w *Homo sapiens* cDNA clone 788839 5', mRNA sequence), AA292888 (zt66c01.r1 Soares testis NHT *Homo sapiens* cDNA clone 727296 5'), and T23348 (Human gene signature HUMGS05169; standard; cDNA to mRNA). Based upon sequence similarity, rd810_6 proteins and each similar protein or peptide may share at least some activity.

rd810_6 protein was expressed in a COS cell expression system, and an expressed protein band of approximately 23 kDa was detected in conditioned medium and membrane fractions using SDS polyacrylamide gel electrophoresis.

Clone "cf85_1"

A polynucleotide of the present invention has been identified as clone "cf85_1". A cDNA clone was first isolated from a human adult placenta library cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. This cDNA clone was then used to isolate cf85_1 from a human adult brain cDNA library. cf85_1 is a full-length clone, including the entire coding sequence of a secreted protein (also referred to herein as "cf85_1 protein").

The nucleotide sequence of cf85_1 as presently determined is reported in SEQ ID NO:39, and includes a poly(A) tail. What applicants presently believe to be the proper reading frame and the predicted amino acid sequence of the cf85_1 protein corresponding to the foregoing nucleotide sequence is reported in SEQ ID NO:40.

The EcoRI/NotI restriction fragment obtainable from the deposit containing clone cf85_1 should be approximately 2000 bp.

The nucleotide sequence disclosed herein for cf85_1 was searched against the GenBank and GeneSeq nucleotide sequence databases using BLASTN/BLASTX and FASTA search protocols. cf85_1 demonstrated at least some similarity with sequences identified as H50932 (yo35f03.r1 *Homo sapiens* cDNA clone 179933 5'), H51595 (yo35f03.s1 *Homo sapiens* cDNA clone 179933 3'), and T24664 (Human gene signature HUMGS06728; standard; cDNA to mRNA). Based upon sequence similarity, cf85_1 proteins and each similar protein or peptide may share at least some activity. The TopPredII computer program predicts three potential transmembrane domains within the cf85_1 protein sequence, centered around amino acids 150, 195, and 220 of SEQ ID NO:40, respectively. The nucleotide sequence of cf85_1 indicates that it may contain an Alu repetitive element.

Clone "dd504_18"

A polynucleotide of the present invention has been identified as clone "dd504_18". dd504_18 was isolated from a human adult testes cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. dd504_18 is a full-length clone, including the entire coding sequence of a secreted protein (also referred to herein as "dd504_18 protein").

The nucleotide sequence of dd504_18 as presently determined is reported in SEQ ID NO:41, and includes a poly(A) tail. What applicants presently believe to be the proper reading frame and the predicted amino acid sequence of the dd504_18 protein corresponding to the foregoing nucleotide sequence is reported in SEQ ID NO:42. Amino acids 134 to 146 of SEQ ID NO:42 are a predicted leader/signal sequence, with the predicted mature amino acid sequence beginning at amino acid 147. Amino acids 7 to 19 of SEQ ID NO:42 are also a possible leader/signal sequence, with a predicted mature amino acid sequence beginning in that case at amino acid 20. Due to the hydrophobic nature of these predicted leader/signal sequences, each is likely to act as a transmembrane domain should it not be separated from the remainder of the dd504_18 protein.

The EcoRI/NotI restriction fragment obtainable from the deposit containing clone dd504_18 should be approximately 2000 bp.

The nucleotide sequence disclosed herein for dd504_18 was searched against the GenBank and GeneSeq nucleotide sequence databases using BLASTN/BLASTX and FASTA search protocols. dd504_18 demonstrated at least some similarity with sequences identified as AA393779 (zt77f07.r1 Soares testis NHT *Homo sapiens* cDNA clone 728389 5' similar to WP:F41E7.1 CE03301; mRNA sequence), AA429420 (zw51f02.r1 Soares total fetus Nb2HHT8 9w *Homo sapiens* cDNA clone 773595 5' similar to WP W02B12.7 CE03767 KINENSIN-LIKE PROTEIN), AC002038 (* SEQUENCING IN PROGRESS * Human chromosome 16p12 BAC clone CIT987SK-101B6; HTGS phase 1, 1 unordered pieces; *Homo sapiens* chromosome 2 clone 101B6 from 2p11, complete sequence), H10672 (yl99g09.r1 *Homo sapiens* cDNA clone 46448 5'), and R59895 (yh07f12.r1 *Homo sapiens* cDNA clone 42477 5'). The predicted amino acid sequence disclosed herein for dd504_18 was searched against the GenPept and GeneSeq amino acid sequence databases using the BLASTX search protocol. The predicted dd504_18 protein demonstrated at least some similarity to sequences identified as AE000854 (Na+/H+-exchanging protein Na+/H+ antiporter [*Methanobacterium thermoautotrophicum*]) and Z68106 (F41E7.1 [*Caeno-rhabditis elegans*]). Based upon sequence similarity, dd504_18 proteins and each similar protein or peptide may share at least some activity. The TopPredU computer program predicts eight potential transmembrane domains within the dd504_18 protein sequence, centered around amino acids 20, 48, 118, 144, 191, 220, 268, and 326 of SEQ ID NO:42, respectively.

dd504_18 protein was expressed in a COS cell expression system, and an expressed protein band of approximately 36 kDa was detected in membrane fractions using SDS polyacrylamide gel electrophoresis.

Clone “np26_3”

A polynucleotide of the present invention has been identified as clone “np26_3”. np26_3 was isolated from a human fetal kidney (293 cell line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. np26_3 is a full-length clone, including the entire coding sequence of a secreted protein (also referred to herein as “np26_3 protein”).

The nucleotide sequence of np26_3 as presently determined is reported in SEQ ID NO:43, and includes a poly(A) tail. What applicants presently believe to be the proper reading frame and the predicted amino acid sequence of the np26_3 protein corresponding to the foregoing nucleotide sequence is reported in SEQ ID NO:44.

The EcoRI/NotI restriction fragment obtainable from the deposit containing clone np26_3 should be approximately 3800 bp.

The nucleotide sequence disclosed herein for np26_3 was searched against the GenBank and GeneSeq nucleotide sequence databases using BLASTN/BLASTX and FASTA search protocols. np26_3 demonstrated at least some similarity with sequences identified as AA118527 (mo99d08.r1 Stratagene mouse heart (#937316) *Mus musculus* cDNA clone 567855 5'), AA284633 (zt15d04.s1 NCI_CGAP_GCB1 *Homo sapiens* cDNA clone IMAGE:713191 3', mRNA sequence), AA427620 (zw30d02.s1 Soares ovary tumor NbHOT *Homo sapiens* cDNA clone 770787 3' similar to contains MER17.b1 MER17 repetitive element; mRNA sequence), and AA496955 (aa42f01.s1 Soares NhHMPu S1 *Homo sapiens* cDNA clone 823609 3', mRNA sequence). The predicted amino acid sequence disclosed herein for np26_3 was searched against the GenPept and GeneSeq amino acid sequence databases using the BLASTX search protocol. The predicted np26_3 protein demonstrated at least some similarity to the sequence identified as M86752 (transformation-sensitive protein [*Homo sapiens*]). Based upon sequence similarity, np26_3 proteins and each similar protein or peptide may share at least some activity. The TopPredII computer program predicts a potential transmembrane domain within the np26_3 protein sequence centered around amino acid 146 of SEQ ID NO:44.

np26_3 protein was expressed in a COS cell expression system, and an expressed protein band of approximately 63 kDa was detected in conditioned medium using SDS polyacrylamide gel electrophoresis.

Clone “pm412_12”

A polynucleotide of the present invention has been identified as clone “pm412_12”. pm412_12 was isolated from a human fetal kidney (293 cell line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. pm412_12 is a full-length clone, including the entire coding sequence of a secreted protein (also referred to herein as “pm412_12 protein”).

The nucleotide sequence of pm412_12 as presently determined is reported in SEQ ID NO:45, and includes a poly(A) tail. What applicants presently believe to be the proper reading frame and the predicted amino acid sequence of the pm412_12 protein corresponding to the foregoing nucleotide sequence is reported in SEQ ID NO:46. Amino acids 607 to 619 of SEQ ID NO:46 are a possible leader/signal sequence, with the predicted mature amino acid sequence beginning at amino acid 620. Due to the hydrophobic nature of this possible leader/signal sequence, it is likely to act as a transmembrane domain should it not be separated from the remainder of the pm412_12 protein.

The EcoRI/NotI restriction fragment obtainable from the deposit containing clone pm412_12 should be approximately 4000 bp.

The nucleotide sequence disclosed herein for pm412_12 was searched against the GenBank and GeneSeq nucleotide sequence databases using BLASTN/BLASTX and FASTA search protocols. pm412_12 demonstrated at least some similarity with sequences identified as AA176820 (zp34a12.s1 Stratagene muscle 937209 *Homo sapiens* cDNA clone 611326 3'), AA425762 (zw47f10.s1 Soares total fetus Nb2HF8 9w *Homo sapiens* cDNA clone 773227 3' similar to TR:G285999 G285999 ORF, COMPLETE CDS), AA568580 (nm21a10.s1 NCI_CGAP_Co10 *Homo*

*sapiens* cDNA clone IMAGE:1060794 similar to TR:G642306 G642306 HYPOTHETICAL 153.8 KD PROTEIN), AA610863 (np98h01.s1 NCI_CGAP_Lu1 *Homo sapiens* cDNA clone IMAGE 1142449 similar to TR G285999 G285999 ORF, COMPLETE CDS), AA769312 (nz39f06.s1 NCI_CGAP_GCB1 *Homo sapiens* cDNA clone IMAGE 1290179 similar to TR Q15393 Q15393 ORF, COMPLETE CDS; mRNA sequence), D13642 (Human mRNA for KIAA0017 gene, complete cds), and T92977 (ye22e09.r1 *Homo sapiens* cDNA clone 118504 5'). The predicted amino acid sequence disclosed herein for pm412__12 was searched against the GenPept and GeneSeq amino acid sequence databases using the BLASTX search protocol. The predicted pm412__12 protein demonstrated at least some similarity to sequences identified as AF043699 (ORF; similar to human UV-damaged DNA binding factor [*C. elegans*]), D13642 (KIAA0017 *[Homo sapiens*]), R72386 (XAP-1, part of the DNA repair complex), and X54413 (alpha1(IX) collagen precursor [*Homo sapiens*]). Based upon sequence similarity, pm412__12 proteins and each similar protein or peptide may share at least some activity. The TopPredII computer program predicts three potential transmembrane domains within the pm412__12 protein sequence, centered around amino acids 277, 415, and 1060 of SEQ ID NO46, respectively.

pm412__12 protein was expressed in a COS cell expression system, and an expressed protein band of approximately 119 kDa was detected in conditioned medium and membrane fractions using SDS polyacrylamide gel electrophoresis.

Clone "pm421__3"

A polynucleotide of the present invention has been identified as clone "pm421__3". pm421__3 was isolated from a human fetal kidney (293 cell line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. pm421__3 is a full-length clone, including the entire coding sequence of a secreted protein (also referred to herein as "pm421__3 protein").

The nucleotide sequence of pm421__3 as presently determined is reported in SEQ ID NO:47, and includes a poly(A) tail. What applicants presently believe to be the proper reading frame and the predicted amino acid sequence of the pm421__3 protein corresponding to the foregoing nucleotide sequence is reported in SEQ ID NO:48. Amino acids 10 to 22 of SEQ ID NO:48 are a predicted leader/signal sequence, with the predicted mature amino acid sequence beginning at amino acid 23. Due to the hydrophobic nature of the predicted leader/signal sequence, it is likely to act as a transmembrane domain should the predicted leader/signal sequence not be separated from the remainder of the pm421__3 protein.

The EcoRI/NotI restriction fragment obtainable from the deposit containing clone pm421__3 should be approximately 2800 bp.

The nucleotide sequence disclosed herein for pm421__3 was searched against the GenBank and GeneSeq nucleotide sequence databases using BLASTN/BLASTX and FASTA search protocols. pm421__3 demonstrated at least some similarity with sequences identified as AA196485 (zq59a06.s1 Stratagene neuroepithelium (#937231) *Homo sapiens* cDNA clone 645874 3'), AA421712 (zu26g11.r1 Soares ovary tumor NbHOT *Homo sapiens* cDNA clone 739172 5', mRNA sequence), AC005026 (*Homo sapiens* clone GS489L14; HTGS phase 1, 3 unordered pieces), AC005028 (*Homo sapiens* clone GS539F22; HTGS phase 1, 1 unordered pieces), Q60534 (Human brain Expressed Sequence Tag EST02540; standard; cDNA), and R13985 (yf68h04.r1 *Homo sapiens* cDNA clone 27722 5'). Based upon sequence similarity, pm421__3 proteins and each similar protein or peptide may share at least some activity. The TopPredII computer program predicts an additional potential transmembrane domain within the pm421__3 protein sequence centered around amino acid 36 of SEQ ID NO:48.

Clone "pv6__1"

A polynucleotide of the present invention has been identified as clone "pv6__1". pv6__1 was isolated from a human adult brain (cerebellum) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. pv6__1 is a full-length clone, including the entire coding sequence of a secreted protein (also referred to herein as "pv6__1 protein").

The nucleotide sequence of pv6__1 as presently determined is reported in SEQ ID NO:49, and includes a poly(A) tail. What applicants presently believe to be the proper reading frame and the predicted amino acid sequence of the pv6__1 protein corresponding to the foregoing nucleotide sequence is reported in SEQ ID NO:50. Amino acids 39 to 51 of SEQ ID NO:50 are a predicted leader/signal sequence, with the predicted mature amino acid sequence beginning at amino acid 52. Amino acids 8 to 20 of SEQ ID NO:50 are also a possible leader/signal sequence, with a predicted mature amino acid sequence beginning at amino acid 21. Due to the hydrophobic nature of these predicted leader/signal sequences, each is likely to act as a transmembrane domain should it not be separated from the remainder of the pv6__1 protein.

The EcoRI/NotI restriction fragment obtainable from the deposit containing clone pv6__1 should be approximately 1800 bp.

The nucleotide sequence disclosed herein for pv6__1 was searched against the GenBank and GeneSeq nucleotide sequence databases using BLASTN/BLASTX and FASTA search protocols. pv6__1 demonstrated at least some similarity with sequences identified as B53192 (CIT-HSP-2009D9.TR CIT-HSP *Homo sapiens* genomic clone 2009D9, genomic survey sequence), R18429 (yg02g05.r1 *Homo sapiens* cDNA clone 31056 5'), T77089 (yc93b02.r1 *Homo sapiens* cDNA clone 23653 5'), and X89480 (*S.scrofa* mRNA for membrane protein). The predicted amino acid sequence disclosed herein for pv6__1 was searched against the GenPept and GeneSeq amino acid sequence databases using the BLASTX search protocol. The predicted pv6__1 protein demonstrated at least some similarity to the sequence identified as X89480 (transmembrane protein [*Sus scrofa*]). Based upon sequence similarity, pv6__1 proteins and each similar protein or peptide may share at least some activity. The TopPredII computer program predicts a potential transmembrane domain within the pv6__1 protein sequence centered around amino acid 21 of SEQ ID NO:50.

Clone "qs14__3"

A polynucleotide of the present invention has been identified as clone "qs14__3". A cDNA clone was isolated from a human whole embryo cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. This cDNA clone was then used to isolate qs14__3 from a human fetal heart cDNA library. qs14_3 is a full-length clone, including the entire coding sequence of a secreted protein (also referred to herein as "qs14_3 protein").

The nucleotide sequence of qs14_3 as presently determined is reported in SEQ ID NO:51, and includes a poly(A) tail. What applicants presently believe to be the proper reading frame and the predicted amino acid sequence of the qs14_3 protein corresponding to the foregoing nucleotide sequence is reported in SEQ ID NO:52. Amino acids 15 to 27 of SEQ ID NO:52 are a predicted leader/signal sequence, with the predicted mature amino acid sequence beginning at amino acid 28. Due to the hydrophobic nature of the predicted leader/signal sequence, it is likely to act as a transmembrane domain should the predicted leader/signal sequence not be separated from the remainder of the qs14_3 protein.

The EcoRI/NotI restriction fragment obtainable from the deposit containing clone qs14_3 should be approximately 5000 bp.

The nucleotide sequence disclosed herein for qs14_3 was searched against the GenBank and GeneSeq nucleotide sequence databases using BLASTN/BLASTX and FASTA search protocols. qs14_3 demonstrated at least some similarity with sequences identified as AA558554 (nl69g02.s1 NCI_CGAP_Pr4.1 *Homo sapiens* cDNA clone IMAGE 1045970 similar to TR G307329 G307329 PROTOCADHERIN 43), AB002343 (Human mRNA for KIAA0345 gene), and L43592 (*Rattus norvegicus* protocadherin-3 (pcdh3) mRNA, and translated products). The predicted amino acid sequence disclosed herein for qs14_3 was searched against the GenPept and GeneSeq amino acid sequence databases using the BLASTX search protocol. The predicted qs14_3 protein demonstrated at least some similarity to sequences identified as AF029343 (protocadherin [*Homo sapiens*]), AF042192 (protocadherin [*Xenopus*]), AF052685 (protocadherin 43 *[Homo sapiens*]), L11373 (protocadherin 43 *[Homo sapiens*]), R49144 (Product of alternative splicing of human protocadherin-43 mRNA), and Y08715 (protocadherin [*Mus musculus*]). The cadherins are a family of calcium-binding membrane glycoproteins. Most cadherins are capable of acting as cell adhesion molecules (CAMs). Motif analysis of the predicted qs14_3 protein also detects the 'cadherins extracellular repeated domain signature'. Based upon sequence similarity, qs14_3 proteins and each similar protein or peptide may share at least some activity. The TopPredII computer program predicts two additional potential transmembrane domains within the qs14_3 protein sequence, one centered around amino acid 510 and another around amino acid 721 of SEQ ID NO:52.

qs14_3 protein was expressed in a COS cell expression system, and an expressed protein band of approximately 132 kDa was detected in membrane fractions using SDS polyacrylamide gel electrophoresis.

Clone "qy338_9"

A polynucleotide of the present invention has been identified as clone "qy338_9". qy338_9 was isolated from a human adult blood (promyelocytic leukemia HL-60) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. qy338_9 is a full-length clone, including the entire coding sequence of a secreted protein (also referred to herein as "qy338_9 protein").

The nucleotide sequence of qy338_9 as presently determined is reported in SEQ ID NO:53, and includes a poly(A) tail. What applicants presently believe to be the proper reading frame and the predicted amino acid sequence of the qy338_9 protein corresponding to the foregoing nucleotide sequence is reported in SEQ ID NO:54. Amino acids 144 to 156 of SEQ ID NO:54 are a predicted leader/signal sequence, with the predicted mature amino acid sequence be inning at amino acid 157. Due to the hydrophobic nature of the predicted leader/signal sequence, it is likely to act as a transmembrane domain should the predicted leader/signal sequence not be separated from the remainder of the qy338_9 protein.

The EcoRI/NotI restriction fragment obtainable from the deposit containing done qy338_9 should be approximately 1300 bp.

The nucleotide sequence disclosed herein for qy338_9 was searched against the GenBank and GeneSeq nucleotide sequence databases using BLASTN/BLASTX and FASTA search protocols. qy338_9 demonstrated at least some similarity with sequences identified as AA205412 (zq66a09.s1 Stratagene neuroepithelium (#937231) *Homo sapiens* cDNA clone 646552 3' similar to contains Alu repetitive element; contains element LTR1 repetitive element; mRNA), AA595068 (no40h10.s1 NCI_CGAP_Pr23 *Homo sapiens* cDNA clone IMAGE 1103203 similar to WP C27F2.4 CE011711 TRANSFERASE), AJ224442 (*Homo sapiens* mRNA for putative methyltransferase), and H40834 (yo05g09.r1 *Homo sapiens* cDNA clone 177088 5'). The predicted amino acid sequence disclosed herein for qy338_9 was searched against the GenPept and GeneSeq amino acid sequence databases using the BLASTX search protocol. The predicted qy338_9 protein demonstrated at least some similarity to sequences identified as AJ224442 (methyl-transferase [*Homo sapiens*]), U40419 (similar to *S. cerevisiae* gene YCR47C, putative 30.7 kd methyltransferase (SP YCT7_YEAST,P25627) [*Caenorhabditis elegans*]), and Z69240 (putative methyltransferase [*S. cerevisiae*]). Based upon sequence similarity, qy338_9 proteins and each similar protein or peptide may share at least some activity.

qy338_9 protein was expressed in a COS cell expression system, and an expressed protein band of approximately 34 kDa was detected in membrane fractions using SDS polyacrylamide gel electrophoresis.

Clone "rc58_1"

A polynucleotide of the present invention has been identified as clone "rc58_1". rc58_1 was isolated from a human fetal kidney cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. rc58_1 is a full-length clone, including the entire coding sequence of a secreted protein (also referred to herein as "rc58_1 protein").

The nucleotide sequence of rc58_1 as presently determined is reported in SEQ ID NO:55, and includes a poly(A) tail. What applicants presently believe to be the proper reading frame and the predicted amino acid sequence of the rc58_1 protein corresponding to the foregoing nucleotide sequence is reported in SEQ ID NO:56. Amino acids 2 to 14 of SEQ ID NO:56 are a predicted leader/signal sequence, with the predicted mature amino acid sequence beginning at amino acid 15. Due to the hydrophobic nature of the predicted leader/signal sequence, it is likely to act as a transmembrane domain should the predicted leader/signal sequence not be separated from the remainder of the rc58_1 protein.

The EcoRI/NotI restriction fragment obtainable from the deposit containing clone rc58__1 should be approximately 1500 bp.

The nucleotide sequence disclosed herein for rc58__1 was searched against the GenBank and GeneSeq nucleotide sequence databases using BLASTN/BLASTX and FASTA search protocols. rc58__1 demonstrated at least some similarity with sequences identified as AA203670 (zx52d04.r1 Soares fetal liver spleen 1NFLS S1 *Homo sapiens* cDNA clone 446119 5' similar to gb X07868_mal PUTATIVE INSULIN-LIKE GROWTH FACTOR II ASSOCIATED (HUMAN); mRNA sequence), AA878778 (oe80h01.s1 NCI_CGAP_Lu5 *Homo sapiens* cDNA clone IMAGE: 1417969 3', mRNA sequence), and U96448 (*Bos taurus* cleavage and polyadenylation specificity factor 30 kDa subunit mRNA, complete cds). The predicted amino acid sequence disclosed herein for rc58__1 was searched against the GenPept and GeneSeq amino acid sequence databases using the BLASTX search protocol. The predicted rc58__1 protein demonstrated at least some similarity to sequences identified as AF033201 (cleavage and polyadenylation specificity factor [*Mus musculus*]) and U96448 (cleavage and polyadenylation specificity factor 30 kDa subunit [*Bos taurus*]). Based upon sequence similarity, rc58__1 proteins and each similar protein or peptide may share at least some activity. The TopPredII computer program predicts an additional potential transmembrane domain within the rc58__1 protein sequence centered around amino acid 53 of SEQ ID NO:56.

Clone "rd232__5"

A polynucleotide of the present invention has been identified as clone "rd232__5". rd232__5 was isolated from a human fetal kidney cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. rd232__5 is a full-length clone, including the entire coding sequence of a secreted protein (also referred to herein as "rd232__5 protein").

The nucleotide sequence of rd232__5 as presently determined is reported in SEQ ID NO:57, and includes a poly(A) tail. What applicants presently believe to be the proper reading frame and the predicted amino acid sequence of the rd232__5 protein corresponding to the foregoing nucleotide sequence is reported in SEQ ID NO:58.

The EcoRI/NotI restriction fragment obtainable from the deposit containing done rd232__5 should be approximately 3800 bp.

The nucleotide sequence disclosed herein for rd232__5 was searched against the GenBank and GeneSeq nucleotide sequence databases using BLASTN/BLASTX and FASTA search protocols. rd232__5 demonstrated at least some similarity with sequences identified as AA768103 (oc16g01.s1 NCI_CGAP_GCB1 *Homo sapiens* cDNA clone IMAGE: 1341072), AA831487 (oc61a11.s1 NCI_CGAP_GCB1 *Homo sapiens* cDNA clone IMAGE:1354172 3', mRNA sequence), and R57296 (F2616 Fetal heart *Homo sapiens* cDNA clone F2616 5' end). The predicted amino acid sequence disclosed herein for rd232__5 was searched against the GenPept and GeneSeq amino acid sequence databases using the BLASTX search protocol. The predicted rd232__5 protein demonstrated at least some similarity to the sequence identified as Z79755 (F43G9.2 *[Caenorhabditis elegans*]). Based upon sequence similarity, rd232__5 proteins and each similar protein or peptide may share at least some activity. The TopPredII computer program predicts a potential transmembrane domain within the rd232__5 protein sequence centered around amino acid 225 of SEQ ID NO:58. The nucleotide sequence of rd232__5 indicates that it may contain a simple AC repeat region.

Clone "ck213__12"

A polynucleotide of the present invention has been identified as clone "ck213__12". ck213__12 was isolated from a human adult testes cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. ck213__12 is a full-length clone, including the entire coding sequence of a secreted protein (also referred to herein as "ck13__12 protein").

The nucleotide sequence of ck213__12 as presently determined is reported in SEQ ID NO:59, and includes a poly(A) tail. What applicants presently believe to be the proper reading frame and the predicted amino acid sequence of the ck213__12 protein corresponding to the foregoing nucleotide sequence is reported in SEQ ID NO:60.

The EcoRI/NotI restriction fragment obtainable from the deposit containing done ck213__12 should be approximately 3500 bp.

The nucleotide sequence disclosed herein for ck213__12 was searched against the GenBank and GeneSeq nucleotide sequence databases using BLASTN/BLASTX and FASTA search protocols. ck213__12 demonstrated at least some similarity with sequences identified as AA062731 (zm01h03.s1 Stratagene corneal stroma (#937222) *Homo sapiens* cDNA clone 512885 3' similar to TR:G1136390 G1136390 KIAA0164 PROTEIN, mRNA sequence), AA173803 (zp30f05.s1 Stratagene neuroepithelium (#937231) *Homo sapiens* cDNA clone 610977 3', mRNA sequence), D79986 (Human mRNA for KIAA0164 protein gene, complete cds), and R01411 (ye77c11.s1 *Homo sapiens* cDNA clone 123764 3'). The predicted amino acid sequence disclosed herein for ck213__12 was searched against the GenPept and GeneSeq amino acid sequence databases using the BLASTX search protocol.

The predicted ck213__12 protein demonstrated at least some similarity to the sequence identified as D79986 (similar to human DNA-binding protein 5 *[Homo sapiens*], KIAA0164 protein [*Homo sapiens*], HUMKIAA04$_{_1}$). Based upon sequence similarity, ck213__12 proteins and each similar protein or peptide may share at least some activity.

Clone "pg195__1"

A polynucleotide of the present invention has been identified as clone "pg195__1". pg195__1 was isolated from a human adult thyroid cDNA library using methods which are selective for cDNAs encoding secreted proteins (see U.S. Pat. No. 5,536,637), or was identified as encoding a secreted or transmembrane protein on the basis of computer analysis of the amino add sequence of the encoded protein. pg195__1 is a full-length clone, including the entire coding sequence of a secreted protein (also referred to herein as "pg195__1 protein").

The nucleotide sequence of pg195__1 as presently determined is reported in SEQ ID NO:61, and includes a poly(A) tail. What applicants presently believe to be the proper reading frame and the predicted amino acid sequence of the pg195__1 protein corresponding to the foregoing nucleotide sequence is reported in SEQ ID NO:62.

The EcoRI/NotI restriction fragment obtainable from the deposit containing clone pg195__1 should be approximately 3300 bp.

The nucleotide sequence disclosed herein for pg195_1 was searched against the GenBank and GeneSeq nucleotide sequence databases using BLASTN/BLASTX and PASTA search protocols. pg195_1 demonstrated at least some similarity with sequences identified as H72617 (yu02g10.r1 *Homo sapiens* cDNA clone 232674 5') and W37280 (zc11a07.r1 Soares parathyroid tumor NbHPA *Homo sapiens* cDNA clone 321972 5', mRNA sequence). The predicted amino acid sequence disclosed herein for pg195_1 was searched against the GenPept and GeneSeq amino acid sequence databases using the BLASTX search protocol. The predicted pg195_1 protein demonstrated at least some similarity to the sequence identified as AF007270 (contains similarity to myosin heavy chain [*Arabidopsis thaliana*]). Based upon sequence similarity, pg195_1 proteins and each similar protein or peptide may share at least some activity. The TopPredII computer program predicts two potential transmembrane domains within the pg195_1 protein sequence, one centered around amino acid 480 and another around amino acid 520 of SEQ ID NO:62. The nucleotide sequence of pg195_1 indicates that it may contain one or more repetitive sequences.

Clone "pw460_5"

A polynucleotide of the present invention has been identified as clone "pw460_5". pw460_5 was isolated from a human adult brain (cerebellum) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. pw460_5 is a full-length clone, including the entire coding sequence of a secreted protein (also referred to herein as "pw460_5 protein").

The nucleotide sequence of pw460_5 as presently determined is reported in SEQ ID NO:63, and includes a poly(A) tail. What applicants presently believe to be the proper reading frame and the predicted amino acid sequence of the pw460_5 protein corresponding to the foregoing nucleotide sequence is reported in SEQ ID NO:64. Amino acids 17 to 29 of SEQ ID NO:64 are a predicted leader/signal sequence, with the predicted mature amino acid sequence beginning at amino acid 30. Due to the hydrophobic nature of the predicted leader/signal sequence, it is likely to act as a transmembrane domain should the predicted leader/signal sequence not be separated from the remainder of the pw460_5 protein.

The EcoRI/NotI restriction fragment obtainable from the deposit containing done pw460_5 should be approximately 1800 bp.

The nucleotide sequence disclosed herein for pw460_5 was searched against the GenBank and GeneSeq nucleotide sequence databases using BLASTN/BLASTX and FASTA search protocols. pw460_5 demonstrated at least some similarity with sequences identified as AA447258 (zw93e03.r1 Soares total fetus Nb2HF8 9w *Homo sapiens* cDNA clone 784540 5', mRNA sequence), AA617801 (nq04f05.s1 NCI_CGAP_Lu1 *Homo sapiens* cDNA clone IMAGE 1142913), AC002486 (Human BAC clone RG367017 from 7p15-p21, complete sequence), AC004837 (human genomic DNA fragments), and H45347 (yo65h03.r1 *Homo sapiens* cDNA clone 182837 5'). Based upon sequence similarity, pw460_5 proteins and each similar protein or peptide may share at least some activity.

Clone "qa136_1"

A polynucleotide of the present invention has been identified as clone "qa136_1". qa136_1 was isolated from a human adult cartilage (chondrosarcoma HTB-94 line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. qa136_1 is a full-length clone, including the entire coding sequence of a secreted protein (also referred to herein as "qa136_1 protein").

The nucleotide sequence of qa136_1 as presently determined is reported in SEQ ID NO:65. What applicants presently believe to be the proper reading frame and the predicted amino acid sequence of the qa136_1 protein corresponding to the foregoing nucleotide sequence is reported in SEQ ID NO:66. Amino acids 15 to 27 of SEQ ID NO:66 are a predicted leader/signal sequence, with the predicted mature amino acid sequence beginning at amino acid 28. Due to the hydrophobic nature of the predicted leader/signal sequence, it is likely to act as a transmembrane domain should the predicted leader/signal sequence not be separated from the remainder of the qa136_1 protein.

The EcoRI/NotI restriction fragment obtainable from the deposit containing clone qa136_1 should be approximately 1600 bp.

The nucleotide sequence disclosed herein for qa136_1 was searched against the GenBank and GeneSeq nucleotide sequence databases using BLASTN/BLASTX and FASTA search protocols. qa136_1 demonstrated at least some similarity with sequences identified as AA758023 (ah67g02.s1 Soares testis NHT *Homo sapiens* cDNA clone 1320722 3', mRNA sequence), R69911 (yi47c02.r1 *Homo sapiens* cDNA clone 142370 5'), and T21835 (Human gene signature HUMGS03376; standard; cDNA to mRNA). Based upon sequence similarity, qa136_1 proteins and each similar protein or peptide may share at least some activity. The TopPredII computer program predicts five additional potential transmembrane domains within the qa136_1 protein sequence, centered around amino acids 59, 136, 171, 201, and 268 of SEQ ID NO:66, respectively. qa136_1 protein was expressed in a COS cell expression system, and an expressed protein band of approximately 24 kDa was detected in conditioned medium and membrane fractions using SDS polyacrylamide gel electrophoresis.

Clone "qy1261_2"

A polynucleotide of the present invention has been identified as clone "qy1261_2". qy1261_2 was isolated from a human adult blood (promyelocytic Leukemia HL-60) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. qy1261_2 is a full-length clone, including the entire coding sequence of a secreted protein (also referred to herein as "qy1261_2 protein").

The nucleotide sequence of qy1261_2 as presently determined is reported in SEQ ID NO:67, and includes a poly(A) tail. What applicants presently believe to be the proper reading frame and the predicted amino acid sequence of the qy1261_2 protein corresponding to the foregoing nucleotide sequence is reported in SEQ ID NO:68. Amino acids 100 to 112 of SEQ ID NO:68 are a predicted leader/signal sequence, with the predicted mature amino acid sequence beginning at amino acid 113. Due to the hydrophobic nature of the predicted leader/signal sequence, it is likely to act as a transmembrane domain should the predicted leader/signal sequence not be separated from the remainder of the qy1261_2 protein.

The EcoRI/NotI restriction fragment obtainable from the deposit containing clone qy1261_2 should be approximately 2500 bp.

The nucleotide sequence disclosed herein for qy1261_2 was searched against the GenBank and GeneSeq nucleotide sequence databases using BLASTN/BLASTX and FASTA search protocols. qy1261_2 demonstrated at least some similarity with sequences identified as AA076472 (zm91b06.r1 Stratagene ovarian cancer (#937219) *Homo sapiens* cDNA clone 545267 5'), AA115700 (zl87g10.r1 Stratagene colon (#937204) *Homo sapiens* cDNA clone 511650 5', mRNA sequence), and AA190522 (zp85e0 7.r1 Stratagene HeLa cell s3 937216 *Homo sapiens* cDNA clone 627012 5'). The predicted amino acid sequence disclosed herein for qy1261_2 was searched against the GenPept and GeneSeq amino acid sequence databases using the BLASTX search protocol. The predicted qy1261_2 protein demonstrated at least some similarity to the sequence identified as U49082 (transporter protein [*Homo sapiens*]). Based upon sequence similarity, qy1261_2 proteins and each similar protein or peptide may share at least some activity. The TopPredII computer program predicts ten additional potential transmembrane domains within the qy1261_2 protein sequence, centered around amino acids 80, 157, 203, 227, 286, 322, 365, 403, 426, and 462 of SEQ ID NO:68. The nucleotide sequence of qy1261_2 indicates that it may contain one or more Alu repeat sequences.

Clone "rd432_4"

A polynucleotide of the present invention has been identified as clone "rd432_4". rd432_4 was isolated from a human kidney (293 embryonal carcinoma cell line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. rd432_4 is a full-length clone, including the entire coding sequence of a secreted protein (also referred to herein as "rd432_4 protein").

The nucleotide sequence of rd432_4 as presently determined is reported in SEQ ID NO:69, and includes a poly(A) tail. What applicants presently believe to be the proper reading frame and the predicted amino acid sequence of the rd432_4 protein corresponding to the foregoing nucleotide sequence is reported in SEQ ID NO:70.

The EcoRI/NotI restriction fragment obtainable from the deposit containing clone rd432_4 should be approximately 2200 bp.

The nucleotide sequence disclosed herein for rd432_4 was searched against the GenBank and GeneSeq nucleotide sequence databases using BLASTN/BLASTX and FASTA search protocols. rd432_4 demonstrated at least some similarity with sequences identified as AA662913 (nu92b03.s1 NCI_CGAP_Pr22 *Homo sapiens* cDNA clone IMAGE: 1218125, mRNA sequence). Based upon sequence similarity, rd432_4 proteins and each similar protein or peptide may share at least some activity. The TopPredII computer program predicts a potential transmembrane domain within the rd432_4 protein sequence, which includes amino adds 102-122 of SEQ ID NO:70. The nucleotide sequence of rd432_4 indicates that it may contain one or more Alu repetitive elements.

rd432_4 protein was expressed in a COS cell expression system, and an expressed protein band of approximately 18 kDa was detected in membrane fractions using SDS polyacrylamide gel electrophoresis.

Clone "rb789_14"

A polynucleotide of the present invention has been identified as clone "rb789_14". rb789_14 was isolated from a human kidney (293 embryonal carcinoma line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. rb789_14 is a full-length clone, including the entire coding sequence of a secreted protein (also referred to herein as "rb789_14 protein").

The nucleotide sequence of rb789_14 as presently determined is reported in SEQ ID NO:71, and includes a poly(A) tail. What applicants presently believe to be the proper reading frame and the predicted amino acid sequence of the rb789_14 protein corresponding to the foregoing nucleotide sequence is reported in SEQ ID NO:72. Amino acids 9 to 21 of SEQ ID NO:72 are a predicted leader/signal sequence, with the predicted mature amino acid sequence beginning at amino acid 22. Due to the hydrophobic nature of the predicted leader/signal sequence, it is likely to act as a transmembrane domain should the predicted leader/signal sequence not be separated from the remainder of the rb789_14 protein.

The EcoRI/NotI restriction fragment obtainable from the deposit containing clone rb789_14 should be approximately 2300 bp.

The nucleotide sequence disclosed herein for rb789_14 was searched against the GenBank and GeneSeq nucleotide sequence databases using BLASTN/BLASTX and FASTA search protocols. rb789_14 demonstrated at least some similarity with sequences identified as AL008582 (Human DNA sequence *SEQUENCING IN PROGRESS* from clone 223H9; HTGS phase 1), AL022393 (*Homo sapiens* DNA sequence from P1 p373c6 on chromosome 6p21.31-21.33. Contains zinc finger proteins, pseudogenes, ESTs and STS), N28823 (yx71f11.r1 *Homo sapiens* cDNA clone 267213 5'), and Q60944 (Human brain Expressed Sequence Tag EST01025; standard; DNA). Based upon sequence similarity, rb789_14 proteins and each similar protein or peptide may share at least some activity. The TopPredII computer program predicts two additional potential transmembrane domains within the rb789_14 protein sequence, one centered around amino acid 30 and another around amino acid 75 of SEQ ID NO:72.

Clone "yd137_1"

A polynucleotide of the present invention has been identified as clone "yd137_1". yd137_1 was isolated from a human adult brain cDNA library and was identified as encoding a secreted or transmembrane protein on the basis of computer analysis of the amino acid sequence of the encoded protein. yd137_1 is a full-length clone, including the entire coding sequence of a secreted protein (also referred to herein as "yd137_1 protein").

The nucleotide sequence of yd137_1 as presently determined is reported in SEQ ID NO:73, and includes a poly(A) tail. What applicants presently believe to be the proper reading frame and the predicted amino acid sequence of the yd137_1 protein corresponding to the foregoing nucleotide sequence is reported in SEQ ID NO:74. Amino acids 27 to 39 of SEQ ID NO:74 are a predicted leader/signal sequence, with the predicted mature amino acid sequence beginning at amino acid 40. Due to the hydrophobic nature of the predicted leader/signal sequence, it is likely to act as a transmembrane domain should the predicted leader/signal sequence not be separated from the remainder of the yd137_1 protein.

The EcoRI/NotI restriction fragment obtainable from the deposit containing clone yd137_1 should be approximately 789 bp.

The nucleotide sequence disclosed herein for yd137_1 was searched against the GenBank and GeneSeq nucleotide sequence databases using BLASTN/BLASTX and FASTA search protocols. yd137_1 demonstrated at least some similarity with sequences identified as AI015619 (ov29g02.x1 Soares_testis_NHT *Homo sapiens* cDNA clone IMAGE: 1638770 3' similar to WP:C34B2.10 CE16898; mRNA sequence). The predicted amino acid sequence disclosed herein for yd137_1 was searched against the GenPept and GeneSeq amino acid sequence databases using the BLASTX search protocol. The predicted yd137_1 protein demonstrated at least some similarity to the sequence identified as AF043693 (*Caenorhabditis elegans* cosmid C34B2). Based upon sequence similarity, yd137_1 proteins and each similar protein or peptide may share at least some activity. The TopPredII computer program predicts two additional potential transmembrane domains within the yd137_1 protein sequence, one centered around amino acid 30 and another around amino acid 55 of SEQ ID NO:74.

Clone "yd218_1"

A polynucleotide of the present invention has been identified as clone "yd218_1". yd218_1 was isolated from a human adult brain cDNA library and was identified as encoding a secreted or transmembrane protein on the basis of computer analysis of the amino acid sequence of the encoded protein. yd218_1 is a full-length clone, including the entire coding sequence of a secreted protein (also referred to herein as "yd218_1 protein").

The nucleotide sequence of yd218_1 as presently determined is reported in SEQ ID NO:75, and includes a poly(A) tail. What applicants presently believe to be the proper reading frame and the predicted amino acid sequence of the yd218_1 protein corresponding to the foregoing nucleotide sequence is reported in SEQ ID NO:76. Amino acids 2 to 14 of SEQ ID NO:76 are a predicted leader/signal sequence, with the predicted mature amino acid sequence beginning at amino acid 15. Due to the hydrophobic nature of the predicted leader/signal sequence, it is likely to act as a transmembrane domain should the predicted leader/signal sequence not be separated from the remainder of the yd218_1 protein.

The EcoRI/NotI restriction fragment obtainable from the deposit containing clone yd218_1 should be approximately 900 bp.

The nucleotide sequence disclosed herein for yd218_1 was searched against the GenBank and GeneSeq nucleotide sequence databases using BLASTN/BLASTX and FASTA search protocols. yd218_1 demonstrated at least some similarity with sequences identified as AA402818 (zu55f06.s1 Soares ovary tumor NbHOT *Homo sapiens* cDNA clone 741923 3', mRNA sequence) and AI150344 (qf35b11.x1 Soares_testis_NHT *Homo sapiens* cDNA clone IMAGE: 1751997 3', mRNA sequence). Based upon sequence similarity, yd218_1 proteins and each similar protein or peptide may share at least some activity. The TopPredII computer program predicts two additional potential transmembrane domains within the yd218_1 protein sequence, one centered around amino acid 66 and another around amino acid 100 of SEQ ID NO:76.

yd218_1 protein was expressed in a COS cell expression system, and an expressed protein band of approximately 15 kDa was detected in membrane fractions using SDS polyacrylamide gel electrophoresis.

Clone "ye11_1"

A polynucleotide of the present invention has been identified as clone "ye11_1". ye11_1 was isolated from a human fetal brain cDNA library and was identified as encoding a secreted or transmembrane protein on the basis of computer analysis of the amino acid sequence of the encoded protein. ye11_1 is a full-length clone, including the entire coding sequence of a secreted protein (also referred to herein as "ye11_1 protein").

The nucleotide sequence of ye11_1 as presently determined is reported in SEQ ID NO:77, and includes a poly(A) tail. What applicants presently believe to be the proper reading frame and the predicted amino acid sequence of the ye11_1 protein corresponding to the foregoing nucleotide sequence is reported in SEQ ID NO:78.

The EcoRI/NotI restriction fragment obtainable from the deposit containing clone ye11_1 should be approximately 2700 bp.

The nucleotide sequence disclosed herein for ye11_1 was searched against the GenBank and GeneSeq nucleotide sequence databases using BLASTN/BLASTX and FASTA search protocols. ye11_1 demonstrated at least some similarity with sequences identified as AC005082 (*SEQUENCING N PROGRESS* *Homo sapiens* clone RG271G13; HTGS phase 1, 7 unordered pieces). The predicted amino acid sequence disclosed herein for ye11_1 was searched against the GenPept and GeneSeq amino acid sequence databases using the BLASTX search protocol. The predicted ye11_1 protein demonstrated at least some similarity to sequences identified as AF059569 (actin binding protein MAYVEN [*Homo sapiens*]) and R94386 (Human neural cell protein marker RR/B). MAYVEN is an actin-binding protein expressed in brain. Hidden markov model analysis reveals the presence of a BTB (BR-c/Ttk) domain in the predicted ye11_1 protein. BTB domains are characteristic of certain bacterial membrane transport proteins. The MAYVEN protein is thought to contain a similar BTB motif, an indication that ye11_1 and MAYVEN may share a similar function. Based upon sequence similarity, ye11_1 proteins and each similar protein or peptide may share at least some activity. The TopPredII computer program predicts two potential transmembrane domains within the ye11_1 protein sequence, one centered around amino acid 20 and another around amino acid 480 of SEQ ID NO:78.

ye11_1 protein was expressed in a COS cell expression system, and an expressed protein band of approximately 57 kDa was detected in conditioned medium and membrane fractions using SDS polyacrylamide gel electrophoresis.

Clone "ye72 1"

A polynucleotide of the present invention has been identified as clone "ye72_1". ye72_1 was isolated from a human fetal brain cDNA library and was identified as encoding a secreted or transmembrane protein on the basis of computer analysis of the amino acid sequence of the encoded protein. ye72_1 is a full-length clone, including the entire coding sequence of a secreted protein (also referred to herein as "ye72_1 protein").

The nucleotide sequence of ye72_1 as presently determined is reported in SEQ ID NO:79, and includes a poly(A) tail. What applicants presently believe to be the proper reading frame and the predicted amino acid sequence of the ye72_1 protein corresponding to the foregoing nucleotide sequence is reported in SEQ ID NO:80. Amino acids 24 to 36 of SEQ ID NO:80 are a predicted leader/signal sequence, with the predicted mature amino acid sequence beginning at amino acid 37. Due to the hydrophobic nature of the predicted leader/signal sequence, it is likely to act as a transmembrane domain should the predicted leader/signal sequence not be separated from the remainder of the ye72__1 protein.

The EcoRI/NotI restriction fragment obtainable from the deposit containing clone ye72__1 should be approximately 2261 bp.

The nucleotide sequence disclosed herein for ye72__1 was searched against the GenBank and GeneSeq nucleotide sequence databases using BLASTN/BLASTX and FASTA search protocols. ye72__1 demonstrated at least some similarity with sequences identified as AA968450 (op49d06.s1 Soares_NFL_T_GBC_S1 *Homo sapiens* cDNA clone IMAGE:1580171 3', mRNA sequence). The predicted amino acid sequence disclosed herein for ye72__1 was searched against the GenPept and GeneSeq amino acid sequence databases using the BLASTX search protocol. The predicted ye72__1 protein demonstrated at least some similarity to sequences identified as U16258 (I kappa BR [*Homo sapiens*]) and W15483 (Human P28). Based upon sequence similarity, ye72__1 proteins and each similar protein or peptide may share at least some activity. Hidden markov model analysis reveals the presence of three ankyrin repeats in the predicted ye72__1 protein at amino acids 273 to 306, 307 to 339, and 341 to 373 of SEQ ID NO:80. The ankyrin 33-residue repeating motif, an L-shaped structure with protruding beta-hairpin tips, mediates specific macromolecular interactions with cytoskeletal, membrane, and regulatory proteins. The TopPredII computer program predicts an additional potential transmembrane domain within the ye72__1 protein sequence centered around amino acid 140 of SEQ ID NO:80.

Clone "ye78__1"

A polynucleotide of the present invention has been identified as clone "ye78__1". ye78__1 was isolated from a human fetal brain cDNA library and was identified as encoding a secreted or transmembrane protein on the basis of computer analysis of the amino acid sequence of the encoded protein. ye78__1 is a full-length clone, including the entire coding sequence of a secreted protein (also referred to herein as "ye78__1 protein").

The nucleotide sequence of ye78__1 as presently determined is reported in SEQ ID NO:81, and includes a poly(A) tail. What applicants presently believe to be the proper reading frame and the predicted amino acid sequence of the ye78__1 protein corresponding to the foregoing nucleotide sequence is reported in SEQ ID NO:82. Amino acids 78 to 90 of SEQ ID NO:82 are a predicted leader/signal sequence, with the predicted mature amino acid sequence beginning at amino acid 91. Amino acids 42 to 54 are also a possible leader/signal sequence, with the predicted mature amino acid sequence beginning at amino acid 55. Due to the hydrophobic nature of leader/signal sequences, both of these predicted and possible leader sequences are likely to act as a transmembrane domain should either of them not be separated from the remainder of the ye78__1 protein.

The EcoRI/NotI restriction fragment obtainable from the deposit containing clone ye78__1 should be approximately 2654 bp.

The nucleotide sequence disclosed herein for ye78__1 was searched against the GenBank and GeneSeq nucleotide sequence databases using BLASTN/BLASTX and FASTA search protocols. ye78__1 demonstrated at least some similarity with sequences identified as AA522797 (ni40c10.s1 NCI_CGAP_Lu1*Homo sapiens* cDNA clone IMAGE: 979314, mRNA sequence). Based upon sequence similarity, ye78__1 proteins and each similar protein or peptide may share at least some activity. The TopPredII computer program predicts four potential transmembrane domains within the ye78__1 protein sequence, centered around amino acids 55, 75, 84, and 480 of SEQ ID NO:12, respectively.

Clone "ye90__1"

A polynucleotide of the present invention has been identified as clone "ye90__1". ye901 was isolated from a human fetal brain cDNA library and was identified as encoding a secreted or transmembrane protein on the basis of computer analysis of the amino acid sequence of the encoded protein. ye90__1 is a full-length clone, including the entire coding sequence of a secreted protein (also referred to herein as "ye90__1 protein").

The nucleotide sequence of ye90__1 as presently determined is reported in SEQ ID NO:83, and includes a poly(A) tail. What applicants presently believe to be the proper reading frame and the predicted amino acid sequence of the ye90__1 protein corresponding to the foregoing nucleotide sequence is reported in SEQ ID NO:84. Amino acids 7 to 19 of SEQ ID NO:84 are a predicted leader/signal sequence, with the predicted mature amino acid sequence beginning at amino acid 20. Due to the hydrophobic nature of the predicted leader/signal sequence, it is likely to act as a transmembrane domain should the predicted leader/signal sequence not be separated from the remainder of the ye90__1 protein.

The EcoRI/NotI restriction fragment obtainable from the deposit containing done ye90__1 should be approximately 1505 bp.

The nucleotide sequence disclosed herein for ye90__1 was searched against the GenBank and GeneSeq nucleotide sequence databases using BLASTN/BLASTX and FASTA search protocols. ye90__1 demonstrated at least some similarity with sequences identified as AI079268 (oz32f06.x1 Soares_total_fetus_Nb2HF8__9w *Homo sapiens* cDNA clone IMAGE:1677059 3', mRNA sequence) and T25543 (Human gene signature HUMGS07715, standard; cDNA to mRNA). Based upon sequence similarity, ye90__1 proteins and each similar protein or peptide may share at least some activity. Motifs analysis reveals the presence of a neutral zinc metallopeptidases, zinc-binding region signature beginning around amino acid residue 236 of SEQ ID NO:84; some known secreted proteins have this motif. The TopPredII computer program predicts two additional potential transmembrane domains within the ye901 protein sequence, one centred around amino acid 195 and another around amino acid 300 of SEQ ID NO:84.

Clone "yi62__1"

A polynucleotide of the present invention has been identified as clone "yi62__1". yi62__1 was isolated from a human adult brain cDNA library and was identified as encoding a secreted or transmembrane protein on the basis of computer analysis of the amino acid sequence of the encoded protein. yi62__1 is a full-length clone, including the entire coding sequence of a secreted protein (also referred to herein as "yi62__1 protein").

The nucleotide sequence of yi62__1 as presently determined is reported in SEQ ID NO:85, and includes a poly(A) tail. What applicants presently believe to be the proper reading frame and the predicted amino acid sequence of the yi62__1 protein corresponding to the foregoing nucleotide sequence is reported in SEQ ID NO:86. Amino acids 2 to 14 are a possible leader/signal sequence, with the predicted mature amino acid sequence beginning at amino acid 15. Due to the hydrophobic nature of the predicted leader/signal sequence, it is likely to act as a transmembrane domain should the predicted leader/signal sequence not be separated from the remainder of the yi62__1 protein.

The EcoRI/NotI restriction fragment obtainable from the deposit containing clone yi62_1 should be approximately 1240 bp.

The nucleotide sequence disclosed herein for yi62_1 was searched against the GenBank and GeneSeq nucleotide sequence databases using BLASTN/BLASTX and FASTA search protocols. yi62_1 demonstrated at least some similarity with sequences identified as R57572 (F3589 Fetal heart *Homo sapiens* cDNA clone F3589 5' end, mRNA sequence). Based upon sequence similarity, yi62_1 proteins and each similar protein or peptide may share at least some activity. The TopPredII computer program predicts four potential transmembrane domains within the yi62_1 protein sequence, centered around amino acids 15, 75, 100, and 125 of SEQ ID NO:86, respectively.

Clone "yk78_1"

A polynucleotide of the present invention has been identified as clone "yk78_1". yk78_1 was isolated from a human adult thymus cDNA library and was identified as encoding a secreted or transmembrane protein on the basis of computer analysis of the amino acid sequence of the encoded protein. yk78_1 is a full-length clone, including the entire coding sequence of a secreted protein (also referred to herein as "yk78_1 protein").

The nucleotide sequence of yk78_1 as presently determined is reported in SEQ ID NO:87, and includes a poly(A) tail. What applicants presently believe to be the proper reading frame and the predicted amino acid sequence of the yk78_1 protein corresponding to the foregoing nucleotide sequence is reported in SEQ ID NO:88. Amino acids 57 to 69 of SEQ ID NO:88 are a predicted leader/signal sequence, with the predicted mature amino acid sequence beginning at amino acid 70. Amino acids 7 to 19 are a possible leader/signal sequence, with the predicted mature amino acid sequence beginning at amino acid 20. Due to the hydrophobic nature of leader/signal sequences, both of these predicted and possible leader sequences are likely to act as a transmembrane domain should either of them not be separated from the remainder of the yk8_1 protein.

The EcoRI/NotI restriction fragment obtainable from the deposit containing clone yk78_1 should be approximately 1088 bp.

The nucleotide sequence disclosed herein for yk78_1 was searched against the GenBank and GeneSeq nucleotide sequence databases using BLASTN/BLASTX and FASTA search protocols. yk78_1 demonstrated at least some similarity with sequences identified as AC004921 (* SEQUENCING IN PROGRESS * *Homo sapiens* clone DJ0899E09; HTGS phase 1, 11 unordered pieces). Based upon sequence similarity, yk78_1 proteins and each similar protein or peptide may share at least some activity. The TopPredII computer program predicts two potential transmembrane domains within the yk78_1 protein sequence, one centered around amino acid 20 and another around amino acids 60 of SEQ ID NO:88.

Clone "yk251_1"

A polynucleotide of the present invention has been identified as clone "yk251_1". yk251_1 was isolated from a human adult thymus cDNA library and was identified as encoding a secreted or transmembrane protein on the basis of computer analysis of the amino acid sequence of the encoded protein. yk251_1 is a full-length clone, including the entire coding sequence of a secreted protein (also referred to herein as "yk251_1 protein").

The nucleotide sequence of yk251_1 as presently determined is reported in SEQ ID NO:89, and includes a poly(A) tail. What applicants presently believe to be the proper reading frame and the predicted amino acid sequence of the yk251_1 protein corresponding to the foregoing nucleotide sequence is reported in SEQ ID NO:90. Amino acids 17 to 29 of SEQ ID NO:90 are a predicted leader/signal sequence, with the predicted mature amino acid sequence beginning at amino acid 30. Due to the hydrophobic nature of the predicted leader/signal sequence, it is likely to act as a transmembrane domain should the predicted leader/signal sequence not be separated from the remainder of the yk251_1 protein.

The EcoRI/NotI restriction fragment obtainable from the deposit containing clone yk251_1 should be approximately 2558 bp.

The nucleotide sequence disclosed herein for yk251_1 was searched against the GenBank and GeneSeq nucleotide sequence databases using BLASTN/BLASTX and FASTA search protocols. No hits were found in the databases. The TopPredII computer program predicts a potential transmembrane domain within the yk251_1 protein sequence centered, around amino acid 20 of SEQ ID NO:90. The nucleotide sequence of yk251_1 indicates that it may contain Alu and SVA repetitive elements.

Clone "yt14_1"

A polynucleotide of the present invention has been identified as clone "yt14_1". yt14_1 was isolated from a human adult retina (WERI-Rb1 retinoblastoma line) cDNA library and was identified as encoding a secreted or transmembrane protein on the basis of computer analysis of the amino acid sequence of the encoded protein. yt14_1 is a full-length clone, including the entire coding sequence of a secreted protein (also referred to herein as "yt14_1 protein").

The nucleotide sequence of yt14_1 as presently determined is reported in SEQ ID NO:91, and includes a poly(A) tail. What applicants presently believe to be the proper reading frame and the predicted amino acid sequence of the yt14_1 protein corresponding to the foregoing nucleotide sequence is reported in SEQ ID NO:92. Amino acids 1 to 9 are a possible leader/signal sequence, with the predicted mature amino acid sequence beginning at amino acid 10. Due to the hydrophobic nature of this possible leader/signal sequence, it is likely to act as a transmembrane domain should the predicted leader/signal sequence not be separated from the remainder of the yk251_1 protein.

The EcoRI/NotI restriction fragment obtainable from the deposit containing clone yt14_1 should be approximately 2429 bp.

The nucleotide sequence disclosed herein for yt14_1 was searched against the GenBank and GeneSeq nucleotide sequence databases using BLASTN/BLASTX and FASTA search protocols. yt14_1 demonstrated at least some similarity with sequences identified as WO7167 (za93b12.r1 Soares fetal lung NbHL19W *Homo sapiens* cDNA clone 300095 5', mRNA sequence). The predicted amino acid sequence disclosed herein for yt14_1 was searched against the GenPept and GeneSeq amino acid sequence databases using the BLASTX search protocol. The predicted yt14_1 protein demonstrated at least some similarity to the sequence identified as AF002196 (weak similarity to *Bacillus* and *Pseudomonas* probable glucarate transporters (GI 709999 and PIR S27616) [*Caenorhabditis elegans*]). Based upon sequence similarity, yt14_1 proteins and each similar protein or peptide may share at least some activity. The TopPredII computer program predicts six potential transmembrane domains within the yt14_1 protein sequence, centered around amino acids 10, 40, 65, 90, 130, and 160 of SEQ ID NO:92, respectively. The nucleotide sequence of yt14_1 indicates that it may contain Alu and L1 repetitive elements.

Clone "bf157_16"

A polynucleotide of the present invention has been identified as clone "bf157_16". bf157_16 was isolated from a human fetal brain cDNA library and was identified as encoding a novel protein on the basis of computer analysis of the amino acid sequence of the encoded protein. bf157_16 is a full-length clone, including the entire coding sequence of a novel protein (also referred to herein as "bf157_16 protein"). The nucleotide sequence of bf157_16 as presently determined is reported in SEQ ID NO:93, and includes a poly(A) tail. What applicants presently believe to be the proper reading frame and the predicted amino acid sequence of the bf157_16 protein corresponding to the foregoing nucleotide sequence is reported in SEQ ID NO:94.

The EcoRI/NotI restriction fragment obtainable from the deposit containing clone bf157_16 should be approximately 3480 bp.

The nucleotide sequence disclosed herein for bf157_16 was searched against the GenBank and GeneSeq nucleotide sequence databases using BLASTN/BLASTX and FASTA search protocols. bf157_16 demonstrated at least some similarity with sequences identified as AA186595 (zo71g04.r1 Stratagene pancreas (#937208) *Homo sapiens* cDNA clone 592374 5' similar to WP C16A3.3 CE04004 HUMAN ALPHA-FETOPROTEIN ENHANCER-BINDING PROTEIN), AA630405 (ac09b05.s1 Stratagene HeLa cell s3 937216 *Homo sapiens* cDNA clone 855921 3' similar to WP C16A3.3 CE04004HUMAN ALPHA-FETOPROTEIN ENHANCER-BINDING PROTEIN; mRNA sequence), AF075104 (*Homo sapiens* full length insert cDNA YR39H06), H49655 (yq20h07.s1 Soares fetal liver spleen 1NFLS *Homo sapiens* cDNA clone 274428 3'), Z28494 (*H. sapiens* partial cDNA sequence; clone 22G07; version 1; strand(−), single read), Z56794 (H.sapiens CpG island DNA genomic Mse1 fragment, done), and Z64553 (*H.sapiens* CpG island DNA genomic Mse1 fragment, clone 139f5, forward read cpg139f5.ft1a). The predicted amino acid sequence disclosed herein for bf157_16 was searched against the GenPept and GeneSeq amino acid sequence databases using the BLASTX search protocol. The predicted bf157_16 protein demonstrated at least some similarity to sequences identified as R23962 (AFP-1. DNA encoding protein binding to alpha-fetoprotein gene enhancer—useful for prodn. of biological active protein), and U41534 (similar to yeast hypothetical protein (SP:YB9M_YEAST,P38344); similar to human alpha-fetoprotein enhancer-binding protein (PIR:A41948) [*Caenorhabditis elegans*]). Based upon sequence similarity, bf157_16 proteins and each similar protein or peptide may share at least some activity. Hidden Markov model and motifs analyses have revealed the presence of the following protein domains in the predicted bf157_16 protein: four Zinc finger, C2H2 type, domains at amino acids 4 to 28, 67 to 91, 252 to 275, and 303 to 330 of SEQ ID NO:94; and a D-isomer-specific 2-hydroxyacid dehydrogenases signature at residues 119 to 131 of SEQ ID NO:94. A number of NAD-dependent 2-hydroxyacid dehydrogenases, with at least some specificity for the D-isomer of their substrate, have been shown to be functionally and structurally related. Clone bf157_16 appears to encode a novel protein which may have NAD-dependent 2-hydroxyacid dehydrogenase activity.

bf157_16 protein was expressed in a COS cell expression system, and an expressed protein band of approximately 16 kDa was detected in conditioned medium and membrane fractions using SDS polyacrylamide gel electrophoresis.

Clone "bk343_2"

A polynucleotide of the present invention has been identified as clone "bk343_2". bk343_2 was isolated from a human adult retina cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. bk343_2 is a full-length clone, including the entire coding sequence of a secreted protein (also referred to herein as "bk343_2 protein").

The nucleotide sequence of bk343 2 as presently determined is reported in SEQ ID NO:95, and includes a poly(A) tail. What applicants presently believe to be the proper reading frame and the predicted amino acid sequence of the bk343_2 protein corresponding to the foregoing nucleotide sequence is reported in SEQ ID NO:96.

Another possible reading frame within the bk343_2 clone extends from nucleotide 45 to nucleotide 188 of SEQ ID NO:95, and encodes the amino acid sequence reported in SEQ ID NO:239. Amino acids 5 to 17 of SEQ ID NO:239 are a predicted leader/signal sequence, with the predicted mature amino acid sequence beginning at amino acid 18. Due to the hydrophobic nature of the predicted leader/signal sequence, it is likely to act as a transmembrane domain should the predicted leader/signal sequence not be separated from the remainder of the protein of SEQ ID NO:239.

The EcoRI/NotI restriction fragment obtainable from the deposit containing clone bk343_2 should be approximately 1600 bp.

The nucleotide sequence disclosed herein for bk343_2 was searched against the GenBank and GeneSeq nucleotide sequence databases using BLASTN/BLASTX and FASTA search protocols. bk343_2 demonstrated at least some similarity with sequences identified as AA156969 (zo51d05.r1 Stratagene endothelial cell 937223 *Homo sapiens* cDNA clone 590409 5'), AA947938 (oe60c08.s1 NCI_CGAP_Lu5 *Homo sapiens* cDNA clone IMAGE:1416014 3', mRNA sequence), N31147 (yx52g05.r1 *Homo sapiens* cDNA clone 265400 5'), N42759 (yy22a09.r1 *Homo sapiens* cDNA clone 271960 5'), N47537 (yy90h10.s1 *Homo sapiens* cDNA clone 280867 3'), R68913 (yi43b04.r1 *Homo sapiens* cDNA clone 141967 5'), T24885 (Human gene signature HUMGS06991; standard; cDNA to mRNA), and T30099 (EST112339 *Homo sapiens* cDNA 5' end similar to None). The predicted amino acid sequence disclosed herein for bk343_2 was searched against the GenPept and GeneSeq amino acid sequence databases using the BLASTX search protocol. The predicted bk343_2 protein demonstrated at least some similarity to sequences identified as Z72508 (F28H7.4 [*Caenorhabditis elegans*]) and Z78417 (C35C5.3 [*Caenorhabditis elegans*]). Based upon sequence similarity, bk343_2 proteins and each similar protein or peptide may share at least some activity. The TopPredII computer program predicts a potential transmembrane domain within the bk343_2 protein sequence centered around amino acid 36 of SEQ ID NO:96.

Clone "cd205_2"

A polynucleotide of the present invention has been identified as clone "cd205_2". cd205_2 was isolated from a human fetal brain cDNA library and was identified as encoding a novel protein on the basis of computer analysis of the amino acid sequence of the encoded protein. cd205_2 is a full-length clone, including the entire coding sequence of a novel protein (also referred to herein as "cd205_2 protein").

The nucleotide sequence of cd205_2 as presently determined is reported in SEQ ID NO:97, and includes a poly(A) tail. What applicants presently believe to be the proper reading frame and the predicted amino acid sequence of the cd205_2 protein corresponding to the foregoing nucleotide sequence is reported in SEQ ID NO:98. Amino acids 92 to 104 of SEQ ID NO:98 are a predicted leader/signal sequence, with the predicted mature amino acid sequence beginning at amino acid 105. Due to the hydrophobic nature of the predicted leader/signal sequence, it is likely to act as a transmembrane domain should the predicted leader/signal sequence not be separated from the remainder of the cd205_2 protein.

Another possible reading frame within the cd205_2 clone extends from nucleotide 59 to nucleotide 478 of SEQ ID NO:97, and encodes the amino acid sequence reported in SEQ ID NO:240. The open reading frames encoding the amino acid sequences of SEQ ID NO:98 and SEQ ID NO:240 could be joined if one or more frame shifts were made in the nucleotide sequence of SEQ ID NO:97.

The EcoRI/NotI restriction fragment obtainable from the deposit containing clone cd205_2 should be approximately 1300 bp.

The nucleotide sequence disclosed herein for cd205_2 was searched against the GenBank and GeneSeq nucleotide sequence databases using BLASTN/BLASTX and FASTA search protocols. cd205_2 demonstrated at least some similarity with sequences identified as AA053543 (zl71f10.r1 Stratagene colon (#937204) *Homo sapiens* cDNA clone 510091 5' similar to gb:M77830 DESMOPLAKIN I AND II (HUMAN)), AC005332 (*Homo sapiens* chromosome 17, clone hRPK.147_L_13, complete sequence), N84944 (J1677F *Homo sapiens* cDNA clone J1677 5' similar to CHROMOSOME 4 (CLONE P4-661) STS4-563), N86274 G7481F Fetal heart, Lambda ZAP Express *Homo sapiens* cDNA clone J7481 5' similar to CHROMOSOME 4 (CLONE P4-661) STS4_563), W68823 (zd37f04.r1 Soares fetal heart NbHH19W *Homo sapiens* cDNA clone 342847 5', mRNA sequence), and Z54387 (H.sapiens CpG island DNA genomic Mse1 fragment, clone 10g3, reverse read cpg10g3.rt1a). Based upon sequence similarity, cd205_2 proteins and each similar protein or peptide may share at least some activity. The TopPredII computer program predicts a potential transmembrane domain within the cd205_2 protein sequence located around amino acid 105 of SEQ ID NO:98.

Clone "cw1292_8"

A polynucleotide of the present invention has been identified as clone "cw1292_8". cw1292_8 was isolated from a human fetal brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. cw1292_8 is a full-length clone, including the entire coding sequence of a secreted protein (also referred to herein as "cw1292_8 protein").

The nucleotide sequence of cw1292_8 as presently determined is reported in SEQ ID NO:99, and includes a poly(A) tail. What applicants presently believe to be the proper reading frame and the predicted amino acid sequence of the cw1292_8 protein corresponding to the foregoing nucleotide sequence is reported in SEQ ID NO:100. Amino acids 18 to 30 of SEQ ID NO:100 are a predicted leader/signal sequence, with the predicted mature amino acid sequence beginning at amino acid 31. Due to the hydrophobic nature of the predicted leader/signal sequence, it is likely to act as a transmembrane domain should the predicted leader/signal sequence not be separated from the remainder of the cw1292_8 protein.

The EcoRI/NotI restriction fragment obtainable from the deposit containing done cw1292_8 should be approximately 1100 bp.

The nucleotide sequence disclosed herein for cw1292_8 was searched against the GenBank and GeneSeq nucleotide sequence databases using BLASTN/BLASTX and FASTA search protocols. cw1292_8 demonstrated at least some similarity with sequences identified as AA017976 (mh46h10.r1 Soares mouse placenta 4NbMP13.5 14.5 *Mus*), AA423855 (zv79c04.s1 Soares total fetus Nb2HF8 9w *Homo sapiens* cDNA clone 759846 3'), AA626784 (ad09f08.s1 Soares NbHFB *Homo sapiens* cDNA clone 877767 3', mRNA sequence), H23387 (ym57f05.r1 *Homo sapiens* cDNA clone 52337 5'), H78534 (yu13d06.r1 *Homo sapiens* cDNA clone 233675 5'), H79021 (yu13d06.s1 *Homo sapiens* cDNA done 233675 3'), R44807 (yg23g06.s1 *Homo sapiens* cDNA clone 33217 3'), T24772 (Human gene signature HUMGS06848; standard; cDNA to mRNA), T97424 (ye53hO8.r1 *Homo sapiens* cDNA clone 121503.5'), and Z44597 (*H. sapiens* partial cDNA sequence; clone c-25a05).

The predicted amino acid sequence disclosed herein for cw1292_8 was searched against the GenPept and GeneSeq amino acid sequence databases using the BLASTX search protocol. The predicted cw1292 8 protein demonstrated at least some similarity to the sequence identified as M33521 (HLA-B-associated transcript 3 (BAT3) [Homo]). Based upon sequence similarity, cw1292_8 proteins and each similar protein or peptide may share at least some activity.

Clone "cw1475_2"

A polynucleotide of the present invention has been identified as clone "cw1475_2". cw1475_2 was isolated from a human fetal brain cDNA library and was identified as encoding a novel protein on the basis of computer analysis of the amino acid sequence of the encoded protein. cw1475_2 is a full-length clone, including the entire coding sequence of a novel protein (also referred to herein as "cw1475 2 protein").

The nucleotide sequence of cw1475_2 as presently determined is reported in SEQ ID NO:101, and includes a poly(A) tail. What applicants presently believe to be the proper reading frame and the predicted amino acid sequence of the cw1475_2 protein corresponding to the foregoing nucleotide sequence is reported in SEQ ID NO:102.

The EcoRI/NotI restriction fragment obtainable from the deposit containing clone cw1475_2 should be approximately 2800 bp.

The nucleotide sequence disclosed herein for cw1475_2 was searched against the GenBank and GeneSeq nucleotide sequence databases using BLASTN/BLASTX and FASTA search protocols. cw1475_2 demonstrated at least some similarity with sequences identified as AA527429 (ng41a10.s1 NCI_CGAP_Co3 *Homo sapiens* cDNA clone IMAGE:937338, mRNA sequence), AD000092 (*Homo sapiens* DNA from chromosome 19p13.2 cosmids R31240, R30272 and R28549 containing the EKLF, GCDH, CRTC, and RAD23A genes, genomic sequence), H98508 (yv90f08.r1 *Homo sapiens* cDNA clone 250023 5'), N25554 (yx76f08.s1 *Homo sapiens* cDNA clone 267687 3'), N50970 (yy94b06.s1 *Homo sapiens* cDNA clone 281171 3'), N81188 (yw36g06.r1 *Homo sapiens* cDNA clone 254362 5'), R32569 (yh54g03.r1 *Homo sapiens* cDNA clone 133588 5'), R81017 (yi94g02.r1 *Homo sapiens* cDNA clone 146930 5' similar to contains Alu repetitive element;contains MER30 repetitive element), T06537 (EST04426 *Homo sapiens* cDNA clone [FBDU83 similar to EST containing Alu repeat), T31594 (Probe (BLUR11) for Alu repeat sequence), and W30895 (zb78e12.r1 Soares senescent fibroblasts NbHSF *Homo*). Based upon sequence similarity, cw1475_2 proteins and each similar protein or peptide may share at least some activity. The nucleotide sequence of cw1475_2 indicates that it may contain noe or more of the following repetitive elements: Alu, SVA.

Clone “dd428_4”

A polynucleotide of the present invention has been identified as clone “dd428_4”. dd428_4 was isolated from a human adult testes cDNA library and was identified as encoding a novel protein on the basis of computer analysis of the amino acid sequence of the encoded protein. dd428_4 is a full-length clone, including the entire coding sequence of a novel protein (also referred to herein as “dd428_4 protein”).

The nucleotide sequence of dd428_4 as presently determined is reported in SEQ ID NO:103, and includes a poly(A) tail. What applicants presently believe to be the proper reading frame and the predicted amino acid sequence of the dd428_4 protein corresponding to the foregoing nucleotide sequence is reported in SEQ ID NO:104.

The EcoRI/NotI restriction fragment obtainable from the deposit containing clone dd428_4 should be approximately 1500 bp.

The nucleotide sequence disclosed herein for dd428_4 was searched against the GenBank and GeneSeq nucleotide sequence databases using BLASTN/BLASTX and FASTA search protocols. dd428_4 demonstrated at least some similarity with sequences identified as AC000057 (Human BAC clone RG067M09 from 7q21-7q22; HTGS phase 3, complete sequence), AC005500 (complete sequence), L27428 (Human L1 putative reverse transcriptase gene insertion in hamster, 3' end), T86176 (yd78c11.s1 *Homo sapiens* cDNA clone 114356 3' similar to gb L25879 EPOXIDE HYDROLASE (HUMAN); contains L1 repetitive element), X61307 (*Staphylococcus aureus* spa gene for protein A), and Z69647 (Human DNA sequence from cosmid E118G4, maps to 10cen and 11q13-q14). Based upon sequence similarity, dd428_4 proteins and each similar protein or peptide may share at least some activity. The nucleotide sequence of dd428_4 indicates that it may contain L1 repeat sequences.

Clone “dh1073_12”

A polynucleotide of the present invention has been identified as clone “dh1073_12”. dh1073_12 was isolated from a human fetal brain cDNA library and was identified as encoding a novel protein on the basis of computer analysis of the amino acid sequence of the encoded protein. dh1073_12 is a full-length clone, including the entire coding sequence of a novel-protein (also referred to herein as “dh1073_12 protein”).

The nucleotide sequence of dh1073_12 as presently determined is reported in SEQ ID NO:105, and includes a poly(A) tail. What applicants presently believe to be the proper reading frame and the predicted amino acid sequence of the dh1073_12 protein corresponding to the foregoing nucleotide sequence is reported in SEQ ID NO:106.

The EcoRI/NotI restriction fragment obtainable from the deposit containing clone dh1073_12 should be approximately 2400 bp.

The nucleotide sequence disclosed herein for dh1073_12 was searched against the GenBank and GeneSeq nucleotide sequence databases using BLASTN/BLASTX and FASTA search protocols. dh1073_12 demonstrated at least some similarity with sequences identified as AA257983 (zs35h03.s1 NCI_CGAP_GCB1 *Homo sapiens* cDNA clone IMAGE 687221 3' similar to TR G666014 G666014 SA SA GENE PRODUCT, COMPLETE CDS PRECURSOR; mRNA sequence), AA526325 (ni59g06.s1 NCI_CGAP_Ov2 *Homo sapiens* cDNA clone 981178 similar to contains Alu repetitive element), AF001549 (Human Chromosome 16 BAC clone CIT987SK-A-270G1, complete sequence), N57823 (yv59e04.s1 Soares fetal liver spleen 1NFLS *Homo sapiens* cDNA clone 247038 3'), and N68408 (za13c05.s1 *Homo sapiens* cDNA clone 292424 3'). The predicted amino acid sequence disclosed herein for cw1292_8 was searched against the GenPept and GeneSeq amino acid sequence databases using the BLASTX search protocol. The predicted dh1073_12 protein demonstrated at least some similarity to the sequence identified as AC003034 (Gene with similarity to rat kidney-specific (KS) gene [*Homo sapiens*]). Based upon sequence similarity, dh1073_12 proteins and each similar protein or peptide may share at least some activity. The nucleotide sequence of dh1073_12 indicates that it may contain an Alu repetitive element.

Clone “dw78_1”

A polynucleotide of the present invention has been identified as clone “dw78_1”. dw78_1 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. dw78_1 is a full-length clone, including the entire coding sequence of a secreted protein (also referred to herein as “dw78_1 protein”).

The nucleotide sequence of dw78_1 as presently determined is reported in SEQ ID NO:107, and includes a poly(A) tail.-What applicants presently believe to be the proper reading frame and the predicted amino acid sequence of the dw78_1 protein corresponding to the foregoing nucleotide sequence is reported in SEQ ID NO:108.

The EcoRI/NotI restriction fragment obtainable from the deposit containing clone dw78_1 should be approximately 1400 bp.

The nucleotide sequence disclosed herein for dw78_1 was searched against the GenBank and GeneSeq nucleotide sequence databases using BLASTN/BLASTX and FASTA search protocols. dw78_1 demonstrated at least some similarity with sequences identified as AA807622 (nv65g11.s1 NCI_CGAP_GCB1 *Homo sapiens* cDNA clone IMAGE 1234724, mRNA sequence), AF086326 (*Homo sapiens* full length insert cDNA clone ZD54A02), D37980 (*Dictyostelium discoidium* DDCOF1 gene for cofilin, complete cds (exon1-2)), 1126207 (yl53c04.r1 *Homo sapiens* cDNA clone 161958 5'), N72717 (za47h03.s1 *Homo sapiens* cDNA clone 295733 3' similar to contains Alu repetitive element;contains element L1 repetitive element), T23963 (Human gene signature HUMGS05917; standard; cDNA to mRNA), U14567 (***ALU WARNING Human Alu-J subfamily consensus sequence), U43572 (Human alpha-N-acetylglucosaminidase (NAGLU) gene, complete cds), W42787 (zc25a04.s1 Soares senescent fibroblasts NbHSF *Homo sapiens* cDNA clone 323310 3'), and W73472 (zd54a02.s1 Soares fetal heart NbHH19W *Homo sapiens* cDNA clone 344426 3', mRNA sequence). The predicted amino acid sequence disclosed herein for dw78_1 was searched against the GenPept and GeneSeq amino acid sequence databases using the BLASTX search protocol. The predicted dw78_1 protein demonstrated at least some similarity to the sequence identified as D32202 (alpha 1C adrenergic receptor isoform 2 *[Homo sapiens*]). Based upon sequence similarity, dw78_1 proteins and each similar protein or peptide may share at least some activity. The TopPredII computer program predicts two potential transmembrane domains within the dw78_1 protein sequence, one centered around amino acid 45 and another around amino acid 93 of SEQ ID NO:108. The nucleotide sequence of dw78_1 indicates that it may contain an Alu repetitive element.

Clone "fh116_11"

A polynucleotide of the present invention has been identified as clone "fh116_11". fh116_11 was isolated from a human fetal brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded-protein. fh116_11 is a full-length clone, including the entire coding sequence of a secreted protein (also referred to herein as "fh116_11 protein").

The nucleotide sequence of fh116_11 as presently determined is reported in SEQ ID NO:109, and includes a poly(A) tail. What applicants presently believe to be the proper reading frame and the predicted amino acid sequence of the fh116_11 protein corresponding to the foregoing nucleotide sequence is reported in SEQ ID NO:110.

The EcoRI/NotI restriction fragment obtainable from the deposit containing done fh116_11 should be approximately 1200 bp.

The nucleotide sequence disclosed herein for fh116_11 was searched against the GenBank and GeneSeq nucleotide sequence databases using BLASTN/BLASTX and FASTA search protocols. fh116_11 demonstrated at least some similarity with sequences identified as AA054185 (zf5c06.r1 Soares retina N2b4HR *Homo sapiens* cDNA clone 380458 5'), AA057975 (mj57b02.r1 Soares mouse embryo N-bME13.5 14.5 *Mus musculus* cDNA clone 480171 5' similar to WP:F57A8.2 CE05983), AA128902 (zn90a05.s1 Stratagene lung carcinoma 937218 *Homo sapiens* cDNA clone 565424 3'), AA426021 (zw49h09.s1 Soares total fetus Nb2HF8 9w *Homo sapiens* cDNA clone 773441 3'), AA505926 (nh98g03.s1 NCI_CGAP_Br2 *Homo sapiens* cDNA clone 966580), AI079540 (oz04e08.x1 Soares_fetal_liver_spleen_1NFLS_S1 *Homo sapiens* cDNA clone IMAGE:1674374 3' similar to WP:F57A8.2 CE05983; mRNA sequence), H68794 (yr91h09.s1 *Homo sapiens* cDNA clone 212705 3'), H86659 (yt02c04.r1 *Homo sapiens* cDNA clone 223110 5'), T24554 (Human gene signature HUMGS06604; standard; cDNA to mRNA), U96490 (*Rattus norvegicus* liver mRNA, complete cds), and WO0635 (yy71d12.r1 *Homo sapiens* cDNA clone 278999 5' similar to contains element PTR5 repetitive element). The predicted amino acid sequence disclosed herein for fh116_11 was searched against the GenPept and GeneSeq amino acid sequence databases using the BLASTX search protocol. The predicted fh116_11 protein demonstrated at least some similarity to sequences identified as AF004876 (54TMp [*Homo sapiens*]), U96490 (unknown [*Rattus norvegicus*]), and Z70781 (F57A8.2 [*Caenorhabditis elegans*]). Based upon sequence similarity, fh116_11 proteins and each similar protein or peptide may share at least some activity. The TopPredII computer program predicts five potential transmembrane domains within the fh116_11 protein sequence, centered around amino acids 35 to 49, 136, 171, 215, and 270 of SEQ ID NO:110, respectively.

fh116_11 protein was expressed in a COS cell expression system, and an expressed protein band of approximately 28 kDa was detected in membrane fractions using SDS polyacrylamide gel electrophoresis.

Clone "fy356_14"

A polynucleotide of the present invention has been identified as clone "fy356_14". fy356_14 was isolated from a human fetal placenta cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. fy356_14 is a full-length clone, including the entire coding sequence of a secreted protein (also referred to herein as "fy356_14 protein").

The nucleotide sequence of fy356_14 as presently determined is reported in SEQ ID NO:111, and includes a poly(A) tail. What applicants presently believe to be the proper reading frame and the predicted amino acid sequence of the fy356_14 protein corresponding to the foregoing nucleotide sequence is reported in SEQ ID NO:112. Amino acids 385 to 397 of SEQ ID NO:112 are a possible leader/signal sequence, with the predicted mature amino acid sequence beginning at amino acid 398. Due to the hydrophobic nature of this possible leader/signal sequence, it is likely to act as a transmembrane domain should the predicted leader/signal sequence not be separated from the remainder of the fy356_14 protein.

The EcoRI/NotI restriction fragment obtainable from the deposit containing done fy356_14 should be approximately 3700 bp.

The nucleotide sequence disclosed herein for fy356_14 was searched against the GenBank and GeneSeq nucleotide sequence databases using BLASTN/BLASTX and FASTA search protocols. fy356_14 demonstrated at least some similarity with sequences identified as AA017639 (ze38c05.r1 Soares retina N2b4R *Homo sapiens* cDNA clone 361256 5' similar to PIR S55385 S55385 PEA-15 protein—mouse), AA181529 (zp51f07.s1 Stratagene HeLa cell s3 937216 *Homo sapiens* cDNA clone 612997 3'), AA687129 (nv63d03.s1 NCI_CGAP_GCB1 *Homo sapiens* cDNA clone IMAGE 1234469), AA811277 (ob68e06.s1 NCI_CGAP_GCB1 *Homo sapiens* cDNA clone IMAGE: 1336546, mRNA sequence), N53623 (yz04e01.r1 *Homo sapiens* cDNA clone 282072 5'), T25935 (Human gene signature HUMGS08167; standard; cDNA to mRNA), T24538 (Human gene signature HUMGS06585; standard; cDNA to mRNA), and X86809 (H.sapiens mRNA for major astrocytic phosphoprotein PEA-15). The predicted amino acid sequence disclosed herein for fy356_14 was searched against the GenPept and GeneSeq amino acid sequence databases using the BLASTX search protocol. The predicted fy356_14 protein demonstrated at least some similarity to the sequence identified as X86809 (PEA-15 gene product [*Homo sapiens*]). Based upon sequence similarity, fy356_14 proteins and each similar protein or peptide may share at least some activity. The TopPredII computer program predicts a potential transmembrane domain within the fy356_14 protein sequence, centered around amino acid 398 of SEQ ID NO:112.

Clone "iw66_1"

A polynucleotide of the present invention has been identified as clone "iw66_1". iw66_1 was isolated from a human adult retina (WER1-Rb1 retinoblastoma line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. iw66_1 is a full-length clone, including the entire coding sequence of a secreted protein (also referred to herein as "iw66_1 protein").

The nucleotide sequence of iw66_1 as presently determined is reported in SEQ ID NO:113, and includes a poly(A) tail. What applicants presently believe to be the proper reading frame and the predicted amino acid sequence of the iw66_1 protein corresponding to the foregoing nucleotide sequence is reported in SEQ ID NO:114.

Amino acids 9 to 21 of SEQ ID NO:114 are a predicted leader/signal sequence, with the predicted mature amino acid sequence beginning at amino acid 22. Due to the hydrophobic nature of the predicted leader/signal sequence, it is likely to act as a transmembrane domain should the predicted leader/signal sequence not be separated from the remainder of the iw66_1 protein.

The EcoRI/NotI restriction fragment obtainable from the deposit containing done iw66_1 should be approximately 1450 bp.

The nucleotide sequence disclosed herein for iw66_1 was searched against the GenBank and GeneSeq nucleotide sequence databases using BLASTN/BLASTX and FASTA search protocols. iw66_1 demonstrated at least some similarity with sequences identified as AA216917 (mv75h11.r1 Soares mouse 3NME12 5 *Mus musculus* cDNA done 660933 5'), AA339406 (EST44484 Fetal brain I *Homo sapiens* cDNA 5' end), AI275861 (ql68b12.x1 Soares_NhHMPu_S1 *Homo sapiens* cDNA clone IMAGE:1877471 3', mRNA sequence), Q61257 (Human brain Expressed Sequence Tag EST01278; standard; DNA), R89651 (ym97c08.r1 *Homo sapiens* cDNA clone 166862 5'), W53584 (md55f06.r1 Soares mouse embryo NbME13.5 14.5 *Mus musculus* cDNA clone 372323 5'), and Z60886 (*H.sapiens* CpG island DNA genomic Mse1 fragment, clone 38a8, reverse read cpg38a8.rt1a). The predicted amino acid sequence disclosed herein for iw66_1 was searched against the GenPept and GeneSeq amino acid sequence databases using the BLASTX search protocol. The predicted iw66_1 protein demonstrated at least some similarity to sequences identified as AF004874 (latent TGF-beta binding protein-2 *[Mus musculus*]), L29029 (amino acid feature Rod protein domain, aa 266 468; amino acid feature globular protein domain, aa 32 . . . 265 *[Chlamydomonas reinhardtii*]), R27150 (PspA fragment), and R79478 (Mouse LTBP-2). Based upon sequence similarity, iw66_1 proteins and each similar protein or peptide may share at least some activity. The TopPredII computer program predicts three additional potential transmembrane domains within the iw66_1 protein sequence, centered around amino acids 45, 74, and 158 of SEQ ID NO:114, respectively. The nucleotide sequence of iw66_1 indicates that it may contain one or more of the following repetitive elements: MIR.

Clone "kh13_4"

A polynucleotide of the present invention has been identified as clone "kh13_4". kh13_4 was isolated from a human adult testes cDNA library and was identified as encoding a novel protein on the basis of computer analysis of the amino acid sequence of the encoded protein. kh13_4 is a full-length clone, including the entire coding sequence of a novel protein (also referred to herein as "kh13_4 protein").

The nucleotide sequence of kh13_4 as presently determined is reported in SEQ ID NO:115, and includes a poly(A) tail. What applicants presently believe to be the proper reading frame and the predicted amino acid sequence of the kh13_4 protein corresponding to the foregoing nucleotide sequence is reported in SEQ ID NO:116.

The EcoRI/NotI restriction fragment obtainable from the deposit containing clone kh13_4 should be approximately 950 bp.

The nucleotide sequence disclosed herein for kh13_4 was searched against the GenBank and GeneSeq nucleotide sequence databases using BLASTN/BLASTX and FASTA search protocols. kh13_4 demonstrated at least some similarity with sequences identified as AA435981 (zu01f08.s1 Soares testis NHT *Homo sapiens* cDNA clone 730599 3'), AA436078 (zu01f08.r1 Soares testis NHT *Homo sapiens* cDNA clone 730599 5'), AA778636 (af87c04.s1 Soares testis NHT *Homo sapiens* cDNA clone 1048998 3' similar to gb:M94856 PSORIASIS-ASSOCIATED FATTY ACID BINDING PROTEIN HOMOLOG (HUMAN); mRNA sequence), M94856 (Human fatty acid binding protein homologue (PA-FABP) mRNA, complete cds), and Q66842 (Melanogenic inhibitor; standard; DNA). The predicted amino acid sequence disclosed herein for kh13_4 was searched against the GenPept and GeneSeq amino acid sequence databases using the BLASTX search protocol. The predicted kh13_4 protein demonstrated at least some similarity to sequences identified as M94856 (fatty acid binding protein homologue [*Homo sapiens*]) and R55866 (Melanogeric inhibitor). Fatty acid binding protein homologue (M94856) is described as "a novel keratinocyte protein (psoriasis-associated fatty acid-binding protein [PA-FABP]) that is highly up-regulated in psoriatic skin and that shares similarity to fatty acid-binding proteins." Based upon sequence similarity, kh13_4 proteins and each similar protein or peptide may share at least some activity.

Clone "ko258_4"

A polynucleotide of the present invention has been identified as clone "ko258_4". ko258_4 was isolated from a human adult uterus cDNA library and was identified as encoding a novel protein on the basis of computer analysis of the amino acid sequence of the encoded protein. ko258_4 is a full-length clone, including the entire coding sequence of a novel protein (also referred to herein as "ko258_4 protein").

The nucleotide sequence of ko258_4 as presently determined is reported in SEQ ID NO:117, and includes a poly(A) tail. What applicants presently believe to be the proper reading frame and the predicted amino acid sequence of the ko258_4 protein corresponding to the foregoing nucleotide sequence is reported in SEQ ID NO:118.

The EcoRI/NotI restriction fragment obtainable from the deposit containing clone ko258_4 should be approximately 2500 bp.

The nucleotide sequence disclosed herein for ko258_4 was searched against the GenBank and GeneSeq nucleotide sequence databases using BLASTN/BLASTX and FASTA search protocols. ko258_4 demonstrated at least some similarity with sequences identified as AC002401 (*SEQUENCING IN PROGRESS* *Homo sapiens* chromosome 17, clone RPC875H18; HTGS phase 1, 4 unordered pieces), AC00240.1 (*Homo sapiens* chromosome 17, clone RPC875H18, complete sequence), C15329 (Human fetal brain cDNA 5'-end GEN-133H10, mRNA sequence), AF035306 (*Homo sapiens* clone 23771 mRNA sequence), and R28382 (IMAGE 3p clone). Based upon sequence similarity, ko258_4 proteins and each similar protein or peptide may share at least some activity. The TopPredII computer program predicts a potential transmembrane domain within the ko258_4 protein sequence, centered around amino acid 28 of SEQ ID NO:118.

Clone "kv10_8"

A polynucleotide of the present invention has been identified as clone "kv10_8". kv10_8 was isolated from a human adult retina cDNA library using methods which are selective for cDNAs encoding secreted proteins (see U.S.

Pat. No. 5,536,637), or was identified as encoding a secreted or transmembrane protein on the basis of computer analysis of the amino acid sequence of the encoded protein. kv10_8 is a full-length clone, including the entire coding sequence of a secreted protein (also referred to herein as "kv10_8 protein").

The nucleotide sequence of kv108 as presently determined is reported in SEQ ID NO:119, and includes a poly(A) tail. What applicants presently believe to be the proper reading frame and the predicted amino acid sequence of the kv10_8 protein corresponding to the foregoing nucleotide sequence is reported in SEQ ID NO:120.

The EcoRI/NotI restriction fragment obtainable from the deposit containing clone kv10_8 should be approximately 4300 bp.

The nucleotide sequence disclosed herein for kv10_8 was searched against the GenBank and GeneSeq nucleotide sequence databases using BLASTN/BLASTX and FASTA search protocols. kv10_8 demonstrated at least some similarity with sequences identified as AA418842 (zw01e12.s1 Soares NhHMu S1 *Homo sapiens* cDNA clone 768046 3'), AC004228 (*SEQUENCING IN PROGRESS* *Homo sapiens* Chromosome 11q12 pac pDJ519o3; HTGS phase 1, 18 unordered pieces), AF052108 (*Homo sapiens* clone 23687 mRNA sequence), R00761 (ye78b11.s1 *Homo sapiens* cDNA clone 123837 3'), T83434 (yd46b04.r1 *Homo sapiens* cDNA clone 111247 5'), T84080 (yd46b04.s1 *Homo sapiens* cDNA clone 111247 3'), and U00594 (*Mustela vison* unknown mRNA down regulated by TGF-beta, partial sequence). Based upon sequence similarity, kv10_8 proteins and each similar protein or peptide may share at least some activity. The TopPredII computer program predicts a potential transmembrane domain within the kv10_8 protein sequence, centered around amino acids 35 to 45 of SEQ ID NO:120. The nucleotide sequence of kv10_8 indicates that it may contain one or more of the following repetitive elements: Alu, SVA.

Clone "LL89_3"

A polynucleotide of the present invention has been identified as clone "LL89_3". LL89_3 was isolated from a human adult thyroid cDNA library and was identified as encoding a novel protein on the basis of computer analysis of the amino acid sequence of the encoded protein. LL89_3 is a full-length clone, including the entire coding sequence of a novel protein (also referred to herein as "LL89_3 protein").

The nucleotide sequence of LL89_3 as presently determined is reported in SEQ ID NO:121, and includes a poly(A) tail. What applicants presently believe to be the proper reading frame and the predicted amino acid sequence of the LL89_3 protein corresponding to the foregoing nucleotide sequence is reported in SEQ ID NO:122.

The EcoRI/NotI restriction fragment obtainable from the deposit containing clone LL89_3 should be approximately 900 bp.

The nucleotide sequence disclosed herein for LL89_3 was searched against the GenBank and GeneSeq nucleotide sequence databases using BLASTN/BLASTX and FASTA search protocols. LL89_3 demonstrated at least some similarity with sequences identified as AL031010 (Human DNA sequence * SEQUENCING IN PROGRESS * from clone 422F24, complete sequence), H78002 (yu82h09.r1 *Homo sapiens* cDNA clone 240353 5'), and W90018 (zh72c08.s1 Soares fetal liver spleen 1NFLS S1 *Homo sapiens* cDNA clone 417614 3'). Based upon sequence similarity, LL89_3 proteins and each similar protein or peptide may share at least some activity.

Clone "mc300_1"

A polynucleotide of the present invention has been identified as clone "mc300_1". mc300_1 was isolated from a human adult thyroid cDNA library and was identified as encoding a novel protein on the basis of computer analysis of the amino acid sequence of the encoded protein. mc300_1 is a full-length clone, including the entire coding sequence of a novel protein (also referred to herein as "mc300_1 protein").

The nucleotide sequence of mc300_1 as presently determined is reported in SEQ ID NO:123, and includes a poly(A) tail. What applicants presently believe to be the proper reading frame and the predicted amino acid sequence of the mc300_1 protein corresponding to the foregoing nucleotide sequence is reported in SEQ ID NO:124.

The EcoRI/NotI restriction fragment obtainable from the deposit containing clone mc300_1 should be approximately 2600 bp.

The nucleotide sequence disclosed herein for mc300_1 was searched against the GenBank and GeneSeq nucleotide sequence databases using BLASTN/BLASTX and FASTA search protocols. mc300_1 demonstrated at least some similarity with sequences identified as AA142942 (IMAGE 3p clone), AA315222 (EST187017 Colon carcinoma (HCC) cell line *Homo sapiens* cDNA 5' end), AA142942 (zl43c04.s1 Soares pregnant uterus NbHPU *Homo sapiens* cDNA clone 504678 3'), AI246503 (qn64a06.x1 NCI_CGAP_HN4 *Homo sapiens* cDNA clone IMAGE:1902994 3', mRNA sequence), D61461 (Human fetal brain cDNA 5'-end GEN-404B08), D79662 (Human aorta cDNA 5'-end GEN-300D05, mRNA sequence), H93575 (yv14h11.s1 *Homo sapiens* cDNA clone 242757 3'), T25928 (Human gene signature HUMGS08160; standard; cDNA to mRNA), and W93059 (zd93h06.s1 Soares fetal heart NbHH19W *Homo sapiens* cDNA clone 357083 3'). Based upon sequence similarity, mc300_1 proteins and each similar protein or peptide may share at least some activity. The nucleotide sequence of mc300_1 indicates that it may contain one or more Alu repetitive elements.

Clone "ml227_1"

A polynucleotide of the present invention has been identified as clone "ml227_1". ml227_1 was isolated from a human adult brain (caudate nucleus) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. ml227_1 is a full-length clone, including the entire coding sequence of a secreted protein (also referred to herein as "ml227_1 protein").

The nucleotide sequence of ml227_1 as presently determined is reported in SEQ ID NO:125, and includes a poly(A) tail. What applicants presently believe to be the proper reading frame and the predicted amino acid sequence of the ml227_1 protein corresponding to the foregoing nucleotide sequence is reported in SEQ ID NO:126.

The EcoRI/NotI restriction fragment obtainable from the deposit containing clone ml227_1 should be approximately 2700 bp.

The nucleotide sequence disclosed herein for ml227_1 was searched against the GenBank and GeneSeq nucleotide sequence databases using BLASTN/BLASTX and FASTA search protocols. ml227_1 demonstrated at least some similarity with sequences identified as AA857826 (oe88e05.s1 NCI_CGAP_Co12 *Homo sapiens* cDNA clone IMAGE:1418720 3', mRNA sequence), F18464 (*H.sapiens* EST sequence (017-T4-16) from skeletal muscle), H30845

(yo78d11.r1 *Homo sapiens* cDNA clone 184053 5'), T06839 (EST04728 *Homo sapiens* cDNA clone HFBDZ66), T19759 (Human gene signature HUMGS00834), T26021 (Human gene signature HUMGS08257; standard; cDNA to mRNA), and Z69043 (*H.sapiens* mRNA translocon-associated protein delta subunit precursor). The predicted amino acid sequence disclosed herein for ml227_1 was searched against the GenPept and GeneSeq amino acid sequence databases using the BLASTX search protocol. The predicted ml227_1 protein demonstrated at least some similarity to the sequence identified as Z69664 (K04D7.5 *[Caenorhabditis elegans*]). Based upon sequence similarity, ml227_1 proteins and each similar protein or peptide may share at least some activity. The TopPredII computer program predicts six potential transmembrane domains within the ml227_1 protein sequence, centered around amino acids 465, 510, 560, 572, 595, and 615 of SEQ ID NO:126, respectively.

Clone "mm367_6"

A polynucleotide of the present invention has been identified as clone "mm367_6". mm367_6 was isolated from a human adult retina (WER1-Rb1 retinoblastoma line) cDNA library and was identified as encoding a protein. mm367_6 is a full-length clone, including the entire coding sequence of a protein (also referred to herein as "mm367_6 protein").

The nucleotide sequence of mm367_6 as presently determined is reported in SEQ ID NO:127, and includes a poly(A) tail. What applicants presently believe to be the proper reading frame and the predicted amino acid sequence of the mm367_6 protein corresponding to the foregoing nucleotide sequence is reported in SEQ ID NO:128.

The EcoRI/NotI restriction fragment obtainable from the deposit containing clone mm367_6 should be approximately 2600 bp.

The nucleotide sequence disclosed herein for mm367_6 was searched against the GenBank and GeneSeq nucleotide sequence databases using BLASTN/BLASTX and FASTA search protocols. mm367_6 demonstrated at least some similarity with sequences identified as AA114127 (zn65fO2.r1 Stratagene HeLa cell s3 937216 *Homo sapiens* cDNA clone 563067 5'), AA127284 (zn91c12.r1 Stratagene lung carcinoma 937218 *Homo sapiens* cDNA clone 565558 5'), AA173842 (zp30d01.r1 Stratagene neuroepithelium (#937231) *Homo sapiens* cDNA clone 610945 5'), AF000364 (*Homo sapiens* heterogeneous nuclear ribonucleoprotein R mRNA, complete CDs), N31934 (yy22d10.s1 *Homo sapiens* cDNA clone 271987 3'), T24354 (Human gene signature HUMGS06385; standard; cDNA to mRNA), U48271 (*Dictyostelium discoideum* UbpA deubiquitinase mRNA, complete CDs), W16579 (zb13g11.r1 Soares fetal lung NbHL19W *Homo sapiens* cDNA clone 301988 5'), and W72461 (zd67f06.s1 Soares fetal heart NbHH19W *Homo sapiens* cDNA clone 345731 3'). The predicted amino acid sequence disclosed herein for mm367_6 was searched against the GenPept and GeneSeq amino acid sequence databases using the BLASTX search protocol. The predicted mm367_6 protein demonstrated at least some similarity to sequences identified as AF000364 (heterogeneous nuclear ribonucleoprotein R [*Homo sapiens*]) and W26553 (Human heterogeneous nuclear ribonucleoprotein (hnRNP) A2). Based upon sequence similarity, mm367_6 proteins and each similar protein or peptide may share at least some activity.

mm367_6 protein was expressed in a COS cell expression system, and an expressed protein band of approximately 79 kDa was detected in membrane fractions using SDS polyacrylamide gel electrophoresis.

Clone "mt124_3"

A polynucleotide of the present invention has been identified as clone "mt124_3". mt124_3 was isolated from a human adult testes cDNA library and was identified as encoding a novel protein on the basis of computer analysis of the amino acid sequence of the encoded protein. mt124_3 is a full-length clone, including the entire coding sequence of a novel protein (also referred to herein as "mt124_3 protein").

The nucleotide sequence of mt124_3 as presently determined is reported in SEQ ID NO:129, and includes a poly(A) tail What applicants presently believe to be the proper reading frame and the predicted amino acid sequence of the mt124_3 protein corresponding to the foregoing nucleotide sequence is reported in SEQ ID NO:130.

The EcoRI/NotI restriction fragment obtainable from the deposit containing clone mt124_3 should be approximately 1100 bp.

The nucleotide sequence disclosed herein for mt124_3 was searched against the GenBank and GeneSeq nucleotide sequence databases using BLASTN/BLASTX and FASTA search protocols. mt124_3 demonstrated at least some similarity with sequences identified as AA435386 (ve15h01.r1 Soares mouse NbMH *Mus musculus* cDNA clone 818257 5' similar to TR:E198756 E198756 PUTATIVE ORF), AI185116 (qe51g07.x1 Soares_fetal_lung_NbHL19W *Homo sapiens* cDNA clone IMAGE 1742556 3' similar to TR Q92564 Q92564 MYELOBLAST KIAA0276; mRNA sequence), C03847 (Human Heart cDNA, clone 3NHC2256), N74186 (za76h03.s1 *Homo sapiens* cDNA clone 298517-3'), T24234 (Human gene signature HUMGS06248; standard; cDNA to mRNA), W87997 (mf65b06.r1 Soares mouse embryo NbME13.5 14.5 *Mus musculus* cDNA clone 419123 5'), and Z86062 (Human DNA sequence from PAC 121G13 on chromosome 6 contains flow sorted chromosome 6 HindIII fragment ESTs, polymorphic CA repeat, CpG island, CpG island genomic fragments). The predicted amino acid sequence disclosed herein for mt124_3 was searched against the GenPept and GeneSeq amino acid sequence databases using the BLASTX search protocol. The predicted mt124_3 protein demonstrated at least some similarity to sequences identified as AL024499 (H38K22.2 *[Caenorhabditis elegans*]) and D87466 (Similar to *S.cerevisiae* hypothetical protein L3111 (S59316) [*Homo sapiens*]). Based upon sequence similarity, mt124_3 proteins and each similar protein or peptide may share at least some activity.

Clone "nf56_3"

A polynucleotide of the present invention has been identified as clone "nf56_3". nf56_3 was isolated from a human adult brain (substantia nigra) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. nf56_3 is a full-length clone, including the entire coding sequence of a secreted protein (also referred to herein as "nf56_3 protein").

The nucleotide sequence of nf56_3 as presently determined is reported in SEQ ID NO:131, and includes a poly(A) tail. What applicants presently believe to be the proper reading frame and the predicted amino acid sequence of the nf56_3 protein corresponding to the foregoing nucleotide sequence is reported in SEQ ID NO:132. Amino acids 3 to 15 of SEQ ID NO:132 are a predicted leader/signal sequence, with the predicted mature amino acid sequence beginning at amino acid 16. Due to the hydrophobic nature of the predicted leader/signal sequence, it is likely to act as a transmembrane domain should the predicted leader/signal sequence not be separated from the remainder of the nf56_3 protein.

The EcoRI/NotI restriction fragment obtainable from the deposit containing clone nf56_3 should be approximately 5000 bp.

The nucleotide sequence disclosed herein for nf56_3 was searched against the GenBank and GeneSeq nucleotide sequence databases using BLASTN/BLASTX and FASTA search protocols. nf56_3 demonstrated at least some similarity with sequences identified as H08054 (yl86a09.s1 *Homo sapiens* cDNA clone 44915 3'), Q60495 (Human brain Expressed Sequence Tag EST02500; standard; cDNA), T25509 (Human gene signature HUMGS07678), W34534 (mc58h01.r1 Soares mouse embryo NbME13.5 14.5 *Mus musculus* cDNA clone 352753 5'), and Z64987 (*H.sapiens* CpG island DNA genomic Mse1 fragment, clone 186b1, reverse read cpg186b1.rt1b). The predicted amino acid sequence disclosed herein for nf56_3 was searched against the GenPept and GeneSeq amino acid sequence databases using the BLASTX search protocol. The predicted nf56_3 protein demonstrated at least some similarity to sequences identified as D86983 (similar to *D.melanogaster* peroxidasin (U11052) [*Homo sapiens*]), R25079 (*Drosophila* SLIT protein involved in axon pathway development), and X53959 (slit protein [*Drosophila melanogaster*]). Based upon sequence similarity, nf56_3 proteins and each similar protein or peptide may share at least some activity. The TopPredII computer program predicts two potential transmembrane domains within the nf56_3 protein sequence, one centered around amino acid 514 and another around amino acid 628 of SEQ ID NO:132.

Clone "qy442_2"

A polynucleotide of the present invention has been identified as clone "qy442_2". qy442_2 was isolated from a human adult blood (promyelocytic leukemia HL-60 line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. qy442_2 is a full-length clone, including the entire coding sequence of a secreted protein (also referred to herein as "qy442_2 protein").

The nucleotide sequence of qy442_2 as presently determined is reported in SEQ ID NO:133, and includes a poly(A) tail. What applicants presently believe to be the proper reading frame and the predicted amino acid sequence of the qy442_2 protein corresponding to the foregoing nucleotide sequence is reported in SEQ ID NO:134. Amino acids 3 to 15 of SEQ ID NO:134 are a predicted leader/signal sequence, with the predicted mature amino acid sequence beginning at amino acid 16. Due to the hydrophobic nature of the predicted leader/signal sequence, it is likely to act as a transmembrane domain should the predicted leader/signal sequence not be separated from the remainder of the qy442_2 protein.

The EcoRI/NotI restriction fragment obtainable from the deposit containing clone qy442_2 should be approximately 1800 bp.

The nucleotide sequence disclosed herein for qy442_2 was searched against the GenBank and GeneSeq nucleotide sequence databases using BLASTN/BLASTX and FASTA search protocols. qy442_2 demonstrated at least some similarity with sequences identified as AI081522 (on04e12.x1 NCI_CGAP_Kid3 *Homo sapiens* cDNA clone IMAGE: 1555726 3' similar to contains Alu repetitive element; mRNA sequence) and AA449854 (zx37a06.r1 Soares total fetus Nb2HF8 9w *Homo sapiens* cDNA clone 788626 5'). Based upon sequence similarity, qy442_2 proteins and each similar protein or peptide may share at least some activity. The TopPredII computer program predicts a potential transmembrane domain within the qy442_2 protein sequence, centered around amino acid 68 of SEQ ID NO:20. The nucleotide sequence of qy442_2 indicates that it may contain one or more Alu repetitive elements.

Clone "rj214_14"

A polynucleotide of the present invention has been identified as clone "rj214_14". rj214_14 was isolated from a human adult neural (neuroepithelioma HTB-10 line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. rj214_14 is a full-length clone, including the entire coding sequence of a secreted protein (also referred to herein as "rj214_14 protein").

The nucleotide sequence of rj214_14 as presently determined is reported in SEQ ID NO:135, and includes a poly(A) tail. What applicants presently believe to be the proper reading frame and the predicted amino acid sequence of the rj214_14 protein corresponding to the foregoing nucleotide sequence is reported in SEQ ID NO:136. Amino acids 3 to 15 of SEQ ID NO:136 are a predicted leader/signal sequence, with the predicted mature amino acid sequence beginning at amino acid 16. Due to the hydrophobic nature of the predicted leader/signal sequence, it is likely to act as a transmembrane domain should the predicted leader/signal sequence not be separated from the remainder of the rj214_14 protein.

The EcoRI/NotI restriction fragment obtainable from the deposit containing clone rj214_14 should be approximately 900 bp.

The nucleotide sequence disclosed herein for rj214_14 was searched against the GenBank and GeneSeq nucleotide sequence databases using BLASTN/BLASTX and FASTA search protocols. rj214_14 demonstrated at least some similarity with sequences identified as AA167035 (zp05c10.s1 Stratagene ovarian cancer (#937219) *Homo sapiens* cDNA clone 595506 3' similar to TR:G563357 G563357 GENES RAS1, RLB1 AND RLC1; mRNA sequence), AA491109 (aa52d09.r1 NCI_CGAP_GCB1 *Homo sapiens* cDNA clone IMAGE 824561 5' similar to TR G563357 G563357 GENES RAS1, RLB1 AND RLC1), and AI189156 (qd04c02.x1 Soares_placenta_8 to 9 weeks_2NbHP8 to 9W *Homo sapiens* cDNA clone IMAGE: 1722722 3' similar to TR:O01437 O01437 SIMILAR TO *DROSOPHILA* RLC1 GENE PRODUCT; mRNA sequence). The predicted amino acid sequence disclosed herein for rj214_14 was searched against the GenPept and GeneSeq amino acid sequence databases using the BLASTX search protocol. The predicted rj214_14 protein demonstrated at least some similarity to sequences identified as U97016 (similar to *drosophila* Rlc1 gene product (NID g563361) and *S. cerevisiae* mitochondrial 60S ribosomal protein L4 (YMLA4) (NID g459259) [*Caenorhabditis elegans*]), and X73219 (Rlc1). *Drosophila* Rlc1 is a basic protein that is bound to the inner face of the cell membrane. Transcription mapping and nucleotide sequence analysis reveal that Rlc1 lies in the same genomic region as *Drosophila* Ras1 and shows expression patterns that are similar to those of Ras1. It has been demonstrated (Ezer et al., 1994, *Dev. Dyn.* 201(2): 179-190, which is incorporated by reference herein) that during embryogenesis Ras1 transcripts are restricted mainly to the embryonic central nervous system, suggesting that the Rlc1 gene product also may have a role in these nerve cells. Based upon sequence similarity, rj214_14 proteins and each similar protein or peptide may share at least some activity. The TopPredII computer program predicts a potential transmembrane domain within the rj214_14 protein sequence, centered around amino acid 32 of SEQ ID NO:136.

rj214_14 protein was expressed in a COS cell expression system, and an expressed protein band of approximately 22 kDa was detected in membrane fractions using SDS polyacrylamide gel electrophoresis.

Clone “rk80_3”

A polynucleotide of the present invention has been identified as clone “rk80_3”. rk80_3 was isolated from a human adult tumor (colorectal adenocarcinoma SW480 line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. rk80_3 is a full-length clone, including the entire coding sequence of a secreted protein (also referred to herein as “rk80_3-protein”).

The nucleotide sequence of rk80_3 as presently determined is reported in SEQ ID NO:137, and includes a poly(A) tail. What applicants presently believe to be the proper reading frame and the predicted amino acid sequence of the rk80_3 protein corresponding to the foregoing nucleotide sequence is reported in SEQ ID NO:138. Amino acids 6 to 18 of SEQ ID NO:138 are a predicted leader/signal sequence, with the predicted mature amino acid sequence beginning at amino acid 19. Due to the hydrophobic nature of the predicted leader/signal sequence, it is likely to act as a transmembrane domain should the predicted leader/signal sequence not be separated from the remainder of the rk80_3 protein.

The EcoRI/NotI restriction fragment obtainable from the deposit containing clone rk80_3 should be approximately 1096 bp.

The nucleotide sequence disclosed herein for rk80_3 was searched against the GenBank and GeneSeq nucleotide sequence databases using BLASTN/BLASTX and FASTA search protocols. rk80_3 demonstrated at least some similarity with sequences identified as AA418955 (zw01c10.r1 Soares NhHMPu S1 *Homo sapiens* cDNA clone 768018 5', mRNA sequence), AB004061 (domestic pig mRNA for STAT2, complete CDs, a signal transducer and activator of transcription), C06368 (similar to none), and U38443 (Human clone JkA3 mRNA induced upon T-cell activation, 3' end). The predicted rk80_3 protein demonstrated at least some similarity to granulocyte-colony stimulating factor (G-CSF) and interleukin-6 (IL-6). Hidden Markov model analysis has revealed the presence of an IL-6/G-CSF/mast cell growth factor (MGF) family signature at amino acids 69 to 181 of SEQ ID NO:138. This family of cytokines are glycoproteins of about 170 to 180 amino acid residues in size that contain four conserved cysteine residues involved in two disulfide bonds. rk80_3 appears to encode a novel cytokine in the IL-6/G-CSF family. Based upon sequence similarity, rk80_3 proteins and each similar protein or peptide may share at least some activity.

rk80_3 protein was expressed in a COS cell expression system, and an expressed protein band of approximately 24 kDa was detected in membrane fractions using SDS polyacrylamide gel electrophoresis.

Clone “au36_42”

A polynucleotide of the present invention has been identified as clone “au36_42”. au36_42 was isolated from a human adult testes cDNA library and was identified as encoding a novel protein on the basis of computer analysis of the amino acid sequence of the encoded protein. au36_42 is a full-length clone, including the entire coding sequence of a novel protein (also referred to herein as “au36_42 protein”).

The nucleotide sequence of au36_42 as presently determined is reported in SEQ ID NO:139, and includes a poly(A) tail. What applicants presently believe to be the proper reading frame and the predicted amino acid sequence of the au36_42 protein corresponding to the foregoing nucleotide sequence is reported in SEQ ID NO:140.

The EcoRI/NotI restriction fragment obtainable from the deposit containing clone au36_42 should be approximately 1400 bp.

The nucleotide sequence disclosed herein for au36_42 was searched against the GenBank and GeneSeq nucleotide sequence databases using BLASTN/BLASTX and FASTA search protocols. No significant hits were found in the database. The nucleotide sequence of au36_42 indicates that it may contain a L1ME repetitive element.

Clone “bo549_13”

A polynucleotide of the present invention has been identified as clone “bo549_13”. bo549_13 was isolated from a human adult retina cDNA library and was identified as encoding a novel protein on the basis of computer analysis of the amino acid sequence of the encoded protein. bo549_13 is a full-length clone, including the entire coding sequence of a novel protein (also referred to herein as “bo549_13 protein”).

The nucleotide sequence of bo549_13 as presently determined is reported in SEQ ID NO:141, and includes a poly(A) tail. What applicants presently believe to be the proper reading frame and the predicted amino acid sequence of the bo549_13 protein corresponding to the foregoing nucleotide sequence is reported in SEQ ID NO:142. The region of SEQ ID NO:141 at nucleotides 518 and 519 may represent the border of an alternatively spliced exon.

The EcoRI/NotI restriction fragment obtainable from the deposit containing clone bo549_13 should be approximately 1200 bp.

The nucleotide sequence disclosed herein for bo549_13 was searched against the GenBank and GeneSeq nucleotide sequence databases using BLASTN/BLASTX and FASTA search protocols. bo549_13 demonstrated at least some similarity with sequences identified as AI261562 (qz30c06.x1 NCI_CGAP_Kid11 *Homo sapiens* cDNA clone IMAGE 2028394 3' similar to TR Q63061 Q63061 HYPOTHETICAL 4.7 KD PROTEIN; mRNA sequence) and J02649 (Rat stomach (H+,K+)-ATPase mRNA, complete cds). The predicted amino acid sequence disclosed herein for bo549_13 was searched against the GenPept and GeneSeq amino acid sequence databases using the BLASTX search protocol. The predicted bo549_13 protein demonstrated at least some similarity to sequences identified as J02649 (unknown protein [*Rattus norvegicus*]). Based upon sequence similarity, bo549_13 proteins and each similar protein or peptide may share at least some activity.

Clone “da529_3”

A polynucleotide of the present invention has been identified as clone “da529_3”. da529_3 was isolated from a human fetal placenta cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. da529_3 is a full-length clone, including the entire coding sequence of a secreted protein (also referred to herein as "da529_3 protein").

The nucleotide sequence of da529_3 as presently determined is reported in SEQ ID NO:143, and includes a poly(A) tail. What applicants presently believe to be the proper reading frame and the predicted amino acid sequence of the da529_3 protein corresponding to the foregoing nucleotide sequence is reported in SEQ ID NO:144. Amino adds 59 to 71 of SEQ ID NO:144 are a predicted leader/signal sequence, with the predicted mature amino acid sequence beginning at amino acid 72. Due to the hydrophobic nature of the predicted leader/signal sequence, it is likely to act as a transmembrane domain should the predicted leader/signal sequence not be separated from the remainder of the da529_3 protein.

The EcoRI/NotI restriction fragment obtainable from the deposit containing clone da529_3 should be approximately 1150 bp.

The nucleotide sequence disclosed herein for da529_3 was searched against the GenBank and GeneSeq nucleotide sequence databases using BLASTN/BLASTX and FASTA search protocols. da529_3 demonstrated at least some similarity with sequences identified as AI189911 (qd33e06.x1 Soares_placenta_8 to 9 weeks_2NbHP8 to 9W *Homo sapiens* cDNA clone IMAGE 1725538 3' similar to TR O42204 O42204 PUTATIVE TRANSMEMBRANE PROTEIN E3-16; mRNA sequence), T35254 (EST82005 *Homo sapiens* cDNA 5' end similar to None), U76253 (*Mus musculus* E25B protein mRNA, complete cds), V43619 (Human secreted protein 19 encoding DNA), W28608 (49b1 Human retina cDNA randomly primed sublibrary *Homo sapiens* cDNA), and W41628 (mc47c10.r1 Soares mouse p3NMF19). The predicted amino acid sequence disclosed herein for da529_3 was searched against the GenPept and GeneSeq amino acid sequence databases using the BLASTX search protocol. The predicted da529_3 protein demonstrated at least some similarity to sequences identified as AF03895 (E25 protein [*Homo sapiens*]) and W63699 (Human secreted protein 19). Based upon sequence similarity, da529_3 proteins and each similar protein or peptide may share at least some activity.

Clone "dm365_3"

A polynucleotide of the present invention has been identified as clone "dm365_3". A cDNA clone was first isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. This cDNA clone was then used to isolate dm365_3 from a human fetal brain cDNA library. dm365_3 is a full-length clone, including the entire coding sequence of a secreted protein (also referred to herein as "dm365_3 protein").

The nucleotide sequence of dm365_3 as presently determined is reported in SEQ ID NO:145, and includes a poly(A) tail. What applicants presently believe to be the proper reading frame and the predicted amino acid sequence of the dm365_3 protein corresponding to the foregoing nucleotide sequence is reported in SEQ ID NO:146. Amino acids 1 to 13 of SEQ ID NO:146 are a predicted leader/signal sequence, with the predicted mature amino acid sequence beginning at amino acid 14. Amino acids 40 to 52 of SEQ ID NO:146 are also a possible leader/signal sequence, with the predicted mature amino acid sequence beginning in that case at amino acid 53. Due to the hydrophobic nature of each of these predicted leader/signal sequences, each predicted leader/signal sequence is likely to act as a transmembrane domain should it not be separated from the remainder of the dm365_3 protein.

The EcoRI/NotI restriction fragment obtainable from the deposit containing clone dm365_3 should be approximately 1300 bp.

The nucleotide sequence disclosed herein for dm365_3 was searched against the GenBank and GeneSeq nucleotide sequence databases using BLASTN/BLASTX and FASTA search protocols. dm365_3 demonstrated at least some similarity with sequences identified as AC005533 (*SEQUENCING IN PROGRESS* *Homo sapiens* clone DJ0794K21; HTGS phase 1,22 unordered pieces), AI125562 (qd94d09.x1 Soares testis NHT *Homo sapiens* cDNA clone IMAGE 1737137 3', mRNA sequence), R02268 (ye85c10.r1 *Homo sapiens* cDNA clone 124530 5' similar to contains LTR5 repetitive element), and V90427 (EST clone DM365). Based upon sequence similarity, dm365_3 proteins and each similar protein or peptide may share at least some activity. The nucleotide sequence of dm365_3 indicates that it may contain repetitive sequences.

dm365_3 protein was expressed in a COS cell expression system, and an expressed protein band of approximately 23 kDa was detected in conditioned medium and membrane fractions using SDS polyacrylamide gel electrophoresis.

Clone "fa171_1"

A polynucleotide of the present invention has been identified as clone "fa171_1". fa171_1 was isolated from a human fetal brain cDNA library and was identified as encoding a novel protein on the basis of computer analysis of the amino acid sequence of the encoded protein. fa171_1 is a full-length clone, including the entire coding sequence of a novel protein (also referred to herein as "fa171_1 protein").

The nucleotide sequence of fa171_1 as presently determined is reported in SEQ ID NO:147, and includes a poly(A) tail. What applicants presently believe to be the proper reading frame and the predicted amino acid sequence of the fa171_1 protein corresponding to the foregoing nucleotide sequence is reported in SEQ ID NO:148.

The EcoRI/NotI restriction fragment obtainable from the deposit containing clone fa171_1 should be approximately 2500 bp.

The nucleotide sequence disclosed herein for fa171_1 was searched against the GenBank and GeneSeq nucleotide sequence databases using BLASTN/BLASTX and FASTA search protocols. fa171_1 demonstrated at least some similarity with sequences identified as AA446057 (zw66d04.r1 Soares testis NHT *Homo sapiens* cDNA clone 781159 5', mRNA sequence), AC002099 (*SEQUENCING IN PROGRESS*Genomic sequence from Human 9q34; HTGS phase 1, 2 unordered pieces), AC002355 (*SEQUENCING IN PROGRESS*Genomic sequence from Human 9q34; HTGS phase 1, 7 unordered pieces), and U10185 (*Xenopus laevis* XPMC2 protein mRNA, complete cds). The predicted amino acid sequence disclosed herein for fa171_1 was searched against the GenPept and GeneSeq amino acid sequence databases using the BLASTX search protocol. The predicted fa171_1 protein demonstrated at least some similarity to sequences identified as R67549 (Fruiting body inducing polypeptide) and U10185 (XPMC2 protein [*Xenopus laevis*]). XPMC2 is a *Xenopus* cDNA clone that can rescue several different yeast mitotic catastrophe mutants-defective in Wee1 kinase function, and is a nuclear protein. Based upon sequence similarity, fa171__1 proteins and each similar protein or peptide may share at least some activity.

Clone "lp572__2"

A polynucleotide of the present invention has been identified as clone "lp572__2". lp572__2 was isolated from a human adult blood (peripheral blood mononuclear cells treated with granulocyte-colony stimulating factor in vivo) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. lp572__2 is a full-length clone, including the entire coding sequence of a secreted protein (also referred to herein as "lp572__2 protein").

The nucleotide sequence of lp572__2 as presently determined is reported in SEQ ID NO:149, and includes a poly(A) tail. What applicants presently believe to be the proper reading frame and the predicted amino acid sequence of the lp572__2 protein corresponding to the foregoing nucleotide sequence is reported in SEQ ID NO:150. Amino acids 79 to 91 of SEQ ID NO:150 are a predicted leader/signal sequence, with the predicted mature amino acid sequence beginning at amino acid 92. Due to the hydrophobic nature of the predicted leader/signal sequence, it is likely to act as a transmembrane domain should the predicted leader/signal sequence not be separated from the remainder of the lp572__2 protein.

The EcoRI/NotI restriction fragment obtainable from the deposit containing clone lp572__2 should be approximately 2100 bp.

The nucleotide sequence disclosed herein for lp572__2 was searched against the GenBank and GeneSeq nucleotide sequence databases using BLASTN/BLASTX and FASTA search protocols. lp572__2 demonstrated at least some similarity with sequences identified as AA489012 (aa56a0 3.s1 NCI_CGAP_GCB1 *Homo sapiens* cDNA clone 824908 3'), AA533633 (nf73b09.s1 NCI_CGAP_Co3 *Homo sapiens* cDNA clone IMAGE 925529, mRNA sequence), AC004686 (*Homo sapiens* chromosome 17, clone hRPC.1073_F__15, complete sequence), T18977 (g07030t Testis 1 *Homo sapiens* cDNA clone g07030 5' end), T21490 (Human gene signature HUMGS02862), and W73324 (zd01h01.r1 Pancreatic Islet *Homo sapiens* cDNA clone 339409 5'). The predicted amino acid sequence disclosed herein for lp572__2 was searched against the GenPept and GeneSeq amino acid sequence databases using the BLASTX search protocol. The predicted lp572__2 protein demonstrated at least some similarity to sequences identified as AL03262 (predicted using Genefinder [*Caenorhabditis elegans*]). Based upon sequence similarity, lp572__2 proteins and each similar protein or peptide may share at least some activity. The TopPredII computer program predicts five additional potential transmembrane domains within the lp572__2 protein sequence, centered around amino acids 129, 263, 286, 326, and 378 of SEQ ID NO:150, respectively.

Clone "pe246__1"

A polynucleotide of the present invention has been identified as clone "pe246__1". pe246__1 was isolated from a human adult blood (chronic myelogenous leukemia line K562) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. pe246__1 is a full-length clone, including the entire coding sequence of a secreted protein (also referred to herein as "pe246__1 protein").

The nucleotide sequence of pe246__1 as presently determined is reported in SEQ ID NO:151, and includes a poly(A) tail. What applicants presently believe to be the proper reading frame and the predicted amino acid sequence of the pe246__1 protein corresponding to the foregoing nucleotide sequence is reported in SEQ ID NO:152. Amino acids 193 to 205 of SEQ ID NO:152 are a predicted leader/signal sequence, with the predicted mature amino acid sequence beginning at amino acid 206. Due to the hydrophobic nature of the predicted leader/signal sequence, it is likely to act as a transmembrane domain should the predicted leader/signal sequence not be separated from the remainder of the pe246__1 protein.

The EcoRI/NotI restriction fragment obtainable from the deposit containing clone pe246__1 should be approximately 1500 bp.

The nucleotide sequence disclosed herein for pe246__1 was searched against the GenBank and GeneSeq nucleotide sequence databases using BLASTN/BLASTX and FASTA search protocols. pe246__1 demonstrated at least some similarity with sequences identified as AA234138 (zr51b06.r1 Soares NhHMPu S1 *Homo sapiens* cDNA clone 666899 5' similar to SW FCEB_HUMAN Q01362 HIGH AFFINITY IMMUNOGLOBULIN EPSILON RECEPTOR BETA-SUBUNIT), AA418443 (zv92e0 5.r1 Soares NhHMPu S1 *Homo sapiens* cDNA clone 767264 5' similar to SW FCEB_RAT P13386 HIGH AFFINITY IMMUNOGLOBULIN EPSILON RECEPTOR BETA-SUBUNIT; mRNA sequence), AC004584 (*Homo sapiens* chromosome 17, clone hRPC1107__A__17, complete sequence), M74509 (Human endogenous retrovirus type C oncovirus sequence), and V57903 (Hereditary haemochromatosis subregion from an HH affected individual). The predicted amino acid sequence disclosed herein for pe246__1 was searched against the GenPept and GeneSeq amino acid sequence databases using the BLASTX search protocol. The predicted pe246__1 protein demonstrated at least some similarity to sequences identified as L35848 (IgE receptor beta subunit [*Homo sapiens*]), R05026 (Beta subunit of rat high affinity IgE receptor Fc(epsilon) R1), and R42341 (Subunit of the human IgE receptor). The first 359 nucleotides of SEQ ID NO:13 is similar in sequence to that of M74509 (Human endogenous retrovirus type C oncovirus sequence) and also to several genomic sequences as a result. It appears that this region may be retroviral DNA that has been incorporated into the genome. Based upon sequence similarity, pe246__1 proteins and each similar protein or peptide may share at least some activity. The TopPredII computer program predicts three additional potential transmembrane domains within the pe246__1 protein sequence, centered around amino acids 86, 115, and 154 of SEQ ID NO:152, respectively.

Clone "qf122__3"

A polynucleotide of the present invention has been identified as clone "qf122__3". qf122__3 was isolated from a human adult bladder (carcinoma line 5637) cDNA library and was identified as encoding a novel protein on the basis of computer analysis of the amino acid sequence of the encoded protein. qf122__3 is a full-length clone, including the entire coding sequence of a novel protein (also referred to herein as "qf122__3 protein").

The nucleotide sequence of qf122__3 as presently determined is reported in SEQ ID NO:153. What applicants presently believe to be the proper reading frame and the predicted amino acid sequence of the qf122_3 protein corresponding to the foregoing nucleotide sequence is reported in SEQ ID NO:154.

The EcoRI/NotI restriction fragment obtainable from the deposit containing clone qf122_3 should be approximately 1700 bp.

The nucleotide sequence disclosed herein for qf122_3 was searched against the GenBank and GeneSeq nucleotide sequence databases using BLASTN/BLASTX and FASTA search protocols. qf122_3 demonstrated at least some similarity with sequences identified as AA206909 (zq80d10.r1 Stratagene hNT neuron (#937233) *Homo sapiens* cDNA clone 647923 5' similar to SW YYAF_BACSU P37518 HYPOTHETICAL 40.1 KD GTP-BINDING PROTEIN IN RPSF—SPO0J INTERGENIC REGION; mRNA sequence), AA237053 (zs01c01.r1 NCI_CGAP_GCB1 *Homo sapiens* cDNA clone IMAGE 683904 5' similar to SW YBN5_YEAST P38219 HYPOTHETICAL 44.2 KD PROTEIN IN SCO2-MRF1 INTERGENIC REGION), AA775776 (ad14e03.s1 Soares NbHFB *Homo sapiens* cDNA clone 878236 3' similar to TR P91917 P91917 WO8E3.3; mRNA sequence), AL021878 (*Homo sapiens* DNA sequence from PAC 257120 on chromosome 22q13.1-13.2; contains cytochrome P450 pseudogenes CYP2D7P, CYP2D8P, CYP2D6(D), TCF20, NADH ubiquinone oxidoreductase B14 subunit, ESTs, CA repeat, STS, GSS), and N32932 (yy10a02.s1 *Homo sapiens* cDNA clone 270794 3' similar to SW:YBN5_YEAST P38219 HYPOTHETICAL 44.2 KD PROTEIN IN SCO2-MRF1 INTERGENIC REGION). The predicted amino acid sequence disclosed herein for qf122_3 was searched against the GenPept and GeneSeq amino acid sequence databases using the BLASTX search protocol. The predicted qf122_3 protein demonstrated at least some similarity to sequences identified as W48670 (*Staphylococcus aureus* gbpA protein), Z92773 (WO8E3.3 [*Caenorhabditis elegans*]), and Z92773 (predicted using Genefinder; Similarity to Yeast hypothetical 44.2 KD protein, putative GTP-binding protein (SW P38219); cDNA EST EMBL D64516 comes from this gene). Based upon sequence similarity, qf122_3 proteins and each similar protein or peptide may share at least some activity. Analysis of protein motifs in SEQ ID NO:154 predicts an ATP/GTP-binding site motif A (P-loop) around amino acid 29 of SEQ ID NO:154.

Clone "qv538_1"

A polynucleotide of the present invention has been identified as clone "qv538_1". qv538_1 was isolated from a human adult testes (embryonal carcinoma NT2D1 cell line) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. qv538_1 is a full-length clone, including the entire coding sequence of a secreted protein (also referred to herein as "qv538_1 protein").

The nucleotide sequence of qv538_1 as presently determined is reported in SEQ ID NO:155, and includes a poly(A) tail. What applicants presently believe to be the proper reading frame and the predicted amino acid sequence of the qv538_1 protein corresponding to the foregoing nucleotide sequence is reported in SEQ ID NO:156. Amino acids 8 to 20 of SEQ ID NO:156 are a predicted leader/signal sequence, with the predicted mature amino acid sequence beginning at amino acid 21. Due to the hydrophobic nature of the predicted leader/signal sequence, it is likely to act as a transmembrane domain should the predicted leader/signal sequence not be separated from the remainder of the qv538_1 protein.

The EcoRI/NotI restriction fragment obtainable from the deposit containing clone qv538_1 should be approximately 2600 bp.

The nucleotide sequence disclosed herein for qv538_1 was searched against the GenBank and GeneSeq nucleotide sequence databases using BLASTN/BLASTX and FASTA search protocols. qv538_1 demonstrated at least some similarity with sequences identified as W44974 (zc22e11.r1 Soares senescent fibroblasts NbHSF *Homo sapiens* cDNA clone 323084 5' similar to SW:FKB2_YEAST P32472 FK506-BINDING PROTEIN PRECURSOR; mRNA sequence), and Z62799 (*H.sapiens* CpG island DNA genomic Mse1 fragment, clone 73c8, reverse read cpg73c8.rt1a). The predicted amino acid sequence disclosed herein for qv538_1 was searched against the GenPept and GeneSeq amino acid sequence databases using the BLASTX search protocol. The predicted qv538_1 protein demonstrated at least some similarity to sequences identified as AF04025 (FK506-binding protein [*Mus musculus*]) and W88556 (Secreted protein encoded by gene 23 clone HSQEO84). FK506-binding protein (or "FKBP") is the major high-affinity binding protein, in vertebrates, for the immunosuppressive drug FK506 (used to aid in organ transplantation acceptance among other indications). It exhibits peptidyl-prolyl cis-trans isomerase activity (PPIase or rotamase). PPIase is an enzyme that accelerates protein folding by catalyzing the cis-trans isomerization of proline imidic peptide bonds in oligopeptides. Based upon sequence similarity, qv538_1 proteins and each similar protein or peptide may share at least some activity. Analysis of protein motifs in SEQ ID NO:156 detects an endoplasmic reticulum targeting sequence around amino acid 208. Hidden Markov Model analysis detects an EF-hand calcium-binding domain at amino acids 183 to 211 of SEQ ID NO:156 (also found by motif analysis) and a FKBP-type peptidyl-prolyl cis-trans isomerase signatures/profile at amino acids 38 to 132 of SEQ ID NO:156. The nucleotide sequence of qv538_1 indicates that it may contain an Alu repetitive element. qv538_1 protein was expressed in a COS cell expression system, and an expressed protein band of approximately 24 kDa was detected in conditioned medium and membrane fractions using SDS polyacrylamide gel electrophoresis.

Clone "ys20_1"

A polynucleotide of the present invention has been identified as clone "ys20_1". ys20_1 was isolated from a human adult thymus cDNA library and was identified as encoding a secreted or transmembrane protein on the basis of computer analysis of the amino acid sequence of the encoded protein. ys20_1 is a full-length clone, including the entire coding sequence of a secreted protein (also referred to herein as "ys20_1 protein").

The nucleotide sequence of ys20_1 as presently determined is reported in SEQ ID NO:157, and includes a poly(A) tail. What applicants presently believe to be the proper reading frame and the predicted amino acid sequence of the ys20_1 protein corresponding to the foregoing nucleotide sequence is reported in SEQ ID NO:158. Amino acids 41 to 53 of SEQ ID NO:158 are a possible leader/signal sequence, with the predicted mature amino acid sequence beginning at amino acid 54. Amino acids 121 to 133 of SEQ ID NO:158 are also a possible leader/signal sequence, with the predicted mature amino acid sequence beginning in that case at amino acid 134. Due to the hydrophobic nature of each of these predicted leader/signal sequences, each predicted leader/signal sequence is likely to act as a transmembrane domain should it not be separated from the remainder of the ys20_1 protein.

The EcoRI/NotI restriction fragment obtainable from the deposit containing clone ys20_1 should be approximately 2229 bp.

The nucleotide sequence disclosed herein for ys20_1 was searched against the GenBank and GeneSeq nucleotide sequence databases using BLASTN/BLASTX and FASTA search protocols. ys20_1 demonstrated at least some similarity with sequences identified as B76357 (RPCI11-15B19.TV RPCI11 *Homo sapiens* genomic clone R-15B19, genomic survey sequence). Based upon sequence similarity, ys20_1 proteins and each similar protein or peptide may share at least some activity. The TopPredII computer program predicts an additional potential transmembrane domain within the ys20_]protein sequence, centered around amino acid 205 of SEQ ID NO:158. The nucleotide sequence of ys20_1 indicates that it may contain one or more mammalian transposon-like long terminal repeat elements, such as MCT1b/c.

Clone "as180_1"

A polynucleotide of the present invention has been identified as clone "as180_1". as180_1 was isolated from a human fetal brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. as180_1 is a full-length clone, including the entire coding sequence of a secreted protein (also referred to herein as "as180_1 protein").

The nucleotide sequence of as180_1 as presently determined is reported in SEQ ID NO:159. What applicants presently believe to be the proper reading frame and the predicted amino acid sequence of the as180_1 protein corresponding to the foregoing nucleotide sequence is reported in SEQ ID NO:160. Amino acids 168 to 180 of SEQ ID NO:160 are a predicted leader/signal sequence, with the predicted mature amino acid sequence beginning at amino acid 181. Due to the hydrophobic nature of the predicted leader/signal sequence, it is likely to act as a transmembrane domain should the predicted leader/signal sequence not be separated from the remainder of the as180_1 protein.

The EcoRI/NotI restriction fragment obtainable from the deposit containing clone as180_1 should be approximately 3580 bp.

The nucleotide sequence disclosed herein for as180_1 was searched against the GenBank and GeneSeq nucleotide sequence databases using BLASTN/BLASTX and FASTA search protocols. as180_1 demonstrated at least some similarity with sequences identified as AB018279 (*Homo sapiens* mRNA for KIAA0736 protein, complete cds), S47919 (p87=transporter-like protein [cattle, mRNA]), V89585 (EST clone CR618), and W28902 (53d 11 Human retina cDNA randomly primed sublibrary *Homo sapiens* cDNA, mRNA sequence). The predicted amino acid sequence disclosed herein for as180_1 was searched against the GenPept and GeneSeq amino acid sequence databases using the BLASTX search protocol. The predicted as180_1 protein demonstrated at least some similarity to sequences identified as AB018279 (KIAA0736 protein [*Homo sapiens*]), L05435 (synaptic vesicle protein 2 *[Rattus norvegicus*]), S47919 (p87 *[Bos* sp.]), and W64538 (Human liver cell clone HP01293 protein). Synaptic vesicle protein 2 (SV2) is a membrane glycoprotein specifically localized to secretory vesicles in neurons and endocrine cells (Bajjalieh, S. M. et al., 1992*, Science August* 28; 257(5074): 1271-1273, which is incorporated by reference herein). Based upon sequence similarity, as180_1 proteins and each similar protein or peptide may share at least some activity. Analysis of amino acid motifs detected a sugar-transport protein signature around amino acid 264 of SEQ ID NO:160, and hidden Markov Model analysis detected a sugar-transporter amino acid profile from amino acid 153 to amino acid 741 of SEQ ID NO:160. The TopPredII computer program predicts twelve potential transmembrane domains within the as 180_1 protein sequence, centered around amino acids 181, 205, 248, 270, 308, 344, 432, 458, 605, 638, 654, and 710 of SEQ ID NO: 160, respectively.

Deposit of Clones

Clones co62_12, lo311_8, ns197_1, pj193_5, pj317_2, pt332_1, qc297_15, qg596_12, and rb649_3 were deposited on Jul. 29, 1998 with the American Type Culture Collection. (10801 University Boulevard, Manassas, Va. 20110-2209 U.S.A.) as an original deposit under the Budapest Treaty and were given the accession number ATCC 98825, from which each clone comprising a particular polynucleotide is obtainable.

Clones ca106_19xx, ci52_2, md124_16, pk366_7, pl741_5, pp314_19, pv35_1, pw337_6, rd610_1, and rd810_6 were deposited on Aug. 11, 1998 with the American Type Culture Collection (10801 University Boulevard, Manassas, Va. 20110-2209 U.S.A.) as an original deposit under the Budapest Treaty and were given the accession number ATCC 98835, from which each clone comprising a particular polynucleotide is obtainable.

Clones cf85_1, dd504_18, np26_3, pm412_12, pm421_3, pv6_1, qs14_3, qy338_9, rc58_1, and rd232_5 were deposited on Aug. 27, 1998 with the American Type Culture Collection (10801 University Boulevard, Manassas, Va. 20110-2209 U.S.A.) as an original deposit under the Budapest Treaty and were given the accession number ATCC 98850, from which each clone comprising a particular polynucleotide is obtainable.

Clones ck213_12, pg195_1, pw460_5, qa136_1, qy1261_2, and rd432_4 were deposited on Oct. 8, 1998 with the American Type Culture Collection (10801 University Boulevard, Manassas, Va. 20110-2209 U.S.A.) as an original deposit under the Budapest Treaty and were given the accession number ATCC 98918, from which each clone comprising a particular polynucleotide is obtainable.

Clones rb789_14, yd137_1, yd218_1, ye11_1, ye72_1, ye78_1, ye90_1, yi62_1, yk78_1, yk251_1, and yt14_1 were deposited on Dec. 15, 1998 with the American Type Culture Collection (10801 University Boulevard, Manassas, Va. 20110-2209 U.S.A.) as an original deposit under the Budapest Treaty and were given the accession number ATCC 207004, from which each clone comprising a particular polynucleotide is obtainable.

Clones bf157_16, bk343_2, cd205_2, cw1292_8, cw1475_2, dd428_4, dh1073_12, dw78_1, fh116_11, fy356_14, and iw66_1 were deposited on Feb. 4, 1999 with the American Type Culture Collection (10801 University Boulevard, Manassas, Va. 20110-2209 U.S.A.) as an original deposit under the Budapest Treaty and were given the accession number ATCC 207088, from which each clone comprising a particular polynucleotide is obtainable.

Clones kh13_4, ko258_4, kv10_8, LL89_3, mc300_1, ml227_1, mm367_6, mt124_3, nf56_3, qy442_2, rj214_1, and rk80_3 were deposited on Feb. 4, 1999 with the American Type Culture Collection (10801 University Boulevard, Manassas, Va. 20110-2209 U.S.A.) as an original deposit under the Budapest Treaty and were given the accession number ATCC 207089, from which each clone comprising a particular polynucleotide is obtainable.

Clones au36_42, bo549_13, da529_3, dm365_3, fa171_1, lp572_2, pe246_1, qf122_3, qv538_1, and ys20_1 were deposited on Apr. 2, 1999 with the American Type Culture Collection (10801 University Boulevard, Manassas, Va. 20110-2209 U.S.A.) as an original deposit under the Budapest Treaty and were given the accession number ATCC 207187, from which each clone comprising a particular polynucleotide is obtainable.

Clone as180_1 was deposited on Aug. 11, 1999 with the American Type Culture Collection (10801 University Boulevard, Manassas, Va. 20110-2209 U.S.A.) as an original deposit under the Budapest Treaty, from which the as180_1 clone comprising a particular polynucleotide is obtainable.

All restrictions on the availability to the public of the deposited material will be irrevocably removed upon the granting of the patent, except for the requirements specified in 37 C.F.R. § 1.808(b), and the term of the deposit will comply with 37 C.F.R. § 1.806.

Figure 1B:
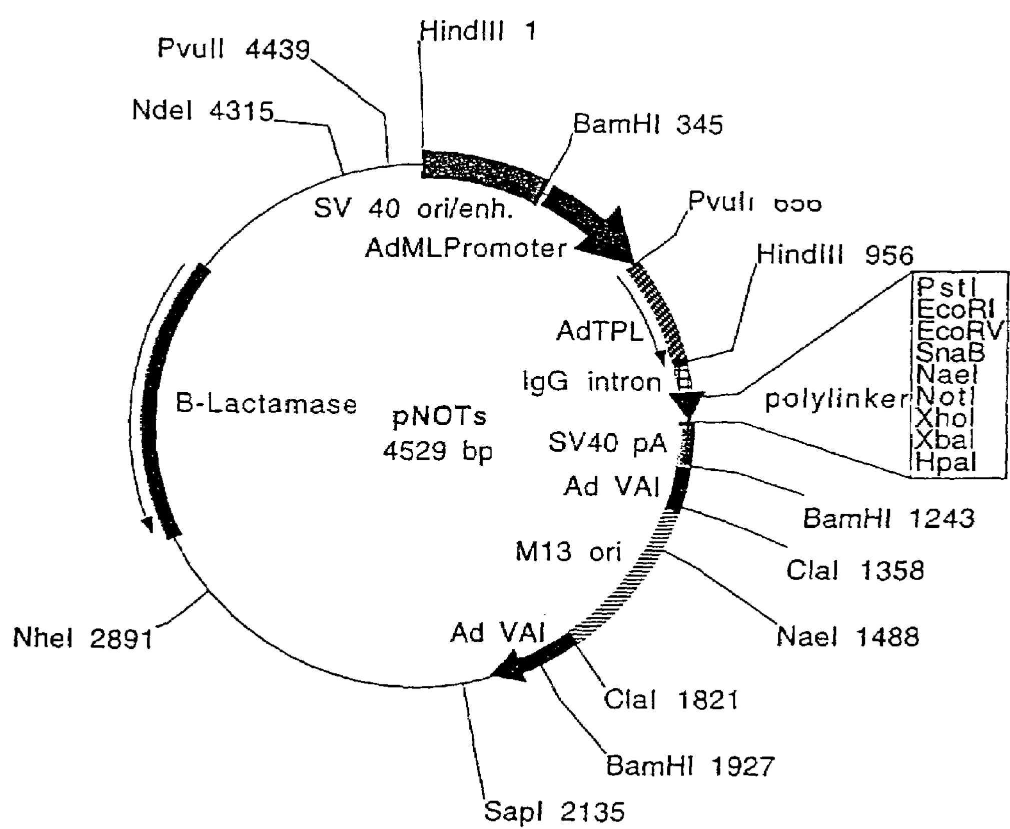
Figure 2:
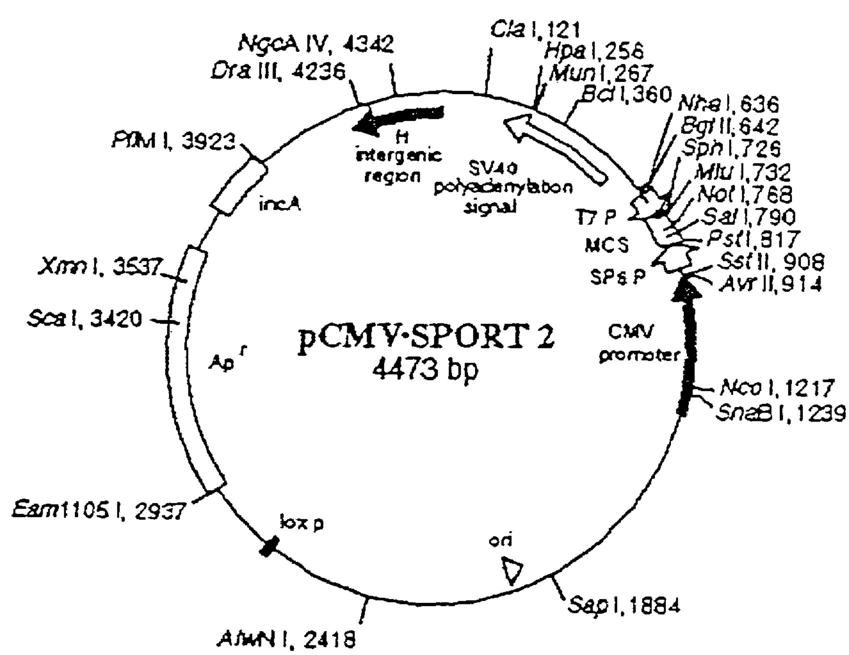
FIG. 2 is a schematic representation of the pCMVSport2 vector used for deposit of clone qs14_3 disclosed herein.

Each clone has been transfected into separate bacterial cells (*E. coli*) in the above composite deposits. Each clone can be removed from the vector in which it was deposited by performing an EcoRI/NotI digestion (5' site, EcoRI; 3' site, NotI) to produce the appropriate fragment for such clone. Each clone was deposited in either the pED6 or pNOTs vector depicted in FIGS. 1A and 1B, respectively, or in the case of clone qs14_3, in the pCMVSport2 vector (Life Technologies, Inc., Rockville, Md. 20850, U.S.A.) depicted in FIG. 2. The pED6dpc2 vector ("pED6") was derived from pED6dpc1 by insertion of a new polylinker to facilitate cDNA cloning (Kaufman et al., 1991, *Nucleic Acids Res.* 19: 4485-4490); the pNOTs vector was derived from pMT2 (Kaufman et al., 1989, *Mol. Cell. Biol.* 9: 946-958) by deletion of the DHFR sequences, insertion of a new polylinker, and insertion of the M13 origin of replication in the ClaI site. In some instances, the deposited clone can become "flipped" (i.e., in the reverse orientation) in the deposited isolate. In such instances, the cDNA insert can still be isolated by digestion with EcoRI and NotI. However, NotI will then produce the 5' site and EcoRI will produce the 3' site for placement of the cDNA in proper orientation for expression in a suitable vector. The cDNA may also be expressed from the vectors in which they were deposited.

Bacterial cells containing a particular clone can be obtained from the composite deposit as follows:

An oligonucleotide probe or probes should be designed to the sequence that is known for that particular clone. This sequence can be derived from the sequences provided herein, or from a combination of those sequences. The sequence of an oligonucleotide probe that was used to isolate or to sequence each full-length clone is identified below, and should be most reliable in isolating the clone of interest.

| Clone | Probe Sequence |
|---|---|
| co62_12 | SEQ ID NO: 161 |
| lo311_8 | SEQ ID NO: 162 |
| ns197_1 | SEQ ID NO: 163 |
| pj193_5 | SEQ ID NO: 164 |
| pj317_2 | SEQ ID NO: 165 |
| pt332_1 | SEQ ID NO: 166 |
| qc297_15 | SEQ ID NO: 167 |
| qg596_12 | SEQ ID NO: 168 |
| rb649_3 | SEQ ID NO: 169 |
| ca106_19x | SEQ ID NO: 170 |
| ci52_2 | SEQ ID NO: 171 |
| md124_16 | SEQ ID NO: 172 |

-continued

| Clone | Probe Sequence |
|---|---|
| pk366_7 | SEQ ID NO: 173 |
| pl741_5 | SEQ ID NO: 174 |
| pp314_19 | SEQ ID NO: 175 |
| pv35_1 | SEQ ID NO: 176 |
| pw337_6 | SEQ ID NO: 177 |
| rd610_1 | SEQ ID NO: 178 |
| rd810_6 | SEQ ID NO: 179 |
| cf85_1 | SEQ ID NO: 180 |
| dd504_18 | SEQ ID NO: 181 |
| np26_3 | SEQ ID NO: 182 |
| pm412_12 | SEQ ID NO: 183 |
| pm421_3 | SEQ ID NO: 184 |
| pv6_1 | SEQ ID NO: 185 |
| qs14_3 | SEQ ID NO: 186 |
| qy338_9 | SEQ ID NO: 187 |
| rc58_1 | SEQ ID NO: 188 |
| rd232_5 | SEQ ID NO: 189 |
| ck213_12 | SEQ ID NO: 190 |
| pg195_1 | SEQ ID NO: 191 |
| pw460_5 | SEQ ID NO: 192 |
| qa136_1 | SEQ ID NO: 193 |
| qy1261_2 | SEQ ID NO: 194 |
| rd432_4 | SEQ ID NO: 195 |
| rb789_14 | SEQ ID NO: 196 |
| yd137_1 | SEQ ID NO: 197 |
| ye11_1 | SEQ ID NO: 198 |
| ye72_1 | SEQ ID NO: 199 |
| ye78_1 | SEQ ID NO: 200 |
| ye90_1 | SEQ ID NO: 201 |
| yk251_1 | SEQ ID NO: 202 |
| yt14_1 | SEQ ID NO: 203 |
| bf157_16 | SEQ ID NO: 204 |
| bk343_2 | SEQ ID NO: 205 |
| cd205_2 | SEQ ID NO: 206 |
| cw1292_8 | SEQ ID NO: 207 |
| cw1475_2 | SEQ ID NO: 208 |
| dd428_4 | SEQ ID NO: 209 |
| dh1073_12 | SEQ ID NO: 210 |
| dw78_1 | SEQ ID NO: 211 |
| fh116_ll | SEQ ID NO: 212 |
| fy356_14 | SEQ ID NO: 213 |
| iw66_1 | SEQ ID NO: 214 |
| kh13_4 | SEQ ID NO: 215 |
| ko258_4 | SEQ ID NO: 216 |
| kv10_8 | SEQ ID NO: 217 |
| LL89_3 | SEQ ID NO: 218 |
| mc300_1 | SEQ ID NO: 219 |
| ml227_1 | SEQ ID NO: 220 |
| mm367_6 | SEQ ID NO: 221 |
| mt124_3 | SEQ ID NO: 222 |
| nf56_3 | SEQ ID NO: 223 |
| qy442_2 | SEQ ID NO: 224 |
| rj214_14 | SEQ ID NO: 225 |
| rk80_3 | SEQ ID NO: 226 |
| au36_42 | SEQ ID NO: 227 |
| bo549_13 | SEQ ID NO: 228 |
| da529_3 | SEQ ID NO: 229 |
| dm365_3 | SEQ ID NO: 230 |
| fa171_1 | SEQ ID NO: 231 |
| lp572_2 | SEQ ID NO: 232 |
| pe246_1 | SEQ ID NO: 233 |
| qf122_3 | SEQ ID NO: 234 |
| qv538_1 | SEQ ID NO: 235 |
| ys20_1 | SEQ ID NO: 236 |
| as180_1 | SEQ ID NO: 237 |

In the sequences listed above which include an N at position 2, that position is occupied in preferred probes/primers by a biotinylated phosphoaramidite residue rather than a nucleotide (such as, for example, that produced by use of biotin phosphoramidite (1-dimethoxytrityloxy-2-(N-biotinyl-4-aminobutyl)-propyl-3-O-(2-cyanoethyl)-(N,N-diisopropyl)-phosphoramadite) (Glen Research, cat. no. 10-1953)).

The design of the oligonucleotide probe should preferably follow these parameters:

(a) It should be designed to an area of the sequence which has the fewest ambiguous bases ("N's"), if any;

(b) It should be designed to have a $T_m$ of approx. 80° C. (assuming 2° for each A or T and 4 degrees for each G or C.).

The oligonucleotide should preferably be labeled with γ-$^{32}$P ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately 4e+6 dpm/pmole.

The bacterial culture containing the pool of full-length clones should preferably be thawed and 100 μl of the stock used to inoculate a sterile culture flask containing 25 ml of sterile L-broth containing ampicilin at 100 μg/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicilin at 100 μg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them.

The filter is then preferably incubated at 65° C. for 1 hour with gentle agitation in 6×SSC (20× stock is 175.3 g NaCl/liter, 88.2 g Na citrate/liter, adjusted to pH 7.0 with NaOH) containing 0.5% SDS, 100 μg/ml of yeast RNA, and 10 mM EDTA (approximately 10 mL per 150 mm filter). Preferably, the probe is then added to the hybridization mix at a concentration greater than or equal to 1e+6 dpm/mL. The filter is then preferably incubated at 65° C. with gentle agitation overnight. The filter is then preferably washed in 500 mL of 2×SSC/0.5% SDS at room temperature without agitation, preferably followed by 500 mL of 2×SSC/0.1% SDS at room temperature with gentle shaking for 15 minutes. A third wash with 0.1×SSC/0.5% SDS at 65° C. for 30 minutes to 1 hour is optional. The filter is then preferably dried and subjected to autoradiography for sufficient time to visualize the positives on the X-ray film. Other known hybridization methods can also be employed.

The positive colonies are picked, grown in culture, and plasmid DNA isolated using standard procedures. The clones can then be verified by restriction analysis, hybridization analysis, or DNA sequencing.

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773-778 (1992) and in R. S. McDowell, et al., J. Amer. Chem. Soc. 114,9245-9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein—IgM fusion would generate a decavalent form of the protein of the invention.

The present invention also provides both full-length and mature forms of the disclosed proteins. The full-length form of the such proteins is identified in the sequence listing by translation of the nucleotide sequence of each disclosed clone. The mature form(s) of such protein may be obtained by expression of the disclosed full-length polynucleotide (preferably those deposited with ATCC) in a suitable mammalian cell or other host cell. The sequence(s) of the mature form(s) of the protein may also be determinable from the amino acid sequence of the full-length form.

The present invention also provides genes corresponding to the polynucleotide sequences disclosed herein. "Corresponding genes" are the regions of the genome that are transcribed to produce the mRNAs from which cDNA polynucleotide sequences are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" is a gene that has been separated from the adjacent coding sequences, if any, present in the genome of the organism from which the gene was isolated.

The chromosomal location corresponding to the polynucleotide sequences disclosed herein may also be determined, for example by hybridizing appropriately labeled polynucleotides of the present invention to chromosomes in situ. It may also be possible to determine the corresponding chromosomal location for a disclosed polynucleotide by identifying significantly similar nucleotide sequences in public databases, such as expressed sequence tags (ESTs), that have already been mapped to particular chromosomal locations. For at least some of the polynucleotide sequences disclosed herein, public database sequences having at least some similarity to the polynucleotide of the present invention have been listed by database accession number. Searches using the GenBank accession numbers of these public database sequences can then be performed at an Internet site provided by the National Center for Biotechnology Information having the address http://www.ncbi.nlm.nih.gov/UniGene/, in order to identify "UniGene clusters" of overlapping sequences. Many of the "UniGene clusters" so identified will already have been mapped to particular chromosomal sites.

Organisms that have enhanced, reduced, or modified expression of the gene(s) corresponding to the polynucleotide sequences disclosed herein are provided. The desired change in gene expression can be achieved through the use of antisense polynucleotides or ribozymes that bind and/or cleave the mRNA transcribed from the gene (Albert and Morris, 1994, *Trends Pharmacol. Sci.* 15(7): 250-254; Lavarosky et al., 1997, *Biochem. Mol. Med.* 62(1): 11-22; and Hampel, 1998, *Prog. Nucleic Acid Res. Mol. Biol.* 58: 1-39; all of which are incorporated by reference herein). The desired change in gene expression can also be achieved through the use of double-stranded ribonucleotide molecules having some complementarity to the mRNA transcribed from the gene, and which interfere with the transcription, stability, or expression of the mRNA ("RNA intereference" or "RNAi"; Fire et al., 1998, *Nature* 391 (6669): 806-811; Montgomery et al., 1998, *Proc. Natl. Acad. Sci. USA* 95

(26): 15502-15507; and Sharp, 1999, *Genes Dev.* 13 (2): 139-141; all of which are incorporated by reference herein). Transgenic animals that have multiple copies of the gene(s) corresponding to the polynucleotide sequences disclosed herein, preferably produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see European Patent No. 0 649 464 B1, incorporated by reference herein). In addition, organisms are provided in which the gene(s) corresponding to the polynucleotide sequences disclosed herein have been partially or completely inactivated, through insertion of extraneous sequences into the corresponding gene(s) or through deletion of all or part of the corresponding gene(s). Partial or complete gene inactivation can be accomplished through insertion, preferably followed by imprecise excision, of transposable elements (Plasterk, 1992, *Bioessays* 14(9): 629-633; Zwaal et al., 1993, *Proc. Natl. Acad. Sci. USA* 90(16): 7431-7435; Clark et al., 1994, *Proc. Natl. Acad. Sci. USA* 91(2): 719-722; all of which are incorporated by reference herein), or through homologous recombination, preferably detected by positive/negative genetic selection strategies (Mansour et al., 1988, *Nature* 336: 348-352; U.S. Pat. Nos. 5,464,764; 5,487,992; 5,627,059; 5,631,153; 5,614,396; 5,616,491; and 5,679,523; all of which are incorporated by reference herein). These organisms with altered gene expression are preferably eukaryotes and more preferably are mammals. Such organisms are useful for the development of non-human models for the study of disorders involving the corresponding gene(s), and for the development of assay systems for the identification of molecules that interact with the protein product(s) of the corresponding gene(s).

Where the protein of the present invention is membrane-bound (e.g., is a receptor), the present invention also provides for soluble forms of such protein. In such forms, part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information. For example, the TopPredII computer program can be used to predict the location of transmembrane domains in an amino acid sequence, domains which are described by the location of the center of the transmembrane domain, with at least ten transmembrane amino acids on each side of the reported central residue(s).

Proteins and protein fragments of the present invention include proteins with amino acid sequence lengths that are at least 25% (more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

In particular, sequence identity may be determined using WU-BLAST (Washington University BLAST) version 2.0 software, which builds upon WU-BLAST version 1.4, which in turn is based on the public domain NCBI-BLAST version 1.4 (Altschul and Gish, 1996, Local alignment statistics, Doolittle ed., *Methods in Enzymology* 266: 460480; Altschul et al., 1990, Basic local alignment search tool, *Journal of Molecular Biology* 215: 403410; Gish and States, 1993, Identification of protein coding regions by database similarity search, *Nature Genetics* 3: 266-272; Karlin and Altschul, 1993, Applications and statistics for multiple high-scoring segments in molecular sequences, *Proc. Natl. Acad. Sci. USA* 90: 5873-5877; all of which are incorporated by reference herein). WU-BLAST version 2.0 executable programs for several UNIX platforms can be downloaded from ftp://blast.wust1.edu/blast/executables. The complete suite of search programs (BLASTP, BLASTN, BLASTX, TBLASTN, and TBLASTX) is provided at that site, in addition to several support programs. WU-BLAST 2.0 is copyrighted and may not be sold or redistributed in any form or manner without the express written consent of the author; but the posted executables may otherwise be freely used for commercial, nonprofit, or academic purposes. In all search programs in the suite—BLASTP, BLASTN, BLASTX, TBLASTN and TBLASTX—the gapped alignment routines are integral to the database search itself, and thus yield much better sensitivity and selectivity while producing the more easily interpreted output. Gapping can optionally be turned off in all of these programs, if desired. The default penalty (Q) for a gap of length one is Q=9 for proteins and BLASTP, and Q=10 for BLASTN, but may be changed to any integer value including zero, one through eight, nine, ten, eleven, twelve through twenty, twenty-one through fifty, fifty-one through one hundred, etc. The default per-residue penalty for extending a gap (R) is R=2 for proteins and BLASTP, and R=10 for BLASTN, but may be changed to any integer value including zero, one, two, three, four, five, six, seven, eight, nine, ten, eleven, twelve through twenty, twenty-one through fifty, fifty-one through one hundred, etc. Any combination of values for Q and R can be used in order to align sequences so as to maximize overlap and identity while minimizing sequence gaps.

The default amino acid comparison matrix is BLOSUM62, but other amino acid comparison matrices such as PAM can be utilized.

Species homologues of the disclosed polynucleotides and proteins are also provided by the present invention. As used herein, a "species homologue" is a protein or polynucleotide with a different species of origin from that of a given protein or polynucleotide, but with significant sequence similarity to the given protein or polynucleotide. Preferably, polynucleotide species homologues have at least 60% sequence identity (more preferably, at least 75% identity; most preferably at least 90% identity) with the given polynucleotide, and protein species homologues have at least 30% sequence identity (more preferably, at least 45% identity; most preferably at least 60% identity) with the given protein, where sequence identity is determined by comparing the nucleotide sequences of the polynucleotides or the amino acid sequences of the proteins when aligned so as to maximize overlap and identity while minimizing sequence gaps. Species homologues may be isolated and identified by making suitable probes or primers from the sequences provided herein and screening a suitable nucleic acid source from the desired species. Preferably, species homologues are those isolated from mammalian species. Most preferably, species homologues are those isolated from certain mammalian species such as, for example, *Pan troglodytes, Gorilla gorilla, Pongo pygmaeus, Hylobates concolor, Macaca mulatta, Papio papio, Papio hamadryas, Cercopithecus aethiops, Cebus capucinus, Aotus trivirgatus, Sanguinus oedipus, Microcebus murinus, Mus musculus, Rattus nor-*

*vegicus, Cricetulus griseus, Felis catus, Mustela vison, Canis familiaris, Oryctolagus cuniculus, Bos taurus, Ovis aries, Sus scrofa*, and *Equus caballus*, for which genetic maps have been created allowing the identification of syntenic relationships between the genomic organization of genes in one species and the genomic organization of the related genes in another species (O'Brien and Seuánez, 1988, *Ann. Rev. Genet.* 22: 323-351; O'Brien et al., 1993, *Nature Genetics* 3:103-112; Johansson et al., 1995, *Genomics* 25: 682-690; Lyons et al., 1997, *Nature Genetics* 15: 47-56; O'Brien et al., 1997, *Trends in Genetics* 13(10): 393-399; Carver and Stubbs, 1997, *Genome Research* 7:1123-1137; all of which are incorporated by reference herein).

The invention also encompasses allelic variants of the disclosed polynucleotides or proteins; that is, naturally-occurring alternative forms of the isolated polynucleotides which also encode proteins which are identical or have significantly similar sequences to those encoded by the disclosed polynucleotides. Preferably, allelic variants have at least 60% sequence identity (more preferably, at least 75% identity; most preferably at least 90% identity) with the given polynucleotide, where sequence identity is determined by comparing the nucleotide sequences of the polynucleotides when aligned so as to maximize overlap and identity while minimizing sequence gaps. Allelic variants may be isolated and identified by making suitable probes or primers from the sequences provided herein and screening a suitable nucleic acid source from individuals of the appropriate species.

The invention also includes polynucleotides with sequences complementary to those of the polynucleotides disclosed herein.

The present invention also includes polynucleotides that hybridize under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A-F; stringent conditions are at least as stringent as, for example, conditions G-L; and reduced stringency conditions are at least as stringent as, for example, conditions M-R.

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≧50 | 65° C.; 1 × SSC -or- 42° C.; 1 × SSC, 50% formamide | 65° C.; 0.3 × SSC |
| B | DNA:DNA | <50 | $T_B$*; 1 × SSC | $T_B$*; 1 × SSC |
| C | DNA:RNA | ≧50 | 67° C.; 1 × SSC -or- 45° C.; 1 × SSC, 50% formamide | 67° C.; 0.3 × SSC |
| D | DNA:RNA | <50 | $T_D$*; 1 × SSC | $T_D$*; 1 × SSC |
| E | RNA:RNA | ≧50 | 70° C; 1 × SSC -or- 50° C; 1 × SSC, 50% formamide | 70° C.; 0.3 × SSC |
| F | RNA:RNA | <50 | $T_F$*; 1 × SSC | $T_F$*; 1 × SSC |
| G | DNA:DNA | ≧50 | 65° C.; 4 × SSC -or- 42° C.; 4 × SSC, 50% formamide | 65° C.; 1 × SSC |
| H | DNA:DNA | <50 | $T_H$*;4 × SSC | $T_H$*; 4 × SSC |
| I | DNA:RNA | ≧50 | 67° C; 4 × SSC -or- 45° C.; 4 × SSC, 50% formamide | 67° C.; 1 × SSC |
| J | DNA:RNA | <50 | $T_J$*; 4 × SSC | $T_J$*; 4 × SSC |
| K | RNA:RNA | ≧50 | 70° C.; 4 × SSC -or- 50° C.; 4 × SSC, 50% formamide | 67° C; 1 × SSC |
| L | RNA:RNA | <50 | $T_L$*; 2 × SSC | $T_L$*;2 × SSC |
| M | DNA:DNA | ≧50 | 50° C.; 4 × SSC -or- 40° C.; 6 × SSC, 50% formamide | 50° C.; 2 × SSC |
| N | DNA:DNA | <50 | $T_N$*; 6 × SSC | $T_N$*; 6 × SSC |
| O | DNA:RNA | ≧50 | 55° C.; 4 × SSC -or- 42° C.; 6 × SSC, 50% formamide | 55° C.; 2 × SSC |
| P | DNA:RNA | <50 | $T_P$*; 6 × SSC | $T_P$*; 6 × SSC |
| Q | RNA:RNA | ≧50 | 60° C.; 4 × SSC -or- 45° C.; 6 × SSC, 50% formamide | 60° C.; 2 × SSC |
| R | RNA:RNA | <50 | $T_R$*; 4 × SSC | $T_R$*; 4 × SSC |

‡The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.

†SSPE (1 × SSPE is 0.15 M NaCl, 10 mM $NaH_2PO_4$, and 1.25 mM EDTA, pH 7.4) can be substituted for SSC (1 × SSC is 0.15 M NaCl and 15 mM sodium citrate) in the hybridization and wash buffers; washes are performed for 15 minutes after hybridization is complete.

*$T_B$-$T_R$: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases).For hybrids between 18 and 49 base pairs in length, $T_m$(° C.) = 81.5 + 16.6($\log_{10}[Na^+]$) + 0.41(% G + C) − (600/N), where N is the number of bases in the hybrid, and $[Na^+]$ is the concentration of sodium ions in the hybridization buffer ($[Na^+]$ for 1 × SSC = 0.165 M).

Additional examples of stringency conditions for polynucleotide hybridization are provided in Sambrook, J., E. F. Fritsch, and T. Maniatis, 1989, *Molecular Cloning: A Laboratory Manual, Cold Spring Harbor Laboratory Press, Cold Spring Harbor, N.Y., chapters* 9 and 11, and *Current Protocols in Molecular Biology,* 1995, F. M. Ausubel et al., eds., John Wiley & Sons, Inc., sections 2.10 and 6.3-6.4, incorporated herein by reference.

Preferably, each such hybridizing polynucleotide has a length that is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

The isolated polynucleotide endcoing the protein of the invention may be operably linked to an expression control sequence such as the pMT2 or pED expression vectors disclosed in Kaufman et al., Nucleic Acids Res. 19, 4485-4490 (1991), in order to produce the protein recombinantly. Many suitable expression control sequences are known in the art. General methods of expressing recombinant proteins are also known and are exemplified in R. Kaufman, Methods in Enzymology 185, 537-566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLabs (Beverly, Mass.), Pharmacia (Piscataway, N.J.) and Invitrogen Corporation (Carlsbad, Calif.), respectively. The protein can also be tagged with an epitope and subsequently purified by using a specific antibody directed to such epitope. One such epitope ("Flag") is commercially available from the Eastman Kodak Company (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

Uses and Biological Activity

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, those described in Gyuris et al., 1993, *Cell* 75: 791-803 and in Rossi et al., 1997, *Proc. Natl. Acad. Sci. USA* 94: 8405-8410, all of which are incorporated by reference herein) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Cytokine and Cell Proliferation/Differentiation Activity

A protein of the present invention may exhibit cytokine, cell proliferation (either inducing or inhibiting) or cell differentiation (either-inducing or inhibiting) activity or may induce production of other cytokines in certain cell populations. Many protein factors discovered to date, including all known cytokines, have exhibited activity in one or more factor-dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+.), 2E8, RB5, DA1, 123, T1165, HT2, CTLL2, TF-1, Mo7e and CMK.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137:3494-3500, 1986; Bertagnolli et al., J. Immunol. 145: 1706-1712, 1990; Bertagnolli et al., Cellular Immunology 133:327-341, 1991; Bertagnolli, et al., J. Immunol. 149: 3778-3783, 1992; Bowman et al., J. Immunol. 152: 1756-1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In *Current Protocols in Immunology. J. E. e.a. Coligan eds. Vol* 1 pp. 3.12.1-3.12.14, John Wiley and Sons, Toronto. 1994; and Measurement of mouse and human Interferon γ, Schreiber, R. D. In *Current Protocols in Immunology*. J. E. e.a. Coligan eds. Vol 1 pp. 6.8.1-6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In *Current Protocols in Immunology*. J. E. e.a. Coligan eds. Vol 1 pp. 6.3.1-6.3.12, John Wiley and Sons, Toronto. 1991; deVries et al., J. Exp. Med. 173:1205-1211, 1991; Moreau et al., Nature 336:690-692, 1988; Greenberger et al., Proc. Natl. Acad. Sci. U.S.A. 80:2931-2938, 1983; Measurement of mouse and human interleukin 6—Nordan, R. In *Current Protocols in Immunology*. J. E. e.a. Coligan eds. Vol 1 pp. 6.6.1-6.6.5, John Wiley and Sons, Toronto. 1991; Smith et al., Proc. Natl. Acad. Sci. U.S.A. 83:1857-1861, 1986; Measurement of human Interleukin 11—Bennett, F., Giannotti, J., Clark, S. C. and Turner, K. J. In *Current Protocols in Immunology*. J. E. e.a. Coligan eds. Vol 1 pp. 6.15.1 John Wiley and Sons, Toronto. 1991, Measurement of mouse and human Interleukin 9—Ciarletta, A., Giannotti, J., Clark, S. C. and Turner, K. J. In *Current Protocols in Immunology*. J. E. e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091-6095, 1980; Weinberger et al., Eur. J. Immun. 11:405-411, 1981; Takai et al., J. Immunol. 137:3494-3500, 1986; Takai et al., J. Immunol. 140:508-512, 1988.

Immune Stimulating or Suppressing Activity

A protein of the present invention may also exhibit immune stimulating or immune suppressing activity, including without Limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, *Leishmania* spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitis, myasthenia gravis, graft-versus-host disease and autoimmune inflammatory eye disease.

Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to regulate immune responses in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789-792 (1992) and Turka et al., Proc. Natl. Acad. Sci USA, 89:11102-11105 (1992). In addition, murine models of GVHD (see Paul ed., Fundamental Immunology, Raven Press, New York, 1989, pp. 846-847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840-856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I $\alpha$ chain protein and $\beta_2$ microglobulin protein or an MHC class $\alpha$ chain protein and an MHC class II $\beta$ chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A.M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1-3.19; Chapter 7, Immunologic studies in Humans); Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., J. Immunol. 137:3494-3500, 1986; Takai et al., J. Immunol. 140:508-512, 1988; Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., J. Immunol. 137:3494-3500, 1986; Bowmanet al., J. Virology 61:1992-1998; Takai et al., J. Immunol. 140:508-512, 1988; Bertagnolli et al., Cellular Immunology 133:327-341, 1991; Brown et al., J. Immunol. 153:3079-3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028-3033, 1990; and Assays for B cell function: In vitro antibody production, Mond, J. J. and Brunswick, M. In *Current Protocols in Immunology*. J. E. e.a. Coligan eds. Vol 1 pp. 3.8.1-3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137:3494-3500,1986; Takai et al., J. Immunol. 140:508-512, 1988; Bertagnolli et al., J. Immunol. 149:3778-3783, 1992.

Dendritic cell-dependent assays (which will identify, among others, proteins expressed by dendritic cells that activate naive T-cells) include, without limitation, those described in: Guery et al., J. Immunol. 134:536-544, 1995; Inaba et al., Journal of Experimental Medicine 173:549-559, 1991; Macatonia et al., Journal of Immunology 154:5071-5079, 1995; Porgador et al., Journal of Experimental Medicine 182:255-260, 1995; Nair et al., Journal of Virology 67:4062-4069, 1993; Huang et al., Science 264:961-965, 1994; Macatonia et al., Journal of Experimental Medicine 169:1255-1264,1989; Bhardwaj et al., Journal of Clinical Investigation 94:797-807, 1994; and Inaba et al., Journal of Experimental Medicine 172:631-640,1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795-808, 1992; Gorczyca et al., Leukemia 7:659-670, 1993; Gorczyca et al., Cancer Research 53:1945-1951, 1993; Itoh et al., Cell 66:233-243, 1991; Zacharchuk, Journal of Immunology 145:40374045, 1990; Zamai et al., Cytometry 14:891-897, 1993; Gorczyca et al., International Journal of Oncology 1:639-648,1992.

Assays for proteins that influence early steps of T-cell commitment and development include, without limitation, those described in: Antica et al., Blood 84:111-117, 1994; Fine et al., Cellular Immunology 155:111-122, 1994; Galy et al., Blood 85:2770-2778, 1995; Toki et al., Proc. Nat. Acad. Sci. USA 88:7548-7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141-151, 1995; Keller et al., Molecular and Cellular Biology 13:473-486, 1993; McClanahan et al., Blood 81:2903-2915, 1993.

Assays for stem cell survival and differentiation (which will identify, among others, proteins that regulate lympho-hematopoiesis) include, without limitation, those described in: Methylcellulose colony forming assays, Freshney, M. G. In *Culture of Hematopoietic Cells*. R. I. Freshney, et al. eds. Vol pp. 265-268, Wiley-Liss, Inc., New York, N.Y. 1994; Hirayama et al., Proc. Natl. Acad. Sci. USA 89:5907-5911, 1992; Primitive hematopoietic colony forming cells with high proliferative potential, McNiece, I. K. and Briddell, R. A. In *Culture of Hematopoietic Cells*. R. I. Freshney, et al. eds. Vol pp. 23-39, Wiley-Liss, Inc., New York, N.Y. 1994; Neben et al., Experimental Hematology 22:353-359, 1994; Cobblestone area forming cell assay, Ploemacher, R. E. In *Culture of Hematopoietic Cells*. R. I. Freshney, et al. eds. Vol pp. 1-21, Wiley-Liss, Inc., New York, N.Y. 1994; Long term bone marrow cultures in the presence of stromal cells, Spooncer, E., Dexter, M. and Allen, T. In *Culture of Hematopoietic Cells*. R. I. Freshney, et al. eds. Vol pp. 163-179, Wiley-Liss, Inc., New York, N.Y. 1994; Long term culture initiating cell assay, Sutherland, H. J. In *Culture of Hematopoietic Cells*. R. I. Freshney, et al. eds. Vol pp. 139-162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein or the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, *Epidermal Wound Healing* pps. 71-112 (Maibach, H I and Rovee, D T, eds.), Year Book Medical Publishers, Inc., Chicago, as modified by Eaglstein and Mertz, J. Invest. Dermatol 71:382-84 (1978).

Activin/Inhibin Activity

A protein of the present invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin a family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562-572, 1972; Ling et al., Nature 321:779-782, 1986; Vale et al., Nature 321:776-779, 198%; Mason et al., Nature 318:659-663, 1985; Forage et al., Proc. Natl. Acad. Sci. USA 83:3091-3095, 1986.

Chemotactic /Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 6.12, Measurement of alpha and beta Chemokines 6.12.1-6.12.28; Taub et al. J. Clin. Invest. 95:1370-1376, 1995; Lind et al. APMIS 103:140-146, 1995; Muller et al Eur. J. Immunol. 25: 1744-1748; Gruber et al. J. of Immunol. 152:5860-5867, 1994; Johnston et al. J. of Immunol. 153: 1762-1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131-140, 1986; Burdick et al., Thrombosis Res. 45: 413-419, 1987; Humphrey et al., Fibrinolysis 5:71-79 (1991); Schaub, Prostaglandins 35:467-474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectin, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1-7.28.22), Takai et al., Proc. Natl. Acad. Sci. USA 84:6864-6868, 1987; Bierer et al., J. Exp. Med. 168:1145-1156, 1988; Rosenstein et al., J. Exp. Med. 169:149-160 1989; Stoltenborg et al., J. Immunol. Methods 175:59-68, 1994; Stitt et al., Cell 80:661-670, 1995.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Cadherin/Tumor Invasion Suppressor Activity

Cadherins are calcium-dependent adhesion molecules that appear to play major roles during development, particularly in defining specific cell types. Loss or alteration of normal cadherin expression can lead to changes in cell adhesion properties linked to tumor growth and metastasis. Cadherin malfunction is also implicated in other human diseases, such as pemphigus vulgaris and pemphigus foliaceus (auto-immune blistering skin diseases), Crohn's disease, and some developmental abnormalities.

The cadherin superfamily includes well over forty members, each with a distinct pattern of expression. All members of the superfamily have in common conserved extracellular repeats (cadherin domains), but structural differences are found in other parts of the molecule. The cadherin domains bind calcium to form their tertiary structure and thus calcium is required to mediate their adhesion. Only a few amino acids in the first cadherin domain provide the basis for homophilic adhesion; modification of this recognition site can change the specificity of a cadherin so that instead of recognizing only itself, the mutant molecule can now also bind to a different cadherin. In addition, some cadherins engage in heterophilic adhesion with other cadherins.

E-cadherin, one member of the cadherin superfamily, is expressed in epithelial cell types. Pathologically, if E-cadherin expression is lost in a tumor, the malignant cells become invasive and the cancer metastasizes. Transfection of cancer cell lines with polynucleotides expressing E-cadherin has reversed cancer-associated changes by returning altered cell shapes to normal, restoring cells' adhesiveness to each other and to their substrate, decreasing the cell growth rate, and drastically reducing anchorage-independent cell growth. Thus, reintroducing E-cadherin expression reverts carcinomas to a less advanced stage. It is likely that other cadherins have the same invasion suppressor role in carcinomas derived from other tissue types. Therefore, proteins of the present invention with cadherin activity, and polynucleotides of the present invention encoding such proteins, can be used to treat cancer. Introducing such proteins or polynucleotides into cancer cells can reduce or eliminate the cancerous changes observed in these cells by providing normal cadherin expression.

Cancer cells have also been shown to express cadherins of a different tissue type than their origin, thus allowing these cells to invade and metastasize in a different tissue in the body. Proteins of the present invention with cadherin activity, and polynucleotides of the present invention encoding such proteins, can be substituted in these cells for the inappropriately expressed cadherins, restoring normal cell adhesive properties and reducing or eliminating the tendency of the cells to metastasize.

Additionally, proteins of the present invention with cadherin activity, and polynucleotides of the present invention encoding such proteins, can used to generate antibodies recognizing and binding to cadherins. Such antibodies can be used to block the adhesion of inappropriately expressed tumor-cell cadherins, preventing the cells from forming a tumor elsewhere. Such an anti-cadherin antibody can also be used as a marker for the grade, pathological type, and prognosis of a cancer, i.e. the more progressed the cancer, the less cadherin expression there will be, and this decrease in cadherin expression can be detected by the use of a cadherin-binding antibody.

Fragments of proteins of the present invention with cadherin activity, preferably a polypeptide comprising a decapeptide of the cadherin recognition site, and polynucleotides of the present invention encoding such protein fragments, can also be used to block cadherin function by binding to cadherins and preventing them from binding in ways that produce undesirable effects. Additionally, fragments of proteins of the present invention with cadherin activity, preferably truncated soluble cadherin fragments which have been found to be stable in the circulation of cancer patients, and polynucleotides encoding such protein fragments, can be used to disturb proper cell-cell adhesion.

Assays for cadherin adhesive and invasive suppressor activity include, without limitation, those described in: Hortsch et al. J Biol Chem 270 (32): 18809-18817, 1995; Miyaki et al. Oncogene 11: 2547-2552, 1995; Ozawa et al. Cell 63: 1033-1038, 1990.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via antibody-dependent cell-mediated cytotoxicity (ADCC)). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

Administration and Dosing

A protein of the present invention (from whatever source derived, including without limitation from recombinant and non-recombinant sources) may be used in a pharmaceutical composition when combined with a pharmaceutically acceptable carrier. Such a composition may also contain (in addition to protein and a carrier) diluents, fillers, salts, buffers, stabilizers, solubilizers, and other materials well known in the art. The term “pharmaceutically acceptable” means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A protein of the present invention may be active in multimers (e.g., heterodimers or homodimers) or complexes with itself or other proteins. As a result, pharmaceutical compositions of the invention may comprise a protein of the invention in such multimeric or complexed form.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other sacchande solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 μg to about 100 mg (preferably about 0.1 μg to about 10 mg, more preferably about 0.1 μg to about 1 mg) of protein of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Protein of the invention may also be used to immunize animals to obtain polyclonal and monoclonal antibodies which specifically react with the protein. As used herein, the term "antibody" includes without limitation a polyclonal antibody, a monoclonal antibody, a chimeric antibody, a single-chain antibody, a CDR-grafted antibody, a humanized antibody, or fragments thereof which bind to the indicated protein. Such term also includes any other species derived from an antibody or antibody sequence which is capable of binding the indicated protein.

Antibodies to a particular protein can be produced by methods well known to those skilled in the art. For example, monoclonal antibodies can be produced by generation of antibody-producing hybridomas in accordance with known methods (see for example, Goding, 1983, Monoclonal antibodies: principles and practice, Academic Press Inc., New York; and Yokoyama, 1992, "Production of Monoclonal Antibodies" in Current Protocols in Immunology, Unit 2.5, Greene Publishing Assoc. and John Wiley & Sons). Polyclonal sera and antibodies can be produced by inoculation of a mammalian subject with the relevant protein or fragments thereof in accordance with known methods. Fragments of antibodies, receptors, or other reactive peptides can be produced from the corresponding antibodies by cleavage of and collection of the desired fragments in accordance with known methods (see for example, Goding, supra; and Andrew et al., 1992, "Fragmentation of Immunoglobulins" in Current Protocols in Immunology, Unit 2.8, Greene Publishing Assoc. and John Wiley & Sons). Chimeric antibodies and single chain antibodies can also be produced in accordance with known recombinant methods (see for example, U.S. Pat. Nos. 5,169,939, 5,194,594, and 5,576,184). Humanized antibodies can also be made from corresponding murine antibodies in accordance with well known methods (see for example, U.S. Pat. Nos. 5,530,101, 5,585,089, and 5,693,762). Additionally, human antibodies may be produced in non-human animals such as mice that have been genetically altered to express human antibody molecules (see for example Fishwild et al., 1996, *Nature Biotechnology* 14: 845-851; Mendez et al., 1997, *Nature Genetics* 15: 146-156 (erratum *Nature Genetics* 16: 410); and U.S. Pat. Nos. 5,877,397 and 5,625,126). Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer.Chem.Soc. 85, 2149-2154 (1963); J. L. Krstenansky, et al., FEBS Lett. 211, 10 (1987).

Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5-20 wt %, preferably 1-10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells.

In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-$\alpha$ and TGF-$\beta$), and insulin-like growth factor (IGF).

The therapeutic compositions are also presently valuable for veterinary applications. Particularly domestic animals and thoroughbred horses, in addition to humans, are desired patients for such treatment with proteins of the present invention.

The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of proteins of the present invention in order to proliferate or to produce a desired effect on or activity in such cells. Treated cells can then be introduced in vivo for therapeutic purposes.

Patent and literature references cited herein are incorporated by reference as if fully set forth.

What is claimed is:

1. An isolated polynucleotide selected from the group consisting of:

(a) a polynucleotide comprising the nucleotide sequence of SEQ ID NO:155;

(b) a polynucleotide comprising the nucleotide sequence of SEQ ID NO:155 from nucleotide 110 to nucleotide 742;

(c) a polynucleotide comprising the nucleotide sequence of SEQ ID NO:155 from nucleotide 170 to nucleotide 742; and (d) a polynucleotide encoding a protein comprising the amino acid sequence of SEQ ID NO:156.

2. The polynucleotide of claim 1, wherein said polynucleotide is operably linked to at least one expression control sequence.

3. An isolated host cell transformed with the polynucleotide of claim 2.

4. The host cell of claim 3, wherein said cell is a mammalian cell.

5. A process for producing a protein encoded by the polynucleotide of claim 2, which process comprises:

(a) growing a culture of a host cell in a suitable culture medium, wherein the host cell has been transformed with said polynucleotide; and (b) purifying said protein from the culture.

* * * * *

SEQUENCE LISTING

```
<160> NUMBER OF SEQ ID NOS: 240

<210> SEQ ID NO 1
<211> LENGTH: 1925
<212> TYPE: DNA
<213> ORGANISM: Homo sapiens

<400> SEQUENCE: 1

aggtcgtcac agacgatgat ggccaggccc cggaggctaa ggacggcagc tcctttagcg     60

gcagagtttt ccgagtgacc ttcttgatgc tggctgtttc tctcaccgtt cccctgcttg    120

gagccatgat gctgctggaa tctcctatag atccacagcc tctcagcttc aaagaacccc    180

cgctcttgct tggtgttctg catccaaata cgaagctgcg acaggcagaa aggctgtttg    240

aaaatcaact tgttggaccg gagtccatag cacatattgg ggatgtgatg tttactggga    300

cagcagatgg cccggtcgta aaacttgaaa atggtgaaat agagaccatt gcccggtttg    360

gttcgggccc ttgcaaaacc cgagatgatg agcctgtgtg tgggagaccc ctgggtatcc    420

gtgcagggcc caatgggact ctctttgtgg ccgatgcata caagggacta tttgaagtaa    480

atccctggaa acgtgaagtg aaactgctgc tgtcctccga gacacccatt gaggggaaga    540

acatgtcctt tgtgaatgat cttacagtca ctcaggatgg gaggaagatt tatttcaccg    600

attctagcag caaatggcaa agacgagact acctgcttct ggtgatggag ggcacagatg    660

acgggcgcct gctggagtat gatactgtga ccagggaagt aaaagtttta ttggaccagc    720

tgcggttccc gaatggagtc cagctgtctc ctgcagaaga ctttgtcctg gtggcagaaa    780

caaccatggc caggatacga agctctttag tcaagagacg gtgatgaagt ttgtgccgcg    840

gtacagcctc gtcctagaac tcagcgacag cggtgccttc cggagaagcc tgcatgatcc    900

cgatgggctg gtggccacct acatcaccga ggtgcacgaa cacgatgggc acctgtacct    960

gggctctttc aggtccccct tcctctgcag actcagcctc caggctgttt agccctccca   1020

gatagctgcc cctgccacgc aggccaggag tcttcacact caggcaccag gcctggtcca   1080

ggaggagctg tggacacagt cgtggttcaa gtgtccacat gcacctgtta gtccctgaga   1140

ggtggtggga atggctgctt cattcctcga ggatgcccgg gccccacctg ggcttgtctt   1200

tctgtttaga gggaagtgta acatatctgc catgaggaac ataaattcat gtaaagccat   1260

tttctcttaa acaaaacaaa actttctaag tacaatcatt ctctaggatt tgggaagctc   1320

cttgcacttg gaacagggct caggtgggtg gagcagtaag gcactaccca gagagcttgc   1380

tgctgcggcc ctgtcctgcg gcctcaaagt tcttctttac tatatataac gtgcggtcat   1440

acctttcttc gttgtggtgg ggatggaaga gcagagggag catggcccag ggtgttgag    1500

gccagcggtg agagccgtgt tagccaagac atggaactgt gttctcaagg gttatgtggg   1560
```

-continued

```
gcgtgggctc tccatagtgt gtatgaaaag cttgttgact ctagcggctc agagaggact   1620

ttgctgggtt tctttctgtg aatatctccg tgctgaccat gctggaattg gatgattctg   1680

caattcggga cctactgcag gggtccgttt agtaacgtct tgtctgtgat ctttgttctt   1740

gacctctaga ccccaagatg tgaacagtgc acgtgttaat gtcatctttg ctcatgtgtt   1800

ataagcccca agttgctgta tattttcaca agtatgtcta cacactggtc atgattttga   1860

taataaataa cgataaatcg acttctgctg attaaccttt aaaaaaaaaa aaaaaaaaaa   1920

aaaaa                                                                1925
```

<210> SEQ ID NO 2
<211> LENGTH: 245
<212> TYPE: PRT
<213> ORGANISM: Homo sapiens

<400> SEQUENCE: 2

```
Met Leu Ala Val Ser Leu Thr Val Pro Leu Leu Gly Ala Met Met Leu
  1               5                  10                  15

Leu Glu Ser Pro Ile Asp Pro Gln Pro Leu Ser Phe Lys Glu Pro Pro
             20                  25                  30

Leu Leu Leu Gly Val Leu His Pro Asn Thr Lys Leu Arg Gln Ala Glu
         35                  40                  45

Arg Leu Phe Glu Asn Gln Leu Val Gly Pro Glu Ser Ile Ala His Ile
     50                  55                  60

Gly Asp Val Met Phe Thr Gly Thr Ala Asp Gly Pro Val Val Lys Leu
 65                  70                  75                  80

Glu Asn Gly Glu Ile Glu Thr Ile Ala Arg Phe Gly Ser Gly Pro Cys
                 85                  90                  95

Lys Thr Arg Asp Asp Glu Pro Val Cys Gly Arg Pro Leu Gly Ile Arg
            100                 105                 110

Ala Gly Pro Asn Gly Thr Leu Phe Val Ala Asp Ala Tyr Lys Gly Leu
        115                 120                 125

Phe Glu Val Asn Pro Trp Lys Arg Glu Val Lys Leu Leu Leu Ser Ser
    130                 135                 140

Glu Thr Pro Ile Glu Gly Lys Asn Met Ser Phe Val Asn Asp Leu Thr
145                 150                 155                 160

Val Thr Gln Asp Gly Arg Lys Ile Tyr Phe Thr Asp Ser Ser Ser Lys
                165                 170                 175

Trp Gln Arg Arg Asp Tyr Leu Leu Leu Val Met Glu Gly Thr Asp Asp
            180                 185                 190

Gly Arg Leu Leu Glu Tyr Asp Thr Val Thr Arg Glu Val Lys Val Leu
        195                 200                 205

Leu Asp Gln Leu Arg Phe Pro Asn Gly Val Gln Leu Ser Pro Ala Glu
    210                 215                 220

Asp Phe Val Leu Val Ala Glu Thr Thr Met Ala Arg Ile Arg Ser Ser
225                 230                 235                 240

Leu Val Lys Arg Arg
                245
```

<210> SEQ ID NO 3
<211> LENGTH: 3508
<212> TYPE: DNA
<213> ORGANISM: Homo sapiens

<400> SEQUENCE: 3

```
gagcgaacat ggcagcgcgt tggcggtttt ggtgtgtctc tgtgaccatg gtggtggcgc     60
```

-continued

```
tgctcatcgt ttgcgacgtt ccctcagcct ctgcccaaag aaagaaggag atggtgttat    120
ctgaaaaggt tagtcagctg atggaatgga ctaacaaaag acctgtaata agaatgaatg    180
gagacaagtt ccgtcgcctt gtgaaagccc caccgagaaa ttactccgtt atcgtcatgt    240
tcactgctct ccaactgcat agacagtgtg tcgtttgcaa gcaagctgat gaagaattcc    300
agatcctggc aaactcctgg cgatactcca gtgcattcac caacaggata ttttttgcca    360
tggtggattt tgatgaaggc tctgatgtat ttcagatgct aaacatgaat tcagctccaa    420
ctttcatcaa ctttcctgca aaagggaaac ccaaacgggg tgatacatat gagttacagg    480
tgcggggttt ttcagctgag cagattgccc ggtggatcgc cgacagaact gatgtcaata    540
ttagagtgat tagacccccca aattatgctg gtccccttat gttgggattg cttttggctg    600
ttattggtgg acttgtgtat cttcgaagaa gtaatatgga atttctcttt aataaaactg    660
gatgggcttt tgcagctttg tgttttgtgc ttgctatgac atctggtcaa atgtggaacc    720
atataagagg accaccatat gcccataaga atccccacac gggacatgtg aattatatcc    780
atggaagcag tcaagcccag tttgtagctg aaacacacat tgttcttctg tttaatggtg    840
gagttacctt aggaatggtg cttttatgtg aagctgctac ctctgacatg gatattggaa    900
agcgaaagat aatgtgtgtg gctggtattg gacttgttgt attattcttc agttggatgc    960
tctctatttt tagatctaaa tatcatggct acccatacag ctttctgatg agttaaaaag   1020
gtcccagaga tatatagaca ctggagtact ggaaattgaa aaacgaaaat cgtgtgtgtt   1080
tgaaaagaag aatgcaactt gtatattttg tattacctct tttttttca agtgatttaa   1140
atagttaatc atttaaccaa agaagatgtg tagtgcctta acaagcaatc ctctgtcaaa   1200
atctgaggta tttgaaaata attatcctct taaccttctc ttcccagtga actttatgga   1260
acatttaatt tagtacaatt aagtatatta taaaaattgt aaaactacta ctttgtttta   1320
gttagaacaa agctcaaaac tactttagtt aacttggtca tctgatttta tattgcctta   1380
tccaaagatg ggaaagtaa gtcctgacca ggtgttccca catatgcctg ttacagataa   1440
ctacattagg aattcattct tagcttcttc atctttgtgt ggatgtgtat actttacgca   1500
tctttccttt tgagtagaga aattatgtgt gtcatgtggt cttctgaaaa tggaacacca   1560
ttcttcagag cacacgtcta gccctcagca agacagttgt ttctcctcct ccttgcatat   1620
ttcctactga aatacagtgc tgtctatgat tgtttttgtt ttgttgtttt tttgagacgg   1680
tctcgctgtg tcacacaggc ggagattgca gtgagccgag atcacgctac tgcgctcagc   1740
ctgagtgata gagtgagact ctgtctcaaa aaaaagtatc tctaaataca ggattataat   1800
ttctgcttga gtatggtgtt aactaccttg tatttagaaa gatttcagat tcattccatc   1860
tccttagttt tcttttaagg tgacccatct gtgataaaaa tatagcttag tgctaaaatc   1920
agtgtaactt atacatggcc taaaatgttt ctacaaatta gagtttgtca cttattccat   1980
ttgtacctaa gagaaaaata tgctcagtta gaaaaggact ccctggccag gcgcagtgac   2040
ttacgcctgt tatctcagca ctttgggagg ccaaggcagg cagatcacga ggtcaggagt   2100
tcgagaccat cctggccaac atggtgaaac cccgtctcta ctaaaaaatat aaaaaattagc   2160
tgggtgtggt ggcaggagcc tgtaatccca gctacacagg aggctgaggc acgagaatca   2220
cttgaactca gggagatgga ggtttcagtg agccaagatc acaccactgc actccagcct   2280
ggcaacagag cgagaattcc atctcaaaaa aaaaaaaaaa agtaagaaaa gaaaaggact   2340
cccttagaat gggaaagaaa aatcataaaa tattgagctg aagcctgtat atagaaatta   2400
```

-continued

```
agcgtttctc gaaagctgtt ctatgttctg ccgttattta gtctttattc tcttccttga   2460

ggtggagaaa caaagtacca atttgaaggg attttttta ttttgtcttt tggtttctgt   2520

cagtagaaat aaccatatgt gctaaccaaa tttctgtgaa gaatgttttc atggttatca   2580

ttatatctaa ctataacctc ccccatagtt atgaagagta acctgaaatg ccactattgt   2640

ggaaatagga taattgtaat tgtgaaaaaa taattttaag gaaatcttac aagtattaca   2700

ttaaaaagat actatgactg ccacctgcca tttaccttct aataaccctg ccatgtggtt   2760

tgcagaaaga gatggatata gtagcctcag aagaaatatt ttatgtgggt tttttgtttt   2820

tcgttactag atttcttgga tgaggggtta tggttgacct tttacttttt aatggagcag   2880

ccagtttttg ttaattactc acttgtaaat tgtgagattc tgaattcctt acctgctatt   2940

cttgtacttg tctcaggcca aatctatgct gtggttctta tgagacttgt atgaagatgc   3000

cctgatttgt acagattgac cacgggaata ctactgccat gtaatctgta tagttccaga   3060

taatttgtca tgaacattga cagaatgaca attttttgta tttgcttttt ctccctttaa   3120

gagcacattc ttctgtaagg agaaaggcag cattctggct aaaatgtgta gaaggtaatt   3180

tactacactt ataaaatagt gtgacttttg tgaaaatttt gaattagctt tcatatgaag   3240

tgccttaagt agactcttca tttacttttc tggtaatggt ttaaatatca tttgttatgc   3300

atttttaaga tacagttcag aatgacacat tgtagtggca aagataacca aatgtctggc   3360

tgtttgcttt ttgaccatat caataaactt ttacaatctt aaaaaaaaaa aaaaaaaaaa   3420

aaaaaaaaaa aaaaaaaaaa aaaaaaaaaa aaaaaaaaaa aaaaaaaaaa aaaaaaaaaa   3480

aaaaaaaaaa aaaaaaaaaa aaaaaaaa                                      3508
```

```
<210> SEQ ID NO 4
<211> LENGTH: 335
<212> TYPE: PRT
<213> ORGANISM: Homo sapiens

<400> SEQUENCE: 4

Met Ala Ala Arg Trp Arg Phe Trp Cys Val Ser Val Thr Met Val Val
  1               5                  10                  15

Ala Leu Leu Ile Val Cys Asp Val Pro Ser Ala Ser Ala Gln Arg Lys
             20                  25                  30

Lys Glu Met Val Leu Ser Glu Lys Val Ser Gln Leu Met Glu Trp Thr
         35                  40                  45

Asn Lys Arg Pro Val Ile Arg Met Asn Gly Asp Lys Phe Arg Arg Leu
     50                  55                  60

Val Lys Ala Pro Pro Arg Asn Tyr Ser Val Ile Val Met Phe Thr Ala
 65                  70                  75                  80

Leu Gln Leu His Arg Gln Cys Val Val Cys Lys Gln Ala Asp Glu Glu
                 85                  90                  95

Phe Gln Ile Leu Ala Asn Ser Trp Arg Tyr Ser Ser Ala Phe Thr Asn
            100                 105                 110

Arg Ile Phe Phe Ala Met Val Asp Phe Asp Glu Gly Ser Asp Val Phe
        115                 120                 125

Gln Met Leu Asn Met Asn Ser Ala Pro Thr Phe Ile Asn Phe Pro Ala
    130                 135                 140

Lys Gly Lys Pro Lys Arg Gly Asp Thr Tyr Glu Leu Gln Val Arg Gly
145                 150                 155                 160

Phe Ser Ala Glu Gln Ile Ala Arg Trp Ile Ala Asp Arg Thr Asp Val
                165                 170                 175
```

-continued

```
Asn Ile Arg Val Ile Arg Pro Pro Asn Tyr Ala Gly Pro Leu Met Leu
            180                 185                 190

Gly Leu Leu Leu Ala Val Ile Gly Gly Leu Val Tyr Leu Arg Arg Ser
        195                 200                 205

Asn Met Glu Phe Leu Phe Asn Lys Thr Gly Trp Ala Phe Ala Ala Leu
    210                 215                 220

Cys Phe Val Leu Ala Met Thr Ser Gly Gln Met Trp Asn His Ile Arg
225                 230                 235                 240

Gly Pro Pro Tyr Ala His Lys Asn Pro His Thr Gly His Val Asn Tyr
                245                 250                 255

Ile His Gly Ser Ser Gln Ala Gln Phe Val Ala Glu Thr His Ile Val
            260                 265                 270

Leu Leu Phe Asn Gly Gly Val Thr Leu Gly Met Val Leu Leu Cys Glu
        275                 280                 285

Ala Ala Thr Ser Asp Met Asp Ile Gly Lys Arg Lys Ile Met Cys Val
    290                 295                 300

Ala Gly Ile Gly Leu Val Val Leu Phe Phe Ser Trp Met Leu Ser Ile
305                 310                 315                 320

Phe Arg Ser Lys Tyr His Gly Tyr Pro Tyr Ser Phe Leu Met Ser
                325                 330                 335
```

<210> SEQ ID NO 5
<211> LENGTH: 1697
<212> TYPE: DNA
<213> ORGANISM: Homo sapiens

<400> SEQUENCE: 5

```
ttcaatgaaa acgagggggg cgcggaggag gaggcggcgg cgtcggtggc ggcggcgacg     60

gcggcgcgga ggcgaaggca gcggcgggcg cagcgaggag ggcgaggccg ggggccgaga    120

gggcgggagg gcgtagtggc ggcccgtcgg ggcggctgag gcgggcagcc gaagcagtgg    180

ctctcggagg gggaacaaag agcagcgact aaggcggcag aggagcggcg gcggtggcgg    240

cgctgcagca gcgggcggga ctggtatggt ggttccacag ggcagacccc gctgcactca    300

cagggaggag gaggcggcag cggcggagga aggcggcgca ccccgagagg catgcccaaa    360

gaaaaatacg agccccctga ccctcggagg atgtatacaa ttatgtcttc tgaggaagca    420

gcaaatggaa agaaatccca ctgggcagag cttgaaataa gtggaaaagt aagaagctta    480

agcgcatctt tgtggtcact aactcacctg acagctttgc atttgagtga caattccctg    540

tcccgaattc cttcagacat tgccaagctt cacaatctgg tgtatttgga cctgtcatct    600

aataaaattc gtagcttacc cgcagaactc ggaaacatgg tatcactcag ggagctccat    660

ttaaataaca acctgttacg agttctacct tttgagctgg gaaaactgtt tcagttgcag    720

actttaggcc tgaaaggtat gacttccata tttgtacttc ttatggtttg tgtatatgtc    780

tttgaatcta aggaagccaa gaagctttct gctaggggat tcttttaaag actcattttc    840

ccccagactt catcagtttc ttagctatat cgcaatggtt ttatcttctc tgttcagctg    900

tagactatct actagtcttt gttttctttt tttttgctcc ggacccagcc cttcttttct    960

agcctctgtt ttaatgaacc ctgtgttctg gtgatacatc cctgaggcta tgctttattt   1020

catcatgtta taaacagctg tttttcttag attcaaatct caaaaaacat ggagcctctc   1080

atatagtaca gaaaacagga agtcgaaaat gttgaccatt tgaacctgct gatgatcaag   1140

atttaagcat atttaaaaaa acttgattta tgaggacttg tgattatagg gccataattg   1200

atccagcaag aactattagg aaataaatat tttttaagcc aacaatattg aaagttatat   1260
```

```
tttgacagta tgtcaatgcc tataaatttt ttatcatgtt aagcagttct tcaccagcct   1320

tgggtaggtg tgtctagcct actgtacagt tgcttcttca aaaaagtcac tagatgaagt   1380

cgtcaagatt tgcaccctta ggccgggcac agtggctcac acctgtaatc acaaaacttt   1440

gggaggctga ggtgggtgga tatcttgagg ccaagagttc aagaccagca tgagcaacat   1500

ggcaaaaccc aatctctacc aaaaatacaa aagtcagctt ggcatggtgg ttcccacctg   1560

tagtaccacc tacttgggag gctgaggcat gagatttgct tgaacctggg aagcagaggt   1620

tgaagtgagg tgacattgtg gcattgcact ccagcctggg tgacagagcg agactctgtc   1680

ttaaaaaaaa aaaaaaa                                                  1697
```

```
<210> SEQ ID NO 6
<211> LENGTH: 158
<212> TYPE: PRT
<213> ORGANISM: Homo sapiens

<400> SEQUENCE: 6

Met Pro Lys Glu Lys Tyr Glu Pro Pro Asp Pro Arg Arg Met Tyr Thr
  1               5                  10                  15

Ile Met Ser Ser Glu Glu Ala Ala Asn Gly Lys Lys Ser His Trp Ala
             20                  25                  30

Glu Leu Glu Ile Ser Gly Lys Val Arg Ser Leu Ser Ala Ser Leu Trp
         35                  40                  45

Ser Leu Thr His Leu Thr Ala Leu His Leu Ser Asp Asn Ser Leu Ser
     50                  55                  60

Arg Ile Pro Ser Asp Ile Ala Lys Leu His Asn Leu Val Tyr Leu Asp
 65                  70                  75                  80

Leu Ser Ser Asn Lys Ile Arg Ser Leu Pro Ala Glu Leu Gly Asn Met
                 85                  90                  95

Val Ser Leu Arg Glu Leu His Leu Asn Asn Asn Leu Leu Arg Val Leu
            100                 105                 110

Pro Phe Glu Leu Gly Lys Leu Phe Gln Leu Gln Thr Leu Gly Leu Lys
        115                 120                 125

Gly Met Thr Ser Ile Phe Val Leu Leu Met Val Cys Val Tyr Val Phe
    130                 135                 140

Glu Ser Lys Glu Ala Lys Lys Leu Ser Ala Arg Gly Phe Phe
145                 150                 155
```

```
<210> SEQ ID NO 7
<211> LENGTH: 1462
<212> TYPE: DNA
<213> ORGANISM: Homo sapiens

<400> SEQUENCE: 7

gctagccgcc tgggaattta agggacccac actaccttcc cgaagttgaa ggcaagcggt     60

gattgtttgt agacggcgct ttgtcatggg acctgtgcgg ttgggaatat tgcttttcct    120

tttttggcc gtgcacgagg cttgggctgg gatgttgaag gaggaggacg atgacacaga     180

acgcttgccc agcaaatgcg aagtgtgtaa gctgctgagc acagagctac aggcggaact    240

gagtcgcacc ggtcgatctc gagaggtgct ggagctgggg caggtgctgg atacaggcaa    300

gaggaagaga cacgtgcctt acagcgtttc agagacaagg ctggaagagg ccttagagaa    360

tttatgtgag cggatcctgg actatagtgt tcacgctgag cgcaagggct cactgagata    420

tgccaagggt cagagtcaga ccatggcaac actgaaaggc ctagtgcaga agggggtgaa    480
```

-continued

```
ggtggatctg gggatccctc tggagctttg ggatgagccc agcgtggagg tcacatacct    540

caagaagcag tgtgagacca tgttggagga gtttgaagac attgtgggag actggtactt    600

ccaccatcag gagcagcccc tacaaaattt tctctgtgaa ggtcatgtgc tcccagctgc    660

tgaaactgca tgtctacagg aaacttggac tggaaaggag atcacagatg ggaagagaa     720

aacagaaggg gaggaagagc aggaggagga ggaggaagag gaggaagagg aagggggaga    780

caagatgacc aagacaggaa gccaccccaa acttgaccga gaagatcttt gacccttgcc    840

tttgagcccc caggaggga agggatcatg gagagccctc taaagcctgc actctccctg     900

ctccacagct ttcagggtgt gtttatgagt gactccaccc aagcttgtag ctgttctctc    960

ccatctaacc tcaggcaaga tcctggtgaa acagcatgac atggcttctg gggtggaggg   1020

tgggggtgga ggtcctgctc ctagagatga actctatcca gccccttaat tggcaggtgt   1080

atgtgctgac agtactgaaa gctttcctct ttaactgatc ccaccccccac ccaaaagtca  1140

gcagtggcac tggagctgtg ggctttgggg aagtcactta gctccttaag gtctgttttt   1200

agacccttcc aaggaagagg ccagaacgga cattctctgc gatctatata cattgcctgt   1260

atccaggagg ctacacacca gcaaaccgtg aaggagaatg ggacactggg tcatggcctg   1320

gagttgctga taatttaggt gggatagata cttggtctac ttaagctcaa tgtaacccag   1380

agcccaccat atagttttat aggtgctcaa ttttctatat cgctattaaa ctttttttctt  1440

tttttctaaa aaaaaaaaaa aa                                            1462


<210> SEQ ID NO 8
<211> LENGTH: 248
<212> TYPE: PRT
<213> ORGANISM: Homo sapiens

<400> SEQUENCE: 8

Met Gly Pro Val Arg Leu Gly Ile Leu Leu Phe Leu Phe Leu Ala Val
1               5                   10                  15

His Glu Ala Trp Ala Gly Met Leu Lys Glu Glu Asp Asp Asp Thr Glu
            20                  25                  30

Arg Leu Pro Ser Lys Cys Glu Val Cys Lys Leu Leu Ser Thr Glu Leu
        35                  40                  45

Gln Ala Glu Leu Ser Arg Thr Gly Arg Ser Arg Glu Val Leu Glu Leu
    50                  55                  60

Gly Gln Val Leu Asp Thr Gly Lys Arg Lys Arg His Val Pro Tyr Ser
65                  70                  75                  80

Val Ser Glu Thr Arg Leu Glu Glu Ala Leu Glu Asn Leu Cys Glu Arg
                85                  90                  95

Ile Leu Asp Tyr Ser Val His Ala Glu Arg Lys Gly Ser Leu Arg Tyr
            100                 105                 110

Ala Lys Gly Gln Ser Gln Thr Met Ala Thr Leu Lys Gly Leu Val Gln
        115                 120                 125

Lys Gly Val Lys Val Asp Leu Gly Ile Pro Leu Glu Leu Trp Asp Glu
    130                 135                 140

Pro Ser Val Glu Val Thr Tyr Leu Lys Lys Gln Cys Glu Thr Met Leu
145                 150                 155                 160

Glu Glu Phe Glu Asp Ile Val Gly Asp Trp Tyr Phe His His Gln Glu
                165                 170                 175

Gln Pro Leu Gln Asn Phe Leu Cys Glu Gly His Val Leu Pro Ala Ala
            180                 185                 190

Glu Thr Ala Cys Leu Gln Glu Thr Trp Thr Gly Lys Glu Ile Thr Asp
```

-continued

```
        195                 200                 205

Gly Glu Glu Lys Thr Glu Gly Glu Glu Glu Gln Glu Glu Glu Glu Glu
    210                 215                 220

Glu Glu Glu Glu Glu Gly Gly Asp Lys Met Thr Lys Thr Gly Ser His
225                 230                 235                 240

Pro Lys Leu Asp Arg Glu Asp Leu
                245


<210> SEQ ID NO 9
<211> LENGTH: 2104
<212> TYPE: DNA
<213> ORGANISM: Homo sapiens

<400> SEQUENCE: 9

ccccttgccg ctccggtgac agtctctgcg gaaagtcacg tktgtgattt cgggagagca      60

cagaacggga cgacggcgct cttgctgggt catctgggcc aggtgacgaa gaaacagttt     120

cctggtgaag cagtccctca cccctagtca gcccacaccc ctagggccta aagatgctga     180

ggtctgtatg gaattttctg aaacgccaca aaaagaaatg catcttcctg ggcacggtcc     240

ttggaggagt atatattctg ggaaaatatg gacagaagaa aatcagagaa atacaggaaa     300

gggaggctgc agaatacatt gcccaagcac gacgacaata tcattttgaa agtaaccaga     360

ggacttgcaa tatgacagtg ctgtccatgc ttccaacact gagagaggcc ttaatgcagc     420

aactgaattc cgagagcctc acagctctgc taaaaaacag gccttcaaac aagctagaaa     480

tatgggagga tctgaagata ataagtttca caagaagtac tgtggctgta tacagtacct     540

gtatgctggt tgttcttttg cgggtccagt taaacataat tggtggatat atttacctgg     600

ataatgcagc agttggcaaa aatggcacta caattcttgc tcccccagat gtccaacagc     660

agtatttatc aagtattcag cacctacttg gagatggcct gacagaattg atcactgtca     720

ttaaacaagc tgtgcagaag gttttaggaa gtgtttctct taaacattct ttgtcccttt     780

tggacttgga gcaaaaacta aaagaaatca gaaatctcgt tgagcagcat aagtcttctt     840

cttggattaa taaagatgga tccaaacctt tattatgcca ttatatgatg ccagatgaag     900

aaactccatt agcagtgcag gcctgtggac tttctcctcg agacattacc actattaaac     960

ttctcaatga aactagagac atgttggaaa gcccagattt tagtacagtt ttgaatacct    1020

gtttaaaccg aggttttagt agacttctag acaatatggc tgagttcttt cgacctactg    1080

aacaggacct gcaacatggt aactctatga atagtctttc cagtgtcagc ctgcctttag    1140

ctaagataat tccaatagta aacggacaga tccattcagt ttgcagtgaa acacctagtc    1200

attttgttca ggatctgttg acaatggagc aagtgaaaga ctttgctgct aatgtgtatg    1260

aagcttttag taccccctcag caactggaga aatgattttt ccttcaagaa aaactacagt    1320

gggattcatt tactttttaa aatacactgg gtaaatcacc tatacttaga gtaacagttt    1380

gttatcaaaa tgcctgataa aatatattct taataaaagt cttcatttca taatgaaatc    1440

aatttatttg gcatcttaat atattttttt agattcatca acagaccagt ttttgtgggc    1500

atatatatat acacgtgcaa atatcagaat tgttaataat ttgttacaca tggacatttg    1560

ttccaaactg actaaaaatc aatatagata ttttatatac atatatatat ataaaaatac    1620

aaaattcagt gtactttacc atattaatac tgaggaaaaa tctgttggag acataggtct    1680

aggatgtgtg aagtttggaa aaatatgcta tttaattata atgttcccta gactgctgta    1740

aacagaagtg aatcagactt ttctccagct acctttcaaa ataataaatt atttgtctca    1800
```

```
aatatacctt gatggaggac ttttttattc ttatggaaat agtgaattcc aacaactatg   1860

atgaactatg ttctttgcta tttcttcact atatttttta aggttttatt aaaaagcctt   1920

agaaagttac atattggttt agaggctaaa attgtgttga tgctgtttac tcacctaatt   1980

acatagtttt aatcatttgt acataatttt aaaaacttac tttgtattga ttttgaatac   2040

agtgaaaatc ttattgcaat aaactatttt agtaaaaaaa aaaaaaaaaa aaaaaaaaaa   2100

aaaa                                                                2104


<210> SEQ ID NO 10
<211> LENGTH: 373
<212> TYPE: PRT
<213> ORGANISM: Homo sapiens

<400> SEQUENCE: 10

Met Leu Arg Ser Val Trp Asn Phe Leu Lys Arg His Lys Lys Lys Cys
 1               5                  10                  15

Ile Phe Leu Gly Thr Val Leu Gly Gly Val Tyr Ile Leu Gly Lys Tyr
            20                  25                  30

Gly Gln Lys Lys Ile Arg Glu Ile Gln Glu Arg Glu Ala Ala Glu Tyr
        35                  40                  45

Ile Ala Gln Ala Arg Arg Gln Tyr His Phe Glu Ser Asn Gln Arg Thr
    50                  55                  60

Cys Asn Met Thr Val Leu Ser Met Leu Pro Thr Leu Arg Glu Ala Leu
65                  70                  75                  80

Met Gln Gln Leu Asn Ser Glu Ser Leu Thr Ala Leu Leu Lys Asn Arg
                85                  90                  95

Pro Ser Asn Lys Leu Glu Ile Trp Glu Asp Leu Lys Ile Ile Ser Phe
            100                 105                 110

Thr Arg Ser Thr Val Ala Val Tyr Ser Thr Cys Met Leu Val Val Leu
        115                 120                 125

Leu Arg Val Gln Leu Asn Ile Ile Gly Gly Tyr Ile Tyr Leu Asp Asn
   130                 135                 140

Ala Ala Val Gly Lys Asn Gly Thr Thr Ile Leu Ala Pro Pro Asp Val
45                 150                 155                 160

Gln Gln Gln Tyr Leu Ser Ser Ile Gln His Leu Leu Gly Asp Gly Leu
               165                 170                 175

Thr Glu Leu Ile Thr Val Ile Lys Gln Ala Val Gln Lys Val Leu Gly
           180                 185                 190

Ser Val Ser Leu Lys His Ser Leu Ser Leu Leu Asp Leu Glu Gln Lys
       195                 200                 205

Leu Lys Glu Ile Arg Asn Leu Val Glu Gln His Lys Ser Ser Ser Trp
   210                 215                 220

Ile Asn Lys Asp Gly Ser Lys Pro Leu Leu Cys His Tyr Met Met Pro
25                 230                 235                 240

Asp Glu Glu Thr Pro Leu Ala Val Gln Ala Cys Gly Leu Ser Pro Arg
               245                 250                 255

Asp Ile Thr Thr Ile Lys Leu Leu Asn Glu Thr Arg Asp Met Leu Glu
           260                 265                 270

Ser Pro Asp Phe Ser Thr Val Leu Asn Thr Cys Leu Asn Arg Gly Phe
       275                 280                 285

Ser Arg Leu Leu Asp Asn Met Ala Glu Phe Phe Arg Pro Thr Glu Gln
   290                 295                 300

Asp Leu Gln His Gly Asn Ser Met Asn Ser Leu Ser Ser Val Ser Leu
05                 310                 315                 320
```

-continued

```
Pro Leu Ala Lys Ile Ile Pro Ile Val Asn Gly Gln Ile His Ser Val
                325                 330                 335

Cys Ser Glu Thr Pro Ser His Phe Val Gln Asp Leu Leu Thr Met Glu
            340                 345                 350

Gln Val Lys Asp Phe Ala Ala Asn Val Tyr Glu Ala Phe Ser Thr Pro
        355                 360                 365

Gln Gln Leu Glu Lys
    370


<210> SEQ ID NO 11
<211> LENGTH: 3262
<212> TYPE: DNA
<213> ORGANISM: Homo sapiens

<400> SEQUENCE: 11

gccaagatgg agccggcagt cggcggtccg ggcccactga tcgtgaacaa caaacagccc      60

cagcccccgc cacctccgcc gccggcagcc gcacagccac cacccggggc accgcgggcc     120

gccgcgggcc tcctgcctgg gggcaaagcc cgcgagttca accgcaacca gcgcaaagac     180

tcagagggct attcggagtc accagacctg gagtttgagt atgctgacac agacaagtgg     240

gctgcagagc tctcggagct ttacagctac acggaagggc cagaattcct gatgaatcga     300

aaatgctttg aggaggactt ccggatccat gtgacagaca agaagtggac tgagctggat     360

accaaccagc accggaccca tgccatgagg ctcctggatg gcttggaagt cactgccagg     420

gagaagagac tcaaggtggc tcgagcaatt ctctatgttg ctcaaggcac gtttggggag     480

tgcagctcgg aggcagaggt gcagtcctgg atgcgctaca acatctttct cctcctggag     540

gtgggcacgt tcaatgcttt ggtggagctt ctgaacatgg aaatagacaa cagtgccgcc     600

tgcagcagtg ctgtgaggaa gcctgccatc tccctggctg acagcacaga cctcagggtc     660

ctgctcaaca tcatgtacct gatagtggag accgttcatc aggagtgtga gggtgacaag     720

gctgagtgga ggaccatgcg gcagaccttc agagccgagc tgggctcccc gctgtacaac     780

aatgagccat ttgccatcat gctgtttggg atggtgacca aattttgcag tggtcacgcc     840

cctcactttc ccatgaagaa agttctcttg ctgctctgga agacagtatt gtgcacgcta     900

ggcggctttg aggagctgca gagcatgaag gctgagaagc gcagcatcct gggcctcccc     960

ccgcttcctg aggacagcat caaagtgatt cgcaacatga gagcagcctc tccaccagca    1020

tctgcttcag acttgattga gcagcagcag aaacggggcc gccgagagca caaggctctg    1080

ataaagcagg acaacctaga tgccttcaac gagcgggatc cctacaaggc tgatgactct    1140

cgagaagagg aagaggagaa tgatgatgac aacagtctgg agggggagac gtttcccctg    1200

gaacgggatg aagtgatgcc tcccccgcta cagcacccac agactgacag gctgacttgc    1260

cccaaagggc tcccgtgggc tcccaaggtc agagagaaag acattgagat gttccttgag    1320

tccagccgca gcaaatttat aggttacact ctaggcagtg acacgaacac agtggtgggg    1380

ctgcccaggc caatccacga aagcatcaag actctgaaac agcacaagta cacgtcgatt    1440

gcagaggtcc aggcacagat ggaggaggaa tacctccgct cccctctctc agggggagaa    1500

gaagaagttg agcaagtccc tgcagaaacc ctctaccaag gcttgctccc cagcctgcct    1560

cagtatatga ttgccctcct gaagatcctg ttggctgcag cacccacctc aaaagccaaa    1620

acagactcaa tcaacatcct agcggacgtc ttgcctgagg agatgcccac cacagtgttg    1680

cagagcatga agctgggggt ggatgtaaac cgccacaaag aggtcattgt taaggccatt    1740
```

-continued

```
tctgctgtcc tgctgctgct gctcaagcac tttaagttga accatgtcta ccagtttgaa   1800

tacatggccc agcacctggt gtttgccaac tgcattcctt tgatcctaaa gttcttcaat   1860

caaaacatca tgtcctacat cactgccaag aacagcattt ctgtcctgga ttaccctcac   1920

tgcgtggtgc atgagctgcc agagctgacg gcggagagtt tggaagcagg tgacagtaac   1980

caattttgct ggaggaacct cttttcttgt atcaatctgc ttcggatctt gaacaagctg   2040

acaaagtgga agcattcaag gacaatgatg ctggtggtgt tcaagtcagc ccccatcttg   2100

aagcgggccc taaaggtgaa acaagccatg atgcagctct atgtgctgaa gctgctcaag   2160

gtacagacca aatacttggg gcggcagtgg cgaaagagca acatgaagac catgtctgcc   2220

atctaccaga aggtgcggca tcggctgaac gacgactggg catacggcaa tgatcttgat   2280

gcccggcctt gggacttcca ggcagaggag tgtgcccttc gtgccaacat tgaacgcttc   2340

aacgcccggc gctatgaccg ggcccacagc aaccctgact tcctgccagt ggacaactgc   2400

ctgcagagtg tcctgggcca acgggtggac ctccctgagg actttcagat gaactatgac   2460

ctctggttag aaagggaggt cttctccaag cccatttcct gggaagagct gctgcagtga   2520

ggctgttggt taggggactg aaatggagag aaaagatgat ctgaaggtac ctgtgggact   2580

gtcctagttc attgctgcag tgctcccatc ccccaccagg tggcagcaca gccccactgt   2640

gtcttccgca gtctgtcctg ggcttgggtg agcccagctt gacctcccct tggttcccag   2700

ggtcctgctc cgaagcagtc atctctgcct gagatccatt cttcctttac ttcccccacc   2760

ctcctctctt ggatatggtt ggttttggct catttcacaa tcagcccaag gctgggaaag   2820

ctggaatggg atgggaaccc ctccgccgtg catctgaatt tcaggggtca tgctgatgcc   2880

tctcgagaca tacaaatcct tgctttgtca gcttgcaaag gaggagagtt taggattagg   2940

gccagggcca gaaagtcggt atcttggttg tgctctgggg tgggggtggg gtgtttctga   3000

tgttattcca gcctcctgct acattatatc cagaagtaat tgcggaggct ccttcagctg   3060

cctcagcact ttgattttgg acagggacaa ggtaggaaga gaagcttccc ttaaccagag   3120

gggccatttt tccttttggc tttcgagggc ctgtaaatat ctatatataa ttctgtgtgt   3180

attctgtgtc atgttggggt ttttaatgtg attgtgtatt ctgtttacat taaaaagaag   3240

caaaaataaa aaaaaaaaaa aa                                            3262
```

<210> SEQ ID NO 12
<211> LENGTH: 837
<212> TYPE: PRT
<213> ORGANISM: Homo sapiens

<400> SEQUENCE: 12

```
Met Glu Pro Ala Val Gly Gly Pro Gly Pro Leu Ile Val Asn Asn Lys
  1               5                  10                  15

Gln Pro Gln Pro Pro Pro Pro Pro Pro Pro Ala Ala Ala Gln Pro Pro
             20                  25                  30

Pro Gly Ala Pro Arg Ala Ala Ala Gly Leu Leu Pro Gly Gly Lys Ala
         35                  40                  45

Arg Glu Phe Asn Arg Asn Gln Arg Lys Asp Ser Glu Gly Tyr Ser Glu
     50                  55                  60

Ser Pro Asp Leu Glu Phe Glu Tyr Ala Asp Thr Asp Lys Trp Ala Ala
 65                  70                  75                  80

Glu Leu Ser Glu Leu Tyr Ser Tyr Thr Glu Gly Pro Glu Phe Leu Met
                 85                  90                  95

Asn Arg Lys Cys Phe Glu Glu Asp Phe Arg Ile His Val Thr Asp Lys
```

-continued

```
            100                 105                 110

Lys Trp Thr Glu Leu Asp Thr Asn Gln His Arg Thr His Ala Met Arg
        115                 120                 125

Leu Leu Asp Gly Leu Glu Val Thr Ala Arg Glu Lys Arg Leu Lys Val
    130                 135                 140

Ala Arg Ala Ile Leu Tyr Val Ala Gln Gly Thr Phe Gly Glu Cys Ser
145                 150                 155                 160

Ser Glu Ala Glu Val Gln Ser Trp Met Arg Tyr Asn Ile Phe Leu Leu
                165                 170                 175

Leu Glu Val Gly Thr Phe Asn Ala Leu Val Glu Leu Leu Asn Met Glu
            180                 185                 190

Ile Asp Asn Ser Ala Ala Cys Ser Ser Ala Val Arg Lys Pro Ala Ile
        195                 200                 205

Ser Leu Ala Asp Ser Thr Asp Leu Arg Val Leu Leu Asn Ile Met Tyr
    210                 215                 220

Leu Ile Val Glu Thr Val His Gln Glu Cys Glu Gly Asp Lys Ala Glu
225                 230                 235                 240

Trp Arg Thr Met Arg Gln Thr Phe Arg Ala Glu Leu Gly Ser Pro Leu
                245                 250                 255

Tyr Asn Asn Glu Pro Phe Ala Ile Met Leu Phe Gly Met Val Thr Lys
            260                 265                 270

Phe Cys Ser Gly His Ala Pro His Phe Pro Met Lys Lys Val Leu Leu
        275                 280                 285

Leu Leu Trp Lys Thr Val Leu Cys Thr Leu Gly Gly Phe Glu Glu Leu
    290                 295                 300

Gln Ser Met Lys Ala Glu Lys Arg Ser Ile Leu Gly Leu Pro Pro Leu
305                 310                 315                 320

Pro Glu Asp Ser Ile Lys Val Ile Arg Asn Met Arg Ala Ala Ser Pro
                325                 330                 335

Pro Ala Ser Ala Ser Asp Leu Ile Glu Gln Gln Gln Lys Arg Gly Arg
            340                 345                 350

Arg Glu His Lys Ala Leu Ile Lys Gln Asp Asn Leu Asp Ala Phe Asn
        355                 360                 365

Glu Arg Asp Pro Tyr Lys Ala Asp Asp Ser Arg Glu Glu Glu Glu Glu
    370                 375                 380

Asn Asp Asp Asp Asn Ser Leu Glu Gly Glu Thr Phe Pro Leu Glu Arg
385                 390                 395                 400

Asp Glu Val Met Pro Pro Pro Leu Gln His Pro Gln Thr Asp Arg Leu
                405                 410                 415

Thr Cys Pro Lys Gly Leu Pro Trp Ala Pro Lys Val Arg Glu Lys Asp
            420                 425                 430

Ile Glu Met Phe Leu Glu Ser Ser Arg Ser Lys Phe Ile Gly Tyr Thr
        435                 440                 445

Leu Gly Ser Asp Thr Asn Thr Val Val Gly Leu Pro Arg Pro Ile His
    450                 455                 460

Glu Ser Ile Lys Thr Leu Lys Gln His Lys Tyr Thr Ser Ile Ala Glu
465                 470                 475                 480

Val Gln Ala Gln Met Glu Glu Glu Tyr Leu Arg Ser Pro Leu Ser Gly
                485                 490                 495

Gly Glu Glu Glu Val Glu Gln Val Pro Ala Glu Thr Leu Tyr Gln Gly
            500                 505                 510

Leu Leu Pro Ser Leu Pro Gln Tyr Met Ile Ala Leu Leu Lys Ile Leu
        515                 520                 525
```

```
Leu Ala Ala Ala Pro Thr Ser Lys Ala Lys Thr Asp Ser Ile Asn Ile
    530                 535                 540

Leu Ala Asp Val Leu Pro Glu Glu Met Pro Thr Thr Val Leu Gln Ser
545                 550                 555                 560

Met Lys Leu Gly Val Asp Val Asn Arg His Lys Glu Val Ile Val Lys
                565                 570                 575

Ala Ile Ser Ala Val Leu Leu Leu Leu Leu Lys His Phe Lys Leu Asn
            580                 585                 590

His Val Tyr Gln Phe Glu Tyr Met Ala Gln His Leu Val Phe Ala Asn
        595                 600                 605

Cys Ile Pro Leu Ile Leu Lys Phe Phe Asn Gln Asn Ile Met Ser Tyr
    610                 615                 620

Ile Thr Ala Lys Asn Ser Ile Ser Val Leu Asp Tyr Pro His Cys Val
625                 630                 635                 640

Val His Glu Leu Pro Glu Leu Thr Ala Glu Ser Leu Glu Ala Gly Asp
                645                 650                 655

Ser Asn Gln Phe Cys Trp Arg Asn Leu Phe Ser Cys Ile Asn Leu Leu
            660                 665                 670

Arg Ile Leu Asn Lys Leu Thr Lys Trp Lys His Ser Arg Thr Met Met
        675                 680                 685

Leu Val Val Phe Lys Ser Ala Pro Ile Leu Lys Arg Ala Leu Lys Val
    690                 695                 700

Lys Gln Ala Met Met Gln Leu Tyr Val Leu Lys Leu Leu Lys Val Gln
705                 710                 715                 720

Thr Lys Tyr Leu Gly Arg Gln Trp Arg Lys Ser Asn Met Lys Thr Met
                725                 730                 735

Ser Ala Ile Tyr Gln Lys Val Arg His Arg Leu Asn Asp Asp Trp Ala
            740                 745                 750

Tyr Gly Asn Asp Leu Asp Ala Arg Pro Trp Asp Phe Gln Ala Glu Glu
        755                 760                 765

Cys Ala Leu Arg Ala Asn Ile Glu Arg Phe Asn Ala Arg Arg Tyr Asp
    770                 775                 780

Arg Ala His Ser Asn Pro Asp Phe Leu Pro Val Asp Asn Cys Leu Gln
785                 790                 795                 800

Ser Val Leu Gly Gln Arg Val Asp Leu Pro Glu Asp Phe Gln Met Asn
                805                 810                 815

Tyr Asp Leu Trp Leu Glu Arg Glu Val Phe Ser Lys Pro Ile Ser Trp
            820                 825                 830

Glu Glu Leu Leu Gln
        835


<210> SEQ ID NO 13
<211> LENGTH: 1264
<212> TYPE: DNA
<213> ORGANISM: Homo sapiens

<400> SEQUENCE: 13

cttgaacgca cctcaggatg gcccgtactt tggaaccact agcaaagaag atctttaaag      60

gagttttggt agccgaactt gtaggcgttt ttggagcata ttttttgttt agcaagatgc     120

acacaagcca agatttcagg caaacaatga gcaagaaata tcccttcatc ttggaagttt     180

attacaaatc cactgagaag tctggaatgt atggaatcag agagctagat caaaaaacat     240

ggttgaacag caaaaattag atgtaaggaa gatctgcatt caaatgtgag tgggcaccat     300
```

-continued

```
ccaatctgct ggggccctgg agagaacaaa acaaagaggc aaacatgttg atctgctgtg     360
ctgaggagga aaatggcgga taaggggaca ggactaacgt gcagctccca catggatgga     420
cagaacagcg tgtggcaacg tgtttagtct ccttaaaagg atttcactct gtcacccagg     480
ctggagtgca gtggcgtaat cttggctcac ggcaacctct gactcctgga ttcaggcgat     540
tctcgtgcct ctgcttctcg agtagctggg actacaggtg cgtgccacca tgcccagctc     600
atttttgggg gtttttagtg gagacagggt ttcaccgtgt tggccaggct ggtctcgaac     660
tcctgacctc aaacaatctt cctgcctcgg cctgccgagg tgctgggatt acaggtgtga     720
gccacagcgc ctggccccaa atatttctta atcttccact gtgatttgca tgatattctt     780
agctaagtga ttttttaaaa ctaaggccac ttctcccact aatgttccat ggtctattaa     840
cacatagtag tagattattt tacaaagagt caacaaaaca aattaccaat cagctcttca     900
aattcttcat catccacgtc ttctatactt tcttcatctg catcccgttt ttgtttctct     960
ttaacagcaa ctttttata atacctataa tattcatgtt atatatttga caattttatt    1020
aaaggtctaa tcttactata tatcatcaaa gcacctatga ccagtggcaa accacaactg    1080
taaaatctta agtatactca attggaaata aatgactgaa atttgtatct aatatacaaa    1140
aaatagttta actcaataaa aagtagctgg aaaaaaaaaa aaaaaaaaaa aaaaaaaaaa    1200
aaaaaaaaaa aaaaaaaaaa aaaaaaaaaa aaaaaaaaaa aaaaaaaaaa aaaaaaaaaa    1260
aaaa                                                                1264
```

<210> SEQ ID NO 14
<211> LENGTH: 80
<212> TYPE: PRT
<213> ORGANISM: Homo sapiens

<400> SEQUENCE: 14

```
Met Ala Arg Thr Leu Glu Pro Leu Ala Lys Lys Ile Phe Lys Gly Val
  1               5                  10                  15

Leu Val Ala Glu Leu Val Gly Val Phe Gly Ala Tyr Phe Leu Phe Ser
             20                  25                  30

Lys Met His Thr Ser Gln Asp Phe Arg Gln Thr Met Ser Lys Lys Tyr
         35                  40                  45

Pro Phe Ile Leu Glu Val Tyr Tyr Lys Ser Thr Glu Lys Ser Gly Met
     50                  55                  60

Tyr Gly Ile Arg Glu Leu Asp Gln Lys Thr Trp Leu Asn Ser Lys Asn
 65                  70                  75                  80
```

<210> SEQ ID NO 15
<211> LENGTH: 2671
<212> TYPE: DNA
<213> ORGANISM: Homo sapiens

<400> SEQUENCE: 15

```
ccgtacacgc gcgctgcggc atggcggccc accgccccgg cccgctcaag cagcagaata      60
aagctcataa aggcggacgg catcggggtc ggggatctgc acagcgggac ggcaagggcc     120
gtctggcact gaaaacccta agcaagaagg tgagaaaaga actcagcaga gtcgaccaga     180
ggcatcgcgc cagccagctc cgaaagcaga agaaggaggc ggttctggca gagaagagac     240
agctgggtgg caaggatggc cctcctcatc aggtactggt ggtgcccctg cacagcagaa     300
tttccctgcc agaggccatg cagctgcttc aagataggga cactggaaca gtacacttga     360
atgaattggg aaacacccag aactttatgc tgctgtgccc ccgcttgaaa catctgtggt     420
```

-continued

```
ttttcacctc agcaaggcca ggggatctgc acgttgtgtt agacatggct aaagtagctg    480

ataccatcct gttcctcctt gatccactag aaggctggga cagcacccgt gattactgtc    540

tttcctgcct ctttgctcag ggccttccga cctatacact agctgtccag ggatttctg    600

gcctcccact gaagaaacaa atagatacca ggaagaagct aagtaaagca gtggagaagc    660

gctttccgca tgacaaactc ctcttgttag acactcaaca ggaggcaggg atgctgctta    720

ggcagttggc taaccagaag caacagcatc ttgcttttcg agatcggcgg gcctacctat    780

ttgcccatgc tgttgatttt gttcctagtg aagagaataa cttggtgggc accttgaaaa    840

tttcaggcta tgttcgaggg cagactctga atgtcaatag gttgctgcat atcgttggat    900

atggtgattt gccagatgaa cagatagatg cccccggaga ccctttccct ttaaatccta    960

gaggaattaa accccaaaag gacccagaca tggcaatgga gatttgtgct acggatgctg   1020

tagatgatat ggaagaaggt cttaaagtcc taatgaaggc agaccctggt agacaggaat   1080

ccttgcaagc agaggttatc ccagatccaa tggaggggaga gcaaacctgg cccactgagg   1140

aggagctgag cgaggcaaag gatttcttga aggaaagttc taaggtggta aagaaggtcc   1200

ccaaaggaac atccagttac caagctgaat ggattttgga tggtggcagc caaagtggtg   1260

gggaaggaga tgaatatgaa tatgatgata tggaacatga ggattttatg gaggaggaat   1320

ctcaggatga gagtagtgaa gaagaggaag aatatgaaac tatgactatt ggggagtctg   1380

tgcatgatga tctgtatgat aagaaagtag atgaagaagc tgaggcaaaa atgttggaga   1440

aatataaaca agaaagactg gaagagatgt ttccagatga agtggacacg ccccgtgatg   1500

tggctgctcg aattcgattt cagaaataca gaggccttaa gagcttccgg acatctccat   1560

gggatcctaa ggaaaacctt cctcaagatt atgctcgaat atttcagttt cagaacttta   1620

ctaacactag gaaaagcatc tttaaagagg ttgaagaaaa agaggttgaa ggagctgagg   1680

ttggctggta tgtcacactt catgtctctg aagtccccgt ctcagtggtc gagtgcttca   1740

ggcaaggaac acccttgatt gcattttctt tactacctca tgaacagaag atgtcagtat   1800

tgaatatggt ggtgaggcgt gaccctggca acactgaacc tgtgaaagcc aaggaagagc   1860

tcatatttca ctgtggattc aggcgcttcc gagcctcacc tttattctct cagcacactg   1920

cagcggacaa acataaattg cagagattcc tgactgctga catggccctg gtggcgacag   1980

tctatgcgcc aatcactttt cctcctgcat ctgtgctgct tttcaagcaa aaaagcaatg   2040

gaatgcacag cctcattgct acaggccatc ttatgtcagt agatccagac agaatggtca   2100

tcaagagagt tgttctgagt ggtcatcctt tcaaaatttt tactaagatg gcagtagtac   2160

gttacatgtt cttcaacaga gaggatgtgc tgtggtttaa accagtggaa ctgagaacga   2220

agtggggccg gagaggacat atcaaggaac ctttaggtac ccatggccac atgaaatgca   2280

gctttgatgg gaagctaaaa tctcaagaca cagtactgat gaacctgtat aaacgagtct   2340

tccccaaatg gacttatgat ccatatgtac cagaaccagt accctggctg aaaagtgaga   2400

tttcttcaac agtgcctcaa gggggcatgg agtaatggat tcaaagagat tctgtcttac   2460

cggtgccagt cagtactcca gggatgggag gcacaagttg tgattgggca aagtttattt   2520

tctatgtcag cctgtcagtc cactgcccca ttttgcaaga cttttttta gccttgacaa   2580

aatgtctcag ttaagtataa aagtttttcc actacttagt ccaaaaaaaa ctattaaatc   2640

ttaatgaaat aaaaaaaaaa aaaaaaaaaa a                                  2671
```

<210> SEQ ID NO 16
<211> LENGTH: 804

```
<212> TYPE: PRT
<213> ORGANISM: Homo sapiens

<400> SEQUENCE: 16

Met Ala Ala His Arg Pro Gly Pro Leu Lys Gln Gln Asn Lys Ala His
  1               5                  10                  15

Lys Gly Gly Arg His Arg Gly Arg Gly Ser Ala Gln Arg Asp Gly Lys
             20                  25                  30

Gly Arg Leu Ala Leu Lys Thr Leu Ser Lys Lys Val Arg Lys Glu Leu
         35                  40                  45

Ser Arg Val Asp Gln Arg His Arg Ala Ser Gln Leu Arg Lys Gln Lys
     50                  55                  60

Lys Glu Ala Val Leu Ala Glu Lys Arg Gln Leu Gly Gly Lys Asp Gly
 65                  70                  75                  80

Pro Pro His Gln Val Leu Val Val Pro Leu His Ser Arg Ile Ser Leu
                 85                  90                  95

Pro Glu Ala Met Gln Leu Leu Gln Asp Arg Asp Thr Gly Thr Val His
            100                 105                 110

Leu Asn Glu Leu Gly Asn Thr Gln Asn Phe Met Leu Leu Cys Pro Arg
        115                 120                 125

Leu Lys His Leu Trp Phe Phe Thr Ser Ala Arg Pro Gly Asp Leu His
    130                 135                 140

Val Val Leu Asp Met Ala Lys Val Ala Asp Thr Ile Leu Phe Leu Leu
145                 150                 155                 160

Asp Pro Leu Glu Gly Trp Asp Ser Thr Arg Asp Tyr Cys Leu Ser Cys
                165                 170                 175

Leu Phe Ala Gln Gly Leu Pro Thr Tyr Thr Leu Ala Val Gln Gly Ile
            180                 185                 190

Ser Gly Leu Pro Leu Lys Lys Gln Ile Asp Thr Arg Lys Lys Leu Ser
        195                 200                 205

Lys Ala Val Glu Lys Arg Phe Pro His Asp Lys Leu Leu Leu Leu Asp
    210                 215                 220

Thr Gln Gln Glu Ala Gly Met Leu Leu Arg Gln Leu Ala Asn Gln Lys
225                 230                 235                 240

Gln Gln His Leu Ala Phe Arg Asp Arg Arg Ala Tyr Leu Phe Ala His
                245                 250                 255

Ala Val Asp Phe Val Pro Ser Glu Glu Asn Asn Leu Val Gly Thr Leu
            260                 265                 270

Lys Ile Ser Gly Tyr Val Arg Gly Gln Thr Leu Asn Val Asn Arg Leu
        275                 280                 285

Leu His Ile Val Gly Tyr Gly Asp Leu Pro Asp Glu Gln Ile Asp Ala
    290                 295                 300

Pro Gly Asp Pro Phe Pro Leu Asn Pro Arg Gly Ile Lys Pro Gln Lys
305                 310                 315                 320

Asp Pro Asp Met Ala Met Glu Ile Cys Ala Thr Asp Ala Val Asp Asp
                325                 330                 335

Met Glu Glu Gly Leu Lys Val Leu Met Lys Ala Asp Pro Gly Arg Gln
            340                 345                 350

Glu Ser Leu Gln Ala Glu Val Ile Pro Asp Pro Met Glu Gly Glu Gln
        355                 360                 365

Thr Trp Pro Thr Glu Glu Glu Leu Ser Glu Ala Lys Asp Phe Leu Lys
    370                 375                 380

Glu Ser Ser Lys Val Val Lys Lys Val Pro Lys Gly Thr Ser Ser Tyr
385                 390                 395                 400
```

-continued

```
Gln Ala Glu Trp Ile Leu Asp Gly Gly Ser Gln Ser Gly Gly Glu Gly
                405                 410                 415

Asp Glu Tyr Glu Tyr Asp Asp Met Glu His Glu Asp Phe Met Glu Glu
            420                 425                 430

Glu Ser Gln Asp Glu Ser Ser Glu Glu Glu Glu Glu Tyr Glu Thr Met
        435                 440                 445

Thr Ile Gly Glu Ser Val His Asp Asp Leu Tyr Asp Lys Lys Val Asp
    450                 455                 460

Glu Glu Ala Glu Ala Lys Met Leu Glu Lys Tyr Lys Gln Glu Arg Leu
465                 470                 475                 480

Glu Glu Met Phe Pro Asp Glu Val Asp Thr Pro Arg Asp Val Ala Ala
                485                 490                 495

Arg Ile Arg Phe Gln Lys Tyr Arg Gly Leu Lys Ser Phe Arg Thr Ser
            500                 505                 510

Pro Trp Asp Pro Lys Glu Asn Leu Pro Gln Asp Tyr Ala Arg Ile Phe
        515                 520                 525

Gln Phe Gln Asn Phe Thr Asn Thr Arg Lys Ser Ile Phe Lys Glu Val
    530                 535                 540

Glu Glu Lys Glu Val Glu Gly Ala Glu Val Gly Trp Tyr Val Thr Leu
545                 550                 555                 560

His Val Ser Glu Val Pro Val Ser Val Val Glu Cys Phe Arg Gln Gly
                565                 570                 575

Thr Pro Leu Ile Ala Phe Ser Leu Leu Pro His Glu Gln Lys Met Ser
            580                 585                 590

Val Leu Asn Met Val Val Arg Arg Asp Pro Gly Asn Thr Glu Pro Val
        595                 600                 605

Lys Ala Lys Glu Glu Leu Ile Phe His Cys Gly Phe Arg Arg Phe Arg
    610                 615                 620

Ala Ser Pro Leu Phe Ser Gln His Thr Ala Ala Asp Lys His Lys Leu
625                 630                 635                 640

Gln Arg Phe Leu Thr Ala Asp Met Ala Leu Val Ala Thr Val Tyr Ala
                645                 650                 655

Pro Ile Thr Phe Pro Pro Ala Ser Val Leu Leu Phe Lys Gln Lys Ser
            660                 665                 670

Asn Gly Met His Ser Leu Ile Ala Thr Gly His Leu Met Ser Val Asp
        675                 680                 685

Pro Asp Arg Met Val Ile Lys Arg Val Val Leu Ser Gly His Pro Phe
    690                 695                 700

Lys Ile Phe Thr Lys Met Ala Val Val Arg Tyr Met Phe Phe Asn Arg
705                 710                 715                 720

Glu Asp Val Leu Trp Phe Lys Pro Val Glu Leu Arg Thr Lys Trp Gly
                725                 730                 735

Arg Arg Gly His Ile Lys Glu Pro Leu Gly Thr His Gly His Met Lys
            740                 745                 750

Cys Ser Phe Asp Gly Lys Leu Lys Ser Gln Asp Thr Val Leu Met Asn
        755                 760                 765

Leu Tyr Lys Arg Val Phe Pro Lys Trp Thr Tyr Asp Pro Tyr Val Pro
    770                 775                 780

Glu Pro Val Pro Trp Leu Lys Ser Glu Ile Ser Ser Thr Val Pro Gln
785                 790                 795                 800

Gly Gly Met Glu
```

-continued

<210> SEQ ID NO 17
<211> LENGTH: 2321
<212> TYPE: DNA
<213> ORGANISM: Homo sapiens

<400> SEQUENCE: 17
ccgaccttgg aatcagaagc ctggggctcc tctagggagt ggctggcccc ccgggaggcc 60
agaggaggcc catcgctgtc ttctgtgctg aacgagctgc ccagtgctgc cacccttcgg 120
taccgagacc ctggggtgct gccttggggg gcgctggagg aggaggagga ggatggagga 180
aggagcagaa aggccttcac agaagtcacc cagacagagc tgcaggaccc tcacccttcc 240
cgggaactgc cctggcccat gcaggccaga cgggcataca ggcaaagaaa tgccagcagg 300
gaccaggtgg tctatggctc tggaactaag acggaccgat gggcgcggct acttcggagg 360
tccaaggaga aaacaaagga aggcttgcga agctgcagcc ctgggcgtgg acactgaaga 420
ggatcggggg ccagtttggc gccggcacgg agtcctactt ctccctgctg cgcttcctgc 480
tccttcttaa cgtgctggcc tctgtgctca tggcctgcat gacgctgctg cccacctggt 540
tgggaggcgc tcccccaggc cctcccggcc ccgacatctc ctcgccctgc ggctcctata 600
acccccactc ccagggcctg gtcacctttg ccacccagct cttcaacttg ctctcgggtg 660
agggttacct ggaatggtcc cctctcttct atggcttcta cacgccccgc ccacgcctgg 720
cggtcaccta cctgtgctgg gcctttgccg ttggcctcat ctgcctcctg ctcatcctgc 780
atcgctcggt gtctgggctg aagcagacac tgctggcgga gtccgaggct ctgaccagct 840
acagccaccg ggtgttctcg gcctgggact tcggtctctg cggggacgtc cacgtgcggc 900
tgcgccagcg catcatcttg tacgaattaa aggtggagct ggaggagaca gtggtgcggc 960
gccaggctgc ggtgcggacg ctgggccagc aagccagggt ttggttggtg cgggtgctgc 1020
tcaacctgct ggtggtcgcg ctcctggggg cagccttcta tggcgtctac tgggctacgg 1080
ggtgcaccgt ggagctgcag gagatgcccc ttgtccagga gttgccactg ctgaagcttg 1140
gggtgaatta ccttccgtcc atcttcatcg ctggggtcaa ttttgtgctg ccgcccgtgt 1200
tcaagctcat tgctccactg gagggctaca ctcggagtcg ccagatcgtt tttatcctgc 1260
tcaggaccgt gtttcttcgc ctcgcctccc tggtggtcct gctcttctct ctctggaatc 1320
agatcacttg tgggggcgac tccgaggctg aggactgcaa aacctgtggc tacaattaca 1380
aacaacttcc gtgctgggag actgtcctgg gccaggaaat gtacaaactt ctgctctttg 1440
atctgctgac tgtcttggca gtcgcgctgc tcatccagtt tcctagaaag ctcctctgtg 1500
gcctctgtcc tggggcgctg ggtcttctgg cggggaccca ggagttccag gtgcccgacg 1560
aggtgctggg gctcatctac gcgcagacgg tggtctgggt ggggagtttt ttctgccctt 1620
tactgcccct gcttaacacg gtcaagttcc tgctgctttt ctacctgaag aagcttaccc 1680
tcttctccac ctgctccccg gctgcccgca ccttccgggc ctccgcggcg aatttctttt 1740 tcccccttggt ccttctcctg ggtctggcca tctccagcgt tcccctgctt tacagcatct 1800
tcctgatccc gccttctaag ctgtgtggtc cattccgggg gcagtcgtcc atctgggccc 1860
agatccctga gtctatttcc agcctccctg agaccaccca gaatttcctc ttcttcctgg 1920
ggacccaggc ttttgctgtg ccccttctgc tgatctccag catcctgatg gcgtacactg 1980
tggctctggc taactcctac ggacgcctca tctctgagct caaacgtcag agagagacgg 2040
aggcgcagaa taaagtcttc ctggcacggc gcgctgtggc gctgacctcc accaaaccgg 2100
ctctttgacc cccgcagccc acgtcccgct ttcagacccc aggcccattg taagcctagg 2160

```
tcacaacatc tgtaaactag gagaactgga gaagactcca cgcccttcca gctttggtat   2220

ctggagattt ccagggcccc tcgccgccac gtccctgact ctcgggtgat cttccttgta   2280

tcaataaata cagccgaggt tgcaaaaaaa aaaaaaaaaa a                        2321


<210> SEQ ID NO 18
<211> LENGTH: 589
<212> TYPE: PRT
<213> ORGANISM: Homo sapiens

<400> SEQUENCE: 18

Met Gly Ala Ala Thr Ser Glu Val Gln Gly Glu Asn Lys Gly Arg Leu
1               5                   10                  15

Ala Lys Leu Gln Pro Trp Ala Trp Thr Leu Lys Arg Ile Gly Gly Gln
            20                  25                  30

Phe Gly Ala Gly Thr Glu Ser Tyr Phe Ser Leu Leu Arg Phe Leu Leu
        35                  40                  45

Leu Leu Asn Val Leu Ala Ser Val Leu Met Ala Cys Met Thr Leu Leu
    50                  55                  60

Pro Thr Trp Leu Gly Gly Ala Pro Pro Gly Pro Pro Gly Pro Asp Ile
65                  70                  75                  80

Ser Ser Pro Cys Gly Ser Tyr Asn Pro His Ser Gln Gly Leu Val Thr
                85                  90                  95

Phe Ala Thr Gln Leu Phe Asn Leu Leu Ser Gly Glu Gly Tyr Leu Glu
            100                 105                 110

Trp Ser Pro Leu Phe Tyr Gly Phe Tyr Thr Pro Arg Pro Arg Leu Ala
        115                 120                 125

Val Thr Tyr Leu Cys Trp Ala Phe Ala Val Gly Leu Ile Cys Leu Leu
    130                 135                 140

Leu Ile Leu His Arg Ser Val Ser Gly Leu Lys Gln Thr Leu Leu Ala
145                 150                 155                 160

Glu Ser Glu Ala Leu Thr Ser Tyr Ser His Arg Val Phe Ser Ala Trp
                165                 170                 175

Asp Phe Gly Leu Cys Gly Asp Val His Val Arg Leu Arg Gln Arg Ile
            180                 185                 190

Ile Leu Tyr Glu Leu Lys Val Glu Leu Glu Glu Thr Val Val Arg Arg
        195                 200                 205

Gln Ala Ala Val Arg Thr Leu Gly Gln Gln Ala Arg Val Trp Leu Val
    210                 215                 220

Arg Val Leu Leu Asn Leu Leu Val Val Ala Leu Leu Gly Ala Ala Phe
225                 230                 235                 240

Tyr Gly Val Tyr Trp Ala Thr Gly Cys Thr Val Glu Leu Gln Glu Met
                245                 250                 255

Pro Leu Val Gln Glu Leu Pro Leu Leu Lys Leu Gly Val Asn Tyr Leu
            260                 265                 270

Pro Ser Ile Phe Ile Ala Gly Val Asn Phe Val Leu Pro Pro Val Phe
        275                 280                 285

Lys Leu Ile Ala Pro Leu Glu Gly Tyr Thr Arg Ser Arg Gln Ile Val
    290                 295                 300

Phe Ile Leu Leu Arg Thr Val Phe Leu Arg Leu Ala Ser Leu Val Val
305                 310                 315                 320

Leu Leu Phe Ser Leu Trp Asn Gln Ile Thr Cys Gly Gly Asp Ser Glu
                325                 330                 335

Ala Glu Asp Cys Lys Thr Cys Gly Tyr Asn Tyr Lys Gln Leu Pro Cys
            340                 345                 350
```

```
Trp Glu Thr Val Leu Gly Gln Glu Met Tyr Lys Leu Leu Leu Phe Asp
        355                 360                 365

Leu Leu Thr Val Leu Ala Val Ala Leu Leu Ile Gln Phe Pro Arg Lys
    370                 375                 380

Leu Leu Cys Gly Leu Cys Pro Gly Ala Leu Gly Leu Leu Ala Gly Thr
385                 390                 395                 400

Gln Glu Phe Gln Val Pro Asp Glu Val Leu Gly Leu Ile Tyr Ala Gln
                405                 410                 415

Thr Val Val Trp Val Gly Ser Phe Phe Cys Pro Leu Leu Pro Leu Leu
            420                 425                 430

Asn Thr Val Lys Phe Leu Leu Leu Phe Tyr Leu Lys Lys Leu Thr Leu
        435                 440                 445

Phe Ser Thr Cys Ser Pro Ala Ala Arg Thr Phe Arg Ala Ser Ala Ala
    450                 455                 460

Asn Phe Phe Phe Pro Leu Val Leu Leu Leu Gly Leu Ala Ile Ser Ser
465                 470                 475                 480

Val Pro Leu Leu Tyr Ser Ile Phe Leu Ile Pro Pro Ser Lys Leu Cys
                485                 490                 495

Gly Pro Phe Arg Gly Gln Ser Ser Ile Trp Ala Gln Ile Pro Glu Ser
            500                 505                 510

Ile Ser Ser Leu Pro Glu Thr Thr Gln Asn Phe Leu Phe Phe Leu Gly
        515                 520                 525

Thr Gln Ala Phe Ala Val Pro Leu Leu Leu Ile Ser Ser Ile Leu Met
    530                 535                 540

Ala Tyr Thr Val Ala Leu Ala Asn Ser Tyr Gly Arg Leu Ile Ser Glu
545                 550                 555                 560

Leu Lys Arg Gln Arg Glu Thr Glu Ala Gln Asn Lys Val Phe Leu Ala
                565                 570                 575

Arg Arg Ala Val Ala Leu Thr Ser Thr Lys Pro Ala Leu
            580                 585
```

<210> SEQ ID NO 19
<211> LENGTH: 5263
<212> TYPE: DNA
<213> ORGANISM: Homo sapiens
<220> FEATURE:
<221> NAME/KEY: unsure
<222> LOCATION: (848)
<220> FEATURE:
<221> NAME/KEY: unsure
<222> LOCATION: (1060)
<220> FEATURE:
<221> NAME/KEY: unsure
<222> LOCATION: (1248)
<220> FEATURE:
<221> NAME/KEY: unsure
<222> LOCATION: (1377)
<220> FEATURE:
<221> NAME/KEY: unsure
<222> LOCATION: (2310)
<220> FEATURE:
<221> NAME/KEY: unsure
<222> LOCATION: (2319)
<220> FEATURE:
<221> NAME/KEY: unsure
<222> LOCATION: (2839)

<400> SEQUENCE: 19

```
agtggaagga gcaggcgctt gagctcgagc gacggcgctg gcggagacgc cggctgctcc      60

tcccctcccc gccggtatta atctctggag aagacacatc cacagttagc actttcttca     120
```

-continued

```
gatgctgacg ctcggtgaac agttgccttt ggtcacaaga tttagaagac acagtgtcca    180
tcctcccaga ttggatctct ttttcatatg gatcttctgt ttctatgtct ttttaaaaaa    240
taactttttg ggaaaccttt tggattacaa ctgttcatcc tcacctatgc aaagaaaggg    300
aagctattgc tgggattttg aggagctttt cctaaaagga ttgtacacct tagaagtgct    360
taaggaagag tgatgaagat aggcatgaag ccttcgtctc acagctgcat gcgtagtcac    420
tgttgaagca aatgcctacc taatttgaca ctcttggtgt gtttaaaaaa ttttttttgag   480
tttgcaaata agcatattaa gtctactgat ggagccttcg ggcagtgaac agttatttga    540
ggaccctgat cctggaggca aatcccaaga tgcagaggcc agaaagcaga cagaatcaga    600
acaaaaattg tctaaaatga cccacaatgc tttggagaac attaacgtga ttggccaagg    660
cttgaagcat ctcttccagc accagcgcag gaggtcatca gtgtctccac atgatgtgca    720
gcaaattcag gcagatccag aacctgaaat ggatctggaa agccagaacg catgtgctga    780
gattgatggt gtccccaccc accccacagc tctgaatcgt gtcctgcagc agattcgagt    840
gccacccnag atgaagagag ggacaagctt gcatagtagg cggggcaagc cagaggcccc    900
aaagggaagt ccccaaatca acaggaagtc tggtcaggag atgacagctg ttatgcagtc    960
aggccgaccc atgtcttcat ccacaactga tgcacctacc ggctctgcta tgatggaaat   1020
agcttgtgct gctgctgctg ctgctgctgc atgtctaccn ggagaggagg gaactgcgga   1080
gcggatcgaa cggttggaag taagcagcct tgcccaaaca tccagtgcag tggcctccag   1140
taccgatggc agcatccaca cagactctgt ggatggaaca ccagaccctc agcgcacaaa   1200
ggctgccatt gctcacctgc agcagaagat cctgaagctc acagaacnaa tcaagattgc   1260
acaaacagcc cgggacgaca acgttgctga atacttgaag cttgccaaca gtgcagacaa   1320
acagcaggct gcccgcatca agcaagtctt tgagaagaag aaccagaaat ctgcccnaac   1380
tatcctccag ctgcaaaaga aacttgagca ctaccacagg aagctcagag aggtagagca   1440
gaatgggatc ccccggcagc caaaggatgt cttcagggac atgcaccagg gtctgaagga   1500
tgtaggagca aaggtgactg gcttcagtga aggtgtggtg gatagtgtca aaggtgggtt   1560
ttccagcttc tcccaggcca cccattcagc agcaggcgct gtagtctcaa agcccagaga   1620
gattgcctca ctcattcgga acaaatttgg cagtgcagac aacatcccca acctgaagga   1680
ctctttagag gaagggcaag tggatgatgc ggggaaggct ttgggagtga tttcaaactt   1740
tcagtctagc ccaaaatatg gtagtgaaga agattgttct agtgccactt caggctcagt   1800
gggagccaac agcaccacag gggcatcgc tgtaggagca tccagctcca aaacaaacac    1860
cctggacatg cagagctcag gatttgatgc actactacat gagatccagg agatccggga   1920
aacccaggcc agactagagg aatcctttga gactctcaag gaacattatc agagggacta   1980
ttccttaata atgcagacct tacaggagga gcgatataga tgtgaacgat tggaagaaca   2040
gctaaatgac ctaacagagc tccaccagaa tgaaatcttg aacttgaagc aggaactggc   2100
aagcatggaa gaaaaaatcg cgtatcagtc ctatgaacgg gcccgggaca tccaggaggc   2160
cctggaggca tgccagacgc gcatctccaa gatggagctg cagcagcagc agcagcaggt   2220
ggtgcagcta gaagggctgg agaatgccac tgcccggaac cttctgggca aactcatcaa   2280
catcctcctg gctgtcatgg cagtcctttn ggtctttgnc tccactgtag ccaactgtgt   2340
ggtcccccctc atgaagactc gcaacaggac gttcagcact ttattccttg tggtttttat  2400
tgcctttctc tggaagcact gggacgccct cttcagctat gtggaacggt tcttttcatc   2460
ccctagatga tgctggcaca gaaggcattg ttccctaccc tctggcgagt gcatgcagca   2520
```

```
gagagttaga cagcaactta cctactctga agttttctac aacaaaaaaa gagttgagtg   2580
aatctgttta catttagaat aatgtttttt tcttcaagag acgcaattgc aatagtattt   2640
tttagatttt atccaagaag ttttttgggc gaaaatcttg gatcattttt atgtagcatg   2700
attttccttg ggatgcaaat cttaaaacag tcctttaata tgaaccaaca atctggagca   2760
caccgaaggg caatctaaat tgtggcttga aggactgcac taaaacccac taaaaagatg   2820
cgaaaacctg atgagggcna accagttaaa cctaacaccc tgccttgtct gggctcatca   2880
cctctcccta tcccagacta actttactgt gaaatcctac acattccatg tctgaatttt   2940
tggattcggg gtggattttc gttgtccgtg gaagaacaca tggatctctc tggctttctc   3000
acccaagttg gccacttacg ctaatcctgg aagtatgatc acttttgaac ctgcccctta   3060
accttgacga ggatacaaaa gtgaaagcat catcccccaa aggatcactg cacagtccta   3120
ctacagtatt tttaagtagc cctctaaata cttaatttta agcaaaatcc cttggccgca   3180
cttttaaggt ttttttatat gtgtatagtt accaacctaa aaataaaaaa tccgaacagc   3240
atacttgaag aatgtaatac tcaaactctc agtgcttcct tatggtttct aataggattt   3300
tttattattg ttattattat tattgggttt ttttggacag ggttgggagg gtcttttatt   3360
tttcctttga aataaagaag tgatgttttt aaatgaagaa atgtgtggat atttaagtgt   3420
gctgctccct cttgtcttga aacagtttga gtaagaaagt cttgctgtaa atgctgccct   3480
ctgccgcctt tgttttgaga tgcagtttaa actccctctg gctgctgctg ctgctttttg   3540
gtgtcccgac atacctacgc ccccgtttta tgggtttggc ttagttgaag aggaaagggt   3600
tgtgcaagga gagcaggagg ctgtttccaa aaaccagtgt agtaggatag ggattttttt   3660
tttttttttg ccccaagaaa acgttcaccc agtgatcttg ggctggggtt gtctttagga   3720
aaagttgaga ctataagagt cataaataag tccttgtgtt tccttaattt attttgttaa   3780
cacccctaat tacaaccaaa gtgatgatgt ggagtcttct gtcttcattt tggccccagc   3840
attcttaatt tcaaagcttt attctgtctg cctaagagaa tcaaccaaag gtgattctcc   3900
taaagagcag tgaaggaaat gtcaggttag caggacccaa gttttgggtg tgaaatgttg   3960
ccagcttcct ataatgtaaa cggacttgtt aacctaacct aattatgctc agtggacttc   4020
tatagatggt tttgaaaaat gaactgagct gccttcccgc atcgcataac cagttccatc   4080
atcctggtgg aacttgaaca tttagagttt atctagagag cttggttaat ctttccatat   4140
tatttgtagt attggtcaca aatgctgttc cctcttagcc tcattctgtg caaccaagtg   4200
catataagat gccctgaaaa gagtaacaaa gtatgctttg cctgtttcca cttaccagga   4260
aattccttca gaactagatt agcattgccc tgcctgtctg aaaggacagt ttacctaatg   4320
gtgccagcct ccttttgctt tggcaagctg gatttctcag agccagcatg ttgtttccat   4380
aactactttg atattttaac tcaggtactc cagtcttcac cccaacctca gctgattgta   4440
gtacacctgc tagctctgtt gccccctcaa aactgcaccc agagcagggc cacaagggtg   4500
cttttttttct ttaaaaaaaa aaaaattaga accaattcat gttcatgcca aaaacaaatt   4560
gtccccaagc ctatatgtat taaaatgtta actttgccta aaaatattgc agtgactttt   4620
taggcaggag tgccaaagga cactatgaac tttttgaact gacagtttct cctaactttc   4680
tgctttagcg taattgctca gagtagagag cccccacaaa gttatttaaa agatgcccta   4740
gcagcaatcc accagttttt ctaagctaga acctttgagt cccccaaact gcctgaagac   4800
ttaagttttg tgggcactgg aagtcacttt gatagatgga ttgaaactgt tcctatttgc   4860
```

-continued

```
cctgggacgg tttctatcta tcaaaggaag gttttcacct gtagaaagcc ccctgcctcc   4920

agccaaatag tcccatgctg actttctatc ttcctttctc aaactgtctt aggaaggacc   4980

ttcagtgcag atcaggtgca gtaatggctt tcttgtccct taattattca ccagacccag   5040

aagttgtacg catttaatgc tgtttgtaac catgcatctg ttttcattct ttgctgtacc   5100

ttttgctgcc catcctgtta cttttgagtt tctttcattg tggttgttct tgggttcttt   5160

tgtcttgtca gagctcttct ataacctcgc tctaatggct taacagttgt tctgggtgga   5220

aacgtcccct catttgaatg ctcctctaaa aaaaaaaaaa aaa                     5263
```

```
<210> SEQ ID NO 20
<211> LENGTH: 653
<212> TYPE: PRT
<213> ORGANISM: Homo sapiens
<220> FEATURE:
<221> NAME/KEY: UNSURE
<222> LOCATION: (114)
<220> FEATURE:
<221> NAME/KEY: UNSURE
<222> LOCATION: (247)
<220> FEATURE:
<221> NAME/KEY: UNSURE
<222> LOCATION: (290)
<220> FEATURE:
<221> NAME/KEY: UNSURE
<222> LOCATION: (601)
<220> FEATURE:
<221> NAME/KEY: UNSURE
<222> LOCATION: (604)

<400> SEQUENCE: 20

Met Glu Pro Ser Gly Ser Glu Gln Leu Phe Glu Asp Pro Asp Pro Gly
  1               5                  10                  15

Gly Lys Ser Gln Asp Ala Glu Ala Arg Lys Gln Thr Glu Ser Glu Gln
             20                  25                  30

Lys Leu Ser Lys Met Thr His Asn Ala Leu Glu Asn Ile Asn Val Ile
         35                  40                  45

Gly Gln Gly Leu Lys His Leu Phe Gln His Gln Arg Arg Arg Ser Ser
     50                  55                  60

Val Ser Pro His Asp Val Gln Gln Ile Gln Ala Asp Pro Glu Pro Glu
 65                  70                  75                  80

Met Asp Leu Glu Ser Gln Asn Ala Cys Ala Glu Ile Asp Gly Val Pro
                 85                  90                  95

Thr His Pro Thr Ala Leu Asn Arg Val Leu Gln Gln Ile Arg Val Pro
            100                 105                 110

Pro Xaa Met Lys Arg Gly Thr Ser Leu His Ser Arg Arg Gly Lys Pro
        115                 120                 125

Glu Ala Pro Lys Gly Ser Pro Gln Ile Asn Arg Lys Ser Gly Gln Glu
    130                 135                 140

Met Thr Ala Val Met Gln Ser Gly Arg Pro Met Ser Ser Ser Thr Thr
145                 150                 155                 160

Asp Ala Pro Thr Gly Ser Ala Met Met Glu Ile Ala Cys Ala Ala Ala
                165                 170                 175

Ala Ala Ala Ala Ala Cys Leu Pro Gly Glu Glu Gly Thr Ala Glu Arg
            180                 185                 190

Ile Glu Arg Leu Glu Val Ser Ser Leu Ala Gln Thr Ser Ser Ala Val
        195                 200                 205

Ala Ser Ser Thr Asp Gly Ser Ile His Thr Asp Ser Val Asp Gly Thr
    210                 215                 220
```

-continued

```
Pro Asp Pro Gln Arg Thr Lys Ala Ala Ile Ala His Leu Gln Gln Lys
225                 230                 235                 240

Ile Leu Lys Leu Thr Glu Xaa Ile Lys Ile Ala Gln Thr Ala Arg Asp
                245                 250                 255

Asp Asn Val Ala Glu Tyr Leu Lys Leu Ala Asn Ser Ala Asp Lys Gln
            260                 265                 270

Gln Ala Ala Arg Ile Lys Gln Val Phe Glu Lys Lys Asn Gln Lys Ser
        275                 280                 285

Ala Xaa Thr Ile Leu Gln Leu Gln Lys Lys Leu Glu His Tyr His Arg
    290                 295                 300

Lys Leu Arg Glu Val Glu Gln Asn Gly Ile Pro Arg Gln Pro Lys Asp
305                 310                 315                 320

Val Phe Arg Asp Met His Gln Gly Leu Lys Asp Val Gly Ala Lys Val
                325                 330                 335

Thr Gly Phe Ser Glu Gly Val Val Asp Ser Val Lys Gly Gly Phe Ser
            340                 345                 350

Ser Phe Ser Gln Ala Thr His Ser Ala Ala Gly Ala Val Val Ser Lys
        355                 360                 365

Pro Arg Glu Ile Ala Ser Leu Ile Arg Asn Lys Phe Gly Ser Ala Asp
    370                 375                 380

Asn Ile Pro Asn Leu Lys Asp Ser Leu Glu Glu Gly Gln Val Asp Asp
385                 390                 395                 400

Ala Gly Lys Ala Leu Gly Val Ile Ser Asn Phe Gln Ser Ser Pro Lys
                405                 410                 415

Tyr Gly Ser Glu Glu Asp Cys Ser Ser Ala Thr Ser Gly Ser Val Gly
            420                 425                 430

Ala Asn Ser Thr Thr Gly Gly Ile Ala Val Gly Ala Ser Ser Ser Lys
        435                 440                 445

Thr Asn Thr Leu Asp Met Gln Ser Ser Gly Phe Asp Ala Leu Leu His
    450                 455                 460

Glu Ile Gln Glu Ile Arg Glu Thr Gln Ala Arg Leu Glu Glu Ser Phe
465                 470                 475                 480

Glu Thr Leu Lys Glu His Tyr Gln Arg Asp Tyr Ser Leu Ile Met Gln
                485                 490                 495

Thr Leu Gln Glu Glu Arg Tyr Arg Cys Glu Arg Leu Glu Glu Gln Leu
            500                 505                 510

Asn Asp Leu Thr Glu Leu His Gln Asn Glu Ile Leu Asn Leu Lys Gln
        515                 520                 525

Glu Leu Ala Ser Met Glu Glu Lys Ile Ala Tyr Gln Ser Tyr Glu Arg
    530                 535                 540

Ala Arg Asp Ile Gln Glu Ala Leu Glu Ala Cys Gln Thr Arg Ile Ser
545                 550                 555                 560

Lys Met Glu Leu Gln Gln Gln Gln Gln Gln Val Val Gln Leu Glu Gly
                565                 570                 575

Leu Glu Asn Ala Thr Ala Arg Asn Leu Leu Gly Lys Leu Ile Asn Ile
            580                 585                 590

Leu Leu Ala Val Met Ala Val Leu Xaa Val Phe Xaa Ser Thr Val Ala
        595                 600                 605

Asn Cys Val Val Pro Leu Met Lys Thr Arg Asn Arg Thr Phe Ser Thr
    610                 615                 620

Leu Phe Leu Val Val Phe Ile Ala Phe Leu Trp Lys His Trp Asp Ala
625                 630                 635                 640

Leu Phe Ser Tyr Val Glu Arg Phe Phe Ser Ser Pro Arg
```

645 650

<210> SEQ ID NO 21
<211> LENGTH: 3349
<212> TYPE: DNA
<213> ORGANISM: Homo sapiens

<400> SEQUENCE: 21

```
cccccctccag gccccgctcc tgcgccctat ttggtcattc ggggggcaag cggcgggagg     60
ggaaacgtgc gcggccgaag gggaagcgga gccggcgccg gctgcgcaga ggagccgctc    120
tcgccgccgc cacctcggct gggagcccac gaggctgccg catcctgccc tcggaacaat    180
gggactcggc gcgcgaggtg cttgggccgc gctgctcctg ggacgctgc aggtgctagc    240
gctgctgggg gccgcccatg aaagcgcagc catggcggca tctgcaaaca tagagaattc    300
tgggcttcca cacaactcca gtgctaactc aacagagact ctccaacatg tgccttctga    360
ccatacaaat gaaacttcca acagtactgt gaaaccacca acttcagttg cctcagactc    420
cagtaataca acggtcacca ccatgaaacc tacagcggca tctaatacaa caacaccagg    480
gatggtctca acaaatatga cttctaccac cttaaagtct acacccaaaa caacaagtgt    540
ttcacagaac acatctcaga tatcaacatc cacaatgacc gtaacccaca atagttcagt    600
gacatctgct gcttcatcag taacaatcac aacaactatg cattctgaag caaagaaagg    660
atcaaaattt gatactggga gctttgttgg tggtattgta ttaacgctgg gagttttatc    720
tattctttac attggatgca aaatgtatta ctcaagaaga ggcattcggt atcgaaccat    780
agatgaacat gatgccatca tttaaggaaa tccatggacc aaggatggaa tacagattga    840
tgctgcccta tcaattaatt ttggtttatt aatagtttaa aacaatattc tctttttgaa    900
aatagtataa acaggccatg catataatgt acagtgtatt agtaaatatg taaagattct    960
tcaaggtaac aagggtttgg gttttgaaat aaacatctgg atcttataga ccgttcatac   1020
aatggtttta gcaagttcat agtaagacaa acaagtccta tctttttttt tttggctggg   1080
gtgggggcat tggtcacata tgaccagtaa ttgaaagacg tcatcactga aagacagaat   1140
gccatctggg catacaaata agaagtttgt cacagcactc aggattttgg gtatcttttg   1200
tagctcacat aaagaacttc agtgcttttc agagctggat atatcttaat tactaatgcc   1260
acacagaaat tatacaatca aactagatct gaagcataat ttaagaaaaa catcaacatt   1320
ttttgtgctt taaactgtag tagttggtct agaaacaaaa tactccaaga aaaagaaaat   1380
tttcaaataa aacccaaaat aatagctttg cttagccctg ttagggatcc attggagcat   1440
taaggagcac atatttttat taacttcttt tgagctttca atgttgatgt aatttttgtt   1500
ctctgtgtaa tttaggtaaa ctgcagtgtt taacataata atgttttaaa gacttagttg   1560
tcagtattaa ataatcctgg cattataggg aaaaaacctc ctagaagtta gattatttgc   1620
tactgtgaga atattgtcac cactggaagt tactttagtt catttaattt taattttata   1680
ttttgtgaat attttaagaa ctgtagagct gctttcaata tctagaaatt tttaattgag   1740
tgtaaacaca cctaacttta agaaaaagaa ccccttgtat gattttcaaa agaacattta   1800
gaattctata gagtcaaaac tatagcgtaa tgctgtgttt attaagccag ggattgtggg   1860
acttccccca ggctactaaa cctgcaggat gaaaatgcta tattttcttt catgcactgt   1920
cgatattact cagatttggg gaaatgacat ttttatacta aaacaaacac caaaatattt   1980
tagaataaat tcttagaaag ttttgagagg aatttttaga gaggacattt cctccttcct   2040
gatttggata ttccctcaaa tccctcctct tactccatgc tgaaggagaa gtactctcag   2100
```

-continued

```
atgcattatg ttaatggaga gaaaaagcac agtattgtag agacaccaat attagctaat   2160
gtattttgga gtgttttcca ttttacagtt tatattccag cactcaaaac tcagggtcaa   2220
gttttaacaa aagaggtatg tagtcacagt aaatactaag atggcatttc tatctcagag   2280
ggccaaagtg aatcacacca gtttctgaag gtcctaaaaa tagctcagat gtcctaatga   2340
acatgcacct acatttaata ggagtacaat aaaactgttg tcagcttttg ttttacagag   2400
aacgctagat attaagaatt ttgaaatgga tcatttctac ttgctgtgca ttttaaccaa   2460
taatctgatg aatatagaaa aaaatgatcc aaaatatgga tatgattgga tgtatgtaac   2520
acatacatgg agtatggagg aaattttctg aaaaatacat ttagattagt ttagtttgaa   2580
ggagaggtgg gctgatggct gagttgtatg ttactaactt ggccctgact ggttgtgcaa   2640
ccattgcttc atttctttgc aaaatgtagt taagatatac tttattctaa tgaaggcctt   2700
ttaaatttgt ccactgcatt cttggtattt cactacttca agtcagtcag aacttcgtag   2760
accgacctga agtttctttt tgaatacttg tttctttagc actttgaaga tagaaaaacc   2820
actttttaag tactaagtca tcatttgcct tgaaagtttc ctctgcattg ggtttgaagt   2880
agtttagtta tgtctttttc tctgtatgta agtagtataa tttgttactt tcaaataccc   2940
gtactttgaa tgtaggtttt tttgttgttg ttatctataa aaattgaggg aaatggttat   3000
gcaaaaaaat attttgcttt ggaccatatt tcttaagcat aaaaaaaatg ctcagttttg   3060
cttgcattcc ttgagaatgt atttatctga agatcaaaac aaacaatcca gatgtataag   3120
tactaggcag aagccaattt taaaatttcc ttgaataatc catgaaagga ataattcaaa   3180
tacagataaa cagagttggc agtatattat agtgataatt ttgtattttc acaaaaaaaa   3240
agttaaactc ttcttttctt tttattataa tgaccagctt ttggtatttc attgttacca   3300
agttctattt ttagaataaa attgttctcc ttctaaaaaa aaaaaaaaa              3349
```

<210> SEQ ID NO 22
<211> LENGTH: 208
<212> TYPE: PRT
<213> ORGANISM: Homo sapiens

<400> SEQUENCE: 22

```
Met Gly Leu Gly Ala Arg Gly Ala Trp Ala Ala Leu Leu Leu Gly Thr
  1               5                  10                  15

Leu Gln Val Leu Ala Leu Leu Gly Ala Ala His Glu Ser Ala Ala Met
             20                  25                  30

Ala Ala Ser Ala Asn Ile Glu Asn Ser Gly Leu Pro His Asn Ser Ser
         35                  40                  45

Ala Asn Ser Thr Glu Thr Leu Gln His Val Pro Ser Asp His Thr Asn
     50                  55                  60

Glu Thr Ser Asn Ser Thr Val Lys Pro Pro Thr Ser Val Ala Ser Asp
 65                  70                  75                  80

Ser Ser Asn Thr Thr Val Thr Thr Met Lys Pro Thr Ala Ala Ser Asn
                 85                  90                  95

Thr Thr Thr Pro Gly Met Val Ser Thr Asn Met Thr Ser Thr Thr Leu
            100                 105                 110

Lys Ser Thr Pro Lys Thr Thr Ser Val Ser Gln Asn Thr Ser Gln Ile
        115                 120                 125

Ser Thr Ser Thr Met Thr Val Thr His Asn Ser Ser Val Thr Ser Ala
    130                 135                 140

Ala Ser Ser Val Thr Ile Thr Thr Thr Met His Ser Glu Ala Lys Lys
```

-continued

```
145                 150                 155                 160

Gly Ser Lys Phe Asp Thr Gly Ser Phe Val Gly Gly Ile Val Leu Thr
                165                 170                 175

Leu Gly Val Leu Ser Ile Leu Tyr Ile Gly Cys Lys Met Tyr Tyr Ser
            180                 185                 190

Arg Arg Gly Ile Arg Tyr Arg Thr Ile Asp Glu His Asp Ala Ile Ile
        195                 200                 205


<210> SEQ ID NO 23
<211> LENGTH: 2361
<212> TYPE: DNA
<213> ORGANISM: Homo sapiens

<400> SEQUENCE: 23

aagaggccta gacttaagaa gcttctgaaa gaccatgcct catccatgcc taacgcagag     60

tcctggcctg tcgtaggtca gttttcaagc gttggctcct tgggagccga tgaatcaaag    120

tggttatgtt ctgagtttaa agagagcatg ctgacactgg ggaaggaaag caagactcca    180

ggaaaaagct ctgttcctct ttacttgatc tatccttctg tggaaaatgt gcggaccagt    240

ttagaaggat atcctgctgg gggctctctt ccctatagca tccagacagc tgaaaaacag    300

aattggctgc attcctattt tcacaaatgg tcagctgaga cttctggccg cagcaatgcc    360

atgccacata ttaagacata tatgaggcct tctccagact tcagtaaaat tgcttggttc    420

cttgtcacaa gcgcaaatct gtccaaggct gcctggggag cattggagaa gaatggcacc    480

cagctgatga tccgctccta cgagctcggg gtccttttcc tcccttcagc atttggtcta    540

gacagtttca aagtgaaaca gaagttcttc gctggcagcc aggagccaat ggccaccttt    600

cctgtgccat atgatttgcc tccagaactg tatggaagta aagatcggcc atggatatgg    660

aacattcctt atgtcaaagc accggatacg catgggaaca tgtgggtgcc ctcctgagaa    720

tcttgaggca ctgtgaaatt taagtgtaag acattgagcc acaaacatgg aatctcttct    780

ttgtactgga tgtccacttc ccttaaagtc ttatttgcac ccttacaaaa tctttccaaa    840

ggtcactctt atgaatggat gttggttata cttttaatgg acattaacat tcctaataaa    900

gtattagttt cttaattcac ttttatatgt tttggaaaga aaattagtga acttctctat    960

gttaaaaata cgtactgctt gagtatcccc tgtctgaaat gcttgggacc agaagtgttt   1020

cagcttttgg attttttga attttggaat atttgcatag cataatgaga tatcttggga    1080

atgggaccca aatctaaaca caaaattcat ttatgtttca tatacacctt atatacaata   1140

acctaaaggt gattttatat gatattttga gtaattttat gcatgaaaca aagttttgac   1200

aggcttttga ccgtgattca tcacatgagt tcaggcatgg aaattttcat ttggagcatc   1260

atgtcagcac tcaaaaagtt ctggatcttg gagcagttca gattttcaga ttagggatgc   1320

tcaaatctat atagatataa aattatcctc acagtaacat agaatctctt ggtgctgtca   1380

gctgttggga attgaagatt gactttgtgc ttccaccctc catccagaaa ggcacccttc   1440

attccaccag aattttaccc aggaagaaca cgatcatttc ctttttcacc gatgccctct   1500

ctcagctttc tgagtacgtc tcttggggtc gctggaggtg atcctaggat ctgtctctga   1560

gaccaatgtg ctgtttcagc cccctgcagc taagaattgt attgactgtc ctcacagcgg   1620

cttttcatag ctttcagctt cagctttacg aggcttctcc tctctccctg gcacctgctg   1680

gctgcctcac tgcttacaga caggtcccac caaacccaaa cacctgccta gggtaaatgg   1740

gtctctcttc tatccccaga aactttcaga ggaagcagct catagaaaca tacaaaagca   1800
```

-continued

```
cacaagtatt ttgggaaaaa atcctaaaag gtgacttaat ttgatgcctt aaattcacaa   1860

gtgaggaagc taaggcctag aaggttaagg atgtccccag ggtcacacag tgagcggggc   1920

tcagagcttg agtgtctttg tgctttgtgt acattgtgtt ctccctaggg tgctttagac   1980

cctgtttgtt ttcttctgca tgaggctgat ttccagtttg tcatcaacct ctttatctta   2040

taatttagga tagagttgaa cgttagtctt gaaagatttt ctaaagtagt ctttcaaact   2100

gttcctcaga ggcctaggat tttccaaaag taccttagga accttgtagg ctgcagtggg   2160

ggtgtggcga tagagcagga ggcagggaga cagggctgca gggcctccca ccttccaaca   2220

gacaggctct gctgtatctg ttgtacatac tgggattctg taaaggacat tatctggggt   2280

gtcgtaggta tttttgtgtg ttctgctttt tttaaataaa cttgaaaagc tactgaacta   2340

aaaaaaaaaa aaaaaaaaaa a                                             2361
```

<210> SEQ ID NO 24
<211> LENGTH: 223
<212> TYPE: PRT
<213> ORGANISM: Homo sapiens

<400> SEQUENCE: 24

```
Met Pro Asn Ala Glu Ser Trp Pro Val Val Gly Gln Phe Ser Ser Val
  1               5                  10                  15

Gly Ser Leu Gly Ala Asp Glu Ser Lys Trp Leu Cys Ser Glu Phe Lys
             20                  25                  30

Glu Ser Met Leu Thr Leu Gly Lys Glu Ser Lys Thr Pro Gly Lys Ser
         35                  40                  45

Ser Val Pro Leu Tyr Leu Ile Tyr Pro Ser Val Glu Asn Val Arg Thr
     50                  55                  60

Ser Leu Glu Gly Tyr Pro Ala Gly Gly Ser Leu Pro Tyr Ser Ile Gln
 65                  70                  75                  80

Thr Ala Glu Lys Gln Asn Trp Leu His Ser Tyr Phe His Lys Trp Ser
                 85                  90                  95

Ala Glu Thr Ser Gly Arg Ser Asn Ala Met Pro His Ile Lys Thr Tyr
            100                 105                 110

Met Arg Pro Ser Pro Asp Phe Ser Lys Ile Ala Trp Phe Leu Val Thr
        115                 120                 125

Ser Ala Asn Leu Ser Lys Ala Ala Trp Gly Ala Leu Glu Lys Asn Gly
    130                 135                 140

Thr Gln Leu Met Ile Arg Ser Tyr Glu Leu Gly Val Leu Phe Leu Pro
145                 150                 155                 160

Ser Ala Phe Gly Leu Asp Ser Phe Lys Val Lys Gln Lys Phe Phe Ala
                165                 170                 175

Gly Ser Gln Glu Pro Met Ala Thr Phe Pro Val Pro Tyr Asp Leu Pro
            180                 185                 190

Pro Glu Leu Tyr Gly Ser Lys Asp Arg Pro Trp Ile Trp Asn Ile Pro
        195                 200                 205

Tyr Val Lys Ala Pro Asp Thr His Gly Asn Met Trp Val Pro Ser
    210                 215                 220
```

<210> SEQ ID NO 25
<211> LENGTH: 3370
<212> TYPE: DNA
<213> ORGANISM: Homo sapiens

<400> SEQUENCE: 25

```
cgcgctgtgg ctgctgctgc tgctgctgcc ccggacccgg gcggacgagc acgaacacac     60
```

-continued

```
gtatcaagat aaagaggaag ttgtcttatg gatgaatact gttgggccct accataatcg    120
tcaagaaaca tataagtact tttcacttcc attctgtgtg gggtcaaaaa aaagtatcag    180
tcattaccat gaaactctgg gagaagcact tcaaggggtt gaattggaat ttagtggtct    240
ggatattaaa tttaaagatg atgtgatgcc agccacttac tgtgaaattg atttagataa    300
agaaaagaga gatgcatttg tatatgccat aaaaaatcat tactggtacc agatgtacat    360
agatgattta ccaatatggg gtattgttgg tgaggctgat gaaaatggag aagattacta    420
tctttggacc tataaaaaac ttgaaatagg ttttaatgga aatcgaattg ttgatgttaa    480
tctaactagt gaaggaaagg tgaaactggt tccaaatact aaaatccaga tgtcatattc    540
agtaaaatgg aaaaagtcag atgtgaaatt tgaagatcga tttgacaaat atcttgatcc    600
gtcctttttt caacatcgga ttcattggtt ttcaattttc aactccttca tgatggtgat    660
cttcttggtg ggcttagttt caatgatttt aatgagaaca ttaagaaaag attatgctcg    720
gtacagtaaa gaggaagaaa tggatgatat ggatagagac ctaggagatg aatatggatg    780
gaaacaggtg catggagatg tatttagacc atcaagtcac ccactgatat tttcctctct    840
gattggttct ggatgtcaga tatttgctgt gtctctcatc gttattattg ttgcaatgat    900
agaagattta tatactgaga ggggatcaat gctcagtaca gccatatttg tctatgctgc    960
tacgtctcca gtgaatggtt attttggagg aagtctgtat gctagacaag gaggaaggag   1020
atggataaag cagatgttta ttggggcatt ccttatccca gctatggtgt gtggcactgc   1080
cttcttcatc aatttcatag ccatttatta ccatgcttca agagccattc cttttggaac   1140
aatggtggcc gtttgttgca tctgtttttt tgttattctt cctctaaatc ttgttggtac   1200
aatacttggc cgaaatctgt caggtcagcc caactttcct tgtcgtgtca atgctgtgcc   1260
tcgtcctata ccggagaaaa aatggttcat ggagcctgcg gttattgttt gcctgggtgg   1320
aattttacct tttggttcaa tctttattga aatgtatttc atcttcacgt ctttctgggc   1380
atataagatc tattatgtct atggcttcat gatgctggtg ctggttatcc tgtgcattgt   1440
gactgtctgt gtgactattg tgtgcacata ttttctacta aatgcagaag attacccgtg   1500
gcaatggaca agttttctct ctgctgcatc aactgcaatc tatgtttaca tgtattcctt   1560
ttactactat tttttcaaaa caaagatgta tggcttattt caaacatcat tttactttgg   1620
atatatggcg gtatttagca cagccttggg gataatgtgt ggagcgattg gttacatggg   1680
aacaagtgcc tttgtccgaa aaatctatac taatgtgaaa attgactaga gacccaagaa   1740
aacctggaac tttggatcaa tttctttttc ataggggtgg aacttgcaca gcaaaaacaa   1800
acaaacgcaa gaagagattt gggctttaac acactgggta ctttgtgggt ctgtctttcg   1860
tcggtggctt aaagtaacat ctatttccat tgatcctagg ttcttcctga ctgctttctc   1920
caactgttca cagcaaatgc ttggatttta tgcagtaggc attactacag tacatggcta   1980
atcttcccaa aaactagctc attaaagatg aaatagacca gctctcttca gtgaagagga   2040
caaatagttt atttaaagca tttgttccaa taaaataaat agagggaaac ttggatgcta   2100
aaattacatg aataggaatc ttcctggcac ttagtgtttc tatgttattg aaaaatgatg   2160
ttccagaaag attacttttt tcctcttatt tttactgcca ttgtcgacct attgtgggac   2220
atttttatat attgaatctg ggttcttttt tgactttttt ttttcccaat ccaacagcat   2280
cctttttttt aaaagagaga attagaaaat attaaatcct gcatgtaata tatctgctgt   2340
catcttagtt ggaccaactt cccatttatt tatcttaaaa ctatacagtt acatcttaat   2400
```

-continued

```
tccatccaaa gaagatacag tttgaagaca gaagtgtact ctctacaatg caatttactg   2460

tacagttaga aagcaaagtg ttaaatggag aagatacttg tttttattaa acattttgag   2520

atttagataa actacatttt aactgaatgt ctaaagtgat tatctttttt ccccccaagt   2580

tagtcttaaa tcttttgggt ttgaatgaag gttttacata agaaattatt aaaaacaagg   2640

ggggtgggta ataaatgtat ataacattaa ataatgtaac gtaggtgtag attcccaaat   2700

gcatttggat gtacagatcg actacagagt acttttttct tatgatgatt ggtgtagaaa   2760

tgtgtgattt gggtgggctt ttacatcttg cctaccattg catgaaacat tggggtttct   2820

tcaaaatgtg tgtgtcatac ttcttttggg aggggggttg ttttcttctg tttattttct   2880

gagactccta caggacccaa atttgtaatt tagagacact taattttgtt aatcctgcct   2940

gggacactta agtaacatct aaagcattat tgctttagaa tgttcaaata aaatttcctg   3000

accaaattgt tttgtggaaa tagatgtgtt tgcaatttga agatatcttt ctgtccagaa   3060

ggcaaaatta ccgaatgcca tttttaaaag tatgctataa actatgctac tctcatacag   3120

gggacccgta ttttaaaatc tccagacttg cttacatcta gattatccag cacaatcata   3180

aagtgaatga caaacccttt gaatgaaatt gtggcacaaa atctgttcag gttggtgtac   3240

cgtgtaaagt ggggatgggg taaaagtggt taacgtactg ttggatcaac aaataaaggt   3300

tacagttttg tttgagaaaa aaaaaaaaaa aaaaaaaaaa aaaaaaaaaa aaaaaaaaaa   3360

aaaaaaaaaa                                                          3370
```

<210> SEQ ID NO 26
<211> LENGTH: 545
<212> TYPE: PRT
<213> ORGANISM: Homo sapiens

<400> SEQUENCE: 26

```
Met Asn Thr Val Gly Pro Tyr His Asn Arg Gln Glu Thr Tyr Lys Tyr
  1               5                  10                  15

Phe Ser Leu Pro Phe Cys Val Gly Ser Lys Lys Ser Ile Ser His Tyr
             20                  25                  30

His Glu Thr Leu Gly Glu Ala Leu Gln Gly Val Glu Leu Glu Phe Ser
         35                  40                  45

Gly Leu Asp Ile Lys Phe Lys Asp Asp Val Met Pro Ala Thr Tyr Cys
     50                  55                  60

Glu Ile Asp Leu Asp Lys Glu Lys Arg Asp Ala Phe Val Tyr Ala Ile
 65                  70                  75                  80

Lys Asn His Tyr Trp Tyr Gln Met Tyr Ile Asp Asp Leu Pro Ile Trp
                 85                  90                  95

Gly Ile Val Gly Glu Ala Asp Glu Asn Gly Glu Asp Tyr Tyr Leu Trp
            100                 105                 110

Thr Tyr Lys Lys Leu Glu Ile Gly Phe Asn Gly Asn Arg Ile Val Asp
        115                 120                 125

Val Asn Leu Thr Ser Glu Gly Lys Val Lys Leu Val Pro Asn Thr Lys
    130                 135                 140

Ile Gln Met Ser Tyr Ser Val Lys Trp Lys Lys Ser Asp Val Lys Phe
145                 150                 155                 160

Glu Asp Arg Phe Asp Lys Tyr Leu Asp Pro Ser Phe Phe Gln His Arg
                165                 170                 175

Ile His Trp Phe Ser Ile Phe Asn Ser Phe Met Met Val Ile Phe Leu
            180                 185                 190

Val Gly Leu Val Ser Met Ile Leu Met Arg Thr Leu Arg Lys Asp Tyr
```

```
        195                 200                 205

Ala Arg Tyr Ser Lys Glu Glu Glu Met Asp Asp Met Asp Arg Asp Leu
    210                 215                 220

Gly Asp Glu Tyr Gly Trp Lys Gln Val His Gly Asp Val Phe Arg Pro
225                 230                 235                 240

Ser Ser His Pro Leu Ile Phe Ser Ser Leu Ile Gly Ser Gly Cys Gln
                245                 250                 255

Ile Phe Ala Val Ser Leu Ile Val Ile Ile Val Ala Met Ile Glu Asp
            260                 265                 270

Leu Tyr Thr Glu Arg Gly Ser Met Leu Ser Thr Ala Ile Phe Val Tyr
        275                 280                 285

Ala Ala Thr Ser Pro Val Asn Gly Tyr Phe Gly Gly Ser Leu Tyr Ala
    290                 295                 300

Arg Gln Gly Gly Arg Arg Trp Ile Lys Gln Met Phe Ile Gly Ala Phe
305                 310                 315                 320

Leu Ile Pro Ala Met Val Cys Gly Thr Ala Phe Phe Ile Asn Phe Ile
                325                 330                 335

Ala Ile Tyr Tyr His Ala Ser Arg Ala Ile Pro Phe Gly Thr Met Val
            340                 345                 350

Ala Val Cys Cys Ile Cys Phe Phe Val Ile Leu Pro Leu Asn Leu Val
        355                 360                 365

Gly Thr Ile Leu Gly Arg Asn Leu Ser Gly Gln Pro Asn Phe Pro Cys
    370                 375                 380

Arg Val Asn Ala Val Pro Arg Pro Ile Pro Glu Lys Lys Trp Phe Met
385                 390                 395                 400

Glu Pro Ala Val Ile Val Cys Leu Gly Gly Ile Leu Pro Phe Gly Ser
                405                 410                 415

Ile Phe Ile Glu Met Tyr Phe Ile Phe Thr Ser Phe Trp Ala Tyr Lys
            420                 425                 430

Ile Tyr Tyr Val Tyr Gly Phe Met Met Leu Val Leu Val Ile Leu Cys
        435                 440                 445

Ile Val Thr Val Cys Val Thr Ile Val Cys Thr Tyr Phe Leu Leu Asn
    450                 455                 460

Ala Glu Asp Tyr Pro Trp Gln Trp Thr Ser Phe Leu Ser Ala Ala Ser
465                 470                 475                 480

Thr Ala Ile Tyr Val Tyr Met Tyr Ser Phe Tyr Tyr Tyr Phe Phe Lys
                485                 490                 495

Thr Lys Met Tyr Gly Leu Phe Gln Thr Ser Phe Tyr Phe Gly Tyr Met
            500                 505                 510

Ala Val Phe Ser Thr Ala Leu Gly Ile Met Cys Gly Ala Ile Gly Tyr
        515                 520                 525

Met Gly Thr Ser Ala Phe Val Arg Lys Ile Tyr Thr Asn Val Lys Ile
    530                 535                 540

Asp
545

<210> SEQ ID NO 27
<211> LENGTH: 3136
<212> TYPE: DNA
<213> ORGANISM: Homo sapiens

<400> SEQUENCE: 27

gctgcgagta cctccatggt cccggtggct gtgacggcgg cagtggcgcc tgtcctgtcc      60

ataaacagcg atttctcaga tttgcgggaa attaaaaagc aactgctgct tattgcgggc     120
```

-continued cttacccggg agcggggcct actacacagt agcaaatggt cggcggagtt ggctttctct 180
ctccctgcat tgcctctggc cgagctgcaa ccgcctccgc ctattacaga ggaagatgcc 240
caggatatgg atgcctatac cctggccaag gcctactttg acgttaaaga gtatgatcgg 300
gcagcacatt tcctgcatgg ctgcaatagc aagaaagcct attttctgta tatgtattcc 360
agatatctgt ctggagaaaa aaagaaggac gatgaaacag ttgatagctt aggccccctg 420
gaaaaaggac aagtgaaaaa tgaggcgctt agagaattga gagtggagct cagcaaaaaa 480
caccaagctc gagaacttga tggatttgga ctttatctgt atggtgtggt gcttcgaaaa 540
ctggacttgg ttaaagaggc cattgatgtg tttgtggaag ctactcatgt tttgcccttg 600
cattggggag cctggttaga actctgtaac ctgatcacag acaaagagat gctgaagttc 660
ctgtctttgc cagacacctg gatgaaagag ttttttctgg ctcatatata cacagagttg 720
cagttgatag aggaggccct gcaaaagtat cagaatctca ttgatgtggg cttctctaag 780
agctcgtata ttgtttccca aattgcagtt gcctatcaca atatcagaga tattgacaaa 840
gccctctcca tttttaatga gctaaggaaa caagaccctt acaggattga aaatatggac 900
acattctcca accttcttta tgtcaggagc atgaaatcgg agttgagtta tctggctcat 960
aacctctgtg agattgataa atatcgtgta gaaacgtgct gtgtaattgg caattattac 1020
agtttacgtt ctcagcatga gaaagcagcc ttatatttcc agagagccct gaaattaaat 1080
cctcggtatc ttggtgcctg gacactaatg ggacatgagt acatggagat gaagaacacg 1140
tctgctgcta tccaggctta tagacatgcc attgaggtca acaaacggga ctacagagct 1200
tggtatggcc tcgggcagac ctatgaaatc cttaagatgc cattttactg cctttattat 1260
tatagacggg cccaccagct tcgacccaat gattctcgca tgctggttgc tttaggagaa 1320
tgttacgaga aactcaatca actagtggaa gccaaaaagt gtttttggat agcttacgcc 1380
gtgggagatg tggagaaaat ggctctggtg aaactggcaa agcttcatga acagttgact 1440
gagtcagaac aggctgccca gtgttacatc aaatatatcc aagatatcta tacctgtggg 1500
gaaatagtag aacacttgga ggaaagcact gcctttcgct atctggccca gtactatttt 1560
aagtgcaaac tgtgggatga agcttcaact tgtgcacaaa agtgttgtgc atttaatgat 1620
acccgggaag aaggtaaggc cttactccgg caaatcctac agcttcggaa ccaaggcgag 1680
actcctacca ccgaggtgcc tgctcccttt ttcctacctg cttcactctc tgctaacaat 1740
acccccacac gcagagtttc tccactcaac ttgtcttctg tcacgccata gttggctact 1800
ctcaagccag cacattgtta gacccatctt aattaagcct tacctccatg taaagaacag 1860
cacgtctgtt ccaaggacct cagctcttct tgtgtctaca gatggcaaca gctccatagg 1920
ggacagcttg tataattacc ttcagaggcc aactgacaga atcctggcag gaacagacat 1980
tatcttgcca gttagaagta cttctgtctc acttatgtcc aaagagtggc tatagatctt 2040
ggccttcttc cctgaatgct tttttttttt tggcccccaa gaaagtccct tttatagcac 2100
tttagcacag gcaatgctac aggaacaaag tttcaatgct gctgagagtg aaagaaagga 2160
ggaaagtctg ccactctacc ctgagctggc agtagggcac tgagtaccct aggaagaagt 2220
cagagcaatg gatacaaatg accttgctct tggatttgct gagcatgatc cctattctga 2280
tgtcagagat taggtttaaa tggaatagag ctatccattt gttcttactc tctagggaga 2340
caatcttcca aaacagtttt ggggggtct tctaaagctt tcaaattgga agtaacttta 2400
ttcaactaga gttgaataaa agaagggcaa aaataatctc acagagcttg gaactgctga 2460

-continued

```
tagcccttac tgagggcaaa agatggctat attgttagct atactcctac caaagcaagc   2520

aaggagatag gattatagat aatttcacgg acatttggaa ataacattgg tgattataca   2580

gacaagaata aactcacttc aagctggtct gttttaataa attttcaacg taattgtcta   2640

ttttttccc tcccatctgc aacagaatac attttttca gcctttatct agatgaggta   2700

aagggaatca ttcttatggt gctcttggag agtttcaggc ctgtgcatgt gtgtacagca   2760

ggaggtaata tgctataatg tctgctgtaa tatatttgca cagtagatgc tatggatcat   2820

tctgagctca gggtccagac tttattctta ttcccagaat tttgtgttac gtttttacct   2880

cctaacatat gacacttcat cttatattaa ggaaggttta gaatatctaa tacgacttga   2940

attcatttgt tactaagcct tctcaggcaa gctgtatact agttactggt ctccactgcc   3000

atgccttttc aaggttccca tggtccagaa tgatgtttga ttcttaattt ttctgtccct   3060

tttataattt gttttaatga ttttgctaca tttggaattc aataaaaaat gtgaacaata   3120

aaaaaaaaaa aaaaaa                                                   3136
```

<210> SEQ ID NO 28
<211> LENGTH: 591
<212> TYPE: PRT
<213> ORGANISM: Homo sapiens

<400> SEQUENCE: 28

```
Met Val Pro Val Ala Val Thr Ala Ala Val Ala Pro Val Leu Ser Ile
  1               5                  10                  15

Asn Ser Asp Phe Ser Asp Leu Arg Glu Ile Lys Lys Gln Leu Leu Leu
             20                  25                  30

Ile Ala Gly Leu Thr Arg Glu Arg Gly Leu Leu His Ser Ser Lys Trp
         35                  40                  45

Ser Ala Glu Leu Ala Phe Ser Leu Pro Ala Leu Pro Leu Ala Glu Leu
     50                  55                  60

Gln Pro Pro Pro Pro Ile Thr Glu Glu Asp Ala Gln Asp Met Asp Ala
 65                  70                  75                  80

Tyr Thr Leu Ala Lys Ala Tyr Phe Asp Val Lys Glu Tyr Asp Arg Ala
                 85                  90                  95

Ala His Phe Leu His Gly Cys Asn Ser Lys Lys Ala Tyr Phe Leu Tyr
            100                 105                 110

Met Tyr Ser Arg Tyr Leu Ser Gly Glu Lys Lys Lys Asp Asp Glu Thr
        115                 120                 125

Val Asp Ser Leu Gly Pro Leu Glu Lys Gly Gln Val Lys Asn Glu Ala
    130                 135                 140

Leu Arg Glu Leu Arg Val Glu Leu Ser Lys Lys His Gln Ala Arg Glu
145                 150                 155                 160

Leu Asp Gly Phe Gly Leu Tyr Leu Tyr Gly Val Val Leu Arg Lys Leu
                165                 170                 175

Asp Leu Val Lys Glu Ala Ile Asp Val Phe Val Glu Ala Thr His Val
            180                 185                 190

Leu Pro Leu His Trp Gly Ala Trp Leu Glu Leu Cys Asn Leu Ile Thr
        195                 200                 205

Asp Lys Glu Met Leu Lys Phe Leu Ser Leu Pro Asp Thr Trp Met Lys
    210                 215                 220

Glu Phe Phe Leu Ala His Ile Tyr Thr Glu Leu Gln Leu Ile Glu Glu
225                 230                 235                 240

Ala Leu Gln Lys Tyr Gln Asn Leu Ile Asp Val Gly Phe Ser Lys Ser
                245                 250                 255
```

-continued

```
Ser Tyr Ile Val Ser Gln Ile Ala Val Ala Tyr His Asn Ile Arg Asp
            260                 265                 270

Ile Asp Lys Ala Leu Ser Ile Phe Asn Glu Leu Arg Lys Gln Asp Pro
        275                 280                 285

Tyr Arg Ile Glu Asn Met Asp Thr Phe Ser Asn Leu Leu Tyr Val Arg
    290                 295                 300

Ser Met Lys Ser Glu Leu Ser Tyr Leu Ala His Asn Leu Cys Glu Ile
305                 310                 315                 320

Asp Lys Tyr Arg Val Glu Thr Cys Cys Val Ile Gly Asn Tyr Tyr Ser
                325                 330                 335

Leu Arg Ser Gln His Glu Lys Ala Ala Leu Tyr Phe Gln Arg Ala Leu
            340                 345                 350

Lys Leu Asn Pro Arg Tyr Leu Gly Ala Trp Thr Leu Met Gly His Glu
        355                 360                 365

Tyr Met Glu Met Lys Asn Thr Ser Ala Ala Ile Gln Ala Tyr Arg His
    370                 375                 380

Ala Ile Glu Val Asn Lys Arg Asp Tyr Arg Ala Trp Tyr Gly Leu Gly
385                 390                 395                 400

Gln Thr Tyr Glu Ile Leu Lys Met Pro Phe Tyr Cys Leu Tyr Tyr Tyr
                405                 410                 415

Arg Arg Ala His Gln Leu Arg Pro Asn Asp Ser Arg Met Leu Val Ala
            420                 425                 430

Leu Gly Glu Cys Tyr Glu Lys Leu Asn Gln Leu Val Glu Ala Lys Lys
        435                 440                 445

Cys Phe Trp Ile Ala Tyr Ala Val Gly Asp Val Glu Lys Met Ala Leu
    450                 455                 460

Val Lys Leu Ala Lys Leu His Glu Gln Leu Thr Glu Ser Glu Gln Ala
465                 470                 475                 480

Ala Gln Cys Tyr Ile Lys Tyr Ile Gln Asp Ile Tyr Thr Cys Gly Glu
                485                 490                 495

Ile Val Glu His Leu Glu Glu Ser Thr Ala Phe Arg Tyr Leu Ala Gln
            500                 505                 510

Tyr Tyr Phe Lys Cys Lys Leu Trp Asp Glu Ala Ser Thr Cys Ala Gln
        515                 520                 525

Lys Cys Cys Ala Phe Asn Asp Thr Arg Glu Glu Gly Lys Ala Leu Leu
    530                 535                 540

Arg Gln Ile Leu Gln Leu Arg Asn Gln Gly Glu Thr Pro Thr Thr Glu
545                 550                 555                 560

Val Pro Ala Pro Phe Phe Leu Pro Ala Ser Leu Ser Ala Asn Asn Thr
                565                 570                 575

Pro Thr Arg Arg Val Ser Pro Leu Asn Leu Ser Ser Val Thr Pro
            580                 585                 590
```

<210> SEQ ID NO 29
<211> LENGTH: 2472
<212> TYPE: DNA
<213> ORGANISM: Homo sapiens

<400> SEQUENCE: 29

```
tatgagcctt cggaacttgt ggagagacta caaagttttg gttgttatgg tccctttagt      60

tgggctcata catttggggt ggtacagaat caaaagcagc cctgttttcc aaatacctaa     120

aaacgacgac attcctgagc aagatagtct gggactttca aatcttcaga agagccaaat     180

ccaggggaag tagcaggctt gcaatcttca ggtaaagaag cagctttgaa tctgagcttc     240
```

```
atatcgaaag aagagatgaa aaataccagt tggattagaa agaactggct tcttgtagct    300
gggatatctt tcataggtgt ccatcttgga acatactttt tgcagaggtc tgcaaagcag    360
tctgtaaaat ttcagtctca aagcaaacaa aagagtattg aagagtgaag taaaataaat    420
atttggaatt actaatttgt cattaaatca ttctatgctg attagcttca taaacattga    480
actttttgat tttatagcca caatgctgca tattcatact ttaattccta aagaataatt    540
tttaatgtta aaacgtgata atgcaataaa tagaaaaatg tggtttacaa aataaaaacg    600
gtcttcacta gttaccacct gaagtaagat gtctcgtttg gaagctaaga agccatcatt    660
gtgtaagagt gaaccactga caactgagag agtcaggacc acactttctg tcttgaaaag    720
aattgtaaca tcatgctatg gcccctcagg taggctgaag cagctgcaca atggctttgg    780
aggttacgtg tgtacaacct cacagtcctc agctctgctc agtcaccttt tggtcacaca    840
tcccatttta aagatcctga cagcctccat acagaatcat gtgtcaagct tcagtgattg    900
tggcttattc acagctattc tttgctgcaa cctgattgaa aatgttcaga gattaggctt    960
gacacccacc actgtcatta gattaaataa acatcttttg agtctttgca tcagttatct   1020
caagtctgat acctgtggtt gtcgaatccc agtggacttt agtagtactc agatcctcct   1080
ttgtttggtg cgtagtatat taacaagtaa acctgcctgt atgctcacca gaaaggaaac   1140
agagcatgtc agtgctttga tcctgagagc ctttttgctt acaattccag aaaatgctga   1200
aggccacatc attttaggaa agagtttaat tgtaccttta aaaggtcaaa gagttataga   1260
ttccactgta ttacctggga tactcattga aatgtcagaa gttcaattaa tgaggctatt   1320
acctatcaaa aaatcaactg ccctcaaggt ggcactcttt tgtacaactt tatccggaga   1380
cacttctgac actggagaag gaactgtggt ggtcagttat ggggtttctc ttgaaaatgc   1440
agtcttggac cagctgctta acctaggaag gcagctaatc agtgaccacg tagatcttgt   1500
cctgtgccaa aaagttatac atccatcttt gaagcagttt ctcaatatgc atcgtattat   1560
tgccatagac agaattggag tgactctgat ggaacccctg actaaaatga caggaacaca   1620
gcctattgga tccctaggct caatatgtcc taatagttat ggaagtgtga aagatgtgtg   1680
cactgcaaaa tttggctccc aacatttttt tcatcttatt cctaatgaag caacaatctg   1740
cagcttgctt ctctgcaaca gaaatgacac tgcctgggat gagctgaagc tcacgtgtca   1800
gacggcactg catgtcctgc agttaacact caaggaacca tgggctttgt tgggaggtgg   1860
ctgtactgaa actcatttgg ctgcatatat cagacacaag actcacaacg acccagaaag   1920
cattctcaaa gatgatgaat gtactcaaac agaacttcaa ttaattgctg aagcattttg   1980
cagtgcccta gaatctgttg ttggctcttt agaacatgat ggaggtgaaa ttctcactga   2040
catgaagtat ggacaccttt ggtcagttca ggcagattct ccctgtgttg ctaactggcc   2100
agatttgctt tcacagtgtg gctgtggatt atacaatagc caggaagaac tcaactggtc   2160
tttcttaaga agcacacgtc gtccatttgt gccacaaagc tgccttccac atgaagctgt   2220
gggctcagcc agcaacctga ccttggactg tttgactgca aagcttagtg gcctacaggt   2280
ggctgtagag acagccaatt tgatttggga tctttcatat gttattgaag ataaaaacta   2340
agagaatagc atgttcgtat tacaagagaa acaaataaac tagtctgttg gcaattgaga   2400
aaaaaaaaaa aaaaaaaaaa aaaaaaaaaa aaaaaaaaaa aaaaaaaaaa aaaaaaaaaa   2460
aaaaaaaaaa aa                                                       2472
```

<210> SEQ ID NO 30

```
<211> LENGTH: 570
<212> TYPE: PRT
<213> ORGANISM: Homo sapiens

<400> SEQUENCE: 30

Met Ser Arg Leu Glu Ala Lys Lys Pro Ser Leu Cys Lys Ser Glu Pro
  1               5                  10                  15

Leu Thr Thr Glu Arg Val Arg Thr Thr Leu Ser Val Leu Lys Arg Ile
             20                  25                  30

Val Thr Ser Cys Tyr Gly Pro Ser Gly Arg Leu Lys Gln Leu His Asn
         35                  40                  45

Gly Phe Gly Gly Tyr Val Cys Thr Thr Ser Gln Ser Ser Ala Leu Leu
     50                  55                  60

Ser His Leu Leu Val Thr His Pro Ile Leu Lys Ile Leu Thr Ala Ser
 65                  70                  75                  80

Ile Gln Asn His Val Ser Ser Phe Ser Asp Cys Gly Leu Phe Thr Ala
                 85                  90                  95

Ile Leu Cys Cys Asn Leu Ile Glu Asn Val Gln Arg Leu Gly Leu Thr
            100                 105                 110

Pro Thr Thr Val Ile Arg Leu Asn Lys His Leu Leu Ser Leu Cys Ile
        115                 120                 125

Ser Tyr Leu Lys Ser Asp Thr Cys Gly Cys Arg Ile Pro Val Asp Phe
    130                 135                 140

Ser Ser Thr Gln Ile Leu Leu Cys Leu Val Arg Ser Ile Leu Thr Ser
145                 150                 155                 160

Lys Pro Ala Cys Met Leu Thr Arg Lys Glu Thr Glu His Val Ser Ala
                165                 170                 175

Leu Ile Leu Arg Ala Phe Leu Leu Thr Ile Pro Glu Asn Ala Glu Gly
            180                 185                 190

His Ile Ile Leu Gly Lys Ser Leu Ile Val Pro Leu Lys Gly Gln Arg
        195                 200                 205

Val Ile Asp Ser Thr Val Leu Pro Gly Ile Leu Ile Glu Met Ser Glu
    210                 215                 220

Val Gln Leu Met Arg Leu Leu Pro Ile Lys Lys Ser Thr Ala Leu Lys
225                 230                 235                 240

Val Ala Leu Phe Cys Thr Thr Leu Ser Gly Asp Thr Ser Asp Thr Gly
                245                 250                 255

Glu Gly Thr Val Val Val Ser Tyr Gly Val Ser Leu Glu Asn Ala Val
            260                 265                 270

Leu Asp Gln Leu Leu Asn Leu Gly Arg Gln Leu Ile Ser Asp His Val
        275                 280                 285

Asp Leu Val Leu Cys Gln Lys Val Ile His Pro Ser Leu Lys Gln Phe
    290                 295                 300

Leu Asn Met His Arg Ile Ile Ala Ile Asp Arg Ile Gly Val Thr Leu
305                 310                 315                 320

Met Glu Pro Leu Thr Lys Met Thr Gly Thr Gln Pro Ile Gly Ser Leu
                325                 330                 335

Gly Ser Ile Cys Pro Asn Ser Tyr Gly Ser Val Lys Asp Val Cys Thr
            340                 345                 350

Ala Lys Phe Gly Ser Gln His Phe Phe His Leu Ile Pro Asn Glu Ala
        355                 360                 365

Thr Ile Cys Ser Leu Leu Leu Cys Asn Arg Asn Asp Thr Ala Trp Asp
    370                 375                 380

Glu Leu Lys Leu Thr Cys Gln Thr Ala Leu His Val Leu Gln Leu Thr
```

-continued

```
385                 390                 395                 400

Leu Lys Glu Pro Trp Ala Leu Leu Gly Gly Gly Cys Thr Glu Thr His
                405                 410                 415

Leu Ala Ala Tyr Ile Arg His Lys Thr His Asn Asp Pro Glu Ser Ile
            420                 425                 430

Leu Lys Asp Asp Glu Cys Thr Gln Thr Glu Leu Gln Leu Ile Ala Glu
        435                 440                 445

Ala Phe Cys Ser Ala Leu Glu Ser Val Val Gly Ser Leu Glu His Asp
    450                 455                 460

Gly Gly Glu Ile Leu Thr Asp Met Lys Tyr Gly His Leu Trp Ser Val
465                 470                 475                 480

Gln Ala Asp Ser Pro Cys Val Ala Asn Trp Pro Asp Leu Leu Ser Gln
                485                 490                 495

Cys Gly Cys Gly Leu Tyr Asn Ser Gln Glu Glu Leu Asn Trp Ser Phe
            500                 505                 510

Leu Arg Ser Thr Arg Arg Pro Phe Val Pro Gln Ser Cys Leu Pro His
        515                 520                 525

Glu Ala Val Gly Ser Ala Ser Asn Leu Thr Leu Asp Cys Leu Thr Ala
    530                 535                 540

Lys Leu Ser Gly Leu Gln Val Ala Val Glu Thr Ala Asn Leu Ile Trp
545                 550                 555                 560

Asp Leu Ser Tyr Val Ile Glu Asp Lys Asn
                565                 570
```

<210> SEQ ID NO 31
<211> LENGTH: 1527
<212> TYPE: DNA
<213> ORGANISM: Homo sapiens

<400> SEQUENCE: 31

```
cactccgcgc gcggggctag cgcgggtttc agcgacggga gccctcaagg gacatggcaa      60

ctacagcggc gccggcgggc ggcgccgaaa tggagctggc ccggaatggg gagggttcga     120

agaaaacatc cagggcggag gctcagctgt gattgacatg gagaacatgg atgatacctc     180

aggctctagc ttcgaggata tgggtgagct gcatcagcgc ctgcgcgagg aagaagtaga     240

cgctgatgca gctgatgcag ctgctgctga agaggaggat ggagagttcc tgggcatgaa     300

gggctttaag ggacagctga gccggcaggt ggcagatcag atgtggcagg ctgggaaaag     360

acaagcctcc agggccttca gcttgtacgc caacatcgac atcctcagac cctactttga     420

tgtggagcct gctcaggtgc gaagcaggct cctggagtcc atgatcccta tcaagatggt     480

caacttcccc cagaaaattg caggtgaact ctatggacct ctcatgctgg tcttcactct     540

ggttgctatc ctactccatg ggatgaagac gtctgacact attatccggg agggcaccct     600

gatgggcaca gccattggca cctgcttcgg ctactggctg ggagtctcat ccttcattta     660

cttccttgcc tacctgtgca acgcccagat caccatgctg cagatgttgg cactgctggg     720

ctatggcctc tttgggcatt gcattgtcct gttcatcacc tataatatcc acctccacgc     780

cctcttctac ctcttctggc ggttggtggg tggactgtcc acactgcgca tggtagcagt     840

gttggtgtct cggaccgtgg gccccacaca gcggctgctc ctctgtggca ccctggctgc     900

cctacacatg ctcttcctgc tctatctgca ttttgcctac cacaaagtgg tagaggggat     960

cctggacaca ctggagggcc ccaacatccc gcccatccag agggtcccca gagacatccc    1020

tgccatgctc cctgctgctc ggcttcccac caccgtcctc aacgccacag ccaaagctgt    1080
```

```
tgcggtgacc ctgcagtcac actgacccca cctgaaattc ttggccagtc ctctttcccg   1140

cagctgcaga gaggaggaag actattaaag gacagtcctg atgacatgtt tcgtagatgg   1200

ggtttgcagc tgccactgag ctgtagctgc gtaagtacct ccttgatgcc tgtcggcact   1260

tctgaaaggc acaaggccaa gaactcctgg ccaggactgc aaggctctgc agccaatgca   1320

gaaaatgggt cagctccttt gagaacccct ccccacctac cccttccttc ctctttatct   1380

ctcccacatt gtcttgctta aatatagaac ttggtcttaa aaaaaaaaaa aaaaaaaaaa   1440

aaaaaaaaaa aaaaaaaaaa aaaaaaaaaa aaaaaaaaaa aaaaaaaaaa aaaaaaaaaa   1500

aaaaaaaaaa aaaaaaaaaa aaaaaaa                                       1527
```

<210> SEQ ID NO 32
<211> LENGTH: 315
<212> TYPE: PRT
<213> ORGANISM: Homo sapiens

<400> SEQUENCE: 32

```
Met Glu Asn Met Asp Asp Thr Ser Gly Ser Ser Phe Glu Asp Met Gly
  1               5                  10                  15

Glu Leu His Gln Arg Leu Arg Glu Glu Glu Val Asp Ala Asp Ala Ala
             20                  25                  30

Asp Ala Ala Ala Ala Glu Glu Glu Asp Gly Glu Phe Leu Gly Met Lys
         35                  40                  45

Gly Phe Lys Gly Gln Leu Ser Arg Gln Val Ala Asp Gln Met Trp Gln
     50                  55                  60

Ala Gly Lys Arg Gln Ala Ser Arg Ala Phe Ser Leu Tyr Ala Asn Ile
 65                  70                  75                  80

Asp Ile Leu Arg Pro Tyr Phe Asp Val Glu Pro Ala Gln Val Arg Ser
                 85                  90                  95

Arg Leu Leu Glu Ser Met Ile Pro Ile Lys Met Val Asn Phe Pro Gln
            100                 105                 110

Lys Ile Ala Gly Glu Leu Tyr Gly Pro Leu Met Leu Val Phe Thr Leu
        115                 120                 125

Val Ala Ile Leu Leu His Gly Met Lys Thr Ser Asp Thr Ile Ile Arg
    130                 135                 140

Glu Gly Thr Leu Met Gly Thr Ala Ile Gly Thr Cys Phe Gly Tyr Trp
145                 150                 155                 160

Leu Gly Val Ser Ser Phe Ile Tyr Phe Leu Ala Tyr Leu Cys Asn Ala
                165                 170                 175

Gln Ile Thr Met Leu Gln Met Leu Ala Leu Leu Gly Tyr Gly Leu Phe
            180                 185                 190

Gly His Cys Ile Val Leu Phe Ile Thr Tyr Asn Ile His Leu His Ala
        195                 200                 205

Leu Phe Tyr Leu Phe Trp Arg Leu Val Gly Gly Leu Ser Thr Leu Arg
    210                 215                 220

Met Val Ala Val Leu Val Ser Arg Thr Val Gly Pro Thr Gln Arg Leu
225                 230                 235                 240

Leu Leu Cys Gly Thr Leu Ala Ala Leu His Met Leu Phe Leu Leu Tyr
                245                 250                 255

Leu His Phe Ala Tyr His Lys Val Val Glu Gly Ile Leu Asp Thr Leu
            260                 265                 270

Glu Gly Pro Asn Ile Pro Pro Ile Gln Arg Val Pro Arg Asp Ile Pro
        275                 280                 285

Ala Met Leu Pro Ala Ala Arg Leu Pro Thr Thr Val Leu Asn Ala Thr
```

-continued

```
    290                 295                 300

Ala Lys Ala Val Ala Val Thr Leu Gln Ser His
305                 310                 315


<210> SEQ ID NO 33
<211> LENGTH: 988
<212> TYPE: DNA
<213> ORGANISM: Homo sapiens

<400> SEQUENCE: 33

caaggctata gtaactaaaa gagaatagta ctggtacaaa aataggatca gatcaatgta      60

acagagtaga gaacccagca ataaagccat gtgcctgcaa ccaactgatc tttgataaag     120

ttgagaaaaa taaacaatga agaaaagaca ctgtattcaa taaatgttgc taggaaaatt     180

ggctagccat atacagaaaa atgaaactga acccgtatct ctcactttat acaaaaatta     240

agttggatta aagacttaaa tgtaaaacct gatactataa aaattataga agaaaaccca     300

ggaaaagctc ttctggacac tggcctaggc aaagaattta tgactaagtc atcaaaagca     360

tatgtaacaa aaaaaaaaaa aaagcgcccg ggtgaggggc ggagctgggg gcatggcgtc     420

cggagcggct cgctggctag tattggcacc cgtcaggtcc ggggctctcc ggagcgggcc     480

tagcttgagg aaagatggcg atgtctccgc cgcatggagc ggctcaggcc ggagcctggt     540

accgtcgagg tcagtcatcg ttacccgcag cggcgccatt ttgcccaaac cggtgaaaat     600

gtccttcggc cttctccgtg tgttctccat tgtgatcccc tttctctatg tcgggacact     660

cattagcaag aactttgctg ctctacttga ggaacatgac atttttgttc cagaggatga     720

tgatgatgat gactaacagg aattacagaa aggagaaagc actaactgaa gaaatggtga     780

tgctctcagt ttctctgcct tccctatcag cagaaaggct cggggaaggc cctcagcctc     840

ccagtctggt gaagcttcct gtatggtcca tgaccgtatt ccaccccagg ctctgggagg     900

ctccctgaga tgtgctgtcc actaagcact gcacaaacaa gcaatcaaat tatgaataaa     960

cataataaat atcaaaaaaa aaaaaaaa                                       988


<210> SEQ ID NO 34
<211> LENGTH: 107
<212> TYPE: PRT
<213> ORGANISM: Homo sapiens

<400> SEQUENCE: 34

Met Ala Ser Gly Ala Ala Arg Trp Leu Val Leu Ala Pro Val Arg Ser
  1               5                  10                  15

Gly Ala Leu Arg Ser Gly Pro Ser Leu Arg Lys Asp Gly Asp Val Ser
             20                  25                  30

Ala Ala Trp Ser Gly Ser Gly Arg Ser Leu Val Pro Ser Arg Ser Val
         35                  40                  45

Ile Val Thr Arg Ser Gly Ala Ile Leu Pro Lys Pro Val Lys Met Ser
     50                  55                  60

Phe Gly Leu Leu Arg Val Phe Ser Ile Val Ile Pro Phe Leu Tyr Val
 65                  70                  75                  80

Gly Thr Leu Ile Ser Lys Asn Phe Ala Ala Leu Leu Glu Glu His Asp
                 85                  90                  95

Ile Phe Val Pro Glu Asp Asp Asp Asp Asp Asp
            100                 105


<210> SEQ ID NO 35
<211> LENGTH: 1759
```

-continued

<212> TYPE: DNA
<213> ORGANISM: Homo sapiens

<400> SEQUENCE: 35

```
tttttttttt tgaggtgtaa tgcaacttca tcactttatt caaatcttca aaatagtctt      60
tattctacat ttttagtata aaaattccac aagttaagtg caccacagtg tagagagaga     120
catacaacgc tgaacttcca taacagtcaa tggtacagtc aaacatcaca tgtacagaac     180
acacaattta gatgaactga aattataaga taaaataaaa taaaatccaa tttcagaaaa     240
caaaaatcaa aacattaagg atccctgaaa tattcttaaa ccctaatgag atttcactgg     300
actcaagtca ttttgtagtg agacattcac aatatgaccc tatcaaccca gtctaggaat     360
tctggggagc cgaatgagtg gccgcatcag acactctgac aaaaaatggt aaccaatttt     420
tgatctgaaa actcctctta atttagctct gaacacagag atttatccaa gtgccagatt     480
actcagtgct ataattttct tttagttaaa caaagggggt cagacagaca ttgcatcatc     540
cagacatgcc ttgttggaca tgtagaatcc gatggagcac tgcacaccag aatgattggc     600
caatgagcag cttctctccc tgaaacaata actgcccatt tggcaaaggg aaagatgaca     660
ataatcagaa gaagaaaatg aatgggatgc ataccataga cgaacgaggc ggagactatt     720
gcgggaatct tactgttcag gagctgttcc tagaactaac tcccttactg tcattgatgt     780
gcattccact ctgtgctttt ctgtacaacc attcaagttt taatttccca ggtgaaccat     840
ctttatctgc cattaccaca agctttcaag tttccagtta ttttcatcat cataaccagt     900
acggtgctat tatttaccta tgtacgtgta gttatgtata attttgtaat tagttacaat     960
ggtaaaaaaa atcgaaatat ataaaaagtg atttgtacag aactttattt tagctctttt    1020
ttaaaaatga tttgcatggt tagaaaacgg cgaggacagc caggggaggg aagggcctct    1080
agggaacttt gcactttcta taacctttgt acttatgcca ctgccctatt tgattctaca    1140
cccaataatg attattactt gaaacccatc tgtaagaaac tgcttcggaa attcatttgt    1200
gtgtatgtaa ataacacaac atagaaacag gaagggaaaa aaagtctgca gtaatgcacg    1260
tatttttttc tttcctgttt attttcggtt ttgctttaag tccttttatt tttaattccc    1320
tttttgtttt tctttttggg ttttggttcc ttttgggttt atgggtgccc tgatactcca    1380
gcagagatca gaaggctaca gatccattct atccatccgt tatgtggctt tgccatccca    1440
gcttggagtg tctttacaaa gataataaca gttgtgttct ttgctctcgt tttggatgca    1500
tagactgaaa aattaaaaca aataacttgt aaaatggctt gttaaaaaat acaattacct    1560
ctaattagta gtacgcgtaa atgttttaca gaatgaaagg cgtgcttttt attttcttac    1620
ttcgttacat tggtggcgaa agaagtctgt atgaaaatca gttctttgct gacacaagtt    1680
ccatttgtta caaatgaatt ctaataaaaa tgtcagtgtt aaaaaaaaaa aaaaaaaaaa    1740
aaaaaaaaaa aaaaaaaaa                                                 1759
```

<210> SEQ ID NO 36
<211> LENGTH: 87
<212> TYPE: PRT
<213> ORGANISM: Homo sapiens

<400> SEQUENCE: 36

```
Met Asn Gly Met His Thr Ile Asp Glu Arg Gly Gly Asp Tyr Cys Gly
  1               5                  10                  15

Asn Leu Thr Val Gln Glu Leu Phe Leu Glu Leu Thr Pro Leu Leu Ser
             20                  25                  30
```

-continued

```
Leu Met Cys Ile Pro Leu Cys Ala Phe Leu Tyr Asn His Ser Ser Phe
        35                  40                  45

Asn Phe Pro Gly Glu Pro Ser Leu Ser Ala Ile Thr Thr Ser Phe Gln
    50                  55                  60

Val Ser Ser Tyr Phe His His His Asn Gln Tyr Gly Ala Ile Ile Tyr
65                  70                  75                  80

Leu Cys Thr Cys Ser Tyr Val
                85
```

<210> SEQ ID NO 37
<211> LENGTH: 643
<212> TYPE: DNA
<213> ORGANISM: Homo sapiens

<400> SEQUENCE: 37

```
tcagcctccg cctccgagcc tcagttgtct tctctgtgag gtgggaatgc cggtgaatcc      60

tgccgctggc gtggatgaga agtgaatgcg tgctcggagc tgcgagtgac agcgggcagg     120

aggcgcccag ggacacttgg tttctccagg gctggaaggc ttctagaagg ttcctcatca     180

agggaagtgt ggctgggggc gccgtctacc tggtgtacga ccaggagctg ctggggccca     240

gcgacaagag ccaggcagcc ctacagaagg ctggggaggt ggtccccccc gccatgtacc     300

agttcagcca gtacgtgtgt cagcagacag gcctgcagat accccagctc ccagcccctc     360

caaagattta ctttcccatc cgtgactcct ggaatgcagg catcatgacg gtgatgtcag     420

ctctgtcggt ggcccccctcc aaggcccgcg agtactccaa ggagggctgg gagtatgtga     480

aggcgcgcac caagtagcga gtcagcaggg gccgcctgcc ccggccagaa cgggcagggc     540

tgccactgac ctgaagactc cggactggga ccccactccg agggcagctc ccggccttgc     600

cggcccaata aaggacttca gaagtgaaaa aaaaaaaaaa aaa                       643
```

<210> SEQ ID NO 38
<211> LENGTH: 140
<212> TYPE: PRT
<213> ORGANISM: Homo sapiens

<400> SEQUENCE: 38

```
Met Arg Ser Glu Cys Val Leu Gly Ala Ala Ser Asp Ser Gly Gln Glu
1               5                   10                  15

Ala Pro Arg Asp Thr Trp Phe Leu Gln Gly Trp Lys Ala Ser Arg Arg
            20                  25                  30

Phe Leu Ile Lys Gly Ser Val Ala Gly Gly Ala Val Tyr Leu Val Tyr
        35                  40                  45

Asp Gln Glu Leu Leu Gly Pro Ser Asp Lys Ser Gln Ala Ala Leu Gln
    50                  55                  60

Lys Ala Gly Glu Val Val Pro Pro Ala Met Tyr Gln Phe Ser Gln Tyr
65                  70                  75                  80

Val Cys Gln Gln Thr Gly Leu Gln Ile Pro Gln Leu Pro Ala Pro Pro
                85                  90                  95

Lys Ile Tyr Phe Pro Ile Arg Asp Ser Trp Asn Ala Gly Ile Met Thr
            100                 105                 110

Val Met Ser Ala Leu Ser Val Ala Pro Ser Lys Ala Arg Glu Tyr Ser
        115                 120                 125

Lys Glu Gly Trp Glu Tyr Val Lys Ala Arg Thr Lys
    130                 135                 140
```

<210> SEQ ID NO 39

-continued

<211> LENGTH: 2015
<212> TYPE: DNA
<213> ORGANISM: Homo sapiens

<400> SEQUENCE: 39

```
aggctgtctg ctagtcagaa ttgcctcaaa aagagtctag aagatgttgt cattgacatc     60
cagtcatctc tttctaaggg aatcagaggc aatgagcccg tatatacttc aactcaagaa    120
gactgcatta attcttgctg ttcaacaaaa aacatatcag gggacaaagc atgtaacttg    180
atgatcttcg acactcgaaa aacagctaga caacccaact gctacctatt tttctgtccc    240
aacgaggaag cctgtccatt gaaaccagca aaaggactta tgagttacag gataattaca    300
gattttccat ctttgaccag aaatttgcca agccaagagt taccccagga agattctctc    360
ttacatggcc aattttcaca agcagtcact cccctagccc atcatcacac agattattca    420
aagcccaccg atatctcatg gagagacaca ctttctcaga agtttggatc ctcagatcac    480
ctggagaaac tatttaagat ggatgaagca agtgcccagc tccttgctta taaggaaaaa    540
ggccattctc agagttcaca attttcctct gatcaagaaa tagctcatct gctgcctgaa    600
aatgtgagtg cgctcccagc tacggtggca gttgcttctc cacataccac ctcggctact    660
ccaaagcccg ccacccttct acccaccaat gcttcagtga caccttctgg gacttcccag    720
ccacagctgg ccaccacagc tccacctgta accactgtca cttctcagcc tcccacgacc    780
ctcatttcta cagtttttac acgggctgcg gctacactcc aagcaatggc tacaacagca    840
gttctgacta ccacctttca ggcacctacg gactcgaaag gcagcttaga aaccataccg    900
tttacagaaa tctccaactt aactttgaac acagggaatg tgtataaccc tactgcactt    960
tctatgtcaa atgtggagtc ttccactatg aataaaactg cttcctggga aggtagggag   1020
gccagtccag gcagttcctc cccagggcag tgttccagaa aatcagtacg gccttccatt   1080
tgaaaaatgg cttcttatcg ggtccctgct ctttggtgtc ctgttcctgg tgataggcct   1140
cgtcctcctg ggtagatcct ctcggaatca ctccgcagga aacgttactc aagactggat   1200
tatttgatca atgggatcta tgtggacatc taaggatgga actcggtgtc tcttaattca   1260
tttagtaacc agaagcccaa atgcaatgag tttctgctga cttgctagtc ttagcaggag   1320
gttgtatttt gaagacagga aaatgccccc ttctgctttc cttttttttt ttggagacag   1380
agtcttgctc tgttgcccag gctggagtgc agtagcacga tctcggctct caccgcaacc   1440
tccgtctcct gggttcaagc gattctcctg cctcagcctc ctagtatctg ggattacagg   1500
catgtgccac cacacctggg tgatttttgt atttttagta gagacgggtt tcaccatgtt   1560
ggtcaggctg gtctcaaact cctgacctag tgatccaccc tcctcggcct cccaaagtgc   1620
tgggataaca ggcatgagcc accacagctg gccccttct gttttatgtt tggtttttga    1680
gaaggaatga agtgggaacc aaattaggta attttgggta atctgtctct aaaatattag   1740
ctgaaaacaa agctgtatgt aaagtaataa ggtataattg ccatataaat ttcaaaattc   1800
aactggcttt tatgcaaaga aacaggttag gacatctagg ttccaattca ttcacattct   1860
tggttccaga taaaatcaac tgtttatatc aatttctaat ggatttgcct ttctttttat   1920
atggattcct ttaaaactta ttccagatgt agttccttcc aattaaatat ttgaataaat   1980
cttttgttac tcaaaaaaaa aaaaaaaaaa aaaaa                              2015
```

<210> SEQ ID NO 40
<211> LENGTH: 300
<212> TYPE: PRT
<213> ORGANISM: Homo sapiens

<400> SEQUENCE: 40

```
Met Ile Phe Asp Thr Arg Lys Thr Ala Arg Gln Pro Asn Cys Tyr Leu
  1               5                  10                  15

Phe Phe Cys Pro Asn Glu Glu Ala Cys Pro Leu Lys Pro Ala Lys Gly
             20                  25                  30

Leu Met Ser Tyr Arg Ile Ile Thr Asp Phe Pro Ser Leu Thr Arg Asn
         35                  40                  45

Leu Pro Ser Gln Glu Leu Pro Gln Glu Asp Ser Leu Leu His Gly Gln
     50                  55                  60

Phe Ser Gln Ala Val Thr Pro Leu Ala His His His Thr Asp Tyr Ser
 65                  70                  75                  80

Lys Pro Thr Asp Ile Ser Trp Arg Asp Thr Leu Ser Gln Lys Phe Gly
                 85                  90                  95

Ser Ser Asp His Leu Glu Lys Leu Phe Lys Met Asp Glu Ala Ser Ala
            100                 105                 110

Gln Leu Leu Ala Tyr Lys Glu Lys Gly His Ser Gln Ser Ser Gln Phe
        115                 120                 125

Ser Ser Asp Gln Glu Ile Ala His Leu Leu Pro Glu Asn Val Ser Ala
    130                 135                 140

Leu Pro Ala Thr Val Ala Val Ala Ser Pro His Thr Thr Ser Ala Thr
145                 150                 155                 160

Pro Lys Pro Ala Thr Leu Leu Pro Thr Asn Ala Ser Val Thr Pro Ser
                165                 170                 175

Gly Thr Ser Gln Pro Gln Leu Ala Thr Thr Ala Pro Pro Val Thr Thr
            180                 185                 190

Val Thr Ser Gln Pro Pro Thr Thr Leu Ile Ser Thr Val Phe Thr Arg
        195                 200                 205

Ala Ala Ala Thr Leu Gln Ala Met Ala Thr Thr Ala Val Leu Thr Thr
    210                 215                 220

Thr Phe Gln Ala Pro Thr Asp Ser Lys Gly Ser Leu Glu Thr Ile Pro
225                 230                 235                 240

Phe Thr Glu Ile Ser Asn Leu Thr Leu Asn Thr Gly Asn Val Tyr Asn
                245                 250                 255

Pro Thr Ala Leu Ser Met Ser Asn Val Glu Ser Ser Thr Met Asn Lys
            260                 265                 270

Thr Ala Ser Trp Glu Gly Arg Glu Ala Ser Pro Gly Ser Ser Ser Pro
        275                 280                 285

Gly Gln Cys Ser Arg Lys Ser Val Arg Pro Ser Ile
    290                 295                 300
```

<210> SEQ ID NO 41
<211> LENGTH: 1549
<212> TYPE: DNA
<213> ORGANISM: Homo sapiens

<400> SEQUENCE: 41

```
tgatcctaat aatactgcac atgaagaaac taaaactgtc ttatcagata cagaagaaat      60

aaaaccacag acaaaaaagg agacatacat ttcttgtcct ctaagaggag tattgaatgt     120

aattattaca aatggagtta tactgtttgt gatatggtgt atgacctggt caatcttagg     180

ctctgaagct ctccctggtg gaaatttatt tgggttgttc attatttttt atagtgccat     240

tattggggga aaaattttac aactcattag aatacottta gtgcctccac ttccacctct     300

tcttgggatg ttactggctg gttttacgat taggaatgtt ccattcatca atgaacatgt     360
```

```
ccatgttcct aacacatggt cttcaatttt aagaagcatt gcccttacca ttattctaat    420

aagagctggg cttggactcg atccacaggc tttgaggcat ttgaaggtcg tttgtttcag    480

attggctgta ggtccatgcc ttatggaggc aagtgcagct gctgtttttt cacacttcat    540

tatgaaattt ccctggcaat gggcatttct attaggtttt gttctaggtg ctgtctctcc    600

tgctgttgtt gtcccttaca tgatggtgct gcaagaaaat ggatatggtg ttgaggaagg    660

cattccaacc ttattaatgg ctgctagcag tatggatgac attctggcta tcactggatt    720

caatacatgc ttgagcatag tcttttcctc aggtggtata cttaataacg ccatagcctc    780

tataaggaac gtatgtatta gtctgctggc aggaattgtt ttgggatttt ttgttcgata    840

ttttccaagt gaagaccaga aaaaacttac attgaagaga ggattccttg ttttgactat    900

gtgtgtttct gccgtcttag gcagccaacg tattggttta catggatctg gaggattatg    960

cacactagtg ttgagtttca ttgcagggac aaaatggtcc caagaaaaga tgaaagtcca   1020

aaagattatt acgactgtat gggatatttt tcaaccactt ctttttggtt tagttggagc   1080

agaagtatct gtttcatcgc ttgaatcaaa tattgttggc atatctgttg ccactctaag   1140

tttggcatta tgtgttcgaa ttttaaccac atatctattg atgtgctttg ctggttttag   1200

ttttaaggag aaaatattta ttgctttagc atggatgccc aaagctacag tacagattaa   1260

tcaagctatc cttctgttgt ttcttcttcg ggaggaatgg acgaactgca aggtagccaa   1320

gaagtgcgag tacaccaagg aaaggcaata accgaagcca ttctgaaact aaacatgtag   1380

atgtgtcaga atctgcagtg ctcttggaaa agaattcaaa atagcatgtc gtttcatcct   1440

tgagcttatt ctttgttact ttttacatta attccttttt aatggatcca taaaactgtg   1500

aataaataac acaataaagc cagctctacc aaaaaaaaaa aaaaaaaaa               1549
```

<210> SEQ ID NO 42
<211> LENGTH: 396
<212> TYPE: PRT
<213> ORGANISM: Homo sapiens

<400> SEQUENCE: 42

```
Met Thr Trp Ser Ile Leu Gly Ser Glu Ala Leu Pro Gly Gly Asn Leu
  1               5                  10                  15

Phe Gly Leu Phe Ile Ile Phe Tyr Ser Ala Ile Ile Gly Gly Lys Ile
             20                  25                  30

Leu Gln Leu Ile Arg Ile Pro Leu Val Pro Pro Leu Pro Pro Leu Leu
         35                  40                  45

Gly Met Leu Leu Ala Gly Phe Thr Ile Arg Asn Val Pro Phe Ile Asn
     50                  55                  60

Glu His Val His Val Pro Asn Thr Trp Ser Ser Ile Leu Arg Ser Ile
 65                  70                  75                  80

Ala Leu Thr Ile Ile Leu Ile Arg Ala Gly Leu Gly Leu Asp Pro Gln
                 85                  90                  95

Ala Leu Arg His Leu Lys Val Val Cys Phe Arg Leu Ala Val Gly Pro
            100                 105                 110

Cys Leu Met Glu Ala Ser Ala Ala Ala Val Phe Ser His Phe Ile Met
        115                 120                 125

Lys Phe Pro Trp Gln Trp Ala Phe Leu Leu Gly Phe Val Leu Gly Ala
    130                 135                 140

Val Ser Pro Ala Val Val Val Pro Tyr Met Met Val Leu Gln Glu Asn
145                 150                 155                 160
```

-continued

```
Gly Tyr Gly Val Glu Glu Gly Ile Pro Thr Leu Leu Met Ala Ala Ser
                165                 170                 175

Ser Met Asp Asp Ile Leu Ala Ile Thr Gly Phe Asn Thr Cys Leu Ser
            180                 185                 190

Ile Val Phe Ser Ser Gly Gly Ile Leu Asn Asn Ala Ile Ala Ser Ile
        195                 200                 205

Arg Asn Val Cys Ile Ser Leu Leu Ala Gly Ile Val Leu Gly Phe Phe
    210                 215                 220

Val Arg Tyr Phe Pro Ser Glu Asp Gln Lys Lys Leu Thr Leu Lys Arg
225                 230                 235                 240

Gly Phe Leu Val Leu Thr Met Cys Val Ser Ala Val Leu Gly Ser Gln
                245                 250                 255

Arg Ile Gly Leu His Gly Ser Gly Gly Leu Cys Thr Leu Val Leu Ser
            260                 265                 270

Phe Ile Ala Gly Thr Lys Trp Ser Gln Glu Lys Met Lys Val Gln Lys
        275                 280                 285

Ile Ile Thr Thr Val Trp Asp Ile Phe Gln Pro Leu Leu Phe Gly Leu
    290                 295                 300

Val Gly Ala Glu Val Ser Val Ser Ser Leu Glu Ser Asn Ile Val Gly
305                 310                 315                 320

Ile Ser Val Ala Thr Leu Ser Leu Ala Leu Cys Val Arg Ile Leu Thr
                325                 330                 335

Thr Tyr Leu Leu Met Cys Phe Ala Gly Phe Ser Phe Lys Glu Lys Ile
            340                 345                 350

Phe Ile Ala Leu Ala Trp Met Pro Lys Ala Thr Val Gln Ile Asn Gln
        355                 360                 365

Ala Ile Leu Leu Leu Phe Leu Leu Arg Glu Glu Trp Thr Asn Cys Lys
    370                 375                 380

Val Ala Lys Lys Cys Glu Tyr Thr Lys Glu Arg Gln
385                 390                 395
```

<210> SEQ ID NO 43
<211> LENGTH: 4433
<212> TYPE: DNA
<213> ORGANISM: Homo sapiens

<400> SEQUENCE: 43

```
ggctcaagta gcggacacgg aacagggaac tatcagcccg tcggcctccg ggccctgcat      60

tctctagcca tggaccggga ccttttgcgg cagtcgctaa attgccacgg gtcgtctttg     120

ctctctctac ttcggagcga acagcaggac aatccacact tccgtagcct cctggggtcg     180

gccgccgagc cagcccgggg cccgccgccc cagcacccgt tgcagggcag aaaagagaag     240

agagttgaca acatcgagat acagaaattc atctccaaaa aagcggatct gctttttgca     300

ctttcctgga aatcagatgc acctgcaact tctgaaatta atgaagacag tgaagatcat     360

tatgcaatca tgccaccttt agagcaattc atggagatac ctagtatgga tcggagagag     420

ctgtttttcc gagatattga gcgtggtgat atagtgattg gaagaattag ttctattcgg     480

gaattcggtt ttttcatggt gttgatctgt ttaggaagtg gtatcatgag agatatagcc     540

cacttagaaa tcacagctct ttgtccctta agagatgtgc cttctcacag taaccatggg     600

gatcctttat catattacca aactggtgac atcattcgag ctggaatcaa ggatattgac     660

agataccatg aaaagctagc agtatctctg tatagctctt ctcttccacc acacctatct     720

ggtattaaat taggtgtaat tagctctgaa gagcttcctt tatactacag gagaagtgtt     780
```

-continued

```
gagctaaata gcaattcttt ggagtcctat gaaaatgtca tgcagagttc cttgggattt    840
gttaatccag gagtagttga attccttcta gaaaaactag gaatagatga atctaatcca    900
ccatctttaa tgagaggcct acaaagcaaa aatttctctg aagatgattt tgcttctgca    960
ttgagaaaaa aacaatccgc atcttgggct ttaaaatgtg tgaagatcgg agttgactat   1020
tttaaagttg gacgccatgt ggatgctatg aatgaataca ataaagcttt ggaaatagac   1080
aaacaaaacg tggaagcttt ggtagctcgt ggagcattat atgcgacaaa aggaagtttg   1140
aacaaagcaa tagaagattt tgagcttgca ttagaaaact gtccaactca cagaaatgca   1200
agaaaatacc tctgccagac acttgtagag agaggaggac agttagaaga agaagaaaag   1260
tttttaaatg ctgaaagtta ctataagaaa gccttggctt tggatgagac ttttaaagat   1320
gcagaggatg ctttgcagaa acttcataaa tatatgcagg tgattcctta tttcctctta   1380
gaaatttagt gatatttgaa ataatgccca aacttaattt tctcctgagg aaaaactatt   1440
ctacattact taagtaaggc attatgaaaa gtttcttttt aggtatagtt tttcctaatt   1500
gggtttgaca ttgcttcata gtgcctctgt tttgtccat aatcgaaagt aaagatagct    1560
gtgagaaaac tattacctaa atttggtatg ttgttttgag aaatgtcctt atagggagct   1620
cacctggtgg tttttaaatt attgttgcta ctataattga gctaattata aaaacctttt   1680
tgagacatat tttaaattgt cttttcctgt aatactgatg atgatgtttt ctcatgcatt   1740
ttcttctgaa ttggaccatt gctgctgtgt ctgtgacatc tggtgctgct catccccatc   1800
cacaaactgg aaaatgattt cctatgtaat catgcattca actgggctgt gctatttttt   1860
taaatggttt gtatttgaac atggtgattc ctccttcact tcaccttaac ggaatgtctt   1920
tatttgaatt ttatttgtaa aatgtgtcct gtttaaattt ttcaatcttt aaaaataatt   1980
tttatgtact tttttttttt tttaaccttt cttgcactct gggtcatggg taccactgca   2040
atggcttccc cttttttat gggataccaa ctgcaatatg gtcctcaatg ctgttctggc    2100
catttcaatg actaatgcca aacatctgta tgactaattt ttttatgtta aaaaaatact   2160
gtttaatgct ggctctatgg tgatttggtt ttactaaatt gggtttctcg ttgggggtgg   2220
tcttttgaat actgggtttt atatattctg ctatttttaa cgtgtggttt ttttcgatat   2280
ctgggttcta aaagaaatct ttggaattaa gagaaaaaca agctgaaaag gaagaaaagc   2340
agaaaacaaa gaaaatagaa acaagtgcag aaaagttgcg taagctctta aaagaagaga   2400
agaggtaaac tataatattc agtattttta aacttaaggc actactgaat tgaacccaaa   2460
gtgccatact ggaagtaaag taaataaaaa tatgaaagta tttcaagtgc caatcagtga   2520
ctgttaagaa tctttagcaa atatgtgttc catgtatttc ctattaaaga gatgaagtgg   2580
aatttaaggc tgaattctac aaaaaagagt acttagaaat taaaatatag aaaaagttac   2640
ttcaattatg ttttaggaag aaatattttt aaaactagag cagtggtctc actaggaggt   2700
gagttcatca gaccggaccc ttgacagatt atttggctga aaataccaat aatcaggtga   2760
agaaaccatg aactagaggt agccaaataa aaaagttgag ttctccttta tgtgttcagt   2820
agtcttaagt ttttaaggta gtgttgaaaa aagtctgtct ttcagagatg atggatttgc   2880
ttacaatgat acctgtctgc aagcattttt tcccccaaaa gtgcttaata gtaaaattag   2940
atcttgtagt agccgagatt attgtatcat ttatctgaac cacagctttt ataaaatctt   3000
taaaggaaac aaatagggcc cacatcttta tgaataattt agaaacattt ttgtatatat   3060
atgacaaatg aactgttttt tttaggctaa agaagaaaag aagaaaatca acttcttctt   3120
caagtgtttc ttctgctgat gaatcagtgt cttcatcatc atcctcttcc tcttctggtc   3180
```

-continued

```
acaaaaggca taagaaacat aagaggaacc gttcagagtc ttctcgcagt tccagaaggc   3240
attcatctag ggcatcctca aatcagatag atcagaatag gaaagatgag tgctacccag   3300
ttccagctaa tacttcagca tcttttctta accataaaca agaagtggag aaactactgg   3360
ggaagcagga taggttacag tatgaaaaga cacagataaa agagaaagat agacgccctc   3420
tctcttcatc ttcacttgaa ataccggatg attttggagt gtactcctat ttatttaaaa   3480
agttaactat aaaacagcct caggcaggtc cttcaggaga tattccagaa gagggcattg   3540
ttatcataga tgacagctcc attcatgtta ctgaccctga agaccttcaa gtgggacaag   3600
atatggaggt ggaagacagt ggtattgatg atcctgacca cgggtaggct taggtttatg   3660
tgtgtgtatg tgtcttagtt tttaacaaaa aaattaaaaa gtaaaaaaac taaaaataga   3720
aaaatgctta gagaataagg atataaagaa tatttttgtg cagttgaaca atgagtgctt   3780
aagctaaatg tcatcacaaa agagtaaaaa aatttacaa aattaaaaat gtttaaagtt    3840
aaaaagctct aggaagctaa ggtcaattta ttattggaga aataaaatta tttttatgaa   3900
tttactgtag cctaggtgta cattatttat catgtctaca gtagtgttca gcaattaggc   3960
cttcacattc tctcaccact cactcactca gtcactcacc cagagcagct tccagtcccg   4020
caagctccat ttatggtaag tgccctgtac aggtgtacca ttttttttaat ccattatacc  4080
atatttttat tgtacctttt ctatgtttag atttgtttag atacacaagt accactgtgt   4140
tacagttgcc tatagtactc agtacagtaa cacactttac aagcttatag cctaggaaca   4200
ataggctata ccatctaggt ttgtgtaagt acactcttat gatgttcaca cagtgacaaa   4260
atcgcccaag gatgcattca tcagaacaca ttcccattgt tatccaatgc atgactgtat   4320
aatggtttta tggattaaat tttttatgta attcaactgg aaagtatttt tatgttattt   4380
tggaaaaaat aaaacaatga caattggaaa aaaaaaaaaa aaaaaaaaaa aaa          4433
```

<210> SEQ ID NO 44
<211> LENGTH: 439
<212> TYPE: PRT
<213> ORGANISM: Homo sapiens

<400> SEQUENCE: 44

```
Met Asp Arg Asp Leu Leu Arg Gln Ser Leu Asn Cys His Gly Ser Ser
  1               5                  10                  15

Leu Leu Ser Leu Leu Arg Ser Glu Gln Gln Asp Asn Pro His Phe Arg
             20                  25                  30

Ser Leu Leu Gly Ser Ala Ala Glu Pro Ala Arg Gly Pro Pro Pro Gln
         35                  40                  45

His Pro Leu Gln Gly Arg Lys Glu Lys Arg Val Asp Asn Ile Glu Ile
     50                  55                  60

Gln Lys Phe Ile Ser Lys Lys Ala Asp Leu Leu Phe Ala Leu Ser Trp
 65                  70                  75                  80

Lys Ser Asp Ala Pro Ala Thr Ser Glu Ile Asn Glu Asp Ser Glu Asp
                 85                  90                  95

His Tyr Ala Ile Met Pro Pro Leu Glu Gln Phe Met Glu Ile Pro Ser
            100                 105                 110

Met Asp Arg Arg Glu Leu Phe Phe Arg Asp Ile Glu Arg Gly Asp Ile
        115                 120                 125

Val Ile Gly Arg Ile Ser Ser Ile Arg Glu Phe Gly Phe Phe Met Val
    130                 135                 140

Leu Ile Cys Leu Gly Ser Gly Ile Met Arg Asp Ile Ala His Leu Glu
```

-continued

```
145                 150                 155                 160

Ile Thr Ala Leu Cys Pro Leu Arg Asp Val Pro Ser His Ser Asn His
                165                 170                 175

Gly Asp Pro Leu Ser Tyr Tyr Gln Thr Gly Asp Ile Ile Arg Ala Gly
            180                 185                 190

Ile Lys Asp Ile Asp Arg Tyr His Glu Lys Leu Ala Val Ser Leu Tyr
        195                 200                 205

Ser Ser Ser Leu Pro Pro His Leu Ser Gly Ile Lys Leu Gly Val Ile
    210                 215                 220

Ser Ser Glu Glu Leu Pro Leu Tyr Tyr Arg Arg Ser Val Glu Leu Asn
225                 230                 235                 240

Ser Asn Ser Leu Glu Ser Tyr Glu Asn Val Met Gln Ser Ser Leu Gly
                245                 250                 255

Phe Val Asn Pro Gly Val Val Glu Phe Leu Leu Glu Lys Leu Gly Ile
            260                 265                 270

Asp Glu Ser Asn Pro Pro Ser Leu Met Arg Gly Leu Gln Ser Lys Asn
        275                 280                 285

Phe Ser Glu Asp Asp Phe Ala Ser Ala Leu Arg Lys Lys Gln Ser Ala
    290                 295                 300

Ser Trp Ala Leu Lys Cys Val Lys Ile Gly Val Asp Tyr Phe Lys Val
305                 310                 315                 320

Gly Arg His Val Asp Ala Met Asn Glu Tyr Asn Lys Ala Leu Glu Ile
                325                 330                 335

Asp Lys Gln Asn Val Glu Ala Leu Val Ala Arg Gly Ala Leu Tyr Ala
            340                 345                 350

Thr Lys Gly Ser Leu Asn Lys Ala Ile Glu Asp Phe Glu Leu Ala Leu
        355                 360                 365

Glu Asn Cys Pro Thr His Arg Asn Ala Arg Lys Tyr Leu Cys Gln Thr
    370                 375                 380

Leu Val Glu Arg Gly Gly Gln Leu Glu Glu Glu Glu Lys Phe Leu Asn
385                 390                 395                 400

Ala Glu Ser Tyr Tyr Lys Lys Ala Leu Ala Leu Asp Glu Thr Phe Lys
                405                 410                 415

Asp Ala Glu Asp Ala Leu Gln Lys Leu His Lys Tyr Met Gln Val Ile
            420                 425                 430

Pro Tyr Phe Leu Leu Glu Ile
        435
```

<210> SEQ ID NO 45
<211> LENGTH: 4017
<212> TYPE: DNA
<213> ORGANISM: Homo sapiens

<400> SEQUENCE: 45

```
acactggcaa agtacatacc ctactcactg tggaagtatt cggtgttatc cggtcactca      60

tggcctttag gctgacaggt ggcaccaaag actacattgt agttggcagt gactctggtc     120

gaattgttat tttggaatac cagccatcta agaatatgtt tgagaagatt caccaagaaa     180

cctttggcaa gagtggatgc agtcgcatcg ttcctggcca gttcttagct gtggatccca     240

aagggcgagc cgttatgatt agtgccattg agaaacagaa attggtgtat attttgaaca     300

gagatgctgc agcccgactt accatttcat ctcccctgga agcccacaaa gcaaacactt     360

tagtgtatca tgtagttgga gtagatgtcg gatttgaaaa tccaatgttt gcttgtctgg     420

aaatggatta tgaggaagca gacaatgatc caacagggga agcagcagct aatacccagc     480
```

-continued

```
agacacttac tttctatgag ctagaccttg gtttaaatca tgtggtccga aaatacagtg    540
aacctttgga ggaacacggc aacttcctta ttacagttcc aggagggtca gatggtccaa    600
gtggagtact gatctgctct gaaaactata ttacttacaa gaactttggt gaccagccag    660
atatccgctg tccaattccc aggaggcgga atgacctgga tgaccctgaa agaggaatga    720
tttttgtctg ctctgcaacc cataaaacca aatcgatgtt cttctttttg gctcaaactg    780
agcagggaga tatctttaag atcactttgg agacagatga agatatggtt actgagatcc    840
ggctcaaata ttttgatact gtacccgttg ctgctgccat gtgtgtgctt aaaacagggt    900
tcctttttgt agcatcagaa tttggaaacc attacttata tcaaattgca catcttggag    960
atgatgatga agaacctgag ttttcatcag ccatgcctct ggaagaagga gacacattct   1020
tttttcagcc aagaccactt aaaaaccttg tgctggttga tgagttggac agcctctctc   1080
ccattctgtt ttgccagata gctgatctgg ccaatgaaga tactccacag ttgtatgtgg   1140
cctgtggtag gggaccccga tcatctctga gagtcctaag acatggactt gaggtgtcag   1200
aaatggctgt ttctgagcta cctggtaacc ccaacgctgt ctggacagtg cgtcgacaca   1260
ttgaagatga gtttgatgcc tacatcattg tgtctttcgt gaatgccacc ctagtgttgt   1320
ccattggaga aactgtagaa gaagtgactg actctgggtt cctggggacc accccgacct   1380
tgtcctgctc cttattagga gatgatgcct tggtgcaggt ctatccagat ggcattcggc   1440
acatacgagc agacaagaga gtcaatgagt ggaagacccc tggaaagaaa acaattgtga   1500
agtgtgcagt gaaccagcga caagtggtga ttgccctgac aggaggagag ctggtctatt   1560
tcgagatgga tccttcagga cagctgaatg agtacacaga acggaaggag atgtcagcag   1620
atgtggtgtg catgagtctg gccaatgtac cccctggaga gcagcggtct cgcttcctgg   1680
ctgtggggct tgtggacaac actgtcagaa tcatctccct ggatccctca gactgtttgc   1740
aacctctaag catgcaggct ctcccagccc agcctgagtc cttgtgtatc gtggaaatgg   1800
gtgggactga gaagcaggat gagctgggtg agaggggctc gattggcttc ctatacctga   1860
atattgggct acagaacggt gtgctgctga ggactgtctt ggaccctgtc actggggatt   1920
tgtctgatac tcgcactcgg tacctggggt cccgtcctgt gaagctcttc cgagtccgaa   1980
tgcaaggcca ggaggcagta ttggccatgt caagccgctc atggttgagc tattcttacc   2040
aatctcgctt ccatctcacc ccactgtctt acgagacact ggaatttgca tcgggttttg   2100
cctcggaaca gtgtcccgag ggcattgtgg ccatctccac caacaccccta cggattttgg   2160
cattagagaa gctcggtgct gtcttcaatc aagtagcctt cccactgcag tacacaccca   2220
ggaaatttgt catccaccct gagagtaaca accttattat cattgaaacg gaccacaatg   2280
cctacactga ggccacgaaa gctcagagaa agcagcagat ggcagaggaa atggtggaag   2340
cagcagggga ggatgagcgg gagctggccg cagagatggc agcagcattc ctcaatgaaa   2400
acctccctga atccatcttt ggagctccca aggctggcaa tgggcagtgg gcctctgtga   2460
tccgagtgat gaatcccatt caagggaaca cactggacct tgtccagctg gaacagaatg   2520
aggcagcttt tagtgtggct gtgtgcaggt tttccaacac tggtgaagac tggtatgtgc   2580
tggtgggtgt ggccaaggac ctgatactaa accccccgatc tgtggcaggg ggcttcgtct   2640
atacttacaa gcttgtgaac aatggggaaa aactggagtt tttgcacaag actcctgtgg   2700
aagaggtccc tgctgctatt gccccattcc aggggagggt gttgattggt gtggggaagc   2760
tgttgcgtgt ctatgacctg ggaaagaaga agttactccg aaaatgtgag aataagcata   2820
```

-continued

```
ttgccaatta tatctctggg atccagacta tcggacatag ggtaattgta tctgatgtcc   2880

aagaaagttt catctgggtt cgctacaagc gtaatgaaaa ccagcttatc atctttgctg   2940

atgataccta cccccgatgg gtcactacag ccagcctcct ggactatgac actgtggctg   3000

gggcagacaa gtttggcaac atatgtgtgg tgaggctccc acctaacacc aatgatgaag   3060

tagatgagga tcctacagga aacaaagccc tgtgggaccg tggcttgctc aatggggcct   3120

cccagaaggc agaggtgatc atgaactacc atgtcgggga gacggtgctg tccttgcaga   3180

agaccacgct gatccctgga ggctcagaat cacttgtcta taccaccttg tctggaggaa   3240

ttggcatcct tgtgccattc acgtcccatg aggaccatga cttcttccag catgtggaaa   3300

tgcacctgcg gtctgaacat cccccctctct gtgggcggga ccacctcagc tttcgctcct   3360

actacttccc tgtgaagaat gtgattgatg gagacctctg tgagcagttc aattccatgg   3420

aacccaacaa acaaaagaac gtctctgaag aactggaccg aaccccaccc gaagtgtcca   3480

agaaactcga ggatatccgg acccgctacg ccttctgagc cctcctttcc cggtggggct   3540

tgccagagac tgtgtgtttt gtttccccca ccaccatcac tgccacctgg cttctgccat   3600

gtggcaggag ggtgactgga taattaagac tgcattatga aagtcaacag ctctttcccc   3660

tcagctcttc tcctggaatg actggcttcc cctcaaattg gcactgagat ttgctacact   3720

tctccccacc tggtacatga tacatgaccc caggttccag tgtagaacct gagtccccca   3780

ttccccaaag ccatccctgc attgatatgt cttgactctc ctgtctactt ttgcacacac   3840

ccttaatttt taattggttt tcttgtaaat acagttttgt acaatgttat ctctgtggga   3900

ggaaggaggc aggctgtggt gggactgggt agggtatagt atcactcctg agttccactg   3960

ctctagaatc taaccagaaa tagaaaccta gtttttaagg tgaaaaaaaa aaaaaaa      4017
```

<210> SEQ ID NO 46
<211> LENGTH: 1152
<212> TYPE: PRT
<213> ORGANISM: Homo sapiens

<400> SEQUENCE: 46

```
Met Ala Phe Arg Leu Thr Gly Gly Thr Lys Asp Tyr Ile Val Val Gly
  1               5                  10                  15

Ser Asp Ser Gly Arg Ile Val Ile Leu Glu Tyr Gln Pro Ser Lys Asn
             20                  25                  30

Met Phe Glu Lys Ile His Gln Glu Thr Phe Gly Lys Ser Gly Cys Ser
         35                  40                  45

Arg Ile Val Pro Gly Gln Phe Leu Ala Val Asp Pro Lys Gly Arg Ala
     50                  55                  60

Val Met Ile Ser Ala Ile Glu Lys Gln Lys Leu Val Tyr Ile Leu Asn
 65                  70                  75                  80

Arg Asp Ala Ala Ala Arg Leu Thr Ile Ser Ser Pro Leu Glu Ala His
                 85                  90                  95

Lys Ala Asn Thr Leu Val Tyr His Val Val Gly Val Asp Val Gly Phe
            100                 105                 110

Glu Asn Pro Met Phe Ala Cys Leu Glu Met Asp Tyr Glu Glu Ala Asp
        115                 120                 125

Asn Asp Pro Thr Gly Glu Ala Ala Ala Asn Thr Gln Gln Thr Leu Thr
    130                 135                 140

Phe Tyr Glu Leu Asp Leu Gly Leu Asn His Val Val Arg Lys Tyr Ser
145                 150                 155                 160

Glu Pro Leu Glu Glu His Gly Asn Phe Leu Ile Thr Val Pro Gly Gly
```

```
                165                 170                 175

Ser Asp Gly Pro Ser Gly Val Leu Ile Cys Ser Glu Asn Tyr Ile Thr
            180                 185                 190

Tyr Lys Asn Phe Gly Asp Gln Pro Asp Ile Arg Cys Pro Ile Pro Arg
        195                 200                 205

Arg Arg Asn Asp Leu Asp Asp Pro Glu Arg Gly Met Ile Phe Val Cys
    210                 215                 220

Ser Ala Thr His Lys Thr Lys Ser Met Phe Phe Phe Leu Ala Gln Thr
225                 230                 235                 240

Glu Gln Gly Asp Ile Phe Lys Ile Thr Leu Glu Thr Asp Glu Asp Met
                245                 250                 255

Val Thr Glu Ile Arg Leu Lys Tyr Phe Asp Thr Val Pro Val Ala Ala
            260                 265                 270

Ala Met Cys Val Leu Lys Thr Gly Phe Leu Phe Val Ala Ser Glu Phe
        275                 280                 285

Gly Asn His Tyr Leu Tyr Gln Ile Ala His Leu Gly Asp Asp Asp Glu
    290                 295                 300

Glu Pro Glu Phe Ser Ser Ala Met Pro Leu Glu Glu Gly Asp Thr Phe
305                 310                 315                 320

Phe Phe Gln Pro Arg Pro Leu Lys Asn Leu Val Leu Val Asp Glu Leu
                325                 330                 335

Asp Ser Leu Ser Pro Ile Leu Phe Cys Gln Ile Ala Asp Leu Ala Asn
            340                 345                 350

Glu Asp Thr Pro Gln Leu Tyr Val Ala Cys Gly Arg Gly Pro Arg Ser
        355                 360                 365

Ser Leu Arg Val Leu Arg His Gly Leu Glu Val Ser Glu Met Ala Val
    370                 375                 380

Ser Glu Leu Pro Gly Asn Pro Asn Ala Val Trp Thr Val Arg Arg His
385                 390                 395                 400

Ile Glu Asp Glu Phe Asp Ala Tyr Ile Ile Val Ser Phe Val Asn Ala
                405                 410                 415

Thr Leu Val Leu Ser Ile Gly Glu Thr Val Glu Glu Val Thr Asp Ser
            420                 425                 430

Gly Phe Leu Gly Thr Thr Pro Thr Leu Ser Cys Ser Leu Leu Gly Asp
        435                 440                 445

Asp Ala Leu Val Gln Val Tyr Pro Asp Gly Ile Arg His Ile Arg Ala
    450                 455                 460

Asp Lys Arg Val Asn Glu Trp Lys Thr Pro Gly Lys Lys Thr Ile Val
465                 470                 475                 480

Lys Cys Ala Val Asn Gln Arg Gln Val Val Ile Ala Leu Thr Gly Gly
                485                 490                 495

Glu Leu Val Tyr Phe Glu Met Asp Pro Ser Gly Gln Leu Asn Glu Tyr
            500                 505                 510

Thr Glu Arg Lys Glu Met Ser Ala Asp Val Val Cys Met Ser Leu Ala
        515                 520                 525

Asn Val Pro Pro Gly Glu Gln Arg Ser Arg Phe Leu Ala Val Gly Leu
    530                 535                 540

Val Asp Asn Thr Val Arg Ile Ile Ser Leu Asp Pro Ser Asp Cys Leu
545                 550                 555                 560

Gln Pro Leu Ser Met Gln Ala Leu Pro Ala Gln Pro Glu Ser Leu Cys
                565                 570                 575

Ile Val Glu Met Gly Gly Thr Glu Lys Gln Asp Glu Leu Gly Glu Arg
            580                 585                 590
```

-continued

```
Gly Ser Ile Gly Phe Leu Tyr Leu Asn Ile Gly Leu Gln Asn Gly Val
        595                 600                 605

Leu Leu Arg Thr Val Leu Asp Pro Val Thr Gly Asp Leu Ser Asp Thr
    610                 615                 620

Arg Thr Arg Tyr Leu Gly Ser Arg Pro Val Lys Leu Phe Arg Val Arg
625                 630                 635                 640

Met Gln Gly Gln Glu Ala Val Leu Ala Met Ser Ser Arg Ser Trp Leu
                645                 650                 655

Ser Tyr Ser Tyr Gln Ser Arg Phe His Leu Thr Pro Leu Ser Tyr Glu
            660                 665                 670

Thr Leu Glu Phe Ala Ser Gly Phe Ala Ser Glu Gln Cys Pro Glu Gly
        675                 680                 685

Ile Val Ala Ile Ser Thr Asn Thr Leu Arg Ile Leu Ala Leu Glu Lys
    690                 695                 700

Leu Gly Ala Val Phe Asn Gln Val Ala Phe Pro Leu Gln Tyr Thr Pro
705                 710                 715                 720

Arg Lys Phe Val Ile His Pro Glu Ser Asn Asn Leu Ile Ile Ile Glu
                725                 730                 735

Thr Asp His Asn Ala Tyr Thr Glu Ala Thr Lys Ala Gln Arg Lys Gln
            740                 745                 750

Gln Met Ala Glu Glu Met Val Glu Ala Ala Gly Glu Asp Glu Arg Glu
        755                 760                 765

Leu Ala Ala Glu Met Ala Ala Ala Phe Leu Asn Glu Asn Leu Pro Glu
    770                 775                 780

Ser Ile Phe Gly Ala Pro Lys Ala Gly Asn Gly Gln Trp Ala Ser Val
785                 790                 795                 800

Ile Arg Val Met Asn Pro Ile Gln Gly Asn Thr Leu Asp Leu Val Gln
                805                 810                 815

Leu Glu Gln Asn Glu Ala Ala Phe Ser Val Ala Val Cys Arg Phe Ser
            820                 825                 830

Asn Thr Gly Glu Asp Trp Tyr Val Leu Val Gly Val Ala Lys Asp Leu
        835                 840                 845

Ile Leu Asn Pro Arg Ser Val Ala Gly Gly Phe Val Tyr Thr Tyr Lys
    850                 855                 860

Leu Val Asn Asn Gly Glu Lys Leu Glu Phe Leu His Lys Thr Pro Val
865                 870                 875                 880

Glu Glu Val Pro Ala Ala Ile Ala Pro Phe Gln Gly Arg Val Leu Ile
                885                 890                 895

Gly Val Gly Lys Leu Leu Arg Val Tyr Asp Leu Gly Lys Lys Lys Leu
            900                 905                 910

Leu Arg Lys Cys Glu Asn Lys His Ile Ala Asn Tyr Ile Ser Gly Ile
        915                 920                 925

Gln Thr Ile Gly His Arg Val Ile Val Ser Asp Val Gln Glu Ser Phe
    930                 935                 940

Ile Trp Val Arg Tyr Lys Arg Asn Glu Asn Gln Leu Ile Ile Phe Ala
945                 950                 955                 960

Asp Asp Thr Tyr Pro Arg Trp Val Thr Thr Ala Ser Leu Leu Asp Tyr
                965                 970                 975

Asp Thr Val Ala Gly Ala Asp Lys Phe Gly Asn Ile Cys Val Val Arg
            980                 985                 990

Leu Pro Pro Asn Thr Asn Asp Glu Val Asp Glu Asp Pro Thr Gly Asn
        995                1000                1005
```

-continued

```
Lys Ala Leu Trp Asp Arg Gly Leu Leu Asn Gly Ala Ser Gln Lys Ala
   1010                1015                1020

Glu Val Ile Met Asn Tyr His Val Gly Glu Thr Val Leu Ser Leu Gln
1025                1030                1035                1040

Lys Thr Thr Leu Ile Pro Gly Gly Ser Glu Ser Leu Val Tyr Thr Thr
                1045                1050                1055

Leu Ser Gly Gly Ile Gly Ile Leu Val Pro Phe Thr Ser His Glu Asp
            1060                1065                1070

His Asp Phe Phe Gln His Val Glu Met His Leu Arg Ser Glu His Pro
        1075                1080                1085

Pro Leu Cys Gly Arg Asp His Leu Ser Phe Arg Ser Tyr Tyr Phe Pro
   1090                1095                1100

Val Lys Asn Val Ile Asp Gly Asp Leu Cys Glu Gln Phe Asn Ser Met
1105                1110                1115                1120

Glu Pro Asn Lys Gln Lys Asn Val Ser Glu Glu Leu Asp Arg Thr Pro
                1125                1130                1135

Pro Glu Val Ser Lys Lys Leu Glu Asp Ile Arg Thr Arg Tyr Ala Phe
            1140                1145                1150


<210> SEQ ID NO 47
<211> LENGTH: 2635
<212> TYPE: DNA
<213> ORGANISM: Homo sapiens

<400> SEQUENCE: 47

aaggggttac acttccagct tttaaaattc tcctttacat gtgctcagtg ttttgttttg     60

tgttttggtt tctgtttttt attttaattc ccacattggg cacaagaatc agaatatgga    120

tagctagttt aagaaacttt tgtgggtgca ctgtagcata gatgacagaa tatttatgag    180

ttgctgtgtt tgttgattag ttccatctct ttcccatttt aactgagaat tgattatata    240

tagctctaag tatataggta tttaaacaac cccacaagcg gctgtatcag taacatttat    300

taattccact atagtgaggg aggatttcca ttctaaatac cttattttga gggatttata    360

aaacttagtt gtaaaagaga aagcccacat agtgggaata aattgcttca gccattttta    420

gtatttgaga gcactaggga agatgtttag tagctgtgtg gatgcctttt ttcacaccct    480

gtctattgaa tgctgcatcc attcacgaag ttaaatgtta catgcagtta gtccttaatg    540

tggactggat ctgtactttt gttttggatt aaaacattta aagatttttg aagtgcagct    600

actccccacg tgcatttgat acacataaaa gtcatactgt gtgtgcacaa agagtacatg    660

gattttccag catattgctt taaaaaatta tataaactgt taaaatatta acacctcagg    720

ctacctgctg tattctgtcc cattgacccc tggaattgga tttactgcaa gtgattgata    780

attcaattat gtggcttttc ccctttaatc ttgccattta aattacagta gaaagacaaa    840

atcaagtaaa ataaagtgtt agataataga aagagtgtta agaccagccc acttttctca    900

tgtttatgtt ctttcatttg gaccaagaat ctccgcatgg aggttgattt gccactgggg    960

actttggcta agactattag gtttgctttc aactagatgt tcctgagaca agcagaggga   1020

cactgcaatt ccccttccat gcctgctgtt ctcccccatg taagtcttct ttgaaattaa   1080

cggatgtgtc tcctttggaa cagccccata acaaaagaga actactgatc tgagcatagg   1140

aaagtagagg ctctaccact tttcagttga aaaagcaaga ctttctctgt gtttctgaaa   1200

caaggcataa tgttgtcaca gaatcagaga tccagtctca cttttccaca aatctccaaa   1260

tctccagtct tatcttgtgt gctctaatgg tttggttcaa tccctttcca actcttgttt   1320
```

-continued

```
tcaaagcatg gggcctgagt gttctccact cctcctaaga aaggagcttg ggtggaaggg   1380

accatgctga cctcctccat cagagggctc ttccagtagt attctcggat gcaacctcca   1440

tttctcagtt accattattt cctgtatcag ctttgtcctt cctggaggga tgcacagtga   1500

tccggcccac cactgttgtt gtcttgtgct tctgctcttt cctatggttt caggttattt   1560

tctgggtttc ccctattctt cttttatttc ttttttttt atatttgctt tcctttctac   1620

tgcttttaga tttgcaggag atgcaagttt cagctcaatg tttggcttct ctcaatatgg   1680

aaatttcaga aggacagagg agaggaggga ggaagaagaa agtatactcc tccagaattt   1740

cagtgatctg ttgtggcagt ccagtggaag gaaggtcttt tgaggtcact tagaagcatc   1800

tttttgggac atccttttgg gatctctgta ggctaggcat ctcatatctt gagactcacc   1860

cccagcctcc aagcctctct ccatttctct aacctatgca ttttagagcg agaggaccgc   1920

ctcactagtg tcaccatcct gccttttcta aaacatgcag gctcacacat tctactcctg   1980

cttaatgtct gtgttaaatg ttttctaacc atttttgttt tatttttctg aaaaagttaa   2040

cccctcccaa ctcctcacac attggctctt cctcttgagc cacaaagttt tgattcttgc   2100

gatgtatgtg ccttatttta tgttaatctt gtcaatgaga gggaccagtt ggtgttgccc   2160

aatcagcact ccaaggctgt gtgtgcacca gccagagagc gcacggtggt agcagagtcg   2220

aggctgtctt gtatcctggt atcatatgtt gttttgaact gataggagga tgttctcttc   2280

tgacaagtta cccttgtgta tcctgcagac atgtaaaata aaatacaagt tcattttttt   2340

cacctttttt agattttttt aaaaaaataaa atgtgtaatc cttttttttaa aagaaacaca   2400

tgtaaataca tttaagtatt gtaggcatag cgttcagatg tgactggccc aggcgttcct   2460

cggacaagcc tgcattcccc gtgatcacgc ccacctcaag cccaggggct gcagcccagc   2520

cacagatgaa ctctaccttt gctttcagaa ccacttagtc cttttgtaac aaagaaaaaa   2580

aaatgtttct tacaatgtca ataaaaaatt ctttgtatgg aaaaaaaaaa aaaaa        2635
```

```
<210> SEQ ID NO 48
<211> LENGTH: 97
<212> TYPE: PRT
<213> ORGANISM: Homo sapiens

<400> SEQUENCE: 48

Met His Ser Asp Pro Ala His His Cys Cys Cys Leu Val Leu Leu Leu
  1               5                  10                  15

Phe Pro Met Val Ser Gly Tyr Phe Leu Gly Phe Pro Tyr Ser Ser Phe
             20                  25                  30

Ile Ser Phe Phe Phe Ile Phe Ala Phe Leu Ser Thr Ala Phe Arg Phe
         35                  40                  45

Ala Gly Asp Ala Ser Phe Ser Ser Met Phe Gly Phe Ser Gln Tyr Gly
     50                  55                  60

Asn Phe Arg Arg Thr Glu Glu Arg Arg Glu Glu Glu Glu Ser Ile Leu
 65                  70                  75                  80

Leu Gln Asn Phe Ser Asp Leu Leu Trp Gln Ser Ser Gly Arg Lys Val
                 85                  90                  95

Phe


<210> SEQ ID NO 49
<211> LENGTH: 1594
<212> TYPE: DNA
<213> ORGANISM: Homo sapiens

<400> SEQUENCE: 49
```

```
gccagtgaga aaggagctta ccaaaggcag tgtacgaaga aggttcctgg gagactgtca     60
gaaatgagtt tttcactgaa cttcaccctg ccggcgaaca caacgtcctc tcctgtcaca    120
ggtgggaaag aaacggactg tgggccctct cttggattag cggcgggcat accattgctg    180
gtggccacag ccctgctggt ggctttacta tttactttga ttcacccaag aagaagcagc    240
attgaggcca tggaggaaag tgacagacca tgtgaaattt cagaaattga tgacaatccc    300
aagatatctg agaatcctag gagatcaccc acacatgaga agaatacgat gggagcacaa    360
gaggcccaca tatatgtgaa gactgtagca ggaagcgagg aacctgtgca tgaccgttac    420
cgtcctacta tagaaatgga aagaaggagg ggattgtggt ggcttgtgcc cagactgagc    480
ctggaatgat gcagctcagt caaggagcag cagacctggc ctggaacagg ttgaaaaccc    540
agggttttgt acttggagag gaaagatgcc aagctgcttc ttaatcaatc caaatttcat    600
ttacagctct ggaacacttt ggggctgatt tgtctcttta ggggacatcc ccaacatggt    660
taattccaac tctcagatct tgtgctttag ttagtacatg tgactcacca gatggggtcc    720
ttagatccta ttcctgctcc cagtgggaat ttgcttttct ttgtcatttt gggaaagggg    780
cttggtttct gagtgtcttg ccttctcatc tttttttttc atatcctttt tctcaaaaaa    840
gccatcagat ctgactttca tggaagtgtt gctgaggtca gcctggtgca agttgggata    900
caaatgaaac ttatgcagga tgtgtgagag gaagcagtta attgtttctg aatatctcag    960
ggtaggaacc atgtggagcc acacattccc tgaccacagg gaagcacctg gctcaatcat   1020
gtcacacagc agtggaaaga atacggactc ttaagtcaca cctaccactg agcagctgta   1080
cgactttgga gaagttgttt aacattttca agcctcagtt tttgcttttt taaaggaggg   1140
gaaatatttg cctcatgtca taattgaaaa gattaaataa gaaataaagg gaagtgtctg   1200
ctacttagtt gccagtcaaa atgttagttc tctctctcta ccaccttctt cctacctctt   1260
cccatattgc ttgcctgata aaacagctaa tcaccagcat ttgttcccca tagtcacagg   1320
gccacacaag ggaacattta ggacaaactt tctccatggc ctatgatcca aattgttatc   1380
taaagatgat tctaggtgtt gctggtagta tgtgaatctt ccaatctagg tgtgatcgtg   1440
tcctcatatg aatcaggaaa aggcagtttc ttacaagttc cgaattccaa atacagagac   1500
tggtggtgtt acatttaacc ttaaagatgt taatgttgat ggaaattcat gtttcatatt   1560
aaaacaacac tttgtcttta aaaaaaaaaa aaaa                               1594
```

```
<210> SEQ ID NO 50
<211> LENGTH: 141
<212> TYPE: PRT
<213> ORGANISM: Homo sapiens

<400> SEQUENCE: 50

Met Ser Phe Ser Leu Asn Phe Thr Leu Pro Ala Asn Thr Thr Ser Ser
  1               5                  10                  15

Pro Val Thr Gly Gly Lys Glu Thr Asp Cys Gly Pro Ser Leu Gly Leu
             20                  25                  30

Ala Ala Gly Ile Pro Leu Leu Val Ala Thr Ala Leu Leu Val Ala Leu
         35                  40                  45

Leu Phe Thr Leu Ile His Pro Arg Arg Ser Ser Ile Glu Ala Met Glu
     50                  55                  60

Glu Ser Asp Arg Pro Cys Glu Ile Ser Glu Ile Asp Asp Asn Pro Lys
 65                  70                  75                  80

Ile Ser Glu Asn Pro Arg Arg Ser Pro Thr His Glu Lys Asn Thr Met
```

-continued

```
                85                  90                  95

Gly Ala Gln Glu Ala His Ile Tyr Val Lys Thr Val Ala Gly Ser Glu
            100                 105                 110

Glu Pro Val His Asp Arg Tyr Arg Pro Thr Ile Glu Met Glu Arg Arg
        115                 120                 125

Arg Gly Leu Trp Trp Leu Val Pro Arg Leu Ser Leu Glu
    130                 135                 140


<210> SEQ ID NO 51
<211> LENGTH: 5160
<212> TYPE: DNA
<213> ORGANISM: Homo sapiens

<400> SEQUENCE: 51

gatatcttaa gcccgggtac gtcgacccac gcgtccggaa tcgctcagga aagacacact     60

gcagactcca ccggcaccct gcaatagatg gattccgact acacaaggga gaaaacgcgg    120

aggtgacact ctcctgcctg gaaagaggac gaacgaccaa acaaacgcaa ggactggact    180

ccatgccgaa ggtatctgga agtcgtgaca cggtgtgtat aaaacaaaag tttgcgagct    240

gttaattgct gtgctgtgtt attaagagac gctttcaagt ttcaagtacc aaatgtagct    300

ttacgttgcc aaaggaagtt gaggcaattg ctttgctgtt ttaacttgct ctgtgaggga    360

aatctcataa actgaccaat gcaccaaatg aatgctaaaa tgcactttag gtttgttttt    420

gcacttctga tagtatcttt caaccacgat gtactgggca agaatttgaa atacaggatt    480

tatgaggaac agagggttgg atcagtaatt gcaagactat cagaggatgt ggctgatgtt    540

ttattgaagc ttcctaatcc ttctactgtt cgatttcgag ccatgcagag gggaaattct    600

cctctacttg tagtaaacga ggataatggg gaaatcagca taggggctac aattgaccgt    660

gaacaactgt gccagaaaaa cttgaactgt tccatagagt ttgatgtgat cactctaccc    720

acagagcatc tgcagctttt ccatattgaa gttgaagtgc tggatattaa tgacaattct    780

ccccagtttt caagatctct catacctatt gagatatctg agagtgcagc agttgggact    840

cgcattcccc tggacagtgc atttgatcca gatgttgggg aaaattccct ccacacatac    900

tcgctctctg ccaatgattt ttttaatatc gaggttcgga ccaggactga tggagccaag    960

tatgcagaac tcatagtggt cagagagtta gatcgggagc tgaagtcaag ctacgagctt   1020

cagctcactg cctcagacat gggagtacct cagaggtctg gctcatccat actaaaaata   1080

agcatttcag actccaatga caacagccct gcttttgagc agcaatctta tataatacaa   1140

ctcttagaaa actccccggt tggcactttg ctcttagatc tgaatgccac ggatccagat   1200

gagggcgcta atgggaaaat tgtatattcc ttcagcagtc atgtgtctcc caaaattatg   1260

gagactttta aaattgattc tgaaagagga catttgactc ttttcaagca agtggattat   1320

gaaatcacca aatcctatga gattgatgtt caggctcaag atttgggtcc aaattcaatc   1380

ccagcccatt gcaaaattat aattaaggtt gtggatgtta atgacaataa acctgaaatt   1440

aacatcaacc tcatgtcccc tggaaaagaa gaaatatctt atatttttga aggggatcct   1500

attgatacat ttgttgcttt ggtcagagtt caggacaagg attctgggct gaatggagaa   1560

atagtttgta agcttcatgg acatggtcac tttaaacttc agaagacata tgaaaacaat   1620

tatttaatct taactaatgc cacactggat agagaaaaga gatctgagta tagtttgact   1680

gtaatcgctg aggacagggg gacacccagt ctctctacag tgaaacattt tacagttcaa   1740

atcaatgata tcaatgacaa tccaccccac ttccagagaa gccgatatga atttgtaatt   1800
```

-continued

```
tcagaaaata actcaccagg ggcatatatc accactgtta cagccacaga tcctgatctt   1860
ggagaaaatg ggcaagtgac atacaccatc ttggagagtt ttattctagg aagttccata   1920
actacatatg taaccattga cccatctaat ggagccatct atgccctcag aatctttgat   1980
catgaagaag tgagtcagat cacttttgtg gtagaagcaa gagatggagg aagcccgaag   2040
caactggtaa gcaataccac agttgtgctc accatcattg acgaaaatga caacgttcct   2100
gtggttatag ggcctgcatt gcgtaataat acggcagaaa tcaccattcc caaaggggct   2160
gaaagtggct ttcatgtcac aagaataagg gcaattgaca gagactctgg tgtgaatgct   2220
gaactcagct gcgccatagt agcaggtaat gaggagaata tcttcataat tgatccacga   2280
tcatgtgaca tccataccaa cgttagcatg gattctgttc cctacacaga atgggagctg   2340
tcagttatca ttcaggacaa aggcaatcct cagctacata ccaaagtcct tctgaagtgc   2400
atgatctttg aatatgcaga gtcggtgaca agtacagcaa tgacttcagt aagccaggca   2460
tccttggatg tctccatgat aataattatt tccttaggag caatttgtgc agtgttgctg   2520
gttattatgg tgctatttgc aactaggtgt aaccgcgaga agaaagacac tagatcctat   2580
aactgcaggg tggccgaatc aacttaccag caccacccaa aaaggccatc ccggcagatt   2640
cacaaagggg acatcacatt ggtgcctacc ataaatggca ctctgcccat cagatctcat   2700
cacagatcgt ctccatcttc atctcctacc ttagaaagag ggcagatggg cagccggcag   2760
agtcacaaca gtcaccagtc actcaacagt ttggtgacaa tctcatcaaa ccacgtgcca   2820
gagaatttct cattagaact cacccacgcc actcctgctg ttgagcaggt ctctcagctt   2880
ctttcaatgc ttcaccaggg gcaatatcag ccaagaccaa gttttcgagg aaacaaatat   2940
tccaggagct acagatatgc ccttcaagac atggacaaat ttagcttgaa agacagtggc   3000
cgtggtgaca gtgaggcagg agacagtgat tatgatttgg ggcgagattc tccaatagat   3060
aggctgttgg gtgaaggatt cagcgacctg tttctcacag atggaagaat tccagcagct   3120
atgagactct gcacggagga gtgcagggtc ctgggacact ctgaccagtg ctggatgcca   3180
ccactgccct caccgtcttc tgattatagg agtaacatgt tcattccagg ggaagaattc   3240
ccaacgcaac cccagcagca gcatccacat cagagtcttg aggatgacgc tcagcctgca   3300
gattccggtg aaaagaagaa gagtttttcc acctttggaa aggactcccc aaacgatgag   3360
gacactgggg ataccagcac atcatctctg ctctcggaaa tgagcagtgt gttccagcgt   3420
ctcttaccgc cttccctgga cacctattct gaatgcagtg aggtggatcg gtccaactcc   3480
ctggagcgca ggaagggacc cttgccagcc aaaactgtgg gttacccaca gggggtagcg   3540
gcatgggcag ccagtacgca ttttcaaaat cccaccacca actgtgggcc gccacttgga   3600
actcactcca gtgtgcagcc ttcttcaaaa tggctgccag ccatggagga gatccctgaa   3660
aattatgagg aagatgattt tgacaatgtg ctcaaccacc tcaatgatgg gaaacacgaa   3720
ctcatggatg ccagtgaact ggtggcagag attaacaaac tgcttcaaga tgtccgccag   3780
agctaggaga ttttagcgaa gcatttttgt ttccatgtat atggaaatag ggaacaacaa   3840
caacaacaaa aaaccctgaa agaactggca ttgccaaata gttgcattta tcataaatgt   3900
gtctgtgtat attgaatatt aaatactgta ttttcgtatg tacacaatgc aagtgtgatt   3960
attttaatct gtattttaaa aatacatttg taccttatat ttatgtgtaa tttaacaaac   4020
aaattttatt tttttactcc catgacagac atgtttttcc tagtcgtgta gaaactagcc   4080
actgttcaaa tctgatacac tattcaacca caaagtgtaa aggcactgct tagattagtt   4140
ttgttgggga agaattatta tgttgtatga acaaccccac tgaagcatta tacaattctt   4200
```

```
aattccatta agtgatccca cttttttca ataacttttt agaaattaag aatcattaaa   4260

attgttaagc tattttattg ttattttctc tactttctac tagccccaat agttgaactc   4320

ttataggaaa atcgaaagat aaagtgaaag tttatttcag gactgagaaa tatcttgaag   4380

gttatttatt agatgactat ctcaaatgaa ctttttatag acaatgatga aaacagaatt   4440

aaagtcaatg tttcctgact cccaggcccc tactattcca ggccatcaca ctggcctgtt   4500

ccggagaata tttctctcac aatattatta tctacttata attatggtaa acaataaatt   4560

ttattccatc cttgtagtat gaaacatgct ccaaggaaat ggaatctgtc ctttaaatgg   4620

ataacagtat gtgttctaat ggcataaaat attactggat aaaaacagtt gtgtcagtgt   4680

ctctcctaag gtagtaaata taattgactt attctgaacc cattctattt tgaatctccc   4740

ctttcctctc acaatacttg aacattttaa tcttttggaa tattgtcttt ctttgttata   4800

actattcatt tttagctttt gtctccagtg catgatctca tatttttgct tttattttta   4860

gtataagaac atttataaaa tcatattttt gttactgcaa ttgttttatt tgttgtgtgg   4920

caaatgagaa atcctttatt tattgtgctg tgatctctct gtgtggaatg ccttggtgag   4980

agagatgctt attatgacta ttatcatttc tgaccaagct tctattaatg ttatttctaa   5040

taatacacta tcttgattgt actctccaga aaatttttct gtcagtgaaa ataaaagaaa   5100

aattaaagta aagctaaaaa aaaaaaaaaa aaaaaaaaaa aaaaaaaaaa aaaaaaaaaa   5160
```

<210> SEQ ID NO 52
<211> LENGTH: 1135
<212> TYPE: PRT
<213> ORGANISM: Homo sapiens

<400> SEQUENCE: 52

```
Met His Gln Met Asn Ala Lys Met His Phe Arg Phe Val Phe Ala Leu
  1               5                  10                  15

Leu Ile Val Ser Phe Asn His Asp Val Leu Gly Lys Asn Leu Lys Tyr
             20                  25                  30

Arg Ile Tyr Glu Glu Gln Arg Val Gly Ser Val Ile Ala Arg Leu Ser
         35                  40                  45

Glu Asp Val Ala Asp Val Leu Leu Lys Leu Pro Asn Pro Ser Thr Val
     50                  55                  60

Arg Phe Arg Ala Met Gln Arg Gly Asn Ser Pro Leu Leu Val Val Asn
 65                  70                  75                  80

Glu Asp Asn Gly Glu Ile Ser Ile Gly Ala Thr Ile Asp Arg Glu Gln
                 85                  90                  95

Leu Cys Gln Lys Asn Leu Asn Cys Ser Ile Glu Phe Asp Val Ile Thr
            100                 105                 110

Leu Pro Thr Glu His Leu Gln Leu Phe His Ile Glu Val Glu Val Leu
        115                 120                 125

Asp Ile Asn Asp Asn Ser Pro Gln Phe Ser Arg Ser Leu Ile Pro Ile
    130                 135                 140

Glu Ile Ser Glu Ser Ala Ala Val Gly Thr Arg Ile Pro Leu Asp Ser
145                 150                 155                 160

Ala Phe Asp Pro Asp Val Gly Glu Asn Ser Leu His Thr Tyr Ser Leu
                165                 170                 175

Ser Ala Asn Asp Phe Phe Asn Ile Glu Val Arg Thr Arg Thr Asp Gly
            180                 185                 190

Ala Lys Tyr Ala Glu Leu Ile Val Val Arg Glu Leu Asp Arg Glu Leu
        195                 200                 205
```

```
Lys Ser Ser Tyr Glu Leu Gln Leu Thr Ala Ser Asp Met Gly Val Pro
    210                 215                 220

Gln Arg Ser Gly Ser Ser Ile Leu Lys Ile Ser Ile Ser Asp Ser Asn
225                 230                 235                 240

Asp Asn Ser Pro Ala Phe Glu Gln Gln Ser Tyr Ile Ile Gln Leu Leu
                245                 250                 255

Glu Asn Ser Pro Val Gly Thr Leu Leu Leu Asp Leu Asn Ala Thr Asp
            260                 265                 270

Pro Asp Glu Gly Ala Asn Gly Lys Ile Val Tyr Ser Phe Ser Ser His
        275                 280                 285

Val Ser Pro Lys Ile Met Glu Thr Phe Lys Ile Asp Ser Glu Arg Gly
    290                 295                 300

His Leu Thr Leu Phe Lys Gln Val Asp Tyr Glu Ile Thr Lys Ser Tyr
305                 310                 315                 320

Glu Ile Asp Val Gln Ala Gln Asp Leu Gly Pro Asn Ser Ile Pro Ala
                325                 330                 335

His Cys Lys Ile Ile Ile Lys Val Val Asp Val Asn Asp Asn Lys Pro
            340                 345                 350

Glu Ile Asn Ile Asn Leu Met Ser Pro Gly Lys Glu Glu Ile Ser Tyr
        355                 360                 365

Ile Phe Glu Gly Asp Pro Ile Asp Thr Phe Val Ala Leu Val Arg Val
    370                 375                 380

Gln Asp Lys Asp Ser Gly Leu Asn Gly Glu Ile Val Cys Lys Leu His
385                 390                 395                 400

Gly His Gly His Phe Lys Leu Gln Lys Thr Tyr Glu Asn Asn Tyr Leu
                405                 410                 415

Ile Leu Thr Asn Ala Thr Leu Asp Arg Glu Lys Arg Ser Glu Tyr Ser
            420                 425                 430

Leu Thr Val Ile Ala Glu Asp Arg Gly Thr Pro Ser Leu Ser Thr Val
        435                 440                 445

Lys His Phe Thr Val Gln Ile Asn Asp Ile Asn Asp Asn Pro Pro His
    450                 455                 460

Phe Gln Arg Ser Arg Tyr Glu Phe Val Ile Ser Glu Asn Asn Ser Pro
465                 470                 475                 480

Gly Ala Tyr Ile Thr Thr Val Thr Ala Thr Asp Pro Asp Leu Gly Glu
                485                 490                 495

Asn Gly Gln Val Thr Tyr Thr Ile Leu Glu Ser Phe Ile Leu Gly Ser
            500                 505                 510

Ser Ile Thr Thr Tyr Val Thr Ile Asp Pro Ser Asn Gly Ala Ile Tyr
        515                 520                 525

Ala Leu Arg Ile Phe Asp His Glu Glu Val Ser Gln Ile Thr Phe Val
    530                 535                 540

Val Glu Ala Arg Asp Gly Gly Ser Pro Lys Gln Leu Val Ser Asn Thr
545                 550                 555                 560

Thr Val Val Leu Thr Ile Ile Asp Glu Asn Asp Asn Val Pro Val Val
                565                 570                 575

Ile Gly Pro Ala Leu Arg Asn Asn Thr Ala Glu Ile Thr Ile Pro Lys
            580                 585                 590

Gly Ala Glu Ser Gly Phe His Val Thr Arg Ile Arg Ala Ile Asp Arg
        595                 600                 605

Asp Ser Gly Val Asn Ala Glu Leu Ser Cys Ala Ile Val Ala Gly Asn
    610                 615                 620
```

-continued

```
Glu Glu Asn Ile Phe Ile Ile Asp Pro Arg Ser Cys Asp Ile His Thr
625                 630                 635                 640

Asn Val Ser Met Asp Ser Val Pro Tyr Thr Glu Trp Glu Leu Ser Val
                645                 650                 655

Ile Ile Gln Asp Lys Gly Asn Pro Gln Leu His Thr Lys Val Leu Leu
            660                 665                 670

Lys Cys Met Ile Phe Glu Tyr Ala Glu Ser Val Thr Ser Thr Ala Met
        675                 680                 685

Thr Ser Val Ser Gln Ala Ser Leu Asp Val Ser Met Ile Ile Ile Ile
    690                 695                 700

Ser Leu Gly Ala Ile Cys Ala Val Leu Leu Val Ile Met Val Leu Phe
705                 710                 715                 720

Ala Thr Arg Cys Asn Arg Glu Lys Lys Asp Thr Arg Ser Tyr Asn Cys
                725                 730                 735

Arg Val Ala Glu Ser Thr Tyr Gln His His Pro Lys Arg Pro Ser Arg
            740                 745                 750

Gln Ile His Lys Gly Asp Ile Thr Leu Val Pro Thr Ile Asn Gly Thr
        755                 760                 765

Leu Pro Ile Arg Ser His His Arg Ser Ser Pro Ser Ser Ser Pro Thr
    770                 775                 780

Leu Glu Arg Gly Gln Met Gly Ser Arg Gln Ser His Asn Ser His Gln
785                 790                 795                 800

Ser Leu Asn Ser Leu Val Thr Ile Ser Ser Asn His Val Pro Glu Asn
                805                 810                 815

Phe Ser Leu Glu Leu Thr His Ala Thr Pro Ala Val Glu Gln Val Ser
            820                 825                 830

Gln Leu Leu Ser Met Leu His Gln Gly Gln Tyr Gln Pro Arg Pro Ser
        835                 840                 845

Phe Arg Gly Asn Lys Tyr Ser Arg Ser Tyr Arg Tyr Ala Leu Gln Asp
    850                 855                 860

Met Asp Lys Phe Ser Leu Lys Asp Ser Gly Arg Gly Asp Ser Glu Ala
865                 870                 875                 880

Gly Asp Ser Asp Tyr Asp Leu Gly Arg Asp Ser Pro Ile Asp Arg Leu
                885                 890                 895

Leu Gly Glu Gly Phe Ser Asp Leu Phe Leu Thr Asp Gly Arg Ile Pro
            900                 905                 910

Ala Ala Met Arg Leu Cys Thr Glu Glu Cys Arg Val Leu Gly His Ser
        915                 920                 925

Asp Gln Cys Trp Met Pro Pro Leu Pro Ser Pro Ser Ser Asp Tyr Arg
    930                 935                 940

Ser Asn Met Phe Ile Pro Gly Glu Glu Phe Pro Thr Gln Pro Gln Gln
945                 950                 955                 960

Gln His Pro His Gln Ser Leu Glu Asp Asp Ala Gln Pro Ala Asp Ser
                965                 970                 975

Gly Glu Lys Lys Lys Ser Phe Ser Thr Phe Gly Lys Asp Ser Pro Asn
            980                 985                 990

Asp Glu Asp Thr Gly Asp Thr Ser Thr Ser Ser Leu Leu Ser Glu Met
        995                 1000                1005

Ser Ser Val Phe Gln Arg Leu Leu Pro Pro Ser Leu Asp Thr Tyr Ser
   1010                1015                1020

Glu Cys Ser Glu Val Asp Arg Ser Asn Ser Leu Glu Arg Arg Lys Gly
1025               1030                1035                1040

Pro Leu Pro Ala Lys Thr Val Gly Tyr Pro Gln Gly Val Ala Ala Trp
```

-continued

```
            1045                1050                1055

Ala Ala Ser Thr His Phe Gln Asn Pro Thr Thr Asn Cys Gly Pro Pro
        1060                1065                1070

Leu Gly Thr His Ser Ser Val Gln Pro Ser Ser Lys Trp Leu Pro Ala
    1075                1080                1085

Met Glu Glu Ile Pro Glu Asn Tyr Glu Glu Asp Asp Phe Asp Asn Val
   1090                1095                1100

Leu Asn His Leu Asn Asp Gly Lys His Glu Leu Met Asp Ala Ser Glu
1105                1110                1115                1120

Leu Val Ala Glu Ile Asn Lys Leu Leu Gln Asp Val Arg Gln Ser
            1125                1130                1135
```

<210> SEQ ID NO 53
<211> LENGTH: 1207
<212> TYPE: DNA
<213> ORGANISM: Homo sapiens

<400> SEQUENCE: 53

```
atggcgtccc gcggccggcg tccggagcat ggcggacccc cagagctgtt ttatgacgag     60

acagaagccc ggaaatacgt tcgcaactca cggatgattg atatccagac caggatggct    120

gggcgagcat tggagcttct ttatctgcca gagaataagc cctgttacct gctggatatt    180

ggctgtggca ctgggctgag tggaagttat ctgtcagatg aagggcacta ttgggtgggc    240

ctggatatca gccctgccat gctggatgag gctgtggacc gagagataga gggagacctg    300

ctgctggggg atatgggcca gggcatccca ttcaagccag gcacatttga tggttgcatc    360

agcatttctg ctgtgcattg gctctgtaat gctaacaaga agtctgaaaa ccctgccaag    420

cgcctgtact gctttttgc ttctcttttt tctgttctcg tccggggatc ccgagctgtc     480

ctgcagctgt accctgagaa ctcagagcag ttggagctga tcacaaccca ggccacaaag    540

gcaggcttct ccggtggcat ggtggtagac taccctaaca gtgccaaagc aaagaaattc    600

tacctctgct tgttttctgg gccttcgacc tttataccag aggggctgag tgaaaatcag    660

gatgaagttg aacccaggga gtctgtgttc accaatgaga ggttcccatt aaggatgtcg    720

aggcggggaa tggtgaggaa gagtcgggca tgggtgctgg agaagaagga gcggcacagg    780

cgccagggca gggaagtcag acctgacacc cagtacaccg gccgcaagcg caagccccgc    840

ttctaagtca ccacgcggtt ctggaaaggc acttgcctct gcacttttct atattgttca    900

gctgacaaag tagtatttta gaaaagttct aaagttataa aaatgttttc tgcagtaaaa    960

aaaaagttct ctgggccggg cgtggtggct cacacctgta atcccagcac cttgggaggc   1020

tgaggtggga ggatcatttg aggccaggag tttgagacct gcctgggcaa cataatgaaa   1080

cttcctttcc agggagaaaa aaaaaaaaaa aaaaaaaagc tctgagagca tcttattttg   1140

tttaaaggca agaaataaaa tttccttttg tggaaaaaaa aaaaaaaaaa aaaaaaaaaa   1200

aaaaaaa                                                             1207
```

<210> SEQ ID NO 54
<211> LENGTH: 281
<212> TYPE: PRT
<213> ORGANISM: Homo sapiens

<400> SEQUENCE: 54

```
Met Ala Ser Arg Gly Arg Arg Pro Glu His Gly Gly Pro Pro Glu Leu
  1               5                  10                  15

Phe Tyr Asp Glu Thr Glu Ala Arg Lys Tyr Val Arg Asn Ser Arg Met
```

-continued

```
            20                  25                  30

Ile Asp Ile Gln Thr Arg Met Ala Gly Arg Ala Leu Glu Leu Leu Tyr
        35                  40                  45

Leu Pro Glu Asn Lys Pro Cys Tyr Leu Leu Asp Ile Gly Cys Gly Thr
    50                  55                  60

Gly Leu Ser Gly Ser Tyr Leu Ser Asp Glu Gly His Tyr Trp Val Gly
65                  70                  75                  80

Leu Asp Ile Ser Pro Ala Met Leu Asp Glu Ala Val Asp Arg Glu Ile
                85                  90                  95

Glu Gly Asp Leu Leu Leu Gly Asp Met Gly Gln Gly Ile Pro Phe Lys
            100                 105                 110

Pro Gly Thr Phe Asp Gly Cys Ile Ser Ile Ser Ala Val His Trp Leu
        115                 120                 125

Cys Asn Ala Asn Lys Lys Ser Glu Asn Pro Ala Lys Arg Leu Tyr Cys
    130                 135                 140

Phe Phe Ala Ser Leu Phe Ser Val Leu Val Arg Gly Ser Arg Ala Val
145                 150                 155                 160

Leu Gln Leu Tyr Pro Glu Asn Ser Glu Gln Leu Glu Leu Ile Thr Thr
                165                 170                 175

Gln Ala Thr Lys Ala Gly Phe Ser Gly Gly Met Val Val Asp Tyr Pro
            180                 185                 190

Asn Ser Ala Lys Ala Lys Lys Phe Tyr Leu Cys Leu Phe Ser Gly Pro
        195                 200                 205

Ser Thr Phe Ile Pro Glu Gly Leu Ser Glu Asn Gln Asp Glu Val Glu
    210                 215                 220

Pro Arg Glu Ser Val Phe Thr Asn Glu Arg Phe Pro Leu Arg Met Ser
225                 230                 235                 240

Arg Arg Gly Met Val Arg Lys Ser Arg Ala Trp Val Leu Glu Lys Lys
                245                 250                 255

Glu Arg His Arg Arg Gln Gly Arg Glu Val Arg Pro Asp Thr Gln Tyr
            260                 265                 270

Thr Gly Arg Lys Arg Lys Pro Arg Phe
        275                 280
```

<210> SEQ ID NO 55
<211> LENGTH: 1490
<212> TYPE: DNA
<213> ORGANISM: Homo sapiens

<400> SEQUENCE: 55

```
agcccacctg gtggggagga ggccctgctg tggaatccct accccaggag ccctggccct      60

cctcctggtg gggctcccta gaggagggtc ctctcagccc gagaacgcag ctcagtgtgt     120

caggctccaa ctgtttttct gtgacttgct cgccgtgtag gctgctaaac atctggctga     180

accaagcgtt catcctgacc tgaagccaga acctcagaaa ccaaagtaag gcctgatcat     240

gccctcgccc cactgcccca gagacctcct cttgtctctt tgatgttttg ttttctattt     300

tatttttcgt ttttgtgtgt ctgcatggtg tttttcgggc agtggcttct gccatcatca     360

ccacatgttt ctctgctgcc cactgtcctg aggtgggccg tcgtggaagc cctgcttcct     420

gccgtttgcg ggacgagtcc cgccctcttt tttcctgtcc ccatcggtag tctgcgtgca     480

cgtgttttcc acagtaaaac cgtgttgtgt aactctttcc agcaaagtaa caatccgcca     540

ttacaaaggt cgtcctcctt gatccagtta acgagtcaga actcttctcc caatcagcag     600

agaaccccgc aggtcatcgg ggtcatgcag agtcaaaaca gcagcggggg caaccgggga     660
```

```
cccggccact ggagcaggtc acctgttaca agtgtggcga gaaaggacac tacgccaaca    720

gatgcaccaa agggcacttg gcctttctca gtggacagtg acagcagctg gagccagctc    780

cgagcagccc gggggccccg ctgttgggag tgtgcattta actgtttcat gcgcttgttg    840

gcgcgactgt ggctcgagct ggcccgcaga cacgtgggtt tcatcactct gaggggccac    900

gtctgttagt ttcctatcat tttgccttag tatttttga aaaaggacat gtgtcctgtg    960

ggtccctgca gtcgacatca tgtttggctg ggcatcgatg cctcctttct gggactcccg   1020

gcacaactcc ctgccctgct gaatcctaaa gctgtgccta tatctgtgat ttgaatgagg   1080

gagccctttg gggcaaattc aggtgccccc attgcctcag gctggccctg gtcccaggtg   1140

gcagcggttg aggaggggta cagggctctc aagcctgagg ttttcttctc tgggcttaat   1200

tttctcttgg ggtacgtgcc tgacagtgtt taaggtgtcc gttgaactgg agttgcagac   1260

ttttaaatag atgacccctt cagatcatct gtgcctacct cctgcccatc aggcgtctac   1320

actgtcactc agacacctgt ggcatgtgga ggagactgcc ctgtcctgag cctggaaaat   1380

gtgaaactgt ctcctgcaac ctgctgggca tgtgggcctg gctgtgttca attgcaagaa   1440

caatttttat gaaatggatt aaagcttgtt ttttaaaaaa aaaaaaaaaa              1490
```

<210> SEQ ID NO 56
<211> LENGTH: 208
<212> TYPE: PRT
<213> ORGANISM: Homo sapiens

<400> SEQUENCE: 56

```
Met Phe Cys Phe Leu Phe Tyr Phe Ser Phe Leu Cys Val Cys Met Val
  1               5                  10                  15

Phe Phe Gly Gln Trp Leu Leu Pro Ser Ser Pro His Val Ser Leu Leu
             20                  25                  30

Pro Thr Val Leu Arg Trp Ala Val Val Glu Ala Leu Leu Pro Ala Val
         35                  40                  45

Cys Gly Thr Ser Pro Ala Leu Phe Phe Pro Val Pro Ile Gly Ser Leu
     50                  55                  60

Arg Ala Arg Val Phe His Ser Lys Thr Val Leu Cys Asn Ser Phe Gln
 65                  70                  75                  80

Gln Ser Asn Asn Pro Pro Leu Gln Arg Ser Ser Ser Leu Ile Gln Leu
                 85                  90                  95

Thr Ser Gln Asn Ser Ser Pro Asn Gln Gln Arg Thr Pro Gln Val Ile
            100                 105                 110

Gly Val Met Gln Ser Gln Asn Ser Ser Gly Gly Asn Arg Gly Pro Gly
        115                 120                 125

His Trp Ser Arg Ser Pro Val Thr Ser Val Ala Arg Lys Asp Thr Thr
    130                 135                 140

Pro Thr Asp Ala Pro Lys Gly Thr Trp Pro Phe Ser Val Asp Ser Asp
145                 150                 155                 160

Ser Ser Trp Ser Gln Leu Arg Ala Ala Arg Gly Pro Arg Cys Trp Glu
                165                 170                 175

Cys Ala Phe Asn Cys Phe Met Arg Leu Leu Ala Arg Leu Trp Leu Glu
            180                 185                 190

Leu Ala Arg Arg His Val Gly Phe Ile Thr Leu Arg Gly His Val Cys
        195                 200                 205
```

<210> SEQ ID NO 57
<211> LENGTH: 4184

<212> TYPE: DNA
<213> ORGANISM: Homo sapiens

<400> SEQUENCE: 57

```
agcagggaaa gaaaaacttg acgtgtggaa tacagaggga ggagatttta acattatggc     60
agggaggcat cagaatcgta gttttcctct tccaggagtt cagtcaagtg gtcaagtaca    120
tgcatttgga aattgttcag acagtgatat tttggaggag gatgctgaag tgtatgagct    180
tcgatccaga ggaaaagaga aagtccgaag aagtacatca agagatagac ttgacgacat    240
tatagtatta acaaaagata tacaagaagg agatacatta aatgcaatag cccttcagta    300
ctgttgtacg gtagcagata tcaagagagt taacaatctc atcagtgatc aagacttttt    360
tgcccttagg tctatcaaaa ttccagtaaa aaagttcagt tccttgaccg aaacactttg    420
tcctccaaaa ggaagacaga cttcacgtca ttcatctgtt caatactctt ccgaacaaca    480
ggaaattttg ccagctaatg attctcttgc ttacagtgac tcagctggta gctttttaaa    540
agaagtagac cgagacatag aacaaatagt aaagtgtaca gacaataaga gagagaacct    600
ccatgaggta gtatcggcct tcacagcaca acaaatgcgt tttgaacctg ataacaaaaa    660
cactcaacgt aaagacccct attatggagc agactgggga atagggtggt ggacagctgt    720
agtgataatg ttgatagtag gtataataac accagtgttt tatttgttgt attatgaaat    780
tttagctaag gtggatgtta gtcatcattc aacagtggac tcttcacatt tacattcaaa    840
aatcacaccc ccatcacagc agagagaaat ggaaaatgga attgtgccaa ctaaaggaat    900
acatttcagc caacaagatg atcataaact gtatagtcaa gattctcagt cacctgctgc    960
tcaacaggaa acatagcaat tagctcataa tcaaatgtta gtggtcaggt cacatgtgca   1020
tctggaatgt ggtgaatcag ttatatccaa taatagcttc aaaggcagaa tttagagaga   1080
ttgaggatgc ttttgttttt aacaaaaggg tttcacactt tgaaaatttt ttgagcaact   1140
agttgttgat gttgagagca gttgatccat aaatctggtg tgtgaatgtt tcaagcagaa   1200
attaatttaa atgtgtgttt aggaagtact taacttggaa gatgtatcat ttttcttaaa   1260
atgcatgttt aaattttatt tttttaagta atttttaaaa agtttattaa tgttaaattt   1320
atgatgcaga atgatagcat cagatgtctg cagctgaaaa aaatttacta ctatgaaccc   1380
ccaaaatatt cagttgcaag aaaatttgat tctaaaatta ttcatggtag gatacgtaac   1440
acaccccttc caaactttta aaaaatacat ttagcacatg tgctatgaaa gcatacgtac   1500
aaagagaaag gggaaagtga tttataattc ctacaacaga ggccaagaaa tagattaaaa   1560
tattttcaag accccaaaat aatgtattat ggttgggaag tcagtagaac actggaatag   1620
gtgaagacct gacagtaatt tttgtcttaa gaatgctttc tttaggacag accctttaac   1680
ctcacctctg tgcatctgtt tttaaaatga ttatatttgc ctctgatatt tgaaagcact   1740
tttgtagttt tgatgatgaa aaatatatta aacgtgcata ttaccattat ttaggaaata   1800
attccttata tactgtgata aatcattgct gttacataca gtaacatgcc ttaattacat   1860
ttaatgcctt actgctttat gtaagtaaat ccaagtttca gaattaaaaa taagcattat   1920
ttcatatggt ccaatcagat tcgttacata ggctatataa atttgtctcc attttcacca   1980
tcaagcacaa ataattgggt caaaactgcc tttgaggtct gttgaagaaa atggttcatt   2040
aagcaaaaaa agagtagagg tattttatat tagcagtaac agacaaatta tttagtaatc   2100
ccttaacctc tgtttttcaa agagaaaata tccaatttag actttttttcc tgatctctat   2160
atatagcatc aaattgggaa acaaaggcca aaggtgtata gattgcttga aagggggtgg   2220
```

-continued

```
taggcctctt tttaagatct gtgagtcggc tacagtctgg ctaagtaaga agcatttgca   2280

tactgattcc atcatttaat ctttaaaagt atgtgtttta aaaatgtaac cagaatgatt   2340

cttcaataga aatgagattt ggtggagtct ggattgcctg ttttgtatat aatatatact   2400

taagatatat aataccacct cattttctgg gcattatttc ctaattgttg atgtttcagg   2460

cttttgataa gtcattttat atatttcaaa tttaactcag aataagtaaa tatttatggc   2520

aaatgcagtt ttatgtactt tcaggagaag accatcagga aaagacagga caaagaagtc   2580

aaacattaaa gcccttgcaa atattagagg accttagaca attaccaaaa agtgtttaat   2640

agggaagttg caaatgattc tcttagtaaa ttaaacattt aaaaagtagt tttaatgtgc   2700

cttgggcatc ttgaaaagaa gagtgtgata taatttatgc ttagtgttaa ctggtcattt   2760

tacattgtat ttattaagtc tgctgaaaaa tgaggtttta aggaagaaaa tgcagattat   2820

tttagggtaa acaggccagg tgtcctttga agaactttgt ttacatcaaa ttgatgaaat   2880

tacagtcagt gattccttac tttttttgct agttgtactt tgaaattgtt atgggttcgt   2940

tttccaaaat atgtaactta ttttttaaag gaataaggtg tgctgtgtat ttgttgatta   3000

aaaatcattt gtcttgcaga gtatcctttt ttgaaggaaa tatacatcct tataacacat   3060

caggtagttt tctttttttct gtatttaaat tatatatttg aattaattga atataatttg   3120

agttacatat aattctatat aaaggttaca tattgaatta tggttctaat ctgtttagga   3180

aagaaatgaa ttttctaagc atttaataca tttggaataa ttttagtttc taaaaagtac   3240

taatgtaagt taagtttata tcaaatgcaa attaccttgt ataactaaca agcacagtta   3300

ttgtttaaca ttatggattt taattgtgtt gacacccttc tttgaatttg ttgctttaca   3360

tgtgtgtctg tgtgtgtgtc tgcatgtgtg cacgcatgta cttgtatgca atgtaaaagt   3420

aacagcagaa tcattgcatt tggtttactt aaaattttgg agttagcaag taaacaaaaa   3480

gctgatagtt ttatgaagtc tcggttaaaa taaaatttct ttgctatctc actcctagga   3540

agttatggag ttcatatttt caaaagatat gttaaaaatg gttacacact ctgctggcca   3600

cattaaaaat tagaagactc atgttaaatt atctcctcca aaggactttt tatttacagc   3660

ttttcttttc ctggactcta cctgcttggt tcagtgtcct gaagagttat ttaaatgaac   3720

cactacttag taattagttc ttttttaaag tatctacttc taaaattacc tagttgaaaa   3780

tatgaaggat atgcttagtt ttagaaatat catgaagcaa ggatctagtc agtgttacag   3840

ggtaaaggtg gagtttttta aagtctgtat ttaaatggtg cactgatgga ttcattttta   3900

atttgcatta caaaaatgtt gctcaggtaa tcagtatttt cttccacgta tgtgcatatt   3960

gcactgttag atcatagaaa tatctgaatg ctttaatttt tatgtatgca aaatctataa   4020

atcttttgta taatgtattt tatacaaatg taactgtaga acattgttag catgtgtatc   4080

tgtaaaacca gtttttaaaa ttttttgccc cttatttttc atattttgaa agatctccaa   4140

catgtaataa agtttctctt attcaatcta aaaaaaaaaa aaaa                    4184
```

<210> SEQ ID NO 58
<211> LENGTH: 306
<212> TYPE: PRT
<213> ORGANISM: Homo sapiens

<400> SEQUENCE: 58

```
Met Ala Gly Arg His Gln Asn Arg Ser Phe Pro Leu Pro Gly Val Gln
  1               5                  10                  15

Ser Ser Gly Gln Val His Ala Phe Gly Asn Cys Ser Asp Ser Asp Ile
             20                  25                  30
```

```
Leu Glu Glu Asp Ala Glu Val Tyr Glu Leu Arg Ser Arg Gly Lys Glu
        35                  40                  45

Lys Val Arg Arg Ser Thr Ser Arg Asp Arg Leu Asp Asp Ile Ile Val
    50                  55                  60

Leu Thr Lys Asp Ile Gln Glu Gly Asp Thr Leu Asn Ala Ile Ala Leu
65                  70                  75                  80

Gln Tyr Cys Cys Thr Val Ala Asp Ile Lys Arg Val Asn Asn Leu Ile
                85                  90                  95

Ser Asp Gln Asp Phe Phe Ala Leu Arg Ser Ile Lys Ile Pro Val Lys
            100                 105                 110

Lys Phe Ser Ser Leu Thr Glu Thr Leu Cys Pro Pro Lys Gly Arg Gln
        115                 120                 125

Thr Ser Arg His Ser Ser Val Gln Tyr Ser Ser Glu Gln Gln Glu Ile
    130                 135                 140

Leu Pro Ala Asn Asp Ser Leu Ala Tyr Ser Asp Ser Ala Gly Ser Phe
145                 150                 155                 160

Leu Lys Glu Val Asp Arg Asp Ile Glu Gln Ile Val Lys Cys Thr Asp
                165                 170                 175

Asn Lys Arg Glu Asn Leu His Glu Val Val Ser Ala Phe Thr Ala Gln
            180                 185                 190

Gln Met Arg Phe Glu Pro Asp Asn Lys Asn Thr Gln Arg Lys Asp Pro
        195                 200                 205

Tyr Tyr Gly Ala Asp Trp Gly Ile Gly Trp Trp Thr Ala Val Val Ile
    210                 215                 220

Met Leu Ile Val Gly Ile Ile Thr Pro Val Phe Tyr Leu Leu Tyr Tyr
225                 230                 235                 240

Glu Ile Leu Ala Lys Val Asp Val Ser His His Ser Thr Val Asp Ser
                245                 250                 255

Ser His Leu His Ser Lys Ile Thr Pro Pro Ser Gln Gln Arg Glu Met
            260                 265                 270

Glu Asn Gly Ile Val Pro Thr Lys Gly Ile His Phe Ser Gln Gln Asp
        275                 280                 285

Asp His Lys Leu Tyr Ser Gln Asp Ser Gln Ser Pro Ala Ala Gln Gln
    290                 295                 300

Glu Thr
305


<210> SEQ ID NO 59
<211> LENGTH: 3191
<212> TYPE: DNA
<213> ORGANISM: Homo sapiens

<400> SEQUENCE: 59

cagaggcttt tatccatggg gccaatataa ccgaggaggc tatggaaact atcgctcaaa      60

ttggcagaat taccggcaag catacagtcc tcgtcgaggc cgttcaagat cccggtcccc     120

aaagagaagg tccccttcac caaggtccag gagccattct agaaactctg ataagtcgtc     180

ttctgaccgg tcaaggcgct cctcatcctc ccgttcttcc tccaaccata gccgagttga     240

atcttctaag cgcaagtctg caaaggagaa aaagtcctct tctaaggata gccggccatc     300

tcaggctgcc ggggataacc agggagatga ggtcaaggag cagacattct ctggaggcac     360

ctctcaagat acaaaagcat ctgagagctc gaagccatgg ccagatgcca cctacggcac     420

tggttctgca tcacgggcct cagcagtttc tgagctgagt cctcgggagc gaagcccagc     480
```

-continued

```
tctcaaaagc cccctccagt ctgtggtggt gaggcggcgg tcacccccgtc ctagcccgtg    540
ccaaaaacct agtcctccac tttccagcac atcccagatg ggctcaactc tgccgagtgg    600
tgccgggtat cagtctggga cacaccaagg tcagttcgac catggttctg ggtccctgag    660
tccatccaaa aagagccctg tgggtaagag tccaccatcc actggctcca catatggctc    720
atctcagaag gaggagagtg ctgcttcagg aggagcagcc tatacaaaga ggtttctaga    780
agagcagaag acagagaatg gaaaagataa ggaacagaaa caaacaaata ccgattaaga    840
aaaaataaaa gagaaaggga gcttctctga cacaggcttg ggtgatggaa aaatgaaatc    900
tgattctttt gctcccaaaa ctgattctga gaagcctttt cggggcagtc agtctcccaa    960
aaggtataag ctccgagatg actttgagaa gaagatggct gacttccaca aggaggagat   1020
ggatgatcaa gataaggaca aagctaaggg aagaaaggaa tctgagtttg atgatgaacc   1080
caaatttatg tctaaagtca taggtgcaaa caaaaaccag gaggaggaga agtcaggcaa   1140
atgggagggc ctggtatatg cacctccagg gaaggaaaag cagagaaaaa cagaggagct   1200
ggaggaggag tctttcccag agagatccaa aaaggaagat cggggcaaga gaagcgaagg   1260
tgggcacagg ggctttgtgc ctgagaagaa tttccgagtg actgcttata aagcagtcca   1320
ggagaaaagc tcatcacctc ccccaagaaa gacctctgag agccgagaca agctgggagc   1380
gaaaggagat ttcccacag gaaagtcttc cttttccatt actcgagagg cacaggtcaa   1440
tgtccggatg gactcttttg atgaggacct cgcacgaccc agtggcttat tggctcagga   1500
acgcaagctt tgccgagatc tagtccatag caacaaaaag gaacaggagt ttcgttccat   1560
tttccagcac atacaatcag ctcagtctca gcgtagcccc tcagaactgt ttgcccaaca   1620
tatagtgacc attgttcacc atgttaaaga gcatcacttt gggtcctcag gaatgacatt   1680
acatgaacgc tttactaaat acctaaagag aggaactgag caggaggcag ccaaaaacaa   1740
gaaaagccca gagatacaca ggagaataga catttccccc agtacattca gaaaacatgg   1800
tttggctcat gatgaaatga aaagtccccg ggaacctggc tacaaggctg agggaaaata   1860
caaagatgat cctgttgatc tccgccttga tattgaacgt cgtaaaaaac ataaggagag   1920
agatcttaaa cgaggtaaat cgagagaatc agtggattcc cgagactcca gtcactcaag   1980
ggaaaggtca gctgaaaaaa cagagaaaac tcataaagga tcaaagaaac agaagaagca   2040
tccgagagca agagacaggt ccagatcctc ctcctcttcc tcccagtcat ctcactccta   2100
caaagcagaa gagtacactg aagagacaga ggaaagagag gagagcacca cgggctttga   2160
caaatcaaga ctggggacca aagactttgt gggtccaagt gaaagaggag gtggcagagc   2220
tcgaggaacc tttcagtttc gagccagagg aagaggctgg ggcagaggca actactctgg   2280
gaacaataac aacaacagca acaacgattt tcaaaaaaga aaccgggaag aggagtggga   2340
cccagagtac acacccaaaa gcaagaagta taacttgcat gatgaccgtg aaggcgaagg   2400
cagtgacaag tgggtgagcc ggggccgggg ccgaggagcc tttcctcggg gtcggggccg   2460
gttcatgttc cggaaatcaa gtaccagccc caagtgggcc catgacaagt tcagtgggga   2520
ggaaggggag attgaagacg acgagagtgg gacagagaac cgagaagaga aggacaatat   2580
acagcccaca accgagtagg ggccacccctt gacgggattc ctgcccaggg gagagaggcg   2640
ctgggaagat ggctggtgag gagcttaaca gaggaacctc aagaagattc tgaaaatcct   2700
acccccaccc cccaccagcc gcacagattg tactaccgcg agaggcatcc ctggcgctgt   2760
ctcccactgg acagaggagg ctggccatgg ggcccagggg tcaggcccag cttttgagca   2820
gaatacaacg cattgggctt tagctgtttt tctcatttgt tggtgtgtgg ggtgggggca   2880
```

```
ggggtagggc gggagagcga tgcttggatt tttgtttcct attagaaacc aacagttttg   2940

ttctaatttc atttcattgg gagctaagat gactaattgg atgattttcg atctcttttc   3000

ccctgtcctg attttaaaag ccccctcctt ttttttttt tttttctttt tttaggcata   3060

tgtagtaata ttagaaacat ttaatttggg aaactttgat tcttgaaaga gaaaacaaaa   3120

gcatgtgaat aaactttgaa gtgttcacct caaaaaaaaa aaaaaaaaaa aaaaaaaaaa   3180

aaaaaaaaaa a                                                          3191
```

<210> SEQ ID NO 60
<211> LENGTH: 568
<212> TYPE: PRT
<213> ORGANISM: Homo sapiens

<400> SEQUENCE: 60

```
Met Lys Ser Asp Ser Phe Ala Pro Lys Thr Asp Ser Glu Lys Pro Phe
  1               5                  10                  15

Arg Gly Ser Gln Ser Pro Lys Arg Tyr Lys Leu Arg Asp Asp Phe Glu
             20                  25                  30

Lys Lys Met Ala Asp Phe His Lys Glu Glu Met Asp Asp Gln Asp Lys
         35                  40                  45

Asp Lys Ala Lys Gly Arg Lys Glu Ser Glu Phe Asp Asp Glu Pro Lys
     50                  55                  60

Phe Met Ser Lys Val Ile Gly Ala Asn Lys Asn Gln Glu Glu Glu Lys
 65                  70                  75                  80

Ser Gly Lys Trp Glu Gly Leu Val Tyr Ala Pro Pro Gly Lys Glu Lys
                 85                  90                  95

Gln Arg Lys Thr Glu Glu Leu Glu Glu Glu Ser Phe Pro Glu Arg Ser
            100                 105                 110

Lys Lys Glu Asp Arg Gly Lys Arg Ser Glu Gly Gly His Arg Gly Phe
        115                 120                 125

Val Pro Glu Lys Asn Phe Arg Val Thr Ala Tyr Lys Ala Val Gln Glu
    130                 135                 140

Lys Ser Ser Ser Pro Pro Pro Arg Lys Thr Ser Glu Ser Arg Asp Lys
145                 150                 155                 160

Leu Gly Ala Lys Gly Asp Phe Pro Thr Gly Lys Ser Ser Phe Ser Ile
                165                 170                 175

Thr Arg Glu Ala Gln Val Asn Val Arg Met Asp Ser Phe Asp Glu Asp
            180                 185                 190

Leu Ala Arg Pro Ser Gly Leu Leu Ala Gln Glu Arg Lys Leu Cys Arg
        195                 200                 205

Asp Leu Val His Ser Asn Lys Lys Glu Gln Glu Phe Arg Ser Ile Phe
    210                 215                 220

Gln His Ile Gln Ser Ala Gln Ser Gln Arg Ser Pro Ser Glu Leu Phe
225                 230                 235                 240

Ala Gln His Ile Val Thr Ile Val His His Val Lys Glu His His Phe
                245                 250                 255

Gly Ser Ser Gly Met Thr Leu His Glu Arg Phe Thr Lys Tyr Leu Lys
            260                 265                 270

Arg Gly Thr Glu Gln Glu Ala Ala Lys Asn Lys Lys Ser Pro Glu Ile
        275                 280                 285

His Arg Arg Ile Asp Ile Ser Pro Ser Thr Phe Arg Lys His Gly Leu
    290                 295                 300

Ala His Asp Glu Met Lys Ser Pro Arg Glu Pro Gly Tyr Lys Ala Glu
```

-continued

```
305                 310                 315                 320

Gly Lys Tyr Lys Asp Asp Pro Val Asp Leu Arg Leu Asp Ile Glu Arg
                325                 330                 335

Arg Lys Lys His Lys Glu Arg Asp Leu Lys Arg Gly Lys Ser Arg Glu
            340                 345                 350

Ser Val Asp Ser Arg Asp Ser Ser His Ser Arg Glu Arg Ser Ala Glu
        355                 360                 365

Lys Thr Glu Lys Thr His Lys Gly Ser Lys Lys Gln Lys Lys His Pro
    370                 375                 380

Arg Ala Arg Asp Arg Ser Arg Ser Ser Ser Ser Ser Ser Gln Ser Ser
385                 390                 395                 400

His Ser Tyr Lys Ala Glu Glu Tyr Thr Glu Glu Thr Glu Glu Arg Glu
                405                 410                 415

Glu Ser Thr Thr Gly Phe Asp Lys Ser Arg Leu Gly Thr Lys Asp Phe
            420                 425                 430

Val Gly Pro Ser Glu Arg Gly Gly Gly Arg Ala Arg Gly Thr Phe Gln
        435                 440                 445

Phe Arg Ala Arg Gly Arg Gly Trp Gly Arg Gly Asn Tyr Ser Gly Asn
    450                 455                 460

Asn Asn Asn Asn Ser Asn Asn Asp Phe Gln Lys Arg Asn Arg Glu Glu
465                 470                 475                 480

Glu Trp Asp Pro Glu Tyr Thr Pro Lys Ser Lys Lys Tyr Asn Leu His
                485                 490                 495

Asp Asp Arg Glu Gly Glu Gly Ser Asp Lys Trp Val Ser Arg Gly Arg
            500                 505                 510

Gly Arg Gly Ala Phe Pro Arg Gly Arg Gly Arg Phe Met Phe Arg Lys
        515                 520                 525

Ser Ser Thr Ser Pro Lys Trp Ala His Asp Lys Phe Ser Gly Glu Glu
    530                 535                 540

Gly Glu Ile Glu Asp Asp Glu Ser Gly Thr Glu Asn Arg Glu Glu Lys
545                 550                 555                 560

Asp Asn Ile Gln Pro Thr Thr Glu
                565
```

<210> SEQ ID NO 61
<211> LENGTH: 3145
<212> TYPE: DNA
<213> ORGANISM: Homo sapiens

<400> SEQUENCE: 61

```
gtccccgtcc ggcagactac tctcccccat ggcggacttc gctgggccgt cttctgccgg      60

ccgcaaggcc ggggctcccc gctgctctcg aaaagccgca ggtactaaac agacgagtac     120

tttgaaacaa gaagatgctt ctaaaagggg aggttcatta cgacctgctc actacagtga     180

tgtcgtggat gaacgttcta ttgtcaaact ctgtggttat cctttatgtc agaagaagct     240

gggaattgta ccaaaacaga aatataaaat ttctaccaaa accaataaag tctatgatat     300

tactgaaaga aagtcttttt gcagcaattt ttgttatcaa gcatctaagt tttttgaagc     360

acaaattccc aaaactccag tatgggttcg agaagaagag aggcatcctg attttcaact     420

gctaaaggaa gaacaaagtg gccattctgg agaagaagta cagttatgca gtaaagccat     480

taaaacatca gatatcgaca atcctagcca ctttgaaaag caatatgaat ctagttcttc     540

tagcactcac agtgatagta gcagtgacaa tgagcaagac tttgtttcct ccattctacc     600

aggaaacaga ccaaattcaa caaatattag accacagctg caccaaaaaa gcataatgaa     660
```

-continued

```
aaagaaagct ggtcacaaag ctaactccaa acacaagcac aaagaacaga cagtagtaga    720
tgtcactgag cagttaggcg attgcaaatt agatagtcag gagaaagatg ctacatgtga    780
acttccttta cagaaagtaa atactcagag ttcttcaaat agcactttgc ctgaaagatt    840
aaaagcgtca gaaaattctg aaagtgaata cagtaggtca gaaataactc tggtaggcat    900
aagtaagaaa agtgcagagc attttaagag aaaatttgcc aaatcaaacc aagtgtctag    960
gtcagtgtct aattcagtgc aggtgtgtcc tgaagttgga aagagaaact tacttaaagt   1020
tttgaaggag actttgattg agtggaagac agaagaaaca ttgaggtttt tgtatggcca   1080
gaattatgct tctgtgtgtc tgaaacccga agcctctctg gttaaagaag aacttgatga   1140
agatgacata atctcagatc cagatagtcc tttccctgcc tggagggaat ctcagaacag   1200
cttggatgag tctttacctt ttaggggctc aggtacagcc attaaaccac tgccaagtta   1260
cgagaatttg aaaaaagaaa ctgaaaagtt aaatctgagg atcagggagt tttacagagg   1320
acggtatgtt ttgggtgaag aaaccaccaa atcacaagac tcagaagagc atgattccac   1380
ctttccactg atagactcaa gttcccagaa ccagattaga aaacgcatcg tacttgaaaa   1440
gttgagtaaa gtgttgcctg ggcttctggt tcctcttcag attacattgg gagatattta   1500
cacacaactt aaaaatcttg ttcgaacttt caggttaaca aatagaaata ttatacacaa   1560
acctgcggaa tggactttaa ttgctatggt gttgctgtca ttactgaccc caattcttgg   1620
cattcagaaa cattctcagg aaggtatggt gtttacacgg tttctagaca ccctccttga   1680
agaattacat ctaaaaaatg aagaccttga aagtctaacc atcatattta gaaccagctg   1740
tttaccagag tgatatattc catgaagaca aaatagaaga tgaacttcta ttcaccgttt   1800
ctggaattct agccgccatg atggtctggt ggtgactgat aactagtttt attccaagac   1860
atacctttac ctctttaagt ttcaatctcc catctcccag tccttcagtc cccaactgca   1920
gaggatgacc tccccagata gaggagaatc attactccaa caagaataac caagtctttg   1980
tatccctagt acaagacata gtatttttat tcgaaaatga atgtttaagt attaaattga   2040
aacttgaatg aatattcaag aaaatataat gatctctact ttttctggat gatttccagc   2100
catcatatca gtttgccaaa aaaattgaga aagttatgat tttgacctcc caacctaaac   2160
tctaaattct aaagatcagt aaacaattag gtcaataaat acatacaatt taagatgaag   2220
ccctttggaa gtctagtcca aaacaggaaa atctcagaac tttctggact caaggaaatg   2280
ctttaaatgg aatctgtagt ttgtttgcag gagagacaat ttctagaatt tagattgctt   2340
ttcaaaatgt ttatcaggta ggcaagttag cagttgaggc ggaacacaga caacttgggg   2400
agctttactg gaaggccaag aaaatactct tggacactgg aggaaatgac agctactaaa   2460
gcccaatcat ggaaaaggac cagaaagcag cccactggaa tggggagctt agtgggcaag   2520
gaggtaggga tataatttct cttcttggct ccaccagtaa ttagctctgt ggcccagtca   2580
cctaaacttt ctggacttca gttcaggttg tatggcagta ggccatagaa ttggctactg   2640
ccatacaatc tctatgggaa aggactgcaa aaactaaatt ttatctctgt atgggcaaag   2700
gctactgtca tcctgttgtt ggtctggggc cactctgaca atttttttta acctcatttg   2760
attgtgtaag ggtctaacca caacaaaaaa tcatagtgta atagaattaa tcaagttcag   2820
caaggtcaca ggctagatca atatacagaa aatcaattgt atttttctgt tcagaaaact   2880
ccaaaaatga aataaagaaa attgtgttca caatatcacc aaagagatta aatacttagg   2940
aataaattta acaaaataag tgtaagactt gtataacgaa aactataaaa cattcaagag   3000
```

ggctgggcat ggtggctcat gcctttagtt ctagcgcttt ggaggcagag gcaggaggac 3060
tgcttgagcc caggagttca agaccagcct gggcaacaaa gtgagaccct gtctccacaa 3120
aaaaaaaaaa aaaaaaaaaa aaaaa 3145

<210> SEQ ID NO 62
<211> LENGTH: 574
<212> TYPE: PRT
<213> ORGANISM: Homo sapiens

<400> SEQUENCE: 62

Met Ala Asp Phe Ala Gly Pro Ser Ser Ala Gly Arg Lys Ala Gly Ala
1 5 10 15

Pro Arg Cys Ser Arg Lys Ala Ala Gly Thr Lys Gln Thr Ser Thr Leu
20 25 30

Lys Gln Glu Asp Ala Ser Lys Arg Gly Gly Ser Leu Arg Pro Ala His
35 40 45

Tyr Ser Asp Val Val Asp Glu Arg Ser Ile Val Lys Leu Cys Gly Tyr
50 55 60

Pro Leu Cys Gln Lys Lys Leu Gly Ile Val Pro Lys Gln Lys Tyr Lys
65 70 75 80

Ile Ser Thr Lys Thr Asn Lys Val Tyr Asp Ile Thr Glu Arg Lys Ser
85 90 95

Phe Cys Ser Asn Phe Cys Tyr Gln Ala Ser Lys Phe Phe Glu Ala Gln
100 105 110

Ile Pro Lys Thr Pro Val Trp Val Arg Glu Glu Glu Arg His Pro Asp
115 120 125

Phe Gln Leu Leu Lys Glu Glu Gln Ser Gly His Ser Gly Glu Glu Val
130 135 140

Gln Leu Cys Ser Lys Ala Ile Lys Thr Ser Asp Ile Asp Asn Pro Ser
145 150 155 160

His Phe Glu Lys Gln Tyr Glu Ser Ser Ser Ser Ser Thr His Ser Asp
165 170 175

Ser Ser Ser Asp Asn Glu Gln Asp Phe Val Ser Ser Ile Leu Pro Gly
180 185 190

Asn Arg Pro Asn Ser Thr Asn Ile Arg Pro Gln Leu His Gln Lys Ser
195 200 205

Ile Met Lys Lys Lys Ala Gly His Lys Ala Asn Ser Lys His Lys His
210 215 220

Lys Glu Gln Thr Val Val Asp Val Thr Glu Gln Leu Gly Asp Cys Lys
225 230 235 240

Leu Asp Ser Gln Glu Lys Asp Ala Thr Cys Glu Leu Pro Leu Gln Lys
245 250 255

Val Asn Thr Gln Ser Ser Ser Asn Ser Thr Leu Pro Glu Arg Leu Lys
260 265 270

Ala Ser Glu Asn Ser Glu Ser Glu Tyr Ser Arg Ser Glu Ile Thr Leu
275 280 285

Val Gly Ile Ser Lys Lys Ser Ala Glu His Phe Lys Arg Lys Phe Ala
290 295 300

Lys Ser Asn Gln Val Ser Arg Ser Val Ser Asn Ser Val Gln Val Cys
305 310 315 320

Pro Glu Val Gly Lys Arg Asn Leu Leu Lys Val Leu Lys Glu Thr Leu
325 330 335

Ile Glu Trp Lys Thr Glu Glu Thr Leu Arg Phe Leu Tyr Gly Gln Asn
340 345 350

```
Tyr Ala Ser Val Cys Leu Lys Pro Glu Ala Ser Leu Val Lys Glu Glu
        355                 360                 365

Leu Asp Glu Asp Asp Ile Ile Ser Asp Pro Asp Ser Pro Phe Pro Ala
    370                 375                 380

Trp Arg Glu Ser Gln Asn Ser Leu Asp Glu Ser Leu Pro Phe Arg Gly
385                 390                 395                 400

Ser Gly Thr Ala Ile Lys Pro Leu Pro Ser Tyr Glu Asn Leu Lys Lys
                405                 410                 415

Glu Thr Glu Lys Leu Asn Leu Arg Ile Arg Glu Phe Tyr Arg Gly Arg
            420                 425                 430

Tyr Val Leu Gly Glu Glu Thr Thr Lys Ser Gln Asp Ser Glu Glu His
        435                 440                 445

Asp Ser Thr Phe Pro Leu Ile Asp Ser Ser Ser Gln Asn Gln Ile Arg
    450                 455                 460

Lys Arg Ile Val Leu Glu Lys Leu Ser Lys Val Leu Pro Gly Leu Leu
465                 470                 475                 480

Val Pro Leu Gln Ile Thr Leu Gly Asp Ile Tyr Thr Gln Leu Lys Asn
                485                 490                 495

Leu Val Arg Thr Phe Arg Leu Thr Asn Arg Asn Ile Ile His Lys Pro
            500                 505                 510

Ala Glu Trp Thr Leu Ile Ala Met Val Leu Leu Ser Leu Leu Thr Pro
        515                 520                 525

Ile Leu Gly Ile Gln Lys His Ser Gln Glu Gly Met Val Phe Thr Arg
    530                 535                 540

Phe Leu Asp Thr Leu Leu Glu Glu Leu His Leu Lys Asn Glu Asp Leu
545                 550                 555                 560

Glu Ser Leu Thr Ile Ile Phe Arg Thr Ser Cys Leu Pro Glu
                565                 570
```

<210> SEQ ID NO 63
<211> LENGTH: 1812
<212> TYPE: DNA
<213> ORGANISM: Homo sapiens

<400> SEQUENCE: 63

```
atttacttta aaaagaaatt aatatggctt caccaagaag caaagttcaa cttatttcat     60

aattgcctac atttatcatg gtcctgaatg tagcgtgtaa gcttgtgttt cttgggcagt    120

ctttcttgaa attgaagagg tgaaatgggg gtggggagtg ggaggaaagg tgacttcctc    180

tggtgtttat tataaagctt aaattttata tcattttaaa atgtcttggt cttctactgc    240

cttgaaaaat gacaattgtg aacatgatag ttaaactacc acttttttta accattatta    300

tgcaaaattt agaagaaaag ttattggcat ggttgttgca tatagttaaa ctgagagtaa    360

ttcatctgtg aatctgcttt aattacctgg tgagtaactt agaaaagtgg tgtaaacttg    420

tacatggaat tttttgaata tgccttaatt tagaaactga aaaatatctg gttatatcat    480

tctgggtgtg ttcttactga caccaggggt ccgctgcccc atgtgtcctg gtgagaaata    540

tatgcctggc acagcttttg tatagaaaat tcttgagaag taactgtccg ctagaagtct    600

gtccaaattt aaaatgtgtg ccatattctg gttcttgaaa ataagattcc agagctcttt    660

gatcgctttt ataactgcag ttcattttaa tgaagggcca gcatatatac ttgcaagata    720

attttcagct gcaaggattc agcaccagtt atgtttgaat gaacctcttt tctctgagat    780

tctggtcctg gaaatccctt ctgctagtgg tgagcatgta agtgtaagtt ttaatctggg    840
```

-continued

```
agcagggcat aggaagaaaa tgtcagtagt gctaatgcat tttgcactag aacgcttcgg    900

gaaaatattc atgcttgcca tctgttcatt tctaaattta tattcataaa gttacagttt    960

gatacaggaa ttattaggag taattctttt cttgtttctg tttataatga agaacactgt   1020

agctacattt tcagaagtta acatcaagcc atcaaacctg ggtatagtgc agaaaacgtg   1080

gcacacactg accacacatt aggctgtgtc accattgtgt ggtgtacctg ctggaagaat   1140

tctagcatgc tacttgggga cataatttca gtgggaaata tgccactgac cgattttttt   1200

tttttcctct ttgcagtggg gctaggacag ttgattcaac aaagtatttt tttctttttt   1260

ctcagtccta atttgaacag gtcaaagatg tgttcaggca ttccaggtaa caggtgtgta   1320

tgtaaagtta aaaataggct ttttaggaac tcactcttta gatatttaca tccagcttct   1380

catgttaaat atttgtcctt aaagggtttg agatgtacat ctttcatttc gtatttctca   1440

taggctatgc catgtgcgga attcaagtta ccaatgtaac actggccagc gggcccagca   1500

atctccatgt gtacttatta cagtcttatt taaccagggg tcctaaccac taacattgtg   1560

actttgcttt gagacctttc ctctcctggg tactgaggtg ctatgaagcc aactgacaaa   1620

gatgcatcac gtgtcttagg ctgatgccac tacccgattt gtttatttgc aatttgagcc   1680

atttaaagac caataaactt cctttttttaa aaaaaaaaaa aaaaaaaaaa aaaaaaaaaa   1740

aaaaaaaaaa aaaaaaaaaa aaaaaaaaaa aaaaaaaaaa aaaaaaaaaa aaaaaaaaaa   1800

aaaaaaaaaa aa                                                       1812
```

<210> SEQ ID NO 64
<211> LENGTH: 98
<212> TYPE: PRT
<213> ORGANISM: Homo sapiens

<400> SEQUENCE: 64

```
Met Leu Leu Gly Asp Ile Ile Ser Val Gly Asn Met Pro Leu Thr Asp
  1               5                  10                  15

Phe Phe Phe Phe Leu Phe Ala Val Gly Leu Gly Gln Leu Ile Gln Gln
             20                  25                  30

Ser Ile Phe Phe Phe Phe Leu Ser Pro Asn Leu Asn Arg Ser Lys Met
         35                  40                  45

Cys Ser Gly Ile Pro Gly Asn Arg Cys Val Cys Lys Val Lys Asn Arg
     50                  55                  60

Leu Phe Arg Asn Ser Leu Phe Arg Tyr Leu His Pro Ala Ser His Val
 65                  70                  75                  80

Lys Tyr Leu Ser Leu Lys Gly Leu Arg Cys Thr Ser Phe Ile Ser Tyr
                 85                  90                  95

Phe Ser
```

<210> SEQ ID NO 65
<211> LENGTH: 1558
<212> TYPE: DNA
<213> ORGANISM: Homo sapiens

<400> SEQUENCE: 65

```
gtcgacaggg ccgcagctag agtcggcgcc accagggggc cgagcatggt gcggcggcgg     60

cggggcgctc cggggaggcc aggacagctg atggttgtgg cagaaacatc tcaaggtagc    120

tggtccgccc cccacttccc catctacctc ttgtcctccc ccccaacacc accaccaccc    180

tggctcccct ccctcatgac cgcctggatc ctcctgcctg tcagcctgtc agcgttctcc    240

atcactggca tatggactgt gtatgccatg gctgtgatga accaccatgt atgccctgtg    300
```

```
gagaactggt cctacaacga gtcctgccct cctgaccctg ctgagcaagg gggtcccaag    360

acctgctgca ccctggacga tgtccccctc atcagcaagt gtggctccta tcccccagaa    420

agctgcctct tcagcctcat tggcaacatg ggtgctttca tggtggccct gatctgcctc    480

ctgcgctacg ggcagctcct ggagcagagt cggcactctt gggttaacac cacggcactc    540

atcacaggct gcaccaacgc tgcgggcctc ttggtggttg gcaactttca ggtggatcat    600

gccaggtctc tgcactacgt tggagctggc gtggccttcc ctgcggggct gctctttgtt    660

tgcctgcact gtctctctcc taccaagggg ccaccgcccc gctggacctg gctgtggcct    720

atctgcgaag tgtgctggct gtcatcgcct ttatcaccct ggtcctcagt ggagtcttct    780

ttgtccatga gagttctcag ctgcaacatg ggcagccct gtgtgagtgg gtgtgtgtca    840

tccatatcgt cattttctat ggcaccttca gctacgagtt tggggcagtc tcctcagaca    900

cactggtggc tgcactgcag cctacccctg gccgggcctg caagtcctcc gggagcagca    960

gcactccacc cacctcaact gtgcccccga gagcatcgct atgatctaag gtctggggag   1020

ggtggctggc ccggctccac agcaccccac cccatatctt ctttccattt atttcgtacc   1080

aaaaacaatt ttgagaaagt attctgttgg gatctgggct tcctcacttc tggagaagtg   1140

gccatcccat gcccacctgt gccatggagg agtgggccct gccagctgcc acagctgcat   1200

gacctgcttc ccaccccacg gtgtcgtttt gtttttaaag gtcacctgtc ctcactcacc   1260

cagccagccc ttcaggtgcc ttctactccc agtgccaaag ccagaccact ggggtttcct   1320

gctgcaggaa ttgggggctg ggaacagcag aggggataga agtctggtgg aggtggagtg   1380

ggcacgcctt agcctacgga aaggcccatt tctgggccca ctgagctgca ctgggattct   1440

tcagtctgcc cctcacttcc tttagggcaa ataacacagc agaaccacgt gggtatttta   1500

gtactttttt ttatattaaa agaattctaa tttgaaatcc cgattgaatt ctagacct     1558
```

<210> SEQ ID NO 66
<211> LENGTH: 437
<212> TYPE: PRT
<213> ORGANISM: Homo sapiens

<400> SEQUENCE: 66

```
Met Val Arg Arg Arg Arg Gly Ala Pro Gly Arg Pro Gly Gln Leu Met
  1               5                  10                  15

Val Val Ala Glu Thr Ser Gln Gly Ser Trp Ser Ala Pro His Phe Pro
             20                  25                  30

Ile Tyr Leu Leu Ser Ser Pro Pro Thr Pro Pro Pro Pro Trp Leu Pro
         35                  40                  45

Ser Leu Met Thr Ala Trp Ile Leu Leu Pro Val Ser Leu Ser Ala Phe
     50                  55                  60

Ser Ile Thr Gly Ile Trp Thr Val Tyr Ala Met Ala Val Met Asn His
 65                  70                  75                  80

His Val Cys Pro Val Glu Asn Trp Ser Tyr Asn Glu Ser Cys Pro Pro
                 85                  90                  95

Asp Pro Ala Glu Gln Gly Gly Pro Lys Thr Cys Cys Thr Leu Asp Asp
            100                 105                 110

Val Pro Leu Ile Ser Lys Cys Gly Ser Tyr Pro Pro Glu Ser Cys Leu
        115                 120                 125

Phe Ser Leu Ile Gly Asn Met Gly Ala Phe Met Val Ala Leu Ile Cys
    130                 135                 140

Leu Leu Arg Tyr Gly Gln Leu Leu Glu Gln Ser Arg His Ser Trp Val
```

-continued

```
145                 150                 155                 160

Asn Thr Thr Ala Leu Ile Thr Gly Cys Thr Asn Ala Ala Gly Leu Leu
                165                 170                 175

Val Val Gly Asn Phe Gln Val Asp His Ala Arg Ser Leu His Tyr Val
            180                 185                 190

Gly Ala Gly Val Ala Phe Pro Ala Gly Leu Leu Phe Val Cys Leu His
        195                 200                 205

Cys Leu Ser Pro Thr Lys Gly Pro Pro Pro Arg Trp Thr Trp Leu Trp
    210                 215                 220

Pro Ile Cys Glu Val Cys Trp Leu Ser Ser Pro Leu Ser Pro Trp Ser
225                 230                 235                 240

Ser Val Glu Ser Ser Leu Ser Met Arg Val Leu Ser Cys Asn Met Gly
                245                 250                 255

Gln Pro Cys Val Ser Gly Cys Val Ser Ser Ile Ser Ser Phe Ser Met
            260                 265                 270

Ala Pro Ser Ala Thr Ser Leu Gly Gln Ser Pro Gln Thr His Trp Trp
        275                 280                 285

Leu His Cys Ser Leu Pro Leu Ala Gly Pro Ala Ser Pro Pro Gly Ala
    290                 295                 300

Ala Ala Leu His Pro Pro Gln Leu Cys Pro Arg Glu His Arg Tyr Asp
305                 310                 315                 320

Leu Arg Ser Gly Glu Gly Gly Trp Pro Gly Ser Thr Ala Pro His Pro
                325                 330                 335

Ile Ser Ser Phe His Leu Phe Arg Thr Lys Asn Asn Phe Glu Lys Val
            340                 345                 350

Phe Cys Trp Asp Leu Gly Phe Leu Thr Ser Gly Glu Val Ala Ile Pro
        355                 360                 365

Cys Pro Pro Val Pro Trp Arg Ser Gly Pro Cys Gln Leu Pro Gln Leu
    370                 375                 380

His Asp Leu Leu Pro Thr Pro Arg Cys Arg Phe Val Phe Lys Gly His
385                 390                 395                 400

Leu Ser Ser Leu Thr Gln Pro Ala Leu Gln Val Pro Ser Thr Pro Ser
                405                 410                 415

Ala Lys Ala Arg Pro Leu Gly Phe Pro Ala Ala Gly Ile Gly Gly Trp
            420                 425                 430

Glu Gln Gln Arg Gly
        435


<210> SEQ ID NO 67
<211> LENGTH: 2336
<212> TYPE: DNA
<213> ORGANISM: Homo sapiens
<220> FEATURE:
<221> NAME/KEY: unsure
<222> LOCATION: (418)

<400> SEQUENCE: 67

atttattgag tgtctactgt gtgccaggca ctatatctat gtgcatagaa aaacctggaa      60

gggcctacca caatacatat agagtgatcg tctctgcttg ctgagctaac aggggtgtca     120

agcttccatt ttggtatcta cttctaaata cactcagaac aggagaaatt tggactaatt     180

ttcaaactac agacactttc taatcatgat gcatttcaaa agtggactcg aattaactga     240

gttgcaaaac atgacagtgc ccgaggatga taacatcagc aatgactcca atgatttcac     300

cgaagtagaa aatggtcaga taaatagcaa gtttatttct gatcgtgaaa gtagaagaag     360
```

-continued

```
tctcacaaac agccatttgg aaaaaaagaa gtgtgatgag tatattccag gtacaacntc    420

cttaggcatg tttgttttta acctaagcaa ctccatgatg ggcagtggga tttgggactc    480

gctttgccct ggcaacactg gaatcctact ttttctggta cttttgactt cagtgacatt    540

gctgtctata tattcaataa acctcctatt gatctgttca aaagaaacag gctgcatggt    600

gtatgaaaag ctgggggaac aagtctttgg caccacaggg aagttcgtaa tctttggagc    660

cacctctcta cagaacactg gagcaatgct gagctacctc ttcatcgtaa aaaatgaact    720

accctctgcc ataaagtttc taatgggaaa ggaagagaca ttttcagcct ggtacgtgga    780

tggccgcgtt ctggtggtga tagttacctt tggcataatt ctccctctgt gtctcttgaa    840

gaacttaggg tatcttggct atactagtgg attttccttg agctgtatgg tttttttcct    900

aattgtggtt atttacaaga aatttcaaat tccctgcatt gttccagagc taaattcaac    960

aataagtgct aattcaacaa atgctgacac gtgtacgcca aaatatgtta ccttcaattc   1020

aaagaccgtg tatgctttac ccaccattgc atgtgcattt gtttgccacc cgtcagtcct   1080

gccaatttac agtgagctta aagaccgatc acagaaaaaa atgcagatgg tttcaaacat   1140

ctcctttttc gccatgtttg ttatgtactt cttgactgcc atttttggct acttgacatt   1200

ctatgacaac gtgcagtccg acctccttca caaatatcag agtaaagatg acattctcat   1260

cctgacagtg cggctggctg tcattgttgc tgtgatcctc acagtgccgg tgttattttt   1320

cacggttcgt tcatctttat ttgaactggc taagaaaaca aagtttaatt tatgtcgtca   1380

taccgtggtt acctgcatac tcttggttgt tatcaacttg ttggtgatct tcataccctc   1440

catgaaggat atttttggag tcgtaggagt tacatctgct aacatgctta ttttcattct   1500

tccttcatct ctttatttaa aaatcacaga ccaggatgga gataaaggaa ctcaaagaat   1560

ttgggtatgt ctcttgccag ccactctaac ttttctgatt agttttccat ttaaatttac   1620

aaaataaata gtccacctct ctatcaagac tactttcagt tgccttgaaa ggaggcagaa   1680

gccctgtagc tttgctactt gggagatatt taaaatatca tatcagaatc ttctcccatc   1740

cctccaaata tcttttctgg ttttactctt ttttttgag atggagtctc actctgtcgc   1800

ccaggctgga gtgcagtggc cagatctcag ctcactgtaa gctccacctc ccgggttcat   1860

gccattcttc tgcctcagag agtagctggg actacaggcg cccgccacca tgcctggcta   1920

atttttttc tttttcttt tttcttttt gtatttttag tagagacggg gtttcaccat   1980

gttagccagg atggtctgta tctcctgacc tcatgatccg tctgcctcgg cctcccacag   2040

tgctgggatt acaggcatga gccatcgcgc ccggccctct ggttttactg ttattgtgcc   2100

tcagcttttg ttctgatcca gggcatggcc agtcagaaga atggacattc atcctcctgt   2160

gtctgtatag gacagtgtct agtcttcagc aagagaggaa gtgacgaggg actcacagat   2220

gttatgcagt ccactgtttc catatgattt ctagtcatgt aactcctccc tacagcccag   2280

ggaacatgca atgccttaat taaaatgtct gagttagctt aaaaaaaaaa aaaaaa       2336

<210> SEQ ID NO 68
<211> LENGTH: 473
<212> TYPE: PRT
<213> ORGANISM: Homo sapiens

<400> SEQUENCE: 68

Met Met His Phe Lys Ser Gly Leu Glu Leu Thr Glu Leu Gln Asn Met
  1               5                  10                  15

Thr Val Pro Glu Asp Asp Asn Ile Ser Asn Asp Ser Asn Asp Phe Thr
             20                  25                  30
```

```
Glu Val Glu Asn Gly Gln Ile Asn Ser Lys Phe Ile Ser Asp Arg Glu
        35                  40                  45

Ser Arg Arg Ser Leu Thr Asn Ser His Leu Glu Lys Lys Lys Cys Asp
    50                  55                  60

Glu Tyr Ile Pro Gly Thr Thr Ser Leu Gly Met Phe Val Phe Asn Leu
65                  70                  75                  80

Ser Asn Ser Met Met Gly Ser Gly Ile Trp Asp Ser Leu Cys Pro Gly
                85                  90                  95

Asn Thr Gly Ile Leu Leu Phe Leu Val Leu Leu Thr Ser Val Thr Leu
            100                 105                 110

Leu Ser Ile Tyr Ser Ile Asn Leu Leu Leu Ile Cys Ser Lys Glu Thr
        115                 120                 125

Gly Cys Met Val Tyr Glu Lys Leu Gly Glu Gln Val Phe Gly Thr Thr
    130                 135                 140

Gly Lys Phe Val Ile Phe Gly Ala Thr Ser Leu Gln Asn Thr Gly Ala
145                 150                 155                 160

Met Leu Ser Tyr Leu Phe Ile Val Lys Asn Glu Leu Pro Ser Ala Ile
                165                 170                 175

Lys Phe Leu Met Gly Lys Glu Glu Thr Phe Ser Ala Trp Tyr Val Asp
            180                 185                 190

Gly Arg Val Leu Val Val Ile Val Thr Phe Gly Ile Ile Leu Pro Leu
        195                 200                 205

Cys Leu Leu Lys Asn Leu Gly Tyr Leu Gly Tyr Thr Ser Gly Phe Ser
    210                 215                 220

Leu Ser Cys Met Val Phe Phe Leu Ile Val Val Ile Tyr Lys Lys Phe
225                 230                 235                 240

Gln Ile Pro Cys Ile Val Pro Glu Leu Asn Ser Thr Ile Ser Ala Asn
                245                 250                 255

Ser Thr Asn Ala Asp Thr Cys Thr Pro Lys Tyr Val Thr Phe Asn Ser
            260                 265                 270

Lys Thr Val Tyr Ala Leu Pro Thr Ile Ala Cys Ala Phe Val Cys His
        275                 280                 285

Pro Ser Val Leu Pro Ile Tyr Ser Glu Leu Lys Asp Arg Ser Gln Lys
    290                 295                 300

Lys Met Gln Met Val Ser Asn Ile Ser Phe Phe Ala Met Phe Val Met
305                 310                 315                 320

Tyr Phe Leu Thr Ala Ile Phe Gly Tyr Leu Thr Phe Tyr Asp Asn Val
                325                 330                 335

Gln Ser Asp Leu Leu His Lys Tyr Gln Ser Lys Asp Asp Ile Leu Ile
            340                 345                 350

Leu Thr Val Arg Leu Ala Val Ile Val Ala Val Ile Leu Thr Val Pro
        355                 360                 365

Val Leu Phe Phe Thr Val Arg Ser Ser Leu Phe Glu Leu Ala Lys Lys
    370                 375                 380

Thr Lys Phe Asn Leu Cys Arg His Thr Val Val Thr Cys Ile Leu Leu
385                 390                 395                 400

Val Val Ile Asn Leu Leu Val Ile Phe Ile Pro Ser Met Lys Asp Ile
                405                 410                 415

Phe Gly Val Val Gly Val Thr Ser Ala Asn Met Leu Ile Phe Ile Leu
            420                 425                 430

Pro Ser Ser Leu Tyr Leu Lys Ile Thr Asp Gln Asp Gly Asp Lys Gly
        435                 440                 445
```

-continued

```
Thr Gln Arg Ile Trp Val Cys Leu Leu Pro Ala Thr Leu Thr Phe Leu
    450                 455                 460

Ile Ser Phe Pro Phe Lys Phe Thr Lys
465                 470


<210> SEQ ID NO 69
<211> LENGTH: 1999
<212> TYPE: DNA
<213> ORGANISM: Homo sapiens

<400> SEQUENCE: 69

ttttttttt ttttttttt ttttttaaag acagggtctc actctgtcac tcaggctgga     60

atgtagtggc atgattatgg ctcactgcag cctctacttc ctgggcccag gcaatcctct    120

cacctcagct cctgagtagc tgggactaca ggcgcacacc acctcacttg gctaattaaa    180

aaaaattttt ttttgtagaa atgggggtct tccaatgttg cccatgctgg tcttgaactc    240

ctggcctcaa gtgatcctcc caccttggcc tcctaaattg ctgagattac agatgtgagc    300

caccacgccc aacctaactt caagaactct tgaccatctc tgtttctttc ctgattttag    360

gcccacaatg ttcactgtct tagttttagg atgagactct aaatcttttt ttttttgaga    420

tggagtctcg ctctgttgcc caggctggag tgcagtggca cgatctcggc tcaccacaac    480

ctctgcctcc aggattcaag cgattgtcct gcctcagcta ctcctcggga ggctgaggca    540

ggagaatggc gtgaactccg gaggtggagc ctgtagtgag ccgagatggc accactgcgc    600

tccagcctgg gcgacagagc aagactccat atcaaaaaaa aaaaaaaaaa aaaagataat    660

ccaaagaatt taaattgtaa tcatgtttca tgtatttgtt ttattactta cttttatagc    720

acttagtccc agtggtatta gactgctatt tggtttcata caaaaaggat taaatttaaa    780

ttcattcatg tttagacttg agttattaca tttttaaaac tatcatcttg cctttaatgt    840

ttgtggtcct acacaaacta ttagtacatt tcagtatcct cttacccctt tgtttttaag    900

tttttgattg ctaaagcaag actttttttct tctagaattt aagtcaacca agtgttatct    960

atgttgtaaa aatggataat agtagatttt aggtgataaa acaacttgtt agtaagacat   1020

ttcctagctt aaaaaaaaaa atcaaaaatt ccatgataga aatgcagacc tgtgagggaa   1080

actcctgaaa agcataagaa gcatcccaga gagccatggg ttttctagac cagagaattt   1140

agagggagat tgtggaactg aggcttaggt ggtcagatcg tttcccttat cactgtaata   1200

tttctggggg aaaaatgctt tctgagttgt ttaaacaagc atccttacat tttttttttt   1260

aattaaacag cctgtctagg cttgggattc cctaatacta cagtagcagt atatgaatat   1320

gattttgtga ttgtgttttt taaaagataa gtaatttgat gaactgttct tttgcagtca   1380

gaaaaacact cacaaaaaga caaaaaaagt tccacagtat tatatttcat gtcagttcag   1440

gcctaaaatc ctttgcaaat aagatgttta taggctggtc acaattaaca atgtattatt   1500

ggcagcactt cttggatgga taccttttgg gacctttcat tagaaagagg gaaagaatgg   1560

ggtggttttg tatgggctcc tgtttggggg taaaaatagc agagtcagtt gctgaggaca   1620

atgaccttcc ttataacatt agtttcatac ccatattagg tcttgtcttg aggaccctttt   1680

atatgtgctt gtttactagt ggccttccag ccatagcatt cttacctttt tttcctattc   1740

taagaattaa aaaaaaaaat tatagagcca gcaagggagg aggcaggaaa cagaaatcga   1800

atttcatcat tccagtatag ttgtcccttt ttttgtattt ctgacttggt tttataatta   1860

tatttactta ctaattattg ttttttaaca ttctttattg tggcttactc ttcatactta   1920

gaattgaaat tgttggacat cacatgtata ttcacattat aaatacatca ttcttccact   1980
```

gttaaaaaaa aaaaaaaaa 1999

<210> SEQ ID NO 70
<211> LENGTH: 153
<212> TYPE: PRT
<213> ORGANISM: Homo sapiens

<400> SEQUENCE: 70

```
Met Asn Cys Ser Phe Ala Val Arg Lys Thr Leu Thr Lys Arg Gln Lys
  1               5                  10                  15

Lys Phe His Ser Ile Ile Phe His Val Ser Ser Gly Leu Lys Ser Phe
             20                  25                  30

Ala Asn Lys Met Phe Ile Gly Trp Ser Gln Leu Thr Met Tyr Tyr Trp
         35                  40                  45

Gln His Phe Leu Asp Gly Tyr Leu Leu Gly Pro Phe Ile Arg Lys Arg
     50                  55                  60

Glu Arg Met Gly Trp Phe Cys Met Gly Ser Cys Leu Gly Val Lys Ile
 65                  70                  75                  80

Ala Glu Ser Val Ala Glu Asp Asn Asp Leu Pro Tyr Asn Ile Ser Phe
                 85                  90                  95

Ile Pro Ile Leu Gly Leu Val Leu Arg Thr Leu Tyr Met Cys Leu Phe
            100                 105                 110

Thr Ser Gly Leu Pro Ala Ile Ala Phe Leu Pro Phe Phe Pro Ile Leu
        115                 120                 125

Arg Ile Lys Lys Lys Asn Tyr Arg Ala Ser Lys Gly Gly Gly Arg Lys
    130                 135                 140

Gln Lys Ser Asn Phe Ile Ile Pro Val
145                 150
```

<210> SEQ ID NO 71
<211> LENGTH: 2020
<212> TYPE: DNA
<213> ORGANISM: Homo sapiens

<400> SEQUENCE: 71

```
ggaggggtgt gtgtgtgtgt atttggtttg ctgtcctttt ttaaaggatt ccaagccatg     60

tgaaacttcc cttctggatg tgattctggg tcgcaagtcc ttatttatat gtgaggctgg    120

ggaatgggct gggggtattg gcagtccttt tgcagggcag tgtgtgtggt ggggtgacac    180

cgctgtggct tagcccaaga cactcccaga ggaaaacact gcagaaggaa ctggtttgca    240

gactgtggaa ggatctgcag ttttgttttt gaccaaaaaa ataataataa gttagctctg    300

aagggcagag ggaataccca agcccctgat gcctatgaga agtccctgga cttcaaccct    360

cctgttgttt ggccttagcc cagagggagc tgctcacctg agcacccttg ggggtgggca    420

gagaggcagg gtgggatttt agagttagtg tctgtgcggg ggcagccctg agcctggagt    480

tgagactttg ggtctcttta gtttggaggt gttgagtgca tttgtgcccc tgcctggttg    540

agagcttctt ggtacctctt gccacccctt ctcactgccc tgacccaacc ccactggacc    600

ttgatgctgc gaggagtggt gtcctgacgg actcagcact cccgcctgat gtattggatc    660

ataggagagc acttgctctc ctgcctctgc caggagaggg cttgttcctc caactctagg    720

aggccaggca agcatggaca ggagccaagg gagcagggtc attaactttt tcttctttgc    780

aaagtgggca cttggcatca gggtcccaat caccagaaag caccaaagcc cctggcaccc    840

cacccactcc atcctaccca gggaccccaa gtaggcaact gttatggcag tgggtccagc    900
```

-continued

```
ccaggccagc actggcagcc tcctctccct gcagtatgca ccagctctac ctcccccggc     960

aggcaatgtc ctggcttctc agcccagcac catctgttcc cctatacttc tcaggggcca    1020

gcccagtctg ggccaccctt tgtttccctc atcctcggct cccacacagg tgacagaccc    1080

agcagatagc ttctctctgg gaaaggttgg atgctgcctt acatcccctt ctagccctcc    1140

tcccatccac acacacaggc acccacccac accaggtcgg cttgtttctc acatgtaggg    1200

agagagggga gaccaacccc tttgtgtctt ttgaaatacg aagaaaaatg tgtgttcagg    1260

agcatgactc cagtgctgcg ctcttgggcc cagttcagtc tgtcttgtct caaatctagg    1320

catttttgct tcaattttat tttttttaag aatacaaaaa cagaaatctg cactaattta    1380

cctggtttcg taggaaaact ttttttttatt ttttacattt tttggtgtcc gtttgtattg    1440

aataatttgc tacatttgta aaatgtaaga ggtatataat atatgtatat ttctaacgta    1500

aaaaacataa ttttttttctt ttcaagattt ttttcttaaa aagatgagag aaacatattt    1560

tttcaggaaa aacaaacttt aaaaaaaaaa gaggagaaat aaaacctttt ctcccctttc    1620

cccatcctct atctatccct ctttcccagg aacaaatcaa aaggtggatt atcttctgaa    1680

gaatggaaac tgttagtcca gaatgatgtg tttttctcaa tgcagtgagt gatagattct    1740

ctagttttct ccctagggat gggaaggggg cattgaggca agcctggaga ggagcctggg    1800

gagcagggtc atgaactttt ttctttagtg aaggaggaat acaatcaagg gttttgtatt    1860

cagaatgttg tgcaatattt tggaatggga cattggtgtg tttagagatt ttagtttaaa    1920

aacaaaacaa aaagattgat caaatctgta cagtttctat tgttccagat ttttttaagt    1980

ttgtattaaa agcacgatac ataataaaaa aaaaaaaaaa                          2020
```

<210> SEQ ID NO 72
<211> LENGTH: 104
<212> TYPE: PRT
<213> ORGANISM: Homo sapiens

<400> SEQUENCE: 72

```
Met Ala Val Gly Pro Ala Gln Ala Ser Thr Gly Ser Leu Leu Ser Leu
  1               5                  10                  15

Gln Tyr Ala Pro Ala Leu Pro Pro Pro Ala Gly Asn Val Leu Ala Ser
             20                  25                  30

Gln Pro Ser Thr Ile Cys Ser Pro Ile Leu Leu Arg Gly Gln Pro Ser
         35                  40                  45

Leu Gly His Pro Leu Phe Pro Ser Ser Ser Ala Pro Thr Gln Val Thr
     50                  55                  60

Asp Pro Ala Asp Ser Phe Ser Leu Gly Lys Val Gly Cys Cys Leu Thr
 65                  70                  75                  80

Ser Pro Ser Ser Pro Pro Pro Ile His Thr His Arg His Pro Pro Thr
                 85                  90                  95

Pro Gly Arg Leu Val Ser His Met
            100
```

<210> SEQ ID NO 73
<211> LENGTH: 760
<212> TYPE: DNA
<213> ORGANISM: Homo sapiens

<400> SEQUENCE: 73

```
cttaagtctt ggcgcgctcg cctcgcagcc tgcaacccgc gctcagctgc ccgcctcctc      60

agccagccat gctggagcat ctgagctcgc tgcccacgca gatggattac aagggccaga     120
```

-continued

```
agctagctga acagatgttt cagggaatta ttcttttttc tgcaatagtt ggatttatct    180

acgggtacgt ggctgaacag ttcgggtgga ctgtctatat agttatggcc ggatttgctt    240

tttcatgttt gctgacactt cctccatggc ccatctatcg ccggcatcct ctcaagtggt    300

tacctgttca agaatcaagc acagacgaca agaaaccagg ggaaagaaaa attaagaggc    360

atgctaaaaa taattgaggt tttcatgatt cagcacctgc ttttgtttct gtgagatgag    420

ctaaattgct ttcatacccc agataagagc taaaaccacc taatgctctt atggcacagc    480

tgtgtataga tttagttctc tttatacttc atttctagcc cagttgggtt ttgatttata    540

taagtagttt agaccttctc ttcataatct tgctctgaga tggggaacag aacacacaag    600

tatgaagttt ctttcaggtg taaataatga aaaataaatg cctcataaat gatagtacaa    660

tgtaactatc aaagttttat aattcattat gagttaacca ttttaatgtt tccaattaac    720

cctcatagtg caaaaaaaaa aaaaaaaaaa aaaaaaaaaa                          760
```

<210> SEQ ID NO 74
<211> LENGTH: 102
<212> TYPE: PRT
<213> ORGANISM: Homo sapiens

<400> SEQUENCE: 74

```
Met Leu Glu His Leu Ser Ser Leu Pro Thr Gln Met Asp Tyr Lys Gly
  1               5                  10                  15

Gln Lys Leu Ala Glu Gln Met Phe Gln Gly Ile Ile Leu Phe Ser Ala
             20                  25                  30

Ile Val Gly Phe Ile Tyr Gly Tyr Val Ala Glu Gln Phe Gly Trp Thr
         35                  40                  45

Val Tyr Ile Val Met Ala Gly Phe Ala Phe Ser Cys Leu Leu Thr Leu
     50                  55                  60

Pro Pro Trp Pro Ile Tyr Arg Arg His Pro Leu Lys Trp Leu Pro Val
 65                  70                  75                  80

Gln Glu Ser Ser Thr Asp Asp Lys Lys Pro Gly Glu Arg Lys Ile Lys
                 85                  90                  95

Arg His Ala Lys Asn Asn
            100
```

<210> SEQ ID NO 75
<211> LENGTH: 875
<212> TYPE: DNA
<213> ORGANISM: Homo sapiens

<400> SEQUENCE: 75

```
ctagctcatg ctgctcttgt cagcctctgg ttctcctcga gtccttgggg acgtggcaga     60

tgccagcgac catcagacaa cgtggaggcc ctcatgggca atggctgagg gggccgggct    120

gaggctgtgc acatgcagtc tgcacgccac tcttgggctc tgctggcgga gatccccttc    180

cttctgggtg cagactgcac ctccggatgc agttttgatg tccatcttcc aggagagaga    240

cggtctcggg tccagggagt ggagggggct gcccctgccg tgcaggtcct ggccgatggc    300

gccttaccct gctgccctgg gcttttggcc tgaagcaaat tcctgagtgg ggggtactgg    360

ggcctgccgc atcctgtcct gtccactgcc cacccccgtg tgctggctcc ctcacttctg    420

gctgcagtgg gagccgccag tctgaccctt gtcaccgcac gctctgcccc caccccgttg    480

caagaggtca caccatgtca gcagccttgc actgaccgca gccggccccc aggcctcaga    540

gttctggatg cttccgtgcg gctccaacag gcatcgtctt cccttccgca ggtggagggg    600
```

```
ccgcttcccg caggcatctg agctctgtgc cggggccgtg gccatgggaa gatgttccac    660

gctgcctcct cctcgagttt tcctcggaaa cactcttgaa tgtctgagtg agggtcctgc    720

ttagctcttt ggcctgtgag atgctttgaa aatttttatt tttttaagat gaagcaagat    780

gtctgtagcg gtaattgcct cacattaaac tgtcgccgac tgcaggcgca gtgactgctg    840

aatgtaaaaa aaaaaaaaaa aaaaaaaaaa aaaaa                               875
```

<210> SEQ ID NO 76
<211> LENGTH: 112
<212> TYPE: PRT
<213> ORGANISM: Homo sapiens

<400> SEQUENCE: 76

```
Met Leu Leu Leu Ser Ala Ser Gly Ser Pro Arg Val Leu Gly Asp Val
  1               5                  10                  15

Ala Asp Ala Ser Asp His Gln Thr Thr Trp Arg Pro Ser Trp Ala Met
             20                  25                  30

Ala Glu Gly Ala Gly Leu Arg Leu Cys Thr Cys Ser Leu His Ala Thr
         35                  40                  45

Leu Gly Leu Cys Trp Arg Arg Ser Pro Ser Phe Trp Val Gln Thr Ala
     50                  55                  60

Pro Pro Asp Ala Val Leu Met Ser Ile Phe Gln Glu Arg Asp Gly Leu
 65                  70                  75                  80

Gly Ser Arg Glu Trp Arg Gly Leu Pro Leu Pro Cys Arg Ser Trp Pro
                 85                  90                  95

Met Ala Pro Tyr Pro Ala Ala Leu Gly Phe Trp Pro Glu Ala Asn Ser
            100                 105                 110
```

<210> SEQ ID NO 77
<211> LENGTH: 2848
<212> TYPE: DNA
<213> ORGANISM: Homo sapiens
<220> FEATURE:
<221> NAME/KEY: unsure
<222> LOCATION: (2526)

<400> SEQUENCE: 77

```
ctttgttctg tccttggtgt gtggtgcatt cgtgaaattc tgcagcacat cggcgaaaga     60

aaacgttgtg tgacgtgatc ctcatggtcc aggaaagaaa gatacctgct catcgtgttg    120

ttcttgctgc agccagtcat ttttttaact taatgttcac aactaacatg cttgaatcaa    180

agtcctttga agtagaactc aaagatgctg aacctgatat tattgaacaa ctggtggaat    240

ttgcttatac tgctagaatt tccgtgaata gcaacaatgt tcagtctttg ctggatgcag    300

caaaccaata tcagattgaa cctgtgaaga aaatgtgtgt tgattttttg aaagaacaag    360

ttgatgcttc aaattgtctt ggtataagtg tgctagcgga gtgtctagat tgtcctgaat    420

tgaaagcaac tgcagatgac tttattcatc agcactttac tgaagtttac aaaactgatg    480

aatttcttca acttgatgtc aagcgagtaa cacatcttct caaccaggac actctgactg    540

tgagagcaga ggatcaggtt tatgatgctg cagtcaggtg gttgaaatac gatgaaccta    600

atcgccagcc atttatggtt gatatccttg ctaaagtcag gtttcctctt atatcaaaga    660

atttcttaag taaaacggta caagctgaac cacttattca agacaatcct gaatgcctta    720

agatggtgat aagtggaatg aggtaccatc tactgtctcc agaggaccga gaagaacttg    780

tagatggccc aagacctaga agaaagaaac atgactaccg catagcccta tttggaggct    840

ctcaaccaca gtcttgtaga tattttaacc ccaaggatta tagctggaca gacatccgct    900
```

```
gcccctttga aaaaccaaga gatgcagcat gcgtgttttg ggacaatgta gtatacattt    960

tgggaggctc tcagcttttc ccaataaagc gaatggactg ctataatgta gtgaaggata   1020

gctggtattc gaaactgggt cctccgacac ctcgagacag ccttgctgca tgtgctgcag   1080

aaggcaaaat ttatacatct ggaggttcag aagtaggaaa ctcagctctg tatttatttg   1140

agtgctatga tacgagaact gaaagctggc acacaaagcc cagcatgctg acccagcgct   1200

gcagccatgg gatggtggaa gccaatggcc taatctatgt ttgtggtgga agtttaggaa   1260

acaatgtttc tgggagagtg cttaattcct gtgaagttta tgatcctgcc acagaaacat   1320

ggactgagct gtgtccaatg attgaagcca ggaagaatca tgggctggta tttgtaaaag   1380

acaagatatt tgctgtgggt ggtcagaatg gtttaggtgg tctggacaat gtggaatatt   1440

acgatattaa gttgaacgaa tggaagatgg tctcaccaat gccatggaag ggtgtaacag   1500

tgaaatgtgc agcagttggc tctatagttt atgtcttggc tggttttcaa ggtgttggtc   1560

gattaggaca cattctccaa tataataccg aaacagacaa atgggttgcc aactcccaag   1620

ttcgtgcttt tccagtcaca aagttgttta atttgtgttg tcgatacttg tggagcaaat   1680

gaagagaccc ttgaaacatg aaaaatgagt ggacttcaga ctcatcagag actctaaaat   1740

atagccacca gtgctttgtt ccaggagttt ggtgacaaag ttttggtttg gtgttttggt   1800

aaagaaagtt tcaagtgaaa tgaggttcct ataaaataga tgtttctttt atatggattt   1860

ccttaattca aagatcatat tttagctggc cacaaaacca agaacatatc tagcaagaaa   1920

acttgaaaaa gtataagcat ttgttaaaaa tgtgaatttc ttgaatgaat ttcacatttg   1980

taactatgat tttggcagaa tagaagattg gctcatcagt gaagcgcagt atcttagctc   2040

tagattctat tttcatgcat cacagaagtg ctatacggtt aggtctgttt gtgctcagtc   2100

aagaactaag aaatagtatg aattgtaagt caagatgggc aactcagatg gagcagctta   2160

gtctcacagt ttgcttgtct atttatttta tttagtgcca aatgtattcc attttaaaag   2220

taagccagag tgagtcaagg catatacaca ctttctcaca aaacttccta aacagatttg   2280

ggggtttaat atgtccaact cctcatgaaa tatattcaat ccacttaaat atattccatc   2340

tttttaacat aaaatgtaaa gcttagcacc catcattaat ttatgtctct gttttatcca   2400

gtggttaaaa aaggattctg cctctttagt cctccctgtt aaataaaacc caatcatagt   2460

aggtgattac ctagcaaaaa gtaaagctat ttatagcaaa tttttagatc attagaaaag   2520

cggggnggtt gaacaataac agtgttgact ttgaacttct ttaacgagat catgaattct   2580

tttcccttag ccaaaacatg aaatatttaa cctagttgtc tctaaaagtt ttgtaatcat   2640

gagttagata tatgtcatct cctattcatt gcttttatgt gatcaataaa tcttttacaa   2700

acccaactac tcatttcctt cctagtaata ctttgccttt ttcactgtgt atggaatgaa   2760

acatgtaaag ctgtcacaat caatgttttt atctgataat attaaatatt ttttaacttc   2820

aaaaaaaaaa aaaaaaaaaa aaaaaaaa                                      2848
```

<210> SEQ ID NO 78
<211> LENGTH: 532
<212> TYPE: PRT
<213> ORGANISM: Homo sapiens

<400> SEQUENCE: 78

```
Met Val Gln Glu Arg Lys Ile Pro Ala His Arg Val Val Leu Ala Ala
  1               5                  10                  15

Ala Ser His Phe Phe Asn Leu Met Phe Thr Thr Asn Met Leu Glu Ser
```

-continued

```
            20                  25                  30

Lys Ser Phe Glu Val Glu Leu Lys Asp Ala Glu Pro Asp Ile Ile Glu
        35                  40                  45

Gln Leu Val Glu Phe Ala Tyr Thr Ala Arg Ile Ser Val Asn Ser Asn
    50                  55                  60

Asn Val Gln Ser Leu Leu Asp Ala Ala Asn Gln Tyr Gln Ile Glu Pro
65                  70                  75                  80

Val Lys Lys Met Cys Val Asp Phe Leu Lys Glu Gln Val Asp Ala Ser
                85                  90                  95

Asn Cys Leu Gly Ile Ser Val Leu Ala Glu Cys Leu Asp Cys Pro Glu
            100                 105                 110

Leu Lys Ala Thr Ala Asp Asp Phe Ile His Gln His Phe Thr Glu Val
        115                 120                 125

Tyr Lys Thr Asp Glu Phe Leu Gln Leu Asp Val Lys Arg Val Thr His
    130                 135                 140

Leu Leu Asn Gln Asp Thr Leu Thr Val Arg Ala Glu Asp Gln Val Tyr
145                 150                 155                 160

Asp Ala Ala Val Arg Trp Leu Lys Tyr Asp Glu Pro Asn Arg Gln Pro
                165                 170                 175

Phe Met Val Asp Ile Leu Ala Lys Val Arg Phe Pro Leu Ile Ser Lys
            180                 185                 190

Asn Phe Leu Ser Lys Thr Val Gln Ala Glu Pro Leu Ile Gln Asp Asn
        195                 200                 205

Pro Glu Cys Leu Lys Met Val Ile Ser Gly Met Arg Tyr His Leu Leu
    210                 215                 220

Ser Pro Glu Asp Arg Glu Glu Leu Val Asp Gly Pro Arg Pro Arg Arg
225                 230                 235                 240

Lys Lys His Asp Tyr Arg Ile Ala Leu Phe Gly Gly Ser Gln Pro Gln
                245                 250                 255

Ser Cys Arg Tyr Phe Asn Pro Lys Asp Tyr Ser Trp Thr Asp Ile Arg
            260                 265                 270

Cys Pro Phe Glu Lys Pro Arg Asp Ala Ala Cys Val Phe Trp Asp Asn
        275                 280                 285

Val Val Tyr Ile Leu Gly Gly Ser Gln Leu Phe Pro Ile Lys Arg Met
    290                 295                 300

Asp Cys Tyr Asn Val Val Lys Asp Ser Trp Tyr Ser Lys Leu Gly Pro
305                 310                 315                 320

Pro Thr Pro Arg Asp Ser Leu Ala Ala Cys Ala Ala Glu Gly Lys Ile
                325                 330                 335

Tyr Thr Ser Gly Gly Ser Glu Val Gly Asn Ser Ala Leu Tyr Leu Phe
            340                 345                 350

Glu Cys Tyr Asp Thr Arg Thr Glu Ser Trp His Thr Lys Pro Ser Met
        355                 360                 365

Leu Thr Gln Arg Cys Ser His Gly Met Val Glu Ala Asn Gly Leu Ile
    370                 375                 380

Tyr Val Cys Gly Gly Ser Leu Gly Asn Asn Val Ser Gly Arg Val Leu
385                 390                 395                 400

Asn Ser Cys Glu Val Tyr Asp Pro Ala Thr Glu Thr Trp Thr Glu Leu
                405                 410                 415

Cys Pro Met Ile Glu Ala Arg Lys Asn His Gly Leu Val Phe Val Lys
            420                 425                 430

Asp Lys Ile Phe Ala Val Gly Gly Gln Asn Gly Leu Gly Gly Leu Asp
        435                 440                 445
```

```
Asn Val Glu Tyr Tyr Asp Ile Lys Leu Asn Glu Trp Lys Met Val Ser
    450                 455                 460

Pro Met Pro Trp Lys Gly Val Thr Val Lys Cys Ala Ala Val Gly Ser
465                 470                 475                 480

Ile Val Tyr Val Leu Ala Gly Phe Gln Gly Val Gly Arg Leu Gly His
                485                 490                 495

Ile Leu Gln Tyr Asn Thr Glu Thr Asp Lys Trp Val Ala Asn Ser Gln
            500                 505                 510

Val Arg Ala Phe Pro Val Thr Lys Leu Phe Asn Leu Cys Cys Arg Tyr
        515                 520                 525

Leu Trp Ser Lys
    530


<210> SEQ ID NO 79
<211> LENGTH: 2232
<212> TYPE: DNA
<213> ORGANISM: Homo sapiens
<220> FEATURE:
<221> NAME/KEY: unsure
<222> LOCATION: (2168)

<400> SEQUENCE: 79

gttcttcatg cccttctaga gaacgttcta cagctcttct tcacctgcat cctccttgga     60

agtctccagc catgtcgaga tattatttag agttgtttca gtgtccaact tgtatgaaag    120

gagcatggtc tttagtagaa gtccttatca ggtcttgcct tttcaatgaa agcttttgtc    180

atcaaatttc agaaaatatt ggctccaagg tgctccacct gacgctactc aaatttttct    240

ttaatttaat tgaaagtgaa gtacaacatc tgagtcaaaa gttgtatgac tggtcagatt    300

ctcagaatct gaaaataaca ggaaaggcaa tgcttcttga aatttttttgg tcaggaagtg    360

aaacctctgg gcttttgacc aaaccagtaa atatgctttt ggaatggact atatattctc    420

acaaggaaaa attcaagtct aatgatactt ttcttccaca ggaattagag attttcattt    480

gctccttttc ctcctcctgg cttcaaatgt ttgttgcaga ggcagtcttt aaaaagttgt    540

gtctacagag ctctggcagt gtttcttctg agccactctc tcttcagaaa atggtatatt    600

cctatttacc agccttgggg aaaactggtg tgcttgggtc tggaaagatt caggtgtcaa    660

agaaaatagg acagcggcct tgttttgact ctcagagaac cttactaatg ctgaatggta    720

ctaaacaaaa acaagtcgaa gggctgccag agttactaga cctgaacctt gctaaatgtt    780

cctcatcatt aaaaaaattg aaaaagaagt cagaaggaga attgtcatgt tccaaggaga    840

attgcccctc tgtagttaaa aagatgaatt ttcacaagac taatctaaaa ggagaaacag    900

ccctgcatag agcttgcata aataaccaag tggagaaatt gattcttctt ctctctttgc    960

caggaataga catcaatgtt aaagacaatg ctggctggac gcctttgcat gaagcctgta   1020

actatggcaa cacagtgggt gtccaggaaa ttttgcaacg ttgtccagag gtagatctgc   1080

tcactcaagt ggacggggtg actcctttgc atgatgcact gtcaaacgga catgtagaaa   1140

ttggcaagct gctactacag catgggggcc cagtgctttt acaacagagg aatgctaagg   1200

gagaattgcc cttggattat gtggtttcac ctcaaatcaa agaagaactg tttgctatta   1260

caaaaataga agatacagtg gagaactttc atgcacaagc agagaaacat tttcattacc   1320

agcaacttga atttggctcc tttttactta gtaggatgtt gctaaatttt tgttcaattt   1380

ttgatttatc ttcagagttc attttagctt ccaaagggtt aactcatcta aatgaactgc   1440

ttatggcttg taaaagtcat aaagaaacca ccagtgttca tactgactgg ttactggatc   1500
```

```
tttatgctgg aaatataaag acattgcaga aactcccaca cattcttaag gaactgcctg   1560

agaatttgaa agtgtgtcct ggggtacaca ctgaggcctt gatgataaca ttggaaatga   1620

tgtgtcggtc agtcatggag ttttcatgat gatgctagaa agtatggatt gactttctaa   1680

atctgttcag tttgcattgg tacttactgt ggacttcata gcttactgac agatagtaat   1740

ttgatttatt tattgacaga ctttgcagcc ttgctaaatt ttaaaagcat ttttaaaaaa   1800

acttctacaa aactctagta tgggcttctg actttttcca gggtgtagaa tttgactcaa   1860

aagtaaaaat aattttgttt tagtatattc tactttcatt aatgtttttt tgttctgaaa   1920

gtgatattat attgtacatg taaaattaat ttaaatattt tttcaaataa aaatgtaatg   1980

tcctgtattc tagatgttct aggtcttaga atcatggcaa gcatattcat acaaatgcgt   2040

acctataaac ttgtagctcc tgactcttag ggatggattt tgaggaaaaa acaagactaa   2100

acaaaaacat gtagctccct atttcttctc tctaggttgt tggactgaaa tatgcatttt   2160

agctttgntg tttctaaaat aaacatttct aaaatttaca ggaaaaaaaa aaaaaaaaaa   2220

aaaaaaaaaa aa                                                       2232

<210> SEQ ID NO 80
<211> LENGTH: 525
<212> TYPE: PRT
<213> ORGANISM: Homo sapiens

<400> SEQUENCE: 80

Met Ser Arg Tyr Tyr Leu Glu Leu Phe Gln Cys Pro Thr Cys Met Lys
  1               5                  10                  15

Gly Ala Trp Ser Leu Val Glu Val Leu Ile Arg Ser Cys Leu Phe Asn
             20                  25                  30

Glu Ser Phe Cys His Gln Ile Ser Glu Asn Ile Gly Ser Lys Val Leu
         35                  40                  45

His Leu Thr Leu Leu Lys Phe Phe Phe Asn Leu Ile Glu Ser Glu Val
     50                  55                  60

Gln His Leu Ser Gln Lys Leu Tyr Asp Trp Ser Asp Ser Gln Asn Leu
 65                  70                  75                  80

Lys Ile Thr Gly Lys Ala Met Leu Leu Glu Ile Phe Trp Ser Gly Ser
                 85                  90                  95

Glu Thr Ser Gly Leu Leu Thr Lys Pro Val Asn Met Leu Leu Glu Trp
            100                 105                 110

Thr Ile Tyr Ser His Lys Glu Lys Phe Lys Ser Asn Asp Thr Phe Leu
        115                 120                 125

Pro Gln Glu Leu Glu Ile Phe Ile Cys Ser Phe Ser Ser Ser Trp Leu
    130                 135                 140

Gln Met Phe Val Ala Glu Ala Val Phe Lys Lys Leu Cys Leu Gln Ser
145                 150                 155                 160

Ser Gly Ser Val Ser Ser Glu Pro Leu Ser Leu Gln Lys Met Val Tyr
                165                 170                 175

Ser Tyr Leu Pro Ala Leu Gly Lys Thr Gly Val Leu Gly Ser Gly Lys
            180                 185                 190

Ile Gln Val Ser Lys Lys Ile Gly Gln Arg Pro Cys Phe Asp Ser Gln
        195                 200                 205

Arg Thr Leu Leu Met Leu Asn Gly Thr Lys Gln Lys Gln Val Glu Gly
    210                 215                 220

Leu Pro Glu Leu Leu Asp Leu Asn Leu Ala Lys Cys Ser Ser Ser Leu
225                 230                 235                 240
```

```
Lys Lys Leu Lys Lys Lys Ser Glu Gly Glu Leu Ser Cys Ser Lys Glu
                245                 250                 255

Asn Cys Pro Ser Val Val Lys Lys Met Asn Phe His Lys Thr Asn Leu
            260                 265                 270

Lys Gly Glu Thr Ala Leu His Arg Ala Cys Ile Asn Asn Gln Val Glu
        275                 280                 285

Lys Leu Ile Leu Leu Leu Ser Leu Pro Gly Ile Asp Ile Asn Val Lys
    290                 295                 300

Asp Asn Ala Gly Trp Thr Pro Leu His Glu Ala Cys Asn Tyr Gly Asn
305                 310                 315                 320

Thr Val Gly Val Gln Glu Ile Leu Gln Arg Cys Pro Glu Val Asp Leu
                325                 330                 335

Leu Thr Gln Val Asp Gly Val Thr Pro Leu His Asp Ala Leu Ser Asn
            340                 345                 350

Gly His Val Glu Ile Gly Lys Leu Leu Leu Gln His Gly Gly Pro Val
        355                 360                 365

Leu Leu Gln Gln Arg Asn Ala Lys Gly Glu Leu Pro Leu Asp Tyr Val
    370                 375                 380

Val Ser Pro Gln Ile Lys Glu Glu Leu Phe Ala Ile Thr Lys Ile Glu
385                 390                 395                 400

Asp Thr Val Glu Asn Phe His Ala Gln Ala Glu Lys His Phe His Tyr
                405                 410                 415

Gln Gln Leu Glu Phe Gly Ser Phe Leu Leu Ser Arg Met Leu Leu Asn
            420                 425                 430

Phe Cys Ser Ile Phe Asp Leu Ser Ser Glu Phe Ile Leu Ala Ser Lys
        435                 440                 445

Gly Leu Thr His Leu Asn Glu Leu Leu Met Ala Cys Lys Ser His Lys
    450                 455                 460

Glu Thr Thr Ser Val His Thr Asp Trp Leu Leu Asp Leu Tyr Ala Gly
465                 470                 475                 480

Asn Ile Lys Thr Leu Gln Lys Leu Pro His Ile Leu Lys Glu Leu Pro
                485                 490                 495

Glu Asn Leu Lys Val Cys Pro Gly Val His Thr Glu Ala Leu Met Ile
            500                 505                 510

Thr Leu Glu Met Met Cys Arg Ser Val Met Glu Phe Ser
        515                 520                 525
```

<210> SEQ ID NO 81
<211> LENGTH: 2625
<212> TYPE: DNA
<213> ORGANISM: Homo sapiens
<220> FEATURE:
<221> NAME/KEY: unsure
<222> LOCATION: (2559)
<220> FEATURE:
<221> NAME/KEY: unsure
<222> LOCATION: (2561)

<400> SEQUENCE: 81

```
gtctcctagc accgcatctg tccaggaagc cactgcctgc ttgttgctca tctgtagttt     60

gcaggtgggg gttgcttttc ctttgttctg ccaggcggct tcagggctcc ctgtctgtag    120

gtcagtatat ttcaccagtt ctgaaaaccc caacctactc cttgacagcc attgtttcct    180

ctgcctctgg gacatccatc aaatgtacgt tagccctcat tccatcttcc gcgtccctta    240

ttctgtcctc tgccttccca cgttattctc tgtaataatt tatctgaaat ttttttatct    300
```

-continued

```
tcctattcac tgggtaagtt cttaatcttc ctatttactg tttctctctt ctactgtatc    360
tagactggca ccaaatatgt ccactgagta cattagtgtt tcatttctaa aagagctgtt    420
tggttttctt tcaaatttgc tgtatctgtt tttagaattt tcagttcccg tcatattcag    480
agtttgttgt tcatttctgc aaacgctgag cgtagctgcc tcacggtgcg tctgcggtgc    540
catctgagtg ttcttggcag cactgccagg tctccctggg agctgcgctc tttgaccctg    600
tgacgtcctg aggcctgggc cagatgctgc ttcctccagg gaagatttgt tctccctccc    660
agtagctccc cagggacctc ccacaccact gccctgggcc ctgtgtgtat aggcccagat    720
ttttctctgt gtcctttatt accagctctg tttacagatc cctggagtca ggggaagggg    780
tgagctcaga tctgaggcca agaggccatt tcccagctgg ctgcagctga gcctggtggc    840
tgtgtctgag cgtcgtggag ccagggtcca cggcacccag gtggcggggg gcaggcgccc    900
tgaccagcca cggcctcaaa gtgactctcc tgctctgctc cagccacacc tgcatgctgt    960
ggcgggcgct ggcggtggag cctcgcctag ctgcccaggt cctggggctg ctgctggaga   1020
agatgagtag ggacgtccct ttcaaggaga gccgggcctt cctgctgggc cgcaccccag   1080
accgcgtggc cacgctgctg cctctctcgg ctacctgtgc actgtttgag gtcatgtcca   1140
cgcctgcagc ggggcccgcg gtgctcgagc tctacccccca gctgtttgtg gtgcttctgc   1200
tgcgcgtcag ctgcaccgtg ggtgtccagc tgccccggaa cctgcaggcc caggaaagga   1260
ggggtgccag tccagcccta gccaccagga acctggaacc ctgcagctct gcagtggaca   1320
ccctgcggtc catgctactc cgcagcggca gcgaggatgt ggtacagcgc atggacctgg   1380
agggaggctg ggaactgctc aggacctcgg cggggcatga ggagggggcc accaggttgg   1440
ccagggccat ggctgagcac gcagggcccc gactccccct ggtgctgaag acgctggcat   1500
gcacacacag cagtgcgtat gagaaccaga gggtgaccac caccgccttc ctggccgagc   1560
tgctgaacag caacgtggcc aacgacctca tgctcttgga ctcgctgctg gagagcctgg   1620
cggctcgcca gaaggacaca tgcgccagcg tgcggaggct ggtgctccgc ggcctggcca   1680
acctggcctc cggctgccct gacaaggtgc gaacccacgg cccccagctc ctcacagcca   1740
tgattggcgg gctggacgac ggggacaacc ctcacagccc agtggccctg gaggccatgc   1800
tgggccttgc gaggctggtg cacctggtgg agtcctggga cctgcgctca gggctgctgc   1860
acgtggccat ccgcatccgg cctttcttcg acagtgagaa gatggagttc cggacggcat   1920
ctatccgcct ctttgggcac cttaacaagg tctgccacgg agactgtgag gacgtcttcc   1980
tggaccaggt ggtgggcggg ctggcgcccc tgctgctgca cctgcaggac cctcaggcca   2040
ccgtggccag cgcctgcagg tttgccctgc gcatgtgtgg ccccaatctg gcatgtgagg   2100
agctctcagc tgctttccag aaacacctgc aggagggccg agccctgcac ttcggggagt   2160
tcctcaacac cacctgcaag cacctgatgc accatttccc agacctgctg ggccgtctcc   2220
tgaccacctg cctgttctac ttcaagagca gctgggagaa cgtccgagct gctgcacccc   2280
tgttcaccgg taagcaccac cccctgcccc acccccacgc cgcccggcag ccccgcctga   2340
tgcccccact tcacagggtt cctggtgctg cactcggagc ccaggcagca gccgcaggtg   2400
gacctggacc agctcattgc gggtgagcac ccctccacgg ggcccctccg ctgggccctg   2460
ctgaccctgt aggcacccgc agggactaag tgattttcct ggatttcagg actttttccc   2520
tgtcactggt gacctcatcg tctctagtaa ttcacggana nttcttaact gttccaaaag   2580
agcttaaaaa acaccaaaaa aaaaaaaaaa aaaaaaaaaa aaaaa                   2625
```

<210> SEQ ID NO 82
<211> LENGTH: 490
<212> TYPE: PRT
<213> ORGANISM: Homo sapiens

<400> SEQUENCE: 82

```
Met Leu Trp Arg Ala Leu Ala Val Glu Pro Arg Leu Ala Ala Gln Val
  1               5                  10                  15

Leu Gly Leu Leu Leu Glu Lys Met Ser Arg Asp Val Pro Phe Lys Glu
             20                  25                  30

Ser Arg Ala Phe Leu Leu Gly Arg Thr Pro Asp Arg Val Ala Thr Leu
         35                  40                  45

Leu Pro Leu Ser Ala Thr Cys Ala Leu Phe Glu Val Met Ser Thr Pro
     50                  55                  60

Ala Ala Gly Pro Ala Val Leu Glu Leu Tyr Pro Gln Leu Phe Val Val
 65                  70                  75                  80

Leu Leu Leu Arg Val Ser Cys Thr Val Gly Val Gln Leu Pro Arg Asn
                 85                  90                  95

Leu Gln Ala Gln Glu Arg Arg Gly Ala Ser Pro Ala Leu Ala Thr Arg
            100                 105                 110

Asn Leu Glu Pro Cys Ser Ser Ala Val Asp Thr Leu Arg Ser Met Leu
        115                 120                 125

Leu Arg Ser Gly Ser Glu Asp Val Val Gln Arg Met Asp Leu Glu Gly
    130                 135                 140

Gly Trp Glu Leu Leu Arg Thr Ser Ala Gly His Glu Glu Gly Ala Thr
145                 150                 155                 160

Arg Leu Ala Arg Ala Met Ala Glu His Ala Gly Pro Arg Leu Pro Leu
                165                 170                 175

Val Leu Lys Thr Leu Ala Cys Thr His Ser Ser Ala Tyr Glu Asn Gln
            180                 185                 190

Arg Val Thr Thr Thr Ala Phe Leu Ala Glu Leu Leu Asn Ser Asn Val
        195                 200                 205

Ala Asn Asp Leu Met Leu Leu Asp Ser Leu Leu Glu Ser Leu Ala Ala
    210                 215                 220

Arg Gln Lys Asp Thr Cys Ala Ser Val Arg Arg Leu Val Leu Arg Gly
225                 230                 235                 240

Leu Ala Asn Leu Ala Ser Gly Cys Pro Asp Lys Val Arg Thr His Gly
                245                 250                 255

Pro Gln Leu Leu Thr Ala Met Ile Gly Gly Leu Asp Asp Gly Asp Asn
            260                 265                 270

Pro His Ser Pro Val Ala Leu Glu Ala Met Leu Gly Leu Ala Arg Leu
        275                 280                 285

Val His Leu Val Glu Ser Trp Asp Leu Arg Ser Gly Leu Leu His Val
    290                 295                 300

Ala Ile Arg Ile Arg Pro Phe Phe Asp Ser Glu Lys Met Glu Phe Arg
305                 310                 315                 320

Thr Ala Ser Ile Arg Leu Phe Gly His Leu Asn Lys Val Cys His Gly
                325                 330                 335

Asp Cys Glu Asp Val Phe Leu Asp Gln Val Val Gly Gly Leu Ala Pro
            340                 345                 350

Leu Leu Leu His Leu Gln Asp Pro Gln Ala Thr Val Ala Ser Ala Cys
        355                 360                 365

Arg Phe Ala Leu Arg Met Cys Gly Pro Asn Leu Ala Cys Glu Glu Leu
    370                 375                 380
```

```
Ser Ala Ala Phe Gln Lys His Leu Gln Glu Gly Arg Ala Leu His Phe
385                 390                 395                 400

Gly Glu Phe Leu Asn Thr Thr Cys Lys His Leu Met His His Phe Pro
                405                 410                 415

Asp Leu Leu Gly Arg Leu Leu Thr Thr Cys Leu Phe Tyr Phe Lys Ser
            420                 425                 430

Ser Trp Glu Asn Val Arg Ala Ala Ala Pro Leu Phe Thr Gly Lys His
        435                 440                 445

His Pro Leu Pro His Pro His Ala Ala Arg Gln Pro Arg Leu Met Pro
    450                 455                 460

Pro Leu His Arg Val Pro Gly Ala Ala Leu Gly Ala Gln Ala Ala Ala
465                 470                 475                 480

Ala Gly Gly Pro Gly Pro Ala His Cys Gly
                485                 490


<210> SEQ ID NO 83
<211> LENGTH: 1476
<212> TYPE: DNA
<213> ORGANISM: Homo sapiens

<400> SEQUENCE: 83

cctctctcca aattggcctc tcaactcaca ggaagacaca gctgcccaga gcagcccagg     60

ccgtggtgag gaggcggagg catcggcggc ggaggctcag ggtggggagc aggcctacct    120

ggcaggcctg gcagggcagt accacttgga gcggtacccg gacagttacg agtccatgtc    180

cgagccgccc attgctcatc ttttgcgccc cgtgcttccc cgggccttcg ccttccccgt    240

ggacccccag gtccagtctg ccgctgatga gactgctgtg cagctgagcg agttgctgac    300

gctgcccgtg ctcatgaagc gctccatcac ggcaccgctg gccgcccaca tctccttggt    360

gaacaaggcc gctgtcgact acttcttcgt ggagctgcac ctggaggcgc actatgaggc    420

actgcggcac ttcctgctga tggaggacgg cgagttcgcc cagtccctca gcgacctgct    480

ctttgagaag cttggagctg ggcaaacgcc ccggagagct gctcaacccg ctggtgctga    540

actctgtgct gacaaggccc tgcagtgcag cctgcatggg gacaccccgc acgcctccaa    600

cctctccctc gctctcaagt acctgcccga ggtgtttgcc cccaacgccc cggatgtgct    660

gagctgcctg gagctcaggt acaaggtgga ctggcctctc aacattgtca tcaccgaggg    720

ctgcctgagc aagtacagcg gcgtcttctc cttcctgctg cagctgaagc tcatgatgtg    780

ggcgctcaag gacgtctgct tccacctcaa gcgcacagcc ctgctgagcc acatggccgg    840

ctctgtgcag ttccgtcagc tgcagctgtt caagcacgag atgcagcatt tcgtgaaggt    900

catccagggc tacatcgcca accagatcct gcacgtcacc tggtgcgagt tcagggccag    960

gttggccacc gtgggcgacc tggaggagat ccagcgtgcg cacgcagagt acctgcacaa   1020

ggccgtcttc aggggcctgc tcacggagaa ggcggcgccc gtcatgaacg tcatccacag   1080

catcttcagc ctcgtgctca agttccgcag ccagctcatc tcccaggcct gggggccccc   1140

tgggggcccg cggggtgcag agcaccccaa ctttgcactc atgcagcagt cctacaacac   1200

cttcaagtac tactcccact ttctcttcaa agtggtgacc aagctggtga accgcggcta   1260

ccagccccac ctggaggact ttctgctgcg catcaacttc aacaactact accaggacgc   1320

ctgaggctgc tctgcggggg acgtgcacaa taaaggtgtt ctcgggaaaa aaaaaaaaaa   1380

aaaaaaaaaa aaaaaaaaaa aaaaaaaaaa aaaaaaaaaa aaaaaaaaaa aaaaaaaaaa   1440

aaaaataaaa aaaaaaaaaa aaaaaaaaaa aaaaaa                             1476
```

<210> SEQ ID NO 84
<211> LENGTH: 382
<212> TYPE: PRT
<213> ORGANISM: Homo sapiens

<400> SEQUENCE: 84

```
Met Ser Glu Pro Pro Ile Ala His Leu Leu Arg Pro Val Leu Pro Arg
  1               5                  10                  15

Ala Phe Ala Phe Pro Val Asp Pro Gln Val Gln Ser Ala Ala Asp Glu
             20                  25                  30

Thr Ala Val Gln Leu Ser Glu Leu Leu Thr Leu Pro Val Leu Met Lys
         35                  40                  45

Arg Ser Ile Thr Ala Pro Leu Ala Ala His Ile Ser Leu Val Asn Lys
     50                  55                  60

Ala Ala Val Asp Tyr Phe Phe Val Glu Leu His Leu Glu Ala His Tyr
 65                  70                  75                  80

Glu Ala Leu Arg His Phe Leu Leu Met Glu Asp Gly Glu Phe Ala Gln
                 85                  90                  95

Ser Leu Ser Asp Leu Leu Phe Glu Lys Leu Gly Ala Gly Gln Thr Pro
            100                 105                 110

Arg Arg Ala Ala Gln Pro Ala Gly Ala Glu Leu Cys Ala Asp Lys Ala
        115                 120                 125

Leu Gln Cys Ser Leu His Gly Asp Thr Pro His Ala Ser Asn Leu Ser
    130                 135                 140

Leu Ala Leu Lys Tyr Leu Pro Glu Val Phe Ala Pro Asn Ala Pro Asp
145                 150                 155                 160

Val Leu Ser Cys Leu Glu Leu Arg Tyr Lys Val Asp Trp Pro Leu Asn
                165                 170                 175

Ile Val Ile Thr Glu Gly Cys Leu Ser Lys Tyr Ser Gly Val Phe Ser
            180                 185                 190

Phe Leu Leu Gln Leu Lys Leu Met Met Trp Ala Leu Lys Asp Val Cys
        195                 200                 205

Phe His Leu Lys Arg Thr Ala Leu Leu Ser His Met Ala Gly Ser Val
    210                 215                 220

Gln Phe Arg Gln Leu Gln Leu Phe Lys His Glu Met Gln His Phe Val
225                 230                 235                 240

Lys Val Ile Gln Gly Tyr Ile Ala Asn Gln Ile Leu His Val Thr Trp
                245                 250                 255

Cys Glu Phe Arg Ala Arg Leu Ala Thr Val Gly Asp Leu Glu Glu Ile
            260                 265                 270

Gln Arg Ala His Ala Glu Tyr Leu His Lys Ala Val Phe Arg Gly Leu
        275                 280                 285

Leu Thr Glu Lys Ala Ala Pro Val Met Asn Val Ile His Ser Ile Phe
    290                 295                 300

Ser Leu Val Leu Lys Phe Arg Ser Gln Leu Ile Ser Gln Ala Trp Gly
305                 310                 315                 320

Pro Pro Gly Gly Pro Arg Gly Ala Glu His Pro Asn Phe Ala Leu Met
                325                 330                 335

Gln Gln Ser Tyr Asn Thr Phe Lys Tyr Tyr Ser His Phe Leu Phe Lys
            340                 345                 350

Val Val Thr Lys Leu Val Asn Arg Gly Tyr Gln Pro His Leu Glu Asp
        355                 360                 365

Phe Leu Leu Arg Ile Asn Phe Asn Asn Tyr Tyr Gln Asp Ala
    370                 375                 380
```

-continued

<210> SEQ ID NO 85
<211> LENGTH: 1212
<212> TYPE: DNA
<213> ORGANISM: Homo sapiens
<220> FEATURE:
<221> NAME/KEY: unsure
<222> LOCATION: (1146)..(1147)

<400> SEQUENCE: 85
taggctcttt ggccgcccag ctctccctgt gctaactgcc tgcaccttgg acagagcggg 60
tgcgcaaatc agaaggatta gttgggacct gccttggcga ccccatggca tcccccagaa 120
ccgtaactat tgtggccctc tcagtggccc tgggactctt ctttgttttc atggggacta 180
tcaagctgac ccccaggctc agcaaggatg cctacagtga gatgaaacgt gcttacaaga 240
gctatgttcg agccctccct ctgctgaaga aaatggggat caattccatt ctcctccgaa 300
aaagcattgg tgcccttgaa gtggcctgtg gcatcgtcat gacccttgtg cctgggcgtc 360
ccaaagatgt ggccaacttc ttcctactgt tgctggtgtt ggctgtgctc ttcttccacc 420
agctggtcgg tgatcctctc aaacgctacg cccatgctct ggtgtttgga atcctgctca 480
cttgccgcct gctgattgct cgcaagcccg aagaccggtc ttctgagaag aagcctttgc 540
cagggaatgc tgaggagcaa ccctccttat atgagaaggc ccctcagggc aaagtgaagg 600
tgtcatagaa aagtggaagt gcaaagagtg gaccttccag gcagttgcgt ccatgacacc 660
aggaagatgt cagtgtgtgt ttttcatttg atttatttat cttggggaaa gtgaaaaatg 720
taatctgcaa gttaatgatc tattggcttg tgtacatcta tatgctaaaa tgacttcccc 780
acattgacat ttgtgcgcca cctttaatca ctctggggca actctcacat cttgctgcat 840
gtacatgtat acggctacta ttgaagtgta attgtgagat ggactccaac aagcatgtga 900
ctgtgagatt gtgtgtggga aaatgtattt aactactctg tgtgtgtgtg tgtgtgtgtg 960
tgcgcgcgcg cgcacgcgca cacactcacg cacacacaag cagagaaggc gctgatcttg 1020
aactaatcct gcacaggcat ccttcccttt atagattgat tccagcaaag gcggaataaa 1080
acaaatttcc tatgaagaga atcctgatat gaaacaagtc atgtagtctc atggccggga 1140
atctcnncac agatactaac aacttaaact tactacttta ggaaaaaaaa aaaaaaaaaa 1200
aaaaaaaaaa aa 1212

<210> SEQ ID NO 86
<211> LENGTH: 167
<212> TYPE: PRT
<213> ORGANISM: Homo sapiens

<400> SEQUENCE: 86

Met Ala Ser Pro Arg Thr Val Thr Ile Val Ala Leu Ser Val Ala Leu
1 5 10 15

Gly Leu Phe Phe Val Phe Met Gly Thr Ile Lys Leu Thr Pro Arg Leu
20 25 30

Ser Lys Asp Ala Tyr Ser Glu Met Lys Arg Ala Tyr Lys Ser Tyr Val
35 40 45

Arg Ala Leu Pro Leu Leu Lys Lys Met Gly Ile Asn Ser Ile Leu Leu
50 55 60

Arg Lys Ser Ile Gly Ala Leu Glu Val Ala Cys Gly Ile Val Met Thr
65 70 75 80

Leu Val Pro Gly Arg Pro Lys Asp Val Ala Asn Phe Phe Leu Leu Leu
85 90 95

```
Leu Val Leu Ala Val Leu Phe Phe His Gln Leu Val Gly Asp Pro Leu
            100                 105                 110

Lys Arg Tyr Ala His Ala Leu Val Phe Gly Ile Leu Leu Thr Cys Arg
        115                 120                 125

Leu Leu Ile Ala Arg Lys Pro Glu Asp Arg Ser Ser Glu Lys Lys Pro
    130                 135                 140

Leu Pro Gly Asn Ala Glu Glu Gln Pro Ser Leu Tyr Glu Lys Ala Pro
145                 150                 155                 160

Gln Gly Lys Val Lys Val Ser
                165


<210> SEQ ID NO 87
<211> LENGTH: 1059
<212> TYPE: DNA
<213> ORGANISM: Homo sapiens

<400> SEQUENCE: 87

tcaggattta aacttgtcaa ctttggatgt gattatcatc aataccgaga taaattttcc      60

aaacacctga ctctgtgtgt ttttaccaac catacaggaa gtttgtgtgt atgttacagc     120

ccgaagtgtg cctcttggga acaaatcaca tattcagtgt tttacattca taaaggacac     180

agcaagacct tcaccacttc tcttgagaat gttggctcac acatgacaaa gggcattact     240

tttctcaacc ttgactatta tgtggctgtt tacttacctg gtcatttctt ccacctactt     300

aatgttcaac atccagacct gatctgccac aatctctttc tgacaggaaa taatgaaatg     360

attgatatgc tacctcattg ccctttacag tcattgtcag ggtccctggt attggattgt     420

tgttctggaa agctctatag agcactgctc agccagtcgt ctttattaca gcttctgcag     480

aacacttgct tagactgtga gaagatggct gcgttgcact gtgcgctcta ctgcggtcaa     540

ggtgcgcagt tcctggaagc ccagattatt cagtggattt ctgagaatgt ctctgcctgc     600

cattcatttg acctcattca ggaatttata attgcttctt catactggag tgtatattca     660

gagacaagta acatggacaa actattgcca cattcctcag tgctcacttg gaatacagaa     720

attcctggaa taactcttgt gacagaagac attgcattgc ctcttatgaa ggttttgaaa     780

aatgtcctgg gcagtaaata aatttagcag gaaagtacgc ctactccatt tatccaaatg     840

ttaatgaact ttctcttagt gaacatggca ctgttgacac cacctaagtc ataaaaaacgg    900

gtctcaaggg aggaaatgac tcagtgtgtt taatacaggt ttccctgcta agcctcaatc     960

tggggaagtc ctgttggttt tgggaagtga gcagcagttc tctatgtggt ttaaaaaaac    1020

aacgacaaca aaaaaaaaaa aaaaaaaaaa aaaaaaaaa                           1059


<210> SEQ ID NO 88
<211> LENGTH: 192
<212> TYPE: PRT
<213> ORGANISM: Homo sapiens

<400> SEQUENCE: 88

Met Thr Lys Gly Ile Thr Phe Leu Asn Leu Asp Tyr Tyr Val Ala Val
  1               5                  10                  15

Tyr Leu Pro Gly His Phe Phe His Leu Leu Asn Val Gln His Pro Asp
             20                  25                  30

Leu Ile Cys His Asn Leu Phe Leu Thr Gly Asn Asn Glu Met Ile Asp
         35                  40                  45

Met Leu Pro His Cys Pro Leu Gln Ser Leu Ser Gly Ser Leu Val Leu
     50                  55                  60
```

```
Asp Cys Cys Ser Gly Lys Leu Tyr Arg Ala Leu Leu Ser Gln Ser Ser
 65                  70                  75                  80

Leu Leu Gln Leu Leu Gln Asn Thr Cys Leu Asp Cys Glu Lys Met Ala
                 85                  90                  95

Ala Leu His Cys Ala Leu Tyr Cys Gly Gln Gly Ala Gln Phe Leu Glu
            100                 105                 110

Ala Gln Ile Ile Gln Trp Ile Ser Glu Asn Val Ser Ala Cys His Ser
        115                 120                 125

Phe Asp Leu Ile Gln Glu Phe Ile Ile Ala Ser Ser Tyr Trp Ser Val
    130                 135                 140

Tyr Ser Glu Thr Ser Asn Met Asp Lys Leu Leu Pro His Ser Ser Val
145                 150                 155                 160

Leu Thr Trp Asn Thr Glu Ile Pro Gly Ile Thr Leu Val Thr Glu Asp
                165                 170                 175

Ile Ala Leu Pro Leu Met Lys Val Leu Lys Asn Val Leu Gly Ser Lys
            180                 185                 190
```

<210> SEQ ID NO 89
<211> LENGTH: 2529
<212> TYPE: DNA
<213> ORGANISM: Homo sapiens

<400> SEQUENCE: 89

```
attttgcctt atgaaaacta agctgaatcg actgctgcca aacatctatt aggcaaaatt     60

ggcctcttgc ccatgatttg actttccagc acagccagtt ctttttctcc tctgcagctg    120

attggctctg gagtgtggcc agaagcctct ctcctgcaat taaaggagtc gggtctctaa    180

ctgttgatct gtttttttcc cttctgagca atggagctta ccatctttat cctgagactg    240

gccatttaca tcctgacatt tcccttgtac ctgctgaact ttctgggctt gtggagctgg    300

atatgcaaaa aatggttccc ctacttcttg gtgaggttca ctgtgatata caacgaacag    360

atggcaagca agaagcggga gctcttcagt aacctgcagg agtttgcggg cccctccggg    420

aaactctccc tgctggaagt gggctgtggc acgggggcca acttcaagtt ctacccacct    480

gggtgcaggg tgacctgtat tgaccccaac cccaactttg agaagttttt gatcaagagc    540

attgcagaga accgacacct gcagtttgag cgctttgtgg tagctgccgg ggagaacatg    600

caccaggtgg ctgatggctc tgtggatgtg gtggtctgca ccctggtgct gtgctctgtg    660

aagaaccagg agcggattct ccgcgaggtg tgcagagtgc tgagaccggg aggggctttc    720

tatttcatgg agcatgtggc agctgagtgt tcgacttgga attacttctg gcaacaagtc    780

ctggatcctg cctggcacct tctgtttgat gggtgcaacc tgaccagaga gagctggaag    840

gccctggagc gggccagctt ctctaagctg aagctgcagc acatccaggc cccactgtcc    900

tgggagttgg tgcgccctca tatctatgga tatgctgtga aatagtgtga gctggcagtt    960

aagagctgaa tggctcaaag aatttaaagc ttcagtttta catttaaaat gctaagtggg   1020

agaagagaaa cctttttttt ggggggcggt ttttttggtt tgttgttggt tttttttttt   1080

tttttggcgg gaagaaagag ttttgctctt gttgcccagg ctggagtgca atggcgtgat   1140

ctccgctcac tgcaacctcc acctcgcggg tttaagcgat tcttctgcct cagcctccct   1200

agtagctggg attacaggtg cccaccacca tgcccagcta atttgtattt ttagttgaga   1260

cagggtttca ctacgttggc caggctggtc ttgaactcct gatctcaggc aatccaccca   1320

cctcagcctc ccaaagtgct gggatgacag gcgtgagcaa ccgcacccag cttaaggttt   1380
```

-continued

```
ttttgttttg ttttgagacg gagttttcgc tcttgttgcc caggctggag tgcaatgctg   1440

tgatctcagc ttaccacaac ctccacctcc cgggttcaag tgattcacct gcctcagcct   1500

cctgagtagc tggtattaca ggcatgcgtc accacgccgg ctaattttgt acttttagta   1560

gagatggtgt ttccccacgt tggtcagtct ggtctcaaat tcctgacctc aggtgatctg   1620

cctgcctcgg cctcccaaag tgctgtgatt acagacgtca gccaccatgc ctggcctgaa   1680

acctttttta ggtaaagttg aattccatcc ttaaaagttt ctgttatcct atttagccat   1740

tttctattgt ctcccaaaga attcacatca aaaaaacagc tttgaactcc cccttcaaag   1800

gaaacagtcg actttcataa ttagcatcta ccattatccc caaatcttat tttattcatt   1860

gacttgaaat tttttccaat tgcttttttt tttttttttt ttaaggttaa gagcagaggt   1920

ttactaggcc aaagaaagag aatagctctc tgttgcagag aggggtcctg gagaaatggg   1980

ttaccccagt tgtcttattt aaatggttac ccatcagatt ttaattttat cttctctttg   2040

agagcttggt aataagaagc acttaaatca ctccaaagaa gactttaaaa agggagcagt   2100

gaaaaggtct taataattta ttgattgaat taagaaatac tagctaatta agaatctgag   2160

tctaaacagc acagattttt tctttctgct tttaaattgt gttttaaaaa aagagacagg   2220

gggctgggcg tggtgctcac gcctgtaatc ctagcacttt gggaggccga ggcgggtgga   2280

tcacgaggta ggagttaaag accagcctgg ccaacatggc aaaaccctac taaagataca   2340

aaaaaaaaaa aaaattagcc aggcgtggtg gtgggtgcct gtaatcccag gtacttggag   2400

ggctgaggca ggagaatctc ttgaacccag aaggcgaagg ttgcagtgaa ccgagatcat   2460

gccattgtac tctagcctgg gtgacaagag caagactccg tctcgaaaaa aaaaaaaaaa   2520

aaaaaaaaa                                                           2529
```

<210> SEQ ID NO 90
<211> LENGTH: 244
<212> TYPE: PRT
<213> ORGANISM: Homo sapiens

<400> SEQUENCE: 90

```
Met Glu Leu Thr Ile Phe Ile Leu Arg Leu Ala Ile Tyr Ile Leu Thr
  1               5                  10                  15

Phe Pro Leu Tyr Leu Leu Asn Phe Leu Gly Leu Trp Ser Trp Ile Cys
             20                  25                  30

Lys Lys Trp Phe Pro Tyr Phe Leu Val Arg Phe Thr Val Ile Tyr Asn
         35                  40                  45

Glu Gln Met Ala Ser Lys Lys Arg Glu Leu Phe Ser Asn Leu Gln Glu
     50                  55                  60

Phe Ala Gly Pro Ser Gly Lys Leu Ser Leu Leu Glu Val Gly Cys Gly
 65                  70                  75                  80

Thr Gly Ala Asn Phe Lys Phe Tyr Pro Pro Gly Cys Arg Val Thr Cys
                 85                  90                  95

Ile Asp Pro Asn Pro Asn Phe Glu Lys Phe Leu Ile Lys Ser Ile Ala
            100                 105                 110

Glu Asn Arg His Leu Gln Phe Glu Arg Phe Val Val Ala Ala Gly Glu
        115                 120                 125

Asn Met His Gln Val Ala Asp Gly Ser Val Asp Val Val Val Cys Thr
    130                 135                 140

Leu Val Leu Cys Ser Val Lys Asn Gln Glu Arg Ile Leu Arg Glu Val
145                 150                 155                 160

Cys Arg Val Leu Arg Pro Gly Gly Ala Phe Tyr Phe Met Glu His Val
```

-continued

```
                165                 170                 175

Ala Ala Glu Cys Ser Thr Trp Asn Tyr Phe Trp Gln Gln Val Leu Asp
            180                 185                 190

Pro Ala Trp His Leu Leu Phe Asp Gly Cys Asn Leu Thr Arg Glu Ser
        195                 200                 205

Trp Lys Ala Leu Glu Arg Ala Ser Phe Ser Lys Leu Lys Leu Gln His
    210                 215                 220

Ile Gln Ala Pro Leu Ser Trp Glu Leu Val Arg Pro His Ile Tyr Gly
225                 230                 235                 240

Tyr Ala Val Lys


<210> SEQ ID NO 91
<211> LENGTH: 2390
<212> TYPE: DNA
<213> ORGANISM: Homo sapiens

<400> SEQUENCE: 91

tgccttcaaa gaaaaacctc ggtatccacc aagtcaggct caagcagctc ttcaagacag     60

tccccctgaa gagtactcct ataagaaatc aataagaaac ctgtttaaaa acattccttt    120

tgtccttctg ttgatcactt atggtatcat gactggtgcc ttttattcag tctcaacgtt    180

attaaatcaa atgatattga catattatga gggagaagaa gtcaatgctg gaaggattgg    240

gctaacgcta gtagtagctg gaatggtggg ctctattctt tgtggcttat ggctggatta    300

tactaaaaca tacaaacaga ctactctgat agtttatatt ttgtctttta ttggaatggt    360

tatctttact ttcacattgg accttagata tattatcatc gtgtttgtta ctggaggggt    420

gcttggcttc ttcatgactg gttacctccc tttgggtttt gaatttgctg ttgaaatcac    480

ttaccctgaa tctgaaggta cttcatctgg tcttcttaat gcttctgcac agatatttgg    540

aattttgttc acattggctc aaggaaagct cacatcagac tatggtccta aggcagggaa    600

catttttctc tgtgtctgga tgtttatagg catcatatta acagcattaa tcaagtctga    660

tctgcgaaga cacaacataa atataggaat tacaaatgtt gatgttaaag ctataccagc    720

tgacagtccc acagaccaag aaccaaaaac ggttatgttg tccaagcagt cagaatcagc    780

aatttgaaga gaaaggcaaa gttactgtcc tgtagtaatt ggggacaatg tgatcatcct    840

tggagagaga tgtgagcacc aaggctgggt ttgtatgtgg tgggggaata aacacactta    900

cttgaaaatt accatatgaa ctctaaatgc ataattattg ttttgcttaa ttgttaaatt    960

aagggaaatt ttcttaaaat tcttctgttt acatcatgtt aacactactg tttatctaat   1020

tagtatccgg tttttagtct catattgtat ctgaaagtaa gcttcttgac gtttactttt   1080

taaaagtcga tgtttttctt ttttgtagaa aatggaagct tagaatactt tttaaagtga   1140

taatatgggg tgttcagtcc ccataagata taatagttca tgcagtttat atattaaagt   1200

atccagtgga actaaatgta caatatattc ctaattggct gcctttttca ctgtgctgac   1260

cagctgttca agccacttca gtttgagtac aacataccaa catgacacta ctcacccaca   1320

aaggacagca ttgggatcag gctttcagat gacctctaag atttttccca tttattgtac   1380

tcttgttaca aagtactttt taacacatgc agtcaatggc tataaaaact attctgtgta   1440

cagattctac ccagactttg gtcttagaat tatgttctaa ttaaggagcc tggttacagg   1500

ttcattctgt cttgagttct tttctgtgct gcctttctat catggataaa tgctaacgct   1560

gtatttttc actccaactt gagatagagt agttttgtac ccattgcctt tttttcttt    1620

taaactctct ttttttttt ttcctgatgt gtaactttct agtaagataa tttcatcatg   1680
```

```
tatgttactg gctatttcat gatttcatgt atcacatcgt atattttgcc ttgaagattc   1740

ctgaaataag gaaatctata ataacttcag atagcctaca tgtccccatt tagtggagac   1800

ctcttgaatg ctatttgaat tctgcagtat catttttatg accattctcc tttgaggaat   1860

actatgccca ggtacatgct ctatcagtgt gccgggagag tggattcttt tcttcactgc   1920

agagtcatca cactgttaga atagtctgct cttttacatg ctcaggtagg gaaaatagga   1980

ccaaatatat ttccacagtg cctaccactg tgtcatgttt acagtgagag tttaaatatt   2040

gttgatgtcc tgactctgtg agctcatagg gagtatcttc atagtaatga catttgatca   2100

gccataaaat ttacattatg ttcatatgca cccaaaaaag ctagtcaggt aatgaatacc   2160

cttgaagtga atagcaattt tgatttaggc agtgtgttag gccatccttg cattgctata   2220

aagaaatatt taggctgggc gtggtggctc acgcctgtaa tcccagcact ttgggaggct   2280

gaagcgtgtg gatcacctga ggtcaggagt tcaagaccag cctggccaac atggtaaaac   2340

cccatctcta ctaaaaaaaa aaaaaaaaaa aaaaaaaaaa aaaaaaaaaa              2390


<210> SEQ ID NO 92
<211> LENGTH: 212
<212> TYPE: PRT
<213> ORGANISM: Homo sapiens

<400> SEQUENCE: 92

Met Thr Gly Ala Phe Tyr Ser Val Ser Thr Leu Leu Asn Gln Met Ile
  1               5                  10                  15

Leu Thr Tyr Tyr Glu Gly Glu Glu Val Asn Ala Gly Arg Ile Gly Leu
             20                  25                  30

Thr Leu Val Val Ala Gly Met Val Gly Ser Ile Leu Cys Gly Leu Trp
         35                  40                  45

Leu Asp Tyr Thr Lys Thr Tyr Lys Gln Thr Thr Leu Ile Val Tyr Ile
     50                  55                  60

Leu Ser Phe Ile Gly Met Val Ile Phe Thr Phe Thr Leu Asp Leu Arg
 65                  70                  75                  80

Tyr Ile Ile Ile Val Phe Val Thr Gly Gly Val Leu Gly Phe Phe Met
                 85                  90                  95

Thr Gly Tyr Leu Pro Leu Gly Phe Glu Phe Ala Val Glu Ile Thr Tyr
            100                 105                 110

Pro Glu Ser Glu Gly Thr Ser Ser Gly Leu Leu Asn Ala Ser Ala Gln
        115                 120                 125

Ile Phe Gly Ile Leu Phe Thr Leu Ala Gln Gly Lys Leu Thr Ser Asp
    130                 135                 140

Tyr Gly Pro Lys Ala Gly Asn Ile Phe Leu Cys Val Trp Met Phe Ile
145                 150                 155                 160

Gly Ile Ile Leu Thr Ala Leu Ile Lys Ser Asp Leu Arg Arg His Asn
                165                 170                 175

Ile Asn Ile Gly Ile Thr Asn Val Asp Val Lys Ala Ile Pro Ala Asp
            180                 185                 190

Ser Pro Thr Asp Gln Glu Pro Lys Thr Val Met Leu Ser Lys Gln Ser
        195                 200                 205

Glu Ser Ala Ile
    210


<210> SEQ ID NO 93
<211> LENGTH: 2922
<212> TYPE: DNA
```

<213> ORGANISM: Homo sapiens

<400> SEQUENCE: 93

```
gaggcgggtt aaggtctgag ggtcttgtgg ggccacggcg ctgatcacca ggtgtttggc     60
ttggtcggtt cttatttctc gcctggcaat ggcgacgtac acctgcataa cttgccgggt    120
ggcgttccgc gacgcggaca tgcagcgggc ccactataag acggactggc accgctacaa    180
cctgcggcgg aaggtggcca gcatggcccc agtgaccgcc gagggcttcc aggagcgagt    240
gcgggcgcag cgggccgtcg cggaggagga gagcaagggc tcggccacct actgcaccgt    300
ttgcagtaag aagtttgcct ctttcaacgc ctacgagaac cacctcaagt cccggcgtca    360
cgttgagctg gagaagaagg ccgtgcaggc agtgaatcgg aaagtggaga tgatgaatga    420
aaagaacttg gagaaaggac tgggcgtgga cagtgtggac aaggatgcca tgaacgcggc    480
catccagcag gccatcaagg cccagccgtc catgtctccc aagaaggcgc ccccagcgcc    540
tgcaaaggag gccaggaatg tcgtggccgt gggtactggt ggccgtggga cccacgaccg    600
agacccgagt gagaaaccac cccggctcca gtggtttgaa cagcaggcga agaagttggc    660
aaagcagcag gaggaggaca gcgaggagga ggaagaggac ctggatggag acgattggga    720
agatattgat tctgatgaag aattggaatg tgaggatact gaagcaatgg acgatgtggt    780
ggagcaggat gcagaggagg aagaggctga ggaaggccca ccccttggtg ccatccctat    840
cacggactgc ttattttgtt cccatcattc cagctcgctg atgaagaatg tggctcacat    900
gaccaaagac cacagtttct ttattcctga tatagaatat ctttcagata ttaagggact    960
gattaaatac ttgggagaga aagttggtgt tggcaagatt tgcttgtggt gcaacgagaa   1020
agggaagtcc ttctactcca cagaagctgt acaggcacat atgaatgaca aaagccactg   1080
taagctcttc acagatggcg atgctgcttt ggaatttgca gacttctatg attttaggag   1140
tagctatcca gatcacaagg aaggggagga ccccaataag gctgaggagt tgccctcaga   1200
aaagaacttg gaatatgatg atgaaaccat ggaattgatt ctgccttctg gtgccagagt   1260
gggtcatcgc tccttgatga gatactacaa acagcgattt ggcttgtcaa gagctgtggc   1320
agttgccaaa aatcggaagg ccgtgggccg agtacttcag cagtacagag ccctgggatg   1380
gactggcagc acaggtacat tgatctttac aactacagac cagtctgaga acttgtattt   1440
ctagaagggg tctggggaaa gttgtttcca tttatgttgt ccatgtggat tctctctagg   1500
ggaaacgtaa cgtcttggct ccagggactt ccattaccac ttgatatgtt taaggcaata   1560
agcccaaagt gctatgactt agaaatttca tattcctggc acagtgattt tatataccat   1620
taactttttc agaagataat agttacaaaa agaattattt agtaatcacc aaaggttgaa   1680
attatcctgg aggttatgca gaggaattag atagtatcct agtggttaat agcttgagct   1740
gtggagtcag acgtgactta tgtgatgtac ttagaggttc ttatatgatg aacatgagta   1800
atttaattaa tataagcttc tgtttcctca tttataaaac agagatgata gtaataagac   1860
ctacctctta gagttgagtg ggttgaatgt catgcatgtg tgatatagtg catgcccata   1920
gtcgaggtta gctatcagtc ccctttttttg taattttccc atagaaaatt tagcaaaagt   1980
tagaagagta aagcatgcca ctgcaattgt tgagttttga aacctcatca gtatggtact   2040
ctttacatct attctgatgt gtcttctgga tgaagctggt tatatcctta gatcttcagg   2100
gaaagcatct atccaactga ggactgtgga gaaaataaga ggcgggctgc cttctgatgg   2160
cctgggaagc tctaggcaac taaaatccat ttgaaaaggc actgtgttta tatgtggttt   2220
ccttcactgt ggctgcttgt gagctgtgtg gccacttgaa tctggcagag acttgacttc   2280
```

```
atcttactct tatcaggaag tattgtctga ctcgatatat agcttctgcc tttctgatta   2340

atggggcttt accttttggg cttataaact cttccagatg atgaaaacta aagctactaa   2400

tcccagataa gtgtatatat acaaaagttc tggtatgcaa ttctggagtc cacagagacc   2460

cctgaggcgc atggcttaga gaccccaagt tagcaactct gttttaaata caagaaccta   2520

gttaccccaa actaaccttt tgaattctct gccaaggttg gattttctct gatcacaaat   2580

aacagaactt tgcctaattt cttaactgcc ttccaatcat aggagcggct cttatgcgag   2640

agcgagacat gcagtatgtc caaaggatga aatcaaaatg gatgctgaag acaggaatga   2700

agaacaatgc caccaagcag atgcactttc gggtccaagt gagattctga gagtctgctg   2760

ggattgagca atcatctcct gcccaagttt cctccttgcc ctgaggacca gtgaaagaca   2820

gatcatagga gagacccttt tgctgctact tcattcgttc tgacctaata ataaaagtta   2880

gaaccataaa aaaaaaaaaa aaaaaaaaaa aaaaaaaaaa aa                      2922
```

```
<210> SEQ ID NO 94
<211> LENGTH: 451
<212> TYPE: PRT
<213> ORGANISM: Homo sapiens

<400> SEQUENCE: 94

Met Ala Thr Tyr Thr Cys Ile Thr Cys Arg Val Ala Phe Arg Asp Ala
  1               5                  10                  15

Asp Met Gln Arg Ala His Tyr Lys Thr Asp Trp His Arg Tyr Asn Leu
             20                  25                  30

Arg Arg Lys Val Ala Ser Met Ala Pro Val Thr Ala Glu Gly Phe Gln
         35                  40                  45

Glu Arg Val Arg Ala Gln Arg Ala Val Ala Glu Glu Glu Ser Lys Gly
     50                  55                  60

Ser Ala Thr Tyr Cys Thr Val Cys Ser Lys Lys Phe Ala Ser Phe Asn
 65                  70                  75                  80

Ala Tyr Glu Asn His Leu Lys Ser Arg Arg His Val Glu Leu Glu Lys
                 85                  90                  95

Lys Ala Val Gln Ala Val Asn Arg Lys Val Glu Met Met Asn Glu Lys
            100                 105                 110

Asn Leu Glu Lys Gly Leu Gly Val Asp Ser Val Asp Lys Asp Ala Met
        115                 120                 125

Asn Ala Ala Ile Gln Gln Ala Ile Lys Ala Gln Pro Ser Met Ser Pro
    130                 135                 140

Lys Lys Ala Pro Pro Ala Pro Ala Lys Glu Ala Arg Asn Val Val Ala
145                 150                 155                 160

Val Gly Thr Gly Gly Arg Gly Thr His Asp Arg Asp Pro Ser Glu Lys
                165                 170                 175

Pro Pro Arg Leu Gln Trp Phe Glu Gln Gln Ala Lys Lys Leu Ala Lys
            180                 185                 190

Gln Gln Glu Glu Asp Ser Glu Glu Glu Glu Glu Asp Leu Asp Gly Asp
        195                 200                 205

Asp Trp Glu Asp Ile Asp Ser Asp Glu Glu Leu Glu Cys Glu Asp Thr
    210                 215                 220

Glu Ala Met Asp Asp Val Val Glu Gln Asp Ala Glu Glu Glu Glu Ala
225                 230                 235                 240

Glu Glu Gly Pro Pro Leu Gly Ala Ile Pro Ile Thr Asp Cys Leu Phe
                245                 250                 255
```

-continued

```
Cys Ser His His Ser Ser Ser Leu Met Lys Asn Val Ala His Met Thr
            260                 265                 270

Lys Asp His Ser Phe Phe Ile Pro Asp Ile Glu Tyr Leu Ser Asp Ile
        275                 280                 285

Lys Gly Leu Ile Lys Tyr Leu Gly Glu Lys Val Gly Val Gly Lys Ile
    290                 295                 300

Cys Leu Trp Cys Asn Glu Lys Gly Lys Ser Phe Tyr Ser Thr Glu Ala
305                 310                 315                 320

Val Gln Ala His Met Asn Asp Lys Ser His Cys Lys Leu Phe Thr Asp
                325                 330                 335

Gly Asp Ala Ala Leu Glu Phe Ala Asp Phe Tyr Asp Phe Arg Ser Ser
            340                 345                 350

Tyr Pro Asp His Lys Glu Gly Glu Asp Pro Asn Lys Ala Glu Glu Leu
        355                 360                 365

Pro Ser Glu Lys Asn Leu Glu Tyr Asp Asp Glu Thr Met Glu Leu Ile
    370                 375                 380

Leu Pro Ser Gly Ala Arg Val Gly His Arg Ser Leu Met Arg Tyr Tyr
385                 390                 395                 400

Lys Gln Arg Phe Gly Leu Ser Arg Ala Val Ala Val Ala Lys Asn Arg
                405                 410                 415

Lys Ala Val Gly Arg Val Leu Gln Gln Tyr Arg Ala Leu Gly Trp Thr
            420                 425                 430

Gly Ser Thr Gly Thr Leu Ile Phe Thr Thr Thr Asp Gln Ser Glu Asn
        435                 440                 445

Leu Tyr Phe
    450
```

<210> SEQ ID NO 95
<211> LENGTH: 1395
<212> TYPE: DNA
<213> ORGANISM: Homo sapiens

<400> SEQUENCE: 95

```
ctgcagtctg tctgagggcg gccgaagtgg ctggctcatt taagatgagg cttctgctgc     60

ttctcctagt ggcggcgtct gcgatggtcc ggagcgaggc ctcggccaat ctgggcggcg    120

tgcccagcaa gagattaaag atgcagtacg ccacggggcc gctgctcaag ttccagattt    180

gtgtttcctg aggttatagg cgggtgtttg aggagtacat gcgggttatt agccagcggt    240

acccagacat ccgcattgaa ggagagaatt acctccctca accaatatat agacacatag    300

catctttcct gtcagtcttc aaactagtat taataggctt aataattgtt ggcaaggatc    360

cttttgcttt ctttggcatg caagctccta gcatctggca gtggggccaa gaaaataagg    420

tttatgcatg tatgatggtt ttcttcttga gcaacatgat tgagaaccag tgtatgtcaa    480

caggtgcatt tgagataact ttaaatgatg tacctgtgtg gtctaagctg gaatctggtc    540

accttccatc catgcaacaa cttgttcaaa ttcttgacaa tgaaatgaag ctcaatgtgc    600

atatggattc aatcccacac catcgatcat agcaccacct atcagcactg aaaactcttt    660

tgcattaagg gatcattgca agagcagcgt gactgacatt atgaaggcct gtactgaaga    720

cagcaagctg ttagtacaga ccagatgctt tcttggcagg ctcgttgtac ctcttggaaa    780

acctcaatgc aagatagtgt ttcagtgctg gcatattttg gaattctgca cattcatgga    840

gtgcaataat actgtatagc tttccccacc tcccacaaag tcacccagtt aatgtgtgtg    900

tgtgtttttt ttttaaggta aacattacta cttgtaactt tttttcttag tcatatttga    960
```

-continued

```
aaaagtagaa aattgagtta caatttgatt ttttttccaa agatgtctgt taaatctgtt   1020

gtgcttttat atgaatattt gtttttata gtttaaaatt gatcctttgg gaatccagtt   1080

gaagttccca aatactttat aagagtttat cagacatctc taatttggcc atgtccagtt   1140

tatacagttt acaaaatata gcagatgcaa gattatgggg gaaatcctat attcagagta   1200

ctctataaat ttttgtgtat gtgtgtatgt gcgtgtgatt accagagaac tactaaaaaa   1260

accaactgct ttttaaatcc tattgtgtag ttaaagtgtc atgccttgac caatctaatg   1320

aattgattaa ttaactgggc ctttatactt aactaaataa aaaactaagc agatatgaaa   1380

aaaaaaaaaa aaaaa                                                    1395
```

<210> SEQ ID NO 96
<211> LENGTH: 137
<212> TYPE: PRT
<213> ORGANISM: Homo sapiens

<400> SEQUENCE: 96

```
Met Arg Val Ile Ser Gln Arg Tyr Pro Asp Ile Arg Ile Glu Gly Glu
  1               5                  10                  15

Asn Tyr Leu Pro Gln Pro Ile Tyr Arg His Ile Ala Ser Phe Leu Ser
             20                  25                  30

Val Phe Lys Leu Val Leu Ile Gly Leu Ile Ile Val Gly Lys Asp Pro
         35                  40                  45

Phe Ala Phe Phe Gly Met Gln Ala Pro Ser Ile Trp Gln Trp Gly Gln
     50                  55                  60

Glu Asn Lys Val Tyr Ala Cys Met Met Val Phe Phe Leu Ser Asn Met
 65                  70                  75                  80

Ile Glu Asn Gln Cys Met Ser Thr Gly Ala Phe Glu Ile Thr Leu Asn
                 85                  90                  95

Asp Val Pro Val Trp Ser Lys Leu Glu Ser Gly His Leu Pro Ser Met
            100                 105                 110

Gln Gln Leu Val Gln Ile Leu Asp Asn Glu Met Lys Leu Asn Val His
        115                 120                 125

Met Asp Ser Ile Pro His His Arg Ser
    130                 135
```

<210> SEQ ID NO 97
<211> LENGTH: 1299
<212> TYPE: DNA
<213> ORGANISM: Homo sapiens

<400> SEQUENCE: 97

```
aggatatcga attcaatcgg gaccaaaggt cagaaagaaa agttatctga gtagactgat     60

gctctcaaac aggcttccgt tctctgcagc gaagagcctc ataaattccc cttcacaagg    120

ggctttttca tccttaagag acctgagtcc tcaagaaaat ccttttctgg aagtatctgc    180

tccttcagaa cattttatag aaaacaataa tacaaaagac acaactgcaa gaaatgcctt    240

tgaagaaaat gtttttatgg aaaacactaa catgccagaa ggaaccatct ctgaaaacac    300

aaactacaat catcctcctg aggcagattc cgctgggact gcattcaact tagggccaac    360

tgttaaacaa actgagacaa aatgggaata caacaacgtg ggcactgacc tgtcccccga    420

gcccaaaagc ttcaattacc cattgctctc gtcccaggtg atcagtttga aattcagcta    480

acccagcagc tgcagtccgt tatccccaac aacaatgtga gaaggctcat tgctcatgtt    540

atccggacct tgaagatgga ctgctctggg gcccatgtgc aagtgacctg tgccaagctc    600
```

-continued

```
gtctccagga caggccacct gatgaagctt ctcagtgggc agcaggaagt aaaggcatcc    660

aagatagaat gggatacgga ccaatggaag actgagaact acattaatga gagcacagaa    720

gcccagagtg aacagaaaga gaagtcgctt gagttcacaa aagaacttcc aggatatggc    780

tataccaaaa aactcatctt ggcgttaatt gtgactggaa tactaacgat tttgattata    840

cttctctgcc tcattgagat ctgttgtcac cgaaggtcat tacaagaaga tgaagaagga    900

ttctcaaggg acagcgaagc cccaacggag gaggagagtg aagccctgcc ataggaggag    960

aacccagccc acctcaggcc tcctgcaaaa atacatagcg taaacaacgg ccatcaaaaa   1020

agcaggactg aagccagcgg cccacacatc cacagaggca gcgggcagag caagcacagg   1080

gccatcgttc ctgcccttgt ttcccagtct aattagtcac ccagacctga aaacatatgc   1140

tcagggggtg gagattttac aattaaataa cattgttttt ggtgccctcc aaaaaaaaaa   1200

aaaaaaaaaa aaaaaaaaaa aaaaaaaaaa aaaaaaaaaa aaaaaaaaaa aaaaaaaaaa   1260

aaaaaaaaaa aaaaaaaaaa aaaaaaaaaa aaaaaaaaa                          1299
```

<210> SEQ ID NO 98
<211> LENGTH: 132
<212> TYPE: PRT
<213> ORGANISM: Homo sapiens

<400> SEQUENCE: 98

```
Met Asp Cys Ser Gly Ala His Val Gln Val Thr Cys Ala Lys Leu Val
  1               5                  10                  15

Ser Arg Thr Gly His Leu Met Lys Leu Leu Ser Gly Gln Gln Glu Val
             20                  25                  30

Lys Ala Ser Lys Ile Glu Trp Asp Thr Asp Gln Trp Lys Thr Glu Asn
         35                  40                  45

Tyr Ile Asn Glu Ser Thr Glu Ala Gln Ser Glu Gln Lys Glu Lys Ser
     50                  55                  60

Leu Glu Phe Thr Lys Glu Leu Pro Gly Tyr Gly Tyr Thr Lys Lys Leu
 65                  70                  75                  80

Ile Leu Ala Leu Ile Val Thr Gly Ile Leu Thr Ile Leu Ile Ile Leu
                 85                  90                  95

Leu Cys Leu Ile Glu Ile Cys Cys His Arg Arg Ser Leu Gln Glu Asp
            100                 105                 110

Glu Glu Gly Phe Ser Arg Asp Ser Glu Ala Pro Thr Glu Glu Glu Ser
        115                 120                 125

Glu Ala Leu Pro
    130
```

<210> SEQ ID NO 99
<211> LENGTH: 915
<212> TYPE: DNA
<213> ORGANISM: Homo sapiens

<400> SEQUENCE: 99

```
cgagcatccc gctgccccgg accctcccgc gggcgcgcac caggctcaac tcaggctcag     60

gactgcaggt agacatctcc actgcccagg aatcactgag cgtgcagaca gcacagcctc    120

ctctgaaggc cggccatacc agagtcctgc ctcggcatgg gcctcaccat tgaggcagct    180

ccactgtctg tgctggtctg agggtgctgc ctgtcatggg ggcagccatc tcccaggggg    240

ccctcatcgc catcgtctgc aacggtctcg tgggcttctt gctgctgctg ctctgggtca    300

tcctctgctg ggcctgccat tctcgctctg ccgacgttga ctctctctct gaatccagtc    360
```

-continued

```
ccaactccag ccctggcccc tgtcctgaga aggccccacc accccagaag cccagccatg    420

aaggcagcta cctgctgcag ccctgaaggc ccctggccta gcctggagcc caggacctaa    480

gtccacctca cctagagcct ggaattagga tcccagagtt cagccagcct ggggtccaga    540

actcaagagt ccgcctgctt ggagctggac ccagcggccc agagtctagc cagcttggct    600

ccaataggag ctcagtggcc ctaaggagat gggcctgggg tgggggctta tgagttggtg    660

ctagagccag ggccatctgg actatgctcc atcccaaggg ccaagggtca ggggccgggt    720

ccactctttc cctaggctga gcacctctag gccctctagg ttggggaagc aaactggaac    780

ccatggcaat aataggaggg tgtccaggct gggcccctcc cctggtcctc ccagtgtttg    840

ctggataata aatggaacta tggctctaaa aaaaaaaaaa aaaaaaaaaa aaaaaaaaaa    900

aaaaaaaaaa aaaaa                                                     915
```

<210> SEQ ID NO 100
<211> LENGTH: 76
<212> TYPE: PRT
<213> ORGANISM: Homo sapiens

<400> SEQUENCE: 100

```
Met Gly Ala Ala Ile Ser Gln Gly Ala Leu Ile Ala Ile Val Cys Asn
  1               5                  10                  15

Gly Leu Val Gly Phe Leu Leu Leu Leu Leu Trp Val Ile Leu Cys Trp
             20                  25                  30

Ala Cys His Ser Arg Ser Ala Asp Val Asp Ser Leu Ser Glu Ser Ser
         35                  40                  45

Pro Asn Ser Ser Pro Gly Pro Cys Pro Glu Lys Ala Pro Pro Pro Gln
     50                  55                  60

Lys Pro Ser His Glu Gly Ser Tyr Leu Leu Gln Pro
 65                  70                  75
```

<210> SEQ ID NO 101
<211> LENGTH: 2915
<212> TYPE: DNA
<213> ORGANISM: Homo sapiens

<400> SEQUENCE: 101

```
caaacttgga gggaaacttc attcatttgg tttattttta tttttatttt tatttatctt     60

tttgagacag aatctcactc tggtttgaga cagaatctca ctgtgtcccc caggttggag    120

tgcggtggtg cgatctcggc tcactgaaac ctctgcctcc tgggttcaag cgattctcct    180

gcttcaccct ccgagtagct gggattacag gtgtgcacca ccacacccgg ctaatttttg    240

tatttttggt agagacggtt tcgccacatt ggctaggttg gtgtcaaact cctggcctca    300

aagtgatccg cccaccttgg cctcccaaag tggagccccc gtgccccttg tttgtgacct    360

gtcaatataa atatgctcag tagcgggggg aggggtgggg ggtgaaaaag gaaatatgtt    420

taatattaag actttggcct tttagtgtaa actgatattc aaaaatttct tcatagaaca    480

tttgcttctt tgcttgatca tttttctaat tctgtacatc taaaatgccc agaatttgag    540

ttgctgttat agtctactaa catagaactt tggagtaata agatgggaat ttgtctctct    600

tttgccaaga caagtattcg taatctaaca cagtattgtt gccacgagta cgagtatgtg    660

atagactgtt gagaataaag aaagcaggca cagttggtca gtcctaagat aaaggagatg    720

ttttttctta tatgtttgtg cattaaagaa aaaaaaatct tgaatctgac caatgatgtt    780

ttttttcctt gtaagaaaat ttaacaaatg tttggcaagc ttctggaatc taaatttgaa    840
```

-continued

```
attatacatt tgtcattttc tttaaatatt tcttcacctt agctttgatt atgagaaatc    900
actgtcctct gctgttcttt tttttttttt ttcttttgag gcggagtctc actctgtgcc    960
aggctggagt gcagtggtgc aatctcggct cactgcaacc tccacttcct gggttcaaat   1020
gattctcctg ccgcagcctc ccgagtagct gggactacag gtgcatgcca ccacacccag   1080
ctaatttttg tatttttggt agagacaggg tttcaccacg ttgtccatgg ccaggatggt   1140
cttgatcttg accttgtgat ccgcccgcct cggcctccca aagtgctggg attgcaggca   1200
tgagccaccg tgcccggcct gtcctctgtg gttttctggg cttatgttaa aattataact   1260
caatcaccag tctttatata tttgcttttt tatatttaaa ccaaacctaa tgctaattgt   1320
gatatgttat ttattctcac ctgatttgaa tcattggatt caattaaatg agtttaatta   1380
tcattaaata attctaagag aaataatgtc tattcggatg gtgggaattt tctttctaca   1440
tgcagcccca ttctgaatga atgaaatcaa atcatgtgaa gatcagggtc ctagagtaac   1500
ctaatatttt gtacattggt tatttgactc ctcattttta tattaaatgt tatatcaagg   1560
gagggggtat aaaagaaata caaaaattgc agaggtatct ggaatgtacc tatttgttaa   1620
ttctatttgt catttctttt gtttcatctt ttgagtaata agctgcttgg aaaagtttct   1680
gttctttagc tgattttta gctataaaaa tgtatttgaa aagctcataa atttcaggat   1740
tgaaaagata attggaagtt taaaaaaaac ctaattcatt gaagtaataa ccaaataatt   1800
ttcaatcttg attcaactgt gattcaaatc ttacaccatt tgcccacttc tatgaatttt   1860
atgtataaaa tttttaaga gtcagagttt ttttttcttg attaattgga tgtatttcac   1920
agaatttcca actgctcacg ttagttttct tccttttaga gttgatctct ctaatgtatt   1980
agatcttcat gcctttgata gtctctctgg aataagttgt ttttagtttg cagaaaaaac   2040
ttcagcatgt gccaggaaca caacctcacc ttgatcagag tattgttaca atcacatttg   2100
aagtaccagg aaatgcaaag gaagaacatc ttaatatgtt tattcagaat ctcctgtggg   2160
aaaagaatgt gagaaacaag gacaatcact gcatggaggt cataaggctg aagggattgg   2220
tgtcaatcaa agacaaatca caacaagtga ttgtccaggg tgtccatgag ctctatgatc   2280
tggaggagac tccagtgagc tggaaggatg acactgagag aacaaatcga ttggtcctca   2340
ttggcagaaa tttagataag gatatcctta aacagctgtt tatagctact gtgacagaaa   2400
cagaaaagca gtggacaaca catttcaaag aagatcaagt ttgtacataa cactagtggc   2460
atttcttatc aaaaggattg gataataaaa ataagtttct actgggtata tttcaagcat   2520
ttatttatta ctttagttac gaattccaat atactttaaa atggtatttg ttttacagca   2580
tacataaaat gtagcaaatc agtactgtaa aacatttaac attcatacaa ttatatataa   2640
tatccttttt tttaaagaat ggtatttcac aaaaatatct tttgaaattg gctttggagt   2700
ttacatatac tgaacatgaa agtttataat aatgatgata caactttcaa cattgtcatt   2760
ttttcttaga acttcagctg attgcagaga tataatgatt acattgttat taaatttttt   2820
taacacaagt aagtgtcacc attttatgac atgaaataaa aggttatgac tgttaaaaaa   2880
aaaaaaaaaa aaaaaaaaaa aaaaaaaaaa aaaaa                              2915
```

<210> SEQ ID NO 102
<211> LENGTH: 104
<212> TYPE: PRT
<213> ORGANISM: Homo sapiens

<400> SEQUENCE: 102

Met Phe Ile Gln Asn Leu Leu Trp Glu Lys Asn Val Arg Asn Lys Asp

-continued

```
  1               5                  10                  15

Asn His Cys Met Glu Val Ile Arg Leu Lys Gly Leu Val Ser Ile Lys
             20                  25                  30

Asp Lys Ser Gln Gln Val Ile Val Gln Gly Val His Glu Leu Tyr Asp
         35                  40                  45

Leu Glu Glu Thr Pro Val Ser Trp Lys Asp Asp Thr Glu Arg Thr Asn
     50                  55                  60

Arg Leu Val Leu Ile Gly Arg Asn Leu Asp Lys Asp Ile Leu Lys Gln
 65                  70                  75                  80

Leu Phe Ile Ala Thr Val Thr Glu Thr Glu Lys Gln Trp Thr Thr His
                 85                  90                  95

Phe Lys Glu Asp Gln Val Cys Thr
            100
```

<210> SEQ ID NO 103
<211> LENGTH: 1530
<212> TYPE: DNA
<213> ORGANISM: Homo sapiens

<400> SEQUENCE: 103

```
atcgggagat atacctaatg ctagatgatg agttagtggg tgcagcgcac cagcacggca     60

catgtataca tatgtaacta acctgcacaa tgtgcacatg taccctaaaa cttaaagtat    120

atatatataa aaaaagacat cgctagtgag cacgctgtat acgacatcgc taatgaggac    180

accatacaag gcatcgctaa cgatgacgct gtacacaaca tcactaatga tgacaccgta    240

taagacatcg ctaattatga cgctgtatac gacatcgcta atgacaccgt acaaggcacg    300

ctaacgagga tgctgtacac gacatcacta atgaggacag tgtacaagcc atcactaatg    360

aggacactgt atatggcatc gctaacgagg acactgtaca aggcattgct aacgaggacg    420

ctgtacacaa catcgctaat gaggacacca tataagacat caccaatgag gatgctgtat    480

atgacatcgc taatggcacc cacaaggcat gctaacgagg acgctgtaga cgacattgct    540

tataaggaca ccgtacaaga catcgctaac gaggacgctg tatacgacat cgctaatgag    600

gacgttgtat atgacatcgc taatgaggat gctttacaag acatagctaa tgaggttgct    660

gtatatgaca tcgctaatga ggacattgta tatgacatcg ctaatgagga cgctctatac    720

gacatcacta atgaggacgc tgtatacaac atcgctaatg aggacgctgt atatggcatc    780

gctaatgagg atgctgtata cgaattcgct aataaggacg ctgtatatga cattgctaat    840

gaggacactg tacaagacat ctgtaaaaaa gaagatgctg ccaatgagcc attgacactg    900

gagaatgata cgtaccctga aataactcac ttcctgagga aaaagcgcca tctctagggg    960

atctcccggg gtgagtgagg aggcgggatc ggaccctggc agtctgacgg cagcacctgt   1020

gttcctctgc actgggccgt ggatgacatt acacaccttg ccactcccac ggtcctgtgt   1080

gttccggata ttttaaaata atggctataa ggttgagcac ttcaggatac gctgttttgc   1140

tgtgtgcaga tggaggcagt ggctggagtg aatgaacggc aacacttgct ggcaaccggc   1200

agaagctgag agacagggaa caggctctcc tccagagcct ccaggagcca ggcctttgga   1260

caccttgaat gtgggcttct gggagaccat gcgtttctgt tataagcagc ccagtctctg   1320

gcagttttta cggctgcccc ggaacactca tctatacctg tctgacaagg tcaagctcca   1380

aggaagggac tctctacata tctacattgt ttgcagattt tacaataatc atttattctt   1440

gcatggctga tcattgttaa ccaatacaaa taaaataata aagaaatgac ccacatttta   1500

aaaaaaaaaa aaaaaaaaaa aaaaaaaaaa                                    1530
```

<210> SEQ ID NO 104
<211> LENGTH: 215
<212> TYPE: PRT
<213> ORGANISM: Homo sapiens

<400> SEQUENCE: 104

```
Met Leu Tyr Thr Thr Ser Leu Met Arg Thr Val Tyr Lys Pro Ser Leu
  1               5                  10                  15

Met Arg Thr Leu Tyr Met Ala Ser Leu Thr Arg Thr Leu Tyr Lys Ala
             20                  25                  30

Leu Leu Thr Arg Thr Leu Tyr Thr Thr Ser Leu Met Arg Thr Pro Tyr
         35                  40                  45

Lys Thr Ser Pro Met Arg Met Leu Tyr Met Thr Ser Leu Met Ala Pro
     50                  55                  60

Thr Arg His Ala Asn Glu Asp Ala Val Asp Asp Ile Ala Tyr Lys Asp
 65                  70                  75                  80

Thr Val Gln Asp Ile Ala Asn Glu Asp Ala Val Tyr Asp Ile Ala Asn
                 85                  90                  95

Glu Asp Val Val Tyr Asp Ile Ala Asn Glu Asp Ala Leu Gln Asp Ile
            100                 105                 110

Ala Asn Glu Val Ala Val Tyr Asp Ile Ala Asn Glu Asp Ile Val Tyr
        115                 120                 125

Asp Ile Ala Asn Glu Asp Ala Leu Tyr Asp Ile Thr Asn Glu Asp Ala
    130                 135                 140

Val Tyr Asn Ile Ala Asn Glu Asp Ala Val Tyr Gly Ile Ala Asn Glu
145                 150                 155                 160

Asp Ala Val Tyr Glu Phe Ala Asn Lys Asp Ala Val Tyr Asp Ile Ala
                165                 170                 175

Asn Glu Asp Thr Val Gln Asp Ile Cys Lys Lys Glu Asp Ala Ala Asn
            180                 185                 190

Glu Pro Leu Thr Leu Glu Asn Asp Thr Tyr Pro Glu Ile Thr His Phe
        195                 200                 205

Leu Arg Lys Lys Arg His Leu
    210                 215
```

<210> SEQ ID NO 105
<211> LENGTH: 2423
<212> TYPE: DNA
<213> ORGANISM: Homo sapiens

<400> SEQUENCE: 105

```
gactgcaccg tgactaacat gcagtgacag cttaattaat gttaaccctt atcattatca      60

tataagaatg tgagttacat aagagaggag tcctgtcagt tcgttctctg ctgtgtcccc     120

aagaccatga atcatggctg gcatgtagta ggcatttaat aatatatgtt caacaagtat     180

ttggcagtct tggagggcag aaaaggaggt ggggaagatt tttaaataac atttttttaaa     240

aagtcacatt gtcctacaat actgattttt cttgcatatt taggaaattg agggtttttt     300

tctaaaacat gcggacatat gggaaatagg atgcaacatt tgcactaatg tttcagacac     360

agttagaggt ttccaagaga ttttgcgctg gggaggctgc ttgctacaag ctcccaaagc     420

tctgggagga catagtattc attcctccct cagcagaagc ggtgaggcaa gaagctctgg     480

ggagcaccca gcgttggact tttagcatag tgtgtcaggt cttcatagtt tgggcccagg     540

gcacagagaa gtcacagctc tccggcatcc tgtgaccttt accctctttg ccaagggaaa     600
```

-continued

```
atgtggccca ccaaagcaag aaacttgagg gcatgggtca ccccagccct ggcatctgcc    660

cagagcccga gaaggaagga acaatgatcc tccagctacc tcacggggct ggcacaggtg    720

accactgccc tggcatcacc cagctgtgtc cggcagcctg aaccccatct gtggggatgc    780

gaggaggaaa atacaaaagt ccttaggtga acactgagaa ggcagatgca gcagaaacct    840

ccaggccaga actacccagt cttggaccta tggtggagat agagcatagc tggcgatcat    900

gtgtacttac actctaaggt cacctggttg cactatggcc tcatctgtgg ctctgaaaat    960

gaagatttgg aaggagatca tcacagctaa tgtttaacaa gcccctcctg tgtgccaaat   1020

cattcacccc tcaccacaac cgaatgagct aaggattctc attatatata gtttatggag   1080

agggaagtgc agacataaag aggtgaatta tcttacccag atcacacagc tgataagtgg   1140

tggaggcaga atagaatcta aacagtgtgg ctccggagcc cacatgcatt gattcgacaa   1200

gtgtttattg agcacctgcc gcggacaagg ccttgtgtga ttaaataggg ttataattag   1260

taatataaaa atgagaaatc actaatgctt tttagactta acattttgtt tttttgtagg   1320

tttcaggcac agaactgtat atccaataat agtgaaatgg atcccactaa ttatgacaga   1380

aatgatgata catttaaatg acttggatgt tttataggta tgatctcgtg aaatcttgag   1440

agaaactgaa tgacgaatga aactattgtt cctgtttcac acagaagaaa actgaggtta   1500

aaaggggtaa agtaattttg catggcatga agtagaaatt caaagtacag gaatttgaac   1560

ttggttctgt ccttttctga agcccttgac cactatagac tcaaacatca ccttgttttt   1620

ccactcattc aacacttttt tttttaaatt atctaatagg ttggcactca tcatgagccc   1680

ctgttctcat tctgcaaatg gtgaagctct ctattgtcct gaccccacag ttcctgtccc   1740

atgaccaggg ccagctcacc aaggagctgc agcagcatgt aaagtcagtg acatgcccat   1800

gcgagtacct gaggaaggtg agtgagtgca gacagatggg gcctggtgcc cttgagcagt   1860

tcccgggtct cagctgccac acatctcata gccggtgatg ctgggggaag cttacgcagt   1920

cacagtactg gcttcttcct ctttttcttt ccatacaagt ggcttaggga tggggtagag   1980

tagttgactt atttggatga aaaccactat cttctgtcag aaactcaaaa ggaatcattg   2040

ctggcatggt aacctaaaga aaaacaacca gacaagtgcc caacgacact taaaaaggtg   2100

atttattatc ttgccaagtt tgggctgggc atggtgactc atgcctctaa tcccagcatt   2160

ttgggaggct gaggctggtg gatcaccgga ggccaggact ttgagaccag cctgaccaat   2220

atggcgaaac ctcgtccctg ctgggaatgc aaaggttagc cgggcatggt ggtgtgagcc   2280

tgtagtccca gctactcagg aggctgagac aggagaattg cttggattcg ggaggtgggg   2340

gttttggtgg gccgagatca cgccattgca ctccagactg tgcgacagag cgagactctg   2400

tcaaaaaaaa aaaaaaaaaa aaa                                           2423
```

<210> SEQ ID NO 106
<211> LENGTH: 66
<212> TYPE: PRT
<213> ORGANISM: Homo sapiens

<400> SEQUENCE: 106

```
Met Val Lys Leu Ser Ile Val Leu Thr Pro Gln Phe Leu Ser His Asp
  1               5                  10                  15

Gln Gly Gln Leu Thr Lys Glu Leu Gln Gln His Val Lys Ser Val Thr
             20                  25                  30

Cys Pro Cys Glu Tyr Leu Arg Lys Val Ser Glu Cys Arg Gln Met Gly
         35                  40                  45
```

-continued

```
Pro Gly Ala Leu Glu Gln Phe Pro Gly Leu Ser Cys His Thr Ser His
     50                  55                  60

Ser Arg
 65


<210> SEQ ID NO 107
<211> LENGTH: 1418
<212> TYPE: DNA
<213> ORGANISM: Homo sapiens

<400> SEQUENCE: 107

cttttgggca gtttgatcac tgatcgagta aggaatgacc tttagattgt gcgacttttg     60

tttttgtttt tttaaatttt tttaaaccaa gaatgatttc tcctgcttcc ttctcctcac    120

catcttccca gacggagttc aaaggccact tctcaagcag cttttggcac cttcagcctc    180

agagtggaat cttttaaaga caggacccct atgtccagga aaggggaaaa ggaactttgc    240

caatgatagt gaccacagca aaagcaaata ataataatat taataataat aaagagaaat    300

aaaataataa aataaaaaac aatagcacag cccttgttga ggtcagcagg gaggaggggc    360

tgcccggagt tgggtccttg cctggatttt gacacagcaa cttcctgtag tgagcacttt    420

gtatgaatcg tggacttcct gttctcaagg cgcaggtatt tattctgtat ctgtctagag    480

cacacaccaa aatccaacct tctaataaac atgatggcgc agtcccactc cctgcctcgc    540

ctgttcccct atccccccca ggcctgggat cttcaggcgt cggtgtgggg aggggcccct    600

gccctccttg ccttgatttt gctcccctgg gtccagctgg ttccaggcct gtgaatgtca    660

gttcgtcggg cactgactcc gtctgctctt ggccttgggt tcatttgaca aatatttgcc    720

cagggcctcc caggcccagc cccatgccac ctgggccccg gcatctcttt gaggttctgc    780

caatgtgctc ttagctgagg acgaaggagg aacacctttc tatgagtctt gcaaagttta    840

cctccttcag gccacaaata tttgagtgca cactacgtgc caggcactgt gcagggctgc    900

aggcatagag acagaatgta atctagctgg gccttggacc ccatagggag aggggaccac    960

tcaggtccat acttcctttg gacttggggc tttggccttg ggaggggtgg aggtggggtg   1020

gcaagatgaa aaagacatcc tgccccccatc cacttcggca gagcttctca aagtctcaag   1080

catgtcttgg gagcttgtta aaagggctga ttccttgctg tggctcacgc ctgtaatcct   1140

gacattttgg gaggccaagg caaattgcct gagctcaggg gtttgagacc agcctgggca   1200

acatgtcgga accctgtttc tacaaaaaat acaagaatta gttgggcgtg gtggggcaca   1260

ccacacctgt ggtcccagct actctgggac tgaggtggga gaactgcttg agcctgggag   1320

gcagaggttg cagtaggtct agatcaggtc actgcactcc agcctgtgca acaaaacaac   1380

agagcaggac cctgtctcaa aaaaaaaaaa aaaaaaaa                           1418


<210> SEQ ID NO 108
<211> LENGTH: 123
<212> TYPE: PRT
<213> ORGANISM: Homo sapiens

<400> SEQUENCE: 108

Met Asn Arg Gly Leu Pro Val Leu Lys Ala Gln Val Phe Ile Leu Tyr
  1               5                  10                  15

Leu Ser Arg Ala His Thr Lys Ile Gln Pro Ser Asn Lys His Asp Gly
             20                  25                  30

Ala Val Pro Leu Pro Ala Ser Pro Val Pro Leu Ser Pro Pro Gly Leu
         35                  40                  45
```

-continued

```
Gly Ser Ser Gly Val Gly Val Gly Arg Gly Pro Cys Pro Pro Cys Leu
     50                  55                  60

Asp Phe Ala Pro Leu Gly Pro Ala Gly Ser Arg Pro Val Asn Val Ser
 65                  70                  75                  80

Ser Ser Gly Thr Asp Ser Val Cys Ser Trp Pro Trp Val His Leu Thr
                 85                  90                  95

Asn Ile Cys Pro Gly Pro Pro Arg Pro Ser Pro Met Pro Pro Gly Pro
            100                 105                 110

Arg His Leu Phe Glu Val Leu Pro Met Cys Ser
        115                 120
```

<210> SEQ ID NO 109
<211> LENGTH: 1199
<212> TYPE: DNA
<213> ORGANISM: Homo sapiens

<400> SEQUENCE: 109

```
gtcggttggc gaggtcactg caggtcagag gtcacgagat caaggatctg gaaccctgag     60

cctcgaagcg gaggatccct gtgtcccagc cgggcatggc cgacccccac cagcttttcg    120

atgacacaag ttcagcccag agccggggct atggggccca gcgggcacct ggtggcctga    180

gttatcctgc agcctctccc acgccccatg cagccttcct ggctgacccg gtgtccaaca    240

tggccatggc ctatgggagc agcctggccg cgcagggcaa ggagctggtg gataagaaca    300

tcgaccgctt catccccatc accaagctca agtattactt tgctgtggac accatgtatg    360

tgggcagaaa gctgggcctg ctgttcttcc cctacctaca ccaggactgg gaagtgcagt    420

accaacagga caccccggtg gcccccccgct ttgacgtcaa tgccccggac ctctacattc    480

cagcaatggc tttcatcacc tacgttttgg tggctggtct tgcgctgggg acccaggata    540

ggttctcccc agacctcctg ggctgcaagg cgagctcagc cctggcctgg ctgaccctgg    600

aggtgctggc catcctgctc agcctctatc tggtcactgt caacaccgac ctcaccacca    660

tcgacctggt ggccttcttg ggctacaaat atgtcgggat gattggcggg gtcctcatgg    720

gcctgctctt cgggaagatt ggctactacc tggtgctggg ctggtgctgc gtagccatct    780

ttgtgttcat gatccggacg ctgcggctga agatcttggc agacgcagca gctgaggggg    840

tcccggtgcg tggggcccgg aaccagctgc gcatgtacct gaccatggcg gtggcggcgg    900

cgcagcctat gctcatgtac tggctcacct tccacctggt gcggtgagcg cgcccgctga    960

acctcccgct gctgctgctg ctgctggggg ccactgtggc cgccgaactc atctcctgcc   1020

tgcaggcccc aaggtccacc ctgtctggcc acaggcaccg cctccatccc atgtcccgcc   1080

cagccccgcc cccaacccaa ggtgctgaga gatctccagc tgcacaggcc accgccccag   1140

ggcgtggccg ctgttacaga aacaataaac cctgatgggc atggaaaaaa aaaaaaaaa    1199
```

<210> SEQ ID NO 110
<211> LENGTH: 283
<212> TYPE: PRT
<213> ORGANISM: Homo sapiens

<400> SEQUENCE: 110

```
Met Ala Asp Pro His Gln Leu Phe Asp Asp Thr Ser Ser Ala Gln Ser
  1               5                  10                  15

Arg Gly Tyr Gly Ala Gln Arg Ala Pro Gly Gly Leu Ser Tyr Pro Ala
             20                  25                  30

Ala Ser Pro Thr Pro His Ala Ala Phe Leu Ala Asp Pro Val Ser Asn
         35                  40                  45
```

```
Met Ala Met Ala Tyr Gly Ser Ser Leu Ala Ala Gln Gly Lys Glu Leu
     50                  55                  60

Val Asp Lys Asn Ile Asp Arg Phe Ile Pro Ile Thr Lys Leu Lys Tyr
 65                  70                  75                  80

Tyr Phe Ala Val Asp Thr Met Tyr Val Gly Arg Lys Leu Gly Leu Leu
                 85                  90                  95

Phe Phe Pro Tyr Leu His Gln Asp Trp Glu Val Gln Tyr Gln Gln Asp
            100                 105                 110

Thr Pro Val Ala Pro Arg Phe Asp Val Asn Ala Pro Asp Leu Tyr Ile
        115                 120                 125

Pro Ala Met Ala Phe Ile Thr Tyr Val Leu Val Ala Gly Leu Ala Leu
    130                 135                 140

Gly Thr Gln Asp Arg Phe Ser Pro Asp Leu Leu Gly Leu Gln Ala Ser
145                 150                 155                 160

Ser Ala Leu Ala Trp Leu Thr Leu Glu Val Leu Ala Ile Leu Leu Ser
                165                 170                 175

Leu Tyr Leu Val Thr Val Asn Thr Asp Leu Thr Thr Ile Asp Leu Val
            180                 185                 190

Ala Phe Leu Gly Tyr Lys Tyr Val Gly Met Ile Gly Gly Val Leu Met
        195                 200                 205

Gly Leu Leu Phe Gly Lys Ile Gly Tyr Tyr Leu Val Leu Gly Trp Cys
    210                 215                 220

Cys Val Ala Ile Phe Val Phe Met Ile Arg Thr Leu Arg Leu Lys Ile
225                 230                 235                 240

Leu Ala Asp Ala Ala Ala Glu Gly Val Pro Val Arg Gly Ala Arg Asn
                245                 250                 255

Gln Leu Arg Met Tyr Leu Thr Met Ala Val Ala Ala Ala Gln Pro Met
            260                 265                 270

Leu Met Tyr Trp Leu Thr Phe His Leu Val Arg
        275                 280
```

<210> SEQ ID NO 111
<211> LENGTH: 2024
<212> TYPE: DNA
<213> ORGANISM: Homo sapiens

<400> SEQUENCE: 111

```
gatatcttaa gcccgggtac gtcgacaaaa tttgctaagt taatccttct gtatttttgt     60

ctcctagagc tgcttatcat ccagactttc caacagttct gacagcttta gaaatagata    120

atgcggttgt ggcaaatagc ctaattgaca tgagaggcat agagacagtg ctactaatca    180

aaaataattc tgtagctcgt gcagtaatgc agtcccaaaa gccacccaaa aattgtagag    240

aagcttttac tgctgatggt gatcaagttt ttgcaggacg ttattattca tctgaaaata    300

caagacctaa gttcctaagc agagatgtgg attctgaaat aagtgacttg gagaatgagg    360

ttgaaaataa gacggcccag atattaaatc ttcagcaaca tttatctgcc cttgaaaaag    420

atattaaaca caatgaggaa cttcttaaaa ggtgccaact acattataaa gaactaaaga    480

tgaaaataag aaaaaatatt tctgaaattc gggaacttga gaacatagaa gaacaccagt    540

ctgtagatat tgcaactttg gaagatgaag ctcaggaaaa taaaagcaaa atgaaaatgg    600

ttgaggaaca tatggagcaa caaaaagaaa atatggagca tcttaaaagt ctgaaaatag    660

aagcagaaaa taagtatgat gcaattaaat tcaaaattaa tcaactatcg gagctagcag    720

acccacttaa ggatgaatta aaccttgctg attctgaagt ggataaccaa aaacgaggga    780
```

```
aacgacatta tgaagaaaaa caaaaagaac acttggatac cttaaataaa aagaaacgag    840

aactggatat gaaagagaaa gaactagagg agaaaatgtc acaagcaaga caaatctgcc    900

cagagcgtat agaagtagaa aaatctgcat caattytgga caaagaaatt aatcgattaa    960

ggcagaagat acaggcagaa catgctagtc atggagatcg agaggaaata atgaggcagt   1020

accaagaagc aagagagacc tatcttgatc tggatagtaa agtgaggact ttaaaaaagt   1080

ttattaaatt actgggagaa atcatggagc acagattcaa gacatatcaa caatttagaa   1140

ggtgtttgac tttacgatgc aaattatact ttgacaactt actatctcag cgggcctatt   1200

gtggaaaaat gaattttgac cacaagaatg aaactctaag tatatcagtt cagcctggag   1260

aaggaaataa agctgctttc aatgacatga gagccttgtc tggaggtgaa cgttctttct   1320

ccacagtgtg ttttattctt tccctgtggt ccatcgcaga atctcctttc agatgcctgg   1380

atgaatttga tgtctacatg gatatggtta ataggagaat tgccatggac ttgatactga   1440

agatggcaga ttcccagcgt tttagacagt ttatcttgct cacacctcaa agcatgagtt   1500

cacttccatc cagtaaactg ataagaattc tccgaatgtc tgatcctgaa agaggacaaa   1560

ctacattgcc tttcagacct gtgactcaag aagaagatga tgaccaaagg tgatttgtaa   1620

cttaacatgc cttgtcctga tgttgaagga tttgtgaagg gaaaaaaaat tctggactct   1680

ttgatataat aaaatgagac tggaggcatt ctgaaatgaa agaaactcct ttatatatcc   1740

aaccacaatc aaacatataa ataagcctgg aaaaccaact acaaccagca atttaagatt   1800

actattactt taagaaaatc aatttcatag tattggtttt aaatcttttt aagttttttt   1860

aatacgatct atttttatag gttctttttc agaagtaaaa ttttgtacat atatacatgt   1920

acatatctgt ttagtttggg ttcatttcta taacattttg taagaaaata aaagtttgag   1980

cacctgatta aaaaaaaaaa aaaaaaaaaa aaaaaaaaaa aaaa                    2024
```

<210> SEQ ID NO 112
<211> LENGTH: 487
<212> TYPE: PRT
<213> ORGANISM: Homo sapiens

<400> SEQUENCE: 112

```
Met Arg Gly Ile Glu Thr Val Leu Leu Ile Lys Asn Asn Ser Val Ala
  1               5                  10                  15

Arg Ala Val Met Gln Ser Gln Lys Pro Pro Lys Asn Cys Arg Glu Ala
             20                  25                  30

Phe Thr Ala Asp Gly Asp Gln Val Phe Ala Gly Arg Tyr Tyr Ser Ser
         35                  40                  45

Glu Asn Thr Arg Pro Lys Phe Leu Ser Arg Asp Val Asp Ser Glu Ile
     50                  55                  60

Ser Asp Leu Glu Asn Glu Val Glu Asn Lys Thr Ala Gln Ile Leu Asn
 65                  70                  75                  80

Leu Gln Gln His Leu Ser Ala Leu Glu Lys Asp Ile Lys His Asn Glu
                 85                  90                  95

Glu Leu Leu Lys Arg Cys Gln Leu His Tyr Lys Glu Leu Lys Met Lys
            100                 105                 110

Ile Arg Lys Asn Ile Ser Glu Ile Arg Glu Leu Glu Asn Ile Glu Glu
        115                 120                 125

His Gln Ser Val Asp Ile Ala Thr Leu Glu Asp Glu Ala Gln Glu Asn
    130                 135                 140

Lys Ser Lys Met Lys Met Val Glu Glu His Met Glu Gln Gln Lys Glu
```

-continued

```
145                 150                 155                 160

Asn Met Glu His Leu Lys Ser Leu Lys Ile Glu Ala Glu Asn Lys Tyr
                165                 170                 175

Asp Ala Ile Lys Phe Lys Ile Asn Gln Leu Ser Glu Leu Ala Asp Pro
            180                 185                 190

Leu Lys Asp Glu Leu Asn Leu Ala Asp Ser Glu Val Asp Asn Gln Lys
        195                 200                 205

Arg Gly Lys Arg His Tyr Glu Glu Lys Gln Lys Glu His Leu Asp Thr
    210                 215                 220

Leu Asn Lys Lys Lys Arg Glu Leu Asp Met Lys Glu Lys Glu Leu Glu
225                 230                 235                 240

Glu Lys Met Ser Gln Ala Arg Gln Ile Cys Pro Glu Arg Ile Glu Val
                245                 250                 255

Glu Lys Ser Ala Ser Ile Leu Asp Lys Glu Ile Asn Arg Leu Arg Gln
            260                 265                 270

Lys Ile Gln Ala Glu His Ala Ser His Gly Asp Arg Glu Glu Ile Met
        275                 280                 285

Arg Gln Tyr Gln Glu Ala Arg Glu Thr Tyr Leu Asp Leu Asp Ser Lys
    290                 295                 300

Val Arg Thr Leu Lys Lys Phe Ile Lys Leu Leu Gly Glu Ile Met Glu
305                 310                 315                 320

His Arg Phe Lys Thr Tyr Gln Gln Phe Arg Arg Cys Leu Thr Leu Arg
                325                 330                 335

Cys Lys Leu Tyr Phe Asp Asn Leu Leu Ser Gln Arg Ala Tyr Cys Gly
            340                 345                 350

Lys Met Asn Phe Asp His Lys Asn Glu Thr Leu Ser Ile Ser Val Gln
        355                 360                 365

Pro Gly Glu Gly Asn Lys Ala Ala Phe Asn Asp Met Arg Ala Leu Ser
    370                 375                 380

Gly Gly Glu Arg Ser Phe Ser Thr Val Cys Phe Ile Leu Ser Leu Trp
385                 390                 395                 400

Ser Ile Ala Glu Ser Pro Phe Arg Cys Leu Asp Glu Phe Asp Val Tyr
                405                 410                 415

Met Asp Met Val Asn Arg Arg Ile Ala Met Asp Leu Ile Leu Lys Met
            420                 425                 430

Ala Asp Ser Gln Arg Phe Arg Gln Phe Ile Leu Leu Thr Pro Gln Ser
        435                 440                 445

Met Ser Ser Leu Pro Ser Ser Lys Leu Ile Arg Ile Leu Arg Met Ser
    450                 455                 460

Asp Pro Glu Arg Gly Gln Thr Thr Leu Pro Phe Arg Pro Val Thr Gln
465                 470                 475                 480

Glu Glu Asp Asp Asp Gln Arg
                485
```

<210> SEQ ID NO 113
<211> LENGTH: 1424
<212> TYPE: DNA
<213> ORGANISM: Homo sapiens

<400> SEQUENCE: 113

```
ggagcaagaa gggcgccgcg gcgtgcggcc cgcgcagccc ccggagccat gggcaagtgc      60

agcgggcgct gcacgctggt cgccttctgc tgcctgcagc tggtggctgc gctggagcgg     120

cagatctttg acttcctggg ctaccagtgg gctcccatcc tagccaactt cctgcacatc     180
```

-continued

```
atggcagtca tcctgggcat ctttggcacc gtgcagtacc gctcccggta cctcatcctg    240

tatgcagcct ggctggtgct ctgggttggc tggaatgcat ttatcatctg cttctacttg    300

gaggttggac agctgtccca ggaccgggac ttcatcatga ccttcaacac atccctgcac    360

cgctcctggt ggatggagaa tgggccaggc tgcctggtga cacctgttct gaactcccgc    420

ctggctctgg aggaccacca tgtcatctct gtcactggct gcctgcttga ctacccctac    480

attgaagccc tcagcagcgc cctgcagatc ttcctggcac tgttcggctt cgtgttcgcc    540

tgctacgtga gcaaagtgtt cctggaggag gaggacagct ttgacttcat cggcggcttt    600

gactcctacg gataccaggc gccccagaag acgtcgcatt tacagctgca gcctctgtac    660

acgtcggggt agcctctgcc ccgcgcccac cccggcgcct cgccctgggc tgaccgcagc    720

tgccgcgagc tcgggccaag gcgcaggcgt gtccccctgg tggcccgcgc gctcactgca    780

gcctgtgccc aaccccgcgt ctgcatctgg agatgcggac ttggacgtgg acttggactt    840

ggacttggat ttgagcttgg ctcttcgcag cccggacttc ggaggagtgg ggcggggcgg    900

gggaggggca ccacggcttt tttgtttttt gtttgtttgt ttttaatctc agccttggcg    960

tgagctgggg ccttcctctc ttctccagcc tctccctttc actcttcacc cagcatcctg   1020

ccccctgtc caaaaacagc aggacatcag acccatccca tcccaccaca ctcactcacc   1080

agctctgggg aaagctactg tgaactagga gcaggattcc tgggttctaa tcgcaggtcc   1140

atcactgact gtgacgtcta gcaaagccct tgccctctct gagcctcggt ttccgcacct   1200

caagtaatta atcccttagc aaatggactc tttcagactt ctcatttaac tcaattccct   1260

gagctagact gggattaaaa ttctcatttt gcagtacatt aaaactgagg cccagagatg   1320

tgatttgctt gaggccacac agctagattt ttggtggaag tgggccttga acacagtgta   1380

ctttctgcag tttctgactg taaaaaaaaa aaaaaaaaaa aaaa                    1424
```

<210> SEQ ID NO 114
<211> LENGTH: 207
<212> TYPE: PRT
<213> ORGANISM: Homo sapiens

<400> SEQUENCE: 114

```
Met Gly Lys Cys Ser Gly Arg Cys Thr Leu Val Ala Phe Cys Cys Leu
  1               5                  10                  15

Gln Leu Val Ala Ala Leu Glu Arg Gln Ile Phe Asp Phe Leu Gly Tyr
             20                  25                  30

Gln Trp Ala Pro Ile Leu Ala Asn Phe Leu His Ile Met Ala Val Ile
         35                  40                  45

Leu Gly Ile Phe Gly Thr Val Gln Tyr Arg Ser Arg Tyr Leu Ile Leu
     50                  55                  60

Tyr Ala Ala Trp Leu Val Leu Trp Val Gly Trp Asn Ala Phe Ile Ile
 65                  70                  75                  80

Cys Phe Tyr Leu Glu Val Gly Gln Leu Ser Gln Asp Arg Asp Phe Ile
                 85                  90                  95

Met Thr Phe Asn Thr Ser Leu His Arg Ser Trp Trp Met Glu Asn Gly
            100                 105                 110

Pro Gly Cys Leu Val Thr Pro Val Leu Asn Ser Arg Leu Ala Leu Glu
        115                 120                 125

Asp His His Val Ile Ser Val Thr Gly Cys Leu Leu Asp Tyr Pro Tyr
    130                 135                 140

Ile Glu Ala Leu Ser Ser Ala Leu Gln Ile Phe Leu Ala Leu Phe Gly
145                 150                 155                 160
```

```
Phe Val Phe Ala Cys Tyr Val Ser Lys Val Phe Leu Glu Glu Glu Asp
                165                 170                 175

Ser Phe Asp Phe Ile Gly Gly Phe Asp Ser Tyr Gly Tyr Gln Ala Pro
            180                 185                 190

Gln Lys Thr Ser His Leu Gln Leu Gln Pro Leu Tyr Thr Ser Gly
        195                 200                 205


<210> SEQ ID NO 115
<211> LENGTH: 843
<212> TYPE: DNA
<213> ORGANISM: Homo sapiens

<400> SEQUENCE: 115

ccagaatctg gcacgctgac ggggacctag ggacagacga ccgcacaaca cgccacgttg      60

caggcgctgc caggccgggt gcctcaccta gctccttcat gtattcatca aagcctttgc     120

tgtccaccag gcgccatctt ccttccagct gctgaactgt ggccatgggt acgcgacggc     180

ctctcgggcg cctcctgcaa gcagggactc gcccggcgcg ccccacgcct catggacgcc     240

ggcgcctgca cgtttcggcg cctctgcagg cccaggaagc cagaggggtc acctggaggc     300

ctggccccgc ctctcctgca cccctccgtt tgacaacata tccaccgccg tttttccttt     360

caaaataccc ggaccaatcg attagccctc gccggactcg gactgcagga agtgattgat     420

cggctgtttg gtttattgat tcattaacta cggtgcctcc ctgaccttct gctcctcgcc     480

agcgcacaag ctcacaatcc acaccctcct aagagaacct gctctcgcca tccgcaggtc     540

tccctggccc aatagtgggg atatacctga gttgagctag aggattttat ccctgttggg     600

atgggggacg tctcgggaag tgtggtttct aaactaaaag actgcaggaa gtgtcaactt     660

tagtgactgt cattgccatt caagaatgtt tgattagttt atattccctt cgtagtgcac     720

ccttcaccgt ttcttctcag acaccagcgg gtttcttctc agacaccagc gggttccctc     780

tttctcttga actataataa taccctacac atgtgcgtaa aaaaaaaaaa aaaaaaaaaa     840

aaa                                                                   843


<210> SEQ ID NO 116
<211> LENGTH: 84
<212> TYPE: PRT
<213> ORGANISM: Homo sapiens

<400> SEQUENCE: 116

Met Gly Thr Arg Arg Pro Leu Gly Arg Leu Leu Gln Ala Gly Thr Arg
  1               5                  10                  15

Pro Ala Arg Pro Thr Pro His Gly Arg Arg Arg Leu His Val Ser Ala
             20                  25                  30

Pro Leu Gln Ala Gln Glu Ala Arg Gly Val Thr Trp Arg Pro Gly Pro
         35                  40                  45

Ala Ser Pro Ala Pro Leu Arg Leu Thr Thr Tyr Pro Pro Pro Phe Phe
     50                  55                  60

Leu Ser Lys Tyr Pro Asp Gln Ser Ile Ser Pro Arg Arg Thr Arg Thr
 65                  70                  75                  80

Ala Gly Ser Asp


<210> SEQ ID NO 117
<211> LENGTH: 2232
<212> TYPE: DNA
<213> ORGANISM: Homo sapiens
<220> FEATURE:
```

<221> NAME/KEY: unsure
<222> LOCATION: (225)

<400> SEQUENCE: 117

```
ataagctggg aggttcctgg cctgtctcct gctctctgct gagttgcttg gggcagggat     60
ggtgaaaaga gcccccagga agtctctgga agtgaggagg gtccttgggc actaactgtg    120
tgaccttggg caagtgactc cccatctctg ggcctcagga ggttgggcag gtccgggcca    180
aggctgaaat actgagtgga ggaatggtgg gggaggagga ggaancgcct aatacccccca   240
accctcatct ttcccaacca cactcattcc aaattcttgc tctgggggtt ctgatccatg    300
ggcaggtcac ggtgtgggag gcggaggctc cactccaggg aggatttgga gctccacaga    360
gtacacctgg ggcaaaagga gcctgggcgt gggaggccag gactgggaag gttctgggac    420
tctctccctc accccggact cctccccaga gcctggggct cagcaactct catgaccggg    480
cactggtgaa gcgcaagttg aaggagatgg cagcagctgc cgagaaggag cgcaaggccc    540
aggagaaggc tgcgcggcag cgggagaagc tccggcgccg agagcaggag gccaagaaga    600
gctaggggag ggtgcacagg cgctggcacc cggcaggggc agccactggc tccgcgggca    660
caggcctcac cagggaggct ggacctgggc gctgcacttg ggctagcctg gtcccacgct    720
ctcagggggg acatgctctc tcttaccctg tcacttggtc tagacccaga gaccccagaa    780
agggagaccc cagggagagg gcctagtaat aaatcctatt ttgaggactt gtttggcaca    840
gagttcctgg gggaggagca gatgaagggg agagggcaga gaggccaggg ctgaggcaag    900
tctgggagcc tgggtcaggc tgtcccattg ccctcaggcc atcgtggggc tggggtggag    960
gggagctagg aggcctgcct gcctgcttgc ctgccagagg ccctgaggcc gggccccagg   1020
gctcagagct gggctgggca tttcagcagg agcccatgtg ggagcggctc ctctccactc   1080
ttccaggggg ctgtgtggtg ggagagctct gtcctgctcc cccaagaggc cagtgggcgc   1140
tgcagcaagt cgcactcagg gtagactccc agccaaactc ctcaacagga gcgcagagaa   1200
agcagcctgg ggcgagtgca gtctttgcca ggactcaaga ggggaggatg aacatcccct   1260
tctccctctc cctcctctg tcctgtgggt cccagggggc gagatgacac cacacaggtc    1320
tgcctctcag ggcccattca agacctggtc tttgacccat tctccaagcc aggactccct   1380
tcacttcctg ctgcttcctc agagggcacc taagtcctct ttgggagctg agcaaacagg   1440
aactgatagg gacagaggac accacttcca ccagccaagg cctaggagct gctgacctgg   1500
tcagccctca ccccagccag gcagagaggc aaaacctggg ggtccccggc agctacgaga   1560
ttggaaaggt tcatcagccc tcccccatct gccccaggca ttgtcaggga atcagtgggc   1620
tcagaactgg caggcggtgc aagctctgct tccctgggcc acactgaggg ctggggccag   1680
ctccctggat gggggtggag tttaccagca gcctggggac agcatgtgtc ctttttagga   1740
aatgtccttg gaggaagtgt tcatgtgtgg cgctggtcag cagctagtcc cgcttccagg   1800
acactggtca gagttaccga tgaggcctgg gggctcccgc ttggaaaccc ctccagctcc   1860
tcccatctgc ccagacagag cggcagatgg caccaatgca tgctggctcc ctcattcctg   1920
cccaggggct gtggcttacg gccagcaccc tgtacctggg actcagccct tatccccccct   1980
ctgctatctg tgctgggaga ggggcttcgg agggaaacag atatgaggac actggcacca   2040
tctgggcctg gtggcagggc catgggaggt tggaaggcac ccacatcctt aaagccatca   2100
gtagctctag tgggtgccca cctgcatgtg aaggggaggc agttctcaat ttatttcaat   2160
aaatccttat gatgtgccag tgaccagaaa aaaaaaaaaa aaaaaaaaaa aaaaaaaaaa   2220
```

aaaaaaaaaa aa 2232

<210> SEQ ID NO 118
<211> LENGTH: 133
<212> TYPE: PRT
<213> ORGANISM: Homo sapiens
<220> FEATURE:
<221> NAME/KEY: UNSURE
<222> LOCATION: (8)

<400> SEQUENCE: 118

Met Val Gly Glu Glu Glu Glu Xaa Pro Asn Thr Pro Asn Pro His Leu
1 5 10 15

Ser Gln Pro His Ser Phe Gln Ile Leu Ala Leu Gly Val Leu Ile His
20 25 30

Gly Gln Val Thr Val Trp Glu Ala Glu Ala Pro Leu Gln Gly Gly Phe
35 40 45

Gly Ala Pro Gln Ser Thr Pro Gly Ala Lys Gly Ala Trp Ala Trp Glu
50 55 60

Ala Arg Thr Gly Lys Val Leu Gly Leu Ser Pro Ser Pro Arg Thr Pro
65 70 75 80

Pro Gln Ser Leu Gly Leu Ser Asn Ser His Asp Arg Ala Leu Val Lys
85 90 95

Arg Lys Leu Lys Glu Met Ala Ala Ala Ala Glu Lys Glu Arg Lys Ala
100 105 110

Gln Glu Lys Ala Ala Arg Gln Arg Glu Lys Leu Arg Arg Arg Glu Gln
115 120 125

Glu Ala Lys Lys Ser
130

<210> SEQ ID NO 119
<211> LENGTH: 4086
<212> TYPE: DNA
<213> ORGANISM: Homo sapiens

<400> SEQUENCE: 119
aaaatagcgg gtactgtggt accggaggct ggcggtacca gtgtggattc caagtgatca 60
tcacaggtac atatagtgat cttccttgtc cgtctcgtcc cactgggtac caggcgaatc 120
ctactgggta ggtcgggtac gcggcatatg tggggtatgt ttggtatcca ggtatttgag 180
gtacgaattc agtgtacgtt gccaggtgtg cttggtcttc taaatttgga atacataggc 240
gaggatactg attctggata gtaaaattgt ttggagctcg gcaatcataa gaaacttgca 300
gtttccaccc cctcttcacc tggagaactt gggctccatt aggtgcaatc gttggagtaa 360
ttagcccatc ttttacattt cttgccacaa aatctcgaag agctgccatt tcaggttcgg 420
acagtgaata cacatgtcca ctgggaatac tgtgtgctcc aggtatcatt tctatgtgag 480
ggtcaaccag gcggtgatct gggtagacgt gctcatctac tggagtgtac acattctgga 540
catagtaata cctcactggt tggtaaactc tgtatccatc tactggataa tagagtggcg 600
gttgtggtgc tggtggtggg agcgatggtg gtattggaga atacatccgg cagtggtagc 660
ggcagtattc agaatcaaag acgatagatc gagtgctcca tgtgatattg ggatcatgtg 720
tgctcagcca gcgaacccct aggacgacag ggaagaatgg agactgagtc acatcaaatg 780
acagcacctc tcggtgatct cccaggtcaa ctatcaggtc gtgagtttcg tggacaactg 840
ggcccgatgc tatggggcgc ccatcaattg cttccacaag tattggccag tccttgattc 900
ttagaggaat tccattttga gcaacatatt cgtgatcaat gaagttgcca gaagcaccag 960

-continued

```
aatcgatcat ggctcggacg aacagggtgt gtctgcccgg aagatgaatc tggagcatca   1020
cttgcaagtg tggagatgag gcatcatctt gtggggacct tattatttct ggcccggtcg   1080
ctgaaggtcc ctctacagcg gggccgggga gtttcccgcc ggcgaagact ttgaggcctt   1140
ggcaggacaa ttgtcagcgt agtgacctcc tgttccacag tagaggcaca ggttcagctt   1200
tctgcgtctt tctttttctt cctgcgtcag gcgcatgcgg gcacctccca ccggctcggt   1260
tggatctacc tggtggtggc ttgcaatgtg aggcaacacc agcgcccggg gtggcgagcg   1320
tggcttgcga gctgcagcag ccctggccag ccttctctca atgtgaatgc actgcccaat   1380
cagagcagac agcgacttgg cgacctcgag caacattaac tgaggaaaaa attgaaaaag   1440
gggcgccctt gcttgggggc ttcctattgt ggaactgtta tggaaaggag ccccatccat   1500
tgcttcctcc ttgaatggca aatgccttta tgatccctat aacttgtccc attatgttta   1560
gacccttggt ggtcagaagg gttctattta gggcagtgtc ccctgcccct ccttgtcctc   1620
caaaaatttt gggaggcact gacgtggatg tcatggggtc agcacaggca tcaacatccc   1680
cagagggatg gaaccaagca gcctattgcc caggcattca ctaacaggca gcccatcctc   1740
agcctcatag ctggccgggg agaagaaagg ctattttggg tcccagatct tttttttttt   1800
ttttgagaca gagtctcgct ctgtcaccca ggctgaagtg caatggtgcg gtctcagctc   1860
actacaacct ccgcctcccg agttcaagag attctcctgc ctcagcctcc tgagtagctg   1920
ggactacagg tgcgtaccac caagcctggc taatttttgt gcttttagta gggacgtggt   1980
ttcaccatgt tgcccaggtt ggtctcaaac tcctgggctc atgcagtccg cctacctcag   2040
cctcccaaag tgctgggatt acaggcatga gccactgcac ccggtctctg tttacaaatt   2100
tatcaccagc ttcatcccct aaggttataa gctccatgag ggtgggaagt ctgtattgtt   2160
cacctctgta tcctaagcat ctagaacata gcccggcaca cagtaggtgc tgaagaattg   2220
aatctgttaa tgtagaaagg atgtttcatc tagctgaagt gtcttgtaca gaataaactc   2280
tcaataaatg aactgtggac acatggaagg gtgagctaga gctctgctca ggggttgagt   2340
gctcctcttg tgcccttgtg gttgtctggt tacctgaact aattggagtg cgatgcagac   2400
atagtcatgg agtgagacag cagaactttg ctgtcttgtt tgtgagccca catcaggggt   2460
tctagactgg ctggttgaca tggtggcccc agcctgtctc ttcagcagct cggcttataa   2520
aaaataacca cctcctattt tggcctcttt ggccgaattc ggccaaagag gcctagcctc   2580
cgattactaa accccttgcc ccacaaacgt ccacattgac gagcctcttt ttagtaactg   2640
cttccccgta attccttcag aggttgctgt acccttcgct gatgtgctgc cctcctgtaa   2700
aacctccaga tgccttccca cgtaatgccc ctttcagatg ctttaagctg agagcttaaa   2760
ccacaggtac catggctgac gcctgccagg tttctgctgc agataatcta tgatgggagg   2820
ggcatatttt ttacttcatt acttatgtaa actcttgttc cagaaagctt taatgtgtgt   2880
gggagtgttc tgggtctatt aggtctgtgc gcatgggtgt gggcatttgc ctgtgtccac   2940
cgggtgggtc tcattatgaa atgtatgttt atgtagggct ttaatggctg aaaatggcaa   3000
agagatgaat agaccacttg gccccatgtg taattgccag gccccttctg tgctcaaatg   3060
aggtgtccga gtgaaggtca gcccttccct tctgtatttg gggcctattt atgccaccag   3120
taattttata agaaatctga atagttctcc cctttgagtg catttaactc tttagtatct   3180
tctctcttac ctatttgagc ccctctagct acagtctggc ttaaatgaaa ggggaattat   3240
atgcttaaga aaaagtagga cacggttgag gcagtttgct gactgaatac gcgaagaagg   3300
```

```
acctgatggg ctcatatgca ccactgccat cacagtcccc atcgtgatgc aagcttatat   3360

gattcttgag gtaactctac cagatacttc cagatttaga aatgtgtcaa aggaaaaatt   3420

ggtgatactc ttctttccct gccagaaaca gcccagatct cctcttaagc ggaaaagaga   3480

ttgaccttct agcagaggca aaggtaaact cctgtaagtt acttctgtta ccaaagggag   3540

gggggcggct tttgtgaatg tatgaggagc ttttgccaga gagatattcg gaggaggggt   3600

gtgcccatat gcacacatat attttcccgc ataaccgtat ccaatgctag catttagagg   3660

aaggcattta gccaccaaaa gtccatccat ctatgctgct tccacagaga aaacattttc   3720

tctttcctcc tcttgaactt acataatatc ctcctcccat tccaacctta gaatggagtc   3780

ttctgggggc agctgcaaag cgttctccct aggacagatg gagcctccct ttcctcatct   3840

actctgtggg tggtttcagg gcccacgagt caacatgagg agttgtgctg gtggtatgtg   3900

tgttggaggc tgggctggct gattcacagt gacgaggatg tcaataataa caagaatgag   3960

aatgatggta cctaataaag actttttttc ccaaaaaaaa aaaaaaaaaa aaaaaaaaaa   4020

aaaaaaaaaa aaaaaaaaaa aaaaaaaaaa aaaaaaaaaa aaaaaaaaaa aaaaaaaaaa   4080

aaaaaa                                                              4086
```

<210> SEQ ID NO 120
<211> LENGTH: 102
<212> TYPE: PRT
<213> ORGANISM: Homo sapiens

<400> SEQUENCE: 120

```
Met Ser Thr Gly Asn Thr Val Cys Ser Arg Tyr His Phe Tyr Val Arg
  1               5                  10                  15

Val Asn Gln Ala Val Ile Trp Val Asp Val Leu Ile Tyr Trp Ser Val
             20                  25                  30

His Ile Leu Asp Ile Val Ile Pro His Trp Leu Val Asn Ser Val Ser
         35                  40                  45

Ile Tyr Trp Ile Ile Glu Trp Arg Leu Trp Cys Trp Trp Trp Glu Arg
     50                  55                  60

Trp Trp Tyr Trp Arg Ile His Pro Ala Val Val Ala Ala Val Phe Arg
 65                  70                  75                  80

Ile Lys Asp Asp Arg Ser Ser Ala Pro Cys Asp Ile Gly Ile Met Cys
                 85                  90                  95

Ala Gln Pro Ala Asn Pro
            100
```

<210> SEQ ID NO 121
<211> LENGTH: 1293
<212> TYPE: DNA
<213> ORGANISM: Homo sapiens

<400> SEQUENCE: 121

```
ggtccagaag aaatgtggct tcagctctgc tgctactgtg cctcccttct cctgccccac     60

tcagcccaca aaataggctg gacactcaaa aaacgttgcg tttatctacc ttttagagag    120

ggtgaatagc agagaactgg aggtgggaat ggtaaggaac tcccagcagg gtagtggagg    180

gaatgggctg acgcatctaa ggctgatgcc aggtctgctc cctatctggg tggcctcagc    240

aaatgacgtc cagcacatcc aggggcaggc tcaagggaga acagccccca aagctaagat    300

cctgccaagc taaatacagt agttctaatg aaatgtgaga ggctataatc ccatttggga    360

aattcctaaa aagtcatgag gcaggggatt ggtttatgtt attatcatga cctgagagtc    420
```

-continued

```
atggctcaga gccaaatgtt caggattgaa ttcaacagca tttaaatgtc tttagagcag    480
gatggaaata tgttagcaat gcctgcagag tgccaagtaa acgcaaaagc caatgagatc    540
ataaaggaag ttgttagcta acctagtgga gtcgccaact tccttctact ctaataatta    600
aaataaaaat aatacttggg aggtaactgg aataaaggtt ctaaaatcaa aaccctctga    660
agggtgaaaa ctgggagcct cctgttccca tagtaaccac agcactcagg gcactgtctc    720
ccagcgctgg agtactgtct tatgaccaga gatcctaagc aacctctgct catctgagtt    780
gtccaccata ttgtgggcat gagtccttga caatagtaaa tagcacctct gttcccttat    840
tgggtaaatg attttccaac tctgggaatg tgtagaattc attatggaaa taatgcaata    900
attcaaatcc ataatattga tactttcatg ttaagtttag gactaatctt gtgtatgctc    960
cttaagtgat ttgaatcttt aaaaagctta tgattccaat ttgaaatgtg aaattgattt   1020
tacgtttgtg atttgaagtt gaaaggtata agaatattta acttagctca tgaaaagtat   1080
tagactagat ttactataag tttaatgtat tagatttaca agagatgctt aaatatatga   1140
gaatgttttg tcttaattgg ttataatctt gtcatatcaa tgatttgaag tgctaaaata   1200
gaaaattaaa tatgataaat tacacaagaa gtttagaatg tttaaaagat tttaataaac   1260
aaagcctata actaagaaaa aaaaaaaaaa aaa                                1293
```

<210> SEQ ID NO 122
<211> LENGTH: 54
<212> TYPE: PRT
<213> ORGANISM: Homo sapiens

<400> SEQUENCE: 122

```
Met Val Arg Asn Ser Gln Gln Gly Ser Gly Gly Asn Gly Leu Thr His
  1               5                  10                  15

Leu Arg Leu Met Pro Gly Leu Leu Pro Ile Trp Val Ala Ser Ala Asn
             20                  25                  30

Asp Val Gln His Ile Gln Gly Gln Ala Gln Gly Arg Thr Ala Pro Lys
         35                  40                  45

Ala Lys Ile Leu Pro Ser
     50
```

<210> SEQ ID NO 123
<211> LENGTH: 2509
<212> TYPE: DNA
<213> ORGANISM: Homo sapiens

<400> SEQUENCE: 123

```
gagctgcatc gcgggaggcg catggcgggg atggcgctgg cgcgggcctg gaagcagatg     60
tcctggttct actaccagta cctgctggtc acggcgctct acatgctgga gccctgggag    120
cggacggtgt tcagctggtt tccattgtgg ggatggcact atacacagga tacgtcttca    180
tgccccagca catcatggcg atattgcact actttgaaat cgtacaatga ccaagatgcg    240
accaggatca gaggttcctt ggggaagacc caccctacga agttggaatg agaccatcag    300
atgtgataag aaactcttct agatgtcaac ataaccaacc ttataaagac taaaattcat    360
gagtagaaca ggaaaatcat cctgactcat gtgttgtgtt ctttattttt aattttcaaa    420
gaggctcttg tatagcagtt tttgtctatt ttaacattgt agtcatttgt actttgatat    480
cagtattttc ttaacctttg tgactgtttc aatattaccc ccgtgaaagc ttttcttaat    540
gtaactttga gtacatttta attgccttct atttttaaaa ctcaaaatca ttagttgggc    600
tttactgttc ttgctattgt atggcatata catctgcctg gatatatttc tactcttgac    660
```

-continued

```
caaagttttg taaagaacaa tataagattt cgggtagggg tatggggagg gaagatattt    720
tattgagaac tacttaacaa aagatttatc tgtaagcttg aactcaggag tacagtttta    780
gctatctaga ctctaacagc ttttgcttta aaattattaa agtgtttctt aatgaaaaag    840
aaaagatctt gctaaagtta aaataaggaa catttcacct tttaaatatt taattcttat    900
gtggacttat ttccagaaaa ctttggtgat aattcttgag acaaaaggtg gttaagtagc    960
attattatgt aatgcttata taccatagag tttttaatag aagagaaatc catttcctcc   1020
gagggtcact attaacaatg tacttcctta aatttagttt aatgattgta atgggtgctg   1080
catttgcaca ttgcattaag ttatgatgag acgaattgtt gttaaaaatt atagcaaaaa   1140
gaaatgtaaa cttggttaaa atcctttcac tctttgtatt gttttttta aggtttttat   1200
tccttaaatg taaaatgact acctaatttt ttgatgtaaa tacattaaat tcaaagagaa   1260
aaaaaatcag ctgatgtagc agtatatctt ttccttgatg gttaaatatt gatctagtat   1320
ttatattgct gaattatttt ctgtggagga ccagataagc agtaagtatg tcttatccta   1380
tatgttttgc aacataaaaa tattgctaat tgaaaagaat taggcaatta tgtgtgttgc   1440
tgggttgttt ttttgttttt tttttttgag acggagtctt gccctgtcgc ccaggatgga   1500
gtgcaacagc atgatctcgg ttcactgcaa cctccatctc ctgggatcaa gtgattctcc   1560
tgcctcagcc tcctgaatag ctgggattac aggcacctgc caccatgcct ggctaatttt   1620
ttgtatctgt agtagagacg gggtttcact gtgttggcca ggatggtctc aaactcctga   1680
cctcctgatc cacctgcctc ggcctcccaa agtgctgggt ttacaggcgt gagccaccgc   1740
gcccggccaa aattgaggta ttttttgccc tacgttttaa ggactagact tttgaagtat   1800
tttatagtct agaggtctca agtaatatat atgtgtttaa tatttttaga gccaattgat   1860
accacaatta gataggagta gtgagaataa tatggaatta cttggtttga agtagttaaa   1920
aattggatat ggttatatct gagctgtagt catattatct caagaaaaat aatacgagga   1980
tttaacataa gatttgttct attaatgccc aaatttggct ttcctctact atcccccata   2040
gagaaccact aacaagtgga tgtctaatat tcctctggtg agttgaaggc aggagaagtt   2100
gagaatcatt agtttcaatg agtatccagg tgacctatcc tggccctcta ctcagaaacc   2160
ggcaatttgt cttcactctg agattcatta aattgctgtt gtataactga tggttattat   2220
gaacactgac ctgtgagaca tatggaagat aaagtttggt cttacaggaa atcttgagga   2280
gagtcaaaag agaaatggga gatgtctctt gagaggtgat cagagaagtt tatgctcact   2340
gtctgatgca aatgtctggt ctatttgtta gtaaataaca gggaaatcat tttcactttt   2400
tgttaaaaat aaggtattta caagcatacc ttgtagttat tgtgggttca gtttcagacc   2460
actgcaataa agtgaatatc tcaataaaaa aaaaaaaaaa aaaaaaaaa               2509
```

<210> SEQ ID NO 124
<211> LENGTH: 89
<212> TYPE: PRT
<213> ORGANISM: Homo sapiens

<400> SEQUENCE: 124

```
Met Ala Gly Met Ala Leu Ala Arg Ala Trp Lys Gln Met Ser Trp Phe
  1               5                  10                  15

Tyr Tyr Gln Tyr Leu Leu Val Thr Ala Leu Tyr Met Leu Glu Pro Trp
             20                  25                  30

Glu Arg Thr Val Phe Ser Trp Phe Pro Leu Trp Gly Trp His Tyr Thr
         35                  40                  45
```

```
Gln Asp Thr Ser Ser Cys Pro Ser Thr Ser Trp Arg Tyr Cys Thr Thr
     50                  55                  60

Leu Lys Ser Tyr Asn Asp Gln Asp Ala Thr Arg Ile Arg Gly Ser Leu
 65                  70                  75                  80

Gly Lys Thr His Pro Thr Lys Leu Glu
                 85


<210> SEQ ID NO 125
<211> LENGTH: 2672
<212> TYPE: DNA
<213> ORGANISM: Homo sapiens

<400> SEQUENCE: 125

ggaggagaga agaggaggtg gagaaggctt gggctcgcgc cgctgaagtc ggcttacccg     60

ctggccgcct cctgacaagc gggagggatc cgcggtggac ccagggaagc ggaggagcct    120

ggcggccacc ccctcttcct cacttccctg tactctcatc gctctcggcc tccgacacga    180

aaaggaagca aatgagctga tggaagatct gtttgaaact ttccaagatg agatgggatt    240

ctccaacatg gaagatgatg gcccagaaga ggaggagcgt gtggctgagc ctcaagctaa    300

ctttaacacc cctcaagctc tacggtttga ggaactactg gccaacctac taaatgaaca    360

acatcagata gcgaaggaac tatttgaaca gctgaagatg aagaaacctt cagccaaaca    420

gcagaaggag gtagagaagg ttaaacccca gtgtaaggaa gttcatcaga ccctgattct    480

ggacccagca caaaggaaga gactccagca gcagatgcag cagcatgttc agctcttgac    540

acaaatccac cttcttgcca cctgcaaccc caatctcaat ccggaggcca gtagcaccag    600

gatatgtctt aaagagctgg gaacctttgc tcaaagctcc atcgcccttc accatcagta    660

caaccccaag tttcagaccc tgttccaacc ctgtaacttg atgggagcta tgcagctgat    720

tgaagacttc agcacacatg tcagcattga ctgcagccct cataaaactg tcaagaagac    780

tgccaatgaa tttccctgtt tgccaaagca agtggcttgg atcctggcca caagcaaggt    840

tttcatgtat ccagagttac ttccagtgtg ttccctgaag gcaaagaatc cccaggataa    900

gatcctcttc accaaggctg aggacaattt gttagcttta ggactgaagc attttgaagg    960

gactgagttt cttaaccctc taatcagcaa gtaccttcta acctgcaaga ctgcccgcca   1020

actgacagtg agaatcaaga acctcaacat gaacagagct cctgacaaca tcattaaatt   1080

ttataagaag accaaacagc tgccagtcct aggaaaatgc tgtgaagaga tccagccaca   1140

tcagtggaag ccacctatag agagagaaga acaccggctc ccattctggt taaaggccag   1200

tctgccatcc atccaggaag aactgcggca catggctgat ggtgctagag aggtaggaaa   1260

tatgactgga accactgaga tcaactcaga tcaaggccta gaaaaagaca actcagagtt   1320

ggggagtgaa actcggtacc cactgctatt gcctaagggt gtagtcctga aactgaagcc   1380

agttgccgac cgtttcccca agaaggcttg gagacagaag cgttcatcag tcctgaaacc   1440

cctccttatc caacccagcc cctctctcca gcccagcttc aaccctggga aaacaccagc   1500

ccaatcaact cattcagaag cccctccgag caaaatggtg ctccggattc ctcacccaat   1560

acagccagcc actgttttac agacagttcc aggtgtccct ccactggggg tcagtggagg   1620

tgagagtttt gagtctcctg cagcactgcc tgctatgccc cctgaggcca ggacaagctt   1680

ccctctgtct gagtcccaga ctttgctctc ttctgcccct gtgcccaagg taatgatgcc   1740

ctcccctgcc tcttccatgt ttcgaaagcc atatgtgaga cggagaccct caaaaagaag   1800

gggagccagg gcctttcgct gtatcaaacc tgcccctgtt atccaccctg catctgttat   1860
```

-continued

```
cttcactgtt cctgctacca ctgtgaagat tgtgagcctt ggcggtggct gtaacatgat   1920

ccagcctgtc aatgcggctg tggcccagag tccccagact attcccatcg ccaccctctt   1980

ggttaaccct acttccttcc cctgtccatt gaaccagccc cttgtggcct cctctgtctc   2040

acccttaatt gtttctggca attctgtgaa tcttcctata ccatccaccc ctgaagataa   2100

ggcccacatg aatgtggaca ttgcttgtgc tgtggctgat ggggaaaatg cctttcaggg   2160

cctagaaccc aaattagagc cccaggaact atctcctctc tctgctactg ttttccccaa   2220

agtggaacat agcccagggc ctccaccagt cgataaacag tgccaagaag gattgtcaga   2280

gaacagtgcc tatcgctgga ccgttgtgaa aacagaggag ggaaggcaag ctctggagcc   2340

gctccctcag ggcatccagg agtctctaaa caactcttcc cctggggatt tagaggaagt   2400

tgtcaagatg gaacctgaag atgctacaga ggaaatcagt ggatttcttt gagctaggag   2460

aataagagtc tggagactgg gagccttcac ttcggcctcc gattggtggc gcatagggtg   2520

taaccaatag gaaaccccta aagggtactt aaaccccaga ttttgcaact ggggctcttg   2580

agcagcttgc tttagcctgc tcccactctg tggaatatac ttttgcttca ataaatctgt   2640

gcttttattg cttcaaaaaa aaaaaaaaaa aa                                 2672
```

<210> SEQ ID NO 126
<211> LENGTH: 750
<212> TYPE: PRT
<213> ORGANISM: Homo sapiens

<400> SEQUENCE: 126

```
Met Glu Asp Leu Phe Glu Thr Phe Gln Asp Glu Met Gly Phe Ser Asn
  1               5                  10                  15

Met Glu Asp Asp Gly Pro Glu Glu Glu Glu Arg Val Ala Glu Pro Gln
             20                  25                  30

Ala Asn Phe Asn Thr Pro Gln Ala Leu Arg Phe Glu Glu Leu Leu Ala
         35                  40                  45

Asn Leu Leu Asn Glu Gln His Gln Ile Ala Lys Glu Leu Phe Glu Gln
     50                  55                  60

Leu Lys Met Lys Lys Pro Ser Ala Lys Gln Gln Lys Glu Val Glu Lys
 65                  70                  75                  80

Val Lys Pro Gln Cys Lys Glu Val His Gln Thr Leu Ile Leu Asp Pro
                 85                  90                  95

Ala Gln Arg Lys Arg Leu Gln Gln Gln Met Gln Gln His Val Gln Leu
            100                 105                 110

Leu Thr Gln Ile His Leu Leu Ala Thr Cys Asn Pro Asn Leu Asn Pro
        115                 120                 125

Glu Ala Ser Ser Thr Arg Ile Cys Leu Lys Glu Leu Gly Thr Phe Ala
    130                 135                 140

Gln Ser Ser Ile Ala Leu His His Gln Tyr Asn Pro Lys Phe Gln Thr
145                 150                 155                 160

Leu Phe Gln Pro Cys Asn Leu Met Gly Ala Met Gln Leu Ile Glu Asp
                165                 170                 175

Phe Ser Thr His Val Ser Ile Asp Cys Ser Pro His Lys Thr Val Lys
            180                 185                 190

Lys Thr Ala Asn Glu Phe Pro Cys Leu Pro Lys Gln Val Ala Trp Ile
        195                 200                 205

Leu Ala Thr Ser Lys Val Phe Met Tyr Pro Glu Leu Leu Pro Val Cys
    210                 215                 220
```

-continued

```
Ser Leu Lys Ala Lys Asn Pro Gln Asp Lys Ile Leu Phe Thr Lys Ala
225                 230                 235                 240

Glu Asp Asn Leu Leu Ala Leu Gly Leu Lys His Phe Glu Gly Thr Glu
                245                 250                 255

Phe Leu Asn Pro Leu Ile Ser Lys Tyr Leu Leu Thr Cys Lys Thr Ala
            260                 265                 270

Arg Gln Leu Thr Val Arg Ile Lys Asn Leu Asn Met Asn Arg Ala Pro
        275                 280                 285

Asp Asn Ile Ile Lys Phe Tyr Lys Lys Thr Lys Gln Leu Pro Val Leu
    290                 295                 300

Gly Lys Cys Cys Glu Glu Ile Gln Pro His Gln Trp Lys Pro Pro Ile
305                 310                 315                 320

Glu Arg Glu Glu His Arg Leu Pro Phe Trp Leu Lys Ala Ser Leu Pro
                325                 330                 335

Ser Ile Gln Glu Glu Leu Arg His Met Ala Asp Gly Ala Arg Glu Val
            340                 345                 350

Gly Asn Met Thr Gly Thr Thr Glu Ile Asn Ser Asp Gln Gly Leu Glu
        355                 360                 365

Lys Asp Asn Ser Glu Leu Gly Ser Glu Thr Arg Tyr Pro Leu Leu Leu
    370                 375                 380

Pro Lys Gly Val Val Leu Lys Leu Lys Pro Val Ala Asp Arg Phe Pro
385                 390                 395                 400

Lys Lys Ala Trp Arg Gln Lys Arg Ser Ser Val Leu Lys Pro Leu Leu
                405                 410                 415

Ile Gln Pro Ser Pro Ser Leu Gln Pro Ser Phe Asn Pro Gly Lys Thr
            420                 425                 430

Pro Ala Gln Ser Thr His Ser Glu Ala Pro Pro Ser Lys Met Val Leu
        435                 440                 445

Arg Ile Pro His Pro Ile Gln Pro Ala Thr Val Leu Gln Thr Val Pro
    450                 455                 460

Gly Val Pro Pro Leu Gly Val Ser Gly Gly Glu Ser Phe Glu Ser Pro
465                 470                 475                 480

Ala Ala Leu Pro Ala Met Pro Pro Glu Ala Arg Thr Ser Phe Pro Leu
                485                 490                 495

Ser Glu Ser Gln Thr Leu Leu Ser Ser Ala Pro Val Pro Lys Val Met
            500                 505                 510

Met Pro Ser Pro Ala Ser Ser Met Phe Arg Lys Pro Tyr Val Arg Arg
        515                 520                 525

Arg Pro Ser Lys Arg Arg Gly Ala Arg Ala Phe Arg Cys Ile Lys Pro
    530                 535                 540

Ala Pro Val Ile His Pro Ala Ser Val Ile Phe Thr Val Pro Ala Thr
545                 550                 555                 560

Thr Val Lys Ile Val Ser Leu Gly Gly Gly Cys Asn Met Ile Gln Pro
                565                 570                 575

Val Asn Ala Ala Val Ala Gln Ser Pro Gln Thr Ile Pro Ile Ala Thr
            580                 585                 590

Leu Leu Val Asn Pro Thr Ser Phe Pro Cys Pro Leu Asn Gln Pro Leu
        595                 600                 605

Val Ala Ser Ser Val Ser Pro Leu Ile Val Ser Gly Asn Ser Val Asn
    610                 615                 620

Leu Pro Ile Pro Ser Thr Pro Glu Asp Lys Ala His Met Asn Val Asp
625                 630                 635                 640

Ile Ala Cys Ala Val Ala Asp Gly Glu Asn Ala Phe Gln Gly Leu Glu
```

-continued

```
                645                 650                 655

Pro Lys Leu Glu Pro Gln Glu Leu Ser Pro Leu Ser Ala Thr Val Phe
            660                 665                 670

Pro Lys Val Glu His Ser Pro Gly Pro Pro Pro Val Asp Lys Gln Cys
        675                 680                 685

Gln Glu Gly Leu Ser Glu Asn Ser Ala Tyr Arg Trp Thr Val Val Lys
    690                 695                 700

Thr Glu Glu Gly Arg Gln Ala Leu Glu Pro Leu Pro Gln Gly Ile Gln
705                 710                 715                 720

Glu Ser Leu Asn Asn Ser Ser Pro Gly Asp Leu Glu Glu Val Val Lys
                725                 730                 735

Met Glu Pro Glu Asp Ala Thr Glu Glu Ile Ser Gly Phe Leu
            740                 745                 750


<210> SEQ ID NO 127
<211> LENGTH: 2673
<212> TYPE: DNA
<213> ORGANISM: Homo sapiens

<400> SEQUENCE: 127

aggtctagaa ttcaatcggg acgcctcgcg ctgattctca cgggcccggc tgccggcccc     60

cgctctgccc tgcataataa aatggctaat caggtgaatg gtaatgcggt acagttaaaa    120

gaagaggaag aaccaatgga tacttccagt gtaactcaca cagaacacta caagacactg    180

atagaggcag gcctcccaca gaaggtggca gaaagacttg atgaaatatt tcagacagga    240

ttggtagctt atgtcgatct tgatgaaaga gcaattgatg ctctcaggga atttaatgaa    300

gaaggagctc tgtctgtact acagcagttc aaggaaagtg acttatcaca tgttcagaac    360

aaaagtgcat ttttatgtgg agttatgaag acctacaggc agagagagaa acaggggagc    420

aaggtgcaag agtccacaaa gggacctgat gaagcgaaga tcaaggcctt gcttgagaga    480

actggttata ctctggatgt aaccacagga cagaggaagt atggtggtcc tccaccagac    540

agtgtgtact ctggcgtgca acctggaatt ggaacggagg tatttgtagg caaaatacca    600

agggatttat atgaggatga gttggtgccc ctttttgaga aggccggacc catttgggat    660

ctacgtctta tgatggatcc actgtccggt cagaatagag ggtatgcatt tatcaccttc    720

tgtggaaagg aagctgcaca ggaagccgtg aaactgtgtg acagctatga aattcgccct    780

ggtaaacacc ttggagtgtg catttctgtg gcaaacaaca gactttttgt tggatccatt    840

ccgaagaata agactaaaga aaacattttg gaagaattca gtaaagtcac agagggtttg    900

gtggacgtta ttctctatca tcaacccgat gacaaaaaga agaatcgggg gttctgcttc    960

cttgaatatg aggatcacaa gtcagcagca caagccagac gccggctgat gagtggaaaa   1020

gtaaaagtgt ggggaaatgt agttacagtt gaatgggctg accctgtgga agaaccagat   1080

ccagaagtca tggctaaggt aaaagttttg tttgtgagaa acttggctac tacggtgaca   1140

gaagaaatat tggaaaagtc attttctgaa tttggaaaac tcgaaagagt aaagaagttg   1200

aaagattatg catttgttca ttttgaagac agaggagcag ctgttaaggc tatggatgaa   1260

atgaatggca aagaaataga aggggaagaa attgaaatag tcttagccaa gccaccagac   1320

aagaaaagga aagagcgcca agctgctaga caggcctcca gaagcactgc gtatgaagat   1380

tattactacc accctcctcc tcgcatgcca cctccaatta gaggtcgggg tcgtggtggg   1440

gggagaggtg gatatggcta ccctccagat tactacggct atgaagatta ctatgatgat   1500

tactatggtt atgattatca cgactatcgt ggaggctatg aagatcccta ctacggctat   1560
```

-continued

```
gatgatggct atgcagtaag aggaagagga ggaggaaggg gagggcgagg tgctccacca   1620
ccaccaaggg ggaggggagc accacctcca agaggtagag ctggctattc acagaggggg   1680
gcacctttgg gaccaccaag aggctctagg ggtggcagag ggggtcctgc tcaacagcag   1740
agaggccgtg gttcccgtgg atctcggggc aatcgtgggg gcaatgtagg aggcaagaga   1800
aaggcagatg ggtacaacca gcctgattcc aagcgtcgtc agaccaacaa ccaacagaac   1860
tggggttccc aacccatcgc tcagcagccg cttcagcaag gtggtgacta ttctggtaac   1920
tatggttaca ataatgacaa ccaggaattt tatcaggata cttatgggca acagtggaag   1980
tagacaagta agggcttgaa aatgatactg gcaagatacg attggctcta gatctacatt   2040
cttcaaaaaa aaaaattggc ttaactgttt catctttaag tagcattttg ctgccatttg   2100
tattgggctg aagaaatcac tattgtgtat atactcaagt ctttttattt ttcctctttt   2160
cataaatgct cttggacatt attgggcttg cagagttccc ttattctggg gattacaatg   2220
cttttatcgt ttcaggcttc attttagctt caaaacaagc tgggcacact gttaaatcat   2280
gattttgcag aacctttggt tttggacagt ttcatttttt tggatttggg atagattaca   2340
taggagtatg gagtatgctg taaataaaaa tacaagctag tgctttgtct tagtagtttt   2400
aagaaattaa agcaaacaaa tttaagtttt cttgtattga aaataaccta tgattgtatg   2460
ttttgcattc ctagaagtag gttaactgtg tttttaaatt gttataactt cacacctttt   2520
tgaaatctgc cctacaaaat ttgtttggct taaacgtcaa aagccgtgac aatttgttct   2580
ttgatgtgat tgtatttcca atttcttgtt catgtaagat ttcaataaaa ctaaaaaatc   2640
tattcaaaac aaaaaaaaaa aaaaaaaaaa aaa                                2673
```

<210> SEQ ID NO 128
<211> LENGTH: 633
<212> TYPE: PRT
<213> ORGANISM: Homo sapiens

<400> SEQUENCE: 128

```
Met Ala Asn Gln Val Asn Gly Asn Ala Val Gln Leu Lys Glu Glu Glu
  1               5                  10                  15

Glu Pro Met Asp Thr Ser Ser Val Thr His Thr Glu His Tyr Lys Thr
             20                  25                  30

Leu Ile Glu Ala Gly Leu Pro Gln Lys Val Ala Glu Arg Leu Asp Glu
         35                  40                  45

Ile Phe Gln Thr Gly Leu Val Ala Tyr Val Asp Leu Asp Glu Arg Ala
     50                  55                  60

Ile Asp Ala Leu Arg Glu Phe Asn Glu Glu Gly Ala Leu Ser Val Leu
 65                  70                  75                  80

Gln Gln Phe Lys Glu Ser Asp Leu Ser His Val Gln Asn Lys Ser Ala
                 85                  90                  95

Phe Leu Cys Gly Val Met Lys Thr Tyr Arg Gln Arg Glu Lys Gln Gly
            100                 105                 110

Ser Lys Val Gln Glu Ser Thr Lys Gly Pro Asp Glu Ala Lys Ile Lys
        115                 120                 125

Ala Leu Leu Glu Arg Thr Gly Tyr Thr Leu Asp Val Thr Thr Gly Gln
    130                 135                 140

Arg Lys Tyr Gly Gly Pro Pro Pro Asp Ser Val Tyr Ser Gly Val Gln
145                 150                 155                 160

Pro Gly Ile Gly Thr Glu Val Phe Val Gly Lys Ile Pro Arg Asp Leu
                165                 170                 175
```

-continued

```
Tyr Glu Asp Glu Leu Val Pro Leu Phe Glu Lys Ala Gly Pro Ile Trp
            180                 185                 190

Asp Leu Arg Leu Met Met Asp Pro Leu Ser Gly Gln Asn Arg Gly Tyr
        195                 200                 205

Ala Phe Ile Thr Phe Cys Gly Lys Glu Ala Ala Gln Glu Ala Val Lys
    210                 215                 220

Leu Cys Asp Ser Tyr Glu Ile Arg Pro Gly Lys His Leu Gly Val Cys
225                 230                 235                 240

Ile Ser Val Ala Asn Asn Arg Leu Phe Val Gly Ser Ile Pro Lys Asn
                245                 250                 255

Lys Thr Lys Glu Asn Ile Leu Glu Glu Phe Ser Lys Val Thr Glu Gly
            260                 265                 270

Leu Val Asp Val Ile Leu Tyr His Gln Pro Asp Asp Lys Lys Lys Asn
        275                 280                 285

Arg Gly Phe Cys Phe Leu Glu Tyr Glu Asp His Lys Ser Ala Ala Gln
    290                 295                 300

Ala Arg Arg Arg Leu Met Ser Gly Lys Val Lys Val Trp Gly Asn Val
305                 310                 315                 320

Val Thr Val Glu Trp Ala Asp Pro Val Glu Glu Pro Asp Pro Glu Val
                325                 330                 335

Met Ala Lys Val Lys Val Leu Phe Val Arg Asn Leu Ala Thr Thr Val
            340                 345                 350

Thr Glu Glu Ile Leu Glu Lys Ser Phe Ser Glu Phe Gly Lys Leu Glu
        355                 360                 365

Arg Val Lys Lys Leu Lys Asp Tyr Ala Phe Val His Phe Glu Asp Arg
    370                 375                 380

Gly Ala Ala Val Lys Ala Met Asp Glu Met Asn Gly Lys Glu Ile Glu
385                 390                 395                 400

Gly Glu Glu Ile Glu Ile Val Leu Ala Lys Pro Pro Asp Lys Lys Arg
                405                 410                 415

Lys Glu Arg Gln Ala Ala Arg Gln Ala Ser Arg Ser Thr Ala Tyr Glu
            420                 425                 430

Asp Tyr Tyr Tyr His Pro Pro Pro Arg Met Pro Pro Pro Ile Arg Gly
        435                 440                 445

Arg Gly Arg Gly Gly Gly Arg Gly Gly Tyr Gly Tyr Pro Pro Asp Tyr
    450                 455                 460

Tyr Gly Tyr Glu Asp Tyr Tyr Asp Asp Tyr Tyr Gly Tyr Asp Tyr His
465                 470                 475                 480

Asp Tyr Arg Gly Gly Tyr Glu Asp Pro Tyr Tyr Gly Tyr Asp Asp Gly
                485                 490                 495

Tyr Ala Val Arg Gly Arg Gly Gly Gly Arg Gly Gly Arg Gly Ala Pro
            500                 505                 510

Pro Pro Pro Arg Gly Arg Gly Ala Pro Pro Pro Arg Gly Arg Ala Gly
        515                 520                 525

Tyr Ser Gln Arg Gly Ala Pro Leu Gly Pro Pro Arg Gly Ser Arg Gly
    530                 535                 540

Gly Arg Gly Gly Pro Ala Gln Gln Gln Arg Gly Arg Gly Ser Arg Gly
545                 550                 555                 560

Ser Arg Gly Asn Arg Gly Gly Asn Val Gly Gly Lys Arg Lys Ala Asp
                565                 570                 575

Gly Tyr Asn Gln Pro Asp Ser Lys Arg Arg Gln Thr Asn Asn Gln Gln
            580                 585                 590
```

-continued

```
Asn Trp Gly Ser Gln Pro Ile Ala Gln Gln Pro Leu Gln Gln Gly Gly
        595                 600                 605

Asp Tyr Ser Gly Asn Tyr Gly Tyr Asn Asn Asp Asn Gln Glu Phe Tyr
    610                 615                 620

Gln Asp Thr Tyr Gly Gln Gln Trp Lys
625                 630


<210> SEQ ID NO 129
<211> LENGTH: 938
<212> TYPE: DNA
<213> ORGANISM: Homo sapiens

<400> SEQUENCE: 129

gcaagtccat gcctctacca tgagggtgga ggagttaaga tcaacagatc cacatgtacc      60

ttgaggtgac agactggctc tgaacaagtt gaaatcatcg cagaaggata aagttcgtca     120

gtttatgatc ttcacacaat ctagtgaaaa aacagcagta agttgtcttt ctcaaaatga     180

ctggaagtta gatgttgcaa cagataattt tttccaaaat cctgaacttt atatacgaga     240

gagtgtaaaa ggatcattgg acaggaagaa gttagaacag ctgtacaata gataccaaga     300

ccctcaagat gagaataaaa ttggaataga tggcatacag cagttctgtg atgacctggc     360

actcgatcca gccagcatta gtgtgttgat tattgcatgg aagttcagag cagcaacaca     420

gtgcgagttc tccaaacagg agttcatgga tggcatgaca gaattaggat gtgacagcat     480

agaaaaacta aaggcccaga tacccaagat ggaacaagaa ttgaaagaac caggacgatt     540

taaggatttt taccagttta cttttaattt tgcaaagaat ccaggacaaa aaggattaga     600

tctagaaatg gccattgcct actggaactt agtgcttaat ggaagattta aattcttaga     660

cttatggaat aaatttttgt tggaacatca taaacgatca ataccaaaag acacttggaa     720

tcttctttta gacttcagta cgatgattgc agatgacatg tctaattatg atgaagaagg     780

agcatggcct gtttttattg atgactttgt ggaatttgca cgccctcaaa ttgctgggac     840

aaaaagtaca acagtgtagc actaaaggaa ccttctagaa tgtacatagt ctgtacaata     900

aatacaacag aaaattgcaa aaaaaaaaaa aaaaaaaa                             938


<210> SEQ ID NO 130
<211> LENGTH: 244
<212> TYPE: PRT
<213> ORGANISM: Homo sapiens

<400> SEQUENCE: 130

Met Ile Phe Thr Gln Ser Ser Glu Lys Thr Ala Val Ser Cys Leu Ser
  1               5                  10                  15

Gln Asn Asp Trp Lys Leu Asp Val Ala Thr Asp Asn Phe Phe Gln Asn
             20                  25                  30

Pro Glu Leu Tyr Ile Arg Glu Ser Val Lys Gly Ser Leu Asp Arg Lys
         35                  40                  45

Lys Leu Glu Gln Leu Tyr Asn Arg Tyr Gln Asp Pro Gln Asp Glu Asn
     50                  55                  60

Lys Ile Gly Ile Asp Gly Ile Gln Gln Phe Cys Asp Asp Leu Ala Leu
 65                  70                  75                  80

Asp Pro Ala Ser Ile Ser Val Leu Ile Ile Ala Trp Lys Phe Arg Ala
                 85                  90                  95

Ala Thr Gln Cys Glu Phe Ser Lys Gln Glu Phe Met Asp Gly Met Thr
            100                 105                 110

Glu Leu Gly Cys Asp Ser Ile Glu Lys Leu Lys Ala Gln Ile Pro Lys
```

-continued

```
        115                 120                 125

Met Glu Gln Glu Leu Lys Glu Pro Gly Arg Phe Lys Asp Phe Tyr Gln
    130                 135                 140

Phe Thr Phe Asn Phe Ala Lys Asn Pro Gly Gln Lys Gly Leu Asp Leu
145                 150                 155                 160

Glu Met Ala Ile Ala Tyr Trp Asn Leu Val Leu Asn Gly Arg Phe Lys
                165                 170                 175

Phe Leu Asp Leu Trp Asn Lys Phe Leu Leu Glu His His Lys Arg Ser
            180                 185                 190

Ile Pro Lys Asp Thr Trp Asn Leu Leu Leu Asp Phe Ser Thr Met Ile
        195                 200                 205

Ala Asp Asp Met Ser Asn Tyr Asp Glu Glu Gly Ala Trp Pro Val Phe
    210                 215                 220

Ile Asp Asp Phe Val Glu Phe Ala Arg Pro Gln Ile Ala Gly Thr Lys
225                 230                 235                 240

Ser Thr Thr Val


<210> SEQ ID NO 131
<211> LENGTH: 5170
<212> TYPE: DNA
<213> ORGANISM: Homo sapiens

<400> SEQUENCE: 131

ccgggtcgac ccacgcgtcc gcgtaattcc gaaagagcag aagaaagaga aggagaacag     60

gaaaagaaga gctagtaagc gagagcgaga gcacagaaaa gaaaaaaaaa agccttaaga    120

ggaccgaagg ggaggaaagg aaaaggatgg acaaccacaa aacgcagcga ttgcggaaat    180

tttccagcgc cattggctgg gcagcgtgag tccttcggtc gggcgtgatt tcagcaccgg    240

gggaactgga cagcacctcg gggggacttc tgggcaaccc gcaaccacag caagaactcc    300

accagcagcc tcaacaacag aagccgcgga aaaccctgct ttgtatcaga gaggcaaggt    360

cagtccgacg cacagccatg cacaggcagt gcgcctgtac tacgctgcaa accctctgct    420

tgtttctcta acatgcactt gcttctaatt actagcattg tttcatttct gatcagtgaa    480

gatcagtaga tgagattctg taagggtgta cttttaattt atatgtatat atttaacttc    540

tttttctgtt atttttaaag tgttgtgggg gagtggggtt tttttcctac tttttttttt    600

tttttttttt tctttgcttg ccttgcacta cgtgcctgga tagtttgtgg atataattat    660

tgactggcgt ctgggctatt gcagtgcggg ggggttaggg aggaaggaat ccaccccccac    720

ccccccaaac ccttttcttc tcctttcctg gcttcggaca ttggagcact aaatgaactt    780

gaattgtgtc tgtggcgagc aggatggtcg ctgttacttt gtgatgagat cggggatgaa    840

ttgctcgctt taaaaatgct gctttggatt ctgttgctgg agacgtctct ttgttttgcc    900

gctggaaacg ttacagggga cgtttgcaaa gagaagatct gttcctgcaa tgagatagaa    960

ggggacctac acgtagactg tgaaaaaaag ggcttcacaa gtctgcagcg tttcactgcc   1020

ccgacttccc agttttacca tttatttctg catggcaatt ccctcactcg acttttccct   1080

aatgagttcg ctaactttta taatgcggtt agtttgcaca tggaaaacaa tggcttgcat   1140

gaaatcgttc cgggggcttt tctggggctg cagctggtga aaaggctgca catcaacaac   1200

aacaagatca agtcttttcg aaagcagact tttctggggc tggacgatct ggaatatctc   1260

caggctgatt ttaatttatt acgagatata gacccggggg ccttccagga cttgaacaag   1320

ctggaggtgc tcattttaaa tgacaatctc atcagcaccc tacctgccaa cgtgttccag   1380
```

-continued

```
tatgtgccca tcacccacct cgacctccgg ggtaacaggc tgaaacgctg ccctatgagg   1440
agtcttggag caaatccctg gtattgcgga gatcctgcta gagataaccc ttgggactgc   1500
acctgtgatc tgctctccct gaaagaatgg ctggaaaaca ttcccaagaa tgccctgatc   1560
ggccgagtgg tctgcgaagc cccccaccaga ctgcagggta aagacctcaa tgaaaccacc   1620
gaacaggact tgtgtccttt gaaaaaccga gtggattcta gtctcccggc gccccctgcc   1680
caagaagaga cctttgctcc tggacccctg ccaactcctt tcaagacaaa tgggcaagag   1740
gatcatgcca caccagggtc tgctccaaac ggaggtacaa agatcccagg caactggcag   1800
atcaaaatca gacccacagc agcgatagcg acgggtagct ccaggaacaa accccttagct   1860
aacagtttac cctgccctgg gggctgcagc tgcgaccaca tcccagggtc gggtttaaag   1920
atgaactgca acaacaggaa cgtgagcagc ttggctgatt tgaagcccaa gctctctaac   1980
gtgcaggagc ttttcctacg agataacaag atccacagca tccgaaaatc gcactttgtg   2040
gattacaaga acctcattct gttggatctg ggcaacaata acatcgctac tgtagagaac   2100
aacactttca agaacctttt ggacctcagg tggctataca tggatagcaa ttacctggac   2160
acgctgtccc gggagaaatt cgcggggctg caaaacctag agtacctgaa cgtggagtac   2220
aacgctatcc agctcatcct cccgggcact ttcaatgcca tgcccaaact gaggatcctc   2280
attctcaaca acaacctgct gaggtccctg cctgtggacg tgttcgctgg ggtctcgctc   2340
tctaaactca gcctgcacaa caattacttc atgtacctcc cggtggcagg ggtgctggac   2400
cagttaacct ccatcatcca gatagacctc cacggaaacc cctgggagtg ctcctgcaca   2460
attgtgcctt tcaagcagtg ggcagaacgc ttgggttccg aagtgctgat gagcgacctc   2520
aagtgtgaga cgccggtgaa cttctttaga aaggatttca tgctcctctc caatgacgag   2580
atctgccctc agctgtacgc taggatctcg cccacgttaa cttcgcacag taaaaacagc   2640
actgggttgg cggagaccgg gacgcactcc aactcctacc tagacaccag cagggtgtcc   2700
atctcggtgt tggtcccggg actgctgctg gtgtttgtca cctccgcctt caccgtggtg   2760
ggcatgctcg tgtttatcct gaggaaccga aagcggtcca agagacgaga tgccaactcc   2820
tccgcgtccg agattaattc cctacagaca gtctgtgact cttcctactg gcacaatggg   2880
ccttacaacg cagatggggc ccacagagtg tatgactgtg gctctcactc gctctcagac   2940
taagacccca accccaatag gggagggcag agggaaggcg atacatcctt ccccaccgca   3000
ggcaccccgg gggctggagg ggcgtgtacc caaatccccg cgccatcagc ctggatgggc   3060
ataagtagat aaataactgt gagctcgcac aaccgaaagg gcctgacccc ttacttagct   3120
ccctccttga aacaaagagc agactgtgga gagctgggag agcgcagcca gctcgctctt   3180
tgctgagagc ccccttttgac agaaagccca gcacgaccct gctggaagaa ctgacagtgc   3240
cctcgccctc ggccccgggg cctgtggggt tggatgccgc ggttctatac atatatacat   3300
atatccacat ctatatagag agatagatat ctatttttcc cctgtggatt agccccgtga   3360
tggctccctg ttggctacgc agggatgggc agttgcacga aggcatgaat gtattgtaaa   3420
taagtaactt tgacttctga caaaaaacaa aaagtgctgc atggctcgca tggaatccac   3480
gcgctccagg gactctgccc gcccccgcga ctggagacgg catctcgttc acagcaccca   3540
ccctcttacc tgataagttc catcgtatca aactttctat aaacaaaata cagtataatc   3600
agaaagtgcc atttcgccat tatttgtgat cggtaggcag ttcagagcat aagttaactg   3660
tgaaaaaaat gtaaaggttt tatttaggac atttgcatgg ctagtcatca gtccatttta   3720
tgagttaaca atgtattttg ttgagggaag tttttagggg ttgttttggg ttcttttatt   3780
```

```
ttgatggtga tgttttattt tattttattt ttttcagggg gtcttttttt taatacatat   3840

ccaataatgc cttccatctg aatgtaaaat aagtacccat gatttctatt atagtatcag   3900

tgtaattatt taaaaaatga ttttgaggca gttaagcatg accaattaat gtcactctag   3960

tgcttaggct gcgatcctat ggtagcaatt ctgtgctggt ataaatctta cttataaagt   4020

aggaaaagag aaccgaggaa gcacgtgaaa cttactaatt ctattcgagg attttataat   4080

ggcatatttt ttcagtatta aagcgaaaat gttttcaact ctgggtcctt accttttttcc   4140

agcttcatat ttgcaagtgg taaattggat ttgcggtgga agagacaggg gagggaaacg   4200

gttggggtta gatcccttcc tgagctacat taaggctctt tctctaatcg ccttacttag   4260

ctttttaccc tttaagtagc tcctcttccc tcgcccccac cctctacccc acccccacct   4320

tcgctcagac tttaccggct ttccccagtc cataaaggtc ttgccccaac actcacccct   4380

tctttttttc ccctctccaa atgcagcagt gaatcccttt attaatactg gaaatccctc   4440

tctgctgctt ttgttggtgc tgcccacact gcagatatat taaggatgtt aggagagatt   4500

tgatttaatt gactctgcct agataggtct cattaaacag agtggagatt tcattggtca   4560

gcactcctca atgaaagaca gacctaatga ctggcatttg agatgctgct ggcattttga   4620

attcaacatc tgctgaaaac ggtaaaacta attagtgccc acccaccctc cccgccccag   4680

caactgcata ttgaaatttg ttaaagcact catctttatg gaaattaatc attatcctaa   4740

agaagtgttt ctctcccatc atccggattt ctggttgtgg cccagcaatt aacaaaaaca   4800

gcttcaactg ttcgaatttt attgaaccaa tgtaactctg gcctcaatca tattcctctg   4860

ggatttctaa acagcagtta agctacaaaa agcaaacaaa accacacata ttgatggagt   4920

ctgcattcca ccacatatcc acccttgaga agtatgtcaa aagactgcag actatagatt   4980

tttttttaat ataggattat aaatcagcta gtgaaagacc tcagagcagt tgtaagtaga   5040

tctgccatct agaactcata ttctaaaggg aagtgatttc tcagaacagt gatgttctgg   5100

aatatgtatt atttatttta acactttttt aataaaatct ttattataaa ccatgaaaaa   5160

aaaaaaaaaa                                                          5170
```

<210> SEQ ID NO 132
<211> LENGTH: 695
<212> TYPE: PRT
<213> ORGANISM: Homo sapiens

<400> SEQUENCE: 132

```
Met Leu Leu Trp Ile Leu Leu Leu Glu Thr Ser Leu Cys Phe Ala Ala
  1               5                  10                  15

Gly Asn Val Thr Gly Asp Val Cys Lys Glu Lys Ile Cys Ser Cys Asn
             20                  25                  30

Glu Ile Glu Gly Asp Leu His Val Asp Cys Glu Lys Lys Gly Phe Thr
         35                  40                  45

Ser Leu Gln Arg Phe Thr Ala Pro Thr Ser Gln Phe Tyr His Leu Phe
     50                  55                  60

Leu His Gly Asn Ser Leu Thr Arg Leu Phe Pro Asn Glu Phe Ala Asn
 65                  70                  75                  80

Phe Tyr Asn Ala Val Ser Leu His Met Glu Asn Asn Gly Leu His Glu
                 85                  90                  95

Ile Val Pro Gly Ala Phe Leu Gly Leu Gln Leu Val Lys Arg Leu His
            100                 105                 110

Ile Asn Asn Asn Lys Ile Lys Ser Phe Arg Lys Gln Thr Phe Leu Gly
```

-continued

```
        115                 120                 125

Leu Asp Asp Leu Glu Tyr Leu Gln Ala Asp Phe Asn Leu Leu Arg Asp
    130                 135                 140

Ile Asp Pro Gly Ala Phe Gln Asp Leu Asn Lys Leu Glu Val Leu Ile
145                 150                 155                 160

Leu Asn Asp Asn Leu Ile Ser Thr Leu Pro Ala Asn Val Phe Gln Tyr
                165                 170                 175

Val Pro Ile Thr His Leu Asp Leu Arg Gly Asn Arg Leu Lys Arg Cys
            180                 185                 190

Pro Met Arg Ser Leu Gly Ala Asn Pro Trp Tyr Cys Gly Asp Pro Ala
        195                 200                 205

Arg Asp Asn Pro Trp Asp Cys Thr Cys Asp Leu Leu Ser Leu Lys Glu
    210                 215                 220

Trp Leu Glu Asn Ile Pro Lys Asn Ala Leu Ile Gly Arg Val Val Cys
225                 230                 235                 240

Glu Ala Pro Thr Arg Leu Gln Gly Lys Asp Leu Asn Glu Thr Thr Glu
                245                 250                 255

Gln Asp Leu Cys Pro Leu Lys Asn Arg Val Asp Ser Ser Leu Pro Ala
            260                 265                 270

Pro Pro Ala Gln Glu Glu Thr Phe Ala Pro Gly Pro Leu Pro Thr Pro
        275                 280                 285

Phe Lys Thr Asn Gly Gln Glu Asp His Ala Thr Pro Gly Ser Ala Pro
    290                 295                 300

Asn Gly Gly Thr Lys Ile Pro Gly Asn Trp Gln Ile Lys Ile Arg Pro
305                 310                 315                 320

Thr Ala Ala Ile Ala Thr Gly Ser Ser Arg Asn Lys Pro Leu Ala Asn
                325                 330                 335

Ser Leu Pro Cys Pro Gly Gly Cys Ser Cys Asp His Ile Pro Gly Ser
            340                 345                 350

Gly Leu Lys Met Asn Cys Asn Asn Arg Asn Val Ser Ser Leu Ala Asp
        355                 360                 365

Leu Lys Pro Lys Leu Ser Asn Val Gln Glu Leu Phe Leu Arg Asp Asn
    370                 375                 380

Lys Ile His Ser Ile Arg Lys Ser His Phe Val Asp Tyr Lys Asn Leu
385                 390                 395                 400

Ile Leu Leu Asp Leu Gly Asn Asn Asn Ile Ala Thr Val Glu Asn Asn
                405                 410                 415

Thr Phe Lys Asn Leu Leu Asp Leu Arg Trp Leu Tyr Met Asp Ser Asn
            420                 425                 430

Tyr Leu Asp Thr Leu Ser Arg Glu Lys Phe Ala Gly Leu Gln Asn Leu
        435                 440                 445

Glu Tyr Leu Asn Val Glu Tyr Asn Ala Ile Gln Leu Ile Leu Pro Gly
    450                 455                 460

Thr Phe Asn Ala Met Pro Lys Leu Arg Ile Leu Ile Leu Asn Asn Asn
465                 470                 475                 480

Leu Leu Arg Ser Leu Pro Val Asp Val Phe Ala Gly Val Ser Leu Ser
                485                 490                 495

Lys Leu Ser Leu His Asn Asn Tyr Phe Met Tyr Leu Pro Val Ala Gly
            500                 505                 510

Val Leu Asp Gln Leu Thr Ser Ile Ile Gln Ile Asp Leu His Gly Asn
        515                 520                 525

Pro Trp Glu Cys Ser Cys Thr Ile Val Pro Phe Lys Gln Trp Ala Glu
    530                 535                 540
```

```
Arg Leu Gly Ser Glu Val Leu Met Ser Asp Leu Lys Cys Glu Thr Pro
545                 550                 555                 560

Val Asn Phe Phe Arg Lys Asp Phe Met Leu Leu Ser Asn Asp Glu Ile
                565                 570                 575

Cys Pro Gln Leu Tyr Ala Arg Ile Ser Pro Thr Leu Thr Ser His Ser
            580                 585                 590

Lys Asn Ser Thr Gly Leu Ala Glu Thr Gly Thr His Ser Asn Ser Tyr
        595                 600                 605

Leu Asp Thr Ser Arg Val Ser Ile Ser Val Leu Val Pro Gly Leu Leu
    610                 615                 620

Leu Val Phe Val Thr Ser Ala Phe Thr Val Val Gly Met Leu Val Phe
625                 630                 635                 640

Ile Leu Arg Asn Arg Lys Arg Ser Lys Arg Arg Asp Ala Asn Ser Ser
                645                 650                 655

Ala Ser Glu Ile Asn Ser Leu Gln Thr Val Cys Asp Ser Ser Tyr Trp
            660                 665                 670

His Asn Gly Pro Tyr Asn Ala Asp Gly Ala His Arg Val Tyr Asp Cys
        675                 680                 685

Gly Ser His Ser Leu Ser Asp
    690                 695


<210> SEQ ID NO 133
<211> LENGTH: 1564
<212> TYPE: DNA
<213> ORGANISM: Homo sapiens

<400> SEQUENCE: 133

attctagacc tcggcctccc aaagtgctgt gattataggt gtaagccacc gtgtctggcc     60

tctgaacaac tttttcagca actaaaaaag ccacaggagt tgaactgcta ggattctgac    120

tatgctgtgg tggctagtgc tcctactcct acctacatta aaatctgttt tttgttctct    180

tgtaactagc ctttaccttc ctaacacaga ggatctgtca ctgtggctct ggcccaaacc    240

tgaccttcac tctggaacga gaacagaggt ttctacccac accgtcccct cgaagccggg    300

gacagcctca ccttgctggc ctctcgctgg agcagtgccc tcaccaactg tctcacgtct    360

ggaggcactg actcgggcag tgcaggtagc tgagcctctt ggtagctgcg gctttcaagg    420

tgggccttgc cctggccgta gaagggattg acaagcccga agatttcata ggcgatggct    480

cccactgccc aggcatcagc cttgctgtag tcaatcactg ccctggggcc aggacgggcc    540

gtggacacct gctcagaagc agtgggtgag acatcacgct gcccgcccat ctaacctttt    600

catgtcctgc acatcacctg atccatgggc taatctgaac tctgtcccaa ggaacccaga    660

gcttgagtga gctgtggctc agacccagaa ggggtctgct tagaccacct ggtttatgtg    720

acaggacttg cattctcctg gaacatgagg gaacgccgga ggaaagcaaa gtggcaggga    780

aggaacttgt gccaaattat gggtcagaaa agatggaggt gttgggttat cacaaggcat    840

cgagtctcct gcattcagtg gacatgtggg ggaagggctg ccgatggcgc atgacacact    900

cgggactcac ctctggggcc atcagacagc cgtttccgcc ccgatccacg taccagctgc    960

tgaagggcaa ctgcaggccg atgctctcat cagccaggca gcagccaaaa tctgcgatca   1020

ccagccaggg gcagccgtct gggaaggagc aagcaaagtg accatttctc ctcccctcct   1080

tccctctgag aggccctcct atgtccctac taaagccacc agcaagacat agctgacagg   1140

ggctaatggc tcagtgttgg cccaggaggt cagcaaggcc tgagagctga tcagaagggc   1200
```

-continued

```
ctgctgtgcg aacacggaaa tgcctccagt aagtacaggc tgcaaaatcc ccaggcaaag   1260

gactgtgtgg ctcaatttaa atcatgttct agtaattgga gctgtcccca agaccaaagg   1320

agctagagct tggttcaaat gatctccaag ggcccttata ccccaggaga ctttgatttg   1380

aatttgaaac cccaaatcca aacctaagaa ccaggtgcat taagaatcag ttattgccgg   1440

gtgtggtggc ctgtaatgcc aacattttgg gaggccgagg cgggtagatc acctgaggtc   1500

aggagttcaa gaccagcctg gccaacatgg tgaaacccct gtctctacta aaaaaaaaaa   1560

aaaa                                                                1564
```

<210> SEQ ID NO 134
<211> LENGTH: 109
<212> TYPE: PRT
<213> ORGANISM: Homo sapiens

<400> SEQUENCE: 134

```
Met Leu Trp Trp Leu Val Leu Leu Leu Leu Pro Thr Leu Lys Ser Val
  1               5                  10                  15

Phe Cys Ser Leu Val Thr Ser Leu Tyr Leu Pro Asn Thr Glu Asp Leu
             20                  25                  30

Ser Leu Trp Leu Trp Pro Lys Pro Asp Leu His Ser Gly Thr Arg Thr
         35                  40                  45

Glu Val Ser Thr His Thr Val Pro Ser Lys Pro Gly Thr Ala Ser Pro
     50                  55                  60

Cys Trp Pro Leu Ala Gly Ala Val Pro Ser Pro Thr Val Ser Arg Leu
 65                  70                  75                  80

Glu Ala Leu Thr Arg Ala Val Gln Val Ala Glu Pro Leu Gly Ser Cys
                 85                  90                  95

Gly Phe Gln Gly Gly Pro Cys Pro Gly Arg Arg Arg Asp
            100                 105
```

<210> SEQ ID NO 135
<211> LENGTH: 839
<212> TYPE: DNA
<213> ORGANISM: Homo sapiens

<400> SEQUENCE: 135

```
aacgcgtttt gccagttatg cgaaaacatg gctgcggccg gtttggccct tctttgtagg     60

agagtttcat ccgccctgaa atcttcccga tcgttaataa ctcctcaggt ccctgcctgc    120

acagggtttt ttcttagttt gttgcctaag agtacaccaa atgtgacatc ctttcaccaa    180

tatagattac ttcataccac attgtcaagg aaaggactag aagaattttt tgatgaccca    240

aaaaactggg ggcaagaaaa agtaaaatct ggagcagcat ggacctgtca gcaactaagg    300

aacaaaagta atgaagattt acacaaactt tggtatgtct tactgaaaga aagaaacatg    360

cttctaaccc tagagcagga ggccaagcgg cagagattgc caatgccaag tccagagcgg    420

ttagataagg tagtagattc catggatgca ttagataaag ttgtccagga aagagaagat    480

gccctaaggc ttcttcagac tggtcaagaa agagctagac ctggtgcttg gagaagagac    540

atctttggaa gaatcatctg gcacaagttc aagcagtggg ttataccttg gcacctaaat    600

aaaagataca ataggaaacg attctttgcc ttgccttatg tggaccattt tctcagactg    660

gaacgtgaga aacgagcccg catcaaagca cggaaggaaa atttagagag aaagaaagca    720

aaaattcttt taaaaaagtt tccacatctt gctgaagccc aaaagtcaag tcttgtctaa    780

gatgtctgaa ctattaaatt taccattttg tttttcttga aaaaaaaaaa aaaaaaaaa     839
```

<210> SEQ ID NO 136
<211> LENGTH: 250
<212> TYPE: PRT
<213> ORGANISM: Homo sapiens

<400> SEQUENCE: 136

Met Ala Ala Ala Gly Leu Ala Leu Leu Cys Arg Arg Val Ser Ser Ala
1 5 10 15

Leu Lys Ser Ser Arg Ser Leu Ile Thr Pro Gln Val Pro Ala Cys Thr
20 25 30

Gly Phe Phe Leu Ser Leu Leu Pro Lys Ser Thr Pro Asn Val Thr Ser
35 40 45

Phe His Gln Tyr Arg Leu Leu His Thr Thr Leu Ser Arg Lys Gly Leu
50 55 60

Glu Glu Phe Phe Asp Asp Pro Lys Asn Trp Gly Gln Glu Lys Val Lys
65 70 75 80

Ser Gly Ala Ala Trp Thr Cys Gln Gln Leu Arg Asn Lys Ser Asn Glu
85 90 95

Asp Leu His Lys Leu Trp Tyr Val Leu Leu Lys Glu Arg Asn Met Leu
100 105 110

Leu Thr Leu Glu Gln Glu Ala Lys Arg Gln Arg Leu Pro Met Pro Ser
115 120 125

Pro Glu Arg Leu Asp Lys Val Val Asp Ser Met Asp Ala Leu Asp Lys
130 135 140

Val Val Gln Glu Arg Glu Asp Ala Leu Arg Leu Leu Gln Thr Gly Gln
145 150 155 160

Glu Arg Ala Arg Pro Gly Ala Trp Arg Arg Asp Ile Phe Gly Arg Ile
165 170 175

Ile Trp His Lys Phe Lys Gln Trp Val Ile Pro Trp His Leu Asn Lys
180 185 190

Arg Tyr Asn Arg Lys Arg Phe Phe Ala Leu Pro Tyr Val Asp His Phe
195 200 205

Leu Arg Leu Glu Arg Glu Lys Arg Ala Arg Ile Lys Ala Arg Lys Glu
210 215 220

Asn Leu Glu Arg Lys Lys Ala Lys Ile Leu Leu Lys Lys Phe Pro His
225 230 235 240

Leu Ala Glu Ala Gln Lys Ser Ser Leu Val
245 250

<210> SEQ ID NO 137
<211> LENGTH: 1067
<212> TYPE: DNA
<213> ORGANISM: Homo sapiens

<400> SEQUENCE: 137
gacaaaggga gaaaaacaac aggaagcagc ttacaaactc ggtgaacaac tgagggaacc 60
aaaccagaga cgcgctgaac agagagaatc aggctcaaag caagtggaag tgggcagaga 120
ttccaccagg actggtgcaa ggcgcagagc cagccagatt tgagaagaag gcaaaaagat 180
gctggggagc agagctgtaa tgctgctgtt gctgctgccc tggacagctc agggcagagc 240
tgtgcctggg ggcagcagcc ctgcctggac tcagtgccag cagctttcac agaagctctg 300
cacactggcc tggagtgcac atccactagt gggacacatg gatctaagag aagagggaga 360
tgaagagact acaaatgatg ttccccatat ccagtgtgga gatggctgtg acccccaagg 420
actcagggac aacagtcagt tctgcttgca aaggatccac cagggtctga ttttttatga 480

```
gaagctgcta ggatcggata ttttcacagg ggagccttct ctgctccctg atagccctgt    540

gggccagctt catgcctccc tactgggcct cagccaactc ctgcagcctg agggtcacca    600

ctgggagact cagcagattc caagcctcag tcccagccag ccatggcagc gtctccttct    660

ccgcttcaaa atccttcgca gcctccaggc ctttgtggct gtagccgccc gggtctttgc    720

ccatggagca gcaaccctga gtccctaaag gcagcagctc aaggatggca ctcagatctc    780

catggcccag caaggccaag ataaatctac caccccaggc acctgtgagc caacaggtta    840

attagtccat taattttagt gggacctgca tatgttgaaa attaccaata ctgactgaca    900

tgtgatgctg acctatgata aggttgagta tttattagat gggaagggaa atttggggat    960

tatttatcct cctggggaca gtttggggag gattatttat tgtatttata ttgaattatg   1020

tactttttc aataaagtct tatttttgtg gcaaaaaaaa aaaaaaa                 1067


<210> SEQ ID NO 138
<211> LENGTH: 189
<212> TYPE: PRT
<213> ORGANISM: Homo sapiens

<400> SEQUENCE: 138

Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185


<210> SEQ ID NO 139
<211> LENGTH: 1785
<212> TYPE: DNA
<213> ORGANISM: Homo sapiens

<400> SEQUENCE: 139

gcccaggaga ctcccctccc accagcctgg cccccagagt gctgactggc aacaatattc     60

caagttaaaa tagtttgcta aatagttata caattagttt acaattcaaa tatatcagag    120

gaaaagacag ggaaaaaaat tctaagatac atgaatccca gaccattgct ctccaaatat    180
```

-continued

```
tttcaagtga ttcatctcct ttatttaaaa aatgaattaa ccaccagatg ggacactcat    240

acattcctga tggttgtagg aatcagtaga ccctgtatgg aaagcaatag gataatattt    300

cataggatca aattaaaatg ttcacagcat tggttccagg aaattggctt ctggagaatt    360

tatactccag aaacaattca acaaaagaac acagctctgt gcatgcagat gctcattagc    420

ccatcaccta gagtaaggga aagtggagat cccaatgaac aacaatgaga tgggttagcg    480

aactgtgacc tatcagccca atggacattt aagcaatcac tgaaaagtag aaacatgaag    540

atattacaca acatggaaac tgtttatgga gtatatttag gtaaaaagga aaaaaaggca    600

gaactgtata tctgtggttg gatatacttt tttttttaa tattaagcac caaccaaaag    660

aagaaaggag gatagaaaaa ataaaatgga agatgtaggg tgggcagatt agggctgcgt    720

ttgttgcttg ctttcatgtt accatcatag cgtttttgcc acttacaaag gaggaaaaaa    780

atcaattctg tgccaaccca gacaacagag acctgagtgg gggttgggaa gagagatttt    840

tcagcacaga atcagactcc ttctccaaag agctgtgtgg ccttcacctg caaggcgacc    900

tcttccacaa gcagaggcca ggacaaaaag aggcacctgt gagcgacaaa gacggtttcc    960

ttggtttccc tcacggcgcc aagcggagtg gccgcctccc accacagggc cccctaatgg   1020

gcgcttttgt cctgcggggc agagggacct cattagaagg cgctggtgct aaagggaaat   1080

gcatttccag aacaggaggt ttcatcattc ctagcgttag cgacagaatg gtgacagaag   1140

ctctgtggac gtattttcca gcgttcagtt cacatcaagg atgggtatgc actggcggaa   1200

aaggccctca ggaggaagca ctcatcttta acaagacctg ctttctcagg actgcaaaca   1260

agagaaaagc ccaataagag gaaagtgaag tgtgaaaatc catttcaaag aactttactg   1320

agaactcacc atgtcagaga gcttccatta atacagttgc ttcaaaacca ataggcagaa   1380

cccaaagtaa tggatgactc accaggactt ttagcagcta atggagtact ctgagaaatg   1440

ctgtaaatcc aatatttttg ctgaaaaatt aatgtgttat gggagggagc ctcttttcta   1500

atcacttacc cacccccacc ctctacttct agttcaccat cagcatcttt agctcttcta   1560

atttttgcca aagctgaatg cagttctttc ccaattttct tatatcattt taagtattat   1620

atatgctatc ttaccaggcc cactcagaga aacagcactt atctttaaaa ttattttta    1680

actactcccc acagcctacg gccaataaaa actctgtaaa ctatgttaaa tataccaaag   1740

taaagtttcc agaattcaca gaaaaaaaaa aaaaaaaaaa aaaaa                   1785
```

```
<210> SEQ ID NO 140
<211> LENGTH: 86
<212> TYPE: PRT
<213> ORGANISM: Homo sapiens

<400> SEQUENCE: 140

Met Gly Ala Phe Val Leu Arg Gly Arg Gly Thr Ser Leu Glu Gly Ala
  1               5                  10                  15

Gly Ala Lys Gly Lys Cys Ile Ser Arg Thr Gly Gly Phe Ile Ile Pro
             20                  25                  30

Ser Val Ser Asp Arg Met Val Thr Glu Ala Leu Trp Thr Tyr Phe Pro
         35                  40                  45

Ala Phe Ser Ser His Gln Gly Trp Val Cys Thr Gly Gly Lys Gly Pro
     50                  55                  60

Gln Glu Glu Ala Leu Ile Phe Asn Lys Thr Cys Phe Leu Arg Thr Ala
 65                  70                  75                  80

Asn Lys Arg Lys Ala Gln
                 85
```

<210> SEQ ID NO 141
<211> LENGTH: 947
<212> TYPE: DNA
<213> ORGANISM: Homo sapiens

<400> SEQUENCE: 141

```
caaactgaag gtaggatgtc tatataccct tcatttcagg ggcccctaga gaatatacct     60

tagctttccc tcttccggca tcctggaaag tggatacctg tggccttcct ttcactttga    120

aagcttacac cctcattttg actacaacta atactaaaag cttggcatct tgcttgagat    180

tagtgtttgc tatgccaaac accttctcct ctttctattg aaagcaaaac ataggaaaat    240

aatttgaaat acttttaagg catcttaaaa acatgacttt ttcatcttat ggaaaagcag    300

accaattttg ctttttttttc ccaacttgtt ctccagactg tgccaataaa atgtgttcat    360

agcaggaaaa tttggaaaat acagaaaagc actatgaaga aaacaaaatg tacccaaaat    420

cccatcactc agataacatc actgttaatg ttttgatatg tatttccagt cttttctatt    480

gtgttaattt ttcattttgt ttttgaataa ataactttca ggaaagaaat tgagcctttt    540

ctgccacctc tgaagcctga ttactgtgtg aagcaggcca tgaaggccat cctcactgac    600

cagcccatga tctgcactcc ccgcctcatg tacatcgtga ccttcatgaa gagcatccta    660

ccatttgaag cagttgtgtg catgtatcgg ttcctaggag cggacaagtg tatgtacccc    720

tttattgctc aaagaaagca agccacaaac aataatgaag caaaaaatgg aatctaagaa    780

tctttttgta tggaatatta cttctatcag aagatgatca agatgtttca gtccagtgca    840

catcagcatt gctgacattt tatggattct aaacttgtgt tgtttctttt ttaaatcaac    900

tttttaaaaa aataaagtgt aaattaaccg acaaaaaaaa aaaaaaa                947
```

<210> SEQ ID NO 142
<211> LENGTH: 65
<212> TYPE: PRT
<213> ORGANISM: Homo sapiens

<400> SEQUENCE: 142

```
Met Lys Ala Ile Leu Thr Asp Gln Pro Met Ile Cys Thr Pro Arg Leu
  1               5                  10                  15

Met Tyr Ile Val Thr Phe Met Lys Ser Ile Leu Pro Phe Glu Ala Val
             20                  25                  30

Val Cys Met Tyr Arg Phe Leu Gly Ala Asp Lys Cys Met Tyr Pro Phe
         35                  40                  45

Ile Ala Gln Arg Lys Gln Ala Thr Asn Asn Asn Glu Ala Lys Asn Gly
     50                  55                  60

Ile
 65
```

<210> SEQ ID NO 143
<211> LENGTH: 1148
<212> TYPE: DNA
<213> ORGANISM: Homo sapiens

<400> SEQUENCE: 143

```
gcgagatccc taccgcagta tccgcctctg ccgccgcgga gcttcccgaa cctcttcagc     60

cgcccggagc cgctcccgga gcccggccgt agaggctgca atcgcagccg ggagcccgca    120

gcccgcgccc cgagcccgcc gccgcccttc gagggcgccc caggccgcgc catggtgaag    180

gtgacgttca actccgctct ggcccagaag gaggccaaga aggacgagcc caagagcggc    240
```

-continued

```
gaggaggcgc tcatcatccc ccccgacgcc gtcgcggtgg actgcaagga cccagatgat    300

gtggtaccag ttggccaaag aagagcctgg tgttggtgca tgtgctttgg actagcattt    360

atgcttgcag gtgttattct aggaggagca tacttgtaca aatattttgc acttcaacca    420

gatgacgtgt actactgtgg aataaagtac atcaaagatg atgtcatctt aaatgagccc    480

tctgcagatg ccccagctgc tctctaccag acaattgaag aaaatattaa aatctttgaa    540

gaagaagaag ttgaatttat cagtgtgcct gtcccagagt ttgcagatag tgatcctgcc    600

aacattgttc atgactttaa caagaaactt acagcctatt tagatcttaa cctggataag    660

tgctatgtga tccctctgaa cacttccatt gttatgccac ccagaaacct actggagtta    720

cttattaaca tcaaggctgg aacctatttg cctcagtcct atctgattca tgagcacatg    780

gttattactg atcgcattga aaacattgat cacctgggtt tctttattta tcgactgtgt    840

catgacaagg aaacttacaa actgcaacgc agagaaacta ttaaaggtat tcagaaacgt    900

gaagccagca attgtttcgc aattcggcat tttgaaaaca aatttgccgt ggaaacttta    960

atttgttctt gaacagtcaa gaaaaacatt attgaggaaa attaatatca cagcataacc   1020

ccaccccttta cattttgtgc agtgattatt ttttaaagtc ttctttcatg taagtagcaa   1080

acagggcttt actatcttct catctcatta attcaattaa aaccattacc ttaaaaaaaa   1140

aaaaaaaa                                                            1148
```

```
<210> SEQ ID NO 144
<211> LENGTH: 266
<212> TYPE: PRT
<213> ORGANISM: Homo sapiens

<400> SEQUENCE: 144

Met Val Lys Val Thr Phe Asn Ser Ala Leu Ala Gln Lys Glu Ala Lys
  1               5                  10                  15

Lys Asp Glu Pro Lys Ser Gly Glu Glu Ala Leu Ile Ile Pro Pro Asp
             20                  25                  30

Ala Val Ala Val Asp Cys Lys Asp Pro Asp Asp Val Val Pro Val Gly
         35                  40                  45

Gln Arg Arg Ala Trp Cys Trp Cys Met Cys Phe Gly Leu Ala Phe Met
     50                  55                  60

Leu Ala Gly Val Ile Leu Gly Gly Ala Tyr Leu Tyr Lys Tyr Phe Ala
 65                  70                  75                  80

Leu Gln Pro Asp Asp Val Tyr Tyr Cys Gly Ile Lys Tyr Ile Lys Asp
                 85                  90                  95

Asp Val Ile Leu Asn Glu Pro Ser Ala Asp Ala Pro Ala Ala Leu Tyr
            100                 105                 110

Gln Thr Ile Glu Glu Asn Ile Lys Ile Phe Glu Glu Glu Glu Val Glu
        115                 120                 125

Phe Ile Ser Val Pro Val Pro Glu Phe Ala Asp Ser Asp Pro Ala Asn
    130                 135                 140

Ile Val His Asp Phe Asn Lys Lys Leu Thr Ala Tyr Leu Asp Leu Asn
145                 150                 155                 160

Leu Asp Lys Cys Tyr Val Ile Pro Leu Asn Thr Ser Ile Val Met Pro
                165                 170                 175

Pro Arg Asn Leu Leu Glu Leu Leu Ile Asn Ile Lys Ala Gly Thr Tyr
            180                 185                 190

Leu Pro Gln Ser Tyr Leu Ile His Glu His Met Val Ile Thr Asp Arg
        195                 200                 205
```

```
Ile Glu Asn Ile Asp His Leu Gly Phe Phe Ile Tyr Arg Leu Cys His
    210                 215                 220

Asp Lys Glu Thr Tyr Lys Leu Gln Arg Arg Glu Thr Ile Lys Gly Ile
225                 230                 235                 240

Gln Lys Arg Glu Ala Ser Asn Cys Phe Ala Ile Arg His Phe Glu Asn
                245                 250                 255

Lys Phe Ala Val Glu Thr Leu Ile Cys Ser
            260                 265


<210> SEQ ID NO 145
<211> LENGTH: 1353
<212> TYPE: DNA
<213> ORGANISM: Homo sapiens

<400> SEQUENCE: 145

aggtctagaa ttcaatcggc cgcttttttt tttttttttt ttgctaacac ccagttctgc     60

ctgctacacc acctgggaat tgaccatcca gctgtgttct ctctgcctct ggcccagtag    120

caactgacct gccctattcc tggctgatct catgctgctg aagttcaagg cgctggacac    180

actaccctga tttttgttgc acctggccta gcctcattaa cttggcaatt agttggtggt    240

tttctttctt tcttcttctt ttttttttta attcatttca tttctgtcac cccttaattt    300

tcatctttct tttttaagta gttgttccat gctgttgttt tttgttttat ctttcattgc    360

ctttccctct gcagtcaaca ttatgacctg gggactccag catccttcaa gcaagccatt    420

tccgaagaag gtgaaaagaa gccaggatga ttggcacctc ctcctcctcc tcctcttctt    480

cctcttccct tgcccagccc cctcctgtgc gtgtgtttca gacaacacag gagccagcac    540

aggagtggaa aatcctgcag cgcaactcag ctcagcccac agaagccttg ggaatggcct    600

cagtttgtgc aataagaaga tttttttttt ctttttaaat cttcattata ttttctttga    660

ttgtctgtga gaaagtaccc aggtccgcct ggaattactc tacagtagaa ataactgaac    720

acaaacaaac tgatggaaaa aaagagttaa ctattttatt tatttcaata tttaaaagga    780

aaaaagtgct gacatggcac agtatttttg tttaaagtac ctcctacttc aaaagttaag    840

cgcaattttg tgaagacatg aaatcataag agtacttaat gtaaaataaa agactgcata    900

ttaactctaa agaaaaaatgc cccacatttt aaataagaaa ataaagatca actctgctct    960

ctcaggcttt ttaaaaagcc attcatgtat gtgctttagg tatttttatt tctgcgagtt   1020

ggatgtggta agtgaggagt gctcagtttt tttttcctcc ttcaaaagtc tattgaaagt   1080

gttggtgatg ttaaatgatt gtgtgttaag atttgactga aataacttag ccacaaatca   1140

gcagtttccc ccaccctcat tgccccctca ccccaggcaa gcccctttta tctgaatgtc   1200

agaagcagcc tgcctcctag ttatcatgtc tgatgaggtc tagctcagga aggaattcca   1260

tctattgatg gaatatatcc cctcaagttc aatagattcg aacacagaga gctttgttta   1320

aaataatgca gcaaaaaaaa aaaaaaaaaa aaa                                 1353


<210> SEQ ID NO 146
<211> LENGTH: 113
<212> TYPE: PRT
<213> ORGANISM: Homo sapiens

<400> SEQUENCE: 146

Met Leu Leu Phe Phe Val Leu Ser Phe Ile Ala Phe Pro Ser Ala Val
  1               5                  10                  15

Asn Ile Met Thr Trp Gly Leu Gln His Pro Ser Ser Lys Pro Phe Pro
```

-continued

```
            20                  25                  30

Lys Lys Val Lys Arg Ser Gln Asp Asp Trp His Leu Leu Leu Leu Leu
        35                  40                  45

Leu Phe Phe Leu Phe Pro Cys Pro Ala Pro Ser Cys Ala Cys Val Ser
    50                  55                  60

Asp Asn Thr Gly Ala Ser Thr Gly Val Glu Asn Pro Ala Ala Gln Leu
 65                 70                  75                  80

Ser Ser Ala His Arg Ser Leu Gly Asn Gly Leu Ser Leu Cys Asn Lys
                85                  90                  95

Lys Ile Phe Phe Phe Phe Leu Asn Leu His Tyr Ile Phe Phe Asp Cys
            100                 105                 110

Leu
```

<210> SEQ ID NO 147
<211> LENGTH: 2312
<212> TYPE: DNA
<213> ORGANISM: Homo sapiens
<220> FEATURE:
<221> NAME/KEY: unsure
<222> LOCATION: (2224)
<220> FEATURE:
<221> NAME/KEY: unsure
<222> LOCATION: (2236)

<400> SEQUENCE: 147

```
gtttcggcct ggcctgggca ggcgcttgtg ctgccagggc gccgggcccg gggaggccgg     60

ggtctcgggt ggccgccggc ccaggcgctg gacggcagca ggatggggaa ggcgaaggtc    120

cccgcctcca agcgcgcccc gagcagcccc gtggctaagc cgggtcctgt caagacgctc    180

actcggaaga aaaacaagaa gaaaaaaagg ttttggaaaa gcaaggcgcg ggaagtaagc    240

aagaagccag caagcggccc cggtgctgtg gtgcgacctc caaaggcacc agaagacttt    300

tctcaaaact ggaaggcgct gcaagagtgg ctgctgaaac aaaaatctca ggccccagaa    360

aagcctcttg tcatctctca gatgggttcc aaaaagaagc ccaaaattat ccagcaaaac    420

aaaaaagaga cctcgcctca agtgaaggga gaggagatgc cggcaggaaa agaccaggag    480

gccagcaggg gctctgttcc ttcaggttcc aagatggaca ggagggcgcc agtacctcgc    540

accaaggcca gtggaacaga gcacaataag aaaggaacca aggaaaggac aaatggtgat    600

attgttccag aacgagggga catcgagcat aagaagcgga aagctaagga ggcagcccca    660

gccccaccca ccgaggaaga catctggttt gacgacgtgg acccagcgga tatcgaagct    720

gccataggtc cagaggcggc caagatagcg aggaaacagt tgggtcagag cgagggcagc    780

gtcagcctca gcctcgtgaa agagcaggcc ttcggcggcc tgacaagagc cttagccttg    840

gactgtgaga tggtgggcgt gggccctaag gggaggaga gcatggccgc ccgtgtgtcc    900

atcgtgaacc agtatgggaa gtgcgtttat gacaagtacg tcaaaccaac cgagcccgtg    960

acggactata ggacagcggt cagtgggatt cggcctgaga acctcaagca gggagaagag   1020

cttgaagttg ttcagaagga agtggcagag atgctgaagg gcagaattct agtggggcac   1080

gctctgcata atgacctaaa ggtactattt cttgatcatc caaaaaagaa gattcgggac   1140

acacagaaat ataaaccttt caagagtcaa gtaaagagtg gaaggccgtc tctgagacta   1200

ctttcagaga agatccttgg gctccaggtc cagcaggcgg agcactgttc aattcaggat   1260

gcccaggcag caatgaggct gtacgtcatg gtgaagaagg agtgggagag catggcccga   1320

gacaggcgcc ccctgctgac tgctccagac cactgcagtg acgacgccta gcagtcctgc   1380
```

```
cctgctgctg ctgccgcccc gctacagagg caatgtgacc agtcacaggg acagatcaca   1440

tctccccaga gtggcaactc tggtgaaacc ttttcagaat catggcagag gggcgtggcg   1500

tggtgctact gagaaggtcc tccttcctct tgactttgtg gtctgaaacc tggtcttact   1560

gtccatgtgt gtttgggccc ggatggtcag ggtggggagc agggacggcc atgggcacgc   1620

ctggccacgc tttaccgact gctgaccccc tgggccaggt gaggttgggg cctgtgggcc   1680

gccagtccat acggtgctgt cactgcccat cttcggtgac accctggggt gaggtgctca   1740

gcaccttcct ctcgaggagc cacattttcc tcctttgtgt taggggacat aacaagctct   1800

gctgggcttg agggacccag accaggtgtc tgcagtcagc tcctgagaca cagctggccg   1860

gcacaacagg tgttacatca ggggtttcct gtggccgttt gaactttgag catttatcta   1920

aattaaattg gcccagggtt ggctggtggg tcacccagca gaggcttctc cccatagcac   1980

gaggatgtgt tgcctgggca cggtgactgc ggttattcct ggaggtcggc agacatgcca   2040

accttgggct atttgagctg gagaagctat gtgatgctag ccggtggctt tctgggctag   2100

gccccagttt gaggctcccc tgggaactag agccaggaac agccagtggc actgacaagg   2160

ggacggagtc caaggcgtta ttgggccacc tgacagctgg acagaaaagg ggcagacaca   2220

ccgnggatgc gatttnaaat aaatgcagat gtttacttgg aaaaaaaaaa aaaaaaaaaa   2280

aaaaaaaaaa aaaaaaaaaa aaaaaaaaaa aa                                 2312
```

```
<210> SEQ ID NO 148
<211> LENGTH: 422
<212> TYPE: PRT
<213> ORGANISM: Homo sapiens

<400> SEQUENCE: 148

Met Gly Lys Ala Lys Val Pro Ala Ser Lys Arg Ala Pro Ser Ser Pro
1               5                   10                  15

Val Ala Lys Pro Gly Pro Val Lys Thr Leu Thr Arg Lys Lys Asn Lys
            20                  25                  30

Lys Lys Lys Arg Phe Trp Lys Ser Lys Ala Arg Glu Val Ser Lys Lys
        35                  40                  45

Pro Ala Ser Gly Pro Gly Ala Val Val Arg Pro Pro Lys Ala Pro Glu
    50                  55                  60

Asp Phe Ser Gln Asn Trp Lys Ala Leu Gln Glu Trp Leu Leu Lys Gln
65                  70                  75                  80

Lys Ser Gln Ala Pro Glu Lys Pro Leu Val Ile Ser Gln Met Gly Ser
                85                  90                  95

Lys Lys Lys Pro Lys Ile Ile Gln Gln Asn Lys Lys Glu Thr Ser Pro
            100                 105                 110

Gln Val Lys Gly Glu Glu Met Pro Ala Gly Lys Asp Gln Glu Ala Ser
        115                 120                 125

Arg Gly Ser Val Pro Ser Gly Ser Lys Met Asp Arg Arg Ala Pro Val
    130                 135                 140

Pro Arg Thr Lys Ala Ser Gly Thr Glu His Asn Lys Lys Gly Thr Lys
145                 150                 155                 160

Glu Arg Thr Asn Gly Asp Ile Val Pro Glu Arg Gly Asp Ile Glu His
                165                 170                 175

Lys Lys Arg Lys Ala Lys Glu Ala Ala Pro Ala Pro Pro Thr Glu Glu
            180                 185                 190

Asp Ile Trp Phe Asp Asp Val Asp Pro Ala Asp Ile Glu Ala Ala Ile
        195                 200                 205
```

```
Gly Pro Glu Ala Ala Lys Ile Ala Arg Lys Gln Leu Gly Gln Ser Glu
    210                 215                 220

Gly Ser Val Ser Leu Ser Leu Val Lys Glu Gln Ala Phe Gly Gly Leu
225                 230                 235                 240

Thr Arg Ala Leu Ala Leu Asp Cys Glu Met Val Gly Val Gly Pro Lys
                245                 250                 255

Gly Glu Glu Ser Met Ala Ala Arg Val Ser Ile Val Asn Gln Tyr Gly
            260                 265                 270

Lys Cys Val Tyr Asp Lys Tyr Val Lys Pro Thr Glu Pro Val Thr Asp
        275                 280                 285

Tyr Arg Thr Ala Val Ser Gly Ile Arg Pro Glu Asn Leu Lys Gln Gly
    290                 295                 300

Glu Glu Leu Glu Val Val Gln Lys Glu Val Ala Glu Met Leu Lys Gly
305                 310                 315                 320

Arg Ile Leu Val Gly His Ala Leu His Asn Asp Leu Lys Val Leu Phe
                325                 330                 335

Leu Asp His Pro Lys Lys Lys Ile Arg Asp Thr Gln Lys Tyr Lys Pro
            340                 345                 350

Phe Lys Ser Gln Val Lys Ser Gly Arg Pro Ser Leu Arg Leu Leu Ser
        355                 360                 365

Glu Lys Ile Leu Gly Leu Gln Val Gln Gln Ala Glu His Cys Ser Ile
    370                 375                 380

Gln Asp Ala Gln Ala Ala Met Arg Leu Tyr Val Met Val Lys Lys Glu
385                 390                 395                 400

Trp Glu Ser Met Ala Arg Asp Arg Arg Pro Leu Leu Thr Ala Pro Asp
                405                 410                 415

His Cys Ser Asp Asp Ala
            420


<210> SEQ ID NO 149
<211> LENGTH: 2103
<212> TYPE: DNA
<213> ORGANISM: Homo sapiens

<400> SEQUENCE: 149

gggaggaacg tatcccttct ggaggctgtc tcagggggca gagggaccgg accggaagtg      60

acgtgagcgg gttccggttg tctggagccc agctgcgggt gtgagagtcc gtaaggagca     120

gcttccagga tcctgagatc cggagcagcc ggggtcggag cggctcctca agagttactg     180

atctatgaaa tggcagagaa tggaaaaaat tgtgaccaga gacgtgtagc aatgaacaag     240

gaacatcata atggaaattt cacagacccc tcttcagtga atgaaaagaa gaggagggag     300

cgggaagaaa ggcagaatat tgtcctgtgg agacagccgc tcattacctt gcagtatttt     360

tctctggaaa tccttgtaat cttgaaggaa tggacctcaa aattatggca tcgtcaaagc     420

attgtggtgt ctttttttact gctgcttgct gtgcttatag ctacgtatta tgttgaagga     480

gtgcatcaac agtatgtgca acgtatagag aaacagtttc ttttgtatgc ctactggata     540

ggcttaggaa ttttgtcttc tgttgggctt ggaacagggc tgcacacctt tctgctttat     600

ctgggtccac atatagcctc agttacatta gctgcttatg aatgcaattc agttaatttt     660

cccgaaccac cctatcctga tcagattatt tgtccagatg aagagggcac tgaaggaacc     720

atttctttgt ggagtatcat ctcaaaagtt aggattgaag cctgcatgtg gggtatcggt     780

acagcaatcg gagagctgcc tccatatttc atggccagag cagctcgcct ctcaggtgct     840

gaaccagatg atgaagagta tcaggaattt gaagagatgc tggaacatgc agagtctgca     900
```

```
caagactttg cctcccgggc caaactggca gttcaaaaac tagtacagaa agttggattt    960

tttggaattt tggcctgtgc ttcaattcca aatcctttat ttgatctggc tggaataacg   1020

tgtggacact ttctggtacc tttttggacc ttctttggtg caaccctaat tggaaaagca   1080

ataataaaaa tgcatatcca gaaaattttt gttataataa cattcagcaa gcacatagtg   1140

gagcaaatgg tggctttcat tggtgctgtc cccggcatag gtccatctct gcagaagcca   1200

tttcaggagt acctggaggc tcaacggcag aagcttcacc acaaaagcga aatgggcaca   1260

ccacagggag aaaactggtt gtcctggatg tttgaaaagt tggtcgttgt catggtgtgt   1320

tacttcatcc tatctatcat taactccatg gcacaaagtt atgccaaacg aatccagcag   1380

cggttgaact cagaggagaa aactaaataa gtagagaaag ttttaaactg cagaaattgg   1440

agtggatggg ttctgcctta aattgggagg actccaagcc gggaaggaaa attccctttt   1500

ccaacctgta tcaattttta caactttttt cctgaaagca gtttagtcca tactttgcac   1560

tgacatactt tttccttctg tgctaaggta aggtatccac cctcgatgca atccaccttg   1620

tgttttctta gggtggaatg tgatgttcag cagcaaactt gcaacagact ggccttctgt   1680

ttgttacttt caaaaggccc acatgataca attagagaat tcccaccgca caaaaaaagt   1740

tcctaagtat gttaaatatg tcaagctttt taggcttgtc acaaatgatt gctttgtttt   1800

cctaagtcat caaaatgtat ataaattatc tagattggat aacagtcttg catgtttatc   1860

atgttacaat ttaatattcc atcctgccca acccttcctc tcccatcctc aaaaaagggc   1920

cattttatga tgcattgcac accctctggg gaaattgatc tttaaatttt gagacagtat   1980

aaggaaaatc tggttggtgt cttacaagtg agctgacacc atttttttatt ctgtgtattt   2040

agaatgaagt cttgaaaaaa actttataaa gacatcttta atcattccaa aaaaaaaaaa   2100

aaa                                                                 2103
```

<210> SEQ ID NO 150
<211> LENGTH: 406
<212> TYPE: PRT
<213> ORGANISM: Homo sapiens

<400> SEQUENCE: 150

```
Met Ala Glu Asn Gly Lys Asn Cys Asp Gln Arg Arg Val Ala Met Asn
1               5                   10                  15

Lys Glu His His Asn Gly Asn Phe Thr Asp Pro Ser Ser Val Asn Glu
            20                  25                  30

Lys Lys Arg Arg Glu Arg Glu Glu Arg Gln Asn Ile Val Leu Trp Arg
        35                  40                  45

Gln Pro Leu Ile Thr Leu Gln Tyr Phe Ser Leu Glu Ile Leu Val Ile
    50                  55                  60

Leu Lys Glu Trp Thr Ser Lys Leu Trp His Arg Gln Ser Ile Val Val
65                  70                  75                  80

Ser Phe Leu Leu Leu Leu Ala Val Leu Ile Ala Thr Tyr Tyr Val Glu
                85                  90                  95

Gly Val His Gln Gln Tyr Val Gln Arg Ile Glu Lys Gln Phe Leu Leu
            100                 105                 110

Tyr Ala Tyr Trp Ile Gly Leu Gly Ile Leu Ser Ser Val Gly Leu Gly
        115                 120                 125

Thr Gly Leu His Thr Phe Leu Leu Tyr Leu Gly Pro His Ile Ala Ser
    130                 135                 140

Val Thr Leu Ala Ala Tyr Glu Cys Asn Ser Val Asn Phe Pro Glu Pro
```

-continued

```
145                 150                 155                 160

Pro Tyr Pro Asp Gln Ile Ile Cys Pro Asp Glu Glu Gly Thr Glu Gly
                165                 170                 175

Thr Ile Ser Leu Trp Ser Ile Ile Ser Lys Val Arg Ile Glu Ala Cys
            180                 185                 190

Met Trp Gly Ile Gly Thr Ala Ile Gly Glu Leu Pro Pro Tyr Phe Met
        195                 200                 205

Ala Arg Ala Ala Arg Leu Ser Gly Ala Glu Pro Asp Asp Glu Glu Tyr
    210                 215                 220

Gln Glu Phe Glu Glu Met Leu Glu His Ala Glu Ser Ala Gln Asp Phe
225                 230                 235                 240

Ala Ser Arg Ala Lys Leu Ala Val Gln Lys Leu Val Gln Lys Val Gly
                245                 250                 255

Phe Phe Gly Ile Leu Ala Cys Ala Ser Ile Pro Asn Pro Leu Phe Asp
            260                 265                 270

Leu Ala Gly Ile Thr Cys Gly His Phe Leu Val Pro Phe Trp Thr Phe
        275                 280                 285

Phe Gly Ala Thr Leu Ile Gly Lys Ala Ile Ile Lys Met His Ile Gln
    290                 295                 300

Lys Ile Phe Val Ile Ile Thr Phe Ser Lys His Ile Val Glu Gln Met
305                 310                 315                 320

Val Ala Phe Ile Gly Ala Val Pro Gly Ile Gly Pro Ser Leu Gln Lys
                325                 330                 335

Pro Phe Gln Glu Tyr Leu Glu Ala Gln Arg Gln Lys Leu His His Lys
            340                 345                 350

Ser Glu Met Gly Thr Pro Gln Gly Glu Asn Trp Leu Ser Trp Met Phe
        355                 360                 365

Glu Lys Leu Val Val Val Met Val Cys Tyr Phe Ile Leu Ser Ile Ile
    370                 375                 380

Asn Ser Met Ala Gln Ser Tyr Ala Lys Arg Ile Gln Gln Arg Leu Asn
385                 390                 395                 400

Ser Glu Glu Lys Thr Lys
                405
```

<210> SEQ ID NO 151
<211> LENGTH: 1330
<212> TYPE: DNA
<213> ORGANISM: Homo sapiens

<400> SEQUENCE: 151

```
gatgtgagtc ttgccaaagc tcctggcgga ataaagccct tccttcttta actcggtgtc      60

tgaggggttt tgtctgtggc ttgtcctgct acatttcttg gttccctgac caggaaacaa     120

ggtgattaat ggatggtcga gacagctcct taggtggctt aggcctgccc tgtggagcat     180

acctgagggg gactccagcc agcttgagtg aagcagatcc tgagagcact cccaggtagg     240

caattgcccc agtggaatgc ctcatcagag cagtgcacag caggcccctg tggaggatca     300

atgcagtggc tgaacaccat gaaggaactg gcacttggag tccggacatc taaaacttgc     360

accttttctg ctgccatgac aaccatgcaa ggaatggaac aggccatgcc aggggctggc     420

cctggtgtgc cccagctggg aaacatggct gtcatacatt cacatctgtg gaaaggattg     480

caagagaagt tcttgaaggg agaacccaaa gtccttgggg ttgtgcagat tctgactgcc     540

ctgatgagcc ttagcatggg aataacaatg atgtgtatgg catctaatac ttatggaagt     600

aaccctattt ccgtgtatat cgggtacaca atttgggggt cagtaatgtt tattatttca     660
```

```
ggatccttgt caattgcagc aggaattaga actacaaaag gcctggtccg aggtagtcta    720

ggaatgaata tcaccagctc tgtactggct gcatcaggga tcttaatcaa cacatttagc    780

ttggcgtttt attcattcca tcacccttac tgtaactact atggcaactc aaataattgt    840

catgggacta tgtccatctt aatgggtctg gatggcatgg tgctcctctt aagtgtgctg    900

gaattctgca ttgctgtgtc cctctctgcc tttggatgta aagtgctctg ttgtacccct    960

ggtggggttg tgttaattct gccatcacat tctcacatgg cagaaacagc atctcccaca   1020

ccacttaatg aggtttgagg ccaccaaaag atcaacagac aaatgctcca gaaatctatg   1080

ctgactgtga cacaagagcc tcacatgaga aattaccagt atccaacttc gatactgata   1140

gacttgttga tattattatt atatgtaatc caattatgaa ctgtgtgtgt atagagagat   1200

aataaattca aaattatgtt ctcatttttt tccctggaac tcaataactc atttcactgg   1260

ctctttatcg agagtactag aagttaaatt aataaataat gcatttaatg aggcaaaaaa   1320

aaaaaaaaaa                                                          1330
```

```
<210> SEQ ID NO 152
<211> LENGTH: 245
<212> TYPE: PRT
<213> ORGANISM: Homo sapiens

<400> SEQUENCE: 152

Met Gln Trp Leu Asn Thr Met Lys Glu Leu Ala Leu Gly Val Arg Thr
  1               5                  10                  15

Ser Lys Thr Cys Thr Phe Ser Ala Ala Met Thr Thr Met Gln Gly Met
             20                  25                  30

Glu Gln Ala Met Pro Gly Ala Gly Pro Gly Val Pro Gln Leu Gly Asn
         35                  40                  45

Met Ala Val Ile His Ser His Leu Trp Lys Gly Leu Gln Glu Lys Phe
     50                  55                  60

Leu Lys Gly Glu Pro Lys Val Leu Gly Val Val Gln Ile Leu Thr Ala
 65                  70                  75                  80

Leu Met Ser Leu Ser Met Gly Ile Thr Met Met Cys Met Ala Ser Asn
                 85                  90                  95

Thr Tyr Gly Ser Asn Pro Ile Ser Val Tyr Ile Gly Tyr Thr Ile Trp
            100                 105                 110

Gly Ser Val Met Phe Ile Ile Ser Gly Ser Leu Ser Ile Ala Ala Gly
        115                 120                 125

Ile Arg Thr Thr Lys Gly Leu Val Arg Gly Ser Leu Gly Met Asn Ile
    130                 135                 140

Thr Ser Ser Val Leu Ala Ala Ser Gly Ile Leu Ile Asn Thr Phe Ser
145                 150                 155                 160

Leu Ala Phe Tyr Ser Phe His His Pro Tyr Cys Asn Tyr Tyr Gly Asn
                165                 170                 175

Ser Asn Asn Cys His Gly Thr Met Ser Ile Leu Met Gly Leu Asp Gly
            180                 185                 190

Met Val Leu Leu Leu Ser Val Leu Glu Phe Cys Ile Ala Val Ser Leu
        195                 200                 205

Ser Ala Phe Gly Cys Lys Val Leu Cys Cys Thr Pro Gly Gly Val Val
    210                 215                 220

Leu Ile Leu Pro Ser His Ser His Met Ala Glu Thr Ala Ser Pro Thr
225                 230                 235                 240

Pro Leu Asn Glu Val
```

-continued

245

<210> SEQ ID NO 153
<211> LENGTH: 1724
<212> TYPE: DNA
<213> ORGANISM: Homo sapiens

<400> SEQUENCE: 153

```
cgttctctcc tccttcctcc ccgcctccag ctgccggcag gacctttctc tcgctgccgc     60
tgggaccccg tgtcatcgcc caggccgagc acgatgcccc ctaaaaaggg aggtgatgga    120
attaaaccac ccccaatcat tggaagattt ggaacctcac tgaaaattgg tattgttgga    180
ttgccaaatg ttgggaaatc tactttcttc aatgtgttaa ccaatagtca ggcttcagca    240
gaaaacttcc cgttctgcac tattgatcct aatgagagca gagtacctgt gccagatgaa    300
aggtttgact ttctttgtca ataccacaaa ccagcaagca aaattcctgc ctttctaaat    360
gtggtggata ttgctggcct tgtgaaagga gctcacaatg ggcagggcct ggggaatgct    420
tttttatctc atattagtgc ctgtgatggc atctttcatc taacacgtgc ttttgaagat    480
gatgatatca cgcacgttga aggaagtgta gatcctattc gagatataga aataatacat    540
gaagagcttc agcttaaaga tgaggaaatg attgggccca ttatagataa actagaaaag    600
gtggctgtga gaggaggaga taaaaaacta aaacctgaat atgatataat gtgcaaagta    660
aaatcctggg ttatagatca aaagacacct gttcgcttct atcatgattg gaatgacaaa    720
gagattgaag tgttgaatac acacttattt ttgacttcaa aaccaatggt ctacttggtt    780
aatctttctg aaaaagacta cattagaaag aaaaacaaat ggttgataaa aattaaagag    840
tgggtggaca agtatgaccc aggtgctttg gtcattcctt ttagtggggc cttggaactc    900
aagttgcaag aattgagtgc tgaggagaga cagaagtatc tggaagcgaa catgacacaa    960
agtgctttgc caaagatcat taaggctggg tttgcagcac tccaactaga atactttttc   1020
actgcaggcc cagatgaagt gcgtgcatgg accatcagga aagggactaa ggctcctcag   1080
gctgcaggaa agattcacac agattttgaa aagggattca ttatggctga agtaatgaaa   1140
tacgaagatt ttaaagagga aggttctgaa aatgcagtca aggctgctgg aaagtacaga   1200
caacaaggca gaaattatat tgttgaagat ggagatatta tcttcttcaa atttaacaca   1260
cctcaacaac cgaagaagaa ataaaattta gttattgctc agataaacat acaacttcca   1320
aaaggcatct gatttttaaa aaattaaaat ttctgaaaac caatgcgaca aataaagttg   1380
gggagatggg aatctttgac aaacaaatta tttttatttg ttttaaaatt aaaatactgt   1440
gtaccccccc ccccccatg aaatgcaggt tcactaaatg tgaacagctt tgcttttcac    1500
gtgattaaga ccctactcca aattgtagaa gcttttcagg aaccatatta ctctcatgat   1560
acttcattaa tctccatcat gtatgccaag cctgacacat ttgacagtga ggacaatgtg   1620
gcttgctcct ttttgaatct acagataatg catgttttac agtactccag atgtctacac   1680
tcaataaaac atttgacaaa accaaaaaaa aaaaaaaaaa aaaa                    1724
```

<210> SEQ ID NO 154
<211> LENGTH: 396
<212> TYPE: PRT
<213> ORGANISM: Homo sapiens

<400> SEQUENCE: 154

```
Met Pro Pro Lys Lys Gly Gly Asp Gly Ile Lys Pro Pro Pro Ile Ile
  1               5                  10                  15
```

-continued

```
Gly Arg Phe Gly Thr Ser Leu Lys Ile Gly Ile Val Gly Leu Pro Asn
            20                  25                  30

Val Gly Lys Ser Thr Phe Phe Asn Val Leu Thr Asn Ser Gln Ala Ser
        35                  40                  45

Ala Glu Asn Phe Pro Phe Cys Thr Ile Asp Pro Asn Glu Ser Arg Val
    50                  55                  60

Pro Val Pro Asp Glu Arg Phe Asp Phe Leu Cys Gln Tyr His Lys Pro
65                  70                  75                  80

Ala Ser Lys Ile Pro Ala Phe Leu Asn Val Val Asp Ile Ala Gly Leu
                85                  90                  95

Val Lys Gly Ala His Asn Gly Gln Gly Leu Gly Asn Ala Phe Leu Ser
            100                 105                 110

His Ile Ser Ala Cys Asp Gly Ile Phe His Leu Thr Arg Ala Phe Glu
        115                 120                 125

Asp Asp Asp Ile Thr His Val Glu Gly Ser Val Asp Pro Ile Arg Asp
    130                 135                 140

Ile Glu Ile Ile His Glu Glu Leu Gln Leu Lys Asp Glu Glu Met Ile
145                 150                 155                 160

Gly Pro Ile Ile Asp Lys Leu Glu Lys Val Ala Val Arg Gly Gly Asp
                165                 170                 175

Lys Lys Leu Lys Pro Glu Tyr Asp Ile Met Cys Lys Val Lys Ser Trp
            180                 185                 190

Val Ile Asp Gln Lys Thr Pro Val Arg Phe Tyr His Asp Trp Asn Asp
        195                 200                 205

Lys Glu Ile Glu Val Leu Asn Thr His Leu Phe Leu Thr Ser Lys Pro
    210                 215                 220

Met Val Tyr Leu Val Asn Leu Ser Glu Lys Asp Tyr Ile Arg Lys Lys
225                 230                 235                 240

Asn Lys Trp Leu Ile Lys Ile Lys Glu Trp Val Asp Lys Tyr Asp Pro
                245                 250                 255

Gly Ala Leu Val Ile Pro Phe Ser Gly Ala Leu Glu Leu Lys Leu Gln
            260                 265                 270

Glu Leu Ser Ala Glu Glu Arg Gln Lys Tyr Leu Glu Ala Asn Met Thr
        275                 280                 285

Gln Ser Ala Leu Pro Lys Ile Ile Lys Ala Gly Phe Ala Ala Leu Gln
    290                 295                 300

Leu Glu Tyr Phe Phe Thr Ala Gly Pro Asp Glu Val Arg Ala Trp Thr
305                 310                 315                 320

Ile Arg Lys Gly Thr Lys Ala Pro Gln Ala Ala Gly Lys Ile His Thr
                325                 330                 335

Asp Phe Glu Lys Gly Phe Ile Met Ala Glu Val Met Lys Tyr Glu Asp
            340                 345                 350

Phe Lys Glu Glu Gly Ser Glu Asn Ala Val Lys Ala Ala Gly Lys Tyr
        355                 360                 365

Arg Gln Gln Gly Arg Asn Tyr Ile Val Glu Asp Gly Asp Ile Ile Phe
    370                 375                 380

Phe Lys Phe Asn Thr Pro Gln Gln Pro Lys Lys Lys
385                 390                 395
```

<210> SEQ ID NO 155
<211> LENGTH: 2291
<212> TYPE: DNA
<213> ORGANISM: Homo sapiens

<400> SEQUENCE: 155

-continued

```
gaacttgtct gaagcccttg tccgtaagcc ttgaactacg ttcttaaatc tatgaagtcg     60
agggaccttt cgctgctttt gtagggactt ctttccttgc ttcagcaaca tgaggctttt    120
cttgtggaac gcggtcttga ctctgttcgt cacttctttg attggggctt tgatccctga    180
accagaagtg aaaattgaag ttctccagaa gccattcatc tgccatcgca agaccaaagg    240
aggggatttg atgttggtcc actatgaagg ctacttagaa aaggacggct ccttatttca    300
ctccactcac aaacataaca atggtcagcc catttggttt accctgggca tcctggaggc    360
tctcaaaggt tgggaccagg gcttgaaagg aatgtgtgta ggagagaaga gaaagctcat    420
cattcctcct gctctgggct atggaaaaga aggaaaaggt aaaattcccc cagaaagtac    480
actgatattt aatattgatc tcctggagat tcgaaatgga ccaagatccc atgaatcatt    540
ccaagaaatg gatcttaatg atgactggaa actctctaaa gatgaggtta aagcatattt    600
aaagaaggag tttgaaaaac atggtgcggt ggtgaatgaa agtcatcatg atgctttggt    660
ggaggatatt tttgataaag aagatgaaga caaagatggg tttatatctg ccagagaatt    720
tacatataaa cacgatgagt tatagagata catctaccct tttaatatag cactcatctt    780
tcaagagagg gcagtcatct ttaaagaaca ttttattttt atacaatgct ctttcttgct    840
ttgcttttta tttttatata ttttttctga ctcctattta aagaacccct taggtttcta    900
agtacccatt tctttctgat aagttattgg gaagaaaaag ctaattggtc tttgaataga    960
agacttctgg acaatttttc actttcacag atatgaagct ttgttttact ttctcactta   1020
taaatttaaa atgttgcaac tggaatata ccacgacatg agaccaggtt atagcacaaa    1080
ttagcaccct atatttctgc ttccctctat tttctccaag ttagaggtca acatttgaaa   1140
agccttttgc aatagcccaa ggcttgctat tttcatgtta taatgaaata gtttatgtgt   1200
aactggctct gagtctctgc ttgaggacca gaggaaaatg gttgttggac ctgacttgtt   1260
aatggctact gctttactaa ggagatgtgc aatgctgaag ttagaaacaa ggttaatagc   1320
caggcatggt ggctcatgcc tgtaatccca gcactttggg aggctgaggc gggcggatca   1380
cctgaggttg ggagttcgag accagcctga ccaacacgga gaaaccctat ctctactaaa   1440
aatacaaaag tagccgggcg tggtgatgcg tgcctgtaat cccagctacc caggaaggct   1500
gaggcggcag aatcacttga acccggaggc ggaggttgcg gtaagccgag atcacctcca   1560
gcctggacac tctgtctcga aaaaaagaaa agaaacacgg ttaataacat ataaatatgt   1620
atgcattgag acatgctacc taggacttaa gctgatgaag cttggctcct agtgattggt   1680
ggcctattat gataaatagg acaaatcatt tatgtgtgag tttctttgta ataaaatgta   1740
tcaatatgtt atagatgagg tagaaagtta tatttatatt caatatttac ttcttaaggc   1800
tagcggaata tccttcctgg ttctttaatg ggtagtctat agtatattat actacaataa   1860
cattgtatca taagataaag tagtaaacca gtctacattt tcccatttct gtctcatcaa   1920
aaactgaagt tagctgggtg tggtggctca tgcctgtaat cccagcactt tgggggccaa   1980
ggagggtgga tcacttgaga tcaggagttc aagaccagcc tggccaacat ggtgaaacct   2040
tgtctctact aaaaatacaa aaattagcca ggcgtggtgg tgcacacctg tagtcccagc   2100
tactcgggag gctgagacag gagatttgct tgaacccggg aggcggaggt tgcagtgagc   2160
caagattgtg ccactgcact ccagcctggg tgacagagca agactccatc tcaaaaaaaa   2220
aaaaaagaag cagacctaca gcagctacta ttgaataaat acctatcctg gattttaaaa   2280
aaaaaaaaaa a                                                        2291
```

<210> SEQ ID NO 156
<211> LENGTH: 211
<212> TYPE: PRT
<213> ORGANISM: Homo sapiens

<400> SEQUENCE: 156

```
Met Arg Leu Phe Leu Trp Asn Ala Val Leu Thr Leu Phe Val Thr Ser
  1               5                  10                  15

Leu Ile Gly Ala Leu Ile Pro Glu Pro Glu Val Lys Ile Glu Val Leu
             20                  25                  30

Gln Lys Pro Phe Ile Cys His Arg Lys Thr Lys Gly Gly Asp Leu Met
         35                  40                  45

Leu Val His Tyr Glu Gly Tyr Leu Glu Lys Asp Gly Ser Leu Phe His
     50                  55                  60

Ser Thr His Lys His Asn Asn Gly Gln Pro Ile Trp Phe Thr Leu Gly
 65                  70                  75                  80

Ile Leu Glu Ala Leu Lys Gly Trp Asp Gln Gly Leu Lys Gly Met Cys
                 85                  90                  95

Val Gly Glu Lys Arg Lys Leu Ile Ile Pro Pro Ala Leu Gly Tyr Gly
            100                 105                 110

Lys Glu Gly Lys Gly Lys Ile Pro Pro Glu Ser Thr Leu Ile Phe Asn
        115                 120                 125

Ile Asp Leu Leu Glu Ile Arg Asn Gly Pro Arg Ser His Glu Ser Phe
    130                 135                 140

Gln Glu Met Asp Leu Asn Asp Asp Trp Lys Leu Ser Lys Asp Glu Val
145                 150                 155                 160

Lys Ala Tyr Leu Lys Lys Glu Phe Glu Lys His Gly Ala Val Val Asn
                165                 170                 175

Glu Ser His His Asp Ala Leu Val Glu Asp Ile Phe Asp Lys Glu Asp
            180                 185                 190

Glu Asp Lys Asp Gly Phe Ile Ser Ala Arg Glu Phe Thr Tyr Lys His
        195                 200                 205

Asp Glu Leu
    210
```

<210> SEQ ID NO 157
<211> LENGTH: 2229
<212> TYPE: DNA
<213> ORGANISM: Homo sapiens

<400> SEQUENCE: 157

```
gaagacgttg acacacttgg agccaacaag aacattagtc atgacaagca tgccatctga      60

aaagcagaat gtcgtcatcc aggttgtgga taaattgaaa ggcttttcaa ttgcaccaga     120

cgtctgtgag accacgactc acgtgctttc cgggaagcca cttcgcaccc tgaatgtgct     180

gctgggaatt gcgcgtggct gctgggttct ctcttatgat tgggtgctat ggtctttaga     240

attgggtcac tggatttctg aggagccgtt cgaactgtct caccacttcc ctgcagctcc     300

cctgtgccga agcgagtgcc acttgtctgc agggccgtac cgcggaaccc tctttgccga     360

ccagccagcg atgtttgtct cgcctgccag cagcccccca gtggccaagc tctgtgaact     420

agtccacctg tgcggaggcc gggtcagcca agtcccccgc caggccagca tcgtcatcgg     480

gccctacagc ggaaagaaga aagccacagt caagtatctg tctgagaaat gggtcttagg     540

taagaatcca ggcacacaga cgctgtggtg tggtccagat ctgtggacag gtttccaggg     600

agggcggcgt caggctcaca ccccccttcca cgcagctggg gcacctgggt tgatgtctca     660
```

-continued

```
gcctccagca tctgccctgg cagcgtcgtg tggtcaccct cggcattccc gctccttgct    720

gttagcagac gtacagttca cgaggaaatg ggaactctaa ctggacttcc ccacttgact    780

tccctggctc gtgtgaaaaa tccaggctac ccaaagccac cccgggccac ccctgtgggc    840

acagactctc cgggcacccc tcttagaccc tccctcccca gtgcctcctt gtcctgcttc    900

aggagtccct ggcagcgccc ggcactgggg cccaagcccc cgtccctgtc atctcctctc    960

ccaggtacat ctcatgatca ctccgtctgc tcatgtgctc aaagggtgtt aaaagacgtc   1020

aaacgactcc atcttttatt tgacaaagtg agcacagtgt gaccgtaatg tcccactctg   1080

gcgttcatgg agctgcgcca ggcgccgtgt gcgattctgg ggaggaagag gtggtaggag   1140

ctgagctgag atcggaggag gctggaaccc cacgccgtgc taacacacgg gctccaggag   1200

acttgcaggt gatccccgga gaagagggtt aaggaagagt gtgaagcaag gacggcctgg   1260

ggaatgcgga ggaagcaggg cagcgtctgt gctagaaatt acctgccctg tggtggagtc   1320

atatgtggcg ggacaagcct agggctccac tgtggggaaa tcccacaccc tcctccatgg   1380

ggttgtgata aacatgttag tttgcttggg ctgccatcgc aaaatactac aggctgggtg   1440

gcttcaaaca acacgcattg tctctcagtt ctggaggctg gaagtctaag atggggtatc   1500

ggcagcgttg gtttcccctg aggcctctct cctgggcttg cagacagctg ccttcttcct   1560

gtgacctcac gtggcctttc ctccatgcac acacatccct ggtatctctg tgtgtgtcca   1620

aatgttctct tctctaagga taccagtcag attggattag ggctcaccca gtggcatcat   1680

tttaacttgt ctttttcaag gccccatctc caaatacagt ctcatcctga gttactgagg   1740

gttaagacat cgacatacga attttgggca gacacaattc agcccataac aatgaatcac   1800

tctagtttca gcccctgggg ccaagatcct tacccgactt tagaggtaca tcccctctct   1860

ctctctcaat ctctctctct ctctcccgtt ctctcattct ttttctctct ctttgcttcc   1920

atctccttcc atgtttccta ttcagtctcc tttcttagta cttttgcatg tctctaaatc   1980

ctaaacttct ggcttttctc atcatctgct caacattatc ccttaataga caagtagata   2040

ctgtgtttgt tcaagttaca ttcgtatcta actacggaca ttttacaagt atcttttaca   2100

tgactgatgg tcatcctttc atatatttta gaagtgtggc aatcaaaagt aatttttttac  2160

tctggtgcag agtaattcat cttttgcctg gaaaccaact tccaaaaaaa aaaaaaaaaa   2220

aaaaaaaaa                                                            2229
```

```
<210> SEQ ID NO 158
<211> LENGTH: 239
<212> TYPE: PRT
<213> ORGANISM: Homo sapiens

<400> SEQUENCE: 158

Met Thr Ser Met Pro Ser Glu Lys Gln Asn Val Val Ile Gln Val Val
  1               5                  10                  15

Asp Lys Leu Lys Gly Phe Ser Ile Ala Pro Asp Val Cys Glu Thr Thr
             20                  25                  30

Thr His Val Leu Ser Gly Lys Pro Leu Arg Thr Leu Asn Val Leu Leu
         35                  40                  45

Gly Ile Ala Arg Gly Cys Trp Val Leu Ser Tyr Asp Trp Val Leu Trp
     50                  55                  60

Ser Leu Glu Leu Gly His Trp Ile Ser Glu Glu Pro Phe Glu Leu Ser
 65                  70                  75                  80

His His Phe Pro Ala Ala Pro Leu Cys Arg Ser Glu Cys His Leu Ser
```

-continued

```
                85                  90                  95

Ala Gly Pro Tyr Arg Gly Thr Leu Phe Ala Asp Gln Pro Ala Met Phe
            100                 105                 110

Val Ser Pro Ala Ser Ser Pro Pro Val Ala Lys Leu Cys Glu Leu Val
        115                 120                 125

His Leu Cys Gly Gly Arg Val Ser Gln Val Pro Arg Gln Ala Ser Ile
    130                 135                 140

Val Ile Gly Pro Tyr Ser Gly Lys Lys Lys Ala Thr Val Lys Tyr Leu
145                 150                 155                 160

Ser Glu Lys Trp Val Leu Gly Lys Asn Pro Gly Thr Gln Thr Leu Trp
                165                 170                 175

Cys Gly Pro Asp Leu Trp Thr Gly Phe Gln Gly Gly Arg Arg Gln Ala
            180                 185                 190

His Thr Pro Phe His Ala Ala Gly Ala Pro Gly Leu Met Ser Gln Pro
        195                 200                 205

Pro Ala Ser Ala Leu Ala Ala Ser Cys Gly His Pro Arg His Ser Arg
    210                 215                 220

Ser Leu Leu Leu Ala Asp Val Gln Phe Thr Arg Lys Trp Glu Leu
225                 230                 235


<210> SEQ ID NO 159
<211> LENGTH: 3580
<212> TYPE: DNA
<213> ORGANISM: Homo sapiens

<400> SEQUENCE: 159

aggtctagaa gtgccccaag ccccatcatg gaagagggct tccgagaccg ggcagctttc      60

atccgtgggg ccaaagacat tgctaaggaa gtcaaaaagc atgcggccaa gaaggtggtg     120

aagggcctgg acagagtcca ggacgaatat tcccgaagat cgtactcccg ctttgaggag     180

gaggatgatg atgatgactt ccctgctccc agtgatggtt attacccagg agaagggacc     240

caggatgagg aggaaggtgg tgcatccagt gatgctactg agggccatga cgaggatgat     300

gacatctatg aaggggaata tcagggcatt ccccgggcag agtctggggg caaaggcgag     360

cggatggcag atggggcgcc cctggctgga gtaagggggg gcttgagtga tggggagggt     420

ccccctgggg gccgggggga ggcacaacga cggaaagaac gagaagaact ggcccaacag     480

tatgaagcca tcctacggga gtgtggccac ggccgcttcc agtggacact gtattttgtg     540

cttggtctgg cgctgatggc tgacggtgtg gaggtctttg tggtgggctt cgtgctgccc     600

agcgctgaga aagacatgtg cctgtccgac tccaacaaag gcatgctagg cctcatcgtc     660

tacctgggca tgatggtggg agccttcctc tggggaggtc tggctgaccg gctgggtcgg     720

aggcagtgtc tgctcatctc gctctcagtc aacagcgtct tcgccttctt ctcatctttt     780

gtccagggtt acggcacttt cctcttctgc cgcctacttt ctggggttgg gattggaggg     840

tccatcccca ttgtcttctc ctatttctcc gagtttctgg cccaggagaa acgaggggag     900

catttgagct ggctctgcat gttttggatg attggtggcg tgtacgcagc tgctatggcc     960

tgggccatca tcccccacta tgggtggagt tttcagatgg gttctgccta ccagttccac    1020

agctggaggg tcttcgtcct cgtctgcgcc tttccttctg tgtttgccat tggggctctg    1080

accacgcagc ctgagagccc ccgtttcttc ctagagaatg gaaagcatga tgaggcctgg    1140

atggtgctga agcaggtcca tgataccaac atgcgagcca aaggacatcc tgagcgagtg    1200

ttctcagtaa cccacattaa gacgattcat caggaggatg aattgattga gatccagtcg    1260
```

-continued

```
gacacaggga cctggtacca gcgctggggg gtccgggcct tgagcctagg ggggcaggtt   1320
tgggggaatt ttctctcctg ttttggtccc gaatatcggc gcatcactct gatgatgatg   1380
ggtgtgtggt tcaccatgtc attcagctac tatggcctga ccgtctggtt tcctgacatg   1440
atccgccatc tccaggcagt ggactacgca tcccgcacca aagtgttccc cggggagcgc   1500
gtagagcatg taacttttaa cttcacgttg gagaatcaga tccaccgagg cgggcagtac   1560
ttcaatgaca agttcattgg gctgcggctc aagtcagtgt cctttgagga ttccctgttt   1620
gaagagtgtt attttgagga tgtcacatcc agcaacacgt tttccgcaa ctgcacattc    1680
atcaacactg tgttctataa cactgacctg ttcgagtaca agtttgtgaa cagccgtctg   1740
ataaacagta cattcctgca caacaaggag ggctgcccgc tagacgtgac agggacgggc   1800
gaaggtgcct acatggtata ctttgtgagc ttcctgggga cactggcagt gcttcctggg   1860
aatatcgtgt ctgccctgct catggacaag atcggcaggc tcagaatgct tgctggctcc   1920
agcgtgatgt cctgtgtctc ctgcttcttc ctgtcttttg ggaacagtga gtcggccatg   1980
atcgctctgc tctgcctttt tggcggggtc agcattgcat cctggaatgc gctggacgtg   2040
ttgactgttg aactttaccc ctcagacaag aggaccacag cttttggctt cctgaatgcc   2100
ctgtgtaagc tggcagctgt gctggggatc agcatcttca catccttcgt gggaatcacc   2160
aaggctgcac ccatcctctt tgcctcagct gcccttgccc ttggcagctc tctggccctg   2220
aagctgcctg agacccgggg gcaggtgctg cagtgaaggg gtctctaggg ctttgggatt   2280
ggcaggcaca ctgtgagacc aacaactcct tccttcccct ccctgccctg ccatcctgac   2340
ctccagagcc ctcactcccc actccccgtg tttggtgtct tagctgtgtg tgcgtgtgcg   2400
tgtgcatgtg tgtaaacccc gtgggcaggg actacaggga aggctccttc atcccagttt   2460
tgagatgaag ctgtactccc catttcccac tgcccttgac tttgcacaag agaaggctga   2520
gccccatcct tctcccctg ttagagaggg gcccttgctt ccctgttcca ggggttccag    2580
aataggcttc ctgccttccc catcattccc tctgcctagg ccctggtgaa accacaggta   2640
tgcaattatg ctaggggctg gggctctggt gtagaccatg gaccaaaaga acttcttaga   2700
gtctgaagag tgggcctcgg gtgccctctc acatctcctg ttggatgctg gggagaagc    2760
aataaacctc agccctctgg cctccacttt cctctcaatt tgggctgcaa atatgaagcc   2820
tgaattttat gaaattagct ttctgattct tatttattaa tagattaagt tctgaggcag   2880
ctccgcagga ctgtgtgtga atgtgtatgt atacttacat atgtgtgtgc atgtgccatg   2940
gggcgggggg tatcactata ctgtcctcaa atataagcca agggtaattt cagcggatgc   3000
acacacaacc ctgcctccca cagttcctcc cctaatctgg tttctgtgtt gagcctggga   3060
tggaggagcc ctaggccagc ctgggataag agtcccacag tctagggaga tctgagggca   3120
tccgacaagg cccatctcct tccctcctca agaagcagag gcctcctctg gagtgagagg   3180
ctccacccac tacagcacag gcgggaatag cacagctgcc ctcccatgct ccctacctgt   3240
cccctcacag ggaggggagc aggggaggga aagaaaccag gcatctggtc aaaccagcag   3300
atcaaaaagc acaaagagct ggggcagagg caggaagcag gggccctcct ggcagctcct   3360
ctgagtgggg agaggttggg cagtgagtga gggaccccta atgcagggac tagaagcctc   3420
agtttcccca ttttaccctt ccacacaata gcctctgtag gttaggctgc cccatcccac   3480
cctactctgt gtggctgctt tctttggtgc cctcccctca ccccactgta gctgtgacgt   3540
gttgtagttt ttagatgttt gtaaaatgtt taaaaaaatg                         3580
```

-continued

```
<210> SEQ ID NO 160
<211> LENGTH: 742
<212> TYPE: PRT
<213> ORGANISM: Homo sapiens

<400> SEQUENCE: 160

Met Glu Glu Gly Phe Arg Asp Arg Ala Ala Phe Ile Arg Gly Ala Lys
  1               5                  10                  15

Asp Ile Ala Lys Glu Val Lys Lys His Ala Ala Lys Lys Val Val Lys
             20                  25                  30

Gly Leu Asp Arg Val Gln Asp Glu Tyr Ser Arg Arg Ser Tyr Ser Arg
         35                  40                  45

Phe Glu Glu Glu Asp Asp Asp Asp Asp Phe Pro Ala Pro Ser Asp Gly
     50                  55                  60

Tyr Tyr Pro Gly Glu Gly Thr Gln Asp Glu Glu Glu Gly Gly Ala Ser
 65                  70                  75                  80

Ser Asp Ala Thr Glu Gly His Asp Glu Asp Asp Asp Ile Tyr Glu Gly
                 85                  90                  95

Glu Tyr Gln Gly Ile Pro Arg Ala Glu Ser Gly Gly Lys Gly Glu Arg
            100                 105                 110

Met Ala Asp Gly Ala Pro Leu Ala Gly Val Arg Gly Gly Leu Ser Asp
        115                 120                 125

Gly Glu Gly Pro Pro Gly Gly Arg Gly Glu Ala Gln Arg Arg Lys Glu
    130                 135                 140

Arg Glu Glu Leu Ala Gln Gln Tyr Glu Ala Ile Leu Arg Glu Cys Gly
145                 150                 155                 160

His Gly Arg Phe Gln Trp Thr Leu Tyr Phe Val Leu Gly Leu Ala Leu
                165                 170                 175

Met Ala Asp Gly Val Glu Val Phe Val Val Gly Phe Val Leu Pro Ser
            180                 185                 190

Ala Glu Lys Asp Met Cys Leu Ser Asp Ser Asn Lys Gly Met Leu Gly
        195                 200                 205

Leu Ile Val Tyr Leu Gly Met Met Val Gly Ala Phe Leu Trp Gly Gly
    210                 215                 220

Leu Ala Asp Arg Leu Gly Arg Arg Gln Cys Leu Leu Ile Ser Leu Ser
225                 230                 235                 240

Val Asn Ser Val Phe Ala Phe Phe Ser Ser Phe Val Gln Gly Tyr Gly
                245                 250                 255

Thr Phe Leu Phe Cys Arg Leu Leu Ser Gly Val Gly Ile Gly Gly Ser
            260                 265                 270

Ile Pro Ile Val Phe Ser Tyr Phe Ser Glu Phe Leu Ala Gln Glu Lys
        275                 280                 285

Arg Gly Glu His Leu Ser Trp Leu Cys Met Phe Trp Met Ile Gly Gly
    290                 295                 300

Val Tyr Ala Ala Ala Met Ala Trp Ala Ile Ile Pro His Tyr Gly Trp
305                 310                 315                 320

Ser Phe Gln Met Gly Ser Ala Tyr Gln Phe His Ser Trp Arg Val Phe
                325                 330                 335

Val Leu Val Cys Ala Phe Pro Ser Val Phe Ala Ile Gly Ala Leu Thr
            340                 345                 350

Thr Gln Pro Glu Ser Pro Arg Phe Phe Leu Glu Asn Gly Lys His Asp
        355                 360                 365

Glu Ala Trp Met Val Leu Lys Gln Val His Asp Thr Asn Met Arg Ala
    370                 375                 380
```

-continued

```
Lys Gly His Pro Glu Arg Val Phe Ser Val Thr His Ile Lys Thr Ile
385                 390                 395                 400

His Gln Glu Asp Glu Leu Ile Glu Ile Gln Ser Asp Thr Gly Thr Trp
            405                 410                 415

Tyr Gln Arg Trp Gly Val Arg Ala Leu Ser Leu Gly Gly Gln Val Trp
        420                 425                 430

Gly Asn Phe Leu Ser Cys Phe Gly Pro Glu Tyr Arg Arg Ile Thr Leu
    435                 440                 445

Met Met Met Gly Val Trp Phe Thr Met Ser Phe Ser Tyr Tyr Gly Leu
    450                 455                 460

Thr Val Trp Phe Pro Asp Met Ile Arg His Leu Gln Ala Val Asp Tyr
465                 470                 475                 480

Ala Ser Arg Thr Lys Val Phe Pro Gly Glu Arg Val Glu His Val Thr
            485                 490                 495

Phe Asn Phe Thr Leu Glu Asn Gln Ile His Arg Gly Gly Gln Tyr Phe
        500                 505                 510

Asn Asp Lys Phe Ile Gly Leu Arg Leu Lys Ser Val Ser Phe Glu Asp
    515                 520                 525

Ser Leu Phe Glu Glu Cys Tyr Phe Glu Asp Val Thr Ser Ser Asn Thr
    530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Ile Asn Ser Thr Phe
            565                 570                 575

Leu His Asn Lys Glu Gly Cys Pro Leu Asp Val Thr Gly Thr Gly Glu
        580                 585                 590

Gly Ala Tyr Met Val Tyr Phe Val Ser Phe Leu Gly Thr Leu Ala Val
    595                 600                 605

Leu Pro Gly Asn Ile Val Ser Ala Leu Leu Met Asp Lys Ile Gly Arg
    610                 615                 620

Leu Arg Met Leu Ala Gly Ser Ser Val Met Ser Cys Val Ser Cys Phe
625                 630                 635                 640

Phe Leu Ser Phe Gly Asn Ser Glu Ser Ala Met Ile Ala Leu Leu Cys
            645                 650                 655

Leu Phe Gly Gly Val Ser Ile Ala Ser Trp Asn Ala Leu Asp Val Leu
        660                 665                 670

Thr Val Glu Leu Tyr Pro Ser Asp Lys Arg Thr Thr Ala Phe Gly Phe
    675                 680                 685

Leu Asn Ala Leu Cys Lys Leu Ala Ala Val Leu Gly Ile Ser Ile Phe
    690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
            725                 730                 735

Arg Gly Gln Val Leu Gln
        740
```

<210> SEQ ID NO 161
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)

<223> OTHER INFORMATION: biotinylated phosphoaramidite residue

<400> SEQUENCE: 161
cnccaagcag gggaacggtg agagaaaca 29

<210> SEQ ID NO 162
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 162
cnagcacaaa acacaaagct gcaaaagcc 29

<210> SEQ ID NO 163
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 163
gntgagttag tgaccacaaa gatgcgctt 29

<210> SEQ ID NO 164
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 164
gncatcgtcc tcctccttca acatcccag 29

<210> SEQ ID NO 165
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 165
gngtttcaga aaattccata cagacctca 29

<210> SEQ ID NO 166
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature -continued
<222> LOCATION: (2)
<223> OTHER INFORMATION: biotinylated phosphoaramidite residue

<400> SEQUENCE: 166
angacattga gatgttcctt gagtccagc 29

<210> SEQ ID NO 167
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 167
tngtggttcc aaagtacggg ccatcctga 29

<210> SEQ ID NO 168
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 168
tncagcatcc gtagcacaaa tctccattg 29

<210> SEQ ID NO 169
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 169
gngcacagag gccagcacgt taagaagga 29

<210> SEQ ID NO 170
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 170
cntcatgagg gggaccacac agttggcta 29

<210> SEQ ID NO 171
<211> LENGTH: 29
<212> TYPE: DNA
<213> ORGANISM: Artificial Sequence
<220> FEATURE:
<223> OTHER INFORMATION: oligonucleotide
<220> FEATURE:

<221> NAME/KEY: misc_feature
<222> LOCATION: (2)
<223> OTHER INFORMATION: biotinylated phosphoaramidite residue

<400> SEQUENCE: 171
gnattctcta tgtttgcaga tgccgccat 29

<210> SEQ ID NO 172
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 172
tncgcttgtg acaaggaacc aagcaattt 29

<210> SEQ ID NO 173
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 173
gngctaaata ccgccatata tccaaagta 29

<210> SEQ ID NO 174
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 174
tncagagttc taaccaggct ccccaatgc 29

<210> SEQ ID NO 175
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 175
cnactaaagg gaccataaca accaaaact 29

<210> SEQ ID NO 176
<211> LENGTH: 29
<212> TYPE: DNA
<213> ORGANISM: Artificial Sequence
<220> FEATURE:
<223> OTHER INFORMATION: oligonucleotide -continued
<220> FEATURE:
<221> NAME/KEY: misc_feature
<222> LOCATION: (2)
<223> OTHER INFORMATION: biotinylated phosphoaramidite residue

<400> SEQUENCE: 176
cnagacacca acactgctac catgcgcag 29

<210> SEQ ID NO 177
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 177
gntcacaatg gagaacacac ggagaaggc 29

<210> SEQ ID NO 178
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 178
cnggctgtcc tcgccgtttt ctaaccatg 29

<210> SEQ ID NO 179
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 179
tnctgtaggg ctgcctggct cttgtcgct 29

<210> SEQ ID NO 180
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 180
antcccttag aaagagatga ctggatgtc 29

<210> SEQ ID NO 181
<211> LENGTH: 29
<212> TYPE: DNA
<213> ORGANISM: Artificial Sequence
<220> FEATURE:

-continued

<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 181
gngcataatc ctccagatcc atgtaaacc 29

<210> SEQ ID NO 182
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 182
tncttccaat cactatatca ccacgctca 29

<210> SEQ ID NO 183
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 183
gnatagacga agccccctgc cacagatcg 29

<210> SEQ ID NO 184
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 184
gnccttcctt ccactggact gccacaaca 29

<210> SEQ ID NO 185
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 185
cnggaacctt cttcgtacac tgcctttgg 29

<210> SEQ ID NO 186
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 186
gncttgcaat tactgatcca accctctgt 29

<210> SEQ ID NO 187
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 187
tnctgtctcg tcataaaaca gctctgggg 29

<210> SEQ ID NO 188
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 188
gngaaacatg tggtgatgat ggcagaagc 29

<210> SEQ ID NO 189
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 189
angagtccac tgttgaatga tgactaaca 29

<210> SEQ ID NO 190
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 190
gnccagagat acacaggaga atagacatt 29

<210> SEQ ID NO 191
<211> LENGTH: 29
<212> TYPE: DNA

<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 191
cntgtagcat ctttctcctg actatctaa 29

<210> SEQ ID NO 192
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 192
gnaacttgaa ttccgcacat ggcatagcc 29

<210> SEQ ID NO 193
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 193
tnctccacag ggcatacatg gtggttcat 29

<210> SEQ ID NO 194
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 194
cntctgcatt tttttctgtg atcggtctt 29

<210> SEQ ID NO 195
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 195
tngtcttttt gtgagtgttt tctgactgc 29

<210> SEQ ID NO 196
<211> LENGTH: 29

```
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 196

gncactaact ctaaaatccc accctgcct                                    29


<210> SEQ ID NO 197
<211> LENGTH: 23
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 197

cactatgagg tttaattgga aac                                          23


<210> SEQ ID NO 198
<211> LENGTH: 21
<212> TYPE: DNA
<213> ORGANISM: Artificial Sequence
<220> FEATURE:
<223> OTHER INFORMATION: oligonucleotide

<400> SEQUENCE: 198

      tcctgaattg aaagcaactg c                                        21


<210> SEQ ID NO 199
LENGTH:     21
<212> TYPE: DNA
<213> ORGANISM: Artificial Sequence
<220> FEATURE:
<223> OTHER INFORMATION: oligonucleotide

<400> SEQUENCE: 199

      aactccatga ctgaccgaca c                                        21


<210> SEQ ID NO 200
<211> LENGTH: 20
<212> TYPE: DNA
<213> ORGANISM: Artificial Sequence
<220> FEATURE:
OTHER INFORMATION: oligonucleoti    de

<400> SEQUENCE: 200

      tcagttcccg tcatattcag                                          20


<210> SEQ ID NO 201
<211> LENGTH: 18
<212> TYPE: DNA
<213> ORGANISM: Artificial Sequence
<220> FEATURE:
<223> OTHER INFORMATION: oligonucleotide

<400> SEQUENCE: 201

gaccaagctg gtgaaccg                                                18


<210> SEQ ID NO 202
```

<211> LENGTH: 21
<212> TYPE: DNA
<213> ORGANISM: Artificial Sequence
<220> FEATURE:
<223> OTHER INFORMATION: oligonucleotide

<400> SEQUENCE: 202
gtgctgttta gactcagatt c 21

<210> SEQ ID NO 203
<211> LENGTH: 21
<212> TYPE: DNA
<213> ORGANISM: Artificial Sequence
<220> FEATURE:
<223> OTHER INFORMATION: oligonucleotide

<400> SEQUENCE: 203
agctcacaga gtcaggacat c 21

<210> SEQ ID NO 204
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 204
cnacgcccag tcctttctcc aagttcttt 29

<210> SEQ ID NO 205
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 205
tnattctctc cttcaatgcg gatgtctgg 29

<210> SEQ ID NO 206
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 206
antctatctt ggatgccttt acttcctgc 29

<210> SEQ ID NO 207
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature -continued
<222> LOCATION: (2)
<223> OTHER INFORMATION: biotinylated phosphoaramidite residue

<400> SEQUENCE: 207
anagagagag tcaacgtcgg cagagcgag 29

<210> SEQ ID NO 208
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 208
tngattgaca ccaatccctt cagccttat 29

<210> SEQ ID NO 209
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 209
anagcgtcat cgttagcgat gccttgtat 29

<210> SEQ ID NO 210
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 210
gngacacagc agagaacgaa ctgacagga 29

<210> SEQ ID NO 211
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 211
cnttgtatga atcgtggact tcctgttct 29

<210> SEQ ID NO 212
<211> LENGTH: 29
<212> TYPE: DNA
<213> ORGANISM: Artificial Sequence
<220> FEATURE:
<223> OTHER INFORMATION: oligonucleotide
<220> FEATURE:

<221> NAME/KEY: misc_feature
<222> LOCATION: (2)
<223> OTHER INFORMATION: biotinylated phosphoaramidite residue

<400> SEQUENCE: 212
tnggtgttga cagtgaccag atagaggct 29

<210> SEQ ID NO 213
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 213
antggtgttc ttctatgttc tcaagttcc 29

<210> SEQ ID NO 214
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 214
gntgggtctg atgtcctgct gtttttgga 29

<210> SEQ ID NO 215
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 215
angtcaggga ggcaccgtag ttaatgaat 29

<210> SEQ ID NO 216
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 216
ancggtaact ctgaccagtg tcctggaag 29

<210> SEQ ID NO 217
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 217
tnctgtggaa caggaggtca ctacgctga 29

<210> SEQ ID NO 218
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 218
cnctggtcat aagacagtac tccagcgct 29

<210> SEQ ID NO 219
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 219
tnataatgct acttaaccac cttttgtct 29

<210> SEQ ID NO 220
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 220
cntgacacaa atccaccttc ttgccacct 29

<210> SEQ ID NO 221
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 221
tnagtgtctt gtagtgttct gtgtgagtt 29

<210> SEQ ID NO 222
<211> LENGTH: 29
<212> TYPE: DNA
<213> ORGANISM: Artificial Sequence
<220> FEATURE:

<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 222
gntcatggat ggcatgacag aattaggat 29

<210> SEQ ID NO 223
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 223
anattgtcat ttaaaatgag cacctccag 29

<210> SEQ ID NO 224
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 224
cnctagccac cacagcatag tcagaatcc 29

<210> SEQ ID NO 225
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 225
gngcagcatg gacctgtcag caactaagg 29

<210> SEQ ID NO 226
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 226
gntcagcgcg tctctggttt ggttccctc 29

<210> SEQ ID NO 227
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 227
gnacaccatc agatgtatga aatgtgggt 29

<210> SEQ ID NO 228
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 228
tnccacctct gaagcctgat tactgtgtg 29

<210> SEQ ID NO 229
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 229
tnttgggctc gtccttcttg gcctccttc 29

<210> SEQ ID NO 230
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 230
cntaatgttg actgcagagg gaaaggcaa 29

<210> SEQ ID NO 231
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 231
tngataattt tgggcttctt tttggaacc 29

<210> SEQ ID NO 232
<211> LENGTH: 29
<212> TYPE: DNA

-continued

<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 232
tnagcggctg tctccacagg acaatattc 29

<210> SEQ ID NO 233
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 233
tncccgatat acacggaaat agggttact 29

<210> SEQ ID NO 234
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 234
tngatttccc aacatttggc aatccaaca 29

<210> SEQ ID NO 235
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 235
angcagcgaa aggtccctcg acttcatag 29

<210> SEQ ID NO 236
<211> LENGTH: 20
<212> TYPE: DNA
<213> ORGANISM: Artificial Sequence
<220> FEATURE:
<223> OTHER INFORMATION: oligonucleotide

<400> SEQUENCE: 236
cggaaagaag aaagccacag 20

<210> SEQ ID NO 237
<211> LENGTH: 29
<212> TYPE: DNA
<213> ORGANISM: Artificial Sequence
<220> FEATURE:
<223> OTHER INFORMATION: oligonucleotide

```
<220> FEATURE:
<221> NAME/KEY: misc_feature
<222> LOCATION: (2)
<223> OTHER INFORMATION: biotinylated phosphoaramidite residue

<400> SEQUENCE: 237

tngtcagagc cccaatggca aacacagaa                                         29


<210> SEQ ID NO 238
<211> LENGTH: 86
<212> TYPE: PRT
<213> ORGANISM: Homo sapiens

<400> SEQUENCE: 238

Met Ser Gly His Ser Leu Ala Arg Thr Leu Leu Leu Tyr Leu Arg Asn
  1               5                  10                  15

Met Thr Phe Leu Phe Gln Arg Met Met Met Met Met Thr Asn Arg Asn
             20                  25                  30

Tyr Arg Lys Glu Lys Ala Leu Thr Glu Glu Met Val Met Leu Ser Val
         35                  40                  45

Ser Leu Pro Ser Leu Ser Ala Glu Arg Leu Gly Glu Gly Pro Gln Pro
     50                  55                  60

Pro Ser Leu Val Lys Leu Pro Val Trp Ser Met Thr Val Phe His Pro
 65                  70                  75                  80

Arg Leu Trp Glu Ala Pro
                 85


<210> SEQ ID NO 239
<211> LENGTH: 48
<212> TYPE: PRT
<213> ORGANISM: Homo sapiens

<400> SEQUENCE: 239

Met Arg Leu Leu Leu Leu Leu Leu Val Ala Ala Ser Ala Met Val Arg
  1               5                  10                  15

Ser Glu Ala Ser Ala Asn Leu Gly Gly Val Pro Ser Lys Arg Leu Lys
             20                  25                  30

Met Gln Tyr Ala Thr Gly Pro Leu Leu Lys Phe Gln Ile Cys Val Ser
         35                  40                  45


<210> SEQ ID NO 240
<211> LENGTH: 140
<212> TYPE: PRT
<213> ORGANISM: Homo sapiens

<400> SEQUENCE: 240

Met Leu Ser Asn Arg Leu Pro Phe Ser Ala Ala Lys Ser Leu Ile Asn
  1               5                  10                  15

Ser Pro Ser Gln Gly Ala Phe Ser Ser Leu Arg Asp Leu Ser Pro Gln
             20                  25                  30

Glu Asn Pro Phe Leu Glu Val Ser Ala Pro Ser Glu His Phe Ile Glu
         35                  40                  45

Asn Asn Asn Thr Lys Asp Thr Thr Ala Arg Asn Ala Phe Glu Glu Asn
     50                  55                  60

Val Phe Met Glu Asn Thr Asn Met Pro Glu Gly Thr Ile Ser Glu Asn
 65                  70                  75                  80

Thr Asn Tyr Asn His Pro Pro Glu Ala Asp Ser Ala Gly Thr Ala Phe
                 85                  90                  95

Asn Leu Gly Pro Thr Val Lys Gln Thr Glu Thr Lys Trp Glu Tyr Asn
```

-continued

```
            100                 105                 110

Asn Val Gly Thr Asp Leu Ser Pro Glu Pro Lys Ser Phe Asn Tyr Pro
        115                 120                 125

Leu Leu Ser Ser Gln Val Ile Ser Leu Lys Phe Ser
    130                 135                 140
```